US011473097B2

(12) United States Patent
Miller et al.

(10) Patent No.: US 11,473,097 B2
(45) Date of Patent: Oct. 18, 2022

(54) METHODS OF INCREASING SEED YIELD

(71) Applicant: Plant Bioscience Limited, Norwich (GB)

(72) Inventors: Charlotte Miller, La Jolla, CA (US); Michael Bevan, Norwich (GB)

(73) Assignee: PLANT BIOSCTENCE LIMITED, Norwich (GB)

( * ) Notice: Subject to any disclaimer, the term of this patent is extended or adjusted under 35 U.S.C. 154(b) by 0 days.

(21) Appl. No.: 16/476,641

(22) PCT Filed: Jan. 10, 2018

(86) PCT No.: PCT/GB2018/050063
§ 371 (c)(1),
(2) Date: Jul. 9, 2019

(87) PCT Pub. No.: WO2018/130828
PCT Pub. Date: Jul. 19, 2018

(65) Prior Publication Data

US 2020/0131524 A1 Apr. 30, 2020

(30) Foreign Application Priority Data

Jan. 10, 2017 (GB) ..................................... 1700380

(51) Int. Cl.
*C12N 15/82* (2006.01)
*C12Q 1/6895* (2018.01)

(52) U.S. Cl.
CPC ..... *C12N 15/8261* (2013.01); *C12N 15/8213* (2013.01); *C12N 15/8218* (2013.01); *C12N 15/8245* (2013.01); *C12N 15/8247* (2013.01); *C12N 15/8251* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2016/0208243 A1* 7/2016 Zhang .................... C12N 15/82

FOREIGN PATENT DOCUMENTS

WO WO2013122472 * 8/2013 ............. C12N 15/82
WO WO2013122472 A1 8/2013

OTHER PUBLICATIONS

Downes et al. The HEXT ubiquitin-protein ligase (UPL) family in *Arabidopsis*: UPL3 has a specific role in trichome development. The Plant Journal. 2003. 35:729-742.*
Yunhai Li et al. Control of final seed and organ size by the DA1 gene family in *Arabidopsis thaliana*. Genes & Development. 2008. 22:1331-1336.*
Na Li et al. Ubiquitin mediated control of seed size in plants. Current Opinion in Plant Biology. 2016. 33:23-32.*
Smith et al. (Nature Biotechnology, 15:1222-1223, 1997).*
Bork et al. (TIG, 12:425-427, 1996).*
Doerks et al., (TIG, 14:248-250, 1998).*
Kim et al. (Plant Molecular Biology, 24:105-117, 1994).*
Benfey et al., Science 250:959-966, 1990.*
Feke et al. (Genetics, 215:699-712, 2020).*
Lourenco et al. (Plant Physiol., 169:2275-2287, p. 2015).*
Chen et al. (J Integr Plant Biol., 3:494-509, 2021).*
Bailey et al. (Nature Communications, 12:251; pp. 1-15, 2021).*
Min et al. (Mol. Cells, 39:250-257, 2016).*
Wells, Biochemistry 29:8509-8517, 1990.*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41(5):583-590, 2000).*
Yang et al. (PNAS, 98:11438-11443, 2001).*
Donald et al. (EMBO J. 9:1717-1726, 1990).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Downes et al. (Plant Journal, 35:729-742, 2003).*
Joseph Ecker (Germplasm / Stock: SALK¬_015534 submitted and available on public domain on Aug. 9, 2008).*
Alonso et al. (Science, 301:653-657, 2003).*
Na Li et al, “Ubiquitin-mediated control of seed size in plants”, Frontiers in Plant Science,vol. 5, Jul. 11, 2014 (Jul. 11, 2014).
McFarlane, H. et al., “Seed Coat Ruthenium Red Staining Assay” Bio-protocol, Apr. 5, 2014, pp. 1-4, vol. 4., No. 7.
Varshavsky, A., “The Ubiquitin System, an Immense Realm”, Annual Review of Biochemistry, 2012, pp. 167-176, vol. 81.
Shi, L. et al., “*Arabidopsis* glabra2 mutant seeds deficient in mucilage biosynthesis produce more oil”, The Plant Journal, 2012, pp. 37-46, vol. 69.
Sadras, V., “Evolutionary aspects of the trade-off between seed size and number in crops”, Elsevier, ScienceDirect, 2007, pp. 125-138, vol. 100.
Peng, F. et al., “Gene coexpression clusters and putative regulatory elements underlying seed storage reserve accumulation in *Arabidopsis*”, BMC Genomics, 2011, pp. 1-14, vol. 12, No. 286.

(Continued)

*Primary Examiner* — Vinod Kumar
(74) *Attorney, Agent, or Firm* — Greer, Burns & Crain, Ltd.

(57) ABSTRACT

The invention relates to methods for increasing seed yield, increasing the total content of protein and/or lipid in seeds and reducing glucosinolate levels by reducing the expression or activity of UPL3. The invention also relates to genetically altered plants characterised by the above phenotypes and methods of producing such plants.

16 Claims, 9 Drawing Sheets

Specification includes a Sequence Listing.

(56) References Cited

OTHER PUBLICATIONS

Mithen, R., "Leaf glucosinolate profiles and their relationship to pest and disease resistance in oilseed rape", Euphytica, 1992, pp. 71-83, vol. 63.

Ohto, M. et al., "Effects of APETALA2 on embryo, endosperm, and seed coat development determine seed size in *Arabidopsis*", Sex Plant Reprod, 2009, pp. 227-289, vol. 22.

Patra, B., "Ubiquitin protein ligase 3 mediates the proteasomal degradation of GLABROUS 3 and Enhancer of Glabrous 3, regulators of trichome development and flavonoid biosynthesis in *Arabidopsis*", The Plant Journal, 2013, pp. 435-447, vol. 74.

Ma, X., "A Robust CRISPR/Cas9 System for Convenient, High-Efficiency Multiplex Genome Editing in Monocot and Dicot Plants", Molecular Plant, Aug. 2015, pp. 1274-1284, vol. 8.

Kunkel, T., Rapid and Efficient Site-Specific Mutagenesis without Phenotypic Selection, Methods in Enzymology, pp. 367-382, vol. 154.

Chen, M., Transparent Testa GLABRA1 Regulates the Accumulation of Seed Storage Reserves in *Arabidopsis*1, Plant Physiology, Sep. 2015, pp. 391-402, vol. 169.

Cermak, T., "Efficient design and assembly of custom TALEN and other TAL effector-based constructs for DNA targeting", Nucleic Acid Research, 2011, pp. 1-11, vol. 39, No. 12.

Belhaj, K. et al., "Plant genome editing made easy: targeted mutagenesis in model and crop plants using the CRISPR/Cas system", Plant Methods, 2013, pp. 1-10, vol. 9, No. 39.

Alahakoon et al., "Hairy Canola (*Brasssica napus*) re-visited: Downregulating TTG1 in an AtGL3-enhanced hairy leaf background improves growth, leaf trichome coverage, and metabolite gene expression diversity" BMC Plant Biology, 2016, pp. 1-24, vol. 16, No. 12.

Li, Y., et al., "Oil content of *Arabidopsis* seeds: The influence of seed anatomy, light and plant-to-plant variation", Elsevier, Phytochemistry, 2006, pp. 904-915.

Le, B., et al., "Global analysis of gene activity during *Arabidopsis* seed development and identification of seed-specific transcription factors", PNAS, May 4, 2010, pp. 8063-8070, vol. 107, No. 18.

Clough S., et al., "Floral dip: a simplified method for Agrobacterium-mediated transformation of *Arabidopsis thaliana*", The Plant Journal, 1998, pp. 735-743, vol. 16, No. 6.

Mendoza, M., et al., "Leafy Cotyledon 2 activation is sufficient to trigger the accumulation of oil and seed specific mRNAs in *Arabidopsis* leaves", FEBS Letters, 579, 2005, pp. 4666-4670.

Zhang, Y., et al., "Efficient and transgene-free genome editing in wheat through transient expression of CRISPR/Cas9 DNA or RNA", Nature Communications, 2016, pp. 1-8, 7:12617.

Harper, A. et al., "Associative transcriptomics of traits in the polyploid crop species *Brassica napus*", Nature Biotechnology, Aug. 2012, pp. 798-804, vol. 30, No. 8.

Gutierrez L. et al., Combined networks regulating seed maturation, TRENDS in Plant, 2007, pp. 294-300, vol. 12, No. 7.

Gil-Humanes J., "High-efficiency gene targeting in hexaploid wheat using DNA replicons and CRISPR/Cas9", The Plant Journal, 2017, pp. 1251-1262, vol. 89.

Downes, B. et al., "The Hect ubiquitin-protein ligase (UPL) family in*Arabidopsis*: UPL3 has a specific role in trichome develoment", The Plant Journal, 2003, pp. 729-742, vol. 35.

Dong H. et al., "Ubiquitylation activates a peptidase that promotes cleavage and destabilization of its activating E3 ligases and diverse growth regulatory proteins to limit cell proliferation in *Arabidopsis*", 2017, Genes & Development, pp. 197-208, vol. 31.

Comai L. et al., "Efficient discovery of DNA polymorphisms in natural populations by Ecotilling" The Plant Journal, 2004, pp. 778-786, vol. 37.

Krysan P. et al., "T-DNA as an Insertional Mutagen in *Arabidopsis*", The Plant Cell, Dec. 1999, pp. 2283-2290, vol. 11.

Komander, D. et al., "The Ubiquitin Code", Annual Review of Biochemistry, 2012, pp. 203-232, vol. 81.

Kunkel T., Rapid and efficient site-specific mutagenesis without phenotypic selection, Proc. Natl. Acad. Sci, USA, Jan. 1985, pp. 488-492, vol. 82.

* cited by examiner

METHODS OF INCREASING SEED YIELD

CROSS-REFERENCE TO RELATED APPLICATIONS

This application is the U.S. National phase application corresponding to PCT/GB2018/050063 which was assigned an international filing date of Jan. 10, 2018 and associated with publication WO 2018/130828 A1 and which claims priority to UK patent application 1700380.7 filed on Jan. 10, 2017, the disclosures of which are expressly incorporated herein by reference.

FIELD OF THE INVENTION

The invention relates to methods for increasing seed yield, increasing the total content of protein and/or lipid in seeds and reducing glucosinolate levels as well as genetically altered plants characterised by the above phenotypes and methods of producing such plants.

INTRODUCTION

Seeds provide the bulk of nutrients for humans and our domesticated animals. Seeds accumulate starch, protein and lipid reserves that are mobilised to support the early growth and development of seedlings. Crop plants have been bred to accumulate high levels of different types of storage compounds in their seeds, and inflorescence development has been adapted by domestication and breeding to increase seed size and seed number. Seeds are of two basic types in flowering plants. Monocotyledonous seeds have a seed coat surrounding the embryo and also have a large endosperm reserve of starch and protein that is mobilised to support seedling growth. Dicotyledonous seeds also have a seed coat and embryo, but the endosperm is transiently formed. Instead, the cotyledons of dicotyledonous embryos contain lipid and protein that is mobilised to support embryo growth. The seed coat is a highly specialised tissue derived from both maternal and zygotic tissues that protects the embryo, and promotes seed dispersal and germination in appropriate conditions.

The development of testa and embryo tissues is coordinated closely over time in dicotyledonous seeds, and is relatively well characterised genetically. Seeds develop in two distinct phases (Gutierrez et al., 2007). In early stages cells and tissues are specified after double fertilization to form the diploid zygote and triploid endosperm, and the genes controlling these processes are reasonably well known (summarised by (Le et al., 2010)). After embryo and seed coat (testa) cell specification, a maturation phase is initiated in which lipid and protein storage products are deposited in the embryo, and pigments, tannin and mucilage are deposited in the testa. The final stages of maturation involves the acquisition of dormancy and dehydration.

Genes encoding enzymes of storage lipid synthesis and storage proteins are co-ordinately expressed during seed maturation, with high levels of expression in mid-maturation, and lower levels at later stages of maturation as dormancy is imposed (FIG. 1). This leads to metabolic changes in lipid deposition and the massive accumulation of proteins in the embryo. The expression of these storage reserve genes is tightly coordinated in distinct networks (Peng and Weselake, 2011). The expression of these sets of genes is controlled by a well-characterised set of master regulatory transcription factors, which are themselves transcriptionally regulated in a temporal pattern. These include the transcription factors abscisic acid insensitive 3 (AB13), Leafy cotyledon 1 (LEC1) and LEC2, FUSCA 3 (FUS3) and WRINKLED 1 (WR1). Among these, the B3 family transcription factor LEC2 has a major role. The expression of this transcription factor is known to enhance the expression of several further key seed maturation genes including, WRI1, MYB118 and LEC1 (FIG. 1). Activation of LEC2 transcription factor activity using a glucocorticoid receptor fusion (LEC2:GR) also led to the expression of S3 oleosin (S3) and At2S3 genes, accumulation of seed lipids and proteins, and also the expression of LEC1, FUS3 and AB13 (Santos Mendoza et al., 2005). This showed that LEC2 has a centrally important role in seed storage gene expression.

Protein ubiquitylation is a universally conserved process in eukaryotes that regulates protein levels and activities. Ubiquitin is a small 76 amino acid protein that is coupled by an N-lysine isopeptide linkage to glycine moieties in proteins. There are several types of ubiquitin chain linkages that serve as different signals. For example, chains of ubiquitin molecules coupled through lysine 48 signals the degradation of the ubiquitylated protein by the 26 proteasome (Komander and Rape, 2012). The levels and activities of many proteins are controlled by tightly regulated processes of ubiquitylation and proteolysis. Ubiquitylation is mediated by a variety of E3 ubiquitin ligases, which either directly transfer ubiquitin moieties to substrates, or facilitate the transfer of ubiquitin from an E2 conjugating enzyme (Varshaysky, 2012) to a substrate.

Ubiquitin E3 ligases form a large and diverse class of proteins in animals and plants. One of the main classes of E3 enzymes is the HECT E3 ligase family in animals and plants. These are characterised by a conserved HECT domain, and directly transfer ubiquitin to substrates. There are seven HECT E3 ligase genes (UPL1-UPL7) in by the *Arabidopsis* genome (Downes et al., 2003), of which UPL3 is the best characterised. UPL3 is characterised by a conserved N-terminal ARM domain and a C-terminal HECT domain. It is required for correct leaf hair formation; loss of function upl3 mutants have trichomes with increased branching. UPL3 was shown to ubiquitylate two bHLH transcription factors, Glabrous 3 (GL3) and enhancer of GL3 (EGL3), which are required for positive regulation of trichome formation. These transcription factors form a complex with two other transcription factors, GL2 and TTG1, to regulate flavonoid biosynthesis genes (Patra et al., 2013). UPL3 is expressed at increased levels during seed embryo development (FIG. 1), suggesting that transcription of UPL3 may have a role in seed embryo development.

(Shi et al., 2011) showed that loss of function gl2 mutants in the testa leads to reduced expression of MUM4, encoding a key enzyme of mucilage production (mucilage is a specialised polysaccharide produced by the testa to promote germination), and also contributed to high embryo lipid levels. ttg and gl2 mutants influence seed testa development by reducing pigment formation and mucilage levels (Chen et al., 2015). TT8 was shown to repress expression of three key transcription factor genes, LEC1, LEC2 and FUSCA3, leading to reduced seed protein and lipid accumulation in embryos. This effect was seen when testa tissue was homozygous for tt8. These observations were interpreted as showing a "balance" of resource allocation between testa mucilage and embryo lipid production, such that reducing mucilage production due to gl2 and tt8 loss of function mutants leads to increased seed lipid accumulation.

Oilseeds form a major source of nutrition for humans and our domesticated animals, and are also a renewable source of transport fuel and industrial feedstocks. Current "00"

varieties of oilseed rape (OSR or canola) have low levels of glucosinolates and erucic acid, and produce a high-quality edible oil with good cooking and nutritional properties. It is second only to soybean as a source of cooking oil, with 20 m tonnes annual production. After oil extraction, OSR seed proteins are a major source of nutrients for domesticated animals. Yields of OSR have been increased steadily by breeding, but its yields are still relatively low compared to soybean.

Therefore, seed yield is a major factor in determining the commercial success of grain crops and thus it is important to not only understand the genetic factors that underlie this trait, but also how to modulate such factors to improve overall seed yield, with the most desirable outcome being an increase in both seed size and seed protein and/or lipid content. The present invention addresses this need.

SUMMARY OF THE INVENTION

Using Associative Transcriptomics we screened a panel of OSR accessions for genetic variation associated with a range of yield component traits. This analysis identified a locus showing high association with seed weight per pod (SWPP). This locus was also identified in the Gene Expression Marker (GEM) analysis where differential expression of a single unigene, corresponding to an orthologue of the *Arabidopsis* UBIQUITIN PROTEIN LIGASE 3 (UPL3), correlates negatively with SWPP. Concordant with this result, we show that *Arabidopsis* mutants lacking a functional copy of this gene produce significantly larger seeds relative to WT plants. This increase in seed size was coupled with a 12% increase in seed lipid and a 13% increase in seed total protein levels. Assessment of gene expression in a seed development time course revealed that a set of regulatory transcription factor genes known for their role in seed maturation are upregulated in mutant seeds relative to WT. Using a cell-free system we showed that UPL3 mediates the proteasomal degradation of LEAFY COTYLEDON 2 (LEC2) protein, which is a master regulator of seed maturation. Closer inspection of the promoter region of the *Brassica napus* orthologues of UPL3 revealed variation which may be causal for the differential expression and consequent phenotypic variation observed.

Therefore, in summary, we have surprisingly demonstrated UPL3 has a negative role in regulating the expression of genes involved in seed lipid and protein accumulation, and as a result, reducing or silencing the expression and/or reducing the activity of UPL3 can increase seed levels of lipids and proteins, and increase seed yields. UPL3 activity also promotes the accumulation of seed glucosinolates, and reducing or silencing the expression or reducing the activity of UPL3, can reduce glucosinolate levels, thus improving the quality of seed oil and protein.

In one aspect of the invention, there is provided a method of increasing seed yield in a plant, the method comprising reducing or abolishing the expression of at least one nucleic acid encoding a ubiquitin protein ligase 3 (UPL3) polypeptide and/or reducing the activity of a UPL3 polypeptide in said plant.

In one embodiment, said increase in seed yield comprises an increase in at least one of seed weight, seed size, seed number per pod, pod length, protein and/or lipid content and weight of seed per pod.

In another aspect of the invention there is provided a method of reducing the levels of glucosinolate in a plant, the method comprising reducing the expression of a nucleic acid encoding a ubiquitin protein ligase 3 (UPL3) polypeptide and/or reducing the activity of a UPL3 polypeptide.

In a further aspect of the invention there is provided a method of increasing lipid and/or protein content in a plant seed, the method comprising reducing or abolishing the expression of at least one nucleic acid encoding a ubiquitin protein ligase 3 (UPL3) polypeptide and/or reducing the activity of a UPL3 polypeptide in said plant.

In one embodiment, the method comprises introducing at least one mutation into the nucleic acid sequence encoding UPL3 or the promoter of said UPL3. Preferably, said mutation is a loss of function mutation. More preferably, said mutation is an insertion, deletion or substitution. In one embodiment, the mutation is introduced using targeted genome modification, preferably ZFNs, TALENs or CRISPR/Cas9. Alternatively, the mutation is introduced using mutagenesis, preferably TILLING or T-DNA insertion.

In another embodiment, the method comprising using RNA interference to reduce or abolish the expression of a UPL3 nucleic acid.

In another aspect of the invention, there is provided, a genetically altered plant, part thereof or plant cell, wherein said plant comprises at least one mutation into at least one ubiquitin protein ligase 3 (UPL3) gene and/or at least one mutation in the UPL3 promoter.

In one embodiment, the increase in seed yield comprises an increase in at least one of seed weight, seed size, seed number per pod, pod length, and weight of seed per pod.

In another embodiment, the plant is characterised by an increase in seed protein and/or lipid content. In a further embodiment, the plant is characterised by reduced glucosinolate levels, wherein preferably said reduction is relative to a wild-type or control plant.

In one embodiment, the mutation is a loss of function mutation, preferably an insertion, deletion or substitution.

In one embodiment, the plant comprises an RNA interference construct that reduces the expression of a UPL3 nucleic acid.

In another embodiment, the plant part is a seed.

In a further aspect of the invention, there is provided a method of producing a plant with increased seed yield and/or increased seed protein and/or lipid content and/or reduced glucosinolate levels, the method comprising introducing at least one mutation into at least one ubiquitin protein ligase 3 (UPL3) gene and/or at least one mutation in the UPL3 promoter.

Preferably, the mutation is a loss of function mutation. More preferably, the mutation is introduced using mutagenesis or targeted genome modification. Even more preferably, the targeted genome modification is selected from ZFNs, TALENs or CRISPR/Cas9.

In another aspect of the invention there is provided a method for producing a plant with increased seed yield and/or increased seed protein and/or lipid content and/or reduced glucosinolate levels, the method comprising introducing and expressing in said plant an RNA interference construct that reduces the expression of a UPL3 nucleic acid.

In one embodiment, the method further comprises regenerating a plant and screening for increased seed yield and/or increased seed protein and/or lipid content and/or reduced glucosinolate levels.

In another aspect of the invention, there is provided a plant, plant part or plant cell obtained by the methods described herein. Preferably, a seed obtained or obtainable from the plant described herein or the methods described herein.

In a further aspect of the invention, there is provided a method for identifying and/or selecting a plant that will have an increased seed yield phenotype, the method comprising detecting in the plant or plant germplasm at least one polymorphism in the promoter of the UPL3 gene, and/or a tandem duplication comprising SEQ ID NO: 18 and wherein said plant or progeny thereof is selected.

Preferably, the deletion of at least one tandem duplication is indicative of a plant with a lower level of UPL3 expression than a plant comprising a different base at the above sites and/or at least two duplications of SEQ ID NO: 18. More preferably, the method further comprises introgressing the chromosomal region comprising at least one of said polymorphisms and/or deletions into a second plant or plant germplasm to produce an introgressed plant or plant germplasm.

In another aspect of the invention, there is provided a nucleic acid construct comprising a nucleic acid sequence as defined in any one of SEQ ID NOs: 11 to 14 or a functional variant or homolog thereof, wherein said sequence is operably linked to a regulatory sequence, wherein preferably said regulatory sequence is a tissue-specific promoter. Also provided is a vector comprising the nucleic acid construct described herein, a host cell comprising the nucleic acid construct described herein and a transgenic plant expressing the nucleic acid construct described herein.

In another aspect of the invention there is provided a method of increasing seed yield and/or increasing seed protein and/or lipid content and/or reducing glucosinolate levels, the method comprising introducing and expressing in said plant the nucleic acid construct described herein.

In yet a further aspect of the invention there is provided a method for producing a plant with increased seed yield and/or increased seed protein and/or lipid content and/or reduced glucosinolate levels, the method comprising introducing and expressing in said plant the nucleic acid construct described herein.

In a final aspect of the invention there is provided a method for producing a food or feed product with increased protein and/or lipid content and/or reduced glucosinolate levels, said method comprising a. producing a plant wherein the expression of UPL3 is reduced or abolished and/or the activity of a UPL3 polypeptide is reduced as described herein;
b. obtaining a seed from said plant; and
c. producing a food or feed product from said seed.

In one embodiment, the UPL3 nucleic acid encoding a UPL3 polypeptide comprises or consists of SEQ ID NO: 4 or 5 or a functional variant or homolog thereof, and wherein the promoter of said UPL3 nucleic acid sequence comprises or consists of SEQ ID NO: 1 or 2 or a functional variant or homolog thereof.

In all described examples, said increase in seed yield may be relative to a control or wild-type plant.

As described herein, the plant is selected from a monocot or dicot plant. Preferably, the plant is selected from any dicotyledonous oilseed crop, such as *Brassica* oilseed crops such as *B. juncea*, soybean, sunflower, linseed, cotton, hemp, oilpalm, coconut, peanut, safflower, Camelina and olive. More preferably, the plant is *Brassica napus*.

Alternatively, the plant is selected from *B. oleracea*, maize, rice, wheat or barley.

DESCRIPTION OF THE FIGURES

The invention is further illustrated in the following non-limiting figures.

DETAILED DESCRIPTION

Figure 1:
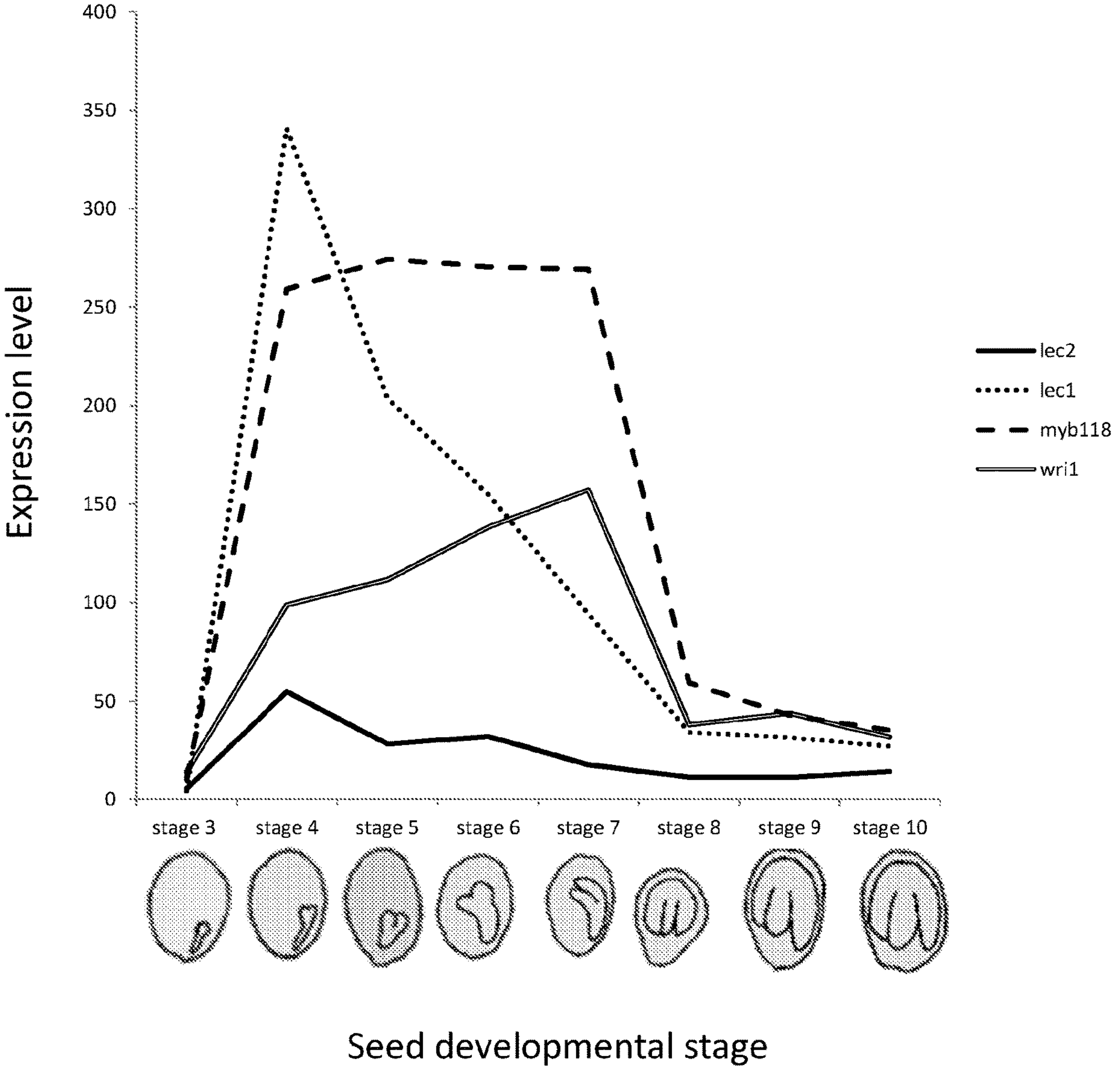
FIG. 1 shows the expression profiles of key seed developmental transcription factors in *Arabidopsis*.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

The terms "seed" and "grain" as used herein can be used interchangeably.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

The aspects of the invention involve recombination DNA technology and exclude embodiments that are solely based on generating plants by traditional breeding methods.

Methods of Increasing Seed Yield

Accordingly, in a first aspect of the invention, there is provided a method of increasing seed yield in a plant, the method comprising reducing or abolishing the expression of at least one nucleic acid encoding a ubiquitin protein ligase 3 (UPL3)-like polypeptide and/or reducing the activity of a UPL3 polypeptide in said plant. The same effects could be generated by modulating the expression of UPL3 to reduce its expression at later stages of seed development, for example by using a promoter that expressed UPL3 at lower levels during seed development. Optimally, the promoter variant identified in this study and described herein that reduces expression can be used in oilseed rape/canola. The promoters of UPL3-related genes in other oilseed crops could be altered to reduce expression by a variety of means, or natural variants of oilseed crop UPL3 promoters could be identified by screening for low UPL3 expression levels.

The term "yield" in general means a measurable produce of economic value, typically related to a specified crop, to an area, and to a period of time. Individual plant parts directly contribute to yield based on their number, size and/or weight. Alternatively, the actual yield is the yield per square meter for a crop and year, which is determined by dividing total production (includes both harvested and appraised production) by planted square meters. Preferably, in the present context, the term "yield" of a plant relates to propagule generation (such as seeds) of that plant. Thus, in a preferred embodiment, the method relates to an increase in seed yield.

The expression of UPL3 correlates negatively with the yield component trait, weight of seed per pod across *Brassica napus* accessions. Weight of seed per pod is a yield component trait comprised of several factors, including seed size, seed weight, pod length and seed number. UPL3 expression contributes to variation in seed weight per pod through its negative effect on seed size. *Arabidopsis* mutants lacking UPL3 expression exhibit increased seed size and *Brassica napus* accessions exhibiting extreme UPL3 transcription show clear segregation of a seed size phenotype. Furthermore, assessment of yield across a subset of GWAS accessions, showed that high weight of seed per pod relates to an increase in harvestable yield—an important observation given the common trade-off between yield component traits, with an increase in one yield component, such as seed size, leading to a reduction in another component, such as seed number (Sadras V O et al.,)

Seed size and number are the main components contributing to seed yield, however, in one embodiment, the increase in seed yield comprises an increase in at least one yield component trait such as pod weight, pod length, seed size, including average seed length, width and/or area, seed weight (single seed or thousand grain weight), seed density, overall seed yield per plant, seed number per pod, protein and/or lipid content and weight of seed per pod. In particular, the inventors have found that increasing at least seed weight per pod results in an overall increase in seed yield.

The terms "increase", "improve" or "enhance" as used herein are interchangeable. In one embodiment, seed yield, and preferably seed weight, seed size, seed number per pod, pod length, protein and/or lipid content and weight of seed per pod is increased by at least 2%, 3%, 4%, 5%, 6%, 7%, 8%, 9%, 10% 11%, 12%, 13%, 14%, 15%, 16%, 17%, 18%, 19%, 20%, 30%, 40% or 50% in comparison to a control plant. Preferably, the increase is at least 2-20%, more preferably 5-15%.

Thus, according to the invention, seed yield can be measured by assessing one or more of seed weight, seed size, seed number per pod, seed number per plant, pod length, seed protein, a combination of both seed size and seed number and/or lipid content and weight of seed per pod. Preferably, yield comprises an increase in seed size, more preferably an increase and/or protein and/or lipid content of the seed. Yield is increased relative to control plants. The skilled person would be able to measure any of the above seed yield parameters using known techniques in the art.

The terms "reducing" means a decrease in the levels of UPL3 expression and/or activity by up to 10%, 20%, 30%, 40%, 50%, 60%, 70%, 80% or 90%. The term "abolish" expression means that no expression of UPL3 is detectable or that no functional UPL3 polypeptide is produced. Method for determining the level of UPL3 expression and/or activity would be well known to the skilled person.

In another aspect of the invention there is provided a method of reducing the levels of a glucosinolate in a plant, the method comprising reducing or abolishing the expression of at least one nucleic acid encoding a ubiquitin protein ligase 3 (UPL3) polypeptide and/or reducing the activity of a UPL3 polypeptide in said plant. Glucosinolates are a class of secondary metabolites that are mainly found in Brassicaceae. Upon damage to the plant (such as any form of food processing etc.) glucosinolate breaks down into a variety of highly bioactive products, such as isothiocyanates, nitriles, epithionitriles and thiocyanates. Some of these breakdown products, isothiocyanates and nitriles in particular, can have toxic effects in both humans and animals at high doses. For this reason it is desirable to produce *brassica* plants with reduced levels of glucosinolates. Glucosinolates are also sulphur-containing proteins that are thought to have health benefits, but high levels in seeds contributes to bitter taste of oil and protein meal. Hence in *Brassica* oilseeds glucosinolate levels are reduced to improve taste. Older varieties of oilseed rape typically have 80 ug/g glucosinolates, while modern "00" varieties have between 10-20 ug/g (Mithen 1992). Typically, reduced expression of UPL3 as shown by the promoter variant described here will reduce total glucosinolate levels approximately 4-fold to levels typically found in low glucosinolate oilseed rape varieties. Preferably said reduction is in the seeds of the plants. More preferably, said reduction is compared to a high glucosinolate control plant and is at least 3 fold, preferably between a 1 to 10 fold, more preferably, between a 2 to 5 fold, and even more preferably 4-fold reduction in plants that have reduced UPL3 expression or function.

In a further aspect of the invention there is provided a method of increasing total lipid and/or protein content in a plant, preferably the total protein and/or lipid content in the seeds (e.g. embryo) of a plant the method comprising reducing or abolishing the expression of at least one nucleic acid encoding a ubiquitin protein ligase 3 (UPL3) polypeptide and/or reducing the activity of a UPL3 polypeptide in said plant. In one embodiment, said increase is between 5 and 50%, more preferably between 10 and 30%, and even more preferably between 10 and 20% compared to a wild-type or control plant. In one embodiment, said increase is up to 10%, 11%, 12%, 13%, 14%, 15%, 16%, 17%, 18%, 19% or 20% compared to a wild-type or control plant. In a preferred embodiment, the method increases both lipid and protein content. Total seed lipid and/or protein levels may be measured using standard techniques in the art, such as, but not limited to, infrared radiation analyses for both protein and lipid, Bradford Reagent to measure protein levels, and gas chromatography or high performance liquid chromatography to measure lipid levels and types of lipids, in particular fatty acids.

By "at least one mutation" is means that where the UPL3 gene is present as more than one copy or homeologue (with the same or slightly different sequence) there is at least one mutation in at least one gene or in a single copy of the gene. For example, in *B. napus* preferably only the copy of UPL3 gene on the A or C genome is mutated, preferably the C genome. In an alternative embodiment, all or all copies of the gene are mutated.

In one embodiment, the method comprises introducing at least one mutation into the, preferably endogenous, gene encoding UPL3 and/or the UPL3 promoter. Preferably said mutation is in the coding region of the UPL3 gene. In one embodiment, at least one mutation or structural alteration may be introduced into the UPL3 promoter such that the UPL3 gene is either not expressed (i.e. expression is abolished) or expression is reduced, as defined herein. In an alternative embodiment, at least one mutation may be introduced into the UPL3 gene such that the altered gene does not express a full-length (i.e. expresses a truncated) UPL3 protein or does not express a fully functional UPL3 protein. In this manner, the activity of the UPL3 polypeptide can be considered to be reduced or abolished as described herein. In any case, the mutation may result in the expression of UPL3 with no, significantly reduced or altered biological activity in vivo. Alternatively, UPL3 may not be expressed at all.

In one embodiment, the sequence of the UPL3 promoter comprises or consists of a nucleic acid sequence as defined in SEQ ID No: 1 or 2 (preferably SEQ ID NO: 1) or a functional variant or homologue thereof.

In another embodiment, the sequence of the UPL3 gene comprises or consists of a nucleic acid sequence as defined in SEQ ID NO: 6 or 7 (genomic) or SEQ ID NO: 4 or 5 (cDNA) or a functional variant or homologue thereof and encodes a polypeptide as defined in SEQ ID NO: 21 or 22 or a functional variant or homologue thereof.

In the above embodiments an 'endogenous' nucleic acid may refer to the native or natural sequence in the plant genome. In one embodiment, the endogenous sequence of the UPL3 gene is defined in any of SEQ ID NOs: 4 to 7 and encodes an amino acid sequence as defined in SEQ ID NO: 21 or 22 or homologs thereof.

Also included in the scope of this invention are functional variants (as defined herein) and homologs of the above identified sequences. Examples of homologs are shown in SEQ ID NOs 3, 8 to 10, and 33, 35, 37, 39, 41, 43, 45, 47, 49 and 51 to 60 and Table 1. In one embodiment, the homolog comprises a nucleic acid sequence as defined in any of SEQ ID Nos 8 to 10 and 33, 35, 37, 39, 41, 43, 45, 47 and 49 and that encodes a UPL3 protein as defined in any of SEQ ID No 27, 28, 34, 36, 38, 40, 42, 44, 46, 48 or 50 or a variant or functional variant thereof. In another embodiment, the homolog comprises a nucleic acid that encodes a UPL3 protein as defined in any of SEQ ID No 27, 28, 34, 36, 38, 40, 42, 44, 46, 48 or 50. Variants or functional variants are defined elsewhere. In another embodiment, the homolog of the UPL3 promoter is selected from SEQ ID NOs 51 to 60.

Further examples of homologues are shown in Table 1 below. Accordingly, in a further embodiment, the homologue may additionally or alternatively be selected from any sequence listed in Table 1 below.

TABLE 1

| UPL3 homologue sequences | |
|---|---|
| Species | Closest homologue to at.UPL3 |
| Sunflower | Ha10_00001502 (e.g. Ha10_00001502.1) |
| Soybean | GLYMA11G11490.1 or GLYMA11G11490.2 |
| Brassica napus | BnaA08g17010D-1; BnaA08g17000D-1; BnaA08g17020D-1 |
| Brassica napus | BnaCO3g60060D-1; BnaC03g60070D-1 |
| Arabidopsis | AT4G38600.1, AT4G38600.2 or AT4G38600.3 |
| peanut | Aradu.QS26M.1 |
| Brassica Oleracea | Bo3g149420.1 |
| Brassica Oleracea | Bo3g149420.1 |
| Brassica rapa | Bra010737.1 |
| *Zea mays* | Zm00001d004139_T007 |
| Rice | LOC_Os02g01170.1 |
| Cotton | gnl\|AD1_NBI\|Gh_Sca004979G01 (Gorai.008G035900.1) |
| Triticum aestivum | TRIAE_UPL3_2A (TraesCS2A01G064700.1) |
| Triticum aestivum | TRIAE_UPL3_2B (TraesCS2B01G076900.1) |
| Triticum aestivum | TRIAE_UPL3_2D (TraesCS2D01G060300LC.1) |
| Hordeum Vulgare | HORVU2Hr1G011040.15 |
| Glycine Max | Glyma04g00530.1 |
| Glycine Max | Glyma12g03640.1 |
| Glycine Max | Glyma11g11490.1 |
| Glycine Max | Glyma06g00600.1 |

The term "functional variant of a nucleic acid sequence" as used herein with reference to any of SEQ ID NOs: 1 to 92 refers to a variant gene sequence or part of the gene sequence which retains the biological function of the full non-variant sequence. A functional variant also comprises a variant of the gene of interest which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence which result in the production of a different amino acid at a given site that do not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

In one embodiment, a functional variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence.

The term homolog, as used herein, also designates a UPL3 promoter or UPL3 gene orthologue from other plant species. A homolog may have, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to any amino acid described herein, for example the proteins represented in Table 1 or by any of SEQ ID NO: 21 to 28, 34, 36, 38, 40, 42, 44, 46, 48 or 50 or to the nucleic acid sequences described herein, for example in Table 1 and as shown by SEQ ID NOs: 1 to 17 or 33, 35, 37, 39, 41, 43, 45, 47 or 49 or 51 to 60. In one embodiment, overall sequence identity is at least 37%. In one embodiment, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%.

Functional variants of UPL3 homologs as defined above are also within the scope of the invention.

The term "UPL3" refers to ubiquitin-protein ligase 3. The UPL3 gene in *B. napus* contains 17 exons, 16 introns and encodes 1888 amino acids. The UPL3 protein is characterised by a conserved C-terminal HECT domain (homologous to the EG-AP carboxyl terminus) and at least one, two, three or up to four N-terminal Armadillo repeat (or ARM domains). Accordingly, in one embodiment, the UPL3 nucleic acid coding sequence encodes a UPL3 protein comprising a C-terminal HECT domain and up to four Armadillo repeats as defined below, or a variant thereof, wherein the variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the HECT domain and/or the Armadillo repeat as defined herein. In a preferred embodiment, the UPL3 polypeptide is characterised by at least one HECT domain and at least one, preferably up to four ARM domains or a HECT or ARM domain with at least 75% homology thereto.

In one embodiment, the sequence of the HECT domain is defined below:

```
                                                (SEQ ID NO: 29)
MRIGRLQR QKVRVSRNRI LDSAAKVMEM YSSQKAVLEVEYFGEVGTGL

GPTLEFYTLL SHDLQKASLG MWRSSSGDKV SMQIGRDEIE

DGKPSAANRD IVLAPLGLFP RPWPSTADIS EGGQFHKVIE

YFRLLGRVMA KALQDGRLLD VPLSTAFYKL ILGQELDLHD

IVLFDAELGK TLQELRVVVA RKHYLEGVGG DNSSTISDLC
```

-continued

```
LRGCRIEDLS LEFTLPGYPE YILRSGDEIV DITNLEEYIS

LVVDATVKRG VTRQIEAFRS GFNQVFDITS LQIFTPSELD

YLLCGRRELW EVETLAEHIK FDHGYNAKSP AIINLLEIMG

ELTADQQRAF CQFVTGAPRL PPGGLAVLNP KLTIVRKHSS

TSSAAANGAG ASETADDDLP SVMTCANYLK LPPYSTKEIM

YKKLLYAINE GQGSFDLS
```

In one embodiment, the UPL3 protein comprises at least one of the following ARM folds and/or ARM helixes:

```
                                                (SEQ ID NO: 30)
RGNNNDNSDKGKEKEHDVRI RERERERDRA REQLNMDAAA

AAARSADEDD DNDSED

                                                (SEQ ID NO: 31)
LNGRMKKILSGLRAEGEEGK QVEALTQLCE MLSIGTEDSL

STFSVDSFVP VLVGLLN HESNPDIMLLAAR ALTHLCDVLP

SSCAAVVHYG AVSCLVARLL TIEYMDLAEQ SLQALKKISQ

EHPTACLRAG ALMAVLSYLD FFSTGVQRVA

LSTAANMCKKLPSDASDYVM EAVPLLTNLL QYHDSKVLEY

ASICLTRIAE AFAPYPEKLDELCNHGLVTQ AASLISTSNS

GGGQASLSVS TYTGLIRLLS TCASGSPLGFRTLLLLGISS

ILKDILLGSG VSANASVSPA LSRPADQIYE

                                                (SEQ ID NO: 32)
GKQEDILKIS PREKLLGDQPELLQQFGLDL LPVLVQIYGS

SVNGTIRHKC LSVIGKLMYF SSSEMIQSLIGDTNISSFLA

GVLAWKDPQV LVPALQVAEI LMEKLPETFS KVFVREGVVHAVDQL.
```

By "UPL3 promoter" is meant a region extending for at least 2 kbp upstream of the ATG codon of the UPL3 ORF.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognised that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Non-limiting examples of algorithms that are suitable for determining percent sequence identity and sequence similarity are the BLAST and BLAST 2.0 algorithms.

Suitable homologues can be identified by sequence comparisons and identifications of conserved domains. There are predictors in the art that can be used to identify such sequences. The function of the homologue can be identified as described herein and a skilled person would thus be able to confirm the function, for example when overexpressed in a plant.

Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologs. Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labelled with a detectable group, or any other detectable marker. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide.

In one embodiment, there is provided a method of increasing seed yield in a plant, as described herein, the method comprising reducing or abolishing the expression of at least one nucleic acid encoding UPL3 and/or activity of UPL3, as also described herein, wherein the method comprises introducing at least one mutation into the UPL3 gene and/or promoter as described herein, wherein the UPL3 gene comprises or consists of a. a nucleic acid sequence encoding a polypeptide as defined in SEQ ID NO:21 or 22 or a homolog or functional variant as defined herein; or
b. a nucleic acid sequence as defined in SEQ ID NO: 4, 5, 6 or 7 or a homolog or functional variant as defined herein; or
c. a nucleic acid sequence encoding a polypeptide, wherein the polypeptide comprises at least a C-terminal HECT domain as defined in SEQ ID NO: 29 or a variant thereof and at least one, two, three or four N-terminal Armadillo repeat domains as defined in SEQ ID NO: 30 and/or 31 and/or 32 or any combination thereof or a variant thereof, wherein the variant has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to any of SEQ ID NO: 29 or 30, 31 or 32; or
d. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to either (a) or (b); or
e. a nucleic acid sequence encoding a MADS1 polypeptide as defined herein that is capable of hybridising under stringent conditions as defined herein to the nucleic acid sequence of any of (a) to (d).

In a preferred embodiment, the mutation that is introduced into the endogenous UPL3 gene or promoter thereof to reduce, or inhibit the biological activity and/or expression levels of the UPL3 gene can be selected from the following mutation types 1. a "missense mutation", which is a change in the nucleic acid sequence that results in the substitution of an amino acid for another amino acid;
2. a "nonsense mutation" or "STOP codon mutation", which is a change in the nucleic acid sequence that results in the introduction of a premature STOP codon and, thus, the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
3. an "insertion mutation" of one or more amino acids, due to one or more codons having been added in the coding sequence of the nucleic acid;
4. a "deletion mutation" of one or more amino acids, due to one or more codons having been deleted in the coding sequence of the nucleic acid;
5. a "frameshift mutation", resulting in the nucleic acid sequence being translated in a different frame downstream of the mutation. A frameshift mutation can have various causes, such as the insertion, deletion or duplication of one or more nucleotides.
6. a "splice site" mutation, which is a mutation that results in the insertion, deletion or substitution of a nucleotide at the site of splicing.

In general, the skilled person will understand that at least one mutation as defined above and which leads to the insertion, deletion or substitution of at least one nucleic acid or amino acid compared to the wild-type UPL3 promoter or UPL3 nucleic acid or protein sequence can affect the biological activity of the UPL3 protein.

In one embodiment, the mutation is introduced into the HECT domain and/or at least one ARM domain in the UPL3 coding sequence or polypeptide. Preferably said mutation is a loss of function mutation such as a premature stop codon, or an amino acid change in a highly conserved region that is predicted to be important for protein structure.

In another embodiment, the mutation is introduced into the UPL3 promoter and is at least the insertion of at least one duplication comprising a sequence as defined in SEQ ID NO: 18 and/or at least on point mutation. Examples of suitable point mutations are described in SEQ ID NO: 19. Other major changes such as deletions that remove functional regions of the promoter are also included as these will reduce the expression of UPL3.

In one example, the mutation may introduce a premature stop codon. As an example we have created a *B. rapa* TILLING mutant, which comprises a premature stop codon resulting in a loss of UPL3 function. The mutations are shown in SEQ ID NO: 17. *B. rapa* is a diploid ancestor of *B. napus*, and moreover the UPL3 gene is very highly conserved between *B. rapa* and *B. napus*. Accordingly, the same mutation shown in SEQ ID NO: 17 can be made to the *B. napus* UPL3 gene to introduce a premature stop codon and thereby abolish UPL3 function, for example abolishing its ubiquitin ligase activity.

In one embodiment, the mutation is introduced using mutagenesis or targeted genome editing. That is, in one embodiment, the invention relates to a method and plant that has been generated by genetic engineering methods as described above, and does not encompass naturally occurring varieties.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Cermak T et al. describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct. Accordingly, using techniques known in the art it is possible to design a TAL effector that targets a UPL3 gene or promoter sequence as described herein.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Accordingly, using techniques known in the art it is possible to design sgRNA molecules that targets a UPL3 gene or promoter sequence as described herein.

Cas9 expression plasmids for use in the methods of the invention can be constructed as described in the art.

Alternatively, more conventional mutagenesis methods can be used to introduce at least one mutation into a UPL3 gene or UPL3 promoter sequence. These methods include both physical and chemical mutagenesis. A skilled person will know further approaches can be used to generate such mutants, and methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein.

In one embodiment, insertional mutagenesis is used, for example using T-DNA mutagenesis (which inserts pieces of the T-DNA from the *Agrobacterium tumefaciens* T-Plasmid into DNA causing either loss of gene function or gain of gene function mutations), site-directed nucleases (SDNs) or transposons as a mutagen. Insertional mutagenesis is an alternative means of disrupting gene function and is based on the insertion of foreign DNA into the gene of interest (see Krysan et al, The Plant Cell, Vol. 11, 2283-2290, December 1999). Accordingly, in one embodiment, T-DNA is used as an insertional mutagen to disrupt UPL3 gene or UPL3 promoter expression. An example of using T-DNA mutagenesis to disrupt the *Arabidopsis* UPL3 gene is described in Downes et al. 2003. T-DNA not only disrupts the expression of the gene into which it is inserted, but also acts as a marker for subsequent identification of the mutation. Since the sequence of the inserted element is known, the gene in which the insertion has occurred can be recovered, using various cloning or PCR-based strategies. The insertion of a piece of T-DNA in the order of 5 to 25 kb in length generally produces a disruption of gene function. If a large enough population of T-DNA transformed lines is generated, there are reasonably good chances of finding a transgenic plant carrying a T-DNA insert within any gene of interest. Transformation of spores with T-DNA is achieved by an *Agrobacterium*-mediated method which involves exposing plant cells and tissues to a suspension of *Agrobacterium* cells.

The details of this method are well known to a skilled person. In short, plant transformation by *Agrobacterium* results in the integration into the nuclear genome of a sequence called T-DNA, which is carried on a bacterial plasmid. The use of T-DNA transformation leads to stable single insertions. Further mutant analysis of the resultant transformed lines is straightforward and each individual insertion line can be rapidly characterized by direct sequencing and analysis of DNA flanking the insertion. Gene expression in the mutant is compared to expression of the UPL3 nucleic acid sequence in a wild type plant and phenotypic analysis is also carried out.

In another embodiment, mutagenesis is physical mutagenesis, such as application of ultraviolet radiation, X-rays, gamma rays, fast or thermal neutrons or protons. The targeted population can then be screened to identify a UPL3 loss of function mutant.

In another embodiment of the various aspects of the invention, the method comprises mutagenizing a plant population with a mutagen. The mutagen may be a fast neutron irradiation or a chemical mutagen, for example selected from the following non-limiting list: ethyl methanesulfonate (EMS), methylmethane sulfonate (MMS), N-ethyl-N-nitrosurea (ENU), triethylmelamine (1'EM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloroethyl)aminopropylamino]acridine dihydrochloride (ICR-170) or formaldehyde.

In another embodiment, the method used to create and analyse mutations is targeting induced local lesions in genomes (TILLING), reviewed in Henikoff et al, 2004. In this method, seeds are mutagenised with a chemical mutagen, for example EMS. The resulting M1 plants are self-fertilised and the M2 generation of individuals is used to prepare DNA samples for mutational screening. DNA samples are pooled and arrayed on microtiter plates and subjected to gene specific PCR. The PCR amplification products may be screened for mutations in the UPL3 target gene using any method that identifies heteroduplexes between wild type and mutant genes. For example, but not limited to, denaturing high pressure liquid chromatography (dHPLC), constant denaturant capillary electrophoresis (CDCE), temperature gradient capillary electrophoresis (TGCE), or by fragmentation using chemical cleavage. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program. Any primer specific to the UPL3 nucleic acid sequence may be utilized to amplify the UPL3 nucleic acid sequence within the pooled DNA sample. Preferably, the primer is designed to amplify the regions of the UPL3 gene where useful mutations are most likely to arise, specifically in the areas of the UPL3 gene that are highly conserved and/or confer activity as explained elsewhere. To facilitate detection of PCR products on a gel, the PCR primer may be labelled using any conventional labelling method. In an alternative embodiment, the method used to create and analyse mutations is EcoTILLING. EcoTILLING is molecular technique that is similar to TILLING, except that its objective is to uncover natural variation in a given population as opposed to induced mutations. The first publication of the EcoTILLING method was described in Comai et al. 2004.

Rapid high-throughput screening procedures thus allow the analysis of amplification products for identifying a mutation conferring the reduction or inactivation of the expression of the UPL3 gene as compared to a corresponding non-mutagenised wild type plant. Once a mutation is identified in a gene of interest, the seeds of the M2 plant carrying that mutation are grown into adult M3 plants and screened for the phenotypic characteristics associated with the target gene UPL3. Loss of and reduced function mutants with increased seed size compared to a control can thus be identified.

Plants obtained or obtainable by such method which carry a functional mutation in the endogenous UPL3 gene or promoter locus are also within the scope of the invention In an alternative embodiment, the expression of the UPL3 gene may be reduced at either the level of transcription or translation. For example, expression of a UPL3 nucleic acid or UPL3 promoter sequence, as defined herein, can be reduced or silenced using a number of gene silencing methods known to the skilled person, such as, but not limited to, the use of small interfering nucleic acids (siNA) against UPL3. “Gene silencing” is a term generally used to refer to suppression of expression of a gene via sequence-specific interactions that are mediated by RNA molecules. The degree of reduction may be so as to totally abolish production of the encoded gene product, but more usually the abolition of expression is partial, with some degree of expression remaining. The term should not therefore be taken to require complete “silencing” of expression.

In one embodiment, the siNA may include, short interfering RNA (siRNA), double-stranded RNA (dsRNA), micro-RNA (miRNA), antagomirs and short hairpin RNA (shRNA) capable of mediating RNA interference.

The inhibition of expression and/or activity can be measured by determining the presence and/or amount of UPL3 transcript using techniques well known to the skilled person (such as Northern Blotting, RT-PCR and so on).

Transgenes may be used to suppress endogenous plant genes. This was discovered originally when chalcone synthase transgenes in *petunia* caused suppression of the endogenous chalcone synthase genes and indicated by easily visible pigmentation changes. Subsequently it has been described how many, if not all plant genes can be “silenced” by transgenes. Gene silencing requires sequence similarity between the transgene and the gene that becomes silenced. This sequence homology may involve promoter regions or coding regions of the silenced target gene. When coding regions are involved, the transgene able to cause gene silencing may have been constructed with a promoter that would transcribe either the sense or the antisense orientation of the coding sequence RNA. It is likely that the various examples of gene silencing involve different mechanisms that are not well understood. In different examples there may be transcriptional or post-transcriptional gene silencing and both may be used according to the methods of the invention.

The mechanisms of gene silencing and their application in genetic engineering, which were first discovered in plants in the early 1990s and then shown in *Caenorhabditis elegans* are extensively described in the literature.

RNA-mediated gene suppression or RNA silencing according to the methods of the invention includes co-suppression wherein over-expression of the target sense RNA or mRNA, that is the UPL3 sense RNA or mRNA, leads to a reduction in the level of expression of the genes concerned. RNAs of the transgene and homologous endogenous gene are co-ordinately suppressed. Other techniques used in the methods of the invention include antisense RNA to reduce transcript levels of the endogenous target gene in a plant. In this method, RNA silencing does not affect the transcription of a gene locus, but only causes sequence-specific degradation of target mRNAs. An "antisense" nucleic acid sequence comprises a nucleotide sequence that is complementary to a "sense" nucleic acid sequence encoding a UPL3 protein, or a part of the protein, i.e. complementary to the coding strand of a double-stranded cDNA molecule or complementary to an mRNA transcript sequence. The antisense nucleic acid sequence is preferably complementary to the endogenous UPL3 gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire UPL3 nucleic acid sequence as defined herein, but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine-substituted nucleotides may be used. Examples of modified nucleotides that may be used to generate the antisense nucleic acid sequences are well known in the art. The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention hybridize with or bind to mRNA transcripts and/or insert into genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using vectors.

RNA interference (RNAi) is another post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

Artificial and/or natural microRNAs (miRNAs) may be used to knock out gene expression and/or mRNA translation. MicroRNAs (miRNAs) miRNAs are typically single stranded small RNAs typically 19-24 nucleotides long. Most plant miRNAs have perfect or near-perfect complementarity with their target sequences. However, there are natural targets with up to five mismatches. They are processed from longer non-coding RNAs with characteristic fold-back structures by double-strand specific RNases of the Dicer family Upon processing, they are incorporated in the RNA-induced silencing complex (RISC) by binding to its main component, an Argonaute protein. miRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes. Artificial microRNA (amiRNA) technology has been applied in *Arabidopsis thaliana* and other plants to efficiently silence target genes of interest. The design principles for amiRNAs have been generalized and integrated into a Web-based tool (wmd-.weigelworld.org).

Thus, according to the various aspects of the invention a plant may be transformed to introduce a RNAi, shRNA, snRNA, dsRNA, siRNA, miRNA, ta-siRNA, amiRNA or cosuppression molecule that has been designed to target the expression of an UPL3 nucleic acid sequence and selectively decreases or inhibits the expression of the gene or stability of its transcript. Preferably, the RNAi, snRNA, dsRNA, shRNA siRNA, miRNA, amiRNA, ta-siRNA or cosuppression molecule used according to the various aspects of the invention comprises a fragment of at least 17 nt, preferably 22 to 26 nt and can be designed on the basis of the information shown in any of SEQ ID Nos. 4 to 7. Guidelines for designing effective siRNAs are known to the skilled person. Briefly, a short fragment of the target gene sequence (e.g., 19-40 nucleotides in length) is chosen as the target sequence of the siRNA of the invention. The short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, 5) a sequence from the target gene mRNA that is unique to the target gene, 6) avoids regions within 75 bases of a start codon. The sequence fragment from the target gene mRNA may meet one or more of the criteria identified above. The selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides that are typically made by chemical synthesis. In addition to siRNA which is complementary to the mRNA target region, degenerate siRNA sequences may be used to target homologous regions. siRNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligonucleotide synthesis suppliers.

siRNA molecules according to the aspects of the invention may be double stranded. In one embodiment, double stranded siRNA molecules comprise blunt ends. In another embodiment, double stranded siRNA molecules comprise overhanging nucleotides (e.g., 1-5 nucleotide overhangs, preferably 2 nucleotide overhangs). In some embodiments, the siRNA is a short hairpin RNA (shRNA); and the two strands of the siRNA molecule may be connected by a linker region (e.g., a nucleotide linker or a non-nucleotide linker). The siRNAs of the invention may contain one or more modified nucleotides and/or non-phosphodiester linkages. Chemical modifications well known in the art are capable of increasing stability, availability, and/or cell uptake of the siRNA. The skilled person will be aware of other types of chemical modification which may be incorporated into RNA molecules.

In one embodiment, recombinant DNA constructs as described in U.S. Pat. No. 6,635,805, incorporated herein by reference, may be used.

The silencing RNA molecule is introduced into the plant using conventional methods, for example a vector and *Agrobacterium*-mediated transformation. Stably transformed plants are generated and expression of the UPL3 gene compared to a wild type control plant is analysed.

Silencing of the UPL3 nucleic acid sequence may also be achieved using virus-induced gene silencing.

Thus, in one embodiment of the invention, the plant expresses a nucleic acid construct comprising a RNAi, shRNA snRNA, dsRNA, siRNA, miRNA, ta-siRNA, amiRNA or co-suppression molecule that targets the UPL3 nucleic acid sequence as described herein and reduces expression of the endogenous UPL3 nucleic acid sequence. A gene is targeted when, for example, the RNAi, snRNA, dsRNA, siRNA, shRNA miRNA, ta-siRNA, amiRNA or cosuppression molecule selectively decreases or inhibits the expression of the gene compared to a control plant. Alternatively, a RNAi, snRNA, dsRNA, siRNA, miRNA, ta-siRNA, amiRNA or cosuppression molecule targets A UPL3 nucleic acid sequence when the RNAi, shRNA snRNA, dsRNA, siRNA, miRNA, ta-siRNA, amiRNA or cosuppression molecule hybridises under stringent conditions to the gene transcript.

A further approach to gene silencing is by targeting nucleic acid sequences complementary to the regulatory region of the gene (e.g., the promoter and/or enhancers) of UPL3 to form triple helical structures that prevent transcription of the gene in target cells. Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

In one embodiment, the suppressor nucleic acids may be anti-sense suppressors of expression of the UPL3 polypeptides. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene.

An anti-sense suppressor nucleic acid may comprise an anti-sense sequence of at least 10 nucleotides from the target nucleotide sequence. It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Suppressor nucleic acids may be operably linked to tissue-specific or inducible promoters. For example, integument and seed specific promoters can be used to specifically down-regulate a UPL3 nucleic acid in developing ovules and seeds to increase final seed size.

Nucleic acid which suppresses expression of a UPL3 polypeptide as described herein may be operably linked to a heterologous regulatory-sequence, such as a promoter, for example a constitutive, inducible, tissue-specific or developmental specific promoter. The construct or vector may be transformed into plant cells and expressed as described herein. Plant cells comprising such vectors are also within the scope of the invention.

In another aspect, the invention relates to a silencing construct obtainable or obtained by a method as described herein and to a plant cell comprising such construct.

Thus, aspects of the invention involve targeted mutagenesis methods, specifically genome editing, and in a preferred embodiment exclude embodiments that are solely based on generating plants by traditional breeding methods.

In a further embodiment, the method may comprise reducing and/or abolishing the activity of UPL3. In one example this may comprise reducing UPL3 ubiquitin ligase activity by reducing the activities of E2 conjugating enzymes that transfer ubiquitin to UPL3. Such reduction can be achieved using several of the approaches described above, for example, by introducing at least one mutation as described above into at least one E2 conjugating enzyme.

In a further embodiment, the method may further comprise introducing and expressing a nucleic acid construct comprising a nucleic acid sequence encoding LEC2 (LEAFY COTYLEDON 2) or a functional variant or homolog thereof. In one embodiment, the nucleic acid sequence for LEC2 is any one of SEQ ID NOs: 11 to 14 and encodes a polypeptide as defined in any one of SEQ ID NOs: 23 to 26. A functional variant or homolog is as defined above. In a preferred embodiment, the nucleic acid construct comprises a LEC2 sequence operably linked to a regulatory sequence. Preferably said regulatory sequence is a tissue-specific, preferably seed-specific promoter such that the expression of LEC2 is temporally restricted to during seed development. Examples of suitable promoters may include, but are not limited to the endogenous LEC2 promoter, the UPL3 promoter as described herein, an altered LEC2 promoter with a sequence that drives reduced expression, or an embryo-specific promoter that is expressed at lower levels than LEC2.

In one embodiment the nucleic acid construct may be stably incorporated into the plant genome.

The term "operably linked" as used herein refers to a functional linkage between the promoter sequence and the gene of interest, such that the promoter sequence is able to initiate transcription of the gene of interest.

In a further aspect of the invention, there is provided a method for increasing seed yield, increasing seed protein and/or lipid content and/or reducing glucosinolate levels, the method comprising introducing and expressing a nucleic acid construct comprising a nucleic acid sequence encoding LEC2 as defined above into a plant. Preferably said LEC2 sequence is operably linked to a tissue-specific promoter as described above. More preferably the nucleic acid construct is stably incorporated into the plant genome.

In a further aspect of the invention, there is provided a method to increase the stability of LEC2 and other proteins that are substrates of UPL3-mediated ubiquitylation, in any plant species containing LEC2-related proteins. Such proteins can be identified using several approaches to anyone skilled in the art, including sequence homology to *Arabidopsis* and *Brassica* LEC2, or functional assays that use interaction of a candidate LEC2 protein (for example those with a conserved B3 DNA binding domain) with other regulatory proteins such as AB13 and LEC1 to form a transcriptional regulatory complex that activates a target gene. Those skilled in the art can identify candidate LEC2-related proteins using these methods. The candidate LEC2-like protein can then be subject to ubiquitylation experiments using UPL3 protein, following procedures that are commonly used for example (Dong et al., 2016). Ubiquitylation involves the covalent attachment of ubiquitin, and polymers or single ubiquitin molecules, to lysine residues on the target protein by a characteristic isopeptide bond. The location of these ubiquitylated lysines can be detected using protein mass spectrometry, a routine method that analyses peptides created by trypsin digestion of ubiquitylated proteins. This releases a characteristic glycine-glycine-lysine peptide generated from ubiquitin and the lysine on the host protein to which it is attached. The peptide sequence containing the lysine defines the location of the lysine. Ubiquitylation of lysine residues targets proteins for degradation, so reducing their levels and activities. By replacing the lysine residues with arginine residues, the protein can no longer be ubiquitylated, thus stabilising the protein. Those skilled in the art can identify lysines on LEC2 and LEC-related proteins that are ubiquitylated by UPL3, and using standard methods of site directed DNA mutagenesis, convert the lysines to arginines. This modified protein can be introduced into a plant by standard methods of transformation, and used to maintain higher levels of LEC2 and LEC2-like proteins in developing seeds. This is predicted to increase expression of target genes, leading to increased seed protein and lipid levels.

Therefore, in a further aspect of the invention, there is provided a method for increasing seed yield, increasing seed protein and/or lipid content and/or reducing glucosinolate levels, the method comprising increasing the stability (e.g. reducing or preventing ubiquitin-mediated degradation) of LEC2, as described above. In other words, the method may comprise mutating by any mutagenesis technique described herein at least one lysine residue on a LEC2 polypeptide as described herein such that LEC2 is not ubiquitinated or ubiquitinated to a lesser extent compared to a wild-type or control LEC2 protein. Accordingly, the mutated LEC2 protein may have no or a reduced number of ubiquitination sites compared to a wild-type or control protein.

In another aspect, the invention extends to a plant obtained or obtainable by a method as described herein.

Genetically Altered or Modified Plants and Methods of Producing Such Plants

In another aspect of the invention there is provided a genetically altered plant, part thereof or plant cell characterised in that the plant does not express UPL3, has reduced levels of UPL3 expression, does not express a functional UPL3 gene or expresses a UPL3 gene with reduced function. For example, the plant is a reduction (knock down) or loss of function (knock out) mutant wherein the function of the UPL3 nucleic acid sequence is reduced or lost compared to a wild type control plant. To this end, a mutation is introduced into either the UPL3 gene sequence or the corresponding promoter sequence which disrupts the transcription of the gene. Therefore, preferably said plant comprises at least one mutation in the promoter and/or gene for UPL3.

In a further aspect of the invention, there is provided a plant, part thereof or plant cell characterised by an increased seed yield compared to a wild-type or control pant, wherein preferably, the plant comprises at least one mutation in the UPL3 gene and/or its promoter. Preferably said increase in seed yield comprises an increase in at least one of seed weight, seed size, seed number per pod, pod length, seed and/or lipid content and weight of seed per pod. In another embodiment, the plant, part thereof or plant cell is characterised by an increase in seed protein and/or lipid content. In a further alternative embodiment, said plant, part thereof or plant cell is characterised by a reduction in glucosinolates levels. Again, such reduction or increase as used above is relative to the levels or content in a wild-type or control plant.

The plant may be producing by introducing a mutation, preferably a deletion, insertion or substitution into the UPL3 gene and/or promoter sequence by any of the above described methods. Preferably said mutation is introduced into a least one plant cell and a plant regenerated from the at least one mutated plant cell.

Alternatively, the plant or plant cell may comprise a nucleic acid construct expressing an RNAi molecule targeting the UPL3 gene as described herein. In one embodiment, said construct is stably incorporated into the plant genome. These techniques also include gene target using vectors that target the gene of interest and which allow integration allows for integration of transgene at a specific site. The targeting construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene will be translated into a nonfunctional protein, if it is translated at all.

In another aspect of the invention there is provided a method for producing a genetically altered plant as described herein. In one embodiment, the method comprises introducing at least one mutation into the UPL3 gene and/or UPL3 promoter of preferably at least one plant cell using any mutagenesis technique described herein. Preferably said method further comprising regenerating a plant from the mutated plant cell.

The method may further comprise selecting one or more mutated plants, preferably for further propagation. Preferably said selected plants comprise at least one mutation in the UPL3 gene and/or promoter sequence. Preferably said plants are characterised by no or a reduced level of UPL3 expression and/or a reduced level of UPL3 polypeptide activity. Expression and/or activity levels of UPL3 can be measured by any standard technique known to the skilled person. UPL3 enzymatic activity on substrates such as LEC2, expression of LEC1 and other target genes can also be measured.

The selected plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In a further aspect of the invention there is provided a plant obtained or obtainable by the above described methods.

For the purposes of the invention, a “genetically altered plant” or “mutant plant” is a plant that has been genetically altered compared to the naturally occurring wild type (WT) plant. In one embodiment, a mutant plant is a plant that has been altered compared to the naturally occurring wild type (WT) plant using a mutagenesis method, such as any of the mutagenesis methods described herein. In one embodiment, the mutagenesis method is targeted genome modification or genome editing. In one embodiment, the plant genome has been altered compared to wild type sequences using a mutagenesis method. Such plants have an altered phenotype as described herein, such as an increased seed yield. Therefore, in this example, increased seed yield is conferred by the presence of an altered plant genome, for example, a mutated endogenous UPL3 gene or UPL3 promoter sequence. In one embodiment, the endogenous promoter or gene sequence is specifically targeted using targeted genome modification and the presence of a mutated gene or promoter sequence is not conferred by the presence of transgenes expressed in the plant. In other words, the genetically altered plant can be described as transgene-free.

A plant according to the various aspects of the invention, including the transgenic plants, methods and uses described herein may be a monocot or a dicot plant. Preferably, the plant is a crop plant. By crop plant is meant any plant which is grown on a commercial scale for human or animal consumption or use. In a preferred embodiment, the plant is a cereal. In another embodiment the plant is *Arabidopsis*.

In a most preferred embodiment, the plant is selected from any dicotyledonous oilseed crop, such as oilseed and protein crops, including *B. napus*, other *Brassica* oilseed crops such as *B. oleracea, B. juncea*, soybean, sunflower, linseed, cotton, hemp, oilpalm, coconut, peanut, safflower, Camelina and olive. In one embodiment the plant is oilseed rape, and the variety is selected from Avatar, Amalie, Incentive, Excalibur, Charger, Trinity, Sy Haranas, Samurai, Lemkes Malchower, Bienvenue, Coriander, Quinta, and Quartz. Alternatively, the variety may be Amber x commanche, Dimension, Eurol, Temple or Licrown x express.

In another embodiment, the plant is selected from maize, rice, wheat and barley.

The term “plant” as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein. The term “plant” also encompasses plant cells, suspension cultures, callus tissue, embryos, meristematic regions, gametophytes, sporophytes, pollen and microspores, again wherein each of the aforementioned comprises the nucleic acid construct as described herein.

The invention also extends to harvestable parts of a plant of the invention as described herein, but not limited to seeds, leaves, fruits, flowers, stems, roots, rhizomes, tubers and bulbs. The aspects of the invention also extend to products derived, preferably directly derived, from a harvestable part of such a plant, such as dry pellets or powders, oil, fat and fatty acids, starch or proteins. Another product that may derived from the harvestable parts of the plant of the invention is biodiesel. The invention also relates to food products and food supplements comprising the plant of the invention or parts thereof. In one embodiment, the food products may be animal feed. In another aspect of the invention, there is provided a product derived from a plant as described herein or from a part thereof.

In a further aspect of the invention there is provided a method for producing a food or feed product with increased protein and/or lipid content and/or reduced glucosinolate levels, said method comprising a. producing a plant wherein the expression of UPL3 is reduced or abolished and/or the activity of a UPL3 polypeptide is reduced;
b. obtaining a seed from said plant; and
c. producing a food or feed product from said seed.

In a preferred embodiment, the plant part or harvestable product is a seed. Therefore, in a further aspect of the invention, there is provided a seed produced from a genetically altered plant as described herein. In an alternative embodiment, the plant part is pollen, a propagule or progeny of the genetically altered plant described herein. Accordingly, in a further aspect of the invention there is provided pollen, a propagule or progeny of the genetically altered plant as described herein.

A control plant as used herein according to all of the aspects of the invention is a plant which has not been modified according to the methods of the invention. Accordingly, in one embodiment, the control plant does not have reduced expression of a UPL3 nucleic acid and/or reduced activity of a UPL3 polypeptide. In an alternative embodiment, the plant been genetically modified, as described above. In one embodiment, the control plant is a wild type plant. The control plant is typically of the same plant species, preferably having the same genetic background as the modified plant.

In another aspect of the invention there is provided a nucleic acid construct comprising a nucleic acid sequence encoding a LEC2 polypeptide or a functional variant or homolog thereof. In one embodiment, the nucleic acid sequence of LEC2 is defined in any one of SEQ ID NOs: 11 to 14 and encodes a polypeptide as defined in any one of SEQ ID NOs: 23 to 26. In a further preferred embodiment, the LEC2 is operably linked to a regulatory sequence, wherein the regulatory sequence is preferably a tissue-specific promoter, such as but not limited to an embryo-specific promoter, such as, but not limited to promoters expressing embryo specific oleosin genes. A functional variant or homolog is as defined above, but in one embodiment, is defined in SEQ ID NO: 15 and encodes a polypeptide defined in SEQ ID NO: 27.

In another aspect of the invention there is provided a vector comprising the nucleic acid sequence described above.

In a further aspect of the invention, there is provided a host cell comprising the nucleic acid construct. The host cell may be a bacterial cell, such as *Agrobacterium tumefaciens*, or an isolated plant cell. The invention also relates to a culture medium or kit comprising a culture medium and an isolated host cell as described below.

In another embodiment, there is provided a transgenic plant expressing the nucleic acid construct as described above. In one embodiment, said nucleic acid construct is stably incorporated into the plant genome.

The nucleic acid sequence is introduced into said plant through a process called transformation. The term “introduction” or “transformation” as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation. According to the invention, the nucleic acid is preferably stably integrated in the transgenic plants genome and the progeny of said plant therefore also comprises the transgene.

To select transformed plants, the plant material obtained in the transformation is, in certain embodiments, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker such as the ones described above.

Following DNA or nucleic acid transfer and regeneration, putatively transformed plants may also be evaluated, for instance using Southern analysis, for the presence of the gene of interest, copy number and/or genomic organisation. Alternatively or additionally, expression levels of the newly introduced nucleic acid may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

A suitable plant is defined above.

In another aspect, the invention relates to the use of a nucleic acid construct as described herein to increase seed yield as defined above, and/or seed protein and/or lipid content and/or reduce glucosinolate levels.

In another aspect of the invention there is provided a method of producing a plant with an increased seed yield phenotype, increased seed protein and/or lipid levels and/or reduced glucosinolates levels, the method comprising introducing and expressing in said plant a nucleic acid construct as described herein.

Method of Screening Plants for Naturally Occurring Low or High Levels of UPL3 Expression In a further aspect of the invention, there is provided a method for screening a population of plants and identifying and/or selecting a plant that has or will have reduced UPL3 expression, an increased seed yield phenotype, increased seed protein and/or lipid levels and/or reduced glucosinolate levels.

In one embodiment the method comprising detecting in a plant or plant germplasm at least one marker that is indicative of high or low UPL3 expression. In one embodiment, this marker may be a SNP or polymorphism in the promoter of the UPL3 gene and/or the UPL3 gene. Alternatively, the marker may be a polymorphism at a highly associated marker locus, wherein the sequence at this locus is indicative of high or low UPL3 expression.

In one embodiment, said screening comprises determining the presence of at least one polymorphism, wherein said polymorphism is at least one substitution or any combination thereof of the residues at the positions described in SEQ ID NO: 20 or its complement and shown in Table 2 (low UPL3-expressing polymorphism) or at a homologous position in a homologous sequence as described herein.

Accordingly, in one example, the method comprises screening and detecting in a plant or plant germplasm at least one polymorphism that is indicative of low UPL3 expression. In one example, the polymorphism may be selected from at least one or any combination thereof, of the following polymorphisms, a T at position −1933 (all positions cited are from the ATG start site);

a A at position −1884;

a G at position −1858;

a C at position −1759;

an insertion of at least one, two, three, four of five nucleotides at position −1718 (1718 to 1722);

a C at position −1660;

a C at position −1609;

an A at position −1605;

a C at position −1600;

an insertion of at least one, two or three nucleotides at positions −1597 (1597-1599);

an insertion of at least one, two or three nucleotides at positions −1580 (1580-182);

a T at position −1469;

a T at position −1456;

an A at position −1418;

a C at position −1370;

an A at position −1367;

a C at position −1354;

an A at position −1352;

an insertion of at least one, two, three four, five, six, seven, eight, nine, ten, eleven, twelve, thirteen, fourteen, fifteen, sixteen, seventeen or eighteen nucleotides at position −1293 (1293 to 1309);

an insertion of at least one, two, three four, five, six, seven, eight, nine, ten, eleven, twelve nucleotides at position −1260 (1260 to 1271);

an A at position 1251 an insertion of at least one or two nucleotides at position −1153 (1153-1154);

a Cat position −1152;

a T at position −1141;

an A at position −1120 an insertion of at least one, two, three four, five or six nucleotides at position −1088 (1083-1088);

an insertion of at least one nucleotide at position −1026;

a T at position −1035 an A at position −929 an A at position −835;

a G at position −805;

a G at position −774 an insertion of between one and 79 nucleotides at position −610 (773 to 852);

a G at position −352;

a C at position −148 a G at position −145; and an A at position −123.

Accordingly, in one example, the method comprises screening and detecting in a plant or plant germplasm at least one polymorphism that is indicative of high UPL3 expression. In one example, the polymorphism may be selected from at least one or any combination thereof, of the following polymorphisms, a C at position −1933 (all positions cited are from the ATG start site);

a G at position −1884;

an A at position −1858;

a T at position −1759;

a T at position −1660;

a T at position −1609;

a T at position −1605;

a T at position −1600;

a C at position −1469;

a C at position −1456;

a G at position −1418;

a T at position −1370;

a G at position −1367;

a T at position −1354;

a G at position −1352;

a G at position 1251 a Tat position −1152;

an A at position −1141;

an A at position −1120 a G at position −1035 a C at position −929 a G at position −835;

an A at position −805;

a C at position −774 a C at position −352;

a T at position −148 a C at position −145; and a T at position −123.

In one embodiment, a plant expressing at least one of these low-UPL3 expressing polymorphisms will express ~3 fold lower level of UPL3 expression compared to a plant wherein the promoter expresses a high-UPL3 expressing polymorphism. As a result such a plant will display an increased seed yield as described above and/or an increased protein and/or lipid seed content and/or reduced levels of glucosinolate. In an alternative embodiment, the method may comprise detecting the presence or absence of an 80 base tandem repeat sequence as defined herein, wherein at least two copies of the repeat sequence is indicative that the plant will express a lower level of UPL3 compared to a plant that expresses only one repeat sequence (defined in SEQ ID NO: 18).

In a further alternative embodiment, the method may comprise detecting the presence of a polymorphism in a marker at the locus JCV_5587:125 in *B. napus* or at a homologous locus in any other plant, for example as described herein. As described in Example 3, the inventors have identified a marker at the above locus that is highly associated with UPL3, and moreover, that specifically, the following sequence at locus JCV_5587:125 in both copies of, preferably, the *B. napus* genome is indicative of low UPL3 expression and a high-yielding phenotype:

(SEQ ID NO: 61)
TATTTCCGCATGTTGCTAAACCGGGAGAATATATCAAATGCAACTGTCATG

ATCCAACCATCGCTGACATCATATACATTCAGTTCACCACCTCAGCCAGCT

TTGCGGCTTCTATTGCAGCCGACAGAATTCTTCTGTTAGATGCATATTTCA

GTGTTGTTGTCTTCCATGGAATGACAATAGCACAATGGCGAAACATGGGTT

ATCATCATCAGGCTGAACATGAGGCATTTGATAGTCCGGGAGCGTTTCCCT

GTCCCCGAGATTAGTTGTGTGTGATCAACA

Conversely, the following sequence at this locus in at least one copy of the genome is indicative of high UPL3 expression and a low-yielding phenotype:

(SEQ ID NO: 62):
TATTTCCGCATGTTGCTAAACCGGGAGAATATATCAAATGCAACTGTCATG

ATTCAACCATCGCTGACATCATATACATTCAGTTCACCACCTCAGCCAGCT

TTGCTGGACGTGGCTTCCATTGCAGCCGACAGAATTCTCCTGTTAGATGCA

TATTTCAGTGTTGTTGTCTTCCATGGAATGACAATWGCACAATGGCGAAAC

ATGGGTTATCATCATCAGGCTGAACATGAGGCATTTGCTCAGCTATTGCAA

GCTCCTCAAGAAGATTCCCAGATGATAGTCCGGGAGCGTTTCCCWGTCCCG

AGATTAGTTGTGTGTGATCAACA

Accordingly, in a further embodiment, the method of screening may comprise detecting the sequence of SEQ ID NO: 61—and preferably the presence of a T or a C at position 134 of SEQ ID NO: 62 or a homologous position thereof, preferably in one or both copies of the genome where the plant is a polyploid, and wherein the presence of T/T in both copies of the genome is indicative of a low UPL3-expressing and high-yielding phenotype and the presence of C/T is indicative of a high UPL3-expressing and low-yielding phenotype As described in Example 4, the primers described in SEQ ID NO: 65 and 66, in one example, may be used to detect this polymorphism.

Suitable tests for assessing the presence of a polymorphism would be well known to the skilled person, and include but are not limited to, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs). In one embodiment, Kompetitive Allele Specific PCR (KASP) genotyping is used.

In one embodiment, the method comprises a) obtaining a nucleic acid sample from a plant and b) carrying out nucleic acid amplification of one or more UPL3 promoter alleles using one or more primer pairs.

In a further embodiment, the method may further comprise introgressing the chromosomal region comprising at least one of said low-UPL3-expressing polymorphisms or the chromosomal region containing the repeat sequence deletion as described above into a second plant or plant germplasm to produce an introgressed plant or plant germplasm. Preferably the expression of UPL3 in said second plant will be reduced or abolished, and more preferably said second plant will display an increase in seed size, and increase in total protein and/or lipid content and/or a reduction in glucosinolate levels.

Alternatively, in another aspect of the invention there is provided a for increasing seed yield, the method comprising a. screening a population of plants for at least one plant with a high-expressing UPL3 polymorphism as described herein;

b. further modulating the expression or activity of a UPL3 polypeptide, as described herein, in said plant by introducing at least one mutation into the nucleic acid sequence encoding UPL3 or at least one mutation into the promoter of UPL3 as described herein or using RNA interference as also described herein.

In a further alternative embodiment, the method may comprise screening plants to detect the level of endogenous UPL3 expression. In one embodiment, RT-PCR may be used to measure expression levels. In one example, the following primers can be used for RT-PCT:

Forward primer:
(SEQ ID NO: 65)
5'-GTAGCTCTCATCAACCTCAAATGC-3'

Reverse primer:
(SEQ ID NO: 66)
5'-AGGGAGCTTAAGGTAGTTGGGG-3'

Accordingly, there is also provided a method of screening and detecting the level of UPL3 expression in a plant, the method comprising using the above primers in RT-PCR to detect the level of UPL3 RNA expression. The method may further comprise detecting plants with a low level of UPL3 expression compared to a control (preferably a high UPL3 expressing plant) and selecting said plant for further propagation. Alternatively, the method may further comprise detecting plants with a high level of UPL3 expression compared to a control (preferably a low UPL3 expressing plant), selecting the plant and reducing the level of UPL3 expression using any of the methods described herein.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Example 1

Results

Associative Transcriptomics Identifies UPL3 as a Novel Regulator of Yield in *Brassica napus*

Figure 2:
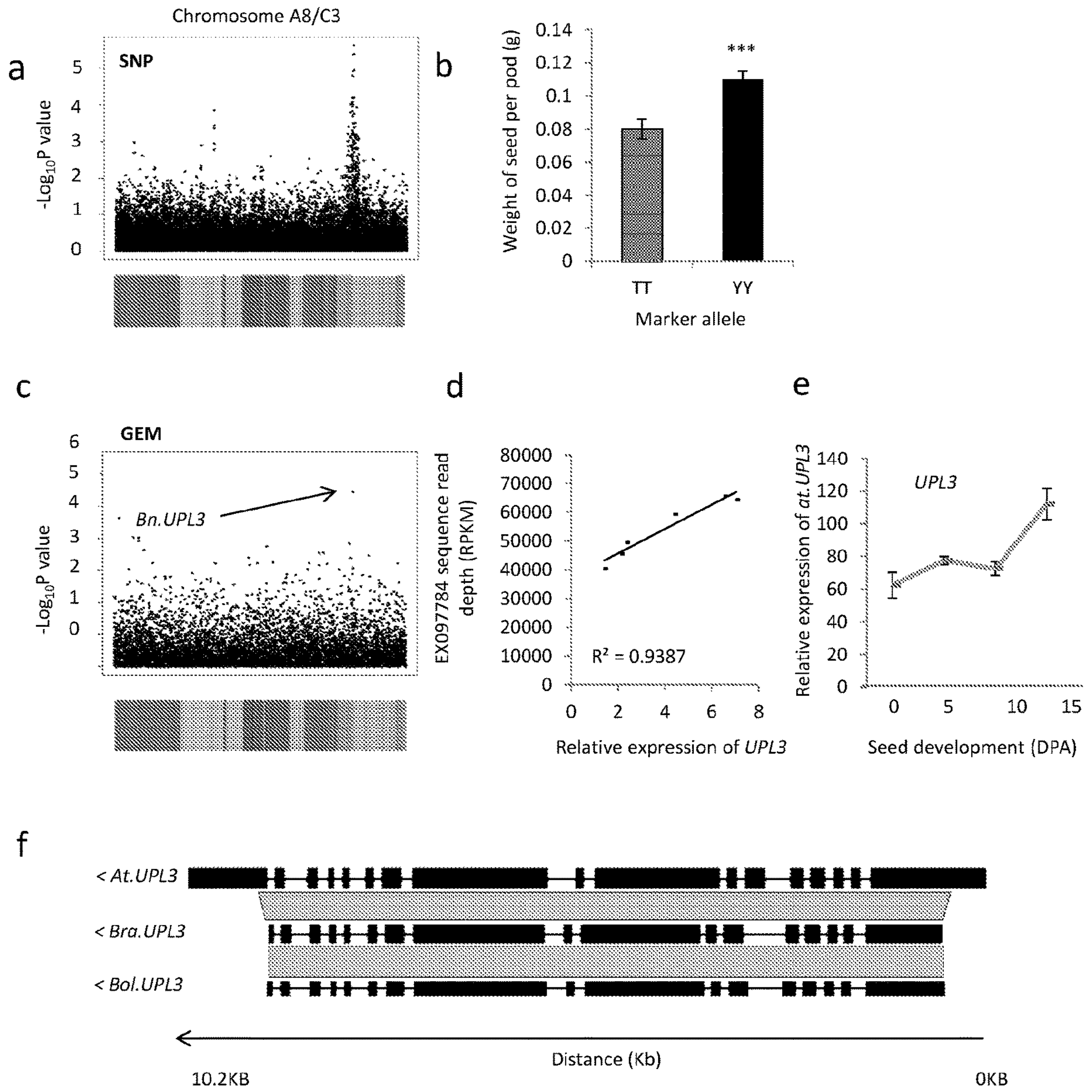
FIG. 2 Associative Transcriptomics identifies UPL3 as a novel regulator of yield in *Brassica napus*. A SNP association peak was identified for weight of seed per pod on chromosome A8/C3 (a). Segregation of the most highly associating marker showed a marker effect of ~20% (b). The GEM analysis revealed that a single unigene, C_EX097784 (corresponding to an orthologue of the *Arabidopsis* UPL3), is differentially expressed between GWAS accessions exhibiting trait variation (C). This differential expression was confirmed in a subset of GWAS accessions using qPCR (d). Assessment of UPL3 expression in developing seeds of *Arabidopsis* shows a steady increase in transcript levels towards seed maturation (e). BLAST analysis indicates that *Brassica rapa* and *Brassica oleracea* each carry a single copy of UPL3 and that there is a high level of conserved synteny between these species and *Arabidopsis* (f). Using Ensembl Plants, despite some misassembly of the *Brassica napus* genome in this region, it is clear that there are two copies of UPL3 in the *B. napus* genome. Alignment of these sequences shows that *Brassica napus* gene models, BnaA08g17020D, BnaA08g17010D and BnaA08g17000D (when combined make up a single copy of Bn.UPL3) show high sequence similarity to the *B. rapa* orthologue, BraC03g010737.1. *B. napus* gene models, BnaC03g60060D and BnaC03g60070D (again each making up part of a single copy of UPL3) show high sequence similarity to the *B. oleracea* orthologue, Bo3g149420. Our GWAS results suggest that variation in the expression of C03 UPL3 transcript is causal for the phenotypic variation in seed weight per pod observed. Sequence information for *B. napus, B. rapa* and *B. oleracea* UPL3 orthologues can be found below.
Figure 3:
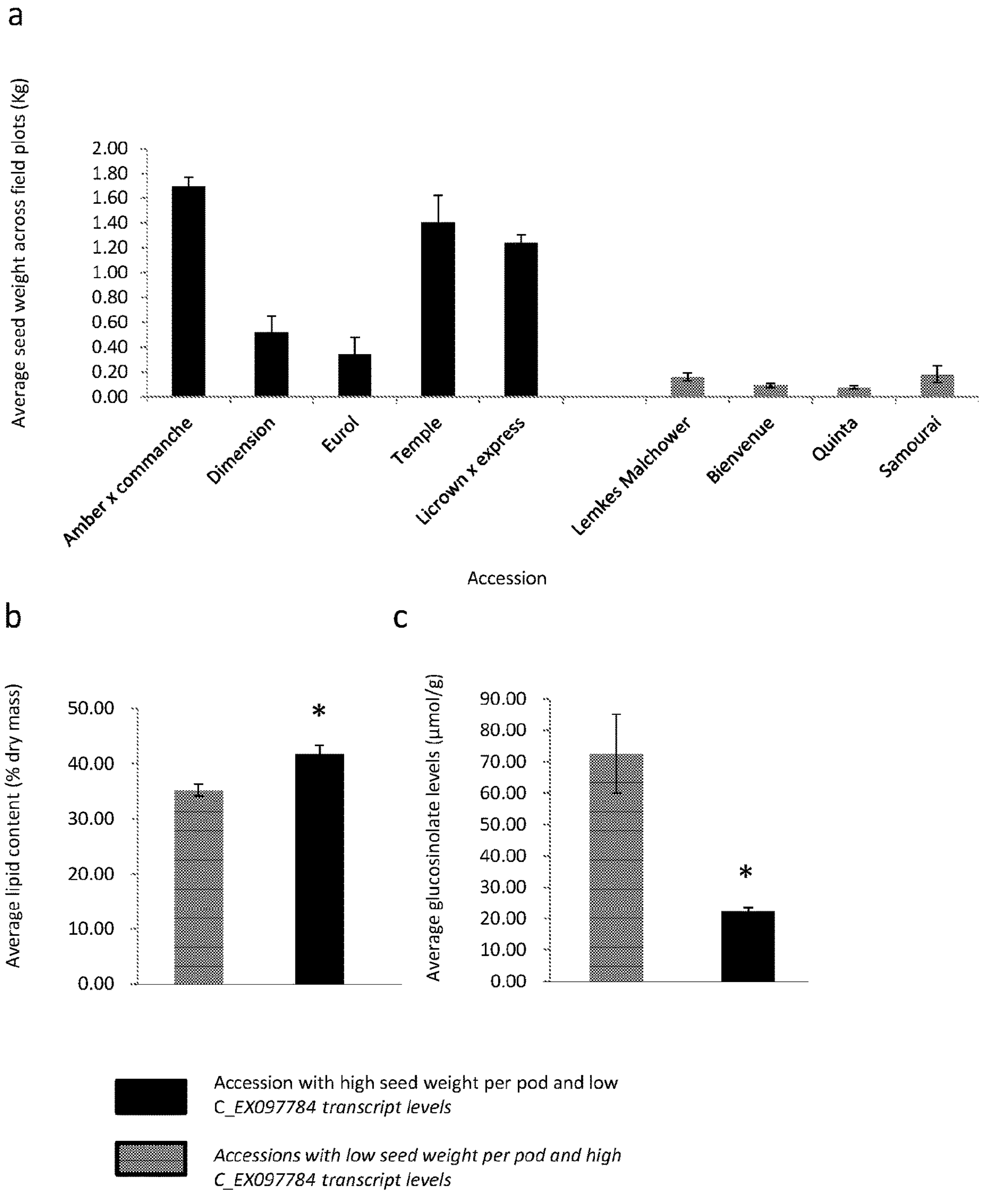
FIG. 3 shows the total plant yield data taken from a 2016 field trial for a subset of GWAS accessions with variation in UPL3 expression. Data shows accessions with high weight of seed per pod (and low UPL3 expression) show increased final yield (a). Across this subset of accessions, those displaying low C_EX097784 expression produce seeds with higher lipid levels (b) and reduced glucosinolate levels (c) relative to high expression genotypes.

To gain insight into the genetic control of yield traits in *Brassica napus,* 69 accessions of oilseed rape (OSR), for which leaf transcriptome data were available were screened for yield-related phenotypic variation (Harper et al., 2012). These traits included: seed weight, seed number per pod, pod length, seed lipid and protein content and weight of seed per pod. Following preliminary statistical analyses, revealing high levels of phenotypic variation, these traits were further assessed using the recently developed method, Associative Transcriptomics (Harper et al., 2012). Associative Transcriptomics is a powerful Genome-Wide Association approach that utilises variation at both the gene sequence (utilising genetic markers such as Single Nucleotide Polymorphisms, or SNPs) and gene expression level (making use of sequence read depth as a measure of gene expression in a Gene Expression Marker, or GEM analysis). These analyses revealed several loci of potential interest, the most promising of which was seen on homologous regions of linkage groups A8 and C3 for seed weight per pod (SWPP) (FIG. 2*a*). Assessment of phenotypic variation segregating with alleles for the most significant SNP marker, revealed a marker effect of ~20% (FIG. 2*b*). This SNP association was also identified, although to a lesser extent, for additional yield traits including pod weight, pod length, seed protein content and seed lipid content. Interestingly, a single C genome-assigned unigene within this region, C_EX097784, also showed high association with trait variation—indicating that differential expression of this unigene between GWAS accessions correlates with the observed variation in weight of seed per pod (FIG. 2*c*). This differential expression was confirmed across a subset of GWAS accessions using qPCR (FIG. 2*d*). This subset of accession was also grown as part of a replicated field trial to allow for measures of overall plant yield to be estimated under field conditions. This revealed that accessions exhibiting high weight of seed per pod (and low levels of C_EX097784) achieve significantly higher overall seed yield across plots than those with low weight of seed per pod (FIG. 3*a*). Furthermore, it was seen that accessions with low expression of the associating unigene produce higher levels of seed lipid (FIG. 3*b*) and reduced levels of seed glucosinolates (FIG. 3*c*) relative to high expressing genotypes.

BLAST analysis revealed that the associating unigene, EX097784, corresponds to an orthologue of the *Arabidopsis* UBIQUITIN PROTEIN LIGASE 3 (UPL3), which encodes a HECT E3 ligase protein known for its role in trichome morphogenesis (Patra et al., 2013). Gene expression at this locus correlates negatively with the weight of seed per pod across GWAS accessions. Assessment of UPL3 expression in the closely related model organism, *Arabidopsis thaliana*, revealed a gradual increase in expression throughout seed development (FIG. 2*e*). Taken together, these results may suggest that, in addition to regulating trichome morphogenesis and xylem development, UPL3 has a further role in negatively regulating seed development.

Using the *Arabidopsis* UPL3 transcript as a reference, *brassica* orthologues of this gene were explored using Ensembl Plants (ensemblgenomes.org). Although some miss-assembly of this region was clear when exploring the *Brassica napus* orthologues, clear gene models were obtained for the ancestral genomes, *Brassica rapa* and *Brassica Oleracea* (FIG. 2*f*), with a single copy of UPL3 found in each ancestral genome. Although some clear differences were observed between these *brassica* orthologues and the *Arabidopsis* UPL3 gene sequence, the coding regions showed a high level of conserved synteny between species.

Figure 4:
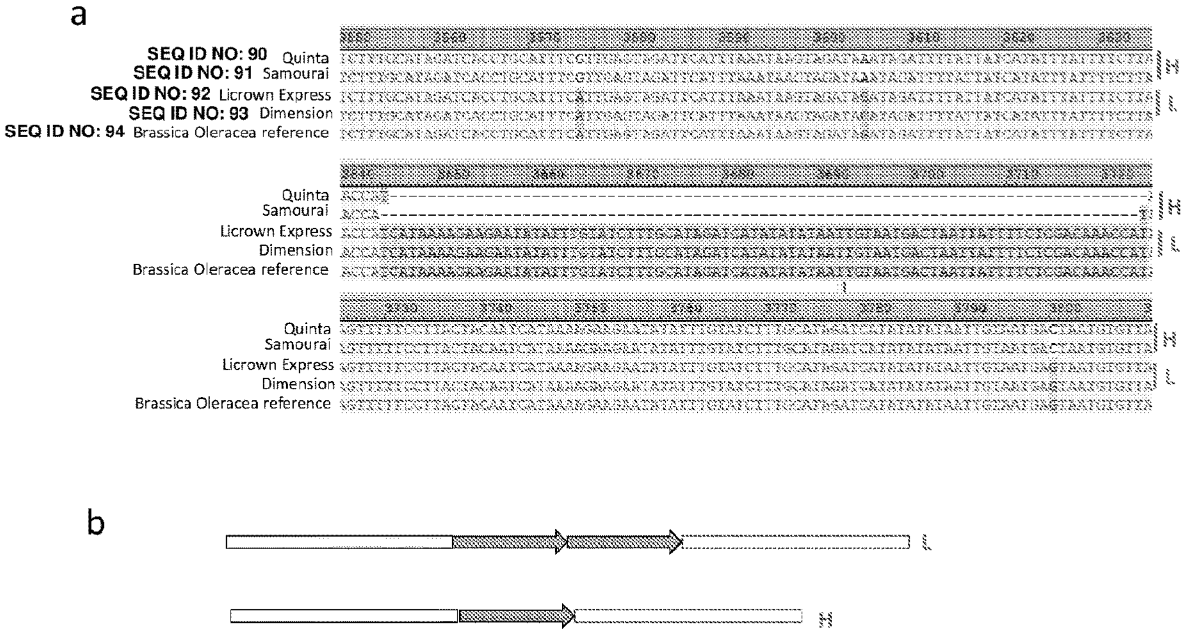
FIG. 4 shows an example of C genome UPL3 promoter variation seen to segregate between *B. napus* GWAS accessions. A high level of variation can be seen segregating between high (marked with "H") and low (marked with "L") C genome UPL3 expression accessions that display high levels of yield trait variation. This includes small changes in the form of SNPs but also larger changes such as the 80 bp InDel (a). This InDel is in fact a tandem duplication present only in low expression accessions. This can be seen represented as a schematic here (b).

Significant Levels of C Genome UPL3 Promoter Variation is Segregating Between GWAS Accessions Given that UPL3 has been identified as a candidate gene based on its differential expression between GWAS accessions, we hypothesised that the genetic variation causal for variation in SWPP may be promoter-based. Using PCR and sequencing, we explored the promoter sequence of the C genome homoeologue of UPL3 across a subset of GWAS accessions. This revealed extensive variation segregating between accessions exhibiting variation in SWPP and UPL3 expression. Much of the observed variation was seen in the form of Single Nucleotide Polymorphisms (SNPs) (FIG. 4*a*). However, more extensive variation was also uncovered, including an 80 bp tandem duplication present only in low C_EX097784 expression accessions FIG. 4*a,b*). Such variation may be causal for the phenotypic variation observed between these genotypes.

*Arabidopsis* Mutants Lacking UPL3 Expression Exhibit Increased Seed Size

Figure 5:
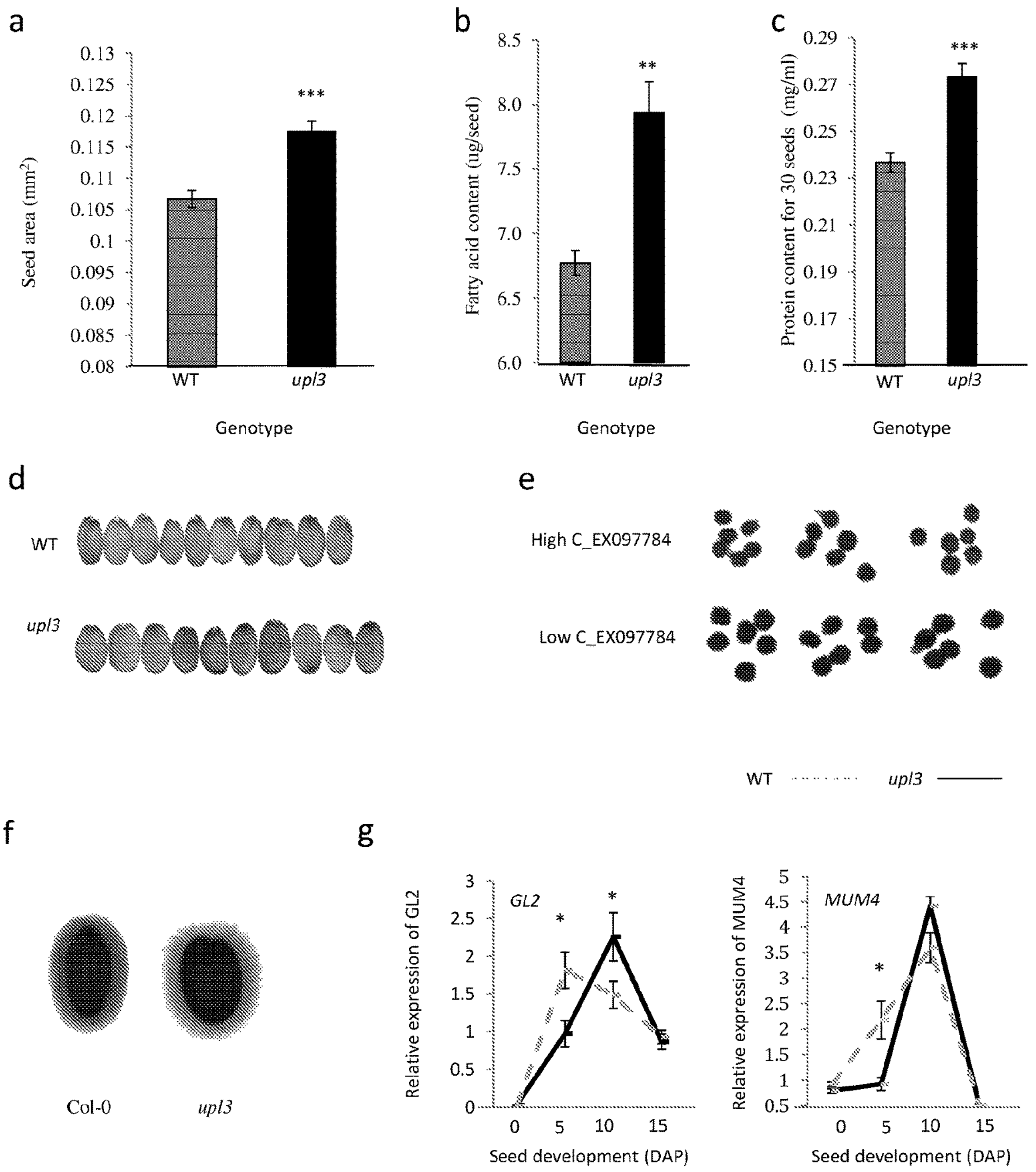
FIG. 5 shows *Arabidopsis* knock-out mutants for UPL3 that exhibit increased seed size. *Arabidopsis* Salk mutant, SALK_015334 exhibits a significant increase in seed size relative to WT plants ($P<0.001$) (a and d). This is coupled with an increase in both seed fatty acid content ($P<0.01$) (b) and seed total protein content ($P<0.001$) (c). *Brassica napus* accession displaying differential expression of C_EX097784 show clear segregation of a seed size phenotype (e). upl3 mutant seeds also exhibit a reduced mucilage extrusion phenotype relative to WT seed (f). This may be explained by the altered expression of GL2 and MUM4 seed between mutant and WT seed (g)

To further explore the potential for UPL3 as a negative regulator of yield, *Arabidopsis* mutant Salk_015534 was obtained from The European *Arabidopsis* Stock Centre (NASC) and assessed for any yield-related phenotypes. UPL3 levels in Salk_015334 homozygous plants, assessed by qPCR, showed complete knockdown of UPL3 expression. Consistent with the hypothesis that UPL3 may function as a negative regulator of yield, mutant plants exhibited significantly increased seed size, relative to wild-type plants (FIGS. 5*a* and *d*). Closer assessment of seed size in *Brassica napus* accessions with high levels of variation in UPL3 expression and weight of seed per pod, also reveal clear differences in seed size (FIG. 5*e*). More in depth analyses of *Arabidopsis* mutant seeds revealed that the increase in seed size was coupled with a 12% increase in seed fatty acid content ($P \leq 0.01$) (FIG. 5*c*) and a 13% increase in seed total protein content ($P \leq 0.001$) (FIG. 5*b*). In addition to these seed phenotypes, upl3 mutant seeds also exhibit altered seed mucilage extrusion relative to WT seed (FIG. 5*f*).

Upl3 Seed Mucilage Phenotype can be Explained by Altered GL2 Expression

Previous studies have shown that UPL3 mediates the proteosomal degradation of GL3/EGL3. GL3/EGL3 are known to positively regulate the expression of GL2, a further transcription factor known to positively regulate both trichome morphogenesis and seed mucilage production. gl2 mutants exhibit a lack of trichomes and reduced mucilage extrusion relative to WT plants. The mucilage phenotype seen in gl2 mutants is thought to, at least in part, be the result of reduced MUM4 expression. MUM4 encodes a RHAMMANOSE SYNTHASE protein required for correct mucilage biosynthesis. Staining of WT and upl3 seeds with ruthinium red, revealed altered seed mucilage extrusion in mutant seeds (FIG. 5*f*). Using qPCR, we assessed MUM4 and GL2 expression throughout seed development in both WT and upl3 seeds. A clear delay in GL2 expression was observed in upl3 seeds relative to WT. In addition, a clear reduction in MUM4 expression is seen at SDPA in upl3 seeds—a trend that would be expected given the reduction in GL2 expression in mutant seeds at this time point (FIG. 5*g*). It is likely that this misregulation of GL2 and consequently MUM4 expression is sufficient to explain the mucilage phenotype observed in upl3 mutant seeds.

Upl3 Mutants Display Increased Expression of Known SSP and Lipid Genes

Figure 6:
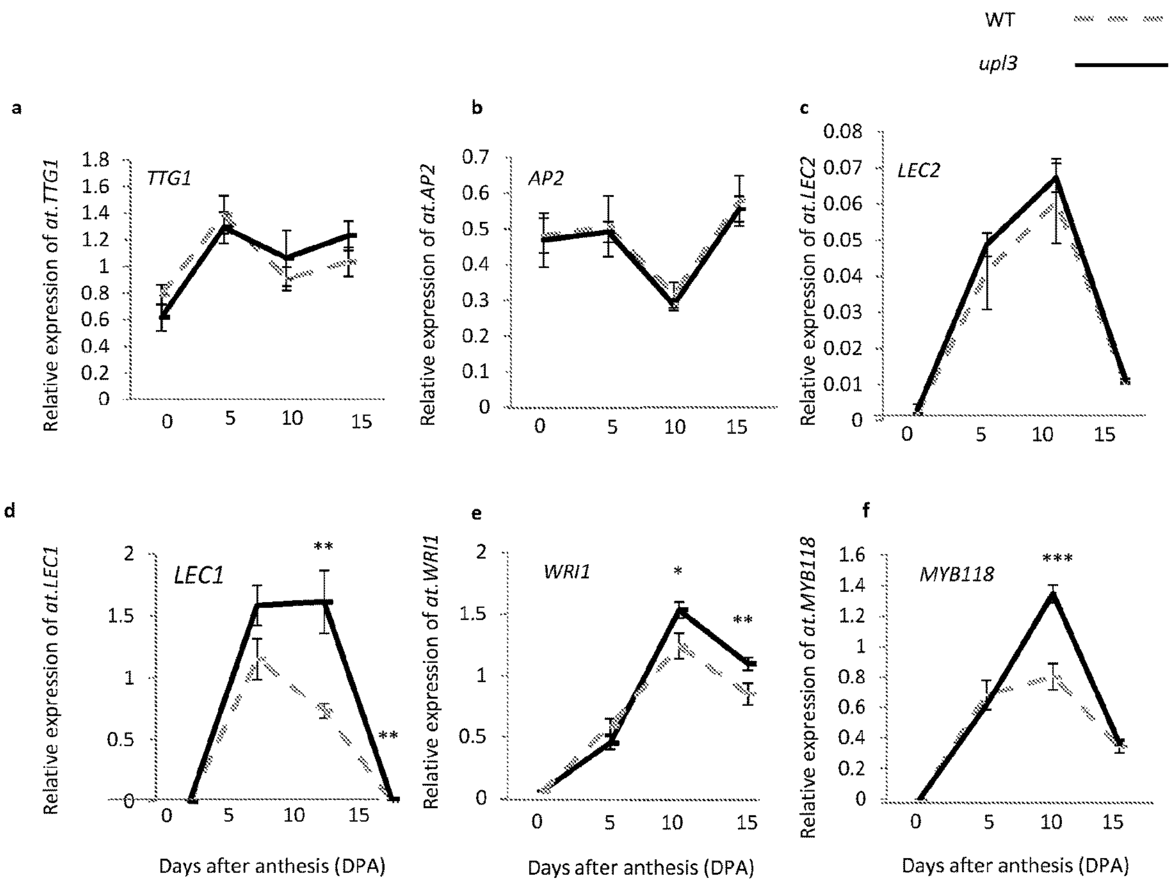
FIG. 6 shows the expression of known regulators of final seed size, seed protein and seed lipid content in *Arabidopsis* WT and upl3 mutant seeds. From 0-15 days after anthesis (DPA). No significant difference in and TRANSPARANT TESTA GLABRA 1 (TTG1) (a) APETELA 2 (AP2) (b) and LEAFY COTYLEDON 2 (LEC2) (c) was seen between WT and mutant seeds. An increase in LEAFY COTYLEDON 1 (LEC1) (d), WRINKLED SEED 1 (WRI1) (e) and MYB118 (f), all of which are targets of LEAFY COTYLEDON 2 (LEC2) is seen from 10DPA in mutant seeds relative to WT. EF1aA4 (At5g60390) was used as internal standard.

Assessment of yield traits in upl3 knockout plants revealed elevated levels of both seed lipid and protein relative to WT plants as well as an increase in final seed size. There are several genes which, at least in *Arabidopsis*, are known to influence these three phenotypes, including TRANSPARENT TESTA GLABRA 1 (TTG1) (Chen et al., 2015), APETELA 2 (AP2) (Ohto et al., 2009) LEAFY COTYLEDON 1 (LEC1) and LEAFY COTYLEDON 2 (LEC2) (Santos Mendoza et al., 2005). To explore the possibility that the seed phenotypes observed in upl3 mutants could be explained by altered expression of such genes, we carried out a qPCR time course on developing seed taken from WT and mutant upl3 plants from 0-15 DPA. Although no difference in the expression of TTG1 (FIG. 6*a*) and AP2 (FIG. 6*b*) was seen, an increase in LEC1 expression was observed in mutant seed at 10 and 15DPA (FIG. 6*c*). LEC1 is known to positively affect the expression of genes required for the accumulation of seed reserves, including SEED STORAGE ALBUMIN 3, AT2S3 (AT4G27160), known for its role in seed protein accumulation and members of the Oleosin family, such as AT3G01570, involved in lipid storage (Santos Mendoza et al., 2005). LEC1 is known to be positively regulated by a closely related transcription factor, LEAFY COTYLEDON 2 (LEC2) (Santos Mendoza et al., 2005). The role of HECT E3 ligases is to transfer ubiquitin to target proteins, which may then be targeted for proteosomal degradation (Downes et al., 2003). Given this, we hypothesised that UPL3 might target LEC2 at the protein level-potentially mediating its proteosomal degradation. This would explain the altered expression levels of LEC1 observed in mutant seeds. Based on this hypothesis we assessed the expression of additional known LEC2 targets, WRINKLED SEED 1 (WRI1) (FIG. 6*d*) and MYB118 (FIG. 6*e*) in both WT and mutant seeds. For both of these transcription factors we found elevated expression at 10DPA in mutant seeds relative to WT—a result concordant with our hypothesis that LEC2 protein levels may be altered in upl3 mutant seeds. Interestingly, MYB118 is known to have a role in negatively regulating seed glucosinolate levels in *Arabidopsis*. This relationship between UPL3 and MYB118 expression may explain the variation in seed glucosinolate levels seen in *Brassica napus* accessions showing high differential expression of C_EX097784.

Promoter Transactivation Assay in Protoplast Shows that UPL3 can Disrupt LEC2-Mediated Upregulation of Downstream Seed Lipid and Protein Targets.

LEC2 is known to be a master regulator of seed protein and lipid accumulation. Previous studies have shown that LEC2 positively regulates the expression of LEC1.

Figure 7:
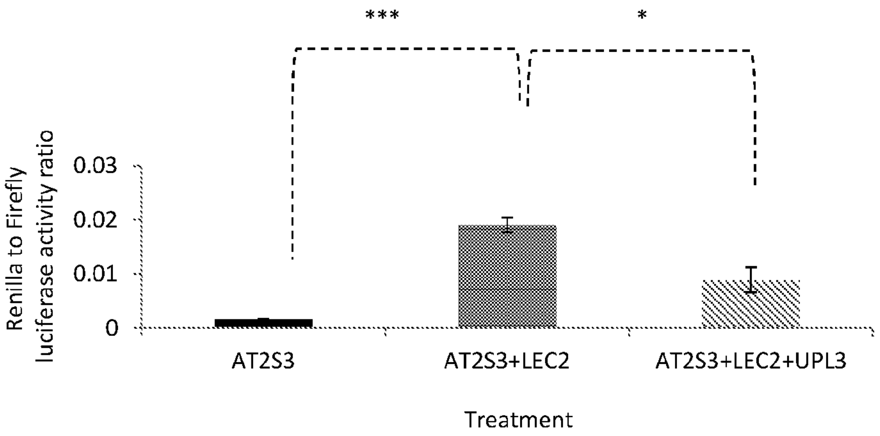
FIG. 7 is a promoter transactivation assay in *Arabidopsis* protoplast and shows that UPL3 can disrupt the LEC2-mediated activation of AT2S3 promoter activity. In the presence of LEC2, AT2S3 promoter activity (measured as a ratio of luciferase to *Renilla* output) is significantly increased ($P<0.001$). When co-transfected with 35s::UPL3, enhancement of AT2S3 promoter activity by LEC2 is significantly reduced ($P<0.05$).

Following this, both LEC1 and LEC2 work to bind the promoters, and activate the expression, of downstream seed protein and lipid biosynthestic genes, such as AT2S3 (AT4G27160) and the Oleosin gene, S3 (At3g01570)[7]. Based on qPCR results in upl3 mutants and WT developing seeds, we hypothesised that UPL3 may have a role in disrupting LEC2-mediated gene regulation. If this were the case, we would expect that, in response to an increase in UPL3 expression that the expression of LEC2 targets, such as S3 and AT2S3 would be reduced. To explore this possibility further we utilised a promoter transactivation assay in mesophyll protoplast taken from upl3 mutant leaves. This analysis allows for direct quantification of the effect of various treatments on the activity of promoters of interest, in this case, the activity of LEC1, AT2S3 and S3 promoters. Firstly, we assessed the baseline promoter activity of these genes by fusing them to Firefly luciferase CDS and measuring luciferase activity relative to the activity of the co-transfected construct (serving as a transfection rate control) carrying *Renilla* luciferase driven by 35S promoter (the output being a ratio of Firefly luciferase to *Renilla* luciferase activity). Secondly, we assess what happens to this baseline promoter activity when a 35s::LEC2 construct is co-transfected. The final treatment assesses the effect of 35s::UPL3 and 35s::LEC2 on promoter activity when co-transfected. An example of the results obtained from this assay can be seen in FIG. 7. Concordant with previous studies, we show that LEC2 is able to promote the promoter activity of AT2S3. Furthermore we show that in the presence of UPL3, this promoter activation is reduced. This supports the hypothesis that UPL3 is able to disrupt LEC2-mediated upregulation of genes involved in the seed filling process.

In the Presence of UPL3, LEC2 Protein Stability is Reduced

Figure 8:
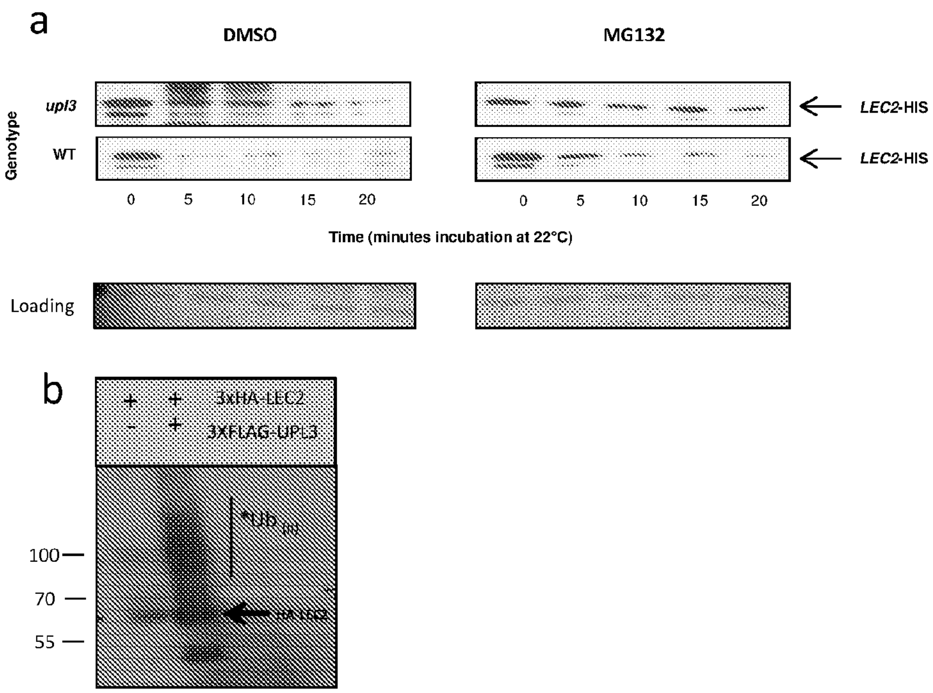
FIG. 8 shows that UPL3 reduced the stability of LEC2 in a cell-free system and increased LEC2 ubiquitylation. Incubation of expressed HA-LEC2 protein in total protein extracts taken from WT and upl3 mutant silliques shows that in the presence of UPL3, LEC2 stability is decreased. LEC2 stability can be enhanced with the addition of MG132 to the protein extracts. (a). HA-LEC2 protein was expressed in *Nicotinia Benthamiana* both alone and co-expressed with 3×FLAG-U-PL3. Protein extracts were immunoprecipitated and immunoblotted with HA antibody. In the presence of UPL3, 3×HA-L-EC2 displays an increased ubiquitylation pattern (b).
Figure 9:
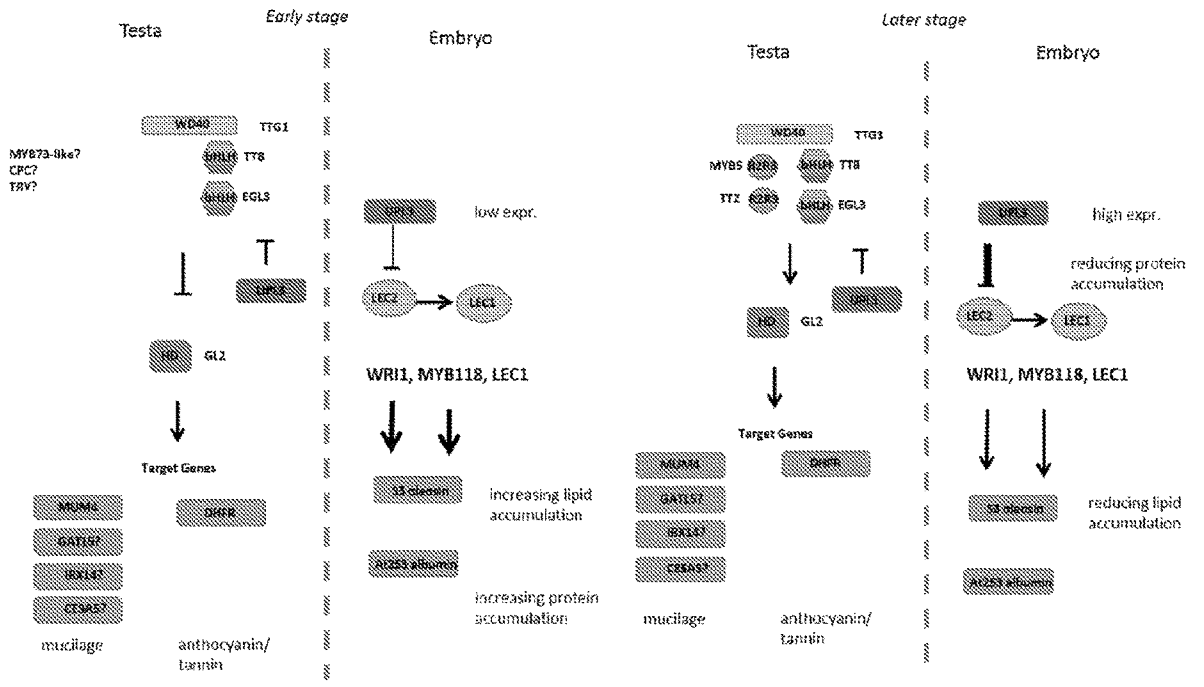
FIG. 9 shows a model describing the roles of UPL3 in regulating gene expression in both the testa and the embryo throughout seed development.

The results of the qPCR and promoter transactivation assays indicate that UPL3 is able to disrupt the protein function of LEC2. Given the known role of Hect E3 ligases in mediating proteosomal degradation through ubiquitination, we wanted to test the stability of LEC2 in the absence and presence of UPL3 using a cell-free degradation assay. Through qPCR, we showed that LEC2 targets were upregulated from 10DPA in mutant siliques. Given this we used total protein extracts taken from 10DPA siliques of WT and upl3 plants in our cell-free system. Following total protein extraction, HIS-at.LEC2 (expressed in *E. coli* and purified using HIS-beads) was incubated at 22° C. for 0-20 minutes within protein extracts taken from WT or mutant siliques. Any degradation taking place during this time was then assessed following western blot analysis. Using this system, we have been able to show that in the presence of UPL3, LEC2 stability is significantly reduced. As FIG. 8*a* shows, in the absence of MG132 (our chosen proteosomal inhibitor), when incubated in total protein extracts taken form WT plants, HIS-LEC2 is barely detectable at 5 minutes. When incubated in mutant protein extract however, a clear signal remains at up to 15 minutes. In addition, we can see that in both cases, when MG132 is added, HIS-LEC2 degradation can be reduced, suggesting that the proteasome is playing a role in this process.

We also show in *Nicotinia Benthamiana* that when co-expressed with 3×FLAG-UPL3, 3×HA-LEC2 ubiquitylation appears enhanced (FIG. 8*b*). Taken together, these data suggest that LEC2 is targeted for degradation by the proteasome and that this degradation takes place following ubiquitylation of LEC2 by UPL3.

Methods

1. Plant Growth and Phenotypic Analyses 69 lines of OREGIN *B. napus* diversity fixed foundation set (DFFS) representing the winter, spring and Chinese oilseed rape crop types were transplanted in a randomised, triplicated experimental design in a Keder plastic soil house in April 2014. The Keder soil house has no lighting or temperature control capabilities but allowed the plants to be grown in near-field conditions with irrigation, increased controls on disease and reduced pest pressures. Pre-transplantation, plants received four weeks pre-growth under standard glasshouse conditions (18/15 C day/night, 16 hours light) before six weeks vernalisation (4 C, 8 hours light).

20 pods per plant were collected and digitally imaged for phenotypic analysis of yield components. Pod length (Podl) was measured using ImageJ (ref). Pods were weighed (PW) before threshing to remove seed and seed number, average seed length (SL), width (SW), area (SA), single seed weight (SSW) and thousand grain weight (TGW) were measured for each sample using Marvin (ref). Number of seed per pod (SPP), seed weight per pod (SWPP) and seed density (SDen) were calculated from this data. Lipid and protein data was analysed from 15 g of whole unbagged plant samples Data was visualised to explore distributions and within line variation before analysis via unbalanced ANOVA (REML) using Genstat (ref) to determine line, block and line x block interactions. Where appropriate mean values were calculated for analysis via associative transcriptomics.

2. Population Structure

All lines used within the study had previously been transcriptome sequenced via Illumina mRNAseq) by Harper et. al 2012, identifying ~255,000 SNPs across the full OREGIN diversity panel for associative transcriptomics. As this study used a different subset of lines to the initial publication it was necessary to recalculate the population structure Q matrix for association mapping with TASSEL (ref). As this requires the use of unlinked markers, one SNP per 500 kb interval along the chromosomes, excluding regions less than 1000 kb from centromeres as defined by Mason et al. and Cheng et al. 2013, was selected for Bayesian population structure analysis via STRUCTURE 2.3.3 (ref). The selected SNP had to show at least 5% frequency for the second most abundant allele. The optimum number of K populations was selected as described by Harper et. al 2012.

3. Associative Transcriptomics

SNP data, STRUCTURE Q matrix and phenotypic data for the 89 accessions was entered into the program TASSEL V4.0 (ref). Following the removal of minor allele (frequency $<0.05$) ~144,000 SNPs were used to calculate a kinship (K) matrix to estimate the pairwise relatedness between individuals. Data sets were entered into both Generalised and Mixed Linear Model (GLM and MLM) respectively. Goodness of fit of the model was determined by a QQ plot of the observed vs. the expected −log 10P values.

4. Assessment of Promoter Variation and Plasmid Construction

Genome specific primers were designed based on variation observed between *Brassica rapa* and *Brassica oleracea*. The chosen promoter sequences comprise of 2 Kb of DNA sequence upstream of the ATG start codon. PCR was carried out using Phusion® HF Buffer Pack, Thermofisher Scientific according to manufacturer's guidelines. The primers use for amplification of the C03 genome promoter variants were (STU1 and XHO1 sites were added to the Forward and reverse primers respectively, with "TAT" overhang to improve enzyme binding): Forward: 5'-TATaggcctGGACGTTTGGGTCATCGCTC-3'; (SEQ ID NO: 67) Reverse: 5'-TATctcgagACAAAGGAAGAAACCCCTCCAC-3'.PCR (SEQ ID NO: 68) products were cleaned using WIZARD SV Gel and PCR clean-Up system (Promega) and sent for Capillary sequencing by GATC Biotech (Germany). Promoter variants were cloned using the pENTR Directional TOPO cloning kit (Invitogen). Following the assessment of sequence, PCR product was digested using STU1 and XHO1 (NEB) according to manufacturer's instructions. Digested PCR was cleaned a second time using WIZARD SV Gel and PCR clean-up system.

*Arabidopsis* UPL3 CDS was amplified form cDNA generated from *Arabidopsis Columbia leaf material using Phusion® HF. The following primers were used with a ASCI and XHO restriction sites added to the forward primer sequence. A CACC was added also, to allow for consequent TOPO cloning.* *Forward* 5'-CACCAtatGGCGCGCCtatCTCGAGATGGAAACTCGGAGCCGC-3' (SEQ ID NO: 69); Reverse: 5'-TATggcgcgccGGCAGAGATTCTTCAAATCAGAA-3' (SEQ ID NO: 70). PCR product was cleaned using WIZARD SV Gel and PCR clean-Up system (Promega) and 4 ul of the PCR clean-up product was incubated with 1 ul pENTR topo vector+salt solution overnight at 25 degrees. The following day, 1 ul of this reaction was added to 25 ul TOP10 competent cells and transformation carried out according to manufacturer's guidelines. Colony PCR was carried out using M13 sequencing primers and positive cloned confirmed by sequencing with GATC Biotech. Following identification of a positive TOPO clone carrying *Arabidopsis* UPL3 CDS with no mutations and LR reaction was prepared according to manufacturer's instruction using Gateway® LR Clonase II Enzyme mix (Invitrogen). The GATEWAY destination vector used was Pearly 103. The LR reaction was incubated at 25 degrees Celsius for 15 hours. The following day this reaction was stopped and 2 ul of the clonase mix used to transform TOP10 competent cells. Positive clones were identified by sequencing and a single clone selected for digestion with STU1 and XHO1. The digested plasmid was cleaned using the WIZARD SV Gel and PCR clean-Up system (Promega). The cleaned promoter variant PCRs and digested Pearly103 plasmid were incubated together with T4 DNA Ligase (Promega) according to manufacturer's instructions.

The resulting construct was transformed into *agrobacterium* (GV3101) using electroporation and the plasmid transferred to *Arabidopsis* knockout mutants using the floral dip method described by Clough et al (1998)[2]. Transgenic plants were identified using BASTA selection and the transgene copy number determined by iDNA genetics, UK. After two generations, stable transgenic lines carrying a single homozygous insertion of the transgene were identified and used for consequent phenotyping experiments.

5. Genotyping T-DNA Mutants

Salk lin Salk_015334 was ordered from The Nottingham *Arabidopsis* Stock Centre (NASC) at: arabidopsis.info/BasicForm. We thank the Salk Institute Genomic Analysis Laboratory for providing the sequence-indexed *Arabidopsis* TDNA insertion mutants. Primers were designed using the primer design tool found at: signal.salk.edu/tdnaprimers.2.html. Using this tool, the following primers were designed for identification of a WT UPL3 transcript: RP: 5'-TAGGGACTTGCATGGACGTAC-3' (SEQ ID NO: 71) and LP: 5'-GATATGTCAGCTGTTGAGGGC-3' (SEQ ID NO: 72). For identification of the T-DNA insertion sequence, the above RP primer was used with LB1.3: 5'ATTTTGCCGATTTCGGAAC-3' (SEQ ID NO: 73)

To extract DNA, leaf material was ground to a fine powder with a pestle and 200 ul of the following Edwards buffer added: (200 mM Tris-HCl (pH 7.5), 250 mM NaCl, 25 mM EDTA, and 0.5% SDS) TE Buffer (10 mM Tris-HCl (pH 8) and 1 mM EDTA). Buffer was dilute 10 fold prior to use. Samples were then vortexed briefly and centrifuges at 13,000 rpm for 3 minutes. The resulting supernatant was added to a fresh centrifuge tube and 150 ul 100% isopropanol added. Samples were inverted several times to ensure mixing and then centrifuged at 13,000 rpm for 7 minutes. Liquid was discarded and the remaining pellet washed using 70% ethanol. The pellet was air-dried for 20 minutes and the resuspended in distilled water.

PCR genotyping was carried out using Takara ExTaq (Clontech) and carried out according to manufacturer's instructions.

6. cDNA Synthesis and Quantitative PCR

RNA was extracted from *Arabidopsis* silliques harvested at 0, 5, 10 and 15 Days after anthesis (DAF) using the Sigma Spectrum Plant Total RNA kit (Sigma). 1 ug of total RNA was processed using GoScript Reverse Transcription system for cDNA synthesis. The resulting cDNA was diluted 10× for use in qPCR. Quantification of gene expression was achieved using SYBR green mastermix (Applied Biosystems) according to manufacturer's instructions. All qPCR assays were carried out using EIF4a as a control gene and using a LightCycler® 480 qPCR machine. The following primers were used:

| Gene | Forward primer (5'-3') | Reverse primer (5'-3') |
|---|---|---|
| EIF4a | CTGGAGGTTTTGAGGCTGGTA (SEQ ID NO: 74) | CCAAGGGTGAAAGCAAGAAGA (SEQ ID NO: 75) |
| LEC2 | CGAGAACACAGGAGAATTTGTG (SEQ ID NO: 76) | TCGACTCATTTTCTCTTCCTTCA (SEQ ID NO: 77) |
| TTG1 | CATCCTCCGGTCCACAGAATC (SEQ ID NO: 78) | TTTCGGCTCTACATCGTTCC (SEQ ID NO: 79) |
| AP2 | AGGAACTCAATGCCGAGTCATC (SEQ ID NO: 80) | GTTCATCCTGAGCCGCATATC (SEQ ID NO: 81) |
| LEC1 | GGCGCCGGTGACAAGA (SEQ ID NO: 82) | GCCACACATGGTGGTTGCT (SEQ ID NO: 83) |
| WRI1 | CACAAAGGAATTGGAAGAAATGC (SEQ ID NO: 84) | TCCCATCTTCCGTTGTGGTG (SEQ ID NO: 85) |
| MYB118 | GTCTCAGATTGCTAAGATGCTTCAA (SEQ ID NO: 86) | CATCCATCTTTCTTGATATCGGG(SEQ ID NO: 87) |

7. Expression of LEC2 and UPL3 in *E. coli* and His-Tag Purification

*Arabidopsis* LEC2 CDS was amplified from cDNA using primers designed to incorporate restriction sites. Following cleaning with WIZARD SV Gel and PCR clean-up system, PCR products were digested with the appropriate enzymes (NEB) and transferred to digested pET-24a vector backbone. Resulting plasmid was transformed into BL21 *E. coli* cells and grown on LB plates. Following growth overnight, a single colony was used to inoculate 10 ml liquid LB with the appropriate antibiotic, Kanamycin, and incubates at 37° C. overnight.

The following day, 4 ml of the resulting culture was used to inoculate 400 ml LB with kanamycin and incubated for 2 hours at 37° C. Following incubation, IPTG was added to final concentration of 100 Mm and the culture incubated at 28° C. for 3 hours to induce protein expression.

Following incubation with IPTG, cultures were transferred to 20 ml Falcon tubes and centrifuged at 3500 rpm for 10 minutes at 4° C. The resulting pellet was resuspended in 5 ml of the following buffer: 1M HEPES (PH 7.5); 3M NaCl; 100% TritonX-100; 1% glycerol; cOmplete™ EDTA-FREE inhibitor cocktail table (Roche). The resuspended mixture was sonicated 4×10 seconds with 20 second intervals. The sonicate was then centrifuged at 12,000 g for 20 minutes at 4° C.

Protein purification was carried out using Dynabeads® His-tag magnetic beads (Novex). Prior to use, beads were washed 3 times in the following wash buffer: 1M HEPES (PH7.5); 3M NaCl; 1% glycerol. Sonicate was then added to washed beads and were incubated at 4° C. rotating for 30 minutes. Beads were then washed 3 times using the above resuspension buffer and 3 times using the above wash buffer. His-tagged protein was eluted from the magnetic beads using 100 ul of the following elution buffer; 300 Mm Imidazole; 50 mM HEPES; 150 Mm NaCl; 10 Mm MgCl2 10% glycerol. Purified protein was quantified using Bradford reagent (Bio-Rad) and stored at −70° C. in 15 ul aliquots.

8. Total Protein Extraction and Cell Free Degradation Assay

Silliques were harvested from both WT and upl3 knock out mutant plants at 10-15 DPA. ~100 mg was used for total protein extraction. Following grinding to a fine powder, 200 ul of the following extraction buffer was added: 25 Mm Tris-HCL (PH 7.5); 10 Mm NaCl; 10 Mm MgCl2; 4 Mm AEBSF. Samples were vortexed briefly to ensure homogenisation and then centrifuged at 17,000 g for 10 minutes at 4° C. The resulting supernatant was transferred to a fresh centrifuge tube and the centrifugation step repeated. The supernatant was transferred to a fresh tube and total protein quantification carried out using Bradford reagent (Bio-Rad) according to manufacturer's instructions.

Two reactions were set up for the cell-free degradation assay—one containing MG132—our chosen proteasomeal inhibitor and the other containing DMSO. Expressed HIS-LEC2 was incubated within protein total extracts in the following 120 ul mixture: 40 Um MG132/DMSO; 20 ug total protein; 5 ug HIS-LEC2; 5 Mm DTT; 10 Mm ATP. This mixture was then aliquoted into 5 20 ul reactions (for 0, 5 10, 15 and 20 minute time points). 0 minute sample was added directly to 10 ul 4×SDS Laemmli sample buffer (Bio-Rad) and heated at 96° C. for 5 minutes. The remaining samples were incubated at 22° C. for the appropriate time before also being added to SDS Laemmli buffer and denatured at 96° C.

Following the time-course, 15 ul of the protein samples were ran on a RunBlue SDS protein gel (4-20%)(Expedon LTD) (20 minutes at 80V and 1 hour at 160V). Following transfer to membrane overnight, proteins were probed using anti-HIS antibody and visualised following application of SuperSignal West Femto Chemiluminescent substrate (LIFE SCIENCE IMAGING LTD Thermofisher scientific).

9. Protoplast Isolation and Transient Expression Analysis

The AT2S3 promoter was cloned into pENTR topo vector following amplification with the following primers: Forward: 5'-caccTAGATTCCAAACAAAAACCCTCG-3' (SEQ ID NO: 88) and reverse: 5'-GTTTTGCTATTTGTGTATGTTTTCTTG-3' (SEQ ID NO: 89). An LR reaction was then performed to transfer the promoter of interest to a GATEWAY Firefly Luciferase reporter construct. LEC2 and UPL3 CDS were cloned into pENTR topo vector and then transferred by LR into PB7HA and PW1266 35S constructs respectively. A 35S::*Renilla*_Luciferase construct was prepared as an internal reference gene (serving as transfection control). All plasmids used were prepared using Qiaprep Maxi kit (Qiagen) according to manufacturer's instructions.

Protoplast were isolated from the mesophyll cells of expanding *Arabidopsis* upl3 knock-out mutant leaves. Using a razor blade, leaves were slices perpendicular to the midvein and placed upper-leaf faced down in the following enzyme solution: 20 Mm MES (PH 5.7); 20 Mm KCL; 0.4M mannitol; 1% Cellulose RIO; 0.4% Maceroenzyme; 10 Mm CaCl2); 0.1% BSA. Leaf material was incubated within the enzyme solution at 40 rpm for 4-6 hours. Protoplast were then filtered through a 70 um sieve and transferred to 2 ml centrifuge tubes. Samples were centrifuged at 200 rcf for 3 minutes. The resulting pellet was then resuspended in 1 ml cold W5 solution: 2 Mm mes (ph 5.7); 154 mm NaCl; 125 mm CaCl2); 5 mm KCl. Resuspended protoplast were the incubated on ice for 30 minutes. Samples were centrifuged again at 200 rcf for 3 minutes and the resulting pellet resuspended in MMg solution: 4 mm MES (PH 5.7); 0.4M mannitol; 15 Mm MgCl2. 5 ug of each plasmid was used per treatment with 35S::*Renilla* included in all treatment. To the plasmid mix, 100 ul prepared protoplast was added with a cut pipette tip. 100 ul of the following PEG solution was then added slowly: 2 g PEG; 0.5 ml 1M CaCl2; 2 ml 0.5M mannitol. Samples were mixed gently by inverting and the incubated at room temperature for 15 minutes. Samples were then diluted with 250 ul cold W5 solution and centrifuged for 3 minutes at 200 rcf. Following removal of liquid, the remaining pellet was re-suspended in 150 ul W5 solution and transferred to a 48 well microtitre plate previously coated with 1% BSA. The plate was wrapped in tissue and kept at room temperature overnight. The following day, samples were transferred to 2 ml tubes and centrifuges at 200 rcf for 3 minutes. These samples were used immediately in the transient expression assay.

The transient expression luciferase assay was carried out using the Dual-Luciferase Reporter Assay System (Promega) according to manufacturer's instructions. Luciferase quantification was carried out using GloMax® 20/20 Single tube luminometer—with the dual promega luciferase assay program selected.

10. Seed Coat Ruthenium Red Staining Assay

To assess changes in seed mucilage extrusion we used the methods described by McFarlane et al (2014).

11. Ubiquitination Assay

UPL3 CDS was cloned into PW1266 GATEWAY vector (3×FLAG) and LEC2 CDS was cloned into PB7HA (3×HA). The resulting plasmid was used to transform *agrobacterium* and 10 ml cultures were grown (with Rifampicin and Spectinomycin) at 28° C. overnight. Following overnight incubation, the OD of the cultures was determined using a spectrometer and the following calculation made to determine an appropriate amount of culture to use in consequent experiments: ((1/OD)×10,000). The determined volume was centrifuged at 3000 rcf for 5 minutes. The resulting pellet was re-suspended in the following solution: 0.1M MES PH6.3; 150 Mm MgCl2; +Acetosyringone. The re-suspended plasmids were transfected either separately or together and the transfected leaves labelled with the relevant information. After 72 hours, leaf material was harvested and stored at −70° C. prior to further processing.

1 g leaf material was ground to a fine powder and 2 ml of the following buffer added: 50 um MG132; 1M NaCl; 1% glycerol; 1M tris-HCL; 0.5M EDTA; 0.05% pvpp; 0.1 ml 100× complete cocktail tablet dissolved in water. Samples were vortexed to ensure homogenisation and then centrifuged at max speed for 10 minutes at 4° C. Supernatant was transferred to a fresh tube and the centrifugation repeated. The supernatant was again added to a fresh tube and 20% NP40 added to achieve a final concentration of 0.15%.

All samples were purified using HA magnetic beads (Pierce) and ubiquitination levels determined following immunoblotting with anti-ubiquitin antibody.

12. Seed Protein Quantification

Seed total protein was quantified using 6 batches of 30 seeds taken from WT and upl3 mutant plants using the DC Protein Assay (Bio-Rad). Quantification of protein content was measured relative to a BSA protein serial dilution curve and according to manufacturer's instructions.

13. Seed Fatty Acid Analysis

Seed fatty acid content was analysed according to the methods described by Li et al (2006).

Example 2: Method of Generating UPL3 Genes with Reduced Expression or Function, or Loss-of-Function Using CRISPR/Cas9

In a further aspect of the invention, there is provided a method for specifically altering the expression levels and patterns of UPL3 genes and/or reducing or abolishing the activities of the UPL3 protein, in any plant species containing a ULP3 gene characterised by HECT and ARM domains. The method comprises using the DNA sequence of genes encoding candidate UPL3-like genes from plants, recognisable by their potential to encode conserved ARM- and HECT-protein domains as described herein (examples of *Brassica napus* and other homologues encoding UPL3 are shown in Table 1) using methods that are well tested and described for plants (Gil-Humanes et al., 2016; Ma et al., 2015; Zhang et al., 2016). According to these well-established protocols, a guide RNA based on direct sequence homology to a region of the UPL3 gene (promoter or coding region for example) targeted for change (e.g. targeted deletion of a functional region, insertion of a stop codon, or any other change in the UPL3 gene and regulatory region designed to influence the expression of the gene) is synthesised or encoded in a vector for expression in plants, preferably together with a gene encoding Cas9 protein (although Cas9 can also be encoded in a separate vector).

Preferably the vectors also comprise a regulatory sequence, which drives expression of the guide RNA and/or Cas 9 sequence. In grasses, the promoter can be, for example, an RNA polymerase type III promoter, such as U3 or U6 snRNA gene from the targeted host species, for example wheat or rice. (Liang et al Sci. Rep. 6:21451 (2016). The Cas9 coding region, suitably optimised for expression in plants, including codon optimisation and with added nuclear targeting sequences, can be expressed from the constitutive 35S promoter, or a ubiquitin gene promoter (Belhaj et al Plant Methods 9:39 (2013). In dicot species, the *Arabidopsis* U6 snRNA gene promoter can be used to express guide RNAs ((Belhaj et al Plant Methods 9:39 (2013). Constructs and vectors that are commonly used for stable or transient gene expression can also be used (Zhang et al Nature Communications 7:12617 (2016), including viral systems (Gil-Humanes et al Plant Journal).

The design of guide RNAs is well known to those skilled in the art. Support systems (e.g. blog.addgene.org/how-to-design-your-grna-for-crispr-genome-editing) are also available for guide RNA design, which is specific for each gene sequence and for the desired changes to be made. For example, if one member of a family is to be targeted, then a gene specific sequence needs to be targeted that is predicted to have the desired effect, such as reducing gene function. If all members of a gene family are to be targeted, for example if they have redundant functions such as in polyploid wheat, then a conserved sequence specific to those genes can be targeted to make the desired changes.

Given the sequence of a target locus, such as the sequence of UPL3 described herein for *B. napus* or from different plant species, also described herein and in Table 1, it is possible to design a guide RNA sequence (commonly recognising 20 nt of target sequence) to which a Protospacer Adjacent Motif (PAM) is added to aid interaction with an SSN such as Cas9. In the case of UPL3, sequences in any part of the coding region can be targeted to introduce changes that can include frameshift mutations that disrupt protein sequences. This will abolish UPL3 gene function, leading to larger seeds with increased lipid content. It is also possible to achieve these phenotypes by reducing UPL3 gene expression. For this, guide RNA sequences can be designed to any part of the UPL3 gene that is transcribed, or to 5' regulatory sequences. For example, changes in intronic, 3' UTR and 5'UTR sequences can destabilise mRNA, leading to reduced UPL3 expression, and larger seeds containing more lipids. This effect can be measured by screening plants for reduced UPL3 expression. Furthermore, changes to promoter regions can be made that could reduce transcription. In general, it is difficult to predict the effects of deletions on promoter functions, but it is well known that sequences adjacent to or close to the first 100-200 bp of the promoter (measured from the Transcriptional Start Site) have a major effect on promoter activity. These regions could be targeted for deletions or insertions that can be predicted to reduce gene expression.

These two genes (encoding the guide RNA and Cas9) can then be introduced into e.g. soybean or any other plant, such as *B. rapa, B. oleracea*, rice, cotton, wheat, barley and maize using *Agrobacterium*-mediated transformation by anyone skilled in the art. Stable transgenic plants are regenerated using standard procedures. Several transgenic plants can be screened, using standard PCR methods and DNA sequencing, to detect predicted changes in the UPL3 promoter region and/or coding region. Correct gene editing events are frequent and accurate. Plant containing the desired changes in the UPL3 promoter and coding region are propagated and tested for the effects on the stability of LEC2 protein and seed protein and lipid levels. In particular, plants may be regenerated and grown to maturity with kernels being analysed for an increase in protein and/or oil content. In an alternative approach, genes expressing guide RNA and Cas9 can be transiently delivered into plant cells by various methods, such as particle bombardment or transfection of protoplasts. Multiple plants can be regenerated using standard tissue culture methods by anyone skilled in the art, and these can be screened for desired changes using the same PCR-based analyses and sequencing as would be used for stable transgenic plants. According to several published reports, between 2%-5% of regenerated plants harbour the expected changes in DNA sequence. This method does not maintain the transgenes encoding Cas9 or the guide RNA, having the advantage of being non-transgenic.

Example 3: Selecting for Low BnC03UPL3 Expression for Marker Assisted Breeding of High Yielding Genotypes Using GWAS, we identified an associating locus for weight of seed per pod across *Brassica napus* accessions. The most highly associating marker at the associating locus was JCVI_5587:125. Variation at this locus or a homologous location in any other plant can be selected for to achieve enhanced yield. The hemi-SNP segregating across the GWAS panel used showed that accessions displaying low weight of seed per pod inherit "Y" (corresponding to a C+T genotype in the polyploid genome) and those accessions displaying high weight of seed per pod inheriting a "T" allele in both genomes.

The following primers have been designed to target the JCVI_5587:125 locus:

```
                                         (SEQ ID NO: 65)
Forward primer: 5'-TATTTCCGCATGTTGCTAAACC-3'
                                         (SEQ ID NO: 66)
Reverse primer: 5'-TGTTGATCACACACAACTAATCTCG-3'
```

*primer regions are dashed underlined.

target SNP highlighted in bold** and underlined

Typical Sequence of a High Yielding Accession:

```
                                                          (SEQ ID NO: 61)
TATTTCCGCATGTTGCTAAACCGGGAGAATATATCAAATGCAACTGTCATGATCCA

ACCATCGCTGACATCATATACATTCAGTTCACCACCTCAGCCAGCTTTGCGGCTTC

TATTGCAGCCGACAGAATTCTTCTGTTAGATGCATATTTCAGTGTTGTTGTCTTCCA

TGGAATGACAATAGCACAATGGCGAAACATGGGTTATCATCATCAGGCTGAACAT

GAGGCATTTGATAGTCCGGGAGCGTTTCCCTGTCCCGAGATTAGTTGTGTGTGAT

CAACA
```

Typical Sequence of a Low Yielding Accession:

```
                                                          (SEQ ID NO: 62)
TATTTCCGCATGTTGCTAAACCGGGAGAATATATCAAATGCAACTGTCATGATTCA

ACCATCGCTGACATCATATACATTCAGTTCACCACCTCAGCCAGCTTTGCTGGACG

TGGCTTCCATTGCAGCCGACAGAATTCTC/TCTGTTAGATGCATATTTCAGTGTTGT

TGTCTTCCATGGAATGACAATWGCACAATGGCGAAACATGGGTTATCATCATCAG

GCTGAACATGAGGCATTTGCTCAGCTATTGCAAGCTCCTCAAGAAGATTCCCAGA

TGATAGTCCGGGAGCGTTTCCCWGTCCCGAGATTAGTTGTGTGTGATCAACA
```

In addition to providing information regarding a SNP marker that may be utilised in Marker Assisted Selection of genotypes with enhanced yield, Associative Transcriptomics also allowed us to identify differential expression of UPL3 in *B. napus* or any other plant across genotypes. This differential expression correlates with variation in weight of seed per pod. We have developed a q-RT-PCR assay that is able to screen for UPL3 expression in *Brassica napus* and other plants, such as *B. rapa, B. oleracea*, rice, cotton, wheat, barley and maize. Identifying genotypes with low expression levels would be an approach that can be exploited to maximise final yield in this species. The following primers have been tested and shown to efficiently and specifically target the locus of interest:

```
Forward primer:
                                      (SEQ ID NO: 63)
5'-GTAGCTCTCATCAACCTCAAATGC-3'

Reverse primer:
                                      (SEQ ID NO: 64)
5'-AGGGAGCTTAAGGTAGTTGGGG-3'
```

REFERENCES

Alahakoon, U. I., Taheri, A., Nayidu, N. K., Epp, D., Yu, M., Parkin, I., Hegedus, D., Bonham-Smith, P., and Gruber, M. Y. (2016). Hairy Canola (*Brasssica napus*) re-visited: Down-regulating TTG1 in an AtGL3-enhanced hairy leaf background improves growth, leaf trichome coverage, and metabolite gene expression diversity. BMC Plant Biology 1-25.

Chen, M., Zhang, B., Li, C., Kulaveerasingam, H., Chew, F. T., and Yu, H. (2015). TRANSPARENT TESTA GLABRA1Regulates the Accumulation of Seed Storage Reserves in *Arabidopsis*. Plant Physiology 169, 391-402.

Downes, B. P., Stupar, R. M., Gingerich, D. J., and Vierstra, R. D. (2003). The HECT ubiquitin-protein ligase (UPL) family in *Arabidopsis*: UPL3 has a specific role in trichome development. Plant J. 35, 729-742.

Gutierrez, L., Van Wuytswinkel, O., Castelain, M., and Bellini, C. (2007). Combined networks regulating seed maturation. Trends in Plant Science 12, 294-300.

Harper, A. L., Trick, M., Higgins, J., Fraser, F., Clissold, L., Wells, R., Hattori, C., Werner, P., and Bancroft, I. (2012). Associative transcriptomics of traits in the polyploid crop species *Brassica napus*. Nat Biotechnol 30, 798-802.

Komander, D., and Rape, M. (2012). The Ubiquitin Code. Annu. Rev. Biochem. 81, 203-229.

Le, B. H., Cheng, C., Bui, A. Q., Wagmaister, J. A., Henry, K. F., Pelletier, J., Kwong, L., Belmonte, M., Kirkbride, R., Horvath, S., et al. (2010). Global analysis of gene activity during *Arabidopsis* seed development and identification of seed-specific transcription factors. Proc. Natl. Acad. Sci. U.S.a. 107, 8063-8070.

Mithen, R. (1992). Leaf glucosinolate profiles and their relationship to pest and disease resistance in oilseed rape. Euphytica 63: 71-83.

Ohto, M.-A., Floyd, S. K., Fischer, R. L., Goldberg, R. B., and Harada, J. J. (2009). Effects of APETALA2 on embryo, endosperm, and seed coat development determine seed size in *Arabidopsis*. Sex Plant Reprod 22, 277-289.

Patra, B., Pattanaik, S., and Yuan, L. (2013). Ubiquitin protein ligase 3 mediates the proteasomal degradation of GLABROUS 3 and ENHANCER OF GLABROUS 3, regulators of trichome development and flavonoid biosynthesis in *Arabidopsis*. Plant J. 74, 435-447.

Peng, F. Y., and Weselake, R. J. (2011). Gene coexpression clusters and putative regulatory elements underlying seed storage reserve accumulation in *Arabidopsis. BMC Genomics* 12, 286.

Sadras V O: Evolutionary aspects of the trade-off between seed size and number in crops. *Field Crops Research* 2007, 100(2-3):125-138.

Clough S J, Bent A F: Floral dip: a simplified method for *Agrobacterium*-mediated transformation of *Arabidopsis thaliana. The Plant Journal* 1998, 16(6):735-743.

Li Y, Beisson F, Pollard M, Ohlrogge J: Oil content of *Arabidopsis* seeds: The influence of seed anatomy, light and plant-to-plant variation. *Phytochemistry* 2006, 67(9): 904-915.

Santos Mendoza, M., Dubreucq, B., Miguel, M., Caboche, M., and Lepiniec, L. (2005). LEAFY COTYLEDON 2 activation is sufficient to trigger the accumulation of oil and seed specific mRNAs in *Arabidopsis* leaves. FEBS Letters 579, 4666-4670.

Shi, L., Katavic, V., Yu, Y., Kunst, L., and Haughn, G. (2011). *Arabidopsis* glabra2 mutant seeds deficient in mucilage biosynthesis produce more oil. The Plant Journal 69, 37-46.

Varshaysky, A. (2012). The Ubiquitin System, an Immense Realm. Annu. Rev. Biochem. 81, 167-176.

Comai L, Young K, Till B J, Reynolds S H, Greene E A, Codomo C A, Enns L C, Johnson J E, Burtner C, Odden A R, Henikoff S. Efficient discovery of DNA polymorphisms in natural populations by Ecotilling. Plant J. 2004; 37:778-786

Cermak, T. et al. Efficient design and assembly of custom TALEN and other TAL effector-based constructs for DNA targeting. Nucleic Acids Res. 39 (2011).

Clough S J, Bent A F: Floral dip: a simplified method forAgrobacterium-mediated transformation of *Arabidopsis thaliana. The Plant Journal* 1998, 16(6):735-743.

McFarlane, H. E., Gendre, D. and Western, T. L. (2014). Seed Coat Ruthenium Red Staining Assay. *Bio-protocol* 4(7): e1096. DOI: 10.21769/BioProtoc.1096; Full Text Dong, H., Dumenil, J., Lu, F.-H., Na, L., Vanhaeren, H., Naumann, C., Klecker, M., Prior, R., Smith, C., McKenzie, N., et al. (2016). Ubiquitylation activates a peptidase that promotes cleavage and destabilization of its activating E3 ligases and diverse growth regulatory proteins to limit cell proliferation in *Arabidopsis*. bioRxiv 090563.

Gil-Humanes, J., Wang, Y., Liang, Z., Shan, Q., Ozuna, C. V., Sanchez-Leon, S., Baltes, N.J., Starker, C., Barro, F., Gao, C., et al. (2016). High efficiency gene targeting in hexaploid wheat using DNA replicons and CRISPR/Cas9. The Plant Journal.

Ma, X., Zhang, Q., Zhu, Q., Liu, W., Chen, Y., Qiu, R., Wang, B., Yang, Z., Li, H., Lin, Y., et al. (2015). A Robust CRISPR/Cas9 System for Convenient, High-Efficiency Multiplex Genome Editing in Monocot and Dicot Plants. Molecular Plant 8, 1274-1284.

Zhang, Y., Liang, Z., Zong, Y., Wang, Y., Liu, J., Chen, K., Qiu, J.-L., and Gao, C. (2016). Efficient and transgene-free genome editing in wheat through transient expression of CRISPR/Cas9 DNA or RNA. Nature Communications 7, 12617.

SEQUENCE INFORMATION
UPL3 promoter sequences
SEQ ID NO: 1: *Brassica napus* UPL3 promoter sequence
>Coriander_BnC03_UPL3_promoter (High UPL3 expression genotype)

AGAGAGGCCTGGACGTTTGGGTCATCGCTCCCGGTCGGTTCCTACTTTTTCTGCA

CCACCGCCATTTGTTGATCCAGAAGTATTTACGGCTCAGTTGAAGGACAAAGATG

ATCGCATATCTTTGTTGGAGACCCAGAAGACGGCTCAACAGGCGGGCTATGAGG

CACAGAAGAGGCTGAACCAGCAAATGATGAAAAGGATGTATCCGAACGAGGTGTT

CCCGAACGTGCAAGACCCGTAGTTTTTTTTTTTTTTCAAAAACTCGGAATGTTTTAT

TTTTATTTGTACAACTTTGAATATTATTTAATATGTTTTCAATTTTAATTTTAATTTTAT

ATTTTCGAATTTAAATTTTAAATTTTTTATTTTTTTAAAAAAAAATATTTTTTTTTTGAA

ATTCCGAGGAAATGAACCCTCGGAAATTTCCGACGAACATTTCCTCAGAATAAGTC

GTCGGAATATACCGAGGGACTCCTTCCTCCTCGGAATTTTCCGAGGGCTCCGTTC

CTCGGAAATTCCCGATGAAAATTCCGAGGAACATTTCGTCGGAACTTCCGAGGAT

TGGACCATCGGAAAGTCCATCGAAATATTCTGAGGAAGTTCTCCCTTGGTATATTC

CGAGAACCTTTCCGACGAACTGGTGGTCCTCGGAGTTTCCTCGGAATTCCTTCGG

AAATTTCCGAGGAAAAATGAATTTCCGAGGAGTTATTTCCGAGGACTTGTTTCGTC

GGTATGTCGTCGGAATAACGTTATTCCGACGACGTACCGACGATTTTTTCCCTTTT

GGTATGTTCAAATTGGATTTATAAATGAATCGTAATTTCTGTTTTTCGGGTTAAATT

AATATGTATATATATATATTAAAAAAATCTGTAAGTTCCAAACAAGGGCACACGTAT

AAAAGAAACTAATGTATTATATACTGTCATGTTTTTTTTATAAAATATGTACAATAAT

TTATATATGTCTTCATCCGATTAACAAACTCAAACCCAAACAACCAAAATTTCTACA

TTTAGATTTTAAATTAGCGTGTGATGGCTAAAGAAAAAAAGAAGAATAAATTTGTAT

CTTTGCATAGATCACCTGCATTTCGTTGAGTAGATTCATTTAAATAAGTAGATAAAT

AGATTTTATTATCATATTTATTTTCTTAACAAACCATAGTTTTTCCTTACTACAATCAT

AAAAGAAGAATATATTTGTATCTTTGCATAGATCATATATATAATTGTAATGACTAAT

GTGTTATATAGTCCATGGATCGTAGTGAGAAGGTAGAGTTGAAAGTATAAGAAAGC

GAACCTCCATCATAGTGGGGGCTTAAACCCGTGCAAGCTTGCAGATATCTATGGC

TGATGGTTGGGCCCAGCCTTATATCTTGGGCTTATTTTGTTTCCATCTGTCCAGCC

CATGATAAAGTGTAAAACGACACCGTATTAAGCTTAATGGAGTAAACGAATCACAC

GTAGCGGGGATCCCCGTGTCAGTTCTTGTCCGAAAAGCTGGACGGAGGAAAACG

GTATCGTATTCGCTTCGCTTGAATCTATATATTTTGCGCAAAAGCCCTTTTCATCCC

TTTCTTCTCTCATTACTCGATTTAGGGTTTTCTAATCTCGAAAGAAATCAAGATCCT

CCTTCCTTCCTCTCTCGATTTCGATCTCGTAGCCCCTTTTGCGTTGATTTCGAATTC

GTTCATCAATAGCTTTGTTTCTCTCTAGCTCCTATCGATCTCGCTAGCAAATTAGG

GTTTCGAGCGAGCTTAATCCGATCGGTTTCTGGATCAGTTGAGATGCGATCGGAA

TCTCTCTGAATAAGAGAGACTCGTGTGGAGGGGTTTCTTCCTTTGT

SEQ ID NO: 2 Dimension_BnC03_UPL3_promoter (Low UPL3 expression genotype)

AGAGAGGCCTGGACGTTTGGGTCATCGCTCTCGGTCGGTTCCTACTTTTTCTGCA

CCACCGCCATTTGTTGATCCAGAAATATTTACGGCTCAGTTGAAGGACAAGGATG

ATCGCATATCTTTGTTGGAGACCCAGAAGACGGCTCAACAGGCGGGCTATGAGG

CACAGAAGAGGCTGAACCAGCAAATGATGAAAAGGATGTACCCGAACGAGGTGTT

CCCGAACGTGCAAGACCCGTAGTTTTTTTTTTCAAAAACTCGGAATGTTTTATTTTT

-continued

ATTTGTACAACTTTGAATATTATCTAATATGTTTTCAATTTTAATTTTAATTTTATATT

TTCGAATTTAAATTTCAAAATTTTCATTTTTAAAAAAAAATTAATTTTTTTTTGAAAT

TCCGAGGAAATGAACCCTCGGAAATTTCCGACGAACATTTCCTCAGAATAAGTCGT

CGGAATATACCGAGGGACTCCTTCCTCCTCGGAATTTTCTGAGGGCTCCGTTTCT

CGGAAATTCCCGATGAAAATTCCGAGGAACATTTCATCGGAACTTCCGAGGATTG

GACCATCGGAAAGTCCATCGAAATATTCCGAAGAAGTTCTCCCTCGATATATTCCG

AGAACCTTTCCGACGAACTGGTGGTCCTCGGAGTTTCCTCGGAAATTCATTTCCTC

GGAATTCCTTCGGAAATTTCTGAGGGATTTCCGAGAAAAAAATGAATTTCCGAGGAG

TTATTTCCGAGGACTTGTTTCGTCGGTATGTCGTCGGAATAACGTTATTCCGACGA

CGTACCGACGATTTTTTCCCTCGGTATGTTCATATTGGATTTATAAATGAATCATAA

TTTCTGTTTTTCGGGTTAAATTAATATGTATATATATATATATATATTAAAAAAATCTG

TAAGTTCCAAACAAGGGCACACTTATAAAAGAACTAATGTATTATATACTGTCATGT

TTTTTTTATAAAATATGTACAATAATTTATATATGTCTTCATCCGATTAACAAACTCA

AACCCAAACAACAAAAATTTCTACATTTAGATTTTAAATTAGCGTGTGATGGCTAAA

GAAAAAAAGAAGAATAAATTTGTATCTTTGCATAGATCACCTGCATTTCATTGAGTA

GATTCATTTAAATAAGTAGATAGATAGATTTTATTATCATATTTATTTTCTTAACAAA

CCATCATAAAAGAAGAATATATTTGTATCTTTGCATAGATCATATATATAATTGTAAT

GACTAATTATTTTCTCGACAAACCATAGTTTTTCCTTACTACAATCATAAAAGAAGA

ATATATTTGTATCTTTGCATAGATCATATATATAATTGTAATGAGTAATGTGTTATAT

AGTCCATGGATCGTAGTGAGAAGGTAGAGTTGAAAGTATAAGAAAGCGAACCTCC

ATCATAGTGGGGGCTTAAACCCGTGCAAGCTTGCAGATATCTATGGCTGATGGTT

GGGCCCAGCCTTATATCTTGGGCTTATTTTGTTTCCATCTGTCCAGCCCATGATAA

AGTGTAAAACGACACCGTATTAAGCTTAATGGAGTAAACGAATCACACGTAGCGG

GGATCCCCGTGTCAGTTCTTGTCGGAAAAGCTGGACGGAGGAAAACGGTATCGTA

TTCGCTTCGCTTGAATCTATATATTTTGCGCAAAAGCCCTTTTCATCCCTTTCTTCT

CTCATTACTCGATTTAGGGTTTTCTAATCTCGAAAGAAATCAAGATCCTCCTTCCTT

CCTCTCTCGATTTCGATCTCGTAGCCCCTTTTGCGTTGATTTCGAATTCGTTCATC

AACAGGTTTGTTTCTCTCTAGCTCCTAACGATCTCGCTAGCAAATTAGGGTTTCGA

GCGAGCTTAATCCGATCGGTTTCTGGATCAGTTGAGATGCGATCGGAATCTCTCT

GAATAAGAGAGACTCGTGTGGAGGGGTTTCTTCCTTTGT

SEQ ID NO: 3 *Glycine max* UPL3 promoter sequence;
Bold identifies the start of the coding region
>Gm12:2441900..2443999 Glyma12g03640
TGTTATTTCCAAAAGCAAAACTATGTCCCTGGTTTATGTTTGAATATTAACTTATGTTTG

TGTTTTATTTCCAAAAAAAAAAAAAGAAGTACAGTCACAATTTATATTTGAAGTTGCTAA

ACTATACTAATAAGGGAGGAAAACTAGGTTATTTGAACATGACCGGCCCCTTGTCGACAA

CAACTGAAAGCTCGATAAATGATCATCACTAAATCACTATAGTAGCCCGATAACTTCTAA

AAAACATTTAGAAAGTCACCTTTCAGTTTTTAAATGTGTAAATATTAATGATTATGATGA

TTTTTTTTTTAAAAATTCTAAACAAGTCAAGTGCAAAGATTATTTATTTCATTCAGGTTA

AGTTAAAATGGGATTTGTGATTGTGATTTCCTAAAGTTAGTGTGATCCGTAATACATGTC

CAGTATTCCGAAAAGTACAAACAATTACTGATCTAATAAACAATATCCTTAAAACTTTCA

AGACTTTATGGAGACAAATAGCAATCAAATGTACATGCAAAAAAAAAAAAAAACAGAAAT

-continued

ATATCCAGGATTTAAGCATTTTCAATAGGAAGACTATGCATTGTATTTGCACATAAAAGT

AGGCCGTAACAAAAAGTCCTATCCCCGCTCCTCTTTCCCCGATCGATAAGAATAGAACAT

CCAATAATCCATTAAGGGATTTCTATCAACGTTAATTCTAGCTAGAAACCTCTGCATGAG

AACACTATCTAGTACTCTACTCGTGTCTTTCATTACATGTTCAAGTGAGCATGCAAAGTA

GGTGGGGGAAGTAATAAACCAGACAATCACCAACCTTTTCCATGAGAGAGACATATATAT

TAGCAAAGCAAGGAACCAAAGACTTCAAATTTGCACTCTCAGTGGGAAGGTCTGGTATAT

AGGCAACTCTGGGGTACATTGGGGCGTAATTTGTTTTAAAAATATAACTATTATTGAAAA

TTAAAATAAAATGTTGTAGCTATTTAGAGTATATAGTTAAAGGTAAAAATATTTAGAAGA

AAAATGACAATTATTGCTTTTATAATAATTATAGATATTGATAGTGATATATAATAGATT

TATATAGTTTTTATTTTTTATTTGTTTTTGAATATTTTATAAATAAAAAATTACAAGTGT

TTAAAATATACTTCTATCAAAAAAATCAAATTAAAATGTGTATATAAACATTACATGATT

ATTGTTTCAATTTTTTAGTATTTTAAGAATTATTGGTTTGTGTGTTATAAGTATTAATTG

CTACTGACTTATAAGAATTAAGAACTAAAATTATTGAAACAAAGCTGATTTGGCAGTATT

TATTTAAAGCAGTTATAGAAAAATTGAAGAAATAATGTGTTGATTTATCATTGGCAATAC

ATTTTTTTAATTTTTTTTAATTACTCAATCCAATTATCTAATCCAACGGCCAATTAATAC

CAGCCTTATGTTTAATTGGATTATATTGTAAATTAGATTAAACTAAACTCAATCCAACCA

GTTACATCTTATATTTTTATCTAAAATTTGTATTATAATACATTTTCTATTAAATACAAT

TTAATAATTTAACTTTATTGTGCAAGTGCAACGTATATTAATACAATGCAGGTGTCTATT

GAAACGACGACGTTGAGGGATCGAAGTGTACGCGCCACATTGCGACAGTGCCACCGAGGA

GCGTAGCTAGTTCAGTTCCGTTTGATGAACGAAAATGACCAATCCACCGAGCGAAATTGT

AATTTTCAACAATAAAAAAGGCAAAGAAAGTTACATATGAAAGCCTGTTTTGTTCTGTCC

CTTTTTATTCTTCCCTTTCTTTCTTACTTACCCCTTTCCCTGGCTTAGGGTTTTCTGCCC

CCCCTGAATCCTCATCGCTATTCATGATTACACTCCTTACAATTCTCACTCAGCGACTCG

TTCGAAATACGTGAAATCCCCTTATCTCCAATTTCTAGGGTTTCGATTCATTCAACTCAC

CACAAAGATTGGATCCATGGTAGCGTGATTGGCGCTCGGTGGCGAGCGAGTTGATAATTA

TCGGGTTGGGTGGATTTTGTATGGAAACTCGGAGCCGGAAGCGGGCGGAGGCTTCCTCAG

UPL3 gene sequences
SEQ ID NO: 4 *Brassica napus* UPL3 coding sequence
BnC03_UPL3_CDS
ATGGAAACTCGGAGCCGCAAGCGTGCGGAGGCGACCTCAACTGCCCCATCTTCTTCTTCTTCGTCTCCTC

CTCCTCCTCCCTCAGGTCCCACCACTCGCAGCAAACGCGCTCGCCTCTCGTCTCCCTCTTCCTCTTCAGC

CGCCGCCGCTACCACCGCTACTGCACCTTCCTCCTCCACCCGCTCTCGTTCTTCTCGCTCTGCCGCTACC

GCTACCGCTACAGCCGCCGTTACTCCCATGGACACATCCACCGAGTCTTCTGGATTCCGCCGCGGCGGGG

GACGAGGTAACAGGGGAAACGATAATACTAATTCTGATAAGGGAAAGGAGAAGGAGCATGAGGTTAGGAT

TAGGGATAGAGAAAGAGACCGAGCCAGACAGCAGCTCAACATGGACGCTGCAGCTGCTGCCGCCGCCGCT

GAAGAGGACGATGACAATGATAGTGAGGATGGCAACGGGGGATTCATGCATCCCAACATGAGCTCAGCCA

GCAGTGCGTTACAAGGGTTGCTGAGGAAGCTTGGAGCTGGACTTGATGACTTGCTTCCTTCTTCAGGTAT

TGGCTCAGGTTCTTCTTCCCATTTAAATGGGAGGATGAAGAAGATACTCGCTGGCTTGCGCTCTGAAGGA

AAAGAGGGAAAGCAAGTCGAGGCTTTGACCCAGCTCTGCGAGATGTTATCCATTGGCACCGAAGACTCCT

TGAGCACCTTCTCTGTTGATTCCTTCGTCCCCGTTCTTGTTGGTCTACTTAACCATGAGAGCAATCCGGA

TATTATGCTTCTTGCTGCCAGGGCTCTTACCCATCTGTGTGATGTTTTGCCCTCTTCTTGTGCTGCTGTT

GTTCATTACGGGGCTGTTTCATGCTTTGTCGCCAGATTGCTAACCATTGAATACATGGACTTGGCCGAGC

-continued

AGTCTCTGCAAGCTCTCAAAAAGATATCTCAGGAACACCCAACGGCCTGTTTGCGAGCTGGTGCTCTTAT

GGCAGTGCTATCATATCTGGATTTCTTCTCCACCGGTGTCCAGCGTGTAGCAGTCTCTACCGCTGCAAAT

ATGTGCAAGAAGTTACCTTCTGATGCATCTGATTATGTTATGGAAGCTGTACCGGTACTGACAAACCTAC

TTCAGTATCATGATGCGAAGGTTTTGGAATATGCTTCTATCTGTTTGACTCGGATTGCCGAAGCATTTGC

ATCGTCCCCTGATAAATTAGATGAATTATGCAACCATGGCCTGGTGACTCAAGCTGCGACTCTTATATCC

GCTAGCAACTCGGGAGGTGGGCAAGCATCTCTTGGTGTTTCAACATACACGGGATTAATCCGATTACTTT

CCACCTGTGCGAGCGGTTCACCTCTTGGGTGCAGGACATTACTTCTTCTCGGTATTAGTAGCATTCTTAA

GGATATTCTGTCGGGTTCTGGTGTCTCTGCTAATGCATCTATATCCCCAGCACTGAGCAGGCCTGCAGAT

CAGATTTTTGAGATAGTCAACCTAGCGAACGAGCTCCTCCCTCCATTGCCAGAAGGAAGTATCTCCCTTC

CTACTAGCGCAAACGCGTTAGTGAAAGGTTCAGGCCAAAAAAATTCTTCTCCAAGTACTTCAGGAAAACA

AGAAGATTCTCCCAAAGTTTCACCTAGAGAAAAATTACTTAGTGATCAACCCGAACTTTTGCAGCAATTT

GGATTGGATCTTCTTCCAGTTTTAGTGCAGATCTATGGTTCTAGTGTCAATGGTACTATTCGTCATAAAT

GTCTCTCCGTTATCGCAAAGTTGATGTATTTCAGCACTCCAGAAATGATTCAATCTCTAATTGGTGACAC

AAATATATCGAGCTTCTTGGCTAGTGTCTTGGCATGGAAAGATCCACAAGTCTTGGTTCCTGCTCTACAA

GTTGCAGAAATTCTGATGGAAAAACTTCCTGAAACTTTCTCGAAAGTGTTTGTGAGGGAAGGGGTGGTTC

ATGCTGTAGATCAACTTGTCTTGGTTGGTAAACCTAGTGCTAATGCTTCTACTGATCAGGAAAATGACTG

TGTGCCTGGATCTGCACGATCTAGGCGTTACAGACGGCGAAGTAGTAATGCCAATTCTGATGGAAATCAG

TCGGAAGAGCTTAAGAATTCTGTGTCAGCTAGCATAGGTGCGACCCATAATTCCATGGAATCTCCTACAG

CGAGCTTCATGCTAAGGGAAACAGTTAGCTCCTGTGCAAAAGCATTCAAAGACAAGCACTTCCCGTCTGA

TGGTGGGGAATTTGATGTTGGAGTTACAGATGATCTCTTGCATCTGAAGAATCTTTGCACGAAGCTAACT

GCTGGTACAAATGATCATAAAGTGAAAGGAAAGGGGAAATCTAAAGTCTCTGGGCCATGCCTTGGCGATT

TTTCTGCTAGCAAAGAAGAATACTTGATTGGTATCATCTCCGAGATACTTGGCGAGCTAAGCAAAGGGGA

TGGCGTCTCAACTTTTGAGTTTATTGGCAGTGGTGTGGTAGCAGCATTGCTTAACTATTTTTCTTATGGA

TACTTTTCCAAAGAGAAGATCTCCGAGGTTGATTTGCCCAAACTTCGCCAGGATGGGCTCAGAAGGTTCA

AAGCTTTTCTAGAAATTGCACTTCCTTCTGATGGTAATGAGGGAAAGATCCCTCCTATGACTGTTTTGAT

TCAGAAACTTCAAGATGCTTTGTCTTCACTGGAACGCTTTCCGGTCGTCCTTAGCCATCCCTCAAGGTCA

CTCAGTGGAAGTGCTCGTCTCTCATCTGGATTGAGTGCTTTGGCACATCCTTTGAAGTTGCGGTTATGCC

GTGCACCTGGAGAGAAGGCTCTACGTGATTACTCCTCCAATATTGTTCTCATAGATCCATTGGCAAGCAT

AGCAGCAGTGGAGGAATTTCTCTGGCCCCGAGTTCAACGCAGTGAATCTGGGGTGAAGGCAGCAGCGCCT

GCTGGAAACACTGAGCCAGGCACATTACCTAGCGGTGCTGGTGTTTCATCACCATCCTCGTCAACTCCAG

CTTCCACCACTCGTCATTCTTCTAGATCTAGATCAGCAATTAAAATAGGCGATGCCTCAAAGAAAGAACC

TGTGCACGAGAAAGGTACCAGCTCATCTAAAGGTAAAGGTGTTATGAAGCCGGCTCAGCCGGATAAGGGG

CCTCAGACAAGGAGCAGTGCTCAAAGGAAAGCTGTTCTTGACAAAGATACACTAATGAAACCAGCTAGCG

GAGACTCCAGCTCTGAGGaCGAAGAAATGGATATATCCCCCGTCGACATGGATGATGCTTTGGTGATTGA

AGAGGAAGACATTTCTGACGACGATGATGATGATGATGAGGAGGATGTCTTGGATGACAGTCTTCCCATG

TGCACCCCTGATAAGGTTCATGATGTAAAATTGGGAGACGCAGTGGATGATGAGGGAGCCGGCCTAGCAC

CTAGCGGCCGACAGATGAATTCAGCTTTGGCAGGAAGTAGTGGAACAGCAACTGCAAGGGGATCTAATTC

TACTGATGCTGGCATTGGGAATCTTTATGGTTCTAGGGGTGCACTCTCCTTCGCTGCTGCGGCGATGGCA

GGGCTTGGAGCTGCCAGTGGTAGAGGTATCAGGGGGAGTAGAGACCTACATGGGCGTACCCTGAATCGAA

GTTCTGATGAGTCCTCTAAGTTGATGTTTACTGCGGGAGGAAAGCAACTTAGTAGGCATATGACGATATA

-continued

TCAGGCTGTGCAACGACAACTTATGCTAGACGAAGATGATGATGACAGGCTCGGTGGCAGCGATTTCATC

TCGAGTGATGGAAGCAGATTAAATGATATATATACTATCATGTACCAGATGCCGGACAGCCAAGCGAATA

GGTTGTCTGCTGGTGGTGCAAGTTCTACCACACCATCTAAATCCACTAAATCTGCTACTACTAATGCAAG

CGTAGAAGCCCAGTCGTATAGGGCATCTCTTTTGGATAGTATCGTACAAGGAAAGCTTCCATGCGACCTT

GAGAAGGCAAATTCTACGTATAATGTTTTGGCGTTGTTGCGTGTACTAGAGGGTTTAAATCAGCTTGGCC

CTCGGTTAAGAGCCCAAACCATTTCTGATCGTTTCGCAGAGGGTAAAATTACAAGTCTGGATGATCTGAA

TACAACTGCTGCAAAGGTTTCTCATGAAGAATTCATCAACAGCAAACTTACACCCAAATTAGCTCGACAG

ATCCAGGACGCGCTTGCTTTGTGCAGTGGAAGTCTTCCCTCTTGGTGCTACCAGTTGACTACAGCATGCC

CGTTTTTGTTTCCGTTTCAGACCCGGAGACAGTATTTCTATTCAACTGCCTTTGGGTTGTCGCGTGCATT

GAACCGCTTGCAGCAGCAGCAAGGTGCTGACGGCAGTGGTTCTACAAATGAACGAGAGATGAGAATAGGG

AGATTGCAGCGCCAGAAAGTGCGTGTATCCCGAAATAGAATATTAGATTCTGCTGCGAAAGTTATGGAGA

TGTATTCTAGCCAAAAAGCTGTGCTTGAAGTAGAATATTTTGGTGAAGTTGGTACTGGTCTAGGCCCCAC

ACTTGAGTTTTACACACTCCTAAGCCATGATTTGCAAAAGGTTTCCCTTGGGATGTGGAGATCAAATTCT

GGTGACAAGTTATCTATGCAAACTGATAGAGATGAGATTCAAGACGGTAAATCAGCAGCAGCTAGGGACA

GAGATATAGTTCAGGCACCATTTGGGTTGTTCCCTCGGCCCTGGCCCTCAACTGCTGACGTATCTGAAGG

TAGTCGGTTTCATAAAGTTGTTGAATATTTCCGCCTTTTAGGGCGCGTGATGGCAAAGGCACTTCAAGAT

GGACGGCTAATGGACGTCCCGTTAAGTACAGCTTTTTATAAGCTCATTCTTGGTCAAGAGCTTGATTTGC

ATGATGTTATATTATTTGATGCTGAACTTGGCAAGACTTTGCAAGAGCTTCGTGTTCTTGTTGGCCGTAA

GCACTATCTGGAAGCAGAAGGTGGTGACAACAGTAGCGTGATTTCTGATTTATGTTTACGTGGATCCCGT

ATTGAAGATCTTTGCTTGGACTTCACCCTACCTGGCTATCCTGAATACATATTGAGACCAGGAGATGACA

TGTTGATATTAATAGTCTTGAGGACTATATATCCCTGGTCGTTGATGCCACTGTCAAGAGAGGAGTTGCC

CGGCAGATTGAAGCCTTCAGATCTGGATTCAAtcCAGGTCTTTGACATAAAATCTTTACAAGTATTCACC

CCTTCTGAGCTGGACTACTTGTTATGTGGTCGTAGAGAGTTGTGGGAGGCGGAGACTCTTGTTGAACATA

TCAAGTTTGATCACGGTTATACTGCAAAAAGTCCGGCAATCATTTTCTTACTGGAGATCATGGGAGAGCT

TACAGCAGATCAACAGCGTGCTTTCTGCCAGTTTGTAACTGGAGCTCCTAGGCTTCCTCCTGGTGGCTTA

GCTGTTCTCAACCCAAAGCTGACGATTGTGAGAAAGCTCTCATCAACCTCAAATGCGGCTGCCAATGGGA

CAGGGGCTTCGGAAACAGCAGACGACGATCTTCCCAGCGTCATGACTTGCGCCAACTACCTTAAGCTCCC

TCCTTATTCTACAAAGGAAATCATGTACAAGAAACTGCTCTACGCGATCAACGAAGGGCAGGGATCGTTC

GACCTCTCCTAG

SEQ ID NO: 5: *Brassica napus* UPL3 coding sequence (BnA08_UPL3_CDS)

ATGGAAACTCGGAGCCGCAAGCGTGCGGAGGCGACCTCAACTGCCCCATCTTCTTCTTCTTCCTCTCCTC

CTCCTCCTCCTTCCTCAGGTCCCACCACTCGCAGCAAACGCGCTCGCCTCTCGTCTCCCTCTTCCTCTTC

AGCCGCCGCTACTGCACCTTCCTCCTCCACTCGCTCTCGTTCTTCTCGCTCTACCACCGCTACAGCCGCC

GTTACTCCCATGGACACATCCACCGAGTCTTCTGGATTCCGCCGCGGCGGAGGACGAGGTAACAGGGGAA

ACGATAATACTAACTCTGATAAGGGAAAGGAGAAGGAGCATGAGGTTAGGATTAGGGATAGAGAAAGAGA

CAGAGCTAGACAGCAGCTCAACATGGACGCTGCAGCTGCTGCAGCCGCCGCCGCTGATGAGGACGACGAC

AATGATAGTGAGGATGGCAACGGGGGATTCATGCATCCCAACATGAGCTCAGCCAGCAGTGCGTTACAAG

GGTTGCTTAGGAAGCTTGGAGCTGGACTTGATGACTTGCTTCCTTCTTCAGGTATTGGCTCAGGTTCGTC

TTCTCACTTGAATGGGAGGATGAAGAAGGTACTCGCTGGCTTGCGCTCTGAAGGAGAAGAGGGAAAGCAG

GTCGAGGCTTTGACGCAGCTGTGCGAGATGTTATCTATTGGGACCGAAGACTCCCTGAGCACCTTCTCTG

TTGATTCCTTCGTCCCGGTTCTTGTTGGTCTACTTAACCATGAGAGCAATCCGGATATTATGCTTCTTGC

-continued

TGCCAGGGCTCTTACTCATCTGTGTGATGTTTTGCCGTCTTCTTGTGCTGCTGTTGTTCATTACGGGGCT

GTTTCGTGCTTTGTCGCCAGATTGTTGACAATAGAATACATGGACTTGGCCGAGCAGTCTCTGCAAGCTC

TCAAAAAGATATCTCAGGAACACCCAACGGCCTGTTTGCGTGCTGGTGCTCTTATGGCAGTGCTATCATA

TCTGGATTTCTTCTCCACCGGTGTCCAGCGTGTAGCAGTATCTACCGCTGCAAATATGTGCAAGAAGTTA

CCTTCTGATGCATCTGATTATGTTATGGAAGCTGTACCGGTACTGACAAACCTACTTCAGTATCATGATG

CGAAGGTTTTGGAATATGCTTCTATCTGTTTGACTCGGATTGCCGAAGCATTTGCATCGTCCCCTGATAA

ATTAGATGAATTATGCAACCATGGCCTGGTGACTCAAGCTGCGACTCTTATATCCGCTAGCAACTCGGGA

GGTGGGCAAGCATCTCTCGGTGTTTCAACATACACGGGATTAATCCGATTACTTTCCACCTGTGCGAGCG

GTTCACCTCTTGGGTGCAGGACATTACTTCTTCTCGGTATTAGTAGCATTCTTAAGGATATTCTGTCGGG

TTCCGGTGTCTCTGCTAATGCATCTATATCCCCAGCACTGAGCAGGCCTGCAGATCAGATTTTTGAGATA

GTCAACCTAGCGAACGAGCTCCTCCCTCCACTGCCAGAAGGAAGTATCTCCCTTCCTACTAGCGCAAACG

CGTTAGTGAAAGGTTCAGGCCAAAAAAAGTCTTCTCCAAGTACTTCAGGAAAACAAGAAGATTCTCCCAA

AGTTTCACCTAGAGAAAAATTACTTAGTGATCAACCCGAACTTCTGCAGCAATTTGGATTGGATCTTCTT

CCAGTTTTAGTGCAGATCTATGGTTCTAGTGTCAATGGTACTATTCGTCATAAATGTCTCTCAGTTATCG

CAAAGTTGATGTATTTCAGCACTCCAGAAATGATTCAATCTCTAATTGGTGACACAAATATATCGAGCTT

CTTGGCTAGTGTCTTGGCATGGAAAGATCCACAAGTCTTGGTTCCTGCTCTACAAGTTGCAGAAATTCTG

ATGGAAAAACTTCCTGAAACTTTCTCGAAAGTGTTTGTGAGGGAAGGGGTGGTTCATGCTGTAGATCAAC

TTGTCTTGGTTGGTAAACCTAGTTCTCATGCTTCTACTGATCAGGAAAATGACTGTGTGCCTGGATCTGC

ACGATCTAGGCGTTATAGACGGCGAAGTAGTAACGCCAATTCTGATGGAAATCAGTCGGAAGAGCTTAAG

AATTCTGTGTCAGCTAGTATAGGTGCAAACCATAATTCCATGGAATCTCCTACAGCGAGCTTCATGCTAA

GGGAAACAGTTAGCTCCTGTGCAAAAGCATTCAAAGACAAGCACTTCCCGTCTGATGGTGGGGAATTTGA

TGTTGGAGTTACAGATGATCTCTTGCATCTGAAGAATCTTTGCACGAAGCTAACTGCTGGTACAAATGAT

CATAAAGTGAAAGGAAAGGGGAAATCTAAAGCCTCTGGGCCATGCCTCGGCGATTTTTCTGCTAGCAAAG

AAGAATACTTGATTGGTATCATCTCCGAGATACTTGGCGAGCTAAGCAAAGGAGATGGTGTCTCAACTTT

TGAGTTTATTGGCAGTGGTGTGGTAGCAGCATTGCTTAACTATTTTTCTTATGGATACTTTTCCAAAGAG

AAGATCTCCGAGGTTGATTTGCCCAAACTTCGCCAGGATGGGCTCAGAAGGTTCACAGCTTTTCTAGAAA

TTGCACTTCCTTCTGATGGTAATGAGGGAAAGATCCCTCCTATGACTGTTTTGATTCAGAAACTTCAAGA

TGCTTTGTCTTCACTGGAACGCTTTCCGGTCGTCCTTAGCCATCCCTCAAAGTCACTCAGTGGAAGTGCT

CGTCTCTCATCTGGATTGAGTGCTTTGGCACATCCTTTGAAGTTGCGGTTATGCCGTGCACCTGGAGAGA

AGGCACTACGTGATTACTCCTCCAATATTGTTCTCATAGATCCTTTGGCAAGCATAGCAGCAGTGGAGGA

ATTTCTCTGGCCCCGAGTTCAACGCAGTGAATCTGGGGTGAAGCCAGCAGCGCCTGTTGGAAACACTGAG

CCAGGCACATTACCTAGCGGTGCTGGTGTTTCATCACCATCCTCGTCAACTCCAGCTTCCACCACTCGTC

ATTCTTCTAGATCTAGATCTGCAATTAAAATAGGCGATGCCTCAAAGAAAGAACCTGTGCACGAGAAAGG

TACCAGCTCATCTAAAGGTAAAGGTGTTATGAAGCCGGCTCAGCCGGATAAGGGGCCTCAGACAAGGAGC

AGTGCTCAAAGGAAAGCTGTTCTTGACAAAGATACACTAATGAAACCAGCTAGCGGAGACTCCAGCTCTG

AGGACGAAGAAATGGATATATCCCCCGTCGACATGGATGATGCTTTGGTTATTGAAGAGGAAGACATTTC

TGACGACGATGAGGATGATGATGATGAGGATGTCTTGGATGACAATCTTCCCATGTGCACCCCTGATAAG

GTTCATGATGTAAAATTGGGAGACGCAGTGGATGATGAGGGAGCCGGTCTAGCACCTAGCGGCCGACAGA

TGAATTCAGCTTTGGCAGGAAGTAGTGGAACAGCAACTGCAAGGGGATCTAATTCTACTGATGCTGGCAT

TGGGAATCTTTATGGTTCTAGGGGTGCACTCTCCTTCGCTGCTGCGGCGATGGCAGGGCTTGGAGCTGCC

AGTGGTAGAGGTATCAGGGGAAGTAGAGACCTACATGGGCGTACCCTGAATCGAAGTTCTGATGAGTCCT

-continued

CTAAGTTGATGTTTACTGCGGGAGGAAAGCAACTTAGTAGGCATATGACGATATATCAGGCTGTGCAACG

ACAACTTATGCTAGACGAAGATGATGATGACAGGCTCGGTGGCAGCGATTTCATCTCCAGTGATGGAAGC

AGATTAAATGATATATATACTATCATGTACCAGATGCCGGACAGCCAAGCGAATAGGTTGTCTGCTGGTG

GTGCAAGTTCTACCACACCATCTAAATCCACCAAATCTGCTACTACTAATGCAAGCGTAGAAGCTCAGTC

GTATAGGGCATCTCTTTTGGATAGTATCGTACAAGGAAAGCTTCCATGCGACCTTGAGAAGTCCAATTCT

ACGTATAATGTTCTGGCGTTGTTACGTGTATTAGAGGGTTTAAATCAGCTTGGCCCTCGCTTAAGAGCCC

AAACCGTTTCTGATCGTTTTGCAGAGGGTAAAATTACAAGTCTGGATGATCTGAATACAACTGCTGCAAA

GGTTTCTCATGAAGAATTCATCAACAGCAAACTTACACCCAAATTAGCTCGACAGATCCAGGACGCGCTT

GCTTTGTGCAGTGGAAGTCTTCCCTCTTGGTGCTACCAGTTGACTACAGCATGCCCGTTTTTGTTTCCGT

TTCAGACCCGGAGACAGTATTTCTATTCAACTGCCTTTGGGTTGTCGCGTGCATTGAACCGCTTGCAGCA

GCAGCAAGGTGCTGACGGCAGTGGTTCTACAAATGAACGAGAGATGAGAATAGGGAGATTGCAGCGCCAG

AAAGTGCGTGTATCCCGAAATAGAATATTAGATTCTGCTGCGAAAGTTATGGAGATGTATTCTAGCCAAA

AAGCTGTGCTTGAAGTAGAATATTTTGGTGAAGTTGGTACTGGTCTAGGCCCCACACTTGAGTTTTACAC

ACTCCTAAGCCATGATTTGCAAAAGGTTTCCCTTGGGATGTGGAGATCAAATTCTGGTGACAAGTTATCT

ATGCAAACTGATAGAGATGAGATTCAAGACGGTAAATCAGCAGCAGCTAGGGACAGAGATATAGTTCAGG

CACCACTTGGGTTGTTCCCTCGGCCCTGGCCCTCAACTGCTGACGTATCTGAAGGTAGTCGGTTTCATAA

AGTTGTTGAATATTTCCGCCTTTTAGGGCGCGTGATGGCAAAGGCACTTCAAGATGGACGGCTAATGGAC

GTCCCGTTAAGTACAGCTTTTTATAAGCTCATTCTTGGTCAAGAGCTTGATTTGCATGATGTTATATTAT

TTGATGCTGAACTTGGCAAGACTTTGCAAGAGCTTCGTGTTCTTGTTGGCCGTAAGCACTATCTGGAAGC

AGGCGGTGGTGACAACAGTAGCGGGATTTCTGATTTATGTTTGCGTGGATCCCGTATTGAAGATCTTTGC

TTGGACTTCACCCTACCTGGCTACCCTGAATACATATTGAGACCAGGAGATGACATTGTTGATATTAATA

GTCTTGAGGACTATATATCCCTGGTCGTTGATGCCACTGTCAAGAGAGGAGTTGCCCGGCAGATTGAAGC

CTTCAGATCTGGATTCAATCAGGTCTTTGACATAAAATCTCTACAAATATTCACCCCTTCTGAGCTGGAC

TACTTGTTGTGTGGTCGTAGAGAGTTGTGGGAGGCGGAGACTCTTGTTGAACATATCAAGTTTGATCACG

GTTATACTGCAAAAAGTCCGGCAATCATTTTCTTATTGGAGATCATGGGAGAGCTAACAGCAGATCAACA

GCGGGCTTTCTGCCAGTTCGTAACTGGAGCTCCTAGGCTTCCTCCTGGTGGCTTAGCTGTTCTCAACCCA

AGGCTGACGATTGTGAGAAAGCTCTCATCAACCTCAAATGCTGCTGCCAATGGGACAGGGGCTTCGGAAA

CAGCAGACGACGATCTTCCCAGCGTCATGACTTGCGCCAACTACCTTAAGCTCCCTCCTTATTCTACAAA

GGAAATCATGTACAAGAAACTGCTCTACGCCATCAACGAAGGGCAGGGGTCGTTCGACCTATCCTAG

SEQ ID NO: 6: *Brassica napus* UPL3 genomic sequence A08 genomic UPL3 sequence

ATGGAAACTCGGAGCCGCAAGCGTGCGGAGGCGACCTCAACTGCCCCATCTTCT

TCTTCTTCCTCTCCTCCTCCTCCTCCTTCCTCAGGTCCCACCACTCGCAGCAAACG

CGCTCGCCTCTCGTCTCCCTCTTCCTCTTCAGCCGCCGCTACTGCACCTTCCTCC

TCCACTCGCTCTCGTTCTTCTCGCTCTACCACCGCTACAGCCGCCGTTACTCCCA

TGGACACATCCACCGAGTCTTCTGGATTCCGCCGCGGCGGAGGACGAGGTAACA

GGGGAAACGATAATACTAACTCTGATAAGGGAAAGGAGAAGGAGCATGAGGTTAG

GATTAGGGATAGAGAAAGAGACAGAGCTAGACAGCAGCTCAACATGGACGCTGC

AGCTGCTGCAGCCGCCGCCGCTGATGAGGACGACGACAATGATAGTGAGGATGG

CAACGGGGGATTCATGCATCCCAACATGAGCTCAGCCAGCAGTGCGTTACAAGG

GTTGCTTAGGAAGCTTGGAGCTGGACTTGATGACTTGCTTCCTTCTTCAGGTATTG

-continued

GCTCAGGTTCGTCTTCTCACTTGAATGGGAGGATGAAGAAGGTACTCGCTGGCTT

GCGCTCTGAAGGAGAAGAGGGAAAGCAGGTCGAGGCTTTGACGCAGCTGTGCGA

GATGTTATCTATTGGGACCGAAGACTCCCTGAGCACCTTCTCTGTTGATTCCTTCG

TCCCGGTTCTTGTTGGTCTACTTAACCATGAGAGCAATCCGGATATTATGCTTCTT

GCTGCCAGGGCTCTTACTCATCTGTGTGATGTTTTGCCGTCTTCTTGTGCTGCTGT

TGTTCATTACGGGGCTGTTTCGTGCTTTGTCGCCAGATTGTTGACAATAGAATACA

TGGACTTGGCCGAGCAGGTTCGATTTCCTAACAATTCTTGAATTTTTTTGCTGAAT

ATATATTGTGGAATGTTTTATGCTGCAGTTTCTACACGTACATATCCAATATTTTAG

TTTACTTAGGACGAAATTTGAAATTTGATTTTATTCTTCATGTGATTTACAACAGTCT

CTGCAAGCTCTCAAAAAGATATCTCAGGAACACCCAACGGCCTGTTTGCGTGCTG

GTGCTCTTATGGCAGTGCTATCATATCTGGATTTCTTCTCCACCGGTGTCCAGGTG

GGTAATTTTGTAACTTTTCTTTAATGCTTTCCATACTCGTTTATCTAATGCACTTTTT

TTTTTACTTTTTGTAGCGTGTAGCAGTATCTACCGCTGCAAATATGTGCAAGAAGTT

ACCTTCTGATGCATCTGATTATGTTATGGAAGCTGTACCGGTACTGACAAACCTAC

TTCAGTATCATGATGCGAAGGTAAACGATCCCTTTTTTTTTTTGCTATAATGTGGTA

TTATCTAGTTCTGCTCTTGCCCCAGTTTCCTTCATAGTATGTTCGTACGGTGGCAG

GTTTTGGAATATGCTTCTATCTGTTTGACTCGGATTGCCGAAGCATTTGCATCGTC

CCCTGATAAATTAGATGAATTATGCAACCATGGCCTGGTGACTCAAGCTGCGACT

CTTATATCCGCTAGCAACTCGGGAGGTGGGCAAGCATCTCTCGGTGTTTCAACAT

ACACGGTATGAGTTAATTCTTTTGTGTTTTCTATATTTCGTTATTCATAGGATGACA

TTTTCATCATATTTTCACAGGGATTAATCCGATTACTTTCCACCTGTGCGAGCGGTT

CACCTCTTGGGTGCAGGACATTACTTCTTCTCGGTATTAGTAGCATTCTTAAGGAT

ATTCTGTCGGGTTCCGGTGTCTCTGCTAATGCATCTATATCCCCAGCACTGAGCA

GGCCTGCAGATCAGGTACGGATTTACTTTTTGACATCACAGACTTTATTTTGTTCA

ATTCCTGATAAAGTCTATTCAGTAAAAAGTGTTTTGTTTAGGGGACACACCTTTAAA

TAGATCATCAACATAAATTGTGTGTTGAGTGAGATGCTTAGGGGACACACCTTCAA

ATAGATCACTTGCATTTAAATGGATCACTTGCATTTAGGAGTTTTGTCTATTCAGTT

CAATGATAATCTTTTTTTTTTGTAACACTCAGCTCAATGATAATCTATGTACATGTAT

TTTGAGCTTTATTTATGTTGTAACCGATGGCTCAACTTTCATATGCTTGTTTTCTGG

TATGGTGTTAGAAGTGGTATAGATAAAAGTGCTTAGCGCTTCATCAGTGTGCTCGG

TCTTGTTTATTTAACTTTTTTTATCCCATGACTCGCTAATTCTTGAATATATTCTTGA

ACATGATCATGTGAGGTCTTTTGTTTCCGAATTATAACTCTTGTTTTGCATCTTAGA

TTTTTGAGATAGTCAACCTAGCGAACGAGCTCCTCCCTCCACTGCCAGAAGGAAG

TATCTCCCTTCCTACTAGCGCAAACGCGTTAGTGAAAGGTTCAGGCCAAAAAAAGT

CTTCTCCAAGTACTTCAGGAAAACAAGAAGATTCTCCCAAAGTTTCACCTAGAGAA

AAATTACTTAGTGATCAACCCGAACTTCTGCAGCAATTTGGATTGGATCTTCTTCC

AGTTTTAGTGCAGGTAATTTTTTGTTGCAGTTGCTACAAGTTAGTGTTCATACAACC

TCCTGTATGTCTAATTACCCTTGTTTTCTTTCCTACAGATCTATGGTTCTAGTGTCA

ATGGTACTATTCGTCATAAATGTCTCTCAGTTATCGCAAAGTTGATGTATTTCAGCA

CTCCAGAAATGATTCAATCTCTAATTGGTGACACAAATATATCGAGGTATGCTGGT

TATGTTTTAAATTAGGTATCACATGGCGCAACTTCTTACATTATTTTTCCTATGTAG

-continued

CTTCTTGGCTAGTGTCTTGGCATGGAAAGATCCACAAGTCTTGGTTCCTGCTCTAC

AAGTTGCAGAAATTCTGATGGAAAAACTTCCTGAAACTTTCTCGAAAGTGTTTGTG

AGGGAAGGGGTGGTTCATGCTGTAGATCAACTTGTCTTGGTTGGTAAACCTAGTT

CTCATGCTTCTACTGATCAGGAAAATGACTGTGTGCCTGGATCTGCACGATCTAG

GCGTTATAGACGGCGAAGTAGTAACGCCAATTCTGATGGAAATCAGTCGGAAGAG

CTTAAGAATTCTGTGTCAGCTAGTATAGGTGCAAACCATAATTCCATGGAATCTCC

TACAGCGAGCTTCATGCTAAGGGAAACAGTTAGCTCCTGTGCAAAAGCATTCAAA

GACAAGCACTTCCCGTCTGATGGTGGGGAATTTGATGTTGGAGTTACAGATGATC

TCTTGCATCTGAAGAATCTTTGCACGAAGCTAACTGCTGGTACAAATGATCATAAA

GTGAAAGGAAAGGGGAAATCTAAAGCCTCTGGGCCATGCCTCGGCGATTTTTCTG

CTAGCAAAGAAGAATACTTGATTGGTATCATCTCCGAGATACTTGGCGAGCTAAGC

AAAGGAGATGGTGTCTCAACTTTTGAGTTTATTGGCAGTGGTGTGGTAGCAGCATT

GCTTAACTATTTTTCTTATGGATACTTTTCCAAAGAGAAGATCTCCGAGGTTGATTT

GCCCAAACTTCGCCAGGATGGGCTCAGAAGGTTCACAGCTTTTCTAGAAATTGCA

CTTCCTTCTGATGGTAATGAGGGAAAGATCCCTCCTATGACTGTTTTGATTCAGAA

ACTTCAAGATGCTTTGTCTTCACTGGAACGCTTTCCGGTCGTCCTTAGCCATCCCT

CAAAGTCACTCAGTGGAAGTGCTCGTCTCTCATCTGGATTGAGTGCTTTGGCACA

TCCTTTGAAGTTGCGGTTATGCCGTGCACCTGGAGAGAAGGCACTACGTGATTAC

TCCTCCAATATTGTTCTCATAGATCCTTTGGCAAGCATAGCAGCAGTGGAGGAATT

TCTCTGGCCCCGAGTTCAACGCAGTGAATCTGGGGTGAAGCCAGCAGCGCCTGT

TGGAAACACTGAGCCAGGCACATTACCTAGCGGTGCTGGTGTTTCATCACCATCC

TCGTCAACTCCAGCTTCCACCACTCGTCATTCTTCTAGATCTAGATCTGCAATTAA

AATAGGCGATGCCTCAAAGAAAGAACCTGTGCACGAGAAAGGTACCAGCTCATCT

AAAGGTAAAGGTGTTATGAAGCCGGCTCAGCCGGATAAGGGGCCTCAGACAAGG

AGCAGTGCTCAAAGGAAAGCTGTTCTTGACAAAGATACACTAATGAAACCAGCTA

GCGGAGACTCCAGCTCTGAGGTATGTCACTGTAGAAAGTTCTGGATTACATGGTT

GTTTATTGTGTAACATTATATTATGTTTGTGGTGTGATCTGCTTATGCAGCACTATC

GTACTTATATTGCTTGCAGGACGAAGAAATGGATATATCCCCCGTCGACATGGAT

GATGCTTTGGTTATTGAAGAGGAAGACATTTCTGACGACGATGAGGATGATGATG

ATGAGGATGTAAGTATTCCCTCCCCAGTATGTACATTACAGACGCAATTATTTCTC

TTGCTAACAACATGAAAGATGATACTTTTCGCAATAATGCTTGCTAGCTTTCCGTAT

TCTTAGATAAGTTTACCATATTGAGCTCACCTTATTTGGCACCTTTCCTTTTAGAAC

TGACTAAAGAGAATAATGAACTTTATACCACAATTTCTCATATTGATCTGGTCTTGA

ATTCAGGTCTTGGATGACAATCTTCCCATGTGCACCCCTGATAAGGTTCATGATGT

AAAATTGGGAGACGCAGTGGATGATGAGGGAGCCGGTCTAGCACCTAGCGGCCG

ACAGATGAATTCAGCTTTGGCAGGAAGTAGTGGAACAGCAACTGCAAGGGGATCT

AATTCTACTGATGCTGGCATTGGGAATCTTTATGGTTCTAGGGGTGCACTCTCCTT

CGCTGCTGCGGCGATGGCAGGGCTTGGAGCTGCCAGTGGTAGAGGTATCAGGG

GAAGTAGAGACCTACATGGGCGTACCCTGAATCGAAGTTCTGATGAGTCCTCTAA

GTTGATGTTTACTGCGGGAGGAAAGCAACTTAGTAGGCATATGACGATATATCAG

-continued

GCTGTGCAACGACAACTTATGCTAGACGAAGATGATGATGACAGGCTCGGTGGCA

GCGATTTCATCTCCAGTGATGGAAGCAGATTAAATGATATATATACTATCATGTAC

CAGATGCCGGACAGCCAAGCGAATAGGTTGTCTGCTGGTGGTGCAAGTTCTACCA

CACCATCTAAATCCACCAAATCTGCTACTACTAATGCAAGCGTAGAAGCTCAGTCG

TATAGGGCATCTCTTTTGGATAGTATCGTACAAGGAAAGCTTCCATGCGACCTTGA

GAAGTCCAATTCTACGTATAATGTTCTGGCGTTGTTACGTGTATTAGAGGGTTTAA

ATCAGCTTGGCCCTCGCTTAAGAGCCCAAACCGTTTCTGATCGTTTTGCAGAGGG

TAAAATTACAAGTCTGGATGATCTGAATACAACTGCTGCAAAGGTTTCTCATGAAG

AATTCATCAACAGCAAACTTACACCCAAATTAGCTCGACAGATCCAGGACGCGCTT

GCTTTGTGCAGTGGAAGTCTTCCCTCTTGGTGCTACCAGTTGACTACAGCATGCC

CGTTTTTGTTTCCGTTTCAGACCCGGAGACAGTATTTCTATTCAACTGCCTTTGGG

TTGTCGCGTGCATTGAACCGCTTGCAGCAGCAGCAAGGTGCTGACGGCAGTGGT

TCTACAAATGAACGAGAGATGAGAATAGGGAGATTGCAGCGCCAGAAAGTGCGTG

TATCCCGAAATAGAATATTAGATTCTGCTGCGAAAGTTATGGAGATGTATTCTAGC

CAAAAAGCTGTGCTTGAAGTAGAATATTTTGGTGAAGTTGGTACTGGTCTAGGCCC

CACACTTGAGTTTTACACACTCCTAAGCCATGATTTGCAAAAGGTTTCCCTTGGGA

TGTGGAGATCAAATTCTGGTGACAAGTTATCTATGCAAACTGATAGAGATGAGATT

CAAGACGGTAAATCAGCAGCAGCTAGGGACAGAGATATAGTTCAGGCACCACTTG

GGTTGTTCCCTCGGCCCTGGCCCTCAACTGCTGACGTATCTGAAGGTAGTCGGTT

TCATAAAGTTGTTGAATATTTCCGCCTTTTAGGGCGCGTGATGGCAAAGGCACTTC

AAGATGGACGGCTAATGGACGTCCCGTTAAGTACAGCTTTTTATAAGCTCATTCTT

GGTCAAGTGAGTTTTTTACTATCAGTAACTTTTTTTATTTAGCTAAGAGTGGACTAG

TAGTTTCGACTTCTTTACGTTGTTCGTAATTTCTTACTGCTTCTTTACTCACCTGAA

CAGGAGCTTGATTTGCATGATGTTATATTATTTGATGCTGAACTTGGCAAGACTTT

GCAAGAGCTTCGTGTTCTTGTTGGCCGTAAGCACTATCTGGAAGCAGGCGGTGGT

GACAACAGTAGCGGGATTTCTGATTTATGTTTGCGTGGATCCCGTATTGAAGATCT

TTGCTTGGACTTCACCCTACCTGGCTACCCTGAATACATATTGAGACCAGGAGAT

GACATTGTACCGTCTAATAAGCTTTACATCCGATATCTTACTATTGTTTTAGTTCTT

GTCCATTGTTGCTGATGCCGTGTACTGTTTTCTGTTCTATTACAGGTTGATATTAAT

AGTCTTGAGGACTATATATCCCTGGTCGTTGATGCCACTGTCAAGAGAGGAGTTG

CCCGGCAGATTGAAGCCTTCAGATCTGGATTCAATCAGGTTAGCAGTTTCACAGA

CTCTCCGCTTTGTCTCTTACTTTTCCTGTAGGCTTTGGCTTTGGCTTTGGCTTTGG

CTTCTAAATTACATAGGAGTGGTTTCTTTTGGTTCATACTTTATAATCTTTTAAACAA

CAGGTTGATGATAATTTAGTCTTACCTTTATTATCTTTACAAGAATTCTCTGTTCTTA

CACATGATTACCAGGTCTTTGACATAAAATCTCTACAAATATTCACCCCTTCTGAGC

TGGACTACTTGTTGTGTGGTCGTAGAGAGTTGTGGGAGGTGAGTTTTCATCTATTT

TTTGAATTTCCACTACCCATTTGACTCGAATCGACTAGATAAAATTTTCTTTTCTAAA

ACCTTTCTTTTATTGCAGGCGGAGACTCTTGTTGAACATATCAAGTTTGATCACGG

TTATACTGCAAAAAGTCCGGCAATCATTTTCGTAAGTTACTTTCCGTACTAGTTTGT

TAAAAAACCAATTTTCTTTTACAATCAAGCTTTTTGCTTCTTTATTGTTGATTCCTTT

TTGACTTTGATTTTCACCCTGGCGGTAGTTATTGGAGATCATGGGAGAGCTAACAG

-continued

CAGATCAACAGCGGGCTTTCTGCCAGTTCGTAACTGGAGCTCCTAGGCTTCCTCC

TGGTGGCTTAGCTGTTCTCAACCCAAGGCTGACGATTGTGAGAAAGGTAAGAAAC

CTTTACTTATATATTCGGTTAAAAAGCGTTTTTGTAATTGAGCCAAGAGGTTCTAGT

CATGTTAAACTAGACCCACCAAGCCATATATCAGAATACATCTACACGTGACGCAT

TGTTGTGTTTGCAAGACTTGCTAAGATGAATTAGCTCTTACTCGATTTAAGTTGTGT

ATTTGCTTCCAATTGATGTGTTTTTGGCTTGATGCAGCTCTCATCAACCTCAAATGC

TGCTGCCAATGGGACAGGGGCTTCGGAAACAGCAGACGACGATCTTCCCAGCGT

CATGACTTGCGCCAACTACCTTAAGCTCCCTCCTTATTCTACAAAGGTAACTCGTC

TCTCTTTTTTTAAGTCTACGGTTTCTGTGTTTGGTTGGTTGGGGTGAGCCTGAACA

CGAGTTTGTACCTGAAACAGGAAATCATGTACAAGAAACTGCTCTACGCCATCAAC

GAAGGGCAGGGGTCGTTCGACCTATCCTAG

SEQ ID NO: 7: UPL3 genomic sequence; *Brassica napus*
(C03 genomic UPL3 sequence)
ATGGAAACTCGGAGCCGCAAGCGTGCGGAGGCGACCTCAACTGCCCCATCTTCT

TCTTCTTCGTCTCCTCCTCCTCCTCCCTCAGGTCCCACCACTCGCAGCAAACGCG

CTCGCCTCTCGTCTCCCTCTTCCTCTTCAGCCGCCGCCGCTACCACCGCTACTGC

ACCTTCCTCCTCCACCCGCTCTCGTTCTTCTCGCTCTGCCGCTACCGCTACCGCT

ACAGCCGCCGTTACTCCCATGGACACATCCACCGAGTCTTCTGGATTCCGCCGCG

GCGGGGGACGAGGTAACAGGGGAAACGATAATACTAATTCTGATAAGGGAAAGG

AGAAGGAGCATGAGGTTAGGATTAGGGATAGAGAAAGAGACCGAGCCAGACAGC

AGCTCAACATGGACGCTGCAGCTGCTGCAGCCGCCGCCGCTGAAGAGGACGATG

ACAATGATAGTGAGGATGGCAACGGGGGATTCATGCATCCCAACATGAGCTCAGC

CAGCAGTGCGTTACAAGGGTTGCTGAGGAAGCTTGGAGCTGGACTTGATGACTTG

CTTCCTTCTTCAGGTATTGGCTCAGGTTCTTCCTCCCACTTAAATGGGAGGATGAA

GAAGATACTCGCTGGCTTGCGCTCTGAAGGAGAAGAGGGAAAGCAGGTCGAGGC

TTTGACCCAGCTCTGCGAGATGTTATCCATTGGCACCGAAGACTCCTTGAGCACC

TTCTCTGTTGATTCCTTCGTCCCCGTTCTTGTTGGTCTACTTAACCATGAGAGCAA

TCCGGATATTATGCTTCTTGCTGCCAGGGCTCTTACCCATCTGTGTGATGTTTTGC

CCTCTTCTTGTGCTGCTGTTGTTCATTACGGGGCTGTTTCATGCTTTGTCGCCAGA

TTGCTAACCATTGAATACATGGACTTGGCCGAGCAGGTTCGCTTTCCTAGCAATTC

TTGAATTTTTTTTTTTTGAATATAATACTTATCTAAAATCTGGATAAAGTGTATGTTG

TGGAATGTTTTATGCTGCAGTTTCTACACGTACATATCCAATATTTTAATTTACTTA

GGACGAAATTTGAAATTTGATTTTATTCTTCATGTGATTTACAACAGTCTCTGCAAG

CTCTCAAAAAGATATCTCAGGAACACCCAACGGCCTGTTTGCGAGCTGGTGCTCT

TATGGCAGTGCTATCATATCTGGATTTCTTCTCCACCGGTGTCCAGGTGGGTAATT

TTGTAACCTTTCTTTTATGCTTTCCATACTCGTTTATCTAATGCACTTTTTTTTACTTT

GACTTTGTAGCGTGTAGCAGTCTCTACCGCTGCAAATATGTGCAAGAAGTTACCTT

CTGATGCATCTGATTATGTTATGGAAGCTGTACCGGTACTGACAAACCTACTTCAG

TATCATGATGCGAAGGTAAACGATCCTTTTTTTTTGCTGTACTGTGGTACTATCTAG

TTCTGCTCTTGCCCCAGTTTCCTTCATAGTATGTTCGTACGGTGACAGGTTTTGGA

ATATGCTTCTATCTGTTTGACTCGGATTGCCGAAGCATTTGCATCGTCCCCTGATA

-continued

AATTAGATGAATTATGCAACCATGGCCTGGTGACTCAAGCTGCGACTCTTATATCC

GCTAGCAACTCGGGAGGTGGGCAAGCATCTCTTGGTGTTTCAACATACACGGTAT

GAGTTAATTCTTTCGTGTTTTCTATATTTCGTTATTCATAGGATGACATTTTCATCAT

ATTTTCACAGGGATTAATCCGATTACTTTCCACCTGTGCGAGCGGTTCACCTCTTG

GGTGCAGGACATTACTTCTTCTCGGTATTAGTAGCATTCTTAAGGATATTCTGTCG

GGTTCTGGTGTCTCTGCTAATGCATCTATATCCCCAGCACTGAGCAGGCCTGCAG

ATCAGGTACGGATTTACTTTTTGACATCACAGACTTTATTTTGTTCATTTCCTGATA

AAATAAATGGTGTACAATGAGATGCTTAGGGGACACACCTTCAAATAGATCACTTG

CATTTAGGAGATTTGTCTATTCAGCTCGATGATAATCTATGTACATGTATTTTGAGC

TTTATTTATGTTGTAGCCGATGGCTCAAGTTTCCTATGCTTGTTTTCTGGTCTGGTG

TTAGAAGTGGTATAGATAAAAGCGCTTAGCGCTTCATCAGTGTGCTCTGTCTTGTT

TATTTAACTTTGATCCCATGACTCTCTAATTCTTGAATATATTCTTGAACATGATCAT

GTGAGGTCCTTTGTTTCCAGAAAGGTTCCGAATTATAACTCTTGTTTTGCGTCTTA

GATTTTTGAGATAGTCAACCTAGCGAACGAGCTCCTCCCTCCATTGCCAGAAGGA

AGTATCTCCCTTCCTACTAGCGCAAACGCGTTAGTGAAAGGTTCAGGCCAAAAAA

ATTCTTCTCCAAGTACTTCAGGAAAACAAGAAGATTCTCCCAAAGTTTCACCTAGA

GAAAAATTACTTAGTGATCAACCCGAACTTTTGCAGCAATTTGGATTGGATCTTCTT

CCAGTTTTAGTGCAGGTAATTTTTTGTTGCGGTTGCTACAAGTTAATGTTCATACAA

CCTCCTGTATGTCTAATTACCCTTGTTTTCTTTCCAACAGATCTATGGTTCTAGTGT

CAATGGTACTATTCGTCATAAATGTCTCTCCGTTATCGCAAAGTTGATGTATTTCAG

CACTCCAGAAATGATTCAATCTCTAATTGGTGACACAAATATATCGAGGTATGCTG

TTTATGTTTTAAATTAGGTATCACATGGCGCAACTTCTTACATTATTTTTCCTATGTA

GCTTCTTGGCTAGTGTCTTGGCATGGAAAGATCCACAAGTCTTGGTTCCTGCTCTA

CAAGTTGCAGAAATTCTGATGGAAAAACTTCCTGAAACTTTCTCGAAAGTGTTTGT

GAGGGAAGGGGTGGTTCATGCTGTAGATCAACTTGTCTTGGTTGGTAAACCTAGT

GCTAATGCTTCTACTGATCAGGAAAATGACTGTGTGCCTGGATCTGCACGATCTA

GGCGTTACAGACGGCGAAGTAGTAATGCCAATTCTGATGGAAATCAGTCGGAAGA

GCTTAAGAATTCTGTGTCAGCTAGCATAGGTGCGACCCATAATTCCATGGAATCTC

CTACAGCGAGCTTCATGCTAAGGGAAACAGTTAGCTCCTGTGCAAAAGCATTCAA

AGACAAGCACTTCCCGTCTGATGGTGGGGAATTTGATGTTGGAGTTACAGATGAT

CTCTTGCATCTGAAGAATCTTTGCACGAAGCTAACTGCTGGTACAAATGATCATAA

AGTGAAAGGAAAGGGGAAATCTAAAGTCTCTGGGCCATGCCTTGGCGATTTTTCT

GCTAGCAAAGAAGAATACTTGATTGGTATCATCTCCGAGATACTTGGCGAGCTAA

GCAAAGGGGATGGCGTCTCAACTTTTGAGTTTATTGGCAGTGGTGTGGTAGCAGC

ATTGCTTAACTATTTTTCTTATGGATACTTTTCCAAAGAGAAGATCTCCGAGGTTGA

TTTGCCCAAACTTCGCCAGGATGGGCTCAGAAGGTTCAAAGCTTTTCTAGAAATTG

CACTTCCTTCTGATGGTAATGAGGGAAAGATCCCTCCTATGACTGTTTTGATTCAG

AAACTTCAAGATGCTTTGTCTTCACTGGAACGCTTTCCGGTCGTCCTTAGCCATCC

CTCAAGGTCACTCAGTGGAAGTGCTCGTCTCTCATCTGGATTGAGTGCTTTGGCA

CATCCTTTGAAGTTGCGGTTATGCCGTGCACCTGGAGAGAAGGCTCTACGTGATT

ACTCCTCCAATATTGTTCTCATAGATCCATTGGCAAGCATAGCAGCAGTGGAGGAA

-continued

TTTCTCTGGCCCCGAGTTCAACGCAGTGAATCTGGGGTGAAGGCAGCAGCGCCT
GCTGGAAACACTGAGCCAGGCACATTACCTAGCGGTGCTGGTGTTTCATCACCAT
CCTCGTCAACTCCAGCTTCCACCACTCGTCATTCTTCTAGATCTAGATCAGCAATT
AAAATAGGCGATGCCTCAAAGAAAGAACCTGTGCACGAGAAAGGTACCAGCTCAT
CTAAAGGTAAAGGTGTTATGAAGCCGGCTCAGCCGGATAAGGGGCCTCAGACAA
GGAGCAGTGCTCAAAGGAAAGCTGTTCTTGACAAAGATACACTAATGAAACCAGC
TAGCGGAGACTCCAGCTCTGAGGTATGTCACTGTAGGAAGTTCTGGATTACATGG
TTGTTTATTGTGTAACATTATATTATGTTTGTGGTGTGATCTGCTTATGCAGCACTA
TCTTACTTATATTGCTTGCAGGACGAAGAAATGGATATATCCCCCGTCGACATGGA
TGATGCTTTGGTGATTGAAGAGGAAGACATTTCTGACGACGATGATGATGATGAT
GAGGAGGATGTAAGTATTCCCTCCCCAGTATGTACATTACAGACGCAATTATTTCT
CTTGCTAACAACATGAAAGATGATACTTCTCGCAATAATGCTTGCTAGCTTTCCGT
ATTCTTAGATAAGTTTACCATATTGAGCTGACCTTATCGGAACCTTTCCTTTTAGAA
CTGACTAAAGAGAATTATGAACTTTATACCACAATTTCTCATATTGATCTGGTCTTG
AATTCAGGTCTTGGATGACAGTCTTCCCATGTGCACCCCTGATAAGGTTCATGATG
TAAAATTGGGAGACGCAGTGGATGATGAGGGAGCCGGCCTAGCACCTAGCGGCC
GACAGATGAATTCAGCTTTGGCAGGAAGTAGTGGAACAGCAACTGCAAGGGGATC
TAATTCTACTGATGCTGGCATTGGGAATCTTTATGGTTCTAGGGGTGCACTCTCCT
TCGCTGCTGCGGCGATGGCAGGGCTTGGAGCTGCCAGTGGTAGAGGTATCAGG
GGGAGTAGAGACCTACATGGGCGTACCCTGAATCGAAGTTCTGATGAGTCCTCTA
AGTTGATGTTTACTGCGGGAGGAAAGCAACTTAGTAGGCATATGACGATATATCA
GGCTGTGCAACGACAACTTATGCTAGACGAAGATGATGATGACAGGCTCGGTGG
CAGCGATTTCATCTCGAGTGATGGAAGCAGATTAAATGATATATATACTATCATGT
ACCAGATGCCGGACAGCCAAGCGAATAGGTTGTCTGCTGGTGGTGCAAGTTCTAC
CACACCATCTAAATCCACTAAATCTGCTACTACTAATGCAAGCGTAGAAGCCCAGT
CGTATAGGGCATCTCTTTTGGATAGTATCGTACAAGGAAAGCTTCCATGCGACCTT
GAGAAGGCAAATTCTACGTATAATGTTTTGGCGTTGTTGCGTGTACTAGAGGGTTT
AAATCAGCTTGGCCCTCGGTTAAGAGCCCAAACCATTTCTGATCGTTTCGCAGAG
GGTAAAATTACAAGTCTGGATGATCTGAATACAACTGCTGCAAAGGTTTCTCATGA
AGAATTCATCAACAGCAAACTTACACCCAAATTAGCTCGACAGATCCAGGACGCG
CTTGCTTTGTGCAGTGGAAGTCTTCCCTCTTGGTGCTACCAGTTGACTACAGCATG
CCCGTTTTTGTTTCCGTTTCAGACCCGGAGACAGTATTTCTATTCAACTGCCTTTG
GGTTGTCGCGTGCATTGAACCGCTTGCAGCAGCAGCAAGGTGCTGACGGCAGTG
GTTCTACAAATGAACGAGAGATGAGAATAGGGAGATTGCAGCGCCAGAAAGTGCG
TGTATCCCGAAATAGAATATTAGATTCTGCTGCGAAAGTTATGGAGATGTATTCTA
GCCAAAAAGCTGTGCTTGAAGTAGAATATTTTGGTGAAGTTGGTACTGGTCTAGG
CCCCACACTTGAGTTTTACACACTCCTAAGCCATGATTTGCAAAAGGTTTCCCTTG
GGATGTGGAGATCAAATTCTGGTGACAAGTTATCTATGCAAACTGATAGAGATGAG
ATTCAAGACGGTAAATCAGCAGCAGCTAGGGACAGAGATATAGTTCAGGCACCAT
TTGGGTTGTTCCCTCGGCCCTGGCCCTCAACTGCTGACGTATCTGAAGGTAGTCG

-continued

GTTTCATAAAGTTGTTGAATATTTCCGCCTTTTAGGGCGCGTGATGGCAAAGGCAC

TTCAAGATGGACGGCTAATGGACGTCCCGTTAAGTACAGCTTTTTATAAGCTCATT

CTTGGTCAAGTGAGTTTTTTTACTATCAGTAACTTTTTTTATTTAGCTAAGAGTGGA

CTAGTAGTTTCGACACTTCTTTACGTTGTTCGTAATTTCTTTTTCTTTTCTCACCTGA

ACAGGAGCTTGATTTGCATGATGTTATATTATTTGATGCTGAACTTGGCAAGACTTT

GCAAGAGCTTCGTGTTCTTGTTGGCCGTAAGCACTATCTGGAAGCAGAAGGTGGT

GACAACAGTAGCGTGATTTCTGATTTATGTTTACGTGGATCCCGTATTGAAGATCT

TTGCTTGGACTTCACCCTACCTGGCTATCCTGAATACATATTGAGACCAGGAGATG

ACATTGTACCGTCTAATAAGCTTTACATCCCATATCTTACTATTCTTTTAGTTCTTGT

CCATTGTTGCTGATGCCGTGTACTGTTTTCTGTTCTATTACAGGTTGATATTAATAG

TCTTGAGGACTATATATCCCTGGTCGTTGATGCCACTGTCAAGAGAGGAGTTGCC

CGGCAGATTGAAGCCTTCAGATCTGGATTCAATCAGGTTAGCAGTTTCACAGACT

CTCCGCTTTGTCTCTTACTTTTCCTGTTGGCTTCTAAATCATATGGAAGGAGTGGT

TTCTTTTGGTTCATTCTTCATAATCTTTTAAACAACAGGTTTATATTAAGTCTTTAAT

TTAGTCTTACCTTTATTATCCTTACAAGACCTCTCTGTTCTTACACATGATTACCAG

GTCTTTGACATAAAATCTTTACAAGTATTCACCCCTTCTGAGCTGGACTACTTGTTA

TGTGGTCGTAGAGAGTTGTGGGAGGTAATTTGTAATTTTTCAACTTTCTTTTGAATT

TCCACTACCCATTTGACTTGAATCAACTAGATAAAATTTTCATTTCTAAAACCTTTCT

TTTATTGCAGGCGGAGACTCTTGTTGAACATATCAAGTTTGATCACGGTTATACTG

CAAAAAGTCCGGCAATCATTTTCGTAAGTTACTTTCCTCACTAGTTTTTTAAAAAAC

CAATTTTCTTTTACAATCAAGCTTTTTGCTTCTTTATTGTTGATTCCTTTTTGACTTT

GATTTTCACCCTGGTGGTAGTTACTGGAGATCATGGGAGAGCTTACAGCAGATCA

ACAGCGTGCTTTCTGCCAGTTTGTAACTGGAGCTCCTAGGCTTCCTCCTGGTGGC

TTAGCTGTTCTCAACCCAAAGCTGACGATTGTGAGAAAGGTAAGAAACCTTTACTT

ATATATTCGGTTAAAAAGCGTTTTTTTAATTGAGCCAAGAGGTTCCTAGTCATGTTA

AACTAGACCCACCAAGCCATATATCAAAATACATCTACACGTGACGCATTTGCTTG

CATTTGCAAGACTTGTTAAGAGGAATTAGCTCTTACTCGATTTAAGTTGTGTATTTG

CTTTCAATTGATGTGTTTTTGGCTTGATGCAGCTCTCATCAACCTCAAATGCGGCT

GCCAATGGGACAGGGGCTTCGGAAACAGCAGACGACGATCTTCCCAGCGTCATG

ACTTGCGCCAACTACCTTAAGCTCCCTCCTTATTCTACAAAGGTAACTCGTGTCTC

TCTTTTTTTAAGTCTATGGTTTCTGTGTTTGGTTGGTTGGAGTGAGCCTGAATAGG

AGTTTGTACCTGAAACAGGAAATCATGTACAAGAAACTGCTCTACGCGATCAACGA

AGGGCAGGGATCGTTCGACCTCTCCTAG

SEQ ID NO: 8; *Arabidopsis Thaliana* UPL3 genomic sequence

*ATGGAAACTCGGAGCCGCAAGCGGGCGGAGGCGACCTCAGCTGCCCCATCTTCT*

*TCTTCTTCTTCTCCTCCTCCTCCTCCCTCTGCCTCTGGTCCCACCACCCGCAGCAA*

*ACGCGCTCGTCTTTCTTCTTCTTCTTCTTCCTCACTTGCCCCCACTCCTCCTTCTTC*

*CTCCACCACCACCCGCTCTCGTTCTTCTCGCTCTGCCGCCGCCGCTGCTCCCATG*

*GACACCTCCACCGACTCTTCTGGATTTCGCCGAGGCGGACGTGGTAACAGGGGA*

*AACAACAACGATAATTCTGACAAAGGTAAGGAGAAGGAACATGACGTTAGGATTA*

*GGGAGCGTGAAAGAGAAAGAGACCGAGCCAGAGAACAACTCAACATGGATGCTG*

-continued

CCGCCGCCGCTGCTAGGAGCGCTGACGAGGATGACGACAATGACAGTGAGGATG

GCAACGGCGGTTTCATGCATCCTAACATGAGCTCTGCGAGCAGTGCTTTACAAGG

CTTGCTCAGGAAGCTCGGTGCTGGATTGGATGACTTGCTTCCTTCTTCCGGTATC

GGCTCTGCTTCTTCCTCCCACTTGAATGGAAGGATGAAGAAGATTCTCTCTGGCTT

GCGCGCTGAAGGAGAAGAGGGAAAACAGGTCGAGGCTTTAACCCAGCTTTGTGA

GATGTTATCCATTGGGACCGAAGACTCGCTTAGCACCTTCTCTGTTGATTCCTTCG

TCCCAGTTCTTGTCGGTCTACTTAACCATGAAAGCAATCCCGACATTATGCTTCTT

GCTGCCAGGGCTCTTACCCATCTATGTGATGTCTTGCCGTCTTCTTGTGCTGCTGT

TGTACATTACGGGGCAGTTTCATGCTTGGTGGCCAGATTGCTAACCATAGAATACA

TGGACTTGGCGGAACAGGTTGGCTATCATACCAATACTTGAATCCTCGATGCTCC

AGCTGCTTTTTTAAAAATTCTTCAGGGATCACACTTGAAATTTGATTCGTATTTATG

TATGTGTTTTAAAACAGTCTCTGCAAGCTCTCAAAAAGATATCTCAGGAGCACCCA

ACTGCCTGTTTGCGAGCTGGTGCTCTTATGGCTGTGCTCTCGTATCTGGATTTCTT

CTCCACTGGTGTTCAGGTGGGTAAATTTCTAACTTCTCTTTTATGCTACACTTACTC

GTGTATCTAATGCACATGTTACTTGGCTTCTTGTAGCGCGTAGCACTATCTACTGC

TGCCAACATGTGCAAGAAACTACCTTCTGATGCATCTGATTATGTTATGGAAGCTG

TACCTTTGCTGACAAACCTACTTCAGTATCATGATTCGAAGGTAATTGACCTGCTTT

CTGTTATAATATGGTACTAATATCTAGTTCCGCTCTTACCCCAGTCTCCTCCATAAT

CTGTTCGTATGATGGTAGGTTTTGGAATATGCTTCTATCTGTCTGACTCGAATTGC

TGAAGCATTTGCACCGTATCCCGAGAAATTAGATGAATTATGTAACCATGGCCTGG

TGACGCAAGCTGCGTCTCTTATTTCCACGAGCAATTCAGGAGGTGGGCAAGCATC

TCTTAGTGTGTCAACATACACGGTAAGCGTAAAATCTTTATTGTGTTTTATTTATCC

TTATACACAAGATGACATTTTCACCATATTGTGCACAGGGGTTAATCCGATTACTTT

CTACCTGTGCGAGCGGGTCACCTCTTGGATTCAGGACATTACTTCTTCTTGGTATT

AGTAGCATTCTTAAGGATATTCTGTTGGGTTCTGGGGTCTCTGCTAATGCATCTGT

ATCCCCAGCACTGAGCCGGCCTGCAGATCAGGTAATTACCTTTTCTGTTTAATACC

TGACTGAAATAAGAATAGCTTAAATTTAGGGTACATTCTCTATTTCGGGCATAGTTT

CCTACTTGTTTTTGTATTACCAAGTTTTACTTAGGTGTTTGTATAGTGTATTGATCAT

AGTCTATATACAGGTCTTATAATCTGTACTTATGTTGGAGTACTCTTATGCCTGTTC

TGCTCTTATGTTAGATCTAGGTTTTTTATCTCATGGTCTCTAATTCTGGAATCTATA

AATTTTGCTTTATATATTAGATTTATGAGATAGTCAACCTAGCGAATGAGCTCCTCC

CTCCATTGCCAGAAGGAGTTATCTCTCTTCCTACTAGCACAAACGCTCTTGTGAAA

GGTTCATGCCAAAAGAAATCTAGTCCAAGTACTTCAGGAAAACAAGAAGATATTCT

AAAAATTTCACCAAGAGAAAAATTACTTGGTGATCAACCTGAACTTCTGCAGCAGT

TTGGATTGGATCTTCTTCCAGTTTTAGTGCAGGTAATTTTTCTCTGCGTTGGCTACA

AGATAATGCTCATACTACCTGCTGTTTTGTCTAATTATTCTTGTTTTCTTTTGCAACA

GATCTATGGTTCTAGTGTCAATGGTACGATTCGCCATAAATGTCTCTCAGTCATTG

GAAAGTTGATGTATTTCAGCAGTTCAGAAATGATTCAATCTCTAATTGGTGACACA

AATATTTCGAGGTATGCTGTTTACGATATAAATTAAGTTTGACACGACAGTGTGTG

CAACTTCTTACATTTTTTTCTTCTTATGTAGCTTCTTGGCTGGTGTCTTGGCATGGA

AAGACCCACAGGTCTTGGTTCCTGCTCTACAAGTTGCAGAGATTTTGATGGAAAA

-continued

*GCTTCCTGAAACATTCTCGAAAGTGTTTGTGAGGGAAGGGGTAGTCCATGCTGTA*

*GATCAACTTGTCTTGGTTGGTAAACCATCCCATGCCTCACCTACTGATAAGGACAA*

*TGACTGTGTACCCGGATCTGCACGATCTAGGCGTTATAGACGGCGCAGTAGTAAT*

*GCCAATTCCGATGGAAACCAGTCGGAAGAGCCTAAGAATCCTGCGTCCCTTACCA*

*TAGGGGCAAACCATAATTCCCTTGATACTCCTACAGCTAGCTTCATGCTAAGGGAA*

*ACAGTTAGTTCCTGCGCCAAAGCATTCAAAGACAAGTACTTCCCGTCTGATGGTG*

GGGATGTTGATGTTGGAGTTACAGATGATCTTTTACATCTGAAGAATCTTTGCACG

*AAGCTAACTGCTGGTATAGATGATCATAAAGTGAAAGGAAAGGGAAAATCTAAAGC*

*CTCTGGGCCATTCCTTGGCGATTTCTCTGCTAGCAAGGAAGAGTACTTGATTGGT*

*GTCATTTCTGAGATACTTGGCGAGATAAGTAAAGGGGATGGTGTCTCAACTTTTGA*

*GTTTATTGGCAGTGGTGTGGTTGCAGCATTGCTTAACTATTTTTCTTGTGGATACTT*

*TTCCAAAGAGAAGATCTCCGAACTTAATTTGCCCAAACTTCGCCAGGAGGGACTC*

*AGAAGGTTTAAAGCTTTTCTAGAAGTCGCTCTTCCTTTTGATGGTAATGAGGGAAA*

*GGTCCCTCCTATGACAGTTTTGATTCAGAAACTTCAAAATGCTTTATCGTCACTGG*

*AGCGCTTTCCTGTTGTCCTTAGCCATCCCTCAAGGTCACTAAGTGGAAGTGCTCG*

*GCTCTCCTCGGGTTTGAGTGCTTTGGCACATCCTTTAAAGTTGCGATTATGCCGA*

*GCATCTGGAGAGAAAACACTACGTGATTACTCCTCCAATATTGTACTTATAGATCC*

*ATTGGCAAGCTTAGCAGCAGTGGAGGAATTTCTGTGGCCCCGAGTTCAACGGAGT*

*GAATCTGCTCTGAAGCCGGCAGCGCCTATTGGCAATACAGAGCCAGGCACGTTA*

*CCTAGCGGTGCTGGTGTTTCATCACCATCTTCGTCAACTCCAGCTTCAACCACTC*

*GTCGTCATTCTTCTAGATCTCGATCGGCAATTAACATCGGTGATACTTCAAAGAAA*

*GATCCTGTGCATGAGAAAGGTACCAGCTCATCGAAAGGAAAAGGTAAAGGCGTTA*

*TGAAACCGGCTCAGGCGGATAAGGGGCCTCAAACAAGGAGCAATGCTCAAAAGA*

*GAGCTGTTCTTGACAAAGATACTCAAATGAAACCAGCTAGCGGAGACTCCAGTTC*

*TGAGGCATGTTACAGTGCTAAGTTTTTGATAACATAAATGTTTTACTTCGTTACTTC*

*GTTACTTCGTTACATCATGATCTTGTGGTGTGATTTACTTACTCAACACAATCTTAC*

*TTGTATGCCTTGCAGGATGAGGAATTGGAAATATCCCCAGTCGACATTGATGATG*

*CCTTGGTGATTGAAGAGGATGACATTTCTGATGATGAAGATGATGATAATGAAGAT*

*GTAAGTTGTCCTTTGGTTTTCTTCTCCGCGATTGTTGTTTTTGCTAACACCGTAATA*

*GATATTGCATTTGGCAATAAAGCTTGACAGCTTTCATATTTTCGAATTATCTTGCCT*

*TGTTGAGTCTGTTTTGTTGATAAGCCGAACTCACTTGGAACCTTTTCTTTTTAGAAT*

*AGACCAAGTAGATTTACTAGCTTATGCCCCTATTTCTCATATTTATCTCGCTGCTAT*

*CAATAACTTTGGCTTTGTACCTTACATGTGCTCTTGATTTTCTTTCAATACCTTCAC*

*AATCATATATACTTTCATGTCCAGGTTTTGGATGACAGTCTTCCCATGTGCACGCC*

*TGATAAAGTCCATGATGTGAAATTGGCGGACTCAGTGGATGATGATGGTCTAGCA*

*ACCAGCGGCCGACAAATGAATCCAGCTTCTGGAGGCACTAGTGGAGCCGCAGCA*

*GCAAGGGCATCTGATTCTATTGATACTGGCATTGGGAATTCCTATGGTTCTAGAGG*

*TGCACTCTCCTTTGCTGCTGCAGCGATGGCTGGGCTTGGAGCTGCCAGTGGTAG*

*AGGTATCAGGGGAAGTAGGGACTTGCATGGACGTACCCTAAATCGAAGTTCAGAT*

*GAGCCCTCTAAGTTGATATTTACTGCGGCAGGAAAACAACTTAGTAGGCATTTGAC*

-continued

*GATTTATCAGGCTGTACAGCGACAACTTATGCTAGATGAAGATGATGATGACAGGT*

*TTGGTGGCAGTGATCTAGTCTCAAGTGATGGAAGCAGATTCAATGATATTTACACC*

*ATCATGTACCAGAGGCCAGACAGCCAAGTGAATAGGTTGTCTGTTGGTGGAGCAA*

*GTTCTACCACACCGTCAAAATCCACGAAATCTGCTACTACCAATTCCAGTGTAGAA*

*TCTCAGTCACATAGGGCATCTCTTTTGGATAGTATCTTACAAGGGGAGCTTCCATG*

*CGACCTTGAGAAGTCGAATTCTACATATAATGTTCTGGCACTGTTACGTGTATTAG*

*AGGGTTTAAATCAGCTTTGCCCTCGTTTAAGAGCCCAAACTCTTTCCGATCGTTTT*

*GCAGAGGGTAAAATTACAAGTCTAGATGATCTGAGTACAACTGCTGCTAAGGTTC*

*CTCTTGATGAATTTGTCAATAGCAAACTTACACCCAAATTGGCTCGACAAATCCAG*

*GATGCGCTTGCTTTGTGCAGTGGAAGTCTTCCCTCTTGGTGCTACCAGTTGACTA*

*GAGCATGCCCATTTTTGTTTCCGTTTCAAACCCGGAGACAGTATTTCTACTCGACT*

*GCTTTTGGGTTGTCTCGTGCATTGAATCGTTTGCAGCAGCAGCAAGGTGCTGACG*

*GCAGTGGGTCTACAAATGAACGAGAGATGAGAATAGGGAGATTGCAGCGCCAGA*

*AAGTCCGTGTATCCCGAAATAGGATATTAGATTCTGCTGCAAAAGTTATGGAGATG*

*TATTCTAGCCAGAAAGCTGTGCTTGAAGTAGAATATTTTGGTGAAGTTGGTACTGG*

*TCTAGGCCCTACCCTTGAGTTTTACACACTTCTAAGCCATGATCTGCAAAAGGCTT*

*CCCTAGGGATGTGGAGATCAAGTTCTGGTGACAAGGTATCTATGCAAATTGGTAG*

*AGATGAGATTGAAGACGGAAAACCATCTGCAGCTAACAGAGATATAGTTCTGGCA*

*CCACTTGGATTGTTTCCTCGGCCTTGGCCCTCAACAGCTGACATATCTGAAGGTG*

*GTCAGTTTCATAAAGTCATTGAATATTTCCGCCTTTTAGGGCGTGTGATGGCCAAA*

*GCACTTCAAGATGGACGGCTATTGGACGTCCCATTGAGTACAGCGTTTTATAAACT*

*TATTCTTGGTCAAGTGAGTTTTTTTTTTACTACTAGTGTTTGTTTAGTTAAAAGTGAA*

*ATAGTGGTTTCTACTTTTTCACTTCTGTCGGCCTTTGCTAATAAGTTCGTCCTCTTT*

*CATTGACTAAGCAGGAGCTTGATTTGCATGATATTGTATTATTTGACGCTGAACTT*

*GGCAAGACCTTGCAAGAGCTGCGTGTTGTTGTTGCCCGCAAGCACTATCTGGAG*

*GGAGTAGGTGGTGACAATAGCAGCACGATTTCTGATTTATGTTTACGTGGATGCC*

*GAATAGAAGATCTCTCCTTGGAATTCACGCTACCTGGCTATCCTGAGTACATCCTG*

*AGATCAGGAGATGAAATTGTACTGTCTTAGCTTACACCCCACCTCTTACTATTCTTT*

*TAGAACATGTCCATGATTGCTGATGACGTGCTGTTTTGTTACAGGTTGATATTACT*

*AATCTTGAGGAGTATATATCCCTTGTCGTTGATGCTACTGTCAAGAGAGGAGTCAC*

*TCGGCAGATCGAAGCCTTCAGATCTGGATTCAATCAGGTTAACAGTCTCGCAGAC*

*TTTCTGTCTCTTTCTTTGTCTATTGCCTTTGGCTTCTAAACATAATATAGAAAATTCT*

*GTAGATTAGAGACTTGCATTTTTTCTTTTTAGGGCGGACCTTAAACTTTTACCTTCA*

*TTTGTTAACTTACAAAACCTTTCTGTTTCTGCACATAATTATCAGGTGTTTGACATA*

*ACATCTCTACAAATATTCACCCCTTCTGAGCTGGACTATTTGCTGTGTGGTCGTAG*

*AGAGTTGTGGGAGGTGAATTTTTCACTTTTCAATTTCCATAACCAAGAGACTTGAA*

*TCCCTTAGATGTAAGAAAATATCATTTCTAAAACTTTCTTTTCTTGCAGGTGGAGAC*

*TCTTGCTGAACATATCAAATTTGATCATGGGTATAATGCCAAAAGTCCGGCAATCA*

*TTAACGTATGTTATCCATCAAGTTGTTAGATATCATATCTTTATTTATTCTTACCTTT*

*CCTTTTGTTTCTGAACCGTTGATTACTTTCTGATTCTGATTTTCACCCCACCCTGTA*

*GTTACTGGAGATCATGGGAGAACTTACAGCAGATCAGCAGAGGGCTTTCTGCCAA*

-continued

*TTTGTAACTGGAGCTCCTAGGCTTCCTCCTGGTGGCTTAGCTGTTCTGAACCCAAA*

*GCTTACGATTGTGAGAAAGGTAAAAAAACTTTAAATCATTTGCAAGTCATTTTTGTA*

*ATTTAGCCACCAAGGATATGTTAGAAGGCATCTATGTGTGGGCAAGGGCTTTTGC*

*TCTTTTTTTCTAAGAGCAGACACGTATTGTGGTGTTTGTTTGCATTGGCAAGAGTTA*

*TTCAGATGAATTATGTCTTACTGTCGTGAAGTTGTTAATTATTGGTTTTGCATGGGA*

*TTCTAAAATTGCATGTGTCTTTGGCTGGTGCAGCACTCATCGACCTCAAGTGCAGC*

*AGCCAACGGAGCAGGGGCTTCGGAGACAGCAGATGATGATTTGCCCAGTGTCAT*

*GACTTGCGCAAACTACCTTAAACTCCCTCCTTATTCTACAAAGGTGAGTCATGTCT*

*TCTATTCTTCTTGAGTCCATGTTAGTGTGGTTGTTGGTGAGCCTGAGGAGTTGTAT*

*GTTATTGAAACAGGAAATCATGTACAAGAAACTGCTCTACGCCATCAACGAAGGG*

*CAAGGATCGTTCGACCTCTCATAAGCAACATATGGCTGTGTTTCTTCCTCCCCTCT*

*CTTGTACATTACATCGGAAGACTGGTTTTGATTTCTCTGCTTTTTTGGGTTTTTATG*

ATCTGACAAAGCCGAAGATACCCCAAAATCCAGGTGACTACTGTTGTTCTCCCGG

*AGACTTTGTAATGGAGGGGATATAGGGTTGTGACTTGTGATGTAAATTTTGTCTTT*

*GCAGGCTCTGCAGAAGGCGCCGCCATTATTGTGTAGATAAAGAAAGATGATAGGC*

*TTATCTTTTCCTTCCTTTTTTTTTTTTTCTTCTTCTTCTTCGTTTCTTAGATTCCCTCT*

*ATGTAAAAGATCGATCATTTCATTTGGTCGGTCAAAACTATGGAAACTCAAGTTCG*

*ATCCGTCTCAGAAAACTAGAATATGGACGGCACTTTGAATATGTTTAACAATGAGT*

*TACATATATAGTTTAGCTTCATTATATAAGCTCTCTTATTACATCA*

SEQ ID NO: 9; *Arabidopsis Thaliana* UPL3 CDS sequence
*ATGGAAACTCGGAGCCGCAAGCGGGCGGAGGCGACCTCAGCTGCCCCATCTTCT*

*TCTTCTTCTTCTCCTCCTCCTCCTCCCTCTGCCTCTGGTCCCACCACCCGCAGCAA*

*ACGCGCTCGTCTTTCTTCTTCTTCTTCTTCCTCACTTGCCCCCACTCCTCCTTCTTC*

*CTCCACCACCACCCGCTCTCGTTCTTCTCGCTCTGCCGCCGCCGCTGCTCCCATG*

*GACACCTCCACCGACTCTTCTGGATTTCGCCGAGGCGGACGTGGTAACAGGGGA*

*AACAACAACGATAATTCTGACAAAGGTAAGGAGAAGGAACATGACGTTAGGATTA*

*GGGAGCGTGAAAGAGAAAGAGACCGAGCCAGAGAACAACTCAACATGGATGCTG*

*CCGCCGCCGCTGCTAGGAGCGCTGACGAGGATGACGACAATGACAGTGAGGATG*

*GCAACGGCGGTTTCATGCATCCTAACATGAGCTCTGCGAGCAGTGCTTTACAAGG*

*CTTGCTCAGGAAGCTCGGTGCTGGATTGGATGACTTGCTTCCTTCTTCCGGTATC*

*GGCTCTGCTTCTTCCTCCCACTTGAATGGAAGGATGAAGAAGATTCTCTCTGGCTT*

*GCGCGCTGAAGGAGAAGAGGGAAAACAGGTCGAGGCTTTAACCCAGCTTTGTGA*

*GATGTTATCCATTGGGACCGAAGACTCGCTTAGCACCTTCTCTGTTGATTCCTTCG*

*TCCCAGTTCTTGTCGGTCTACTTAACCATGAAAGCAATCCCGACATTATGCTTCTT*

*GCTGCCAGGGCTCTTACCCATCTATGTGATGTCTTGCCGTCTTCTTGTGCTGCTGT*

*TGTACATTACGGGGCAGTTTCATGCTTGGTGGCCAGATTGCTAACCATAGAATACA*

*TGGACTTGGCGGAACAGTCTCTGCAAGCTCTCAAAAAGATATCTCAGGAGCACCC*

*AACTGCCTGTTTGCGAGCTGGTGCTCTTATGGCTGTGCTCTCGTATCTGGATTTCT*

*TCTCCACTGGTGTTCAGCGCGTAGCACTATCTACTGCTGCCAACATGTGCAAGAA*

*ACTACCTTCTGATGCATCTGATTATGTTATGGAAGCTGTACCTTTGCTGACAAACC*

*TACTTCAGTATCATGATTCGAAGGTTTTGGAATATGCTTCTATCTGTCTGACTCGAA*

-continued

*TTGCTGAAGCATTTGCACCGTATCCCGAGAAATTAGATGAATTATGTAACCATGGC*

*CTGGTGACGCAAGCTGCGTCTCTTATTTCCACGAGCAATTCAGGAGGTGGGCAAG*

*CATCTCTTAGTGTGTCAACATACACGGGGTTAATCCGATTACTTTCTACCTGTGCG*

*AGCGGGTCACCTCTTGGATTCAGGACATTACTTCTTCTTGGTATTAGTAGCATTCT*

*TAAGGATATTCTGTTGGGTTCTGGGGTCTCTGCTAATGCATCTGTATCCCCAGCAC*

*TGAGCCGGCCTGCAGATCAGATTTATGAGATAGTCAACCTAGCGAATGAGCTCCT*

*CCCTCCATTGCCAGAAGGAGTTATCTCTCTTCCTACTAGCACAAACGCTCTTGTGA*

*AAGGTTCATGCCAAAAGAAATCTAGTCCAAGTACTTCAGGAAAACAAGAAGATATT*

*CTAAAAATTTCACCAAGAGAAAAATTACTTGGTGATCAACCTGAACTTCTGCAGCA*

*GTTTGGATTGGATCTTCTTCCAGTTTTAGTGCAGATCTATGGTTCTAGTGTCAATG*

*GTACGATTCGCCATAAATGTCTCTCAGTCATTGGAAAGTTGATGTATTTCAGCAGT*

*TCAGAAATGATTCAATCTCTAATTGGTGACACAAATATTTCGAGCTTCTTGGCTGG*

*TGTCTTGGCATGGAAAGACCCACAGGTCTTGGTTCCTGCTCTACAAGTTGCAGAG*

*ATTTTGATGGAAAAGCTTCCTGAAACATTCTCGAAAGTGTTTGTGAGGGAAGGGGT*

*AGTCCATGCTGTAGATCAACTTGTCTTGGTTGGTAAACCATCCCATGCCTCACCTA*

*CTGATAAGGACAATGACTGTGTACCCGGATCTGCACGATCTAGGCGTTATAGACG*

*GCGCAGTAGTAATGCCAATTCCGATGGAAACCAGTCGGAAGAGCCTAAGAATCCT*

*GCGTCCCTTACCATAGGGGCAAACCATAATTCCCTTGATACTCCTACAGCTAGCTT*

*CATGCTAAGGGAAACAGTTAGTTCCTGCGCCAAAGCATTCAAAGACAAGTACTTC*

*CCGTCTGATGGTGGGGATGTTGATGTTGGAGTTACAGATGATCTTTTACATCTGAA*

*GAATCTTTGCACGAAGCTAACTGCTGGTATAGATGATCATAAAGTGAAAGGAAAG*

*GGAAAATCTAAAGCCTCTGGGCCATTCCTTGGCGATTTCTCTGCTAGCAAGGAAG*

*AGTACTTGATTGGTGTCATTTCTGAGATACTTGGCGAGATAAGTAAAGGGGATGGT*

*GTCTCAACTTTTGAGTTTATTGGCAGTGGTGTGGTTGCAGCATTGCTTAACTATTTT*

*TCTTGTGGATACTTTTCCAAAGAGAAGATCTCCGAACTTAATTTGCCCAAACTTCG*

*CCAGGAGGGACTCAGAAGGTTTAAAGCTTTTCTAGAAGTCGCTCTTCCTTTTGATG*

*GTAATGAGGGAAAGGTCCCTCCTATGACAGTTTTGATTCAGAAACTTCAAAATGCT*

*TTATCGTCACTGGAGCGCTTTCCTGTTGTCCTTAGCCATCCCTCAAGGTCACTAAG*

*TGGAAGTGCTCGGCTCTCCTCGGGTTTGAGTGCTTTGGCACATCCTTTAAAGTTG*

*CGATTATGCCGAGCATCTGGAGAGAAAACACTACGTGATTACTCCTCCAATATTGT*

*ACTTATAGATCCATTGGCAAGCTTAGCAGCAGTGGAGGAATTTCTGTGGCCCCGA*

*GTTCAACGGAGTGAATCTGCTCTGAAGCCGGCAGCGCCTATTGGCAATACAGAGC*

*CAGGCACGTTACCTAGCGGTGCTGGTGTTTCATCACCATCTTCGTCAACTCCAGC*

*TTCAACCACTCGTCGTCATTCTTCTAGATCTCGATCGGCAATTAACATCGGTGATA*

*CTTCAAAGAAAGATCCTGTGCATGAGAAAGGTACCAGCTCATCGAAAGGAAAAGG*

*TAAAGGCGTTATGAAACCGGCTCAGGCGGATAAGGGGCCTCAAACAAGGAGCAA*

*TGCTCAAAAGAGAGCTGTTCTTGACAAAGATACTCAAATGAAACCAGCTAGCGGA*

*GACTCCAGTTCTGAGGATGAGGAATTGGAAATATCCCCAGTCGACATTGATGATG*

*CCTTGGTGATTGAAGAGGATGACATTTCTGATGATGAAGATGATGATAATGAAGAT*

*GTTTTGGATGACAGTCTTCCCATGTGCACGCCTGATAAAGTCCATGATGTGAAATT*

-continued

GGCGGACTCAGTGGATGATGATGGTCTAGCAACCAGCGGCCGACAAATGAATCC

AGCTTCTGGAGGCACTAGTGGAGCCGCAGCAGCAAGGGCATCTGATTCTATTGAT

ACTGGCATTGGGAATTCCTATGGTTCTAGAGGTGCACTCTCCTTTGCTGCTGCAG

CGATGGCTGGGCTTGGAGCTGCCAGTGGTAGAGGTATCAGGGGAAGTAGGGACT

TGCATGGACGTACCCTAAATCGAAGTTCAGATGAGCCCTCTAAGTTGATATTTACT

GCGGCAGGAAAACAACTTAGTAGGCATTTGACGATTTATCAGGCTGTACAGCGAC

AACTTATGCTAGATGAAGATGATGATGACAGGTTTGGTGGCAGTGATCTAGTCTCA

AGTGATGGAAGCAGATTCAATGATATTTACACCATCATGTACCAGAGGCCAGACA

GCCAAGTGAATAGGTTGTCTGTTGGTGGAGCAAGTTCTACCACACCGTCAAAATC

CACGAAATCTGCTACTACCAATTCCAGTGTAGAATCTCAGTCACATAGGGCATCTC

TTTTGGATAGTATCTTACAAGGGGAGCTTCCATGCGACCTTGAGAAGTCGAATTCT

ACATATAATGTTCTGGCACTGTTACGTGTATTAGAGGGTTTAAATCAGCTTTGCCC

TCGTTTAAGAGCCCAAACTCTTTCCGATCGTTTTGCAGAGGGTAAAATTACAAGTC

TAGATGATCTGAGTACAACTGCTGCTAAGGTTCCTCTTGATGAATTTGTCAATAGC

AAACTTACACCCAAATTGGCTCGACAAATCCAGGATGCGCTTGCTTTGTGCAGTG

GAAGTCTTCCCTCTTGGTGCTACCAGTTGACTAGAGCATGCCCATTTTTGTTTCCG

TTTCAAACCCGGAGACAGTATTTCTACTCGACTGCTTTTGGGTTGTCTCGTGCATT

GAATCGTTTGCAGCAGCAGCAAGGTGCTGACGGCAGTGGGTCTACAAATGAACG

AGAGATGAGAATAGGGAGATTGCAGCGCCAGAAAGTCCGTGTATCCCGAAATAG

GATATTAGATTCTGCTGCAAAAGTTATGGAGATGTATTCTAGCCAGAAAGCTGTGC

TTGAAGTAGAATATTTTGGTGAAGTTGGTACTGGTCTAGGCCCTACCCTTGAGTTT

TACACACTTCTAAGCCATGATCTGCAAAAGGCTTCCCTAGGGATGTGGAGATCAA

GTTCTGGTGACAAGGTATCTATGCAAATTGGTAGAGATGAGATTGAAGACGGAAA

ACCATCTGCAGCTAACAGAGATATAGTTCTGGCACCACTTGGATTGTTTCCTCGGC

CTTGGCCCTCAACAGCTGACATATCTGAAGGTGGTCAGTTTCATAAAGTCATTGAA

TATTTCCGCCTTTTAGGGCGTGTGATGGCCAAAGCACTTCAAGATGGACGGCTAT

TGGACGTCCCATTGAGTACAGCGTTTTATAAACTTATTCTTGGTCAAGAGCTTGAT

TTGCATGATATTGTATTATTTGACGCTGAACTTGGCAAGACCTTGCAAGAGCTGCG

TGTTGTTGTTGCCCGCAAGCACTATCTGGAGGGAGTAGGTGGTGACAATAGCAGC

ACGATTTCTGATTTATGTTTACGTGGATGCCGAATAGAAGATCTCTCCTTGGAATT

CACGCTACCTGGCTATCCTGAGTACATCCTGAGATCAGGAGATGAAATTGTTGATA

TTACTAATCTTGAGGAGTATATATCCCTTGTCGTTGATGCTACTGTCAAGAGAGGA

GTCACTCGGCAGATCGAAGCCTTCAGATCTGGATTCAATCAGGTGTTTGACATAA

CATCTCTACAAATATTCACCCCTTCTGAGCTGGACTATTTGCTGTGTGGTCGTAGA

GAGTTGTGGGAGGTGGAGACTCTTGCTGAACATATCAAATTTGATCATGGGTATAA

TGCCAAAAGTCCGGCAATCATTAACTTACTGGAGATCATGGGAGAACTTACAGCA

GATCAGCAGAGGGCTTTCTGCCAATTTGTAACTGGAGCTCCTAGGCTTCCTCCTG

GTGGCTTAGCTGTTCTGAACCCAAAGCTTACGATTGTGAGAAAGCACTCATCGAC

CTCAAGTGCAGCAGCCAACGGAGCAGGGGCTTCGGAGACAGCAGATGATGATTT

-continued

*GCCCAGTGTCATGACTTGCGCAAACTACCTTAAACTCCCTCCTTATTCTACAAAGG*

*AAATCATGTACAAGAAACTGCTCTACGCCATCAACGAAGGGCAAGGATCGTTCGA*

*CCTCTCATAA*

SEQ ID NO: 10: Soybean (*Glycine_max*)_UPL3_coding sequence
ATGGAAACTCGGAGCCGGAAGCGGGCGGAGGCTTCCTCAGCTGCCCCTTCATCCCCTTCCTCTGGTCCCA

CCACTCGTTCCAGCAAGCGTGCACGCCTCTCTTCTTCTTCCTCCGCTTCCGCCGCCGCTGCCGCCGCATC

CGTTTCTTCCGTGAACACTCGCTCCCGTTCATCCCGGACTAAGGAACCCTTGCCCCCTAAGAATCCTCCT

CCCATGGACTCTGCCAATGAATCCTCTGGCTCCCGCCGCGATCGCCGCAACAAAGACAACTCCGACAAGG

GGAAGGAGAAAGAGCATGATGTTAGGATTAGGGACAGGGATGCTGACAGAGGGCTGGCATTGAACATGGA

TGGTGGCGGAGACGATGATGACAATGACAGCGAAGGCGGTGTGGGGGATTTTGCATCAAAACTTGACCTC

TGCGAGTAGTGCACTTCAGGGGCTTCTTCGGAAACTTGGTGCTGGTTTGGATGATCTGCTTCCATCATCG

GCTATGGGTTCTGCGTCTTCCTCTCACCAGAGTGGGAGGCTGAAAAAGATCCTCTTCGGATTGCGGGCGG

ATGGCGAAGAAGGGCGGCAGGTTGAAGCATTGACACAGCTCTGTGAGATGCTTTCGATTGGGACTGAAGA

GTCACTTAGTACATTCTCTGTTGATTCGTTTGTTCCCGTGCTTGTGGGGTTGTTGAATCACGAGAGCAAC

CCTGACATCATGCTTCTTGCTGCCAGAGCATTGACCCATCTCTGTGATGTGCTCCCTTCATCTTGTGCTG

CTGTTGTGCATTATGGTGCCGTGTCAATCTTTTGTGCGAGGTTGCTCACCATAGAATACATGGACCTGGC

TGAGCAGGTTGTTCCTTGGTTCATGACTATTGTGGAATTAATGAAAATGGTGCTAGAAAGTTATAAAATA

AATATTTGTGTTTCAGTGTTGAACCCTGGTGCTGCCTAATTGTTTTTAAAACTATATATTTCGATGTTTC

TGGGTCAAATTTTCAGTTGTAGAAGAATTATGCCTTTTTTTTTTAATCTAAGACTTAGCATTTTGAAAAT

GAAATTCATATAGTTTGATTACTGTATTTGATGGCATGAACAGTCCCTTCAAGCTCTGAAGAAGATATCT

CAGGAGCATCCCACTGCCTGCCTACGAGCAGGTGCTCTTATGGCCGTGCTTTCCTATTTGGACTTCTTTT

CAACAGGAGTTCAGGTAAATTGTCAGTGAAGTACCTACATTTAGAGGATGATTGCATCCCCACTGGTCCTT

TTGGACAGTCATAAATCATTTGGCCACAGGTGCCATTAGTGAGCAAGTGTATGTTGACATTATTCTTTGT

TTCAGCGGGTTGCATTGTCTACTGCTGCAAATATGTGCAAAAAGCTTCCTTCAGATGCAGCTGATTTTGT

GATGGAAGCTGTTCCTCTTCTGACAAACCTTCTTCAGTACCATGATTCCAAGGTAAGGTCATGTTTTGTT

GCAAGTCTTGTCACATAATGGAAACTGTATTTTTCCTTTTGCATCCATAAACTTGCCTTTTAAGGAAGTT

TAGCTTGAGAAGAGGGAAATTTTGATCCCTATATCCCATGGTATAAAATATTTATCTATAGCTTCACCTT

ATGCATTTTCAATTTTTGTAGGTTCTGGAGCACGCCTCTGTTTGTTTGACTCGAATAGCTGAAGCTTTTG

CGTCATCTCCAGACAAATTAGATGAATTGTGCAACCATGGACTTGTAACACAAGCTGCCTCCCTCATTTC

TAACAGCAGTTCTGGGGGTGGTCAGGCTTCTCTCAGCACGCCGACATATACTGTAAGTGCAATTTTTACT

TTTAGTTAGATGCATTTTGCCTATAGTTTGGTCCTTGACCTGGGTATATGCAGGGTTTAATCCGACTTCT

TTCAACTTGTGCGAGTGGATCTCCTCTTGGAGCTAAAACCTTACTACTTCTTGGAATTAGTGGTATTCTT

AAAGATATTCTATCTGGTTCTGGAGTTTCTTCTAAGGCCTCTGTTTCTCCTGCATTAAGTAGGCCGCCAG

AACAGGTATAGTATAACATCAGAACTTTTCTTTTGGTCATTCATGTGTAGTTTTATCTCGTAATGTTCAT

TAAACAGACACTGACCTTAAATCCATCATTATTCTAATTCTTGGTTTCAAATATATAGATATTTGAGATT

GTAAACCTCACGAATGAGCTTCTGCCTCCATTGCCACATGGAACAATTTCTCTCCCTATCATCTCCAACA

TGTTTTTGAAAGGGCCCATTGTAAAGAAGTCTCCTGCTGGTAGCTCTGGAAAACAAGAAGACACAAATGG

AAATGTTCCTGAGATATCGGCTCGTGAGAAACTATTAAATGATCAGCCTGAACTACTTAAGCAATTTGCG

ATGGATCTCCTTCCAGTTTTAATACAGGTTGATATTTGTGCATCAATTGCTTAAACTTTGCTTGATAAAT

TTGTTAAATTGAAAAAAATGTTCTGATAAATTGCTCCTTTGCTTCCTTATTTGTCTTCTTTGGTTAATTG

ATGATATTGGCTTGCTGTTGATATAGATATATGGTTCTAGTGTCAATGGTCCTGTTCGGCACAAATGCCT

-continued

TTCTGTCATTGGAAAATTGATGTATTTCAGCACAGCAGAGATGATCCAGTCTTTGTTGAGTGTGACAAAT

ATATCAAGGTATGTTGAAATTTAATTGAGTTGATATTGCTTGATACCCTCACTGATTTTATGGGTTTAGA

AAATTTATGCATTGTTGCTTTGATCATATAGTTTCTTAGCTGGCGTCTTAGCATGGAAAGATCCACATGT

TTTGCTTCCTGCCTTGAAAATTGCTGAAATTCTTATGGAAAAGCTTCCTGGGACATTCTCCAAGATGTTC

ATTAGAGAAGGTGTTGTGCATGCAGTGGACCAACTTATTTTAACTGGAAATTCGACCAATATCTCTACAC

AGGCATCTTCTGCCGAGAAGGATAATGATTCTATATCTGGAGCATCATCTCGCTCTAGGCGTTATCGGCG

ACGCAGTGGGAATTCCAATCCTGATGGAAATCCTTTGGACGATTTGAAAACTCCAGTTTCAGTAAATGTT

GGTTCACCTCCTAATTCTGTGGATATGCCAACAGTAAATTCCAGTATTCGGTTATCTGTTAGTACAGCTG

CCAAAGCTTTTAAAGATAAGTATTTTCCTTCAGATCCTGGGGCTGCTGAAGTGGGTATTACTGATGATCT

TTTGCATCTGAAAAATCTTTGCATGAAGTTAAATGCTGGTGCTGATGAACAAAGGACCAATGGAAAGGGG

AAATCTAAAACTTCTGGATTTGGTCTGGAAGAGTATTTAATTGGGATCATAGCTGACATGCTAAAGGAAC

TTGGCAAAGGAGATGGGGTATCTACTTTTGAATTCATTGGTAGTGGTGTTGTTGCAGCTCTGTTGAATTA

TTTTTCTTGTGGGTATTTCTCTAAAGATCGACCATTAGAAACCCACCTTCCCAAGCTTCGCCAACAAGCA

CTTACAAGGTTTAAGTTATTTATAGCTGTTGCACTACCTTCTACTACTGAAGATGGGACTGTGGCTCCTA

TGACTGTCTTGGTCCAGAAGCTTCAAAATGCCTTGTCCTCCTTGGAGCGTTTCCCTGTTGTGCTGAGTCA

TTCATCTAGGTCATCTAGTGGGAGTGCACGCCTCTCCTCTGGACTAAGTGCATTATCTCAGCCCTTCAAG

TTGCGGCTTTGTCGAGCCCAGGGTGAAAGGTCACTTAGGGATTATTCATCCAATGTTGTACTGGTTGATC

CATTAGCAAGTTTAGCAGCAATTGAGGAATTTGTTTGGCCTCGTATCCAACGAAGTGAATTGGGTCAGAA

GTCCACTGTACCTGCTGGGAATTCTGAATCTGGGACAACTCCTACAGGAGCTGGTGTATCCTCTCCAACT

ACCCATCGCCATTCTACTAGATCCAGATCATCTGTTAATATAGGTGATACATCTAGAAAGGAAATAAGTC

AAGATAAAAGCACAAGCTCTTCCAAGGGTAAGGGAAAAGCTGTATTAAAGCCTGCACAAGAGGAGGCAAG

AGGACCTCAGACCAGAAATGCTACTCGCAGAAGAGAAGCTCTTGATAAAGATGCTCAAATAAAGCCTGTA

AACGGTGACTCTACTTCTGAGGTATACTGATGGAAACCGAGTTAGGGGCAGATATGACAGTTATCTGTAG

AAAATAACTGCTTTAGAAATCAATTCTGTATAAGAAACTCAAATAACTGTCTTAGAAAACAGTACTGTAT

TAGAAACTGCAGGATGGTAGTTATGTGTAGAAAATAACTGCTGGTAGTTATGTATTAGGAGTATATGTCT

GTTAGTATGTGGTGTAATTGGGCAGTGTAAAGTCATTTTTAAGTTTGTGGATAGAGAATACTCTGTAGGA

GACTTCTGTCTCTGGGACAGCTAGTGCTGTTTTTTGTATATGATAGGAGACTTTAGTCTCTAGGACGGCA

GGTGTATTGCTGTATTTGTATGTGATAGGAGACTTTTGTCTCTGGGACAGCAAGTGTATTGCTGTATTGT

GTGATTTCAGTGTTCTATATATTTTAGGTAAATGCTAGGGCTCTGGTTGAGGAAGTAAAAAGAGGGATGC

GTAAAAATGTACTCCTCCTATGATTTCCAAAAAAAAACTTTTCTTTTTTAATTCCTTAACCAGTGCCTGG

CACTGGTTAGCAAGACCCTATATTTTATTACTTTATCATTTGGTGTTCTATCATATACTGTGAAATCCTA

GCGATGACTTTACAATGCTTCAACTTTTTTCTTCTGTTAATTTATAACTTCCTTCTGGCTATGTATGACC

TGACTATGAATGCTCTGTTTTCATGTTGGCTTATAAAGTGAAATACGAAGAGAATACTTGATAATGCCAA

TATAAGATGTAAAGATGCATTATTACATTTTTCATTGCAAGCTTGAAAAGACATCTTACATTTCTCTGTA

TCTGTAACTTTGGACATGCTGGATTTTGTTGTCTGTAGATCCTTAAAATGTTACCTCTGCCATTTAGTTT

TATAAATGGTTTTTGATTATAATTATCTATTTAAGATATCATCTCTAATATGAGAAACACTGCCTAGGTT

TTCTTTGGATTATGTTGAACAGTTGCTTTTTTGCACCATTGATTTCTTTACATACATTAAAATTAAGCTG

TTGTAAGGTTTCCCTGCAAAAGTGTTGATTTACTAAAAAATTGAGGCAGAGCTAGCACTGAGAGGATAAC

TTATCTATTTTGCGTTGAAGTAACATTGCTGTAAGTAATAGTGTATTTGGATGTAATCAGATGGATACTT

TGTATATGCTGATCCTCATCCTTCTTTCATTAAGTGCATGTGTCAGAATTTTTAGTATGGTACCACTCAA

-continued

AAAGTCAAAATCGATTCCTATTTTCAGTTTAGCTTAGTTTTTAATTATTTTCTTATAACATTAAACTTGT

CTGTCATGAAGTTGTAGTTTGTATGACTCTCATTGGGGAATATTTTAGATTATTTGTGGGCGGGTTACAT

ATTTTTTCCGTTTAGGTGAAGCTTTCTTGTTTTGTTTTTTGTTGCTTTTGATTATGGCAGTGTTTACATG

CATGTTGTTTAGCTAGGTTCTTGTGGTTGTTAAACTGGTGGAAGCATCTTTGAGTATAAATTTTTTTTTT

TGGAAGGCGTCTTTGAGTATAAATATTAGTCATTTGTTTTTCCTGCTATGCTTTGGACTAAATCATGAAC

CTAATCCAAGTATCTTGAAGTAGTCATTTGTTTTTCCTTTTCTTTTTTTACCCTTCTAGTGACATTTTCC

AATGTCTACATTGTAGGATGAAGATTTGGATATATCCCCTGTTGAGATTGATGAGGCATTGGTGATTGAA

GATGATGATATTTCTGATGATGAAGATGATGACCATGATGATGTATGTTATCTACTGTTTCTTCTTCTTT

GGCTAGGATTTTCTTACTTCCTTGGTGATGAGTATCTCATTTAAGTAATTACTGTGTTTCTGTCTTTTTT

TTTTTTTTGCTTTTCTGACATCATTTCCTTTTTAACATGGCTTTTAAATATGTTAAAATCTGTGTGCAT

CTTTATTTTTTTATTTCCAGTGCTGGTGTCCTTCAATCTTGTTTACAATTTTTTCAAAATGAGTTGCTGC

TGTCTTTCTATCATTTCTTTGTTTTCTATTTTTCTTTTCTGGGTATAATGATGCAATGAAGTTTTGGTTT

ATGACCTTATGCAAACTATCCATAATCCAAGTCTCTGACCAATAGCTCAATCCTGGTGTTTTATTTCCAA

ATTTTTAATTTTAGCTACCATCATTATTGTTAACCAAGATTGAACATTATAATTAAATTCAGTTGTATCT

ATTAAAATTTTTGTGCTTGTTTTGTTTTTTCTGATGCACAGGTACTGAGGGATGATTCTCTTCCTGTTTG

TTCACCTGACAAAGTACATGATGTGAAATTGGGCGACATAGTGGAGGAGAGTAATGTTGCTCCTGCAACT

AGTGATGGTGGCCAGACTAATGCTGCCTCAGGTTCTAGTAGCAAAGCTGGTACAGTCAGGGGATCAGACT

CTGCTGATTTTAGGAGTGGCTATACCTCAAGCTCAAGAGGTGCAATGTCATTTGCTGCTGCTGCTATGGC

TGGACTTGGATCTGCCAATAGCAGAGGTATCAGGGGTGGAAGAGATCGACTAGGGCGTCCATTGTTTGGT

AGTTCTAATGATCCTCCAAAGTTGATATTTACTGCTGGTGGGAAGCAGCTTAATAGGCATTTGACTATTT

ATCAGGCAATTCAAAGGCAGCTTGTGCTAGATGAAGATGATGAGGAGAGATTTGCTGGCAGTAGTGACTA

TGTATCCAGTGATGGAAGCAGGTTGTGGGGTGATATTTATACTATAACTTATCAGAGGGCAGAGAACCAG

ACAGATAGGACTCCCCCTGGAGGTTCAACCTCTAATGCTTCAAAATCTGGCAAATCTGGGTCTGTATTGA

ATTCTAGTTCTGAAGACAAGCTAAATCAGACATCTGTATTAGATAGTATTTTGCAGGGAGAATTGCCCTG

TGAACTGGAGAAATCTAATCCTACATACAATATATTGGCATTATTGCGGGTGCTTGAGGGTTTGAACCAA

CTTGCATCTCGTTTGAGGGCCCAAGTGGTTACTGATAGCTTTGCAGAGGGAAAAATTTTGGATTTAGTTG

AGCTAAGTTTTACCAGTGGTGCTAGGGTTCCTACAGAGGAATTTATAAGCAGCAAACTTACTCCAAAATT

AGCTAGGCAAATACAAGATGCCCTTGCCTTATGTAGTGGGAGTCTTCCCTCATGGTGTTACCAGTTATCT

AAAGCGTGCCCTTTTTTGTTTCCTTTTGAGACCCGGCGACAGTATTTTTATTCAACTGCCTTTGGGTTAT

CTCGTGCATTGTATCGCCTTCAGCAGCAGCAGGGTGCTGATGGTCATGGATCAACAAATGAAAGAGAGGT

CAGGGTTGGGAGATTGCAGCGTCAAAAGGTTCGTGTCTCTCGAAATCGCATTTTGGATTCTGCTGCTAAG

GTGATGGAGTTGTATTCTAGTCAAAAGGCTGTACTTGAAGTAGAATATTTTGGTGAAGTTGGCACCGGTC

TGGGTCCCACTCTGGAGTTCTACACACTTCTCAGTCATGACTTACAAAAAGTTGTACTTCAAATGTGGAG

ATCAGGTTCTTCAGAGAAATATCAAATGGAAATTGATGGAGATGAAAAGAAAATGAAAAATAGTGAAGGC

TCTTTTGTTGGAGATGGAGAACTCGTTCAAGCTCCTCTTGGGCTGTTTCCTCGACCTTGGCCTGCAAATG

CTGATGCATCAGAGGGTACCCAAATTTTCAAAGTGATTGAATATTTCCGATTATTAGGCCGTGTAATGGC

TAAAGCTCTTCAAGATGGACGCTTATTGGATTTACCATTGTCAGTGGCATTTTATAAGCTTGTTCTTGGT

CAAGTAAGTTATGAAATGTTGATGTCTTGTCTGATTTCATGTGTATCTTAAGGTTGATTTTTAGTCTCTA

TATATTTAGCCTTTGATATATTGCAGGAGCTTGATTTGCATGACATTCTTTTCATTGATGCTGAACTTGG

GAAAACTTTGCAAGAGTTAAATGCCCTTGTTTGCCGGAAATGTTTTATAGAATCTATTGGTGGTAGCTAC

ACTGATACCTTTGCTAATTTGCATTTTCGTGGGGCCCCAATAGAAGATCTCTGCTTGGACTTCACACTTC

-continued

CTGGTTATCCAGAGTACATCTTGAAACCTGGAGATGAAATTGTATGTATTCAGTCTGTTTTTTTTACCTG

GTTTTTGTTTTGGTTCTGATTCTGTCTGTAATAAAAATTGCTTTGAACTTACTGTCAAACTTTCAGGTTG

ACATCAATAATCTAGAGGAGTACATATCCATGGTGGTTGAGGCAACGGTTAAGACTGGAATCATGCGTCA

AATGGAAGCTTTTAGAGCAGGGTTTAATCAGGTTATATGTTGTCTCAATAAATTCATGTAACTTTGTCTT

TGACTGTGCATCTTGTTTGGTGATGCTGAGTATAAAAAATATCATGTATTTTTTAACTGATTAATGGTTC

ATTCTTTTTGGTATTCCTTTTCTAGTTTCTCTCAAACAATTTTATTGAAAACTAAACTTGACTGGGGTTT

AATTTGAAAATATTGAGTATGGATTTTTCAGCTTTTAGATTCTTAAGGGGCATTGTTTTCTACTAAAAAT

TGTTACTTTTGGTTATGTCTTGAGCAGTGAACTGTATATATATCCTGAATCTCGGATGTATCAATTAAGA

AATTACTAAATGTTTGTTTCTGACTTTTACTTATGTTTGCTACCAACCTTGTATCCCCCTTCCCCTGCAG

ATGAAGAATGGAAGTTAGAAAATACACATTTTTTTTGTATTGATGTCAAATATTCAGTTATTTAATGTCA

AAATTTTACAAGTGAAATGAGCTACTAGCCTAACTTATATGGAAGAGATGGGCTGGGCAATAGTTTGAAC

TTGGAACAACTAGTTGGATAATTTGTTCATTTGCTTGAGTCCAAAAACTAAACATTTGTCACTTTCCCAC

TTGTTCTTGTCAATTCAGGTTTTTGACATCTCATCTTTACAAATTTTTTCTCCCCAAGAACTGGATTACT

TGCTTTGCGGCCGGAGAGAATTGTGGAAGGTATTCTTTTTTATACAAAAGTATTACTGCTGCTTACAACA

ATCTTTTAGATGTTACCATGGATAATGTAGTTATAATTTTTTTTCTCCTATCTGCAGACTGAGACACTAG

CTGATCATATAAAATTTGACCATGGTTATACTGCCAAGAGCCCTGCCATAGTTAATGTATGTTTTTTTAT

TCCTGTAGAAGGACAATTGTGTTTTTGGAAATTTAGGCTTGTTATATTTGGTGCTGAACCTGTATGATGC

TATTTTCAGTTACTCGAAATTATGGGAGAATTCACACCAGAGCAGCAGCGTGCCTTCTGTCAATTTGTTA

CTGGTGCACCTAGGCTGCCTCCTGGTGGACTGGCAGTTCTAAATCCAAAATTAACGATTGTGAGGAAGGT

ATTGAAAAATATTTTTGATCACTTGCAACCTGTGTTATTCATTCATGCCTTCATGCAATTTTGTACTTGA

TATCTTGAATGTTAAAGTTTTTTGGGGGGCGAGGATCTATTTGAACTTCGGTAGCAAGATGTGTCTGGAT

TTACTGCCTGACATATGTTGCTCCACTATTCCTTTACCTCTTGAAGGGGGGTTTTCAAAATGCAATGTTA

GTAAGTGATTACATTTACATGTCTGGGTGCAGCTTTCGTCAAGTGCAGCTAATGCTTCATCTAACGGGAA

TGGGCCTTCAGAATTAGCAGATGATGACTTGCCAAGTGTGATGACGTGTGCAAATTACCTGAAGCTTCCT

CCTTATTCTACCAAGGTAGAACACTGCAAAGCATTGTTGGTTATATGATCATGCATGTCAAAGTGTCTTT

TGATCTTTGATTTCCATTTTAAAACAGGAAATTATGTACAAGAAGCTACTCTATGCAATCAGTGAAGGCC

AGGGATCCTTTGA

LEC2 sequences
SEQ ID NO: 11; *Brassica napus* LEC2 gene
>BnaA07g08500D
ATGGATAACTTCTTGCCCTTTTCCTCTTCTAACGCAAACTCTGTCCAAGAACTCTCCATGGATCTTAACA

AGAATCGCTCGCACTTCTCCATGGCGCAGCCTCAGCACTTGTTGCCGCCTTACTCGTACGTTGCATGTCC

GGCACTTGATCAGACGGGGACCATGAATCATCAGCCTCTTCACTCATCGGATGCTTTTCCTCAGATCCCG

GTTGTACAAACCGGAGGTGAATTCGGCTATTTGGTTTGTAAGCCCGGTGTGAGGCAGGAACGAGGTGGAT

TTCTTGATCCACACTCCACTAAGATGGCTAGGATCAACAGGAAGAAGGCGATGCTAAGATCAAGAAACAA

CTCTAACCCTAATTCTAGTTCGAATGAGTTGGTTGATTCAAGGAGACAAGTGGCTCTTACCATGAAAAAT

AATGCCGAGATTGCTGCTAGAAAAGATTTTTATCGATTCTCCTCATTCGATAACAAGGTATGTATTTCTT

TGGCCCAAAATAATGGAATATATGCGATTCTACATTCATAACATGATAATGTTTTTGAATTTTTTGTTGA

CTGTACGTAGAAACTTAGGGTTTTGTTGGTGAAGCACTTGAAGAACAGCGATGTTGGGTCACTTGGAAGG

ATTGTTCTACCAAAGGTGTGTAAATTCTTACATTTCTCGTATTCTTTATGGTATAATTAATGTTAAAACA

ATTTTGTAGAGGTAAAAACACTAAATATGTTGGGGATGGATTGATGAAAGATTATCAACTACGTAACTAC

GAATTTTAAAACCTCAATTTCATGAGAAAGTTTTTTAAAAGTAATATAATTTCTGATTTGGCTATTACCA

-continued

TTTAAAAAGATATTATCACTGCGACCACATATTCTCTCATTATGCAATTTCACACATTTTCCTCCATTCA

AACCATCGTTGTTTAACCAATGAGAAGTTTAGTCTCTAAAACACATGGAAAACAAGAGGGATTTTTTTTT

GATAAACCAGAGGAAAATTAAACATGAAAACAAAATGTGAAATATATAATTGTTTAATCAATACGGAGTA

TTTTCGTTCATTCCTTTTGGTGTGAGCTTTTATGTTATACAGTACTATAGTATTTTTTTTAGTTTAGCAA

GAATATGGTGATTAAAAATCTAGTTTAAATTTGGTTTATCTATATTTTAAATTTGAAGGACTAAAAGTCA

AAGTTTTGGAATGAGCACCAAAAATGAAATACAGTATGAAAAAAAATCGAAATAGATTGATCATAGCTCC

TTCAATCTAATATTCCGTGTAAAAACTTACTAACCAATGAATAAAAAACACGAGAAGTAAACGATTTTCT

AGTTGTAGTTAGCTAAAATGGTTAATAAAGTGGTTAAAATGACTTTATTTTGAAACGGGGTTGAAAAAAA

GTCGTATATATATATATATATTCCTTTCCTAATTAATTGCCTCTTAAATGGCATTCCTCGAAATCATTAA

GGAAAAGTAGAAAACAAACAAAAAGCCATTATGGATTAATTGGGGCAGTTTACTAGTTTTATTATAGAAA

AATCATATCAAATCATCCCCTTTATCTATCTTAGTAAGAAAATAATTAGTTTATTTGCACCCAAAAAATA

ATTAGTTTATTAAAAAGTAACTAAGTAAATCATGGGTTTGGAGCGCAGAGAGAAGCAGAAGGAAATCTTC

CGGAGCTATCTGATAAAGAAGGAATGGTATTAGAGATGAGAGATGTTGACTCTGTGCAGTCTTGGTCTTT

CAAATACAAGTGAAGTCTCGTTTCCTTTCTCTTATATATTGATAGAAAACATTTTTATGTTCCATTTTTT

AATCTACCAATAGTTTAACAAACCTTATAAGTTCTTTAGTGATTTTTTGTTAGTGGTATGTTTTATAGCT

TGGAATTTGTTATATCGGTTTCAATTTAATATTTTTGGAACGAGAGAACTTATAAGGCTTGCATTAATGT

GAAACGCAGGTACTGGTCCAATAACAAGAGCAGAATGTATGTCCTCGAAAACACAGGTAATTAAGGAACT

ACTTTGTTCTTTCAACAAGTATAGTTTTTTTTTTAATTCTTTTATGTTGAAAATTAAAGGAGAATTTGTG

AAGAAAAATGGAGTATTGATGGGAGACTATCTAACAATCTACGAGGACGAAAGCAAGAATCTCGTGAGCT

CTCTTATTAACTCTCTTTTCTTATTTTATTTTGGAAAAGACAAAATGTTAAATAATGATTGATTAGTAGT

CCAAAATTGGAAATTTGAAAGTGTGTCATTGAATTTAGTTTGTTCAGCATCCAGACAAAAAAAATTAATT

GCATTTTTATGATTTTTAAATGAAGATTTTAATTGATGTTTCTGCTATATTTGATCATAAATATAACATT

CTACTATCTTATTACATCTTTGAAATAGTAGTCAAGTATTTGGTGATGTTTTATCCTTTCCAAAAAATAG

TTATTTTGAGCAGCCAATTTATTTGGTTTTGAATACATGCATTGTACCAACCGAACAGTTTTTCAGAATT

TGGTTTTCTATTTGAGTTATTATTTTATGTATATATATAAATATATAAAAAATGATATTGAAGTCAATTT

TGACTAGTATGGTTTGAACTAAAAAAAGAAAAGTTAGTAGTCTTAATATTTCTGTTTATCTTCACAGAAT

ATTTTTATCAAAATTAATTTAATATTAATGCTAAAAAAAATTTTTACATATGTAAAAATCAATACTGAAA

GTATATAGTTAAAGTCCTATACATGACTTGTTGAAATTTAATTGAATAATGTTTTGGTCAACAACATAGA

ACTTATTAGAGTTTTTTTTTTTTTTGGTAAAAGAACTTATTAGAGTTTTTTCATGCTTATATTTGGTTTG

GTTATTAAATAATTTTCTAACATTTATTTCTCCTAATTGACCAAAATGATCAACTGCTTTTTTTTTTTTT

TGAACAACCCAAAATGATCAACTGCTAAAACATCTTATATATGTGTATATTTGTTTGGCTTCATTACAGT

ACTTCTCCATCAGAAAGCACCCACACAAACAAAATGATGGAAGAGAGGATGAGTCGATGGAAGTTATCGA

GATGAACTTCTATGAAGATATAATGTTTGATTACATACCAAATGATGAAGACGATTCCATTGCAATGCTC

CTCGGAAATCTAAACGAGCACTATCCCTACCCAAATGATCTTATGGATCTCACTGTCAATCTTGATCAGC

ATCAGCAAGCCACCTCCTCGTCGCCACCTGCTGATCACATGAGCTCGAACGATTTCTTATGGTGATGTGA

TGGA

SEQ ID NO: 12; *Brassica napus* LEC2 gene
>BnaA09g27380D
ATGGATAACTTCTTGCCCTTTTCCTCTTCTAACGCAAACTTTGTCCAAGAACTCTCAATGGATCTTAACA

ACAATCGCTCACGCTTATCAACGTTCCCTACTTATGATCATCATCATCAGGCGCAGCCTCACTCGTTGCA

ACCCTACTCATATGTTGCATGTCCTGTGGATCAGACGGCGGCTATGAATCCTCAGATCCCGGTTACACAA

-continued

ACCGGAAGTGAGTTCGGTTCTCTGGTTTGTAATCCCGGTTTCGGACAAGCAAGAGGTGGATTTCTTGATC

CACACACGGCTAAGATGGCCAGGATCAACAGAAAGAAAGCGATGATAAGATCAAGAAACAATTCTAGCCC

TAACTCTAGTTCGAATGAGCTGGTTGGTTCAAGGAGACAAGTGGTTCTTACCATGAAAAATAATGCCGAG

ATAGCAGCAAGGAAAGATCTCTATCGATATCCCTCATTCGATAACAAGGTTTGTTCCAAATATTAGATAT

TTTCGATTTTATATATATATAAAACTTGATCAAACGTTTTGGATTTTGTGGTTGACTGTAGAAGCTTAGG

GTTTTGTTGGTGAAACACTTGAAGAACAGCGATGTTGGATCACTTGGGAGGATCGTTCTACCAAAGGTGT

GTAAATTCTTACAATTCTTTTATCCATCGTTTTCGTTAAGGTGTAAAGATAAAATAAATTTTATAGGTAA

AACATTAATATGAAATAGTTAACTTTAATATGAAATAGTTATCAATCACGTAACTACGAAATTTGAAACC

TCAATTCCATGGAAAAGTTTTAGAAAAGTAATATGGTTTCAGGATTTGGCTGGCCCCTTTTTCAAAGAAG

GTTTGTGGAACAAAAGTACATAAGTCATTGCGGCCACAAACTCTCATTAAGAAATTTCACTGAGATTTTT

TCTAACATTTCATTCCATTTTTAAAATATAGTAGTAGTATATTTAGCGATTTCGTGGTTTAACCAATTAC

AAGTTCAGTCTCTAAAAACAACACGGAAAACAAGGGGAATGTGAAACATGACAACAAAATGTAGAATGTA

GTAAAGTTGTTTATAGTATTTGTGTTTGTTCAAGTACGAATTTTTATGACATTTTTATAGATTTTTAGTT

TAGGAAGAATATGGATTGTTTGTAAATTCTAACTAAGCTGATTTATTTAAAGATATCTGGAGTTTGAAGG

ATTAACAAATTCTTCAAGTTTTGGAGTGAAAAAATCTAAATAGATTCAATATAGTTTCCTTTTTGTAACC

AATAAGGAAAAGACATGAGTGATAGAACATGAGAAATAATCAATTTTATTCTACTACTAGATAAAGTGAA

ACTGTTTATATGAATTTATTCCAAAATGATGCTGAAGAAAAATAAAGTCGTCTATTTGCCTTTCCTAATT

AATTGACTCTTAAATGGTATACCTCGAAATCATTATGGGAAAGTATCAAGAAACAAAAAAAAACAATTTG

GAAAAGAGGTTCAACGATATTTACTTGATACTGACTGAAACAAATTATAATTGTCTGTTATCTGTCTTAA

TTAAAACAGTAAGAAAGTCATTTTTCGATAAGAAAAGTCATTAAATAATCCCTTAAATAAGTCATGGCTT

TGGAACGCAGAGAGAAGCTGAAGGGAATCTTCCGGAGCTATCTACTAAAGAAGGAATGATAGTAGACATG

AGAGATGCGGACTCTATGCAGAATTGGTCTTTCAAATACAAGTTAAGTCTCGTTTTCATCTCTTATATGA

ACTCAATTATATTCACAAAAGCAATTTATTAATCGTTTTATTTTACCAATGGGTTATAACAATCTTTTAA

GCTCACTTTTTGATGATTTCAAGTTAGAATTTTTATCAATGTCAATTTAATGTCATACTTAAAAAAGCTT

GTATCACTGTGAACATAGGTTCTGGTCCAATAACAAGAGCAGAATGTATGTCCTTGAAAACACAGGTAAT

TAAGGAGCTACTATATTCTTTTTAAAGTATACTACTTATTTAAACTATTTTATTATAATACGTTTTTCCT

TTTGTCTTAAAAATTAAAGGACAATTTGTGACTGAAAAAAGAGTTGAGATTGGAGATTTTTTAACAATCT

ACGAGGACGAAAGCAAGAATCTCGTGAGCTCTCTTATTAACTCTCTTTTCTTGTTTTATTTTAAAAAAGA

CAAAACTCTAAAATAAACTAATAATGATTGATTAGCAGTCCGAAATTGGAAATTTAAAAAGTGAGCCATT

AAATTGTGTTTGTTAAGCATCTAGACAAAAACTTATTGCCTTTTTGACCTTTTCTGTCGATGATAGCTGT

CCGTATAAGGAAGGTACTATAAGAATTTCAAACCTTAGTTTTAATATACTACTGAAAATCGATTCTTTAT

TCTTTTCTTTTTTTTGCTAAACTGAAAATTAAAGACATGATATATTCTTTCAAAAAAAGATGTGAAATAT

ATGAGGGTGACTAGTATTAATTTAAATTTTATGTTTAATAAAATGCTTCTTCTATTTACTCATATTTTTA

TTCTACTATTTTGCTAAGTAGGGAGTGATGTAATATGTTTTTCTCTAGAAAAGTTGTTCTTTTTATCAGC

CAATTTGTTTGGTTTGACTACATAAACTCTTTGTTGACAAAAAAAAAGCCTACATAAACTCTTCCAAATT

AACAAACTGTTTTTAGGATTTGATTTCATATCAGAAATAATTTCTTTTAGAAAAATATTATTTTTATTTA

TCTAAATTTTTTCAATTTTGAAGATAATTTATTTCTCCATTATTTTCGACAAAGTTCAAATTTAATAAAA

ATATTTAGTATACTATTTTCTAGTTATCCTCACAAAATACTTTTTATTAGCATAATAATATAATGTGCAA

AATTTAGTTCATACGTACTTGAATTTTATAACTAAGACAAATTGTTTTGTAATTAGAAACCTGTAAATGA

CATATTGGCATTTAACTGAGTAGGAGTAGTGTTTTGGTTCAAAAACATGGAACTTATTTACTACTCTACA

GTTTTTCATAGGTTATTTAATTTTCCTTTGGATATTAAATAATCTAATATTTATAATATTTAAATCTCCT

-continued

AACTTTTTCAGTTGTTAATCATTTATAAATTCAGCCAATTGCTAAGACACCTTAAAGCATGATTAACCTC

GGTTTTTTAGCCGGGATTCTTAACTCATGATTTGACATTTTTTTATATATTTTTTGGTTAAGAAACAGTT

TTTTTATCTCTTATTTAAGAGACGGTTCTTAGCTATTCTTAGTTAAAATCTAAAAAAAGTTAAGAATCGT

CTCTTATCCAAAATTAAGAACCCCAGTTAAAAGACTGGAGTTAATCATGGTCTTATATATGCATGTTTTG

TTTGTTTGGTCTTACTGCAGTACTTCTCCATAAGAAAGCACGCAGACAAACCAAATGAAGGAAGAGAAGA

TGAGTCGATGGAAGCCAACGACATGAACTTCTACGAAGATATTGCGTTTGATTTCATACCAAAAGATGAA

GACGAAGATTCTATTGCAATGCTCATCGGAAATCTAAATGATCACTATCCCAACCCAAACAATCGTATGG

ACCTCCCAATCGATCTTCATCAGCATCATCAAGCCACCTCATTGCCACCTGCGGATTACATGACCAATCC

TCAGTATGGTGGTTCCTCCAATGATCTCATGAGCTTTAACGACTTCGTATGGTGATGCGATTGA

SEQ ID NO: 13; *Brassica napus* LEC2 gene
>BnaC05g50460D
ATGGATAACTTCTTGCCCTTTTCCTCTTCTAACGCAAACTCTGTCGAAGAACTCTCAATGGATCTTAACA

ACAATCGCTCACGCTTATCAACGTTCCCTACTTATGATCATCATCATCAGGCGCAGCATCACTCGTTGCA

ACCCTACTCATACGTTGCATGTCCTGTGGATCAGACGGCGGCTATGAATCCTCAGATCTCGGTTATACAA

ACCGGAAGTGAGTTCGGTTCTCTGGTTTGTAATCCCGGTTTCAGACAAGCAAGAGGTGGATTCCTTGATC

CACACACGGCTAAGATGGCCAGGATCAACAGAAAGAAAGCGATGATAAGATCAAGAAACAATTCTAGCCC

TAACTCTAGTTCGAATGAGCTGGTTGGTTCAAGGAGACAAGTGGTTCTTACCATGAAAAATAATGCCGAG

ATTGCAGCAAGGAAAGATCTCTATCGATATTCCTCATTCGATAACAAGGTTTGTTCCACATATTAGATAT

TTTAGATTTTATATATATATAAAACTTGATCAAACGTTTTGGATTTTGTGGTTGACTGTAGAAGCTTAGG

GTTTTGCTGGTGAAACACTTGAAGAACAGCGATGTTGGATCACTTGGGAGGATCGTTCTACCAAAGGTGT

GTAAATTCTTACAATTCTTTTATCCATCGTTTTCGTTAAGGTATAAAGATAAAATAAATTTTTTTTTTTT

TTTGGTAACTCTGGTATCTGGGCAGCCACATTCCCAACTATCTCCGTAGGGGGTCCAGCGCCCCAACGGA

AGGGATGTTAAATCCGTTGTGGCCGGGGCTCGAACTCGTGATGGCGGACACCTCAGCCGAGGTTCCTATA

CCACCAGACCACGAGGCCCGGTTAGATAAAATAAATTTTATAGGTAAAACATTAATATGAAATAGTTAAC

TTTAATATGAAATAGTTATCAGTCACGTAACTACGAAATTTGAAACCTCAATTCCATGGAAATTTTTTAG

AAAAGTAATATGGTTTCAGGATTTGGCTGGCCCCTTTTTCAAAGAAGGTTTGTGGAACAAAAGTACATAA

GTCATTGCGGCCACAAACTCTCATTAAGAAATTTCACAGAGATTTATTTCTAACATTTCATTCCACATTT

AAAATATAGTAGTAGTATATTTAGCGATTTCATTGTTTAACCAATTACAAGTTCAGTCTCTAAAAACAAC

ACGGAAAACAAGGGGAATATGAAAGATGACAACAAAATGTAGAATGTAGTAAAGTTGTTTATAGTATTTG

TGTTTGTTCAAGTACGAATTTTTATGACATTTTTATAGTTTTTTAGTTTAGGAAGAATATGGATTGTTTG

TAAATTCTAACTAAACTGATTTATTTAAAGATATCTGGAGTTTGAAGGATTACAAATTCTTCAAGTTTTG

GAGTGAAAAAATGTAAATAGATTCAATATAGTTTCCTTTTAGTAACCAATAATGAAAAAACATGAGTGAA

AGAACATGAGAAATAATCAATTTTATTCTACTAGATAAAGTGAAACTGTTTAAATGAATTTATTCCAAAA

TGATGCTGAAGAAAAATAAAGTCGTCTATTTGCCTTTCCTAATTAATTGCCTCTTAAATGGTATACCTCG

AAATCATTATGGGAAAGTATCAAGAAACAAAAAAAAAACAATTTGGAAAAAAGGTTCAACGATATTACTT

GATAGTTATATTGAAACAAATTATAATTGTGTCTCTTATCTGTCTTAATTAAAACAGTAAAAAAGTCATT

TTTCGATAAGAAAAGTCATTAAATAATCCCTTAAATAAGTCATGGCTTTGGAACGCAGAGAGAAGCTGAA

GGGAATCTTCCGGAGCTATCTACTAAAGAAGGAATGATAGTAGAGATGAGAGATGCGGACTCTATGCAGA

ATTGGTCTTTCAAATACAAGTTAAGTGTCGTTTTCATCTCTTATATGAACTCAATTATATTCACAAAAGC

AATTTCTTAATCGTTTTATTTTACCAATGGGGTTATACTAACAATCTTTTAAGCTCACTTTTTGATGAAT

TCAAGTTAGAATTTTTATCAATGTCAATTTAATGTTATACTTAAAAAAGCTTGCATCACTGTGAACATAG

-continued

GTTCTGGTCCAATAACAAGAGCAGAATGTATGTCCTTGAAAACACAGGTAATTAAGGAGCTACTACATTC

TTTTAAAAGTATACTACTTATTTAAACTATTTTATTATAATATGTTTTTCCTTTTGTCTTAAAAATTAAA

GGAGAATTTGTGGCTGAAAAAAGAGTTGAGATTGGAGATTTTTTAACAATCTACGAGGACGAAAGCAAGA

ATCTCGTGAGCTCTCTTATTAACTCTCTTTTCTTGTTTTATTTTGAAAAAGACAAAACTCTTAAATAAAC

AAATAATGATTGATTAGCAGTCCGAAATTGGAAATTTAAAAAGTGAGTCATTAAATTGTGTTTGTTAAGC

ATCCAGACAAATATTTATTGCCTTTTTGACCTTTTCTGTCGATGATAGCTGTCCGTATGAGGAAGGTACT

ATAAGAATTTCAAACCCTAGTTTTAATATACTACTGAAAATCGATTCTTTATTCTTTTCTTTTTTTGCTA

AACTGAAAATTAAAGACATGATATATTTTTTCAAAAAAGACGTGAAATATATGAGGGTGACTAGTATTAA

TTTAAATTTTATGTTTAATAAAATGCTTCTTCTATTTACTCATATTTTTATTCTTTGCTAAGTAGGGAAT

GATGTAATATGTTTTTCTCTAAAAAGTTGTTCTTTTTAACAGCCAATTTGTTTGGTTTGACTACATAAAC

TCTATGTTGACACAAAAAAAGCCTACATAAACTCTACCAAATTAACAAACTGTTTTTAGGATTTGGTTTC

ATATCAGAAATAATTTCTTTTAGAAAAATACTATTTTTATTTATCTAAATTTTGTCAATTTTGAAGATAA

TTTATTTCCCCATTATTTTCGACCAAGTGAAAATTTAATAAAAAAATTTAGTATACTATTTTCAAGTTAT

CCTCACAAAATACTTTTTATTAGCATAATATAATGTGCGAAATTTAGTTCATACGTACTTGAATTTTATA

ACTAAGACAAATTATTTTGTAATTAGAAACCTGTAAATGTCATGTTGGCATTTAACTGAGTAGGAGTAGT

GTTTTGGTTCAAAAACATGGAACTTATTTACTACTCTACAGTTTTTCATAGGTTATTTAATTTTCGTTTG

GATATTAAATAATCTAATATTTATAACATTTAAATCTCCTAACTTTGTCAGTTGTTAATTATTTATAAAT

TCAGCCAATTGCTAAGACACCTTATATATGCATGTTTTGTTTGTTTGGTCGTACTACAGTACTTCTCCAT

AAGAAAGCACGCAGACAAACCAAATGAAGGAAGAGAAGATGAGTCGATGGAAGCCAACGACATGAACTTC

TACGAAGATATTGCGTTTGATTTCATACCAAAAGATGAAGACGAAGATTCTATTGCAATGCTCATCGGAA

ATCTAAATGATCACTATCCCAACCCAAACAATCTTATGGACCTCCCAATCGATCTTCATCAGCATCATCA

AGCCACCTCCTCGTTGCCACCTGTGGATTACATGACCAATCCTCAGTATAGTGGTTCCTCCAATGATCAC

ATGAGCTTTAACGACTTCGTATGGTGATGCGATTGA

SEQ ID NO: 14; *Brassica napus* LEC2 gene
>BnaC07g10500D
ATGGATAACTTCTTGCCCTTTTCCTCTTCTAACGCAAACTCTGTCCAAGAACTCTCCATGGATCTTAACA

AGAATCGCTCGCACTTCTCCATGGCGCAGCCTCAGCACTTGTTGCCGCCTTACTCGTACGTTGCATGTCC

GGTACTTGATCAGACGGGGGCCATGAATCATCAGCCTCTTCACTCATCGGATGCTTTTCCTCAGATCCCG

GTTGTGCAAACCGGAGGTGAATTCGGCTATTTGGTTTGTAAGCCCGGTGTGAGGCAGGAAAGAGGTGGAT

TTCTTGATCCACACTCGACTAAGATGGCTAGGATCAACAGGAAGAAGGCGATGATAAGATCAAGAAACAA

CTCTAACCTTAATTCTAGTTCGAATGAGTTGGTTGATTCAAGGAGACAAGTGGCTCTTACCATGAAAAAT

AATGCCGAGATTGCTGCTAGAAAAGATTTTTATCGATTCTCCTCATTCGATAACAAGGTTTGTATTTCTT

TGGTCCAAAATAATGGAATATATGCGATTCTACATACACAACATGATAATGTTTTTGAAATTTTTGTTAA

CTGTACGTAGAAACTTAGGGTTTTGTTGGTGAAGCACTTGAAGAACAGCGATGTTGGGTCACTTGGGAGG

ATTGTTCTACCAAAGGTGTGTAAATTTTTACAATTCTCGTATTCTTTATGGTATAATTAATGTTAAAACA

ATTTTGTAGAGGTAAAAACACTAATATGTTGGGGATGGATTGATGAAAGATTATCAATTACGTAACTACG

AATTTTAAAACCTCAATTCATGAGAAAGTTTTTTAAAAGTAATATAATTTCAGGATTTGGCTATTACCAT

TTAAAAAGATATTATCACTGCGACCACATATTCTCTCATTATGCAATTTCACACATTTTCCTCCATTCAA

ACCATCGTTGTTTAACCAATGAGAAGTTTATTCTCTAAAACACATGGAAGACAAGAGGGATTTTTTTATG

ATCAACCAGAGGAAAATTAAACATGAAAACAAAATGTGAAATATATAATTGTTTAATCAATACGGAGTAT

TTTCGTTCATTCCTTCTGGTTTGAGCTTTTATGTTATACAGTACTAGTATTTTTTTAGTTTAGCAAGAAT

ATGGTGATTAAAAATCTAGTTTAAATTTGGTTTATATATATCTTAAATTTGAAGGACTAAAAGTCAAAGT

-continued

TTTGGAATGAGCACCAAAAATGAAATACAGTATGAAAAAAAAATCAAAATAGATTGATCATAGCTCCTTC

AATCTAATATTCCGTGTAAGAACTTAGTAACCAATGAATAAAAAACATGAGAAGTAAACGATTTTCTAGT

TTTAGTTAGCTAAAATGGTTAATAACGTGGTTAAAATGACTTTATTTTGAAACGGGGTTGAAAAAAAGTC

GTATATATTCCTTTCCTAATTAATTGCCTCTTAAATGGCATTCCTCGAAATCATTAAGGAAAAGTAAAAA

ACAAACAAAAAGCCATTATGGATTAATTGGGGTAGTTTACTAGTTTTATTATAGAAAAATCATATCAAAT

CATCCCCTTTATCTATCTTAATAAGAAAATAATTAGTTAGGAATCGCCACTCGCTAGCTAGGAATGCCCG

TTATTTTCATAGATTTCTTAGCTTTATTGGTTGTTCTATTCCGGTCTGGTTACCTAGACCGCCTCAAGTT

TGAGTAATAGAATAACTGTTTGTTGCAAAAAAAAATAAAATAATAATTAGTTTATTAAAAAGTAATTAAG

TAAATCATGGGTTTGGAGCGCAGAGAGAAGCAGAAGGAAATCTTCCGGAGCTATCTGATAAAGAAGGAAT

GGTATTACAGATGAGAGATGTTGACTCTGTGCAGTCTTGGTCTTTCAAATACAAGTTAAGTCTCGTTTCC

TTTCTCATATATATATTGATAGAAAACATTTTATGTTCCATTTTTTAATCTACCAATAGTTTAACAAATT

AACCTTATAAGTTCTTTAGGGCTTTTTTGTTAGTGGTATGTTTTATAGCTTGGAATTTGTTATATCGGTT

TCAATTTAATATTTTTGGAACGAGAGAACTGATAAGGCTTGCATTAATGTGAAACACAGGTACTGGTCCA

ATAACAAGAGCAGAATGTATGTCCTCGAAAACACAGGTAATTAAGAAACTACATTGTTCTTTCAACAAGT

ATAGTTTCTTTTAAAAAAATTCTTTTATGTTGAAAATTAAAGGAGAATTTGTGAAGAAAAATGGAGTATT

GATGGGAGACTATCTAACAATCTACGAGGACGAAAGCAAGAATCTCGTGAGCTCTCTTATTAACTCTCTT

TTCTTATTTTATTTTGGAAAAGGCAAAATGTTAAATAATGATTGATTAGTAGTCCAAAATTGGAAATTTG

AAAGTGTGTCATTGAATTTAGTTTGTTCAGCATCCAGACAAAAAAAATTAATTGCATTTTTATGATTTTT

AAATGAAGATTTTAATTGATGTTTCTGCTATATTTGATCATAAATATAACATTCTACTATCTTATTACAT

CTTTGAAATAGTAGTCAAGTATTTGGTGATGTTTTATCCTTTCCAAAAAATATTTATTTTGAGCAGCCAA

TTTATTTGGTTTTGAATATACATGCATTGTACCAACCGATCAGTTTTTCAGAATTTGGTTTTCTATTTGA

GTTATTATTTTATGTATATATATATATATAAATATATAAAAAATGATATTGAAGTTAGATTTTGACTAGT

ATGGTTTGTCGACCAAGTTGGAACTGAAAAAAGAAAAGTTAGTAGTCTAATATTTCTGTTTATCTTCACA

GAATATTTTTATCAGAATTAATTTTATATTAATGCTAAAAAAAATTTACATATGTAAAAATCAATACTGA

AAGTATCTTATATATTAAAACAGAAGTCACAACTTTGATTCATATGTGATTTTTAAAAACATGGACTTAA

TGGACCTATTACTAAAAAGCCATATTACATTTAATCTCTAATCTTATCATTTAAATTTTTGGCATACCAG

AAATTTTTATTGGGCTATCAATAATTGAATTTAAACAATAGAAGATCCATTGGATTTATAGATAGTATAA

ATTAAATATATATAATTTAATGTTATAATACTATACCTCCATATGTTAATTATTTAAATATTTGTCGATG

TTAACTTTTAAAATTATAAAAAAAAAATTTAAATAACAAAAATCATATTATCTACAATGATTAATCTTTA

CTCCCATAAACCAATGAAAACAAATTTTAAACTATATAGTTTATTTTAAAAATTAAACAAAAACTAAATG

TTTAATTATTTACTCGATAATATAAATCTATGAAGCGAAAAGTTTAATTTTTTAAAAACTTTCTAAATTT

GTGAAATGTTACAATATCTTTGAATACGACAATAAAACAATATTTTACTAATATTTATATATATAGTTAC

GATTTTAATAATGAAATAATAATCCGAAAATATATATATAGAAGAAGATAGAAATACATGTGAAAGTTTG

AAACAATCTATTCAATGAAAAAAATATACCGTAAACTTATTATGTTTAAAAATTGATAGACACATATATA

TTATAATATATACCAATTTAGAATTGAAAATAAAATGTTTATATAAAAATAAATGAAAACAAAAACCCGC

GAATCGAGATCTAGTATTAGTTAAAGTCATATACATGACTTGTTGAAATTTAATTGAATAATGTTTTGGT

CAACAACATAGAACTTATTAGATTTTTTTCATGCTTATATTTGGTTTGGTTATTAAATAATTTTCTAACA

TTTATTTCTCCTAATTGACCAAAAAGATCAACTGCTAAAACATCTTATATATGTGTATATTTGTTTGGTT

TTATTACAGTACTTCTCCATCAGAAAGCACCCACACAAACAAAATGATGGAAGAGAGGATGAGTCAATGG

AAGTCATCGAGATGAACTTCTATGAAGATATAATGTTTGATTACATACCAAATGGTGAAGACGATTCCAT

-continued

TGCAATGCTCCTCGGAAATCTAAACGAGCACTATCCCTACCCAAATGATATTATGGATCTCACTGTCGAT

CTTGATCAGCATCAGCAAGCCACCTCCTCGTCGCCACCTGCTGATCACATGAGCTCGAACGATTTCTTAT

GGTGATGTGATGGA

SEQ ID NO: 15; *Arabidopsis Thaliana* LEC2 genomic sequence

*GATCTCTCTCCCTCTCTCTCTCTCTCTCTCCGGGAAAAATGGATAACTTCTTACCC*

*TTTCCCTCTTCTAACGCAAACTCTGTCCAAGAACTCTCTATGGATCCTAACAACAAT*

*CGCTCGCACTTCACAACAGTCCCTACTTATGATCATCATCAGGCTCAGCCTCATCA*

*CTTCTTGCCTCCGTTTTCATACCCGGTGGAGCAGATGGCGGCGGTGATGAATCCT*

*CAGCCGGTTTACTTATCGGAGTGTTATCCTCAGATCCCGGTTACGCAAACCGGAA*

*GTGAATTCGGTTCTCTGGTTGGTAATCCTTGTTTGTGGCAAGAGAGAGGTGGTTTT*

*CTTGATCCGCGTATGACGAAGATGGCAAGGATCAACAGGAAAAACGCCATGATGA*

*GATCAAGAAACAACTCTAGCCCTAATTCTAGTCCAAGTGAGTTGGTTGATTCAAAG*

*AGACAGCTGATGATGCTTAACTTGAAAAATAACGTGCAGATCTCCGACAAGAAAGA*

*TAGCTACCAACAGTCCACATTTGATAACAAGGTTTGGTTTTTATTCGTCCCAATTTT*

*TGAATATGTACGATTTTCTTATTTATTTTTTGGTTTTCATGTTATTATATGAATATATA*

*CAATTTTGGGTGTATAAAACTTTATGATACAATTTTTAATTATTTTTATTTTGTTTTGG*

*TTGTTGCTTGTAGAAGCTTAGGGTTTTGTGTGAGAAGGAATTGAAGAACAGCGAT*

*GTTGGGTCACTCGGGAGGATAGTTCTACCAAAGGTATGTGAATTCTTAAAATTCTT*

*TTTAATTTCTCGAACCAATACTTGGTAAAAAAATTCTGTTTGTTTTCATGATTTTTCTT*

*CTTTTTCTGTTATTGTATAATGATAAATGAAATGCATTGATGAAAATGATAATCATCA*

*ATCACGTACGTCATTGAAAATTTAAAACACAATCCCATAAAAAAAATTCTTAGAAGAA*

*TAAAGTTATTTTATGAGGATTAGACTTCCGTCATTTTATACAAGAGATTTGTGGAAC*

*ACAAGCACAAAAATCGTTGCGGCCACATATTATCTCATTATTCAATTTCACTGAGTT*

*TTTCTTGCACATTTCATTTTACTTTCAAATTTTACATAATATGTTTATCTAACTGTTTT*

*CTGTTTAACCAATAAAAAGTTTTAAGTCTTTAAAATAAGTATCCACACGAAAACAAG*

*ATGAATAAGAAACATGAGAAGAAAATGTGGACTGAAGTAAAGTTAGTTTAATCAAA*

*TTTTGTTTGGTTTCTGTACGAACTTTTATGTTTTTGATTTTTTATTTATTTAGCAAGTA*

*GTATATGAATTAATTTAATTTTTTATAGTTTTAAACTTGATTTTTTTAAAGATAGCTTA*

*TAATTATTGAATATATGGAATGCTACTTCTTCCTTCAATGTTGTTATTTGTATTTGTT*

*AAATTTGAAATTGGGTTGAAGAAAATGAAAGGTCGTTTATATGCCTTTCCTAATTAA*

*TTGTCCATTGAATGGTTTACCACTTTACCTCGAAAAAGTGAATAAATAAAAATCATT*

*AGGGAAAAAGATTCTACATATCTTGGGGTTTTATCAAACTTTTAATCAATTTTATTTT*

*AATGATATCGTTCTTATTTTTCTTAGCAAGACACTAATACGTGAATCATGGCTTTGG*

*AATGCAGAGAGATGCAGAAGCAAATCTTCCGAAGCTATCTGATAAAGAAGGAATC*

*GTTGTACAGATGAGAGATGTTTTCTCTATGCAGTCTTGGTCTTTCAAATACAAGTAA*

*ATAATTCGCTTTCTAATCCATTTTTCATTTCCCAATTAACACAACTTTAATTTTATGC*

*TCAACTGTTAGTCCCTTTTTGTGTTACCGGTTCTCATACTTAGTTTTAAATTTTGATT*

*TTTTTTTTATCAATTGGGAACAGTATTATAATTAGAAGACTAAATGCTCGTATTAATG*

*ACATAGGTTTTGGTCCAATAACAAGAGCAGAATGTATGTCCTCGAGAACACAGGTA*

*AATTAAGGAGCTCCAATATTATTTCAAAAGTACAAAATCTTATGTAAAACTACTTTTA*

*AATAAATATGATTTACCTTTTCCTTTTTTTTTGTGGTGATAACTAAAGGAGAATTTGT*

-continued

*GAAGCAAAATGGAGCTGAGATAGGAGACTTTTTAACAATATACGAGGACGAAAGC*

*AAGAATCTCGTGAGCTCTCTATTTACTTCATTTCCCTATTTAATTTTGTAAAAAGAC*

*ATGAAAAAGTTAAAAAAAAAATGATTAATTAGTAGTCCAAAATTGGAAATTTAAAAA*

*GTGGTCTTTGAATTGAGTTTGTTAAGCATCCAGACAAAAGTTTTAAAACCTTTTTCT*

*GTCAATGATAACTGTTCTTATATGGTAGGTATTAATAACTTGTGGGCCTAGGGGGA*

*AGTAAATACTATGGAGAAAATTTTATAATAATTGAAATTTGGTTAATTTAGAGTTTAT*

*AATATGGTTTGATTTGGTTTGGTTAGGACTTATGACTTATGTGTCTGTGTGTGATC*

*GCTTGTTCTTATTACAGTACTTCGCCATGAATGGAAATTCGGGAAAACAAAATGAA*

*GGAAGAGAAAATGAGTCGAGGGAAAGGAACCACTACGAAGAGGCAATGCTTGATT*

*ACATACCAAGAGACGAAGAGGAAGCTTCCATTGCAATGCTCATCGGAAATCTAAA*

*CGATCACTATCCCATCCCTAACGATCTCATGGACCTCACCACTGACCTTCAGCAC*

*CATCAAGCCACGTCCTCATCAATGCCACCTGAGGATCACGCGTACGTGGGTTCAT*

*CCGATGATCAGGTGAGCTTTAACGACTTTGAGTGGTGGTGATATGGTGGTGGAAG*

*TTCTCAAGTTCATAACCCCCTTTATGAAAATAGACCTTAAGATATACAAAAGAGATT*

*AAAAGAAAAAAAAGTTAGTATATTTCATCATATCTCTCATTGAAGATGAGATTTATAT*

CTATAATTGTTTAATAGTGTTTTTATTACTTTTCTATCAATATATTAAAGTTTTAATT

SEQ ID NO: 16; *Arabidopsis Thaliana* LEC2 CDS sequence
*ATGGATAACTTCTTACCCTTTCCCTCTTCTAACGCAAACTCTGTCCAAGAACTCTCT*

*ATGGATCCTAACAACAATCGCTCGCACTTCACAACAGTCCCTACTTATGATCATCA*

*TCAGGCTCAGCCTCATCACTTCTTGCCTCCGTTTTCATACCCGGTGGAGCAGATG*

*GCGGCGGTGATGAATCCTCAGCCGGTTTACTTATCGGAGTGTTATCCTCAGATCC*

*CGGTTACGCAAACCGGAAGTGAATTCGGTTCTCTGGTTGGTAATCCTTGTTTGTG*

*GCAAGAGAGAGGTGGTTTTCTTGATCCGCGTATGACGAAGATGGCAAGGATCAAC*

*AGGAAAAACGCCATGATGAGATCAAGAAACAACTCTAGCCCTAATTCTAGTCCAAG*

*TGAGTTGGTTGATTCAAAGAGACAGCTGATGATGCTTAACTTGAAAAATAACGTGC*

*AGATCTCCGACAAGAAAGATAGCTACCAACAGTCCACATTTGATAACAAGAAGCTT*

*AGGGTTTTGTGTGAGAAGGAATTGAAGAACAGCGATGTTGGGTCACTCGGGAGG*

*ATAGTTCTACCAAAGAGAGATGCAGAAGCAAATCTTCCGAAGCTATCTGATAAAGA*

*AGGAATCGTTGTACAGATGAGAGATGTTTTCTCTATGCAGTCTTGGTCTTTCAAAT*

*ACAAGTTTTGGTCCAATAACAAGAGCAGAATGTATGTCCTCGAGAACACAGGAGA*

*ATTTGTGAAGCAAAATGGAGCTGAGATAGGAGACTTTTTAACAATATACGAGGACG*

*AAAGCAAGAATCTCTACTTCGCCATGAATGGAAATTCGGGAAAACAAAATGAAGGA*

*AGAGAAAATGAGTCGAGGGAAAGGAACCACTACGAAGAGGCAATGCTTGATTACA*

*TACCAAGAGACGAAGAGGAAGCTTCCATTGCAATGCTCATCGGAAATCTAAACGA*

*TCACTATCCCATCCCTAACGATCTCATGGACCTCACCACTGACCTTCAGCACCATC*

*AAGCCACGTCCTCATCAATGCCACCTGAGGATCACGCGTACGTGGGTTCATCCGA*

*TGATCAGGTGAGCTTTAACGACTTTGAGTGGTGGTGA*

SEQ ID NO: 17; *Brassica rapa* UPL3 TILLING mutants gene sequence showing location of premature stop codons that abolish UPL3 function Exons Premature stop #1 premature stop #2

Bra010737.1

AATGTGTTTGATATATACCATGGATAGTAGTGAGAAGGTAGAGTTCAAAGTATAAGAAAGCGAACCCCTCCATA

GTGGGGGCTTAAACCCGTGCAAGCTTGCATATATCTATAGCTGATGGTTGGGCCCAAACTTATATCTTGGGCTT

ATTTTGTTTCCATCTGTCCAGCCCATGATAAAGTGTAAAACGACACCGTATAAAGCTTAATGGAGTAAACGAAT

CACACGTAGCGGGGATCCCCGTGTCAGTTCTTGTCCGAAAAGCTGGACGGAGGAAAACGGCATCGTATTCGCTT

CGCTTGAATATATATATTTTGCGCAAAAGCCCTTTTCATCCCTTTCTTCTCTCATTACTCGATTTAGGGTTTTC

TAATCTCGAAAGAAATCAAGATCCTCCTTCCTCCCTCTCTCGATTTCGATCTCTTTCGTGTTGATTTCGAATTC

GTTCGTCAATAGGTTTGTTTCTCTCTAGCTCCGATCGATCTCGCTAGCAAATTAGGGTTTCGAGCGAGCTTAAT

CCGATCGGTTTCTGGATCAGTTGAGATGCGATCGGAATCTCTCTGAATAAGAGAGACTCGTGTGGGGGGTTTCT

TCCTTTGTATGGAAACTCGGAGCCGCAAGCGTGCGGAGGCGACCTCAACTGCCCCATCTTCTTCTTCTTCCTCT

CCTCCTCCTCCTCCTTCCTCAGGTCCCACCACTCGCAGCAAACGCGCTCGCCTCTCGTCTCCCTCTTCATCTTC

AGCCGCCGCTACTGCACCTTCCTCCTCCACCCGCTCTCGTTCTTCTCGCTCTACCACCGCTACAGTCGCCGTTA

CTCCCATGGACACATCCACCGAGTCTTCTGGATTCCACCGCGGCGGAGGACGAGGTAACAGGGGAAACGATAAT

ACTAACTCTGATAAGGGAAAAGAGAAGGAGCATGAGGTTAGGATTAGGGATAGAGAAAGAGACAGAGCTAGGCA

ACAGCTCAACATGGACGCTGCAGCTGCTGCTGCCGCCGCCGCTGACGAGGACGACGACAATGATAGTGAGGATG

GCAACGGGGGATTCATGCATCCCAACATGAGCTCAGCCAGCAGTGCGTTACAAGGGTTGCTGAGGAAGCTTGGA

GCTGGACTTGATGACTTGCTTCCTTCTTCAGGTATTGGCTCAGGTTCGTCTTCTCACTTGAATGGGAGGATGAA

GAAGGTACTCGCTGGCTTGCGCTCTGAAGGAGAAGAGGGAAAGCAGGTCGAGGCTTTGACGCAGCTGTGCGAGA

TGTTATCTATTGGGACCGAAGACTCCCTGAGCACCTTCTCTGTTGATTCCTTCGTCCCGGTTCTTGTTGGTCTA

CTTAACCATGAGAGCAATCCGGATATTATGCTTCTTGCTGCCAGGGCTCTTACTCATCTGTGTGATGTTTTGCC

GTCTTCTTGTGCTGCTGTTGTTCATTACGGGGCTGTTTCGTGCTTTGTCGCCAGATTGTTGACAATAGAATACA

TGGACTTGGCCGAGCAGGTTCGATTTCCTAACAATTCTTGAATTTTTTTGCTGAATATATATTGTGGAATGTTT

TATGCTGCAGTTTCTACACGTACATATCCAATATTTTAGTTTACTTAGGACGAAATTTGAAATTTGATTTTATT

CTTCATGTGATTTACAACAGTCTCTGCAAGCTCTCAAAAAGATATCTCAGGAACACCCAACGGCCTGTTTGCGT

GCTGGTGCTCTTATGGCAGTGCTATCATATCTGGATTTCTTCTCCACCGGTGTCCAGGTGGGTAATTTTGTAAC

TTTTCTTTAATGCTTTCCATACTCGTTTATCTAATGCACTTTTTTTTTTACTTTTTGTAGCGTGTAGCAGTATC

TACCGCTGCAAATATGTGCAAGAAGTTACCTTCTGATGCATCTGATTATGTTATGGAAGCTGTACCGGTACTGA

CAAACCTACTTCAGTATCATGATGCGAAGGTAAACGATCCCTTTTTTTTTGCTATAATGTGGTATTATCTAGTT

CTGCTCTTGCCCCAGTTTCCTTCATAGTATGTTCGTACGGTGGCAGGTTTTGGAATATGCTTCTATCTGTTTGA

CTCGGATTGCCGAAGCATTTGCATCGTCCCCTGATAAATTAGATGAATTATGCAACCATGGCCTGGTGACTCAA

GCTGCGACTCTTATATCCGCTAGCAACTCGGGAGGTGGGCAAGCATCTCTCGGTGTTTCAACATACACGGTATG

AGTTAATTCTTTTGTGTTTTCTATATTTCGTTATTCATAGGATGACATTTTCATCATATTTTCACAGGGATTAA

TCCGATTACTTTCCACCTGTGCGAGCGGTTCACCTCTTGGGTGCAGGACATTACTTCTTCTCGGTATTAGTAGC

ATTCTTAAGGATATTCTGTCGGGTTCCGGTGTCTCTGCTAATGCATCTATATCCCCAGCACTGAGCAGGCCTGC

AGATCAGGTACGGATTTACTTTTTGACATCACAGACTTTATTTTGTTCAATTCCTGATAAAGTCTATTCAGTAA

AAAGTGTTTTGTTTAGGGGACACACCTTTAAATAGATCATCAACATAAATTGTGTGTTGAGTGAGATGCTTAGG

GGACACACCTTCAAATAGATCACTTGCATTTAAATGGATCACTTGCATTTAGGAGTTTTGTCTATTCAGTTCAA

-continued

TGATAATCTTTTTTTTTTTGTAACACTCAGCTCAATGATAATCTATGTACATGTATTTTGAGCTTTATTTATGT

TGTAACCGATGGCTCAACTTTCATATGCTTGTTTTCTGGTATGGTGTTAGAAGTGGTATAGATAAAAGTGCTTA

GCGCTTCATCAGTGTGCTCGGTCTTGTTTATTTAACTTTTTTTATCCCATGACTCGCTAATTCTTGAATATATT

CTTGAACATGATCATGTGAGGTCTTTTGTTTCCGAATTATAACTCTTGTTTTGCATCTTAGATTTTTGAGATAG

TCAACCTAGCGAACGAGCTCCTCCCTCCACTGCCAGAAGGAAGTATCTCCCTTCCTACTAGCGCAAACGCGTTA

GTGAAAGGTTCAGGCCAAAAAAAGTCTTCTCCAAGTACTTCAGGAAAACAAGAAGATTCTCCCAAAGTTTCACC

TAGAGAAAAATTACTTAGTGATCAACCCGAACTTCTGCAGCAATTTGGATTGGATCTTCTTCCAGTTTTAGTGC

AGGTAATTTTTTGTTGCAGTTGCTACAAGTTAGTGTTCATACAACCTCCTGTATGTCTAATTACCCTTGTTTTC

TTTCCTACAGATCTATGGTTCTAGTGTCAATGGTACTATTCGTCATAAATGTCTCTCAGTTATCGCAAAGTTGA

TGTATTTCAGCACTCCAGAAATGATTCAATCTCTAATTGGTGACACAAATATATCGAGGTATGCTGGTTATGTT

TTAAATTAGGTATCACATGGCGCAACTTCTTACATTATTTTTCCTATGTAGCTTCTTGGCTAGTGTCTTGGCAT

GGAAAGATCCACAAGTCTTGGTTCCTGCTCTACAAGTTGCAGAAATTCTGATGGAAAAACTTCCTGAAACTTTC

TCGAAAGTGTTTGTGAGGGAAGGGGTGGTTCATGCTGTAGATCAACTTGTCTTGGTTGGTAAACCTAGTTCTCA

TGCTTCTACTGATCAGGAAAATGACTGTGTGCCTGGATCTGCACGATCTAGGCGTTATAGACGGCGAAGTAGTA

ACGCCAATTCTGATGGAAATCAGTCGGAAGAGCTTAAGAATTCTGTGTCAGCTAGTATAGGTGCAAACCATAAT

TCCATGGAATCTCCTACAGCGAGCTTCATGCTAAGGGAAACAGTTAGCTCCTGTGCAAAAGCATTCAAAGACAA

GCACTTCCCGTCTGATGGTGGGGAATTTGATGTTGGAGTTACAGATGATCTCTTGCATCTGAAGAATCTTTGCA

CGAAGCTAACTGCTGGTACAAATGATCATAAAGTGAAAGGAAAGGGGAAATCTAAAGCCTCTGGGCCATGCCTC

GGCGATTTTTCTGCTAGCAAAGAAGAATACTTGATTGGTATCATCTCCGAGATACTTGGCGAGCTAAGCAAAGG

AGATGGTGTCTCAACTTTTGAGTTTATTGGCAGTGGTGTGGTAGCAGCATTGCTTAACTATTTTTCTTATGGAT

ACTTTTCCAAAGAGAAGATCTCCGAGGTTGATTTGCCCAAACTTCGCCAGGATGGGCTCAGAAGGTTCACAGCT

TTTCTAGAAATTGCACTTCCTTCTGATGGTAATGAGGGAAAGATCCCTCCTATGACTGTTTTGATTCAGAAACT

TCAAGATGCTTTGTCTTCACTGGAACGCTTTCCGGTCGTCCTTAGCCATCCCTCAAAGTCACTCAGTGGAAGTG

CTCGTCTCTCATCTGGATTGAGTGCTTTGGCACATCCTTTGAAGTTGCGGTTATGCCGTGCACCTGGAGAGAAG

GCACTACGTGATTACTCCTCCAATATTGTTCTCATAGATCCTTTGGCAAGCATAGCAGCAGTGGAGGAATTTCT

CTGGCCCCGAGTTCAACGCAGTGAATCTGGGGTGAAGCCAGCAGCGCCTGTTGGAAACACTGAGCCAGGCACAT

TACCTAGCGGTGCTGGTGTTTCATCACCATCCTCGTCAACTCCAGCTTCCACCACTCGTCATTCTTCTAGATCT

AGATCTGCAATTAAAATAGGCGATGCCTCAAAGAAAGAACCTGTGCACGAGAAAGGTACCAGCTCATCTAAAGG

TAAAGGTGTTATGAAGCCGGCTCAGCCGGATAAGGGGCCTCAGACAAGGAGCAGTGCTCAAAGGAAAGCTGTTC

TTGACAAAGATACACTAATGAAACCAGCTAGCGGAGACTCCAGCTCTGAGGTATGTCACTGTAGAAAGTTCTGG

ATTACATGGTTGTTTATTGTGTAACATTATATTATGTTTGTGGTGTGATCTGCTTATGCAGCACTATCGTACTT

ATATTGCTTGCAGGACGAAGAAATGGATATATCCCCCGTCGACATGGATGATGCTTTGGTTATTGAAGAGGAAG

ACATTTCTGACGACGATGAGGATGATGATGATGAGGATGTAAGTATTCCCTCCCCAGTATGTACATTACAGACG

CAATTATTTCTCTTGCTAACAACATGAAAGATGATACTTTTCGCAATAATGCTTGCTAGCTTTCCGTATTCTTA

GATAAGTTTACCATATTGAGCTCACCTTATTTGGCACCTTTCCTTTTAGAACTGACTAAAGAGAATAATGAACT

TTATACCACAATTTCTCATATTGATCTGGTCTTGAATTCAGGTCTTGGATGACAATCTTCCCATGTGCACCCCT

GATAAGGTTCATGATGTAAAATTGGGAGACGCAGTGGATGATGAGGGAGCCGGTCTAGCACCTAGCGGCCGACA

GATGAATTCAGCTTTGGCAGGAAGTAGTGGAACAGCAACTGCAAGGGGATCTAATTCTACTGATGCTGGCATTG

GGAATCTTTATGGTTCTAGGGGTGCACTCTCCTTCGCTGCTGCGGCGATGGCAGGGCTTGGAGCTGCCAGTGGT

AGAGGTATCAGGGGAAGTAGAGACCTACATGGGCGTACCCTGAATCGAAGTTCTGATGAGTCCTCTAAGTTGAT

GTTTACTGCGGGAGGAAAGCAACTTAGTAGGCATATGACGATATATCAGGCTGTGCAACGACAACTTATGCTAG

-continued

ACGAAGATGATGATGACAGGCTCGGTGGCAGCGATTTCATCTCCAGTGATGGAAGCAGATTAAATGATATATAT

ACTATCATGTACCAGATGCCGGACAGCCAAGCGAATAGGTTGTCTGCTGGTGGTGCAAGTTCTACCACACCATC

TAAATCCACCAAATCTGCTACTACTAATGCAAGCGTAGAAGCTCAGTCGTATAGGGCATCTCTTTTGGATAGTA

TCGTACAAGGAAAGCTTCCATGCGACCTTGAGAAGTCCAATTCTACGTATAATGTTCTGGCGTTGTTACGTGTA

TTAGAGGGTTTAAATCAGCTTGGCCCTCGCTTAAGAGCCCAAACCGTTTCTGATCGTTTTGCAGAGGGTAAAAT

TACAAGTCTGGATGATCTGAATACAACTGCTGCAAAGGTTTCTCATGAAGAATTCATCAACAGCAAACTTACAC

CCAAATTAGCTCGACAGATCCAGGACGCGCTTGCTTTGTGCAGTGGAAGTCTTCCCTCTTGGTGCTACCAGTTG

ACTACAGCATGCCCGTTTTTGTTTCCGTTTCAGACCCGGAGACAGTATTTCTATTCAACTGCCTTTGGGTTGTC

GCGTGCATTGAACCGCTTGCAGCAGCAGCAAGGTGCTGACGGCAGTGGTTCTACAAATGAACGAGAGATGAGAA

TAGGGAGATTGCAGCGCCAGAAAGTGCGTGTATCCCGAAATAGAATATTAGATTCTGCTGCGAAAGTTATGGAG

ATGTATTCTAGCCAAAAAGCTGTGCTTGAAGTAGAATATTTTGGTGAAGTTGGTACTGGTCTAGGCCCGACACT

TGAGTTTTACACACTCCTAAGCCATGATTTGCAAAAGGTTTCCCTTGGGATGTGGAGATCAAATTCTGGTGACA

AGTTATCTATGCAAACTGATAGAGATGAGATTCAAGACGGTAAATCAGCAGCAGCTAGGGACAGAGATATAGTT

CAGGCACCACTTGGGTTGTTCCCTCGGCCCTGGCCCTCAACTGCTGACGTATCTGAAGGTAGTCGGTTTCATAA

AGTTGTTGAATATTTCCGCCTTTTAGGGCGCGTGATGGCAAAGGCACTTCAAGATGGACGGCTAATGGACGTCC

CGTTAAGTACAGCTTTTTATAAGCTCATTCTTGGTCAAGTGAGTTTTTTACTATCAGTAACTTTTTTTATTTAG

CTAAGAGTGGACTAGTAGTTTCGACTTCTTTACGTTGTTCGTAATTTCTTACTGCTTCTTTACTCACCTGAACA

GGAGCTTGATTTGCATGATGTTATATTATTTGATGCTGAACTTGGCAAGACTTTGCAAGAGCTTCGTGTTCTTG

TTGGCCGTAAGCACTATCTGGAAGCAGGCGGTGGTGACAACAGTAGCGGGATTTCTGATTTATGTTTGCGTGGA

TCCCGTATTGAAGATCTTTGCTTGGACTTCACCCTACCTGGCTACCCTGAATACATATTGAGACCAGGAGATGA

CATTGTACCGTCTAATAAGCTTTACATCCGATATCTTACTATTGTTTTAGTTCTTGTCCATTGTTGCTGATGCC

GTGTACTGTTTTCTGTTCTATTACAGGTTGATATTAATAGTCTTGAGGACTATATATCCCTGGTCGTTGATGCC

ACTGTCAAGAGAGGAGTTGCCCGGCAGATTGAAGCCTTCAGATCTGGATTCAATCAGGTTAGCAGTTTCACAGA

CTCTCCGCTTTGTCTCTTACTTTTCCTGTAGGCTTTGGCTTTGGCTTTGGCTTTGGCTTCTAAATTACATAGGA

GTGGTTTCTTTTGGTTCATACTTTATAATCTTTTAAACAACAGGTTGATGATAATTTAGTCTTACCTTTATTAT

CTTTACAAGAATTCTCTGTTCTTACACATGATTACCAGGTCTTTGACATAAAATCTCTACAAATATTCACCCCT

TCTGAGCTGGACTACTTGTTGTGTGGTCGTAGAGAGTTGTGG (mutation of G to A to give

"TGA)

GAGGTGAGTTTTCATCTATTTTTTGAATTTCCACTACCCATTTGACTCGAATCGACTAGATAAAATTTTCTTTT

CTAAAACCTTTCTTTTATTGCAGGCGGAGACTCTTGTTGAACATATCAAGTTTGATCACGGTTATACTGCAAAA

AGTCCGGCAATCATTTTCGTAAGTTACTTTCCGTACTAGTTTGTTAAAAAACCAATTTTCTTTTACAATCAAGC

TTTTTGCTTCTTTATTGTTGATTCCTTTTTGACTTTGATTTTCACCCTGGCGGTAGTTATTGGAGATCATGGGA

GAGCTAACAGCAGATCAACAGCGGGCTTTCTGCCAG (mutation of C to T to give "TAG")

TTCGTAACTGGAGCTCCTAGGCTTCCTCCTGGTGGCTTAGCTGTTCTCAACCCAAGGCTGACGATTGTGAGAAA

GGTAAGAAACCTTTACTTATATATTCGGTTAAAAAGCGTTTTTGTAATTGAGCCAAGAGGTTCTAGTCATGTTA

AACTAGACCCACCAAGCCATATATCAGAATACATCTACACGTGACGCATTGTTGTGTTTGCAAGACTTGCTAAG

ATGAATTAGCTCTTACTCGATTTAAGTTGTGTATTTGCTTCCAATTGATGTGTTTTTGGCTTGATGCAGCTCTC

ATCAACCTCAAATGCTGCTGCCAATGGGACAGGGGCTTCGGAAACAGCAGACGACGATCTTCCCAGCGTCATGA

CTTGCGCCAACTACCTTAAGCTCCCTCCTTATTCTACAAAGGTAACTCGTCTCTCTTTTTTTAAGTCTACGGTT

TCTGTGTTTGGTTGGTTGGGGTGAGCCTGAACACGAGTTTGTACCTGAAACAGGAAATCATGTACAAGAAACTG

-continued

CTCTACGCCATCAACGAAGGGCAGGGGTCGTTCGACCTATCCTAGGCATCTCTCTCTGTTGTGGCTGCGGCTAG

AAACCACCAACCCTCTCTCTTCTTTGTACATTTTATATCGGAAGACTCTGATTTTGCACTTTGAATGTTATTTC

TGTTAAACCATGAATTATTAAAATTAGGTTCAATATTTTTCATGTGCAAGTAACATATTAATACATGGAGGATA

AAAATAAAATCAAAAGACAAACTTGAATAATTTTGGTTGCCTTTAAAATTCGTTTGAAAATTCCGAAGCAATTA

TATATAGTGTGAATAAAAGTCGTCAGCTGAAGGAATAAAGGTACAAAGGTACAAAGGTTTAGGTGTTGTATGAT

CCAAAATTCTGTTTTTTTTTAAAGACGGGCTCTATCAGTCACAGCAGTTGACTGTAAGATATCAAAGGAATAAG

AAACAGTTGTTCGTTTGTAGTTTTCTGGAGATTGAACAAGAGAACTCGTCTTCGTTTCATCAGTTTTCTTTTTG

ATAAAAGTCAATTCGACATAGATATCTCTAGACACGAGAAACAAAAGCATAAATAGGAAAACATTACAATTATA

AAAGAGCGTTACGAGTACAGAGTCCAAACTAGGCACAAGAAACCTACCATATG

SEQ ID NO: 18; *Brassica napus* UPL3 promoter repeat region

TCATAAAAGAAGAATATATTTGTATCTTTGCATAGATCATATATATATTGTAATGAC

TAATTATTTTCTCGACAAACCAT

SEQ ID NO: 19; *Brassica napus* LEC2 ptotein

1 METRSRKRAE ATSAAPSSSS SSPPPPPSAS GPTTRSKRAR LSSSSSSSLA

51 PTPPSSSTTT RSRSSRSAAA AAPMDTSTDS SGFRRGGRGN RGNNNDNSDK

101 GKEKEHDVRI RERERERDRA REQLNMDAAA AAARSADEDD DNDSEDGNGG

151 FMHPNMSSAS SALQGLLRKL GAGLDDLLPS SGIGSASSSH LNGRMKKILS

201 GLRAEGEEGK QVEALTQLCE MLSIGTEDSL STFSVDSFVP VLVGLLNHES

251 NPDIMLLAAR ALTHLCDVLP SSCAAVVHYG AVSCLVARLL TIEYMDLAEQ

301 SLQALKKISQ EHPTACLRAG ALMAVLSYLD FESTGVQRVA LSTAANMCKK

351 LPSDASDYVM EAVPLLTNLL QYHDSKVLEY ASICLTRIAE AFAPYPEKLD

401 ELCNHGLVTQ AASLISTSNS GGGQASLSVS TYTGLIRLLS TCASGSPLGF

451 RTLLLLGISS ILKDILLGSG VSANASVSPA LSRPADQIYE INVLANELLP

501 PLPEGVISLP TSTNALVKGS CQKKSSPSTS GKQEDILKIS PREKLLGDQP

551 ELLQQFGLDL LPVLVQIYGS SVNGTIRHKC LSVIGKLMYF SSSEMIQSLI

601 GDTNISSFLA GVLAWKDPQV LVPALQVAEI LMEKLPETFS KVFVREGVVH

651 AVDQLVLVGK PSHASPTDKD NDCVPGSARS RRYRRRSSNA NSDGNQSEEP

701 KNPASLTIGA NHNSLDTPTA SFMLRETVSS CAKAFKDKYF PSDGGDVDVG

751 VTDDLLHLKN LCTKLTAGID DHKVKGKGKS KASGPFLGDF SASKEEYLIG

801 VISEILGEIS KGDGVSTFEF IGSGVVAALL NYFSCGYFSK EKISELNLPK

851 LRQEGLRRFK AFLEVALPFD GNEGKVPPMT VLIQKLQNAL SSLERFPVVL

901 SHPSRSLSGS ARLSSGLSAL AHPLKLRLCR ASGEKTLRDY SSNIVLIDPL

951 ASLAAVEEFL WPRVQRSESA LKPAAPIGNT EPGTLPSGAG VSSPSSSTPA

1001 STTRRHSSPS RSAINIGDTS KKDPVHEKGT SSSKGKGKGV MKPAQADKGP

1051 QTRSNAQKRA VLDKDTQMKP ASGDSSSEDE ELEISPVDID DALVIEEDDI

1101 SDDEDDDNED VLDDSLPMCT PDKVHDVKLA DSVDDDGLAT SGRQMNPASG

1151 GTSGAAAARA SDSIDTGIGN SYGSRGALSF AAAAMAGLGA ASGRGIRGSR

1201 DLHGRTLNRS SDEPSKLIFT AAGKQLSRHL TIYQAVQRQL MLDEDDDDRF

-continued

1251 GGSDLVSSDG SRFNDIYTIM YQRPDSQVNR LSVGGASSTT PSKSTKSATT

1301 NSSVESQSHR ASLLDSILQG ELPCDLEKSN STYNVLALLR VLEGLNQLCP

1351 RLRAQTLSDR FAEGKITSLD DLSTTAAKVP LDEFVNSKLT PKLARQIQDA

1401 LALCSGSLPS WCYQLTRACP FLFPFQTRRQ YFYSTAFGLS RALNRLQQQQ

1451 GADGSGSTNE REMRIGRLQR QKVRVSRNRI LDSAAKVMEM YSSQKAVLEV

1501 EYFGEVGTGL GPTLEFYTLL SHDLQKASLG MWRSSSGDKV SMQIGRDEIE

1551 DGKPSAANRD IVLAPLGLFP RPWPSTADIS EGGQFHKVIE YFRLLGRVMA

1601 KALQDGRLLD VPLSTAFYKL ILGQELDLHD IVLFDAELGK TLQELRVVVA

1651 RKHYLEGVGG DNSSTISDLC LRGCRIEDLS LEFTLPGYPE YILRSGDEIV

1701 DITNLEEYIS LVVDATVKRG VTRQIEAFRS GFNQVFDITS LQIFTPSELD

1751 YLLCGRRELW EVETLAEHIK FDHGYNAKSP AIINLLEIMG ELTADQQRAF

1801 CQFVTGAPRL PPGGLAVLNP KLTIVRKHSS TSSAAANGAG ASETADDDLP

1851 SVMTCANYLK LPPYSTKEIM YKKLLYAINE GQGSFDLS

At4g38600.1 UPL3 ARM fold and ARM helix regions are dashed underlined
The HECT domain is underlined.

SEQ ID NO: 20; Dimension_BnC03_UPL3_promoter (Low UPL3 expression genotype) Underlined sequence indicated polymorphic regions relative to Coriander promoter (high UPL3-expressing) sequence. "-" represents the presence of a deletion in the dimension sequence relative to Coriander sequence. All polymorphisms (substitutions are underlined) are further described in Table 2 that follows.

AGAGAGGCCTGGACGTTTGGGTCATCGCTCTCGGTCGGTTCCTACTTTTTCTGCA

CCACCGCCATTTGTTGATCCAGAAATATTTACGGCTCAGTTGAAGGACAAGGATG

ATCGCATATCTTTGTTGGAGACCCAGAAGACGGCTCAACAGGCGGGCTATGAGG

CACAGAAGAGGCTGAACCAGCAAATGATGAAAAGGATGTACCCGAACGAGGTGTT

CCCGAACGTGCAAGACCCGTAG----

TTTTTTTTTTCAAAAACTCGGAATGTTTTATTTTTATTTGTACAACTTTGAATATTAT

CTAATATGTTTTCAATTTTAATTTTAATTTTATATTTTCGAATTTAAATTTCAAAATTTT

CA

-

TTTTTAAAAAAAAATTAATTTTTTTTTTGAAATTCCGAGGAAATGAACCCTCGGAAAT

TTCCGACGAACATTTCCTCAGAATAAGTCGTCGGAATATACCGAGGGACTCCTTC

CTCCTCGGAATTTTCTGAGGGCTCCGTTTCTCGGAAATTCCCGATGAAAATTCCGA

GGAACATTTC

ATCGGAACTTCCGAGGATTGGACCATCGGAAAGTCCATCGAAATATTCCGAAGAA

GTTCTCCCTCGATATATTCCGAGAACCTTTCCGACGAACTGGTGGTCCTCGGAGT

TTCCTCGGAAATTCATTTCCTCGGAATTCCTTCGGAAATTTCTGAGGGATTTCCGA

GAAAAAATGAATTTCCGAGGAGTTATTTCCGAGGACTTGTTTCGTCGGTATGTCGT

CGGAATAACGTTATCCGACGACGTACCGACGATTTTTTCCC

-

TCGGTATGTTCATATTGGATTTATAAATGAATCATAATTTCTGTTTTTCGGGTTAAAT

TAATATGTATATATATATATATATATATTAAAAAAATCTGTAAGTTCCAAACAAGGGCAC

ACTTATAAAAG-

-continued

```
AACTAATGTATTATATACTGTCATGTTTTTTTATAAAATATGTACAATAATTTATATA
TGTCTTCATCCGATTAACAAACTCAAACCCAAACAACAAAAATTTCTACATTTAGAT
TTTAAATTAGCGTGTGATGGCTAAAGAAAAAAAGAAGAATAAATTTGTATCTTTGCA
TAGATCACCTGCATTTCATTGAGTAGATTCATTTAAATAAGTAGATAGATAGATTTT
ATTATCATATTTATTTTCTTAACAAACCATCATAAAAGAAGAATATATTTGTATCTTT
GCATAGATCATATATATAATTGTAATGACTAATTATTTTCTCGACAAACCATAGTTTT
TCCTTACTACAATCATAAAAGAAGAATATATTTGTATCTTTGCATAGATCATATATAT
AATTGTAATGAGTAATGTGTTATATAGTCCATGGATCGTAGTGAGAAGGTAGAGTT
GAAAGTATAAGAAAGCGAACCTCCATCATAGTGGGGGCTTAAACCCGTGCAAGCT
TGCAGATATCTATGGCTGATGGTTGGGCCCAGCCTTATATCTTGGGCTTATTTTGT
TTCCATCTGTCCAGCCCATGATAAAGTGTAAAACGACACCGTATTAAGCTTAATGG
AGTAAACGAATCACACGTAGCGGGGATCCCCGTGTCAGTTCTTGTCGGAAAAGCT
GGACGGAGGAAAACGGTATCGTATTCGCTTCGCTTGAATCTATATATTTTGCGCAA
AAGCCCTTTTCATCCCTTTCTTCTCTCATTACTCGATTTAGGGTTTTCTAATCTCGA
AAGAAATCAAGATCCTCCTTCCTTCCTCTCTCGATTTCGATCTCGTAGCCCCTTTT
GCGTTGATTTCGAATTCGTTCATCAACAGGTTTGTTTCTCTCTAGCTCCTAACGAT
CTCGCTAGCAAATTAGGGTTTCGAGCGAGCTTAATCCGATCGGTTTCTGGATCAG
TTGAGATGCGATCGGAATCTCTCTGAATAAGAGAGACTCGTGTGGAGGGGTTTCT
TCCTTTGT
```

TABLE 2 summarising the UPL3 promoter variation identified between *brassica napus* accessions, Coriander and Dimension

| Polymorphism type | distance from ATG (BP) | *Brassica napus* variety: Dimension (low UPL3-expressing) | *Brassica napus* variety: Coriander (high UPL3-expressing) |
|---|---|---|---|
| SNP | 1933 | T | C |
| SNP | 1884 | A | G |
| SNP | 1858 | G | A |
| SNP | 1759 | C | T |
| InDel | 1718 | 1718-1722 | N/A |
| SNP | 1660 | C | T |
| SNP | 1609 | C | T |
| SNP | 1605 | A | T |
| SNP | 1600 | C | T |
| InDel | 1597 | 1597-1599 | N/A |
| InDel | 1580 | 1580-1582 | N/A |
| SNP | 1469 | T | C |
| SNP | 1456 | T | C |
| SNP | 1418 | A | G |
| SNP | 1370 | C | T |
| SNP | 1367 | A | G |
| SNP | 1354 | C | T |
| SNP | 1352 | A | G |
| InDel | 1293 | 1293-1309 | N/A |
| InDel | 1260 | 1260-1271 | N/A |
| SNP | 1251 | A | G |
| InDel | 1153 | 1153-1154 | |
| SNP | 1152 | C | T |
| SNP | 1141 | T | A |
| SNP | 1120 | A | G |
| InDel | 1088 | 1083-1088 | N/A |
| InDel | 1026 | 1026 | N/A |
| SNP | 1035 | T | G |
| SNP | 929 | A | C |
| SNP | 835 | A | G |
| SNP | 805 | G | A |
| SNP | 774 | G | C |
| InDel/Duplication | 610 | 773-852 | N/A |
| SNP | 352 | G | C |
| SNP | 148 | C | T |
| SNP | 145 | G | C |
| SNP | 123 | A | T |

Protein Sequences

SEQ ID NO: 21: bA08_Bnapus_UPL3_protein (*B.napus* protein)

```
METRSRKRAEATSTAPSSSSSSPPPPPSSGPTTRSKRARLSSPSSSSAAATAPSSSTRSR
SSRSTTATAAVTPMDTSTESSGFRRGGGRGNRGNDNTNSDKGKEKEHEVRIRDRERDRAR
QQLNMDAAAAAAAAADEDDDNDSEDGNGGFMHPNMSSASSALQGLLRKLGAGLDDLLPSS
GIGSGSSSHLNGRMKKVLAGLRSEGEEGKQVEALTQLCEMLSIGTEDSLSTFSVDSFVPV
LVGLLNHESNPDIMLLAARALTHLCDVLPSSCAAVVHYGAVSCFVARLLTIEYMDLAEQS
```

-continued

LQALKKISQEHFTACLRAGALMAVLSYLDFFSTGVQRVAVSTAANMCKKLPSDASDYVME
AVPVLTNLLQYHDAKVLEYASICLTRIAEAFASSPDKLDELCNHGLVTQAATLISASNSG
GGQASLGVSTYTGLIRLLSTCASGSPLGCRTLLLLGISSILKDILSGSGVSANASISPAL
SRPADQIFEIVNLANELLPPLPEGSISLPTSANALVKGSGQKKSSPSTSGKQEDSPKVSP
REKLLSDQPELLQQFGLDLLPVLVQIYGSSVNGTIRHKCLSVIAKLMYFSTPEMIQSLIG
DTNISSFLASVLAWKDPQVLVPALQVAEILMEKLPETFSKVFVREGVVHAVDQLVLVGKP
SSHASTDQENDCVPGSARSRRYRRRSSNANSDGNQSEELKNSVSASIGANHNSMESPTAS
FMLRETVSSCAKAFKDKHFPSDGGEFDVGVTDDLLHLKNLCTKLTAGTNDHKVKGKGKSK
ASGPCLGDFSASKEEYLIGIISEILGELSKGDGVSTFEFIGSGVVAALLNYFSYGYFSKE
KISEVDLPKLRQDGLRRFTAFLEIALPSDGNEGKIPPMTVLIQKLQDALSSLERFPVVLS
HPSKSLSGSARLSSGLSALAHPLKLRLCRAPGEKALRDYSSNIVLIDPLASIAAVEEFLW
PRVQRSESGVKPAAPVGNTEPGTLPSGAGVSSPSSSTPASTTRHSSRSRSAIKIGDASKK
EPVHEKGTSSSKGKGVMKPAQPDKGPQTRSSAQRKAVLDKDTLMKPASGDSSSEDEEMDI
SPVDMDDALVIEEEDISDDDEDDDDEDVLDDNLPMCTPDKVHDVKLGDAVDDEGAGLAPS
GRQMNSALAGSSGTATARGSNSTDAGIGNLYGSRGALSFAAAAMAGLGAASGRGIRGSRD
LHGRTLNRSSDESSKLMFTAGGKQLSRHMTIYQAVQRQLMLDEDDDDRLGGSDFISSDGS
RLNDIYTIMYQMPDSQANRLSAGGASSTTPSKSTKSATTNASVEAQSYRASLLDSIVQGK
LPCDLEKSNSTYNVLALLRVLEGLNQLGPRLRAQTVSDRFAEGKITSLDDLNTTAAKVSH
EEFINSKLTPKLARQIQDALALCSGSLPSWCYQLTTACPFLFPFQTRRQYFYSTAFGLSR
ALNRLQQQQGADGSGSTNSREMRIGPLQRQKVRVSRNRILDSAAKVMEMYSSQKAVLEVE
YFGEVGTGLGPTLEFYTLLSHDLQKVSLGMWRSNSGDKLSMQTDRDEIQDGKSAAARDRD
IVQAPLGLFPRPWPSTADVSEGSRFHKVVEYFRLLGRVMAKALQDGRLMDVPLSTAFYKL
ILGQELDLHDVILFDAELGKTLQELRVLVGRKHYLEAGGGDNSSGISDLCLRGSRIEDLC
LDFTLPGYPEYILRPGDDIVDINSLEDYISLVVDATVKRGVARQIEAFRSGFNQVFDIKS
LQIFTPSELDYLLCGRRELWEAETLVEHIKFDHGYTAKSPAIIFLLEIMGELTADQQRAF
CQFVTGAPRLPPGGLAVLNPRLTIVRKLSSTSNAAANGTGASETADDDLPSVMTCANYLK
LPPYSTKEIMYKKLLYAINEGQGSFDLS*

SEQ ID NO: 22: C03_Bnapus_UPL3_protein (*B.napus* protein)
METRSRKRAEATSAAPSSSSSSPPPPPSASGPTTRSKRARLSSSSSSSLAPTPPSSSTTT
RSRSSRSAAAAAPMDTSTDSSGFRRGGRGNRGNNNDNSDKGKEKEHDVRIRERERERDRA
REQLNMDAAAAAARSADEDDDNDSEDGNGGFMHPNMSSASSALQGLLRKLGAGLDDLLPS
SGIGSASSSHLNGRMKKILSGLRAEGEEGKQVEALTQLCEMLSIGTEDSLSTFSVDSFVP
VLVGLLNHESNPDIMLLAARALTHLCDVLPSSCAAVVHYGAVSCLVARLLTIEYMDLAEQ
SLQALKKISQEHPTACLRAGALMAVLSYLDFFSTGVQRVALSTAANMCKKLPSDADDYVM
EAVPLLTNLLQYHDSKVLEYASICLTRIAEAFAPYPEKLDELCNHGLVTQAASLISTSNS
GGGQASLSVSTYTGLIRLLSTCASGSPLGFRTLLLLGISSILKDILLGSGVSANASVSPA
LSRPADQIYEIVNLANELLPPLPEGVISLPTSTNALVKGSCQKKSSPSTSGKQEDILKIS
PREKLLGDQPELLQQFGLDLLPVLVQIYGSSVNGTIRHKCLSVIGKLMYFSSSEMIQSLI
GDTNISSFLAGVLAWKDPQVLVPALQVAEILMEKLPETFSKVFVREGVVHAVDQLVLVGK
PSHASPTDKDNDCVPGSARSRRYRRRSSNANSDGNQSEEPKNPASLTIGANHNSLDTPTA
SFMLRSTVSSCAKAFKDKYFPSDGGDVDVGVTDDLLHLKNLCTKLTAGIDDHKVKGKGKS
KASGPFLGDFSASKEEYLIGVISEILGEISKGDGVSTFEFIGSGVVAALLNYFSCGYFSK
EKISELNLPKLRQEGLRRFKAFLEVALPFDGNEGKVPPMTVLIQKLQNALSSLERFPVVL
SHPSRSLSGSARLSSGLSALAHPLKLRLCRASGEKTLRDYSSNIVLIDPLASLAAVEEFL
WPRVQRSESALKPAAPIGNTEPGTLPSGAGVSSPSSSTPASTTRRHSSRSRSAINIGDTS
KKDPVHEKGTSSSKGKGKGVMKPAQADKGPQTRSNAQKRAVLDKDTQMKPASGDSSSEDE
ELEISPVDIDDALVIEEDDISDDEDDDNEDVLDDSLPMCTPDKVHDVKLADSVDDDGLAT
SGRQMNPASGGTSGAAAARASDSIDTGIGNSYGSRGALSFAAAAMAGLGAASGRGIRGSR
DLHGRTLNRSSDEPSKLIFTAAGKQLSRHLTIYQAVQRQLMLDEDDDDRFGGSDLVSSDG
SRFNDIYTIMYQRPDSQVNRLSVGGASSTTPSKSTKSATTNSSVESQSHRASLLDSILQG
ELPCDLEKSNSTYNVLALLRVLEGLNQLCPRLRAQTLSDRFAEGKITSLDDLSTTAAKVP
LDEFYNSKLTPKLARQIQDALALCSGSLPSWCYQLTRACPFLFPFQTRRQYFYSTAFGLS
RALNRLQQQQGADGSGSTNEREMRIGRLQRQKVRVSRNRILDSAAKVMEMYSSQKAVLEV
EYFGEVGTGLGPTLEFYTLLSHDLQKASLGMWRSSSGDKVSMQIGRDEIEDGKPSAANRD
IVLAPLGLFPRPWPSTADISEGGQFHKVIEYFRLLGRVMAKALQDGRLLDVPLSTAFYKL
ILGQELDLHDIVLFDAELGKTLQELRVVVARKHYLEGVGGDNSSTISDLCLRGCRIEDLS
LEFTLPGYPEYILRSGDEIVDITNLEEYISLVVDATVKRGVTRQIEAFRSGFNQVFDITS
LQIFTPSELDYLLCGRRELWEVETLAEHIKFDHGYNAKSPAIINLLEIMGELTADQQRAF
CQFVTGAPRLPPGGLAVLNPKLTIVRKHSSTSSAAANGAGASETADDDLPSVMTCANYLK
LPPYSTKEIMYKKLLYAINEGQGSFDLS*

SEQ ID NO: 23 *B. napus* LEC2 protein
BnaA07g08500D
MDNFLPFSSSNANSVQELSMDLNKNRSHFSMAQPQHLLPPYSYVACPALDQTGTMNHQPL
HSSDAFPQIPVVQTGGEFGYLVCKPGVRQERGGFLDPHSTKMARINRKKAMLRSRNNSNP
NSSSNELVDSRRQVALTMKNNAEIAARKDFYRFSSFDNKKLRVLLVKHLKNSDVGSLGRI
VLPKREAEGNLPELSDKEGMVLEMRDVDSVQSWSFKYKYWSNNKSRMYVLENTGEFVKKN
GVLMGDYLTIYEDESKNLYFSIRKHPHKQNDGREDESMEVIEMNFYEDIMFDYIPNDEDD
SIAMLLGNLNEHYPYPNDLMDLTVNLDQHQQATSSSPPADHMSSNDFLW SEQ ID NO: 24 *B. napus* LEC2 protein
BnaA09g27380D
MDNFLPFSSSNANFVQELSMDLNNNRSRLSTFPTYDHHHQAQPHSLQPYSYVACPVDQTA
AMNPQIPVTQTGSEFGSLVCNPGFGQARGGFLDPHTAKMARINRKKAMIRSRNNSSPNSS
SNELVGSRRQVVLTMKNNAEIAARKDLYRYPSFDNKKLRVLLVKHLKNSDVGSLGRIVLP
KREAEGNLPELSTKEGMIVDMRDADSMQNWSFKYKFWSNNKSRMYVLENTGQFVTEKRVE
IGDFLTIYEDESKNLYFSIRKHADKPNEGREDESMEANDMNFYEDIAFDFIPKDEDEDSI
AMLIGNLNDHYPNPNNRMDLPIDLHQHHQATSLPPADYMTNPQYGGSSNDLMSFNDFVW -continued SEQ ID NO: 25 *B. napus* LEC2 protein
BnaC05g50460D
MDNFLPFSSSNANSVEELSMDLNNNRSRLSTFPTYDHHHQAQHHSLQPYSYVACPVDQTA
AMNPQISVIQTGSEFGSLVCNPGFRQARGGFLDPHTAKMARINRKKAMIRSRNNSSPNSS
SNELVGSRRQVVLTMKNNAEIAARKDLYRYSSFDNKKLRVLLVKHLKNSDVGSLGRIVLP
KREAEGNLPELSTKEGMIVEMRDADSMQNWSFKYKFWSNNKSRMYVLENTGEFVAEKRVE
IGDFLTIYEDESKNLYFSIRKHADKPNEGREDESMEANDMNFYEDIAFDFIPKDEDEDSI
AMLIGNLNDHYPNPNNLMDLPIDLHQHHQATSSLPPVDYMTNPQYSGSSNDHMSFNDFVW SEQ ID NO: 26 *B. napus* LEC2 protein
BnaC07g10500D
MDNFLPFSSSNANSVQELSMDLNKNRSHFSMAQPQHLLPPYSYVACPVLDQTGAMNHQPL
HSSDAFPQIPVVQTGGEFGYLVCKPGVRQERGGFLDPHSTKMARINRKKAMIRSRNNSNL
NSSSNELVDSRRQVALTMKNNAEIAARKDFYRFSSFDNKKLRVLLVKHLKNSDVGSLGRI
VLPKREAEGNLPELSDKEGMVLQMRDVDSVQSWSFKYKYWSNNKSRMYVLENTGEFVKKN
GVLMGDYLTIYEDESKNLYFSIRKHPHKQNDGREDESMEVIEMNFYEDIMFDYIPNGEDD
SIAMLLGNLNEHYPYPNDIMDLTVDLDQHQQATSSSPPADHMSSNDFLW SEQ ID NO: 27 *Arabidopsis*_upl3_protein (*Arabidopsis* UPL3 protein)
METRSRKRAEATSAAPSSSSSSPPPPPSASGPTTRSKRARLSSSSSSSLAPTPPSSSTTT
RSRSSRSAAAAAPMDTSTDSSGFRRGGRGNRGNNNDNSDKGKEKEHDVRIHERERERDRA
REQLNMDAAAAAARSADEDDDNDSEDGNGGFMHPNMSSASSALQGLLRKLGAGLDDLLPS
SGIGSASSSHLNGRMKKILSGLRAEGEEGKQVEALTQLCEMLSIGTEDSLSTFSVDSFVP
VLVGLLNHESNPDIMLLAARALTHLCDVLPSSCAAVVHYGAVSCLVARLLTIEYMDLASQ
SLQALKKISQEHPTACLRAGALMAVLSYLDFFSTGVQRVALSTAANMCKKLPSDASDYVM
EAVPLLTNLLQYHDSKVLEYASICLTRIAEAFAPYPEKLDELCNHGLVTQAASLISTSNS
GGGQASLSVSTYTGLIRLLSTCASGSPLGFRTLLLLGISSILKDILLGSGVSANASVSPA
LSRPADQIYEIVNLANELLPPLFEGVISLPTSTNALVKGSCQKKSSPSTSGKQSDILKIS
PREKLLGDQPELLQQFGLDLLPVLVQIYGS5VNGTIRHKCLSVIGKLMYFSSSEMIQSLI
GDTNISSFLAGVLAWKDPQVLVPALQVAEILMEKLPETFSKVFVREGVVHAVDQLVLVGK
PSHASPTDKDNDCVPGSARSRRYRRRSSNANSDGNQSEEPKNPASLTIGANHNSLDTPTA
SFMLRETVSSCAKAFKDKYFPSDGGDVDVGVTDDLLHLKNLCTKLTAGIDDHKVKGKGKS
KASGPFLGDFSASKEEYLIGVISEILGEISKGDGVSTFEFIGSGVVAALLNYFSCGYFSK
EKISELNLPKLRQEGLRRFKAFLEVALPFDGNEGKVPPMTVLIQKLQNALSSLERFPVVL
SHPSRSLSGSARLSSGLSALAHPLKLRLCRASGEKTLRDYSSNIVLIDPLASLAAVEEFL
WPRVQRSESALKPAAPIGNTEPGTLPSGAGVSSPSSSTPASTTRRHSSRSRSAINIGDTS
KKDPVHEKGTSSSKGKGKGVMKPAQADKGPQTRSNAQKRAVLDKDTQMKPASGDSSSEDE
ELEISPVDIDDALVIEEDDISDDEDDDNEDVLDDSLPMCTPDKVHDVKLADSVDDDGLAT
SGRQMNPASGGTSGAAAARASDSIDTGIGNSYGSRGALSFAAAAMAGLGAASGRGIRGSR
DLHGRTLNRSSDEPSKLIFTAAGKQLSRHLTIYQAVQRQLMLDEDDDDRFGGSDLVSSDG
SRFNDIYTIMYQRPDSQVNRLSVGGASSTTPSKSTKSATTNSSVESQSHRASLLDSILQG
ELPCDLEKSNSTYNVLALLRVLEGLNQLCPRLRAQTLSDRFAEGKITSLDDLSTTAAKVP
LDEFVNSKLTPKLARQIQDALALCSGSLPSWCYQLTRACPFLFPFQTRRQYFYSTAFGLS
RALNRLQQQQGADGSGSTNEREMRIGRLQRQKVRVSRNRILDSAAKVMEMYSSQRAVLEV
EYFGEVGTGLGPTLEFYTLLSHDLQKASLGMWRSSSGDKVSMQIGRDEIEDGKPSAANRD
IVLAPLGLFPRPWPSTADISEGGQFHKVIEYFRLLGRVMAKALQDGRLLDVFLSTAFYKL
ILGQELDLHDIVLFDAELGKTLQELRVVVARKHYLEGVGGDNSSTISDLCLRGCRIEDLS
LEETLPGYPEYILRSGDEIVDITNLEEYISLVVDATVKRGVTRQIEAFRSGFNQVFDITS
LQIFTPSELDYLLCGRRELWEVETLAEHIKFDHGYNAKSPAIINLLEIMGELTADQQRAF
CQEVTGAPRLPPGGLAVLNPKLTIVRKHSSTSSAAANGAGASETADDDLPSVMTCANYLK
LPPYSTKEIMYKKLLYAINEGQGSFDLS*

SEQ ID NO: 28 *Glycine max* UPL3 protein sequence
>GLYMA11G11490.1
METRSRKRASASSAAPSSPSSGPTTRSSKRARLSSSSASAAVNTRSRASNTKSPLPPKN
PPPPLPPMDSANESSGSRRDRRNNKENSSDKGKEKEHDVRIRDRDAALNMDSSGGDEDDD
NDNDSEGGVGILHQNLTSASSALQGLLPKLGAGLDDLLPSSAMGSASSSHQSGRLKKILF
GLPADGEEGRQVEALTQLCEMLSIGTEESLSTFSVDSFVTVLVGLLNHESNPDIMLLAAR
ALTHLCDVLPSSCAAVVHYGAVSIFCARLLTIEYMDLASQSLQALKKISLEHPTACLRAG
ALMAVLSYLDFFSTGVQRVALSTAANMCKKLPSDAADFVMEAVPLLTNLLQYHDSKVLEH
ASVCLTRIAEAFASSPDKLDELCNHGLVTQATSLISNSSSGGGQASLSTPTYTGLIRLLS
TCASGSPLGAKTLLLLGISGILKDILSGSGVSSNASVSPALSRPPEQIFEIVNLANELLP
PLPHGTISLPIISNMFLKGPIVKKSPSGSSGKQEDTNGNVPEISAREKLLNDQPELLKQF
AMDLLPVLIQIYGSSVNGPVPHKCLSVIGKLMYFSTAEMIQSLLSVTNISSFLAGVLAWK
DPKVLLPALKIAEILMEKLPGTFSKMFIREGVVHAVDQLILASNSTMISTQASPASKDND
SISGASSRSRRYRRRSGNSNPDGNPLDDLKTPVSVNVGSPPSSVDMPTLNSSIRLSVSTA
AKAFKDKYFPSDPGAAEVGITDDLLHLKNLCMKLNAGDDSQRTNGKGESKTSGFGPEEYL
IGIIANMLKELGKGDGVSTFEFIGSGVVAALLNYFSCGYFSKDRPLEAHLPKLRQQALTR
FKLFIAVALPSTIEVGTVAPMTVLVQKLQNALSSLERFPVVLSHSSRSSSGSARLSSGLS
ALSQPFKLRLCRAQGEKSLPDYSSNVVLVDPLASLAAIEEFVWPRIQRSESGQKSTVATG
NSESGTTPAGAGVSSPTTRRHSTRSRSSVNIGDTSRKEITQDKSTSSSKGKGKVVLKPAQ
EEARGPQTRNATRRRAALDKDAQMKPVNADSTSEDEDLDISPVSIDEALVIEDDDISDDS
DDDHEDVLPDDSLPVCSPDKVHDVKLGDLAEESNVAPATSDGQANAASGSSSKAGTVRGS
DSTDFRSGYNSSSRGAMSFAAAAMAGLGSANSRGIRGGRDRLGRPLFGSSNDPPKLIFTA
GGKQLNRHLTIYQAIQRQLVLDDDERFAGSSDYVSSDGSRLWGDIYTITYHPAENQTDRT
PPGGSTSNASKSCKSGSVSNSSSSAKLHQTSVLDSILQGELPCSLEKSNPTYNILALLRV
LEGLNQIASRLRAQVVTDSFAEGKILDLDELSVTSGARVPTEEFISSKLTPKLAPQIQDA
LALCSGSLPSWCYQLSKACPFLFPFETRRQYFYSTAFGLSRALYRLQQQQGADGHGSTNE -continued

```
REVRVGRLQRQKVRVSRNRILDSAAKVMELYSSQKAVLEVEYFGEVGTGLGPTLEFYTLL
SHDLQKIILEMWRSGSSEKYQMKIDGDEKKMKRSEGSFVGDGELVQAPLGLFPRPWSANA
DASEGTQFFKVIEYFRLLGRVMAKALQDGRLLDLPMSVAFYKLVLGQELDLHDILFIDAE
LGKTLQELNALVCRKHYIQSTGGSYTDTFANLHFRGAPIEDLCLDFTLPGYPEYILKPGD
EIVDINNLEEYISMVVEATVKTGIMRQMEAFRAGFNQVFDISSLQIFSPQELDYLLCGRR
ELWKTETLADHIKFDHGYTAKSPAIVNLLGIMGEFTPEQQRAFCQFVTGAPRLPPGGLAV
LNPKLTIVRKLSSSAANASSNGNGPSELADDDLPSVMTCANYLKLPPYSTKEIMYKKLLY
AISEGQGSFDLS
```

Other UPL3 Gene Homologues:

SEQ ID NO: 33: *B.Oleracea* genomic UPL3 sequence > Bo3g149420.1_genomic

```
ATATAGTCCATGGATCGTAGTGAGAAGGTAGAGTTGAAAGTATAAGAAAGCGAACCTCCATCATAGTG
GGGGCTTAAACCCGTGCAAGCTTGCAGATATCTATGGCTGATGGTTGGGCCCAGCCTTATATCTTGGGC
TTATTTTGTTTCCATCTGTCCAGCCCATGATAAAGTGTAAAACGACACCGTATTAAGCTTAATGGAGTAA
ACGAATCACACGTAGCGGGGATCCCCGTGTCAGTTCTTGTCGGAAAAGCTGGACGGAGGAAAACGGT
ATCGTATTCGCTTCGCTTGAATCTATATATTTTGCGCAAAAGCCCTTTTCATCCCTTTCTTCTCTCATTACT
CGATTTAGGGTTTTCTAATCTCGAAAGAAATCAAGATCCTCCTTCCTTCCTCTCTCGATTTCGATCTCGTA
GCCCCTTTTGCGTTGATTTCGAATTCGTTCATCAATAGGTTTGTTTCTCTCTAGCTCCTAACGATCTCGCT
AGCAAATTAGGGTTTCGAGCGAGCTTAATCCGATCGGTTTCTGGATCAGTTGAGATGCGATCGGAATCT
CTCTGAATAAGAGAGACTCGTGTGGAGGGGTTTCTTCCTTTGTATGGAAACTCGGAGCCGCAAGCGTG
CGGAGGCGACCTCAACTGCCCCATCTTCTTCTTCTTCGTCTCCTCCTCCTCCTCCCTCAGGTCCCACCACT
CGCAGCAAACGCGCTCGCCTCTCGTCTCCCTCTTCCTCTTCAGCCGCCGCCGCTACCACCGCTACTGCAC
CTTCCTCCTCCACCCGCTCTCGTTCTTCTCGCTCTGCCGCTACCGCTACCGCTACAGCCGCCGTTACTCCC
ATGGACACATCCACCGAGTCTTCTGGATTCCGCCGCGGCGGGGGACGAGGTAACAGGGGAAACGATA
ATACTAATTCTGATAAGGGAAAGGAGAAGGAGCATGAGGTTAGGATTAGGGATAGAGAAAGAGACCG
AGCCAGACAGCAGCTCAACATGGACGCTGCAGCTGCTGCCGCCGCCGCTGAAGAGGACGATGACAAT
GATAGTGAGGATGGCAACGGGGGATTCATGCATCCCAACATGAGCTCAGCCAGCAGTGCGTTACAAG
GGTTGCTGAGGAAGCTTGGAGCTGGACTTGATGACTTGCTTCCTTCTTCAGGTATTGGCTCAGGTTCTT
CTTCCCATTTAAATGGGAGGATGAAGAAGATACTCGCTGGCTTGCGCTCTGAAGGAGAAGAGGGAAA
GCAGGTCGAGGCTTTGACCCAGCTCTGCGAGATGTTATCCATTGGCACCGAAGACTCCTTGAGCACCTT
CTCTGTTGATTCCTTCGTCCCCGTTCTTGTTGGTCTACTTAACCATGAGAGCAATCCGGATATTATGCTTC
TTGCTGCCAGGGCTCTTACCCATCTGTGTGATGTTTTGCCCTCTTCTTGTGCTGCTGTTGTTCATTACGGG
GCTGTTTCATGCTTTGTCGCCAGATTGCTAACCATTGAATACATGGACTTGGCCGAGCAGGTTCGCTTTC
CTAGCAATTCTTGATTTTTTTTTTTTTGAATATAATACTTATCTAAAATCTGGATAAAGTGTATGTTGTGG
AATGTTTTATGCTGCAGTTTCTACACGTACATATCCAATATTTTAATTTACTTAGGACGAAATTTGAAATT
TGATTTTATTCTTCATGTGATTTACAACAGTCTCTGCAAGCTCTCAAAAAGATATCTCAGGAACACCCAA
CGGCCTGTTTGCGAGCTGGTGCTCTTATGGCAGTGCTATCATATCTGGATTTCTTCTCCACCGGTGTCCA
GGTGGGTAATTTTGTAACCTTTCTTTTATGCTTTCCATACTCGTTTATCTAATGCACTTTTTTTTACTTTGA
CTTTGTAGCGTGTAGCAGTCTCTACCGCTGCAAATATGTGCAAGAAGTTACCTTCTGATGCATCTGATTA
TGTTATGGAAGCTGTACCGGTACTGACAAACCTACTTCAGTATCATGATGCGAAGGTAAACGATCCTTT
TTTTTTGCTGTACTGTGGTACTATCTAGTTCTGCTCTTGCCCCAGTTTCCTTCATAGTATGTTCGTACGGT
GACAGGTTTTGGAATATGCTTCTATCTGTTTGACTCGGATTGCCGAAGCATTTGCATCGTCCCCTGATAA
ATTAGATGAATTATGCAACCATGGCCTGGTGACTCAAGCTGCGACTCTTATATCCGCTAGCAACTCGGG
AGGTGGGCAAGCATCTCTTGGTGTTTCAACATACACGGTATGAGTTAATTCTTTTGTGTTTTCTATATTTC
GTTATTCATAGGATGACATTTTCATCATATTTTCACAGGGATTAATCCGATTACTTTCCACCTGTGCGAG
CGGTTCACCTCTTGGGTGCAGGACATTACTTCTTCTCGGTATTAGTAGCATTCTTAAGGATATTCTGTCG
GGTTCTGGTGTCTCTGCTAATGCATCTATATCCCCAGCACTGAGCAGGCCTGCAGATCAGGTACGGATT
TACTTTTTGACATCACAGACTTTATTTGTTCATTTCCTGATAAAATAAATGGTGTACAATGAGATGCTTA
GGGGACACACCTTCAAATAGATCACTTGCATTTAGGAGATTTGTCTATTCAGCTCGATGATAATCTATGT
ACATGTATTTTGAGCTTTATTTATGTTGTAGCCGATGGCTCAAGTTTCCTATGCTTGTTTTCTGGTCTGGT
GTTGGAAGTGGTATAGATAAAAGCGCTTAGCGCTTCATCAGTGTGCTCTGTCTTGTTTATTTAACTTTGA
TCCCATGACTCTCTAATTCTTGAATATATTCTTGAACATGATCATGTGAGGTCCTTTGTTTCCAGAAAGGT
TCCGAATTATAACTCTTGTTTTGCATCTTAGATTTTTGAGATAGTCAACCTAGCGAACGAGCTCCTCCCTC
CATTGCCAGAAGGAAGTATCTCCCTTCCTACTAGCGCAAACGCGTTAGTGAAAGGTTCAGGCCAAAAA
AATTCTTCTCCAAGTACTTCAGGAAAACAAGAAGATTCTCCCAAAGTTTCACCTAGAGAAAAATTACTTT
GTGATCAACCCGAACTTTTGCAGCAATTTGGATTGGATCTTCTTCCAGTTTTAGTGCAGGTAATTTTTTG
TTGCGGTTGCTACAAGTTAATGTTCATACAACCTCCTGTATGTCTAATTACCCTTGTTTTCTTTCCAACAG
ATCTATGGTTCTAGTGTCAATGGTACTATTCGTCATAAATGTCTCTCCGTTATCGCAAAGTTGATGTATTT
CAGCACTCCAGAAATGATTCAATCTCTAATTGGTGACACAAATATATCGAGGTATGCTGTTTATGTTTTA
AATTAGGTATCACATGGCGCAACTTCTTACATTATTTTTCCTATGTAGCTTCTTGGCTAGTGTCTTGGCAT
GGAAAGATCCACAAGTCTTGGTTCCTGCTCTACAAGTTGCAGAAATTCTGATGGAAAAACTTCCTGAAA
CTTTCTCGAAAGTGTTTGTGAGGGAAGGGGTGGTTCATGCTGTAGATCAACTTGTCTTGGTTGGTAAAC
CTAGTGCTAATGCTTCTACTGATCAGGAAAATGACTGTGTGCCTGGATCTGCACGATCTAGGCGTTACA
GACGGCGAAGTAGTAATGCCAATTCTGATGGAAATCAGTCGGAAGAGCTTAAGAATTCTGTGTCAGCT
AGCATAGGTGCGACCCATAATTCCATGGAATCTCCTACAGCGAGCTTCATGCTAAGGGAAACAGTTAGC
TCCTGTGCAAAAGCATTCAAAGACAAGCACTTCCCGTCTGATGGTGGGGAATTTGATGTTGGAGTTACA
GATGATCTCTTGCATCTGAAGAATCTTTGCACGAAGCTAACTGCTGGTACAAATGATCATAAAGTGAAA
GGAAAGGGGAAATCTAAAGTCTCTGGGCCATGCCTTGGCGATTTTTCTGCTAGCAAAGAAGAATACTT
GATTGGTATCATCTCCGAGATACTTGGCGAGCTAAGCAAAGGGGATGGCGTCTCAACTTTTGAGTTTAT
TGGCAGTGGTGTGGTAGCAGCATTGCTTAACTATTTTTCTTATGGATACTTTTCCAAAGAGAAGATCTCC
GAGGTTGATTTGCCCAAACTTCGCCAGGATGGGCTCAGAAGGTTCAAAGCTTTTCTAGAAATTGCACTT
CCTTCTGATGGTAATGAGGGAAAGATCCCTCCTATGACTGTTTTGATTCAGAAACTTCAAGATGCTTTGT
CTTCACTGGAACGCTTTCCGGTCGTCCTTAGCCATCCCTCAAGGTCACTCAGTGGAAGTGCTCGTCTCTC
ATCTGGGTTGAGTGCTTTGGCACATCCTTTGAAGTTGCGGTTATGCCGTGCACCTGGAGAGAAGGCTCT
ACGTGATTACTCCTCCAATATTGTTCTCATAGATCCATTGGCAAGCATAGCAGCAGTGGAGGAATTTCTC
```

-continued

TGGCCCCGAGTTCAACGCAGTGAATCTGGGGTGAAGGCAGCAGCGCCTGCTGGAAACACTGAGCCAG
GCACATTACCTAGCGGTGCTGGTGTTTCATCACCATCCTCGTCAACTCCAGCTTCCACCACTCGTCATTCT
TCTAGATCTAGATCAGCAATTAAAATAGGCGATGCCTCAAAGAAAGAACCTGTGCACGAGAAAGGTAC
CAGCTCATCTAAAGGTAAAGGTGTTATGAAGCCGGCTCAGCCGGATAAGGGGCCTCAGACAAGGAGC
AGTGCTCAAAGGAAAGCTGTTCTTGACAAAGATACACTAATGAAACCAGCTAGCGGAGACTCCAGCTC
TGAGGTATGTCACTGTAGGAAGTTCTGGATTACATGGTTGTTTATTGTGTAACATTATATTATGTTTGTG
GTGTGATCTGCTTATGCAGCACTATCTTACTTATATTGCTTGCAGGACGAAGAAATGGATATATCCCCCG
TCGACATGGATGATGCTTTGGTGATTGAAGAGGAAGACATTTCTGACGACGATGATGATGATGATGAG
GAGGATGTAAGTATTCCCTCCCCAGTATGTACATTACAGACGCAATTATTTCTCTTGCTAACAACATGAA
AGATGATACTTCTCGCAATAATGCTTGCTAGCTTTCCGTATTCTTAGATAAGTTTACCATATTGAGCTGA
CCTTATCGGAACCTTTCCTTTTAGAACTGACTAAAGAGAATTATGAACTTTATACCACAATTTCTCATATT
GATCTGGTCTTGAATTCAGGTCTTGGATGACAGTCTTCCCATGTGCACCCCTGATAAGGTTCATGATGTA
AAATTGGGAGACGCAGTGGATGATGAGGGAGCCGGCCTAGCACCTAGCGGCCGACAGATGAATTCAG
CTTTGGCAGGAAGTAGTGGAACAGCAACTGCAAGGGGATCTAATTCTACTGATGCTGGCATTGGGAAT
CTTTATGGTTCTAGGGGTGCACTCTCCTTCGCTGCTGCGGCGATGGCAGGGCTTGGAGCTGCCAGTGGT
AGAGGTATCAGGGGGAGTAGAGACCTACATGGGCGTACCCTGAATCGAAGTTCTGATGAGTCCTCTAA
GTTGATGTTTACTGCGGGAGGAAAGCAACTTAGTAGGCATATGACGATATATCAGGCTGTGCAACGAC
AACTTATGCTAGACGAAGATGATGATGACAGGCTCGGTGGCAGCGATTTCATCTCGAGTGATGGAAGC
AGATTAAATGATATATATACTATCATGTACCAGATGCCGGACAGCCAAGCGAATAGGTTGTCTGCTGGT
GGTGCAAGTTCTACCACACCATCTAAATCCACTAAATCTGCTACTACTAATGCAAGCGTAGAAGCCCAG
TCGTATAGGGCATCTCTTTGGATAGTATCGTACAAGGAAAGCTTCCATGCGACCTTGAGAAGGCAAAT
TCTACGTATAATGTTTTGGCGTTGTTGCGTGTACTAGAGGGTTTAAATCAGCTTGGCCCTCGGTTAAGA
GCCCAAACCATTTCTGATCGTTTCGCAGAGGGTAAAATTACAAGTCTAGATGATCTGAATACAACTGCT
GCAAAGGTTTCTCATGAAGAATTCATCAACAGCAAACTTACACCCAAATTAGCTCGACAGATCCAGGAC
GCGCTTGCTTTGTGCAGTGGAAGTCTTCCCTCTTGGTGCTACCAGTTGACTACAGCATGCCCGTTTTTGT
TTCCGTTTCAGACCCGGAGACAGTATTTCTATTCAACTGCCTTTGGGTTGTCGCGTGCATTGAACCGCTT
GCAGCAGCAGCAAGGTGCTGACGGCAGTGGTTCTACAAATGAACGAGAGATGAGAATAGGGAGATTG
CAGCGCCAGAAAGTGCGGGTATCCCGAAATAGAATATTAGATTCTGCTGCGAAAGTTATGGAGATGTA
TTCTAGCCAAAAAGCTGTGCTTGAAGTAGAATATTTTGGTGAAGTTGGTACTGGTCTAGGCCCCACACT
TGAGTTTTACACACTCCTAAGCCATGATTTGCAAAAGGTTTCCCTTGGGATGTGGAGATCAAATTCTGGT
GACAAGTTATCTATGCAAACTGATAGAGATGAGATTCAAGACGGTAAATCTGCAGCAGCTAGGGACAG
AGATATAGTTCAGGCACCACTTGGGTTGTTCCCTCGGCCCTGGCCCTCAACTGCTGACGTATCTGAAGG
TAGTCGGTTTCATAAAGTTGTTGAATATTTCCGCCTTTTAGGGCGCGTGATGGCAAAGGCACTTCAAGA
TGGACGGCTAATGGACGTCCCGTTAAGTACAGCTTTTTATAAGCTCATTCTTGGTCAAGTGAGTTTTTTA
CTATCAGTAACTTTTTTATTTAGCTAAGAGTGGACTAGTAGTTTCGACACTTCTTTACGTTGTTCGTAAT
TTCTTTTTCTTTTCTCACCTGAACAGGAGCTTGATTTGCATGATGTTATAATATTTGATACTGAACTTGGC
AAGACTTTGCAAGAGCTTCGTGTTCTTGTTGGCCGTAAGCACTATCTGGAAGCAGAAGGTGGTGACAA
CAGTAGCGTGATTTCTGATTTATGTTTACGTGGATCCCGTATTGAAGATCTTTGCTTGGACTTCACCCTA
CCTGGCTATCCTGAATACATATTGAGACCAGGAGATGACATTGTACCGTCTAATAAGCTTTACATCCCAT
ATCTTACTATTCTTTTAGTTCTTGTCCATTGTTGCTGATGCCGTGTACTGTTTTCTGTTCTATTACAGGTTG
ATATTAATAGTCTTGAGGACTATATATCCCTGGTCGTTGATGCCACTGTCAAGAGAGGAGTTGCCCGGC
AGATTGAAGCCTTCAGATCTGGATTCAATCAGGTTAGCAGTTTCACAGACTCTCCGCTTTGTCTCTTTCTT
TTCCTGTTGGCTTCTAAATCATATGGAAGGAGTGGTTTCTTTTGGTTCATACTTCATAATCTTTTAAACAA
CAGGTTTATATTAAGTCTTTAATTTAGTCTTACCTTTATTATCCTTACAAGACCTCTCTGTTCTTACACATG
ATTACCAGGTCTTTGACATAAAATCTTTACAAGTATTCACCCCTTCTGAGCTGGACTACTTGTTATGTGG
TCGTAGAGAGTTGTGGGAGGTAATTTTTCAACTTTCTTTTGAATTTCCACTACCCATTTGACTTGAATCA
ACTAGATAAAATTTTCATTTCTAAAACCTTTCTTTTATTGCAGGCGGAGACTCTTGTTGAACATATCAAGT
TTGATCACGGTTATACTGCAAAAAGTCCGGCAATCATTTTCGTAAGTTACTTTCCTTGCTAGTTTTTTAAA
AAACCAATTTTCTTTTACAATCAAGCTTTTGCTTATTTATTGTTGATTCCTTTTTGACTTTGATTTTCACCC
TGGTGGTAGTTACTGGAGATCATGGGAGAGCTTACAGCAGATCAACAGCGTGCTTTCTGCCAGTTTGT
AACTGGAGCTCCTAGGCTTCCTCCTGGTGGCTTAGCTGTTCTCAACCCAAAGCTGACGATTGTGAGAAA
GGTAAGAAACCTTTACTTATATATTCGGTTAAAAAGCGTTTTTTAATTGAGCCAAGAGGTTCCTAGTCA
TGTTAAACTAGACCCACGAAGCCATATATCAAAATACATCTACACGTGACGCATTGTGGTGTTTGCTTGC
ATTTGCAAGACTTGTTAAGAGGAATTAGCTCTTACTCGATTTAAGTTGTGTATTTGCTTTCAATTGATGT
GTTTTTGGCTTGGTGCAGCTCTCATCAACCTCAAATGCGGCTGCCAATGGGACAGGGGCTTCGGAAACA
GCAGACGACGATCTTCCCAGCGTCATGACTTGCGCCAACTACCTTAAGCTCCCTCCTTATTCTACAAAGG
TAACTCGTGTCTCTCTTTTTTTAAGTCTATGGTTTCTGTGTTTGGTTGGTTGGAGTGAGCCTGAATAGGA
GTTTGTACCTGAAACAGGAAATCATGTACAAGAAACTGCTCTACGCGATCAACGAAGGGCAGGGATCG
TTCGACCTCTCCTAGGCGTCTCTCTGTTGTCGCTGCGGCTAGAAACCACCAACCCTCTCTCTTCTTTGT
ACATTTTACATCGGAAGACTCTGATTTGCACTTTGAATGTTATTTCTATTAAACCATGAATTATTAAAAT
TAGGTTCAATATTTTTCATGTGCAAGTAATATATTAAAACATGGAGGATAAAAATAAAATCAAAAGACA
AACTTGAATAATTTTGGTTGCCTTTGAAATTCGTTTGAAAATTCCGAAGCAATTGGATAGTGGTGAATA
AAAGCTGTCAGCTGAAAGAAATAAAAAAGGTACAAAGGTTTAGGTGTTGTATGATCCAAAATTCTGTTT
TTTATAAAGACAGGATCTATCAGTCACAGCAGTTGACTGTTAAGATATCAAAGGAATCAAGAAATAATT
GTTCGTTTCTGGAGATTGAACAGAAGACGTTTTCATCAGTTTTCTTTTTGATAAAAGTTAATTGGACATA
GATATCTCTAGACACGAGAAACAAAAGCATAAATAGGAAAACATTACAATTAAAAAGAGCGTTACGAG
TACAGAGTTCAAGCTAGACACAAGAAACCTACCATATGGTGGTATTGACTATTAATATA

SEQ ID NO: 34: *B.Oleracea* genomic UPL3 sequence > Bo3g149420.1protein pep:protein_coding
METRSRKRAEATSTAPSSSSSSPPPPPSGPTTRSKRARLSSPSSSSAAAATTATAPSSSTRSRSSRSAATATATA
AVTPMDTSTESSGFRRGGGRGNRGNDNTNSDKGKEKEHEVRIRDRERDRARQQLNMDAAAAAAAAEED
DDNDSEDGNGGFMHPNMSSASSALQGLLRKLGAGLDDLLPSSGIGSGSSSHLNGRMKKILAGLRSEGEEGK
QVEALTQLCEMLSIGTEDSLSTFSVDSFVPVLVGLLNHESNPDIMLLAARALTHLCDVLPSSCAAVVHYGAVS
CFVARLLTIEYMDLAEQSLQALKKISQEHPTACLRAGALMAVLSYLDFFSTGVQRVAVSTAANMCKKLPSDA
SDYVMEAVPVLTNLLQYHDAKVLEYASICLTRIAEAFASSPDKLDELCNHGLVTQAATLISASNSGGGQASLG
VSTYTGLIRLLSTCASGSPLGCRTLLLLGISSILKDILSGSGVSANASISPALSRPADQIFEIVNLANELLPPLPEGSI
SLPTSANALVKGSGQKNSSPSTSGKQEDSPKVSPREKLLCDQPELLQQFGLDLLPVLVQIYGSSVNGTIRHKCL
SVIAKLMYFSTPEMIQSLIGDTNISSFLASVLAWKDPQVLVPALQVAEILMEKLPETFSKVFVREGVVHAVDQ -continued LVLVGKPSANASTDQENDCVPGSARSRRYRRRSSNANSDGNQSEELKNSVSASIGATHNSMESPTASFMLR
ETVSSCAKAFKDKHFPSDGGEFDVGVTDDLLHLKNLCTKLTAGTNDHKVKGKGKSKVSGPCLGDFSASKEEY
LIGIISEILGELSKGDGVSTFEFIGSGVVAALLNYFSYGYFSKEKISEVDLPKLRQDGLRRFKAFLEIALPSDGNEG
KIPPMTVLIQKLQDALSSLERFPVVLSHPSRSLSGSARLSSGLSALAHPLKLRLCRAPGEKALRDYSSNIVLIDPL
ASIAAVEEFLWPRVQRSESGVKAAAPAGNTEPGTLPSGAGVSSPSSSTPASTTRHSSRSRSAIKIGDASKKEP
VHEKGTSSSKGKGVMKPAQPDKGPQTRSSAQRKAVLDKDTLMKPASGDSSSEDEEMDISPVDMDDALVIE
EEDISDDDDDDEEDVLDDSLPMCTPDKVHDVKLGDAVDDEGAGLAPSGRQMNSALAGSSGTATARGSN
STDAGIGNLYGSRGALSFAAAAMAGLGAASGRGIRGSRDLHGRTLNRSSDESSKLMFTAGGKQLSRHMTIY
QAVQRQLMLDEDDDDRLGGSDFISSDGSRLNDIYTIMYQMPDSQANRLSAGGASSTTPSKSTKSATTNASV
EAQSYRASLLDSIVQGKLPCDLEKANSTYNVLALLRVLEGLNQLGPRLRAQTISDRFAEGKITSLDDLNTTAAK
VSHEEFINSKLTPKLARQIQDALALCSGSLPSWCYQLTTACPFLFPFQTRRQYFYSTAFGLSRALNRLQQQQG
ADGSGSTN+REMRIGRLQRQKVRVSRNRILDSAAKVMEMYSSQKAVLEVEYFGEVGTGLGPTLEFYTLLSH
DLQKVSLGMWRSNSGDKLSMQTDRDEIQDGKSAAARDRDIVQAPLGLFPRPWPSTADVSEGSRFHKVVE
YFRLLGRVMAKALQDGRLMDVPLSTAFYKLILGQELDLHDVIIFDTELGKTLQELRVLVGRKHYLEAEGGDNS
SVISDLCLRGSRIEDLCLDFTLPGYPEYILRPGDDIVDINSLEDYISLVVDATVKRGVARQIEAFRSGFNQVFDIK
SLQVFTPSELDYLLCGRRELWEAETLVEHIKFDHGYTAKSPAIIFLLEIMGELTADQQRAFCQFVTGAPRLPPG
GLAVLNPKLTIVRKLSSTSNAAANGTGASETADDDLPSVMTCANYLKLPPYSTKEIMYKKLLYAINEGQGSFD
LS SEQ ID NO: 35: *Brassica rapa* genomic UPL3 sequence: > Bra010737.1_genomic
AATGTGTTTGATATATACCATGGATAGTAGTGAGAAGGTAGAGTTCAAAGTATAAGAAAGCGAACCCC
TCCATAGTGGGGGCTTAAACCCGTGCAAGCTTGCATATATCTATAGCTGATGGTTGGGCCCAAACTTAT
ATCTTGGGCTTATTTTGTTTCCATCTGTCCAGCCCATGATAAAGTGTAAAACGACACCGTATAAAGCTTA
ATGGAGTAAACGAATCACACGTAGCGGGGATCCCCGTGTCAGTTCTTGTCCGAAAAGCTGGACGGAGG
AAAACGGCATCGTATTCGCTTCGCTTGAATATATATATTTTGCGCAAAAGCCCTTTTCATCCCTTTCTTCT
CTCATTACTCGATTTAGGGTTTTCTAATCTCGAAAGAAATCAAGATCCTCCTTCCTCCCTCTCTCGATTTC
GATCTCTTTCGTGTTGATTTCGAATTCGTTCGTCAATAGGTTTGTTTCTCTCTAGCTCCGATCGATCTCGC
TAGCAAATTAGGGTTTCGAGCGAGCTTAATCCGATCGGTTTCTGGATCAGTTGAGATGCGATCGGAATC
TCTCTGAATAAGAGAGACTCGTGTGGGGGGTTTCTTCCTTTGTATGGAAACTCGGAGCCGCAAGCGTG
CGGAGGCGACCTCAACTGCCCCATCTTCTTCTTCTTCCTCTCCTCCTCCTCCTCCTTCCTCAGGTCCCACCA
CTCGCAGCAAACGCGCTCGCCTCTCGTCTCCCTCTTCATCTTCAGCCGCCGCTACTGCACCTTCCTCCTCC
ACCCGCTCTCGTTCTTCTCGCTCTACCACCGCTACAGTCGCCGTTACTCCCATGGACACATCCACCGAGT
CTTCTGGATTCCACCGCGGCGGAGGACGAGGTAACAGGGGAAACGATAATACTAACTCTGATAAGGG
AAAAGAGAAGGAGCATGAGGTTAGGATTAGGGATAGAGAAAGAGACAGAGCTAGGCAACAGCTCAA
CATGGACGCTGCAGCTGCTGCTGCCGCCGCCGCTGACGAGGACGACGACAATGATAGTGAGGATGGC
AACGGGGGATTCATGCATCCCAACATGAGCTCAGCCAGCAGTGCGTTACAAGGGTTGCTGAGGAAGCT
TGGAGCTGGACTTGATGACTTGCTTCCTTCTTCAGGTATTGGCTCAGGTTCGTCTTCTCACTTGAATGGG
AGGATGAAGAAGGTACTCGCTGGCTTGCGCTCTGAAGGAGAAGAGGGAAAGCAGGTCGAGGCTTTGA
CGCAGCTGTGCGAGATGTTATCTATTGGGACCGAAGACTCCCTGAGCACCTTCTCTGTTGATTCCTTCGT
CCCGGTTCTTGTTGGTCTACTTAACCATGAGAGCAATCCGGATATTATGCTTCTTGCTGCCAGGGCTCTT
ACTCATCTGTGTGATGTTTTGCCGTCTTCTTGTGCTGCTGTTGTTCATTACGGGGCTGTTTCGTGCTTTGT
CGCCAGATTGTTGACAATAGAATACATGGACTTGGCCGAGCAGGTTCGATTTCCTAACAATTCTTGAAT
TTTTTTGCTGAATATATATTGTGGAATGTTTTATGCTGCAGTTTCTACACGTACATATCCAATATTTTAGT
TTACTTAGGACGAAATTTGAAATTTGATTTTATTCTTCATGTGATTTACAACAGTCTCTGCAAGCTCTCAA
AAAGATATCTCAGGAACACCCAACGGCCTGTTTGCGTGCTGGTGCTCTTATGGCAGTGCTATCATATCT
GGATTTCTTCTCCACCGGTGTCCAGGTGGGTAATTTTGTAACTTTTCTTTAATGCTTTCCATACTCGTTTA
TCTAATGCACTTTTTTTTTTACTTTTTGTAGCGTGTAGCAGTATCTACCGCTGCAAATATGTGCAAGAAGT
TACCTTCTGATGCATCTGATTATGTTATGGAAGCTGTACCGGTACTGACAAACCTACTTCAGTATCATGA
TGCGAAGGTAAACGATCCCTTTTTTTTTGCTATAATGTGGTATTATCTAGTTCTGCTCTTGCCCCAGTTTC
CTTCATAGTATGTTCGTACGGTGGCAGGTTTTGGAATATGCTTCTATCTGTTTGACTCGGATTGCCGAAG
CATTTGCATCGTCCCCTGATAAATTAGATGAATTATGCAACCATGGCCTGGTGACTCAAGCTGCGACTCT
TATATCCGCTAGCAACTCGGGAGGTGGGCAAGCATCTCTCGGTGTTTCAACATACACGGTATGAGTTAA
TTCTTTTGTGTTTTCTATATTTCGTTATTCATAGGATGACATTTTCATCATATTTTCACAGGGATTAATCCG
ATTACTTTCCACCTGTGCGAGCGGTTCACCTCTTGGGTGCAGGACATTACTTCTTCTCGGTATTAGTAGC
ATTCTTAAGGATATTCTGTCGGGTTCCGGTGTCTCTGCTAATGCATCTATATCCCCAGCACTGAGCAGGC
CTGCAGATCAGGTACGGATTTACTTTTTGACATCACAGACTTTATTTGTTCAATTCCTGATAAAGTCTAT
TCAGTAAAAAGTGTTTTGTTTAGGGGACACACCTTTAAATAGATCATCAACATAAATTGTGTGTTGAGT
GAGATGCTTAGGGGACACACCTTCAAATAGATCACTTGCATTTAAATGGATCACTTGCATTTAGGAGTT
TTGTCTATTCAGTTCAATGATAATCTTTTTTTTTTGTAACACTCAGCTCAATGATAATCTATGTACATGTA
TTTTGAGCTTTATTTATGTTGTAACCGATGGCTCAACTTTCATATGCTTGTTTTCTGGTATGGTGTTAGAA
GTGGTATAGATAAAAGTGCTTAGCGCTTCATCAGTGTGCTCGGTCTTGTTTATTTAACTTTTTTTATCCCA
TGACTCGCTAATTCTTGAATATATTCTTGAACATGATCATGTGAGGTCTTTTGTTTCCGAATTATAACTCT
TGTTTTGCATCTTAGATTTTTGAGATAGTCAACCTAGCGAACGAGCTCCTCCCTCCACTGCCAGAAGGAA
GTATCTCCCTTCCTACTAGCGCAAACGCGTTAGTGAAAGGTTCAGGCCAAAAAAAGTCTTCTCCAAGTA
CTTCAGGAAAACAAGAAGATTCTCCCAAAGTTTCACCTAGAGAAAAATTACTTAGTGATCAACCCGAAC
TTCTGCAGCAATTTGGATTGGATCTTCTTCCAGTTTTAGTGCAGGTAATTTTTTGTTGCAGTTGCTACAA
GTTAGTGTTCATACAACCTCCTGTATGTCTAATTACCCTTGTTTTCTTTCCTACAGATCTATGGTTCTAGT
GTCAATGGTACTATTCGTCATAAATGTCTCTCAGTTATCGCAAAGTTGATGTATTTCAGCACTCCAG AAA
TGATTCAATCTCTAATTGGTGACACAAATATATCGAGGTATGCTGGTTATGTTTTAAATTAGGTATCACA
TGGCGCAACTTCTTACATTATTTTTCCTATGTAGCTTCTTGGCTAGTGTCTTGGCATGGAAAGATCCACA
AGTCTTGGTTCCTGCTCTACAAGTTGCAGAAATTCTGATGGAAAAACTTCCTGAAACTTTCTCGAAAGTG
TTTGTGAGGGAAGGGGTGGTTCATGCTGTAGATCAACTTGTCTTGGTTGGTAAACCTAGTTCTCATGCT
TCTACTGATCAGGAAAATGACTGTGTGCCTGGATCTGCACGATCTAGGCGTTATAGACGGCGAAGTAG
TAACGCCAATTCTGATGGAAATCAGTCGGAAGAGCTTAAGAATTCTGTGTCAGCTAGTATAGGTGCAA
ACCATAATTCCATGGAATCTCCTACAGCGAGCTTCATGCTAAGGGAAACAGTTAGCTCCTGTGCAAAAG
CATTCAAAGACAAGCACTTCCCGTCTGATGGTGGGGAATTTGATGTTGGAGTTACAGATGATCTCTTGC
ATCTGAAGAATCTTTGCACGAAGCTAACTGCTGGTACAAATGATCATAAAGTGAAAGGAAAGGGGAAA
TCTAAAGCCTCTGGGCCATGCCTCGGCGATTTTTCTGCTAGCAAAGAAGAATACTTGATTGGTATCATCT
CCGAGATACTTGGCGAGCTAAGCAAAGGAGATGGTGTCTCAACTTTTGAGTTTATTGGCAGTGGTGTG -continued GTAGCAGCATTGCTTAACTATTTTTCTTATGGATACTTTTCCAAAGAGAAGATCTCCGAGGTTGATTTGC
CCAAACTTCGCCAGGATGGGCTCAGAAGGTTCACAGCTTTTCTAGAAATTGCACTTCCTTCTGATGGTA
ATGAGGGAAAGATCCCTCCTATGACTGTTTTGATTCAGAAACTTCAAGATGCTTTGTCTTCACTGGAACG
CTTTCCGGTCGTCCTTAGCCATCCCTCAAAGTCACTCAGTGGAAGTGCTCGTCTCTCATCTGGATTGAGT
GCTTTGGCACATCCTTTGAAGTTGCGGTTATGCCGTGCACCTGGAGAGAAGGCACTACGTGATTACTCC
TCCAATATTGTTCTCATAGATCCTTTGGCAAGCATAGCAGCAGTGGAGGAATTTCTCTGGCCCCGAGTTC
AACGCAGTGAATCTGGGGTGAAGCCAGCAGCGCCTGTTGGAAACACTGAGCCAGGCACATTACCTAGC
GGTGCTGGTGTTTCATCACCATCCTCGTCAACTCCAGCTTCCACCACTCGTCATTCTTCTAGATCTAGATC
TGCAATTAAAATAGGCGATGCCTCAAAGAAAGAACCTGTGCACGAGAAAGGTACCAGCTCATCTAAAG
GTAAAGGTGTTATGAAGCCGGCTCAGCCGGATAAGGGGCCTCAGACAAGGAGCAGTGCTCAAAGGAA
AGCTGTTCTTGACAAAGATACACTAATGAAACCAGCTAGCGGAGACTCCAGCTCTGAGGTATGTCACTG
TAGAAAGTTCTGGATTACATGGTTGTTTATTGTGTAACATTATATTATGTTTGTGGTGTGATCTGCTTAT
GCAGCACTATCGTACTTATATTGCTTGCAGGACGAAGAAATGGATATATCCCCCGTCGACATGGATGAT
GCTTTGGTTATTGAAGAGGAAGACATTTCTGACGACGATGAGGATGATGATGATGAGGATGTAAGTAT
TCCCTCCCCAGTATGTACATTACAGACGCAATTATTTCTCTTGCTAACAACATGAAAGATGATACTTTTCG
CAATAATGCTTGCTAGCTTTCCGTATTCTTAGATAAGTTTACCATATTGAGCTCACCTTATTTGGCACCTT
TCCTTTTAGAACTGACTAAAGAGAATAATGAACTTTATACCACAATTTCTCATATTGATCTGGTCTTGAAT
TCAGGTCTTGGATGACAATCTTCCCATGTGCACCCCTGATAAGGTTCATGATGTAAAATTGGGAGACGC
AGTGGATGATGAGGGAGCCGGTCTAGCACCTAGCGGCCGACAGATGAATTCAGCTTTGGCAGGAAGT
AGTGGAACAGCAACTGCAAGGGGATCTAATTCTACTGATGCTGGCATTGGGAATCTTTATGGTTCTAGG
GGTGCACTCTCCTTCGCTGCTGCGGCGATGGCAGGGCTTGGAGCTGCCAGTGGTAGAGGTATCAGGG
GAAGTAGAGACCTACATGGGCGTACCCTGAATCGAAGTTCTGATGAGTCCTCTAAGTTGATGTTTACTG
CGGGAGGAAAGCAACTTAGTAGGCATATGACGATATATCAGGCTGTGCAACGACAACTTATGCTAGAC
GAAGATGATGATGACAGGCTCGGTGGCAGCGATTTCATCTCCAGTGATGGAAGCAGATTAAATGATAT
ATATACTATCATGTACCAGATGCCGGACAGCCAAGCGAATAGGTTGTCTGCTGGTGGTGCAAGTTCTAC
CACACCATCTAAATCCACCAAATCTGCTACTACTAATGCAAGCGTAGAAGCTCAGTCGTATAGGGCATC
TCTTTTGGATAGTATCGTACAAGGAAAGCTTCCATGCGACCTTGAGAAGTCCAATTCTACGTATAATGTT
CTGGCGTTGTTACGTGTATTAGAGGGTTTAAATCAGCTTGGCCCTCGCTTAAGAGCCCAAACCGTTTCT
GATCGTTTTGCAGAGGGTAAAATTACAAGTCTGGATGATCTGAATACAACTGCTGCAAAGGTTTCTCAT
GAAGAATTCATCAACAGCAAACTTACACCCAAATTAGCTCGACAGATCCAGGACGCGCTTGCTTTGTGC
AGTGGAAGTCTTCCCTCTTGGTGCTACCAGTTGACTACAGCATGCCCGTTTTTGTTTCCGTTTCAGACCC
GGAGACAGTATTTCTATTCAACTGCCTTTGGGTTGTCGCGTGCATTGAACCGCTTGCAGCAGCAGCAAG
GTGCTGACGGCAGTGGTTCTACAAATGAACGAGAGATGAGAATAGGGAGATTGCAGCGCCAGAAAGT
GCGTGTATCCCGAAATAGAATATTAGATTCTGCTGCGAAAGTTATGGAGATGTATTCTAGCCAAAAAGC
TGTGCTTGAAGTAGAATATTTTGGTGAAGTTGGTACTGGTCTAGGCCCGACACTTGAGTTTTACACACT
CCTAAGCCATGATTTGCAAAAGGTTTCCCTTGGGATGTGGAGATCAAATTCTGGTGACAAGTTATCTAT
GCAAACTGATAGAGATGAGATTCAAGACGGTAAATCAGCAGCAGCTAGGGACAGAGATATAGTTCAG
GCACCACTTGGGTTGTTCCCTCGGCCCTGGCCCTCAACTGCTGACGTATCTGAAGGTAGTCGGTTTCAT
AAAGTTGTTGAATATTTCCGCCTTTTAGGGCGCGTGATGGCAAAGGCACTTCAAGATGGACGGCTAAT
GGACGTCCCGTTAAGTACAGCTTTTTATAAGCTCATTCTTGGTCAAGTGAGTTTTTTACTATCAGTAACTT
TTTTTATTTAGCTAAGAGTGGACTAGTAGTTTCGACTTCTTTACGTTGTTCGTAATTTCTTACTGCTTCTTT
ACTCACCTGAACAGGAGCTTGATTTGCATGATGTTATATTATTTGATGCTGAACTTGGCAAGACTTTGCA
AGAGCTTCGTGTTCTTGTTGGCCGTAAGCACTATCTGGAAGCAGGCGGTGGTGACAACAGTAGCGGGA
TTTCTGATTTATGTTTGCGTGGATCCCGTATTGAAGATCTTTGCTTGGACTTCACCCTACCTGGCTACCCT
GAATACATATTGAGACCAGGAGATGACATTGTACCGTCTAATAAGCTTTACATCCGATATCTTACTATTG
TTTTAGTTCTTGTCCATTGTTGCTGATGCCGTGTACTGTTTTCTGTTCTATTACAGGTTGATATTAATAGT
CTTGAGGACTATATATCCCTGGTCGTTGATGCCACTGTCAAGAGAGGAGTTGCCCGGCAGATTGAAGC
CTTCAGATCTGGATTCAATCAGGTTAGCAGTTTCACAGACTCTCCGCTTTGTCTCTTACTTTTCCTGTAGG
CTTTGGCTTTGGCTTTGGCTTTGGCTTCTAAATTACATAGGAGTGGTTTCTTTTGGTTCATACTTTATAAT
CTTTTAAACAACAGGTTGATGATAATTTAGTCTTACCTTTATTATCTTTACAAGAATTCTCTGTTCTTACAC
ATGATTACCAGGTCTTTGACATAAAATCTCTACAAATATTCACCCCTTCTGAGCTGGACTACTTGTTGTGT
GGTCGTAGAGAGTTGTGGGAGGTGAGTTTTCATCTATTTTTTGAATTTCCACTACCCATTTGACTCGAAT
CGACTAGATAAAATTTTCTTTTCTAAAACCTTTCTTTTATTGCAGGCGGAGACTCTTGTTGAACATATCAA
GTTTGATCACGGTTATACTGCAAAAAGTCCGGCAATCATTTTCGTAAGTTACTTTCCGTACTAGTTTGTT
AAAAAACCAATTTTCTTTTACAATCAAGCTTTTTGCTTCTTTATTGTTGATTCCTTTTTGACTTTGATTTTCA
CCCTGGCGGTAGTTATTGGAGATCATGGGAGAGCTAACAGCAGATCAACAGCGGGCTTTCTGCCAGTT
CGTAACTGGAGCTCCTAGGCTTCCTCCTGGTGGCTTAGCTGTTCTCAACCCAAGGCTGACGATTGTGAG
AAAGGTAAGAAACCTTTACTTATATATTCGGTTAAAAAGCGTTTTTGTAATTGAGCCAAGAGGTTCTAG
TCATGTTAAACTAGACCCACCAAGCCATATATCAGAATACATCTACACGTGACGCATTGTTGTGTTTGCA
AGACTTGCTAAGATGAATTAGCTCTTACTCGATTTAAGTTGTGTATTTGCTTCCAATTGATGTGTTTTTGG
CTTGATGCAGCTCTCATCAACCTCAAATGCTGCTGCCAATGGGACAGGGGCTTCGGAAACAGCAGACG
ACGATCTTCCCAGCGTCATGACTTGCGCCAACTACCTTAAGCTCCCTCCTTATTCTACAAAGGTAACTCG
TCTCTCTTTTTTTAAGTCTACGGTTTCTGTGTTTGGTTGGTTGGGGTGAGCCTGAACACGAGTTTGTACC
TGAAACAGGAAATCATGTACAAGAAACTGCTCTACGCCATCAACGAAGGGCAGGGGTCGTTCGACCTA
TCCTAGGCATCTCTCTCTGTTGTGGCTGCGGCTAGAAACCACCAACCCTCTCTCTTCTTTGTACATTTTAT
ATCGGAAGACTCTGATTTTGCACTTTGAATGTTATTTCTGTTAAACCATGAATTATTAAAATTAGGTTCA
ATATTTTTCATGTGCAAGTAACATATTAATACATGGAGGATAAAAATAAAATCAAAAGACAAACTTGAA
TAATTTTGGTTGCCTTTAAAATTCGTTTGAAAATTCCGAAGCAATTATATATAGTGTGAATAAAAGTCGT
CAGCTGAAGGAATAAAGGTACAAAGGTACAAAGGTTTAGGTGTTGTATGATCCAAAATTCTGTTTTTTT
TTAAAGACGGGCTCTATCAGTCACAGCAGTTGACTGTAAGATATCAAAGGAATAAGAAACAGTTGTTC
GTTTGTAGTTTTCTGGAGATTGAACAAGAGAACTCGTCTTCGTTTCATCAGTTTTCTTTTTGATAAAAGTC
AATTCGACATAGATATCTCTAGACACGAGAAACAAAAGCATAAATAGGAAAACATTACAATTATAAAA
GAGCGTTACGAGTACAGAGTCCAAACTAGGCACAAGAAACCTACCATATG SEQ ID NO: 36: *B.napus* UPL3 protein sequence > Bra010737.1 protein
METRSRKRAEATSTAPSSSSSSPPPPPSSGPTTRSKRARLSSPSSSSAAATAPSSSTRSRSSRSTTATVAVTPM
DTSTESSGFHRGGGRGNRGNDNTNSDKGKEKEHEVRIRDRERDRARQQLNMDAAAAAAAAADEDDDN
DSEDGNGGFMHPNMSSASSALQGLLRKLGAGLDDLLPSSGIGSGSSSHLNGRMKKVLAGLRSEGEEGKQV
EALTQLCEMLSIGTEDSLSTFSVDSFVPVLVGLLNHESNPDIMLLAARALTHLCDVLPSSCAAVVHYGAVSCF -continued VARLLTIEYMDLAEQSLQALKKISQEHPTACLRAGALMAVLSYLDFFSTGVQRVAVSTAANMCKKLPSDASD
YVMEAVPVLTNLLQYHDAKVLEYASICLTRIAEAFASSPDKLDELCNHGLVTQAATLISASNSGGGQASLGVS
TYTGLIRLLSTCASGSPLGCRTLLLLGISSILKDILSGSGVSANASISPALSRPADQIFEIVNLANELLPPLPEGSISL
PTSANALVKGSGQKKSSPSTSGKQEDSPKVSPREKLLSDQPELLQQFGLDLLPVLVQIYGSSVNGTIRHKCLSV
IAKLMYFSTPEMIQSLIGDTNISSFLASVLAWKDPQVLVPALQVAEILMEKLPETFSKVFVREGVVHAVDQLV
LVGKPSSHASTDQENDCVPGSARSRRYRRRSSNANSDGNQSEELKNSVSASIGANHNSMESPTASFMLRET
VSSCAKAFKDKHFPSDGGEFDVGVTDDLLHLKNLCTKLTAGTNDHKVKGKGKSKASGPCLGDFSASKEEYLI
GIISEILGELSKGDGVSTFEFIGSGVVAALLNYFSYGYFSKEKISEVDLPKLRQDGLRRFTAFLEIALPSDGNEGKI
PPMTVLIQKLQDALSSLERFPVVLSHPSKSLSGSARLSSGLSALAHPLKLRLCRAPGEKALRDYSSNIVLIDPLAS
IAAVEEFLWPRVQRSESGVKPAAPVGNTEPGTLPSGAGVSSPSSSTPASTTRHSSRSRSAIKIGDASKKEPVH
EKGTSSSKGKGVMKPAQPDKGPQTRSSAQRKAVLDKDTLMKPASGDSSSEDEEMDISPVDMDDALVIEEE
DISDDDEDDDDEDVLDDNLPMCTPDKVHDVKLGDAVDDEGAGLAPSGRQMNSALAGSSGTATARGSNS
TDAGIGNLYGSRGALSFAAAAMAGLGAASGRGIRGSRDLHGRTLNRSSDESSKLMFTAGGKQLSRHMTIY
QAVQRQLMLDEDDDDRLGGSDFISSDGSRLNDIYTIMYQMPDSQANRLSAGGASSTTPSKSTKSATTNASV
EAQSYRASLLDSIVQGKLPCDLEKSNSTYNVLALLRVLEGLNQLGPRLRAQTVSDRFAEGKITSLDDLNTTAAK
VSHEEFINSKLTPKLARQIQDALALCSGSLPSWCYQLTTACPFLFPFQTRRQYFYSTAFGLSRALNRLQQQQG
ADGSGSTN+REMRIGRLQRQKVRVSRNRILDSAAKVMEMYSSQKAVLEVEYFGEVGTGLGPTLEFYTLLSH
DLQKVSLGMWRSNSGDKLSMQTDRDEIQDGKSAAARDRDIVQAPLGLFPRPWPSTADVSEGSRFHKVVE
YFRLLGRVMAKALQDGRLMDVPLSTAFYKLILGQELDLHDVILFDAELGKTLQELRVLVGRKHYLEAGGGDN
SSGISDLCLRGSRIEDLCLDFTLPGYPEYILRPGDDIVDINSLEDYISLVVDATVKRGVARQIEAFRSGFNQVFDI
KSLQIFTPSELDYLLCGRRELWEAETLVEHIKFDHGYTAKSPAIIFLLEIMGELTADQQRAFCQFVTGAPRLPPG
GLAVLNPRLTIVRKLSSTSNAAANGTGASETADDDLPSVMTCANYLKLPPYSTKEIMYKKLLYAINEGQGSFD
LS SEQ ID NO: 37: *Zea Mays* genomic UPL3 sequence: > Zm00001d004139_T007_genomic
TTATACGCCTACCTGCCTCTATTACATCTAGTTTTGGGCCTGTTACATGCACATTTGGTTGGCGGGCTCTT
GCACTGCGCCGCAACCCATCGCCAACTGAGCGGCCCACATCTTGCTTGCCGACGGCCTCGCCATTTAAA
TCAACATTCTCCTCATTTACAGACTCCACCGTCGTGCTCACACTAGTGCACAAGACTTATATTAGATGCA
ACAACCACCTAACAACCTTGACTTGACCTAGATACTTGGTTTACATGAGAGGGCCTATCCATCTATAGAT
AACAAATTAAAAAAATCTGTTGGCCAAAGGTTGTTACGGGGAATACAAGATATACAAGGCCACACAAT
AAAGGTGTGCCAAACGAGTAAATTTGGAAATAGAATTATCCTGATATATTTTTAGATTTTTTAAAATAA
AATAAAAATATTTAAACAAATATATACCCTGTGCATATATGTTGTAAGATTTTTGTATCGAGCTGATTCG
TGCATGCGTTACAGTTGAATGGAGACATTTTTGCTGAGCTGATTGATGGATAGCCTTCCGTAGCAATTC
ACGGACGCTGACCTAGCAAAAGCCGTGGGTTTAGCGAAGCCCAGCAACACCCTCGCAGTGTGAAGCAC
CCTCGCAGTGTGAAGCACGTATACCGCATGAAAGCCGGCCCCCAAATCACGAGCTCCTCCCTCTAACCT
CCGGCCTCTTCCTGCGTCACCACCGCGCAGGCGCAGCCATCCCCATCCTTCCTCAAATTCCCAACCCCAC
CCAAGCCAGATCTCACCCCCTCCCCGATCGCTACACCTCCGATGTTCCCGCCTCTTTCGCCTATCCCTTCA
TAGCCGCGTCGCCACCGGCGCCGCTGCGAGGCGGCCGCTGCCTTTCTCCGCTCCCTTTGTATGGAAACG
CGCAGCCGCAAGCGGGCGGAGGCCTCTTCTTCTTCCGCGACCTCCTCCTCCCGCTCCTCCAAGCGCTCG
CGACACAACCCTAACCCTAATCCTCCCGCCGGCCCCTCCCCCGCCCCCAAACTCGTCCCGTTGCCACCAC
GCACCCGCCGCTCGACCGCTGTCAATCCCCTCCCCCCGATGGATTCCTCGGGCGACAACAACTCCAATC
CCGTCCCGCCGCCGCGGCGCCGCGGTCGCCCCTCCAACACAGATAAGGGTAAGGAGCAGCAGCAGCC
GGAGCCGTCTCACAGCTCCCGAGTGCGCGAGGCCGAGCGCCTGCTGGGTCTAGGTTTCGAGGGCATTG
ATGATGATGAAGATTCAGGGTTCGGGGCTGGGGCCATCCCCCACAGCCTGACTTCCGCGAGCACCGCG
CTCCAGGGTCTTCTTAGGAAGCTTGGTGCTGGCCTGGACGATATACTGCCATCGTCGGCACTGTCAGCT
GCAGCTGCAGCCGCGTCATCGTCATCAGCATCCGGGCAGCTGAGTGGGAGGTTGAAGAATATTCTTGC
AGGTTTGCGTGCTGATGGGGAGGATGGAAGGCAGGTCGAGGCGTTAACACAACTCTGTGAGATGCTG
TCCATTGGCACAGAAGAGTCTCTTGGGGCATTCTCGGTGGACTCATTTGTACCTGTCCTGGTCGGTCTG
CTCAATCATGAGAGCAACCCAGACATCATGTTGCTCGCAGCACGAGCCCTAACTCACCTCTGTGATGTG
CTGCCGTCTTCTTGTTCTGCAGTTGTGCATTATGGTGCTGTGCCTTGCTTTTGTGCCCGGCTTCTCACCAT
TGAATACATGGACTTGGCGGAGCAGGTATGCTTTACATTAACACATTGCTTTCAAAATGCTGCTTGTTTG
TCATTTTGCTGCATCCCTTTCATTGATTTGTGAACATGGTTTTATCTTGTGTGCTTCATATGCTGGTGCCT
ACACATTGCCTAGCCTTCCATTTGTTCCTAAATAGTTTGGAATTGCTAATGGTCAGATATTAGTTCATGTT
TCCTATATGAGTGATATAAGGCAAAGACAAGGAGTTAAGGAACACAACTTTGTTCATGGTACACCTTGT
TCTGGAGAAATGCAACAATTACCTTTTTATTTTCTGTTTACACATTACCCTGTCTTGAATGCTACATAGTT
TCTACTGATTAGTTCAGTTTATGACTATATGGTCTTACTTATTCTCTGATACATTTGGCAAAGGTAAAACT
TCAGGGCCAACATAGGCCATGCTCTCCCCCGATCATTTTAGCAACTCTGCAGAATATCTGACAGTATTTT
GAGCTATATTGCTAATGAAACATGTAAATATGCTTTTGGAAACACTGAATTTATCTTCAAATCACAACCC
TCTTTGCCTCCTAACATCGGCTGCAAGCTCTGCCACTGGTTTTTGATAGAACATTTTTTCTGCTTTCTATT
GTTGTTTGGATCTCTAGAAATAATATCTTCACGTTTGAAATACTATGCATACAGATAATAGACGCATACG
TGTACCATCTCTTTGTATTTGTATGCATGCTCTTGATGGTGGCCTAACATATATGCTACGTTTTTTTATTTA
GTCATTGCAAGCTCTTAAAAAAATATCCCTGGAGCATCCAACTGCGTGCTTGCGAGCTGGTGCACTAAT
GGCAGTCCTATCATACCTTGACTTTTTCTCCACAGGTGTTCAGGTAATCACTCTCTGCCTATTATAGACTT
TTGCATCACAAAATACTTTGTTTGTTTCAGCTCATTTATCTCATAGCTTATTCTTATGCATTACTTGTCATT
ATATTGTGACAGATGAACTGTATTATTTATTCTTGTTATTTATTTTTATTACTAACTGTTGTTTTTGTTGAT
GGAATGTTTTCAGAGAGTTGCATTATCTACAGCTGCTAATATGTGTAGGAAACTTCCTTCTGATGCATCA
GATTTTGTAATGGAAGCGGTTCCACTTCTTACTAATCTACTGAACTACCATGATTCAAAAGTACAATTGC
CATTCCAAATGCTGATATCCTCTATGATACCATTTATGTTTCAGATGCTGATATTCCGTTTTGCTTATTCC
AGGTACTGGAGCATGCTTCTGTCTGCCTTACCCGTATTGCGGAATCTTTTTCACCATTTCCAGAAAAATT
GGATGAGTTGTGCAGTCATGGATTGGTTGCACAAGCTGCTAGCTTAGTGTCTGTTAGCAACTCAGCAG
GACAGGCATCCTTGAGTACATCAACATATACGGTACGCTCCATTTTGGCTTTTTGGGTACAATTATTTGT
TTTACGTTTGTGAAGTTTATGCCATGTTTTTATAGGGTGTGATTCGTCTTCTCTCAATATGCGCAAGTGG
ATCACCTCTGGCAGCTAAAACACTTCTCCTTCTTGGAATTAGTGGCATACTTAAAGATATCCTTTCAGGC
TCTGGGTTGGTTGCTGGCACGACTGTGTCCCCTGCTTTAACAAGACCAGCTGATCAGGTGATTTTGTCTT
TTCATAGGCACTTCAAGGCTCTTTGGGTATCATGTGTGCTTGATGTCTACATTTGTTGTTTATCTTAACAA
GCTAAGGCCCCGTTTGGCACTGCTCCACTTCACAAAAACAAGCGCAACTTCATGAACTTCAAAATATAG
CAGCCCAGCTTTGAAGTTGCAGAGTTTTTGAAGAGTTTGGCTTGTAGACCAGCTTTAGTTTCATAAAAA
ATATAATAAAAAAAAACTTGTTTCTTCTTCCTTTGGCCGTGGCGGCCAGAGGCGCACGTGCGCGACTTG
GGAAGACAGACACAACGCTGCGATGGCCTGGCGTGGCTCTGGCGGCCCAGCGCGCTGCACGCAGCCT -continued GGCGGCACGTTGTCGGCCGATGCGGCCCTGCTCGCTAGCGCAGGTGGTGGCACGCGCGCTGCCAGAG
TTTGGTTCAGGCGTGGCTCTGGCAGCGGCACATGGCCTGGCGGTGCGGCTGCCGGTCGGCACGGCCCT
GCTCGCTGGCGTAACTGTGTGCGGCCTGAGTTCCCTTGAGAACAGAACGAAAGAAAACATTTCGTGAG
GGATTGCGTAACTGATGGCAAAGGTGGGTAATTTCACCCCAACTTAATGAGGGAGTTAAAAATACCCA
TTCGTGAAGTATACTTTTGGTTGTTTCATGGATTTGGTGAAGTTAGGGTCAACTTCACCTTTTTTGGTGA
AGCTGGGAGTGTTTGGCTAGAGTTTTATAAAGCTAAGCTAGATTTTGTGAAGTGAAGCAGTCCCAAAC
ATTCCCTAAGTGTAAATTAATGGAGCTAGGCTTACTCTATGCTTCAGATAGTACTTCAACCATTGATTCC
AATTTCCAAGCCTCAGGATATCATCTCTATTAAGGCCCCCTTTGGCACGGCTCTGGCTCTAGCTTCTTGC
AGCCCCTTGGAAGGAGCCCTGCCAAACAGCCATCTAAAACACAGCTCCTGGCAAGGAGCCAGGGCCAG
AAAAATGGTTTCTCCCAGCTCCTTACAAACTTGATACAAATTATTACAAAACTGCCACTGGACCTGTTTT
GACCAAACCTTTTCCAAAACGGCTTCAACTGGCCCAAATTATAAAGGCAGCACAATTAATCCCATACACT
TCCCAACCTTACAAGCCCCTTAATACAGCCCATCTCTGCCTTCATTCTCCATACATATCTGAAAGTCTTCC
ATGTTCTCTCTCTTCTACCACTTCGTGGCGCAGTGAGGGGGGCTTACTTCTAGGAGCGCCTAACATGTG
CTATATAACATCTTTACGCACAATGACATAGGAACAAGTGTCGTCAAAGAAAACAAATAATATTTGTGT
ATATTAAAACATTTTTTGATGAATTTGATGAAATGAAACCAAATCGTCCCATAACATGTTTTTCTCATAAT
GCATTTTGTTTTTTAATCGCCACCAATAATATACTTTGAGCTTGTAGTCAATGTTCGTTTATGGTATGACA
TTGTTTTTCTTTAATGTGAGCATACTCATACTACTTTCCATGTCGAGCATTTGTGAACATGATGTTATCCT
ATGTTCTATTCATGATAGCACAATTTATATTTGTGATGAATTGTCATCTATGTTAAATTTTAATGGGTACT
GTAACTTGTAAAGCTACTGACTTTTTGGTAGTAATAGATTATCACCACACAATTCCATATGCAAATGATG
CCATTATGTGTTTTTTGGTATTACACAGATGAATGAGATTGTGAAGCTTGCAGATGAGTTACTTCCTTCT
CTGCCTGTTGGGACCATTTCTTTACCAGTGTATTCTGGTGTTCACATGAAAGGTTGTTCTGTAAAGAAAT
CCACTTCTAGTAAGCAGGGTGAACATGGTTCAACAGCAAATGAACTATCAGGTCGGGAGAAGTTATTG
CGTGATCAGCCTGAACTTCTGCAGCAATTTGGCATGGACCTGTTACCTACCATGACACAGGTCAGTCTT
GTCTTATTAATGTTCTCTTTGATGTTGTTAATGGTAATGCTGATGTGGTATTACGGGACATTGTTGCTAT
CATGTTGGTGTGATACTTAAGGACTTCAATACCTTGAACAGGTGTATGGCTCTAGTGTAAGTGGACCAA
TACGGCACAGGTGCTTATCTGTCATTGGGAAATTAATGTACTATAGCTCAGCTGAGATGATCCAGTCTC
TCCTTAGCACAACAAACATTTCCAGGTGCTTAACACAATATATTTCATCGAGTTATCTCATGTTATTAGAA
ACTATCTTATCACATGAATTCCAAATATTTGTTTCAAGCTATTAACTTCTATATCAACCATTGCAGCTTTTT
GGCTGGCATTTTAGCTTGGAAAGATCCACAAGTGTTGATCCCTGCTCTTCAGATAGCAGAAGTTTTAAT
GGAAAAACTTCCAGAGATTTTTTTGAAGATGTTTGTGAGGGAAGGCGTTGTTCATGCTGTTGAGTCACT
TATATGCCCAGAATTATCTGGTCAGGTGACTCCTCATGTGGATTCCATTACATCTTCACATAATAGGCGC
AACCGCCGTAGAAATAATGCTGTGAACACTGGAAATAACTTGCCTGATGGACCAAAAGGTTCCAATTCT
ATGATTGCCAATTCACCCCCAAGCATGGCTGAAGTTCCAAATAATAGTCTTCGTGCTTTAGTTAGTAATC
ATGCAAAGTCATTTAAGGATAAATATTTCCCTTCCGAGCCTGGCTCAAGTGACATTGCAGTTACCGATG
ACCTTCTTAAACTGAGGGCACTTTGTGCAAAACTGAATACAACAGCTGACACTATCAAAACAAAAGCTA
AAGGAAAATCAAAGGTAGTGTCTGACAATAGTTTTGATGTCTTGTGCAATATTGAGGAGCAATTGGAT
GATATAATAGCTGAAATGTTGTCTGAGCTTAGCAAGGGTGATGGTGTTTCGACATTTGAGTTCATCGGA
AGTGGAGTTGTTACGGCTTTGCTAACCTATCTGTCATGTGGAACATTTGGGAGGGAAAAGGTGTCTGA
GGCAAACATACCAAATTTGCGTCATCAGGCAGTCAGACGATACAAAACATTTATATCTTTTGCACTTCCA
AATGATAAAGATGGGAATAAAACTCCTATGGCATTCCTAGTCCATAAACTGCAAAGTGCCCTATCTTCG
TTGGAACGTTTCCCAGTTGTGCTCAGCCATTCTGGAAGGGCATCGACTTTGGGAGGATCCCGCCTGACA
ACAGGTTTAGGATCTCTGTCGCAGCCCATCAAATTGCGTCTTTGTCGAGCGCCTGGTGAGAAGTCACTT
AAGGATTTTTCGTCCAATGTTGTTCTTATTGACTCATTAGCTAGTCTGGCAGCTGTTGAAGATTTTCTTTG
GCCTAGAGTCCAGCGCACTGAACCAGTATTGAAGCCTCCAATGTCATCTGCAAATAATTCTGGATCTGG
AGCAGCAAGCTCCACAGCTTGTGCGCCTTCAATTCCATCAGAAACTCAATCTGTCCGTCGCACATCGTTA
AGATCAAAGTCATCAGCTGCCACCAGTGGTGCAATTAAGAAGGATTATCAGGAGGGAAGCATAAACAC
CTCAAAGGGAAAAGGAAAAGCTGTTCTTAAATTGAGTTTGGATGAACCTAAAGGCCCACATACTAGGA
ATGCTGCGCGCAGAAAAGCTACTTCAGAGAAAGATGTTGAACTGAAGCCATCACATGGTCACATCACTT
CAGAGGTTAGATACTCGTGCATTCAATCTTATTTGTTATTTGCATAATATATGCGAAATGGCCTCTAGCC
TAGTGGTTAAAGGCTTCCGAATAGCACCTCCAAGTCTCGGGTTCGATTCCCCTCAGGGGCGAATTTTCC
GGCTTCCTGTGCGCCACCCTCCGGTTGGACCGCTGTAGAGGGGACGGTTGACGTCGGCTCGTTAGTGA
TGGGGAGGGGGGGGGCAGAGTTTGGGGATTTTCTCGGCCGAGACCATTGTTTTAGTCTATCTTGATAT
AATACCGGGATGGCGGTCATTCCTTCCCTGGCTGAGTTTTTTTTATTTGCATAATATATCAATTGAGCCC
TCCTAAGTGAGCTCCGTTGGGAAGTTTAGCTTTAATTTCTGGCTCTAGGACACATTGATTGCAAATGTTT
TTTTAACAATGCCTTTTGTTTACTCAGCTGACAAATGTTATCATAGTAATGATACAACAGTAATGCAGCT
GATTTATTTTGCCTTAAGTGTATCTAGTTTGATCAGTACTTTGTTTTAGTATGTAAGCAATGGATTTCAAA
GGGATGTTCTTCATAGACATGATGTACAGATTGTATAACTATAAAGGAGGGGGGGGCAGTGCTGCAG
GCTCCGACATGAGGAGTCTGGGGAAGGGATAAACCGAGGCAACCCTTCTCCCATAAATACGGAGAGA
CACTGCTTTGAACCCACAACCTGGTGACTCCGGGAGACAATTCACACCACTGACGTACAGATTGTATAA
CTATAAGTCTATAATATCATAAATGTATAACAATGAAAATGCACTGAACTGTGACATTTCTGTGTATCAT
GCATTTATAATATTATATCTGAGATAGGATATAAAAACTGAAGCATTTTTTATAAGAGCAACAAAGATT
AAAGTAGAAATATGCCTGTTTCACTAATATTTTATAATTTAGTCATATTATGTAATGACCTGACTACGCTT
TCGTAACTTAGTATACTGGACTATATTGTGGATACTCACAAATATGAAATATCAGTGTAATCTTTTACTCT
AAACAAGGTTCAGCTAGGCGCTAGGCGGAATCTAGGCGGTGACCCATTGCCTAGCGCCTAGTCGGGA
GTACTCGGTCTTAGGCGCTTCTAGGCGCTTTTCTAGGCGTTTTGGCAATATAGCCATAAATTATATATAT
ATATTATGTATATAACTATATATACGTATATAACTACTATATATGACTATATGAGTCACAGTAAGTATAA
AAAGAAGGCCAGTAGACATATCTGATTCCTAGCTGAGCTTACTCTTGCATGTTCCTAGCTCCTGCAAGG
CTGCAACATATTTTGACAGCTAGTAGTTAGTAAATTAGTCAATAGACAGCTAGCTGTTCATAAAAAAAA
TAGAAAACACTAAATTGTGACTTATCTGGATGATTTCAGCAGCCTCCCATTCATGAGCAGTTGAGCACA
CTGCACACCATATCAGCAGCTGGTAATTACAACACAAGTGGATAGGACAGTAATACAAGTGCAGAACA
CAATTTATAAATAAAGGACAACACAAGCTTCCAACACAAGTGACTTCTTCTGACTCCTCTCCAACCCTAG
ATACATTCACTTCCTCTCTAAGTTCTAGCTCACGAACAGTCTTCTCCTCCCTCTTCCTTTTTGCAGCCTCTA
TTGCTTTCTTGCACTTCTCTTTAGCCTCTAGAGCCTGCGGTGTTGCAGACGTGCATTTCTTCACATTCTTT
CCAACATGGGCAAGATGCTCCTTCAACCTATAAATCCCTCCCCTCATCTCCTTGTCACAGAACTTACACTT
CACCTTGTCTTTGTTGTTAGCATCAACAAGAACACCATATTCCCATCCAACATCATCTGAATTTCTTTTTA
GGAGATTCGCTCTAGCTGCTTCAGTTTCAGAAGGTGCAGCTGCAGTTTCTGATGACATCCTTAATCCTTT
GATTTCTTTCACTTGTACACTGCACAGGGGAGGAAAGCAGTTTCAGCAGGGGAGGAAAGCAGGGGAG
GGGGATGAGCAGGGAGGGGAGCAGCCGACGGGGGAGGAGAACTCACCGGCGGGGGAGCAGGGAG
GGGAGCAGCCGGCGGGGGAGCAGCAGGAGGGGATGAGCGCCGGCGGGGGAGCAATTTCCGTGACC -continued GTGTGGGAGGGAGACTGAGCGGCTGCACAGCGCGCGCGCTAAAAATTGCCGCGCGCTCGCCTGCGCG
CCCGCCTAGGCGCCTGCGCGCCGCCTAGGCGCGGCTGAGCGCTGCCTAGTCGCTGCGGCCGCCTAGAC
GCCGCACAGAGCCCTAGGCTACGCGGCAGCCTATCGACTAGCGCCTAGGCGCGCCTAATCGCCGCCTA
GTCGGCGCCTTGCCGAACACTGACTCTAAATAAAAGATATTGTTGTATTTTGATTTTAAATATCTAAGTG
AAGTTTTCAGGGGAAACAACTTTATGAATTATTATTTGGAATAGTACGTGCATGTTCTTTTATAAGTTTG
ATATCTGAATTTTAGAAATTAAAAAGTTTGAAAGCCCTGCAACATATATTTATATTATTATACCTGCAGG
ATGAAGATCTTGATGCTTCTCCTGTTGAGATTGATGATGCTTTAATTCTTGATGATGATGACGAGGATGT
CCCAGATGATGAAGATGATGATCATGAGGCGGTAATTATTTTTTAAATCTTGCTTATTACTACAAAGGTT
TGTATTGAGGGGACATGATTTGGAACTCAGTAGATTTTGTTGAAATGATCAGGTTCTCCGAGGTTCTCT
TCCTTCCTGTGTTCCTGAGAGAGTGCATGATGTGAAATTAGGAGATGCTGATGATTCTAGTGTTGCCTC
ATTGGCAAATGATAACCAGGCACAGCCCTCATCTGGTTCTAGTACAAAAAATACTTCTAGCAGGGGATT
GGACACTGCTGAATTTAGAAGTCCAGCCACATTTGGTTCACGAGGTGCAATGTCGTTTGCTGCAGCTGC
AATGGCTGGATTAACTCCAGTAGGTGGTCGTGGAATTAGAGGTAGCCGAGATCGGAATGGCCTTCCAT
TGGGTGCTCGTGCAACTGAGCATTACAACAAATTGATATTTACAGCTGCTGGGAAGCAGCTGAACAAA
CATTTGACTGTATATCAAGCTGTTCAAAGACAAGTAGTTCATGCCGAGGATGATGAAGATCGATTCGGT
GGATCTGATTTACCTGATGATGGTAACCACTTCTGGGATGATATAAGGGGTGATGTGTTCACTATAACG
TATCAGAAGGCTGATAACACAGCGGAGAAGGGGTCTGTTGGAGGTTCAGCTTCAGTGCCAAAATCTTC
CAAATCAGATTCTTGCAGAACTTTGTCTGAAAAACAGTGTACTTCTCTTCTTGATAGTATTTTGCAAGGA
GAGCTTCCCTGTGATTTAGAGAAATCAAACCAAACCTACAATATCTTATCACTATTACATGTGTTGGAGG
GTTTGAATCAGTTATCACCTCGTCTGAGACTGCAGTCAGCCTGTGATGATTTTGCTGAAGGAAAAGTTG
CTACATTAAATGGGCTATACGATGTTGGAGCTAAGGTACCCTCAAAGGAGTTTATCAACAGTAAGATGA
CCCCAAAACTTGCTCGGCAAATTCAGGATGTTCTTGCACTGTGTAGTGGCAGTTTACCATCTTGGTGTTA
TCAGCTGACGAAAGCTTGTCCTTTTCTGTTTCCTTTCGAAACACGAAGGCAATACTTCTATTCCACAGCTT
TTGGGTTGTCTCGTGCACTTCATCGTCTTCAGCAACAACCGGGCAATGATAATAACACTGCTTTTGAAAG
AGAAGTCAGGATTGGTAGATTGCAACGCCAGAAAGTCCGTGTTTCTCGTAACCGTATCTTGGATTCTGC
AGCTAAAGTTATGGAGATGTTCTCTAATCAAAAGGCTGTCCTAGAAGTTGAATACTTTGGTGAAGTTGG
AACTGGTCTTGGTCCAACTTTGGAGTTTTATACTCTCTTAAGCCGTGAGCTGCAAAGGGTTGACTTAGG
ATTGTGGAGATCTCATTCTTCAGATAATTCTGGGATGCAAATTGATGCGAATGCTGATGATTTAATAAG
AAGTAAAAATCATGAATCAGAATCACTTACTGAGAGCAGGAACATAGTACAATCACCTCTTGGATTATT
TCCTCAGCCTTGGCCACCTACTGCTGCTGCATCAGAAGGTAGCAAATTCTTCAAAGTTGTCGAGTATTTC
CGCTTAGTTGGTCGAGTGATGGCAAAAGCATTGCAAGATGGAAGGCTTCTCGATTTGCCTTTGTCGACA
GCATTTTACAAACTTTTGCTTGGACAAGTAAGCATGAGGGCCTCCTTGAGCTAGTTTTATCTTATGTTGT
CTTCTAAAACCTTCCTCTTTTCGGTTGGCACTTAACTTTCTGTGCCTTTTCCTTATTAATTTACCAAATTTG
CTTTAATAGGAACTTGATTTATATGATATATTATCTTTTGATACCGAGTTCGGAAAGACATTGCAAGAAT
TGCAAATTCTCGTTGCACGTAAACAATTTTTGGACTCCTGCTCTAGTGAGAGCCAAAAGATAGATCTAT
GTTTCCGTGGTGCTCCCGTTGAAGATTTATATTTGGACTTCACTCTTCCGGGCTATCCTGAATATGTTCTC
AAGGAAGGTGGAGAGAATGCAGAGGTAAGTTATATGATACCCTAGTTTGTTTTTTTCTTCTAGTGTTGC
TGCAGATGACTCATTGTTATCCTGTCTTATAGGTCAACATTTGTAACTTAGAAGAGTATATTTCTTTGGTT
GTGGATGCTACTGTTAAGACCGGCATAATGCGGCAAGTAGAGGCATTTAAGGCAGGATTCAATCAGGT
CTTCTTTCTTATTTTGTGATTTGTGGGCAATTTCTATTAATAATTGATCCTAGAACTAACTAGCACATTTAT
TTATTTATTCAGAAAAAAATACTCATTGTATATTTCTCACTTCAGGTGTTTGACATATCATCACTGCAAAT
ATTTTCTCCTCAAGAACTTGATTATCTGATTTGTGGTCGCTGTGAACTTTGGGAGGTATTGCTTTTGTGG
TCATTCTTGATGTTGTACTTCCTCTGTCCCAGAATGATAAGCATAGTTTGTATAGGAAAAAGTCAAATTT
AGAATTTTATTTCCCAGAAATTGCTTGTATTATACTAGTTTATGTGGCTTTGTGTCCCGCTGCCATAGGTC
AATGTTAGCTATTGAAAGCTAGTTGCTCTAGTCTACTGCTTCCCTTTTTTTCGGGCCGGGGGGGGGGGT
ATTCTCCCTCCTTTGCACTTCACCTTTTTTCTCTCTTAATGAAATGATACACAATTCTCTTTTGTGTTCGAG
AATTCTTTTTACAAACTTTGGCCAACAATTAATCAAATTATATACATGTTTTGGACAAACTTGCATCAATA
GATTCATATTCAGAGTGCATTTGAGATGAGATTAATTGTTTAGCAAACATAAACATATTGTACGAGAAA
TTAATGGTCAATTTTTTAATAGATTATGTGAGTTATTGTACTCAGTCTAAGTGTTATGGACCCTGGTCCC
GCCCATGTAACTCCTTTTCCAATATATGCAACGTAGCCCACCCTGATTGGAGTTAACATGGTATCAAGCT
TGGTCTTTTCTCTCCCTCCCTTCCCTAGCCGCCACCTCCTGGCCGCCATCACTACCGTCGGGTCGCTATTG
TCGTCTGCGCCTCCATCTCCTCCCTAGCGCCTTTCTTGCTCATCGGCCACCCATATTTATTAAGGCGGTGT
TAATAACCATGGGGCCACCACCTTCACTTTAGCTTTCTAGGCGCGACTGGTGGCCTTGTTGGCCCTACG
GTTGGCGCCTTGCCCACCGGTGCTTTAGTCCCGGTCACCTCGATTGCTGCCCCAGTCGCTCCCGTCGCCC
TTGCCTTTGCTGTGGCCATCTATGGCATGGGTGCCGCCAGCCAGGGCCCAGACCTAGCTGACTCTGGCC
TAGCTTATCTTTCGGTCGCGTTACTTCCCCCTGATGTCGCTTTCGCTCACTCCACCTTGGCCATAGCCCCC
ATTGCTGCCAAGACGGTGTTTGCTGCTGCTCGGGATCGGGAACATGTTGCTGCCCTTGCTTAGGGGCAC
AAACGCACCACGACGGATGCACTCGCTCGATAGCAGACCAATGCTGAGGGTCACCTGCTCGGCTCCTC
CTGCATCGAGACCCTCCCAGCGCTCTAGTGGTCGCCCCTTTGTCGGAGTACGAGGTCGAGATCATCACC
AACCTCTATGCCGAGGTGGCGTGTGTCCAGAACATTTGCTCTATGATTCTCGTCATCCTTGATACAACTT
CCTCCAACTACGCCTTCTGGCGGGCGATCTTGTCTACACTCTCCATCACTACGCCTTGGACTACCACGTC
CTCACCAACACTGTCTCCCTCACTAACCTATCCTGGCGGCAGATGGATAGTGTGGTCCTCTCGTGGATCC
CCAGGACCGCCATCGTTGCGCTGCATGACGTGGTTTGCGAGCGTGGTGGCACTATCCGTCTTGGACGT
CGTCGAGTAGTTCCTTGGCAATCGTGAGGCTTGCACTCTCTACCTTGATGTCGCCTTTCAGACTTTTGTC
TAGGGGAACCTCTTTGTCACTGAGTACTTTTGTCAGAGGAAGGGCATGCCAGCCTCCCTCTATGACCTT
GGGGAGCCCGTCTCCCATAGCATGCTCATCCTCAACCTCCTGCATGGCCTTCACCTCCACACTTCGATCA
CTTCCTCAGTCCCGTTCCACAAGGTCAAGGTCAACAACGACCTCATTTCCGAGGAGCTCACCAAGGGGC
TGCTACCACCCTCTACAACTCCACCACTGGGGGGCCAGCGCATGCACCCTCTTCTACTACTATCTTGGGA
GGATCGTCGTTGACTCGTTGCGCTCGTCTGTTCATCAAATCTCAAGCATTGCACATCCTCCCCACTTGCC
TTGGTCTGAGGGGAGGGGTCTAGGGTGGCGGTCGACGAAAGGGCGGTCGTGGTGGTGGCCATGGGG
ACACTCCTTGGCCTTCCATCTACAACCTGTGGACTGATCGCATCTCCATGTGGCCTGGTCCTTCTCCGAG
AGTCCCTTCTCAGCGTATCACTCCACCGTAGCCAGCTCACTTGACATTGCTCGGTCTGGGGTATCACCTT
GGCCATCCTACGCCATTAGCACCTGAGTCACCACTTCTGTCACCGCCACCCCACCTCGCTTTGTCCTGGA
ACCCGTGGCCAGGTGGGTGGGATCAACAGTCTCTTGCTAGCTCCTTCAACACGATGACCTTGACTCCTC
CCACTGTCACCTACTAGGTGGCTGATTCCTGGTGCCTCCTATCACACCACTTTGGACGCGAGTATGCTAT
ATTCTTATCCACCTCTTCGTCTACTCCTACCATTGTGGGTAACGAGAACATTCTCTCGGTCACCTCTGTCA
GTGATTCGGTTCTTCCTAGGCCCTTTCACCTTCACAATGTTCTTGTTGCCCCACATATCCTTTAATATTTA
TCCGTTCACCTATTGAGCATCGGTAATTCTTGTTCCATAGATTTGATCCTTTTGGCTTGTCTGTGAAGGA
TCTTGCTACCTAGAGTCTTCTTGCTTGTTTTGATAGATCTAGGCCCCTGTACACCCATGCAGGCCTGCGT -continued CTACCTCCCCACATACTGGTTTCGCTACATCATCACATTCGTCCTCGCTACAGTCGCCTGCTTTGACTACT
TCCACTATTTGTAGTACTTGGCATCGTCGACTTGTCCATCCCAACCTTGTAGCGTAGTCCAAGCTATGTA
GTACTTTAGTAATTTCTTGTAGTAGGGGCACCCTTGAGCATCTATGCCAGTTGTGTAAGTTAGGTCGTCA
TTTTCGACTTCCTTTCTCTAGCTTCTCACAGCATACGCTGTGATTTGTGGACCTCTCCTGTTACCAATGTTT
TGGGATATAAATATTATTTGGTGATTCTTGATGATTGCTATCATTGTTTGTGGATTTTTCCATTGAGTTTA
AAGTCTGACACCTTTACGACTCTGCTCGGTTACTTCGCTTGGGTTTACACTCAGTTTGGTTGCACTATGA
AGATCGTCCAGTGTGACAATGGTCGTGAGTTTGATAACTTCTCTCGATCCTTTACCTCAATTGGAGTCTA
GCTTCGAATGTCTTGCCCCTACACTTCCCATCAGAGTGGTAAGGCTGAGTGTATGATTTGCACCACGAA
TAATGTAATGTGTTCCTTGATATTTCAATCATCTGTTTCCGCTCGCTAGTGGGATGGGAGCCTCCACACT
GCTACCTACCTCCTTAATTGTCTTCCTACAACGACAACTCTTATGTCATGCCCCCACCCCACTTTGCTCG
AATGGCAAGGCTTAGCGCATGAATTAATGTCATGTTTTTCTTGCTATTTTACTATTTTAGGCATCCGTTCC
TTCTCCTTACTGGTCTGAGAGCCTCCACACCACCACCTACCTCTTTAATTGTTTTCCTATTACGACGACTC
GTGCCCCCACTTCCCACTTTGCTCTTTTTGTCAACACTCCAATGACCATCTTCGTGTTTTGGGTATGTGTG
CCACCCTAACCTTTCCACCACTACTCTCCATCTTGTTCTTTGTTCTGCTCGCTGTGTCTTTCTCGGGTACTC
ATCTGATCACAAAGGGTACTGGTGTCTTGGCCTCACCACTCCTCGCCATTTGATCTCTCATCACGTCATA
TTCGTTGGGATGGATGTCCCCTTCTCAACTAACACCTAGCCCACCACCGCCTCCCCTTTCGAGTTGTATTT
TCTTCATGATCCTGACTCCGTGGTGCCCTTTGTCCAACCACTGTTTTTCTAGTTGCTGTTTTCCTCTCCACT
GTTTCAGCCGGTGGCCCCTGTGTGCCCATGGTGGATCATACGCCCTTGAATTCCTTCCGGGTTGCACCG
TTGCCCCTCGTCGACCCGTGTGTCACCTCGTCAACCCATGTTGGGTCCCTAGGCCCCGGTGGCCCCACTT
TTGACATTGCCTTCGTTGCTAGGGCCCTCTTTATTGCCCTCGCCTGTGCCCTCGCCTTGTTGCTATGCCCA
ACCTGTGCATTTCTATCAGCGACATGCCCGAGTGGGTACACCGCCTCGCTCTTGCGACGAGCCGACAAT
GTATCACCCCTTCATCGTGACTCTCACCACATCCACTTGATGGCGAATTGCCAGGCCACTGGGGTCCTTA
GCCCTGTTGATTGCCTCATCCTCTCCGTGACCTCCTCATTGTCGGTTTCTCATGTGTCGTCTTGCGTTGAT
TGCACCCTTTCTAATACTCATTGGCGCCACGCTATGAAGAAAGAGTACCTGACTATCCTTGCCAACCACA
CCTGGGTTCTGGTATTCTGGTGCCCCATCTTTCGTGCGACAATGTGGTGATTGACAAGTGGGTCTGGAC
ACATAAGCGGCAGGCGGCTGGCTCGCTGGGCTACTCAGTGTCGTGCTGTTGACTACGATGAGACGTTA
ATTCTCGTTGTGAAGCCTGCTACCGACCGTGCCATCCTCACTTTGGCCCTCTCCCATTTTTGGCCAATTCA
TCACTTGGATGTCAAAAATGCTTTTCTGCATGGGACTCTCACTTAGACTTGTCTACTGCTGTCAGCCTAC
TAGCTTTGTTGATCATGCACACCCCGATATGGTATGCAAGCTCAACAAAGTATGCAAACTCAACAAGTC
CCTCTATGGTTCGAGGCAAGCCCCACGTTTGGTACAACCGCTTCACCATATATCTGCTCTCTTTGTTTTGT
TGAGGCCAAGTCAGACACATTTCTGTTCATCTATCGGTGTGGTAGTGACACTGTATACCTACTCCTATAT
GTTGATGACATCGTGCTCACTACCTCCTTTCTCATGCACTAGATCACCACCGCTCTTCAGCATGAGTTCAC
CATGAAGGATTTAGGCCCCCTTCACTTTATGGGGATTGCTGTTGAGCATCGCTTTGATGGCCTCTTTTTT
CAGCAGCGACGATACACCCTGGACATCCTCGAGCGTGCTGGCATTCTGGATTGCAAGCCTTGTGTGGC
GTCAGTGGACATGTAGGCCAAGCTCTCTGGCGTCAGTGCTCCAGTCAGTGGCCCCATCACCTACCATAG
CCTCATCGGTGCTCTTCACCATCTCACCTTCACCAGACCTGACATCGTGTATGCCATCCAACAAGTATGT
CTTTATATGCATGATCCCTGTGACCTGTACTTGGGTGTGGTCAAGTGGAATCCTTATTGTTGACTATGGT
CTCCTCCTTTGGCGCTCCTTCATCCATGAGCTAATCATCTATACTGACGCCGATGGGCCGAGTGTCCTGG
ACACCTGTCGGTATACCTCGGCGAACCTCATCTCCTGGTCCTCCAAGCGGTAGCCAGTGGTCTCCCGTTC
CAGTGCTGACGTTGAGTACTGGCTGTTGCTAATGGGGTGGCTGAGGCGAGCAAGCTGCACCAACTTCT
CCAGTAGCTTCACAACCCACTCACCATGAGTACCCTGGTCTACTACGACAACGTCAGCATCGTCTACCTC
TCTGTCAACCCTTTTCAACACCACCGTATTGACCGTTTTACTATTGGGGACGTCCGCGTATGTTTCAACG
AGCTCGTAGTTTGATGACACCTTCACTAAGGGTTTTCCCTTGTTCTTGGAGTTTCGGTTGTTGGGGCAGG
AGACAGAACCGGTCCTCAACTACCAATTGTACTCACCACTCACCAAGATTCCTAATGCAGAGTAACCGA
CTAGGAGGTGCGAAGGCCTATGGCAGAAGGGGCAAGCCACGGAGGCCGACCCCAACTTCGGTCCTTC
CTAACAATCGCGAAGGCTACTTGACTACGCAGGGACCTTGGCCAAACCTCGACGAGGGACAAACACGT
TCAGCGAGGGCAGGCGGGGGCTAGGACGCGTCGAAGACCCCCGAAGCACCGAACGAAGACCCAACT
GCTACCAGCCGATGTTGACCGAGGCGAGATCGCTCCTCTTTGGTAGGCCGTCGTGAGGCAGTTTTTCTC
TAAGGCCCCCACGCAGAGGCCATAAGACGAGGAATGTTGGATTCCGCCAAGCGGCGGCTCAGTTGTG
GGCGTAGACTCGCCTACTCCACACGTCAGCCTTTGATGTGGGTGAGAAAGATGGTGTAATATGGAATG
TAGCCAGGGGACCTGTAATTACCCCGTTGCACACCTGTTGCACGGTATATCTATGGCATGTAGTAGGTA
ACCAAGGGCATTACGATATTTTAGGCCTTGGGCCCTTGGCCGCCCTATAGATAGCCCCATCCTGTAGCT
GGATGGGACACACTTGACAAGACATTTGTGCTCCCAGCCAATTGTTTTGTCGTGCCACCTGTAACACCA
CTCTCGAGTGCTTGGGCACACTGTTCTAAGTCCCAACATCGGTCCAGTCTCAACATCTTTCACGACTAGA
GTTTCATCTGCGGGGGTGGGGGTAGGGGTGTTAGATTCTTGTGCGTTATTGTACTCAATTTATGTGTTA
TGGGCCTTGGCCCAGCCCATGTAACCCATGCAACACAGTTTACCCTAATTTGGGTTAGGTTTCCAACAAT
TTTGTTTGACTTTTCCATTATCAAAACACACTTAGGCCTTGTTTGTTTACGTCGGATTGCACCCGGAAAC
GTTCCAGCTAATCAAAGTTTATATAAATTAGAGAAGCAATCCGGCTAGGAATCGTTCCGACCCACCAAT
CCGACACAAACGAACAAGACCTTAATATTTCACGATGAATACTCAATTTAAGTGTTATGGGCCTTGGCC
CAGCCCATGTAACCCATGCAACACAGTTCACCCTAATTTGGGTTAGGTTTCCAACAATTTTGTTTGACTTT
TCCATTATCAAAACACACTTAATATTTCACGATGAATGTAGTTGTTTTGGCTTATTCTGAACAATTTCACA
TCATGCAGCCGGAAACACTGCCTGAACATATAAAATTCGACCATGGTTATACCTCTAAGAGTCCTGCAA
TTATTAATGTAAGTTTCCCTGCTTCTTTGTAATTCATTTGTAGGTTTCGTAAGTTTATTTGGATGTTTCTAA
TGTTGTGTTTTGCAGTTTCTTGAGATCATGGCAGAATTTACTCCTGAGCAGCAACATGCTTTCTGCCAGT
TTGTGACCGGTGCTCCTCGGCTTCCACCTGGGGGTTTGGCTGCTCTAAATCCTAAGTTGACCATTGTTAG
GAAGGTAAATTGGCTATCTTTGTTCTTATTTCTACTTTATGGTTGACATGCCTGCCCACATTGTTGAAGTT
TTGAATTCTTAAATTCCAGCACTCTTCTGTGGCAAATAATAATTCAAATGCAACTGGAGCGACAGAGTCT
GCAGATGATGATTTGCCTAGTGTCATGACTTGCGCCAACTATCTTAAACTACCACCATACTCCACCAAGG
TATGCTTCTTTCTGCTTTTTGGCTAACTGTGGTTATATCTCCTGTATTGTCTTATAAATTGAGGATTCAGA
AACCCAGTCACCAAAGAATTACTTCATATAGCCTTATCGTAACAGGTAACTGGACAAATTTTCAACTAAG
GACGTGGAAACTAAAATTTAATGTGGGCAGCACCTTCCAGCCACTCATTAGTTAGAATTATTATTTCGTT
AGTTTAAATCAAATAGCATATTCCACATTGCTTGAACCCTTTATATTGACGCATGCTGGTTTTTTTTCTGG
AAGGAAATATTTACAGTGCTACTCGTGCTAGTGTGTGGCTTGTTATCTCTGTCTGAATTTTGTTGAAAAC
TTCTTGCAGGCTATCATGCTAAAGAAACTGCTTTATGCGATCAACGAAGGCCAAGGGTCATTTGATCTTT
CGTGAATCTCAACACTAACATAGGTATTGGTCCACCTAGAAATCTGCGTCATTGTTACCCAGAGTTAGTT
TCTACCTCATTCATGTATGACATAGGTTAAACTCAGCTCTCCGGAGTCCCACCGAAGGTTTGGAGCCCGT
ACCTTTGGGTGTGGATGTCTATACTCTCTTTTCTTCTTGGTTGTATATTCTTGCGGATCTTTATAGTGAAT
AATAGTAATAAATTGTTTTGCGCTTCTTACTATGCTAATCATCAGTGCCCCACCCGAAGCGTCAGTCGTA
CAAATTTTGCTCGATGGTTTCGCTGCCCACGAATCGGATGGATGGGGGCCCATGAACAAGGGCACGGG -continued ATTTCCGGGGCTATCTGAAATAGTGACGGGCATGCAAACACACCTAAGGTTCACGGCCTGCTTTTGGTC
GACACAGTGCCACGCGACCGTGCTGGATCTTATCACTGGCCTGTCCGAGGCATCTGAGGATGTCAAGTT
GTCAACCGAGGCGCCTATGTGGGCACGGGACTGATCACTTTCACTCGGGTCACAGCGTTCGGTTCAAG
AGCATTGGGCACAGTCACACACTTCTTCAGGTCTTGGCGCTTCAGCCACAACCCCAAGGATGACGATAG
ATGGGCACAAGACACAGCCGTGCCGGCCACGACAGTTGCACAGATCCCCTCGTCTCGTTTGCAGGTAC
CAGCGAAATTGCTAACGTGCGATGCGACCCGCTGCGAAAACGACGGATCACGTATCAGCGGTCGTTGT
CATATATGATCAGTCGGCCGTGCCTTGGCACTGCACAAGCCAATAAAACTCCGCCAGAACTGAGGAAA
GATGGAACCGTCCAGGAGT SEQ ID NO: 38: *Zea Mays* UPL3 protein sequence:
MECFQRVALSTAANMCRKLPSDASDFVMEAVPLLTNLLNYHDSKVLEHASVCLTRIAESFSPFPEKLDELCSH
GLVAQAASLVSVSNSAGQASLSTSTYTGVIRLLSICASGSPLAAKTLLLLGISGILKDILSGSGLVAGTTVSPALTR
PADQMNEIVKLADELLPSLPVGTISLPVYSGVHMKGCSVKKSTSSKQGEHGSTANELSGREKLLRDQPELLQ
QFGMDLLPTMTQVYGSSVSGPIRHRCLSVIGKLMYYSSAEMIQSLLSTTNISSFLAGILAWKDPQVLIPALQIA
EVLMEKLPEIFLKMFVREGVVHAVESLICPELSGQVTPHVDSITSSHNRRNRRRNNAVNTGNNLPDGPKGS
NSMIANSPPSMAEVPNNSLRALVSNHAKSFKDKYFPSEPGSSDIAVTDDLLKLRALCAKLNTTADTIKTKAKG
KSKVVSDNSFDVLCNIEEQLDDIIAEMLSELSKGDGVSTFEFIGSGVVTALLTYLSCGTFGREKVSEANIPNLRH
QAVRRYKTFISFALPNDKDGNKTPMAFLVHKLQSALSSLERFPVVLSHSGRASTLGGSRLTTGLGSLSQPIKLR
LCRAPGEKSLKDFSSNVVLIDSLASLAAVEDFLWPRVQRTEPVLKPPMSSANNSGSGAASSTACAPSIPSETQ
SVRRTSLRSKSSAATSGAIKKDYQEGSINTSKGKGKAVLKLSLDEPKGPHTRNAARRKATSEKDVELKPSHGHI
TSEDEDLDASPVEIDDALILDDDDEDVPDDEDDDHEAVLRGSLPSCVPERVHDVKLGDADDSSVASLANDN
QAQPSSGSSTKNTSSRGLDTAEFRSPATFGSRGAMSFAAAAMAGLTPVGGRGIRGSRDRNGLPLGARATE
HYNKLIFTAAGKQLNKHLTVYQAVQRQVVHAEDDEDRFGGSDLPDDGNHFWDDIRGDVFTITYQKADNT
AEKGSVGGSASVPKSSKSDSCRTLSEKQCTSLLDSILQGELPCDLEKSNQTYNILSLLHVLEGLNQLSPRLRLQS
ACDDFAEGKVATLNGLYDVGAKVPSKEEINSKMTPKLARQIQDVLALCSGSLPSWCYQLTKACPFLFPFETR
RQYFYSTAFGLSRALHRLQQQPGNDNNTAFEREVRIGRLQRQKVRVSRNRILDSAAKVMEMFSNQKAVLE
VEYFGEVGTGLGPTLEFYTLLSRELQRVDLGLWRSHSSDNSGMQ1DANADDLIRSKNHESESLTESRNIVQSP
LGLFPQPWPPTAAASEGSKFFKVVEYFRLVGRVMAKALQDGRLLDLPLSTAFYKLLLGQELDLYDILSFDTEF
GKTLQELQILVARKQFLDSCSSESQKIDLCFRGAPVEDLYLDFTLPGYPEYVLKEGGENAEVNICNLEEYISLVV
DATVKTGIMRQVEAFKAGFNQVFDISSLQIFSPQELDYLICGRCELWEPETLPEHIKFDHGYTSKSPAIINFLEI
MAEFTPEQQHAFCQFVTGAPRLPPGGLAALNPKLTIVRKHSSVANNNSNATGATESADDDLPSVMTCANY
LKLPPYSTKAIMLKKLLYAINEGQGSFDLS SEQ ID NO: 39: Rice UPL3 genomic sequence > LOC_Os02g01170.1_genomic
GTCCTGTGGGACATTTGGAAAGGAGAGGGTATCTGAGGCAAACCTGCCAAAGCTTCGTCAGCAGGCG
CTTAGGCGATACAAGTCTTTTATATCTGTTGCCCTTTCTATTGACCATGAAAGGAATGAGACTCCTATGG
CTTTTTTGGTCCAAAAACTGCAAAGTGCTTTGTGTTCATTGGAGCGCTTCCCTGTTGTGCTCAGCCAGTC
CAGCAGAATAGGTATTGGAGGCTCCCGTTTGACTTCAGGTTTGAGTGCTCTAGCTCAGCCCTTCAAGTT
GCGCCTTTGTCGAGGTCAGGGTGAAAAATCACTTCGGGATTATTCGTCAAATATTGTGCTTATTGATCC
CTTTGCGAGTCTAGCAGCTGTTGAAGAGTTTCTTTGGCCCAGAGTTCAGCGTAGTGAGGCTGCTTCGAA
GCCTACAGTTCCATCAGGAAATAATTCTGAATCTGGCATACCTGGCACCGCAGCTGGTGCGTCATCCAC
AGCTGCACCAGCTCCATCTGGCAGGCGTCCAACAACAAGATCAAAATCATCTGCTGCAAGTAGTGGTG
CATCTAAGAAGGATTCTCAGGAGGAAAGCACAAACACTGCCAAGGGAAAGGGGAAGGCTGTTGCAAA
ACCAAACTCAGAAGAACCAAAAGGACCTAATACACGGAATGCTACTCGCAGAAAAGCTGCTTCAGAGA
AAGATCTGGAAATGAAGCGAGCACATGGTGACAGCAGCTCTGAGGTATTTCTTTCATTTCTCTGAATGA
ACATGAAAAATTCTAATAGAGATTACGAATGCAGTTGTCAGTTTTATTTAGCTCTATACAAGATTCTAGT
GCATGTTAATTCTATGTTGAGAGGCATATAGACATAATAATTGTCCAACAAGTATTAAATTAAAGATAA
TGTACAATCTCCTTTTTGTATACCAAGATTTGACCTCAGCGCCTTATAAACTACTTCCTCCGTTTCACAAT
GTAAGACTTTCTAGCATTGCCCACATTCATATAGATGTTAATAAATCTAGACATATCTATATGAATGTGA
ACAATGCTAGAAAGTCTTACAATATGAAACGGAGGGAGTACATTTTCATTTTTCTTTTATAATATTTCAT
GTTGGTTTCATAGCAAACCTATGTGGTTTTCCACCTAGCTATTAGTTTGCGCTAGATGTGGCCATTTAAT
TTATAGAGTAAACAAATCATAACAATTCTGTATCTGATACCCATGTTCGACATAGAGTTCAGTCTCCGAT
TGCCATTCCCAACAGAGTTGTATGTGAAACAAGGTATATTATATTTTACTGATGAGGACAATTATTGTTA
AAAAAGATGACTTGAAGTTCCAATGCATTTTTATATGAGAAACTAGCTGTGTGTATGCATACTATCTGCT
AATTATTGGATATGACTTGCATGGACTGGGAGCAATGCAAGTAGTAAATTTGTGTTTTTGTGCATGCAG
GATGAGGAGCTTGACACATCTCCTATTGAAATTGATGACGCTTTAATGATTGATGATGATGACATGTCA
GAGGATGAAGAAGATGATCATGAGGTAATGTTTACCACTTTCCAAAATTTATTGTGCTTCTAATTTTGTA
TTGTTGCAACCTGCACTAATTTGTAGGTTTATATATAAGTTTGTTCACATGGCATTTTAGAGCTAGCTTG
ACCTTATTTAAGTTTCGGCATACACCAATGATAAGCATAAGTTTGGTCTAACCAGCTATCGAGTCTTTTC
GGCTTGATATTCAAATATAAGCTTTTCTTCCACAGAGAAGATGTATTATAAATGAAGTGGGGTGGTGCG
CTTATGCTAGGGCTCACAAGTCACAATGGGATTTTATGCAAACAACATGTTGTGCTTGTTGATATATAA
GCTGTAAGCTTTTATTTGATAGGCCTGCCTGTAAGATCAGCATATTATATCATATGCCAATAAAGCTCTT
AGTTTTTCATTATTACAGATATTATTTGCTCTGGTCTGTAAATAAATAACTGTACTACTATTTATCAGGTT
CTCCAAGATGGCTCTCTTCCTATTTGTGTTCAAGATGGGGTGCATGACGTGAAATTGGGTGACACTGAT
GACTCTAACATTGGTTCAGCAAGTGATAGCCAAGTGCAGCCCTCATCTGGTTCCAGCACTAGGAACATC
ATGAGCAGGGGAGTAGATCCAAATACCTTTGGTTCACGAGGTGCAATGTCATTTGTTGCTGCGACAAT
GGCTGGGCTGGCTTCTGTTGGTGGTCGGGGGGTTAGAGGTAGTCGCGATCGACGTGGCCTGTCACTTG
GAGGTAGCATAAATGAGCACAATAAACTGATATTTATGGCTGGGGGGAAGCAGCTCAGCAAACATCTG
ACTGTGTATCAAGCTCTCCAACGTCAGCTGATGTTTGAAGAGGATGATGATGAGAAGTTTAATGGATCT
GATTTGTCAAATGATGGAAATCGATTTTGGGGTGATGTGTTCACGATAACATACCAGAAGGCTGATAG
CCAGGCTGAGAAGGTATCCCAAGGTGGTTCCACCTCGTTGAACTCAAAATCAGATCCTTCAAGATCTAT
ATCTGAATTGAAAGGTGTTTCTCTCCTTGATAGCATCTTACAGGCAGAACTCCCATGTGATCTAGAGAG
AACAAACTCAACTTACAACATTTTAGCACTATTGCGTGTATTAGAGGGGCTCAATCAGTTGTCCCCTCGT
TTAAGAGTACATGCTGCTTCTGATGATTTTGCTGAGGGAAAAATCACCACACTGGATGAGCTATATAGA
ACTGGAGCCAAGGTACCGTCAGAAGAGTTTGTTAATAGTAAGTTGACACCAAAGCTTGCTCGGCAAAT
GCAGGATGTTCTTGCCCTCTGTAGTGGCAGTTTACCTTCTTGGTGTTACCAGATGACCAAAGCCTGCCCT
TTCTTGTTTCCCTTTGAAACAAGGAGACAGTACTTTTACTCCACAGCATTTGGGTTGTCCCGTGCTTTGA
ATCGACTTCAGCAACAACAGGGTGACAACCAAAATGCTGGTGGCGAAAGGGAGATCCGATTTGGAAG
GCTACAACGTCAAAAAGTTCGTGTTTCCCGTAACCGTATTCTGGATTCTGCTGCTAAAGTTATGGAGAT -continued GTTCTCCAGTCAGAGAGCTGTTCTTGAGGTAGAATACTTTGGTGAAGTTGGAACAGGGCTTGGGCCCA
CTTTGGAGTTCTATACTCTCTTAAGCCATGAACTCCAGAGTGTTCGCCTTGGATTATGGAGATCTAGTTC
TCCATCTGATACGGGAATGCAAATTGATAGGAGCGCAAGTCCCGACGATGACTTGGCAGCCAAAGAAC
TCAGCTCAGATTTACCTGACAATGGCAGCCACTTGATACAAGCTCCCTTTGGATTGTTTCCTCGGCCTTG
GCCACTTACCGTTGATGCTTCAGAAGGCAGTAGATTTTCTAAGGTCATCGAACATTTCCGCTTGGTTGG
GCGAGTGATGGCAAAAGTTTTGCAAGATGGAAGACTTTTAGATTTGCCTCTATCAACAGCACTTTATAA
GCTTATACTTGGACAAGTAAGTGATATACTCTTACTGGATTAATATCAGTTTTTCCTTTTGTTACATTTGT
TTTATTGAAGTTAGTCTGAACAAATGAACTGTATGTGCCAGGAGCTGGACTTATTTGACATAATCTCATT
TGATGCTGAATTCGGAAAGACATTGCAAGAACTGCAAATTCTTGTTGAACGGAAGAGGTTCCTTGAATC
CACTTATGGCATGAATCAGCTAGAAGTCACGGACTTGCGTTTCCGTGGCACTCCTATCGAAGATTTGTG
TTTAGATTTTACTCTTCCAGGTTATCCTGATTATATTCTTAAAGAAGGCGAGGAAAACACAATTGTAAGT
GATGAAACCCATCTTAGTTTTGTGTTTGTCCCAGTGACTAGTGTCTGCATTTGCTCCTTTTTGTGGTAATA
AATAGTATTACTCTGTTTTGCAGGTAAATATTTACAACTTGGAAGAGTATGTTACTTTGGTAGTGGATGC
TACAGTTAAATCAGGGATAATGAGGCAAGTCGAAGCATTTAGATCAGGATTTAACCAGGTGCAACGTC
ATTTTCTCTCTCTTGTAATCATTTTATTAGCTGTTTTTTTTTGTTTACTGTAATTGTTCATGTTTACCTTTCT
GTTTTAGGTCTTTGACATCTCATCCCTGAAAATATTTTCACCTGAAGAGCTTGACTATCTAATATGTGGTC
GCCGAGAAATTTGGGAGGTAATGCTCTCTCTCTCTCTCTCACACACACACACACACACACGCACACAGTT
TTAGTTTGTTACATTTCACTGAATAAACCTGTGCTGCAGCCTGATTCATTGGTGGATAATATAAAATTTG
ATCATGGGTATACTGCTAAAAGTCCTGCAATTGTAAATGTAAGTGCGCTATATGCATTTCAATATCTGAA
TTGGCCTTCTGTAAGTTTAGTTACTTAATTGCTCTACATGTTTGTAGCTACTCGAGATCATGGCTGAATTC
ACCCCAGAGCAACAACATGCATTCTGCCAGTTTGTAACTGGTGCTCCTCGGCTTCCGCCTGGTGGTTTA
GCTGCCCTTAATCCCAAGCTTACTATAGTTAGGAAGGTAACATTCTTGGTATATCTTATTAGCATGTTAT
AACGTATGAATATTGTCGCCTCATTTTGGGTGATATAACTTTGTTGTTGCTTTTGATCATTAGCACCCCTC
AAGTGCGGTGAATACTTCAAATATCGCTGGAGTTACAGAGTCTGCAGATGATGATCTGCCAAGTGTTAT
GACATGTGCTAATTATCTTAAATTGCCTCCATACTCCACAAAAGTACGGTTTCTTTCTCTGGTACATGGT
GAATTTTTCGTTTTCTCTTGTACATGTGCTAATTATCTTAACTGGCTTTATGCTTTTGCTTTTTGCAGGAAG
TGATGCGCAAGAAATTGCTTTATGCGATCCTAGAAGGCCGTGGATCATTTGATCTATCATGAGTTGATG
ATAACTAACATACAGGGCTCACCATTGAATGCCCTATCAATTTTATCCAGAATTAGTTTCTTTGTTGCCCG
TGTGACATAATAGGTTGAGGCTACCAGCCGCTGTGGACAAAGCTTGAAGGACAGAGTCTCCCTTCAGA
CACAGGTGCTGAACTGGAGTATTTCTCATGTTAAATACTCCCATATATATAAGCTGATACATAAATAGAT
AATGTAGTATTGGTTTTTGCAGTGAAATCAAGTTCCATATATGTGGCGTGGGCAGCCTCGCGAGCACCG
AGAAGAGGAGCTCTATCCTTTGCCGTACATGTAAATAAAGAAAAAAAAAGAAGGGGCAATAGTAGTTT
ACATATTTGTCGAAAGAAGGATTGATTCGTTGGTGAAACCCTTTGCTGTGTATCTGGAATGTTATTACTT
TGCTATTATTATGTTGTTAACCATCATGTGTACATGTGTGATCGATAATATCGTACTGTTTTTGTACTAAT
AAATGTGGTGTAGTGCTAGTACATAGACGGTATTGTCTTGCCCCCCCCCCCCCCCCCCCCAAGGAGCGA
AAAGCAAAGATTTTGCTCAAAGACGACATCAGTTAGCTCCGAATCATTTATATAGCTCCGAATCATTTAG
CTCCAAATCATTTATATAGCTCCGAATCATTTATAGTAAATCTAATAGACAATTCATATGTATAATAGTTA
ACTTATGTACTACATCATTAATAATTAGTTCTATTATACACATATAATGGGCTTGTTTGGTTTAATACCAT
CTTATTGCCTTATCCAATAGTACCCAATGTTAGTCACTAATAAAATTTTGGTAGGGCAAAAATTGGTTCC
GAATCAAACAAGCCCAATGTTTCCTTTCTAATCCACACAAATTTGCAGTTCGTTCTCTTCTTTCTTATCTAC
TTAAAAGCCATAATTTACTTTGCAAGAACTACCTCCCCAGTATGTGGCATGTGAAATGTTCAAATCAGTT
TCAACTCTATTTGCTACTACAGTAGTATCTTGCAACACATTCCTACTAGTGTATTTATTTTCGTTTATAGTT
TCCAGAAGCTATGTCCTCTTTGATTCAAAGGAAAGTTAAAGTAATTTTTGGAGGAATTCATTCCTATGGG
ATTTTTCCCCTAGATGATCCTTTTTCAAAGGAATGAATAAAATTGAATCCTATGAAATCTTATGGAATAC
TCATGCCATACAAGTTTTGGAGGAAATTTAACATGAGGTAAAACCTCATGGAAACTTTCCTTTAAATCTT
TCTCTCTTCTGTAATTCTTGTATTTTTTTATACGGTCGAAACAAACGGTCGTTCCTATGTTTCGTAATCCTA
CGATTTAAAG SEQ ID NO: 40: Rice UPL3 protein sequence > LOC_Os02g01170.1 protein
MKRAHGDSSSEDEELDTSPIEIDDALMIDDDDMSEDEEDDHEVLQDGSLPICVQDGVHDVKLGDTDDSNI
GSASDSQVQPSSGSSTRNIMSRGVDPNTFGSRGAMSFVAATMAGLASVGGRGVRGSRDRRGLSLGGSINE
HNKLIFMAGGKQLSKHLTVYQALQRQLMFEEDDDEKFNGSDLSNDGNRFWGDVFTITYQKADSQAEKVS
QGGSTSLNSKSDPSRSISELKGVSLLDSILQAELPCDLERTNSTYNILALLRVLEGLNQLSPRLRVHAASDDFAE
GKITTLDELYRTGAKVPSEEFVNSKLTPKLARQMQDVLALCSGSLPSWCYQMTKACPFLFPFETRRQYFYSTA
FGLSRALNRLQQQQGDNQNAGGEREIRFGRLQRQKVRVSRNRILDSAAKVMEMFSSQRAVLEVEYFGEV
GTGLGPTLEFYTLLSHELQSVRLGLWRSSSPSDTGMQIDRSASPDDDLAAKELSSDLPDNGSHLIQAPFGLFP
RPWPLTVDASEGSRFSKVIEHFRLVGRVMAKVLQDGRLLDLPLSTALYKLILGQELDLFDIISFDAEFGKTLQEL
QILVERKRFLESTYGMNQLEVTDLRFRGTPIEDLCLDFTLPGYPDYILKEGEENTIVNIYNLEEYVTLVVDATVK
SGIMRQVEAFRSGFNQVFDISSLKIFSPEELDYLICGRREIWEPDSLVDNIKFDHGYTAKSPAIVNLLEIMAEFT
PEQQHAFCQFVTGAPRLPPGGLAALNPKLTIVRKHPSSAVNTSNIAGVTESADDDLPSVMTCANYLKLPPYS
TKEVMRKKLLYAILEGRGSFDLS SEQ ID NO: 41: Barley UPL3 genomic sequence > HORVU2Hr1G011040.15_genomic
TTGTTGGTTTTTGGTTTATGTGTTCCTTACCTTAACTGTGCTATCTTACTNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNCGCGGATGAAGAGCATGCTCGCGGGCCTCCGCGCCGACGGGGAGGAGGGCCGCCAGGTGGA -continued GGCGCTGACGCAGCTCGGCGAGATGCTGTCCATTGGCACCGAGGACACCCTCGCCGGCTTCTCGGTTG
ACTCCTTCGTGCCTGTTCTGGTCGGGCTGCTCAACCATGAGAGCAACCCCGACATCATGCTGCTCGCAG
CCCGGGCCCTGACCCACCTCTGCGACGTGCTCCCGTCATCCTGCTCCGCCGTTGTGCACTATGGTGCAG
TGGCATGCTTCTGCGCCCGGCTTCTCACCATTGAGTACATGGACCTTGCGGAGCAGGTGAGCACTGTTC
TGTTGCATCGTTTGTTCTGTTTATAGTATATGCTGCTTCTATATCATGTTGCCTGATCCAGATCAATGCTT
ATTGAACCATTTTTTTTACTGTATTATGCATGATTATGCCTTAACCCACGGTAGATGAGTTTCCTTCAAGT
GTTGCAGCTCATTTGTAATATTTGGACTTGCTGGTGAGTAGTGTGCCTTTTGTGTAGCTGTGTTTTTTCT
CTCCCCATTTTAGTTCTAAAATGAATATGGGTGAGAAGGTTAAATACTTCCTAGTTCAGTACCTCACCAT
TTAACGATATTACAAGAAATATCTAGAGGGTTAGGCTGAAGGTGAATCCTTAGCAGCCTAGGGTCCTG
CCTAGGATCTAGTCACTGCCCGCTCTGGGAGGGAAGAAGCTAAGGATAGGAGACACATGAAAGAAAA
AATGGTTGGATGAAAAAAGGCCTGATAGTCACCTCAAGGATGTTGGCTGAAGCCTTAGGGAGCTTGTC
GGCATGGAGAGGTCTTCCCTTCCTCTGCTGCCGCAGGAGGACTCGGACTCCAAATCCTCACCAGCGAAC
TCAAATCCATCTAAGGACCTCATCGGCCCCTTAGAAGACTTTCTAGGCCTGATCATGGTGTCCTCCTGCC
GAGCACATAGGTGCTGTTTAACACGGTTTTGCTGTGCCAGATCACCTATTGCTGCATGACTAAGCTAGC
TATTTGAACATGTTTTTCATCTGTAATATTCAGGGTCTAATATCATGCCTGTGTATGTGGTACTGTAACG
ATCCATCTGAAATACTAAGAAGTGGGTTGGAAATCAGATGCTAAGATTCATGTATCCGGTTTCTGGCTG
TGTTTTCTCTCTGCCTTCCTATCTTATGGATATTATACTTCTACTTTTCTTGGGTCTAATTCAAAACAATGT
GAATTAACTTGATATCATCAGTTTGAATTCCTTTGTAACCATTTGTGCTATTGAATCTAATTTGCCGCTCC
GAATATGTTATTGAGTAGTATCTACCACTATCAGCTTTATCACCTAGGACACTTGAATTACTTTGTTAGAT
TTTGGTATTTTATTGCTTCTGTGGCACTTTAGATTAGCCATTTTCCTTATTTTGTGCTGTCGTTTAAAATAT
GCTGCACAAAGAATCTGTCATTGCTAGGATTTGCATATTTGTATGAATGGTCTTGATGTGGTGCTAACA
TTTCTTATGCCTTTTCTGGGTATTTTAGTCATTGCAAGCACTTAAGAAGATATCCCAGGAGCATCCAACT
GCCTGCTTGAGGGCTGGCGCGCTAATGGCAGTGCTATCATATCTTGACTTCTTCTCCACCGGTGTTCAA
GTAATTTTGCTAAATACTTTTATGTTTTGCCAGCATTTAGACGTAACATTCTCAATACGAACTTATTCTTTT
TGCAGCATTTAGAACTTGGGACATAATAATTTGTCATATCACTTTATCTTTTTGTTGTACACATGTACTAC
ATTTTTATTATTACTCACAGTTGTTTTTTTGGTTAAATGTATACAGAGAGTTGCGTTATCTACAGCCGCTA
ATATATGTAGGAAGCTTCCTTCAGATGCCTCAGATTTTGTAATGGAAGCGGTTCCACTGCTAACAAATCT
TCTGAACTACCATGACGCAAAAGTATGCTTGTTGTTTGTATTTGGATACCCTTATCATGCCATGATATCA
TCTATTCTTAGATGCTGTTGTTCTGTATCGATTTATTTCAGGTGCTGGAACATGCTTCCGTTTGCCTGACT
CGTATAGCAGAATCATTTGCTTCATCTTCAGAGAAACTGGATCAGTTGTGCAATCATGGATTGGTTGCA
CAAGCTGCTAGCTTAATAGCTGTTAGCAACTCAGCGGGACAAGCATCACTGAGTACATTAACATACACA
GTATGCTTCTATTTCACTTTGTATTGCTACTACTGTAGTATTTACGCAAATTTGCTAACTCTGGCTCATAT
ATCCTTGAAGGGAGTAATTCGTGTTCTGTCAATATGTGCAAGTGGATCTCCATTGGCAGCTAAAACGCT
CCTCCTCCATGGAATTAGCGGCACACTCAAAGATATCCTTTCAGGTTCTGGTTTGGTTGCTGGTACAACT
GTATCCCCCACTAGGCCAGCTGATCAGGTGATTATTATTGCTTTATGAAGGCTATATCGAGCTAGATTAT
AGCTACTTACCGTTTTATTTGAATGCCATCGGTTGATGACTCTGTTCGGTTGTTGTTTTATCTGACTTAGC
TGATGAAGCTTTTTGAGTGATATTTTGTTTTTCAGTTTTAGATTCACTCAAGTGTGCATACAATTCAGTTT
TGTTTGGCAAACTGAAATTAATATCACACAACAGAAATTTCAAAATTTGGAAGAAAGTTGCATGCTAGA
TACTTATTCTGTGGTTTGTGTAGTCCAGTAAAAATTTAAATGTTTGTAAGAAAGTTCAGAACATGTATTG
TGAACAGTATATAATAATTTGCCAAACGTTTCCCGTGCTCCTGGTCTTTGTGCGGTGCTGCAAGCTATAA
CAGTGAGCAAACAATGTGGTAGATAGAATTAGGGATTTGACTTGAACTCTCTGTTTAACTGCTCATAGA
CCTCTCTGTTGTCTACCTGATTTTCTCCTTCCAGTCGTAATATGAAATTCACAATGATGTTATTGACTTTG
ATCAAGGTTTAGAGATGCGCTAGACTGGCGGTAGGTGACCCACATAGATGGCGCTCTGCCACTGTTTG
TTAACCTTAATAATCTTGACATCATACCTATATTACTTGTTCCATTTTCTTTTTAAATCAAAGCCAAGAGTT
TCTTATAGTAGTTCTATGGTAATTTGCAGCTTGTTTTCATATGCTAATATTCTTTGTTGTGTCACACAGAT
GTATGAAATTGTGAACCTCGCCAACGAATTGCTTCCTCCTCTACCTGCTGGAACCATTTCTTTACCAGCG
CATTCCCATGTTTTTATGAAAGGCTCTTCTGTAAAGAAACCTGGTTCTAGCAAGCAAGGCGAGTCTGGT
TCAACAGATATTAAAGTCTCAGGCCGGGAGAAGTTACTGCATGATCAGCCTGAACTTCTCCAGCAATTT
GGCATGGATATATTGCCTACCATGACACAGGTCAGTCCCTTGGTTTGCTGATGTATCAGTTGATGTTGA
TTGCTGATGATAAACATTATTGAAATACTGTTATCTGATACATTGTTTGGATACGCTCTATCCCTTGCAG
GTGTATGGCTCCAGTGTAAATGGACCAATACGTCATAAATGCTTATCTGTTATTGCTAAATTAATGTATT
ACAGCTCAGCGGAAATGATTGAAATTCTCCATGGCACAACAAACATATCCAGGTGCTAATACGAAACTT
CAGATGCCATTCCGGCTTACTGTTGTACATATACTTGTGTACCTCTGGTTCCATCTAACCTGATATTCACC
TTTGCAGCTTCTTAGCTGGCATCTTAGCTTGGAAAGATCCACATGTGTTGGTTCCTGCTCTTCAGATAGC
TGAAATTCTGATGGAAAAGCTCCCTGGAACATTTTCGAAGATGTTTGTGAGGGAAGGTGTTGTTCATGC
TGTAGAGTCGCTTATATGCCAGGAAATCTCAAGTCCAATGCTTTTTCAAGTACCACCACAGGATAAGGA
TATTGATTCTGGTACATGTACATCTTCACGTTCAAGACGCAGCCGCCGACGCAGCAGTGCTGGGAATAC
TGATAATAATTCCTTGGATGAACCAAAGAGTTCCCATACTACTATTGCCAATTCACTACCAAGCACGCTA
GAAAGTCCAAATACTAGTATTCGTGCTTCAGTTAGTGATCGCGCAAAGTTATTCAAAGATAAGTACTTC
CCCTCTGAACCCGGCTCAAGTGATATTGCAGTTACTGATGACCTTTTGAAGCTACGGGCACTCTGTGCA
AAATTAAATGCCACTGCAGACACTGTTAAAACAAAAGCTAAAGGGAAATCAAAGTCACTGGGAGGTGA
TGATTTTGATATCTTATGCAATGTTGAGGAACAGTTAGACGACATCATAGCTAAAATATTGTCTGAACTT
AGCAATGGGGATGGGGTTTCCACGTTTGAGTTTATTGGGAGTGGAGTTATCTCAGCGTTGCTTAATTAT
TTGTCCTGTGGAACCTTTGGAAAGGAAAAGGTGTCCGAAGCAAACCTACCCAAGTTGCGTCACCTGGC
ACTCAGGCGATATAAAACATTTATATATGTTGCCCTTCCAAATGATGCGGCAGGGAATCAAACTCCAAT
GGCATTCTTAGTTCAAAAACTGCAAAGTGCGCTGTCTTCACTGGAACGGTTCCCTGTTGTGATTAGCCAT
TCTGGAAGGACGTCCAGTTTGGGAGGATCTCGTCCATCCTCTGGATTAAGTGCTCTATCCCAGCCCCTG
AAGCTGCGCCTGTGTCGAGCACCGGGTGAAAAGACACTCAAGGATTATTCATCCAATATAGTTCTTATT
GATCCCTTGGCAAGTCTAGCAGCAGTTGAAGATTTCCTTTGGCCTAGAATCCAGCGTAGCGAGTCAATA
TCTTATCCTGCAGTGTCATCTGGAAAGAATTCTGAATCTGGGGTGCCTAGTGCAACAGCACCAGTGGCT
TCGTCAACTCAATCTGTTCGGCGGCCCTCGACTAGGTCGAAATCATTGGCTGATGCTGATTCTGCAACTA
AGAAGGATATTCAGGAGGGGAGTGGAAACACATCCAAGGGAAAAGGCAAAGCTGTTGTTAAATCGAC
GTCGGATGAACCAAAAGGACCACATACTAGGACTGCAGCACGCAGAAAAGTTGCTTTAGAGAAAGAC
GCAGAAGTGAAGCCAGCGCACGGTCACAGTAGCTCAGAGGTTTGTTGTTCATTATGGACTCATTTCCTT
AATAATCTATAGAATATATATTTCCTCTAGTACGTCTTGAATTTTTGCTAGTTCCCCAAAATTTGATGAAG
ATGCTTGACTACATATGCTTTGTTTGGTAGTGCCTCTCCACAGTTACTCAGCTGCCAAGCTGATTTTCGTT
ATACAACTGTCCTACTGTTTTCGTCGACGTTTCATGATTATATCTGCCCTCCTTCATTAGTAATTTGATGT
GCATCTGTTAAGGGAAATATACATGATTAATACCATTATGAAATTATTATTTAACACAAATTTCATTGTG
AAACCAATGTGTGAATTTCATAAAATTAGATCTACAGACTACAATGCCTTTTGACCTGCAGTTTGATATG -continued GCATCTAGGGGGCACATATTGTCTCGCCATGTCTACAATGCTTTGGTAGATGAAGACATTGTCTAACTA
AAATCAATGGTTTAGGTAAAGGTTGGTGCTCCCACTATCTCGACCATTGAATGTGCCTAAATGTTGTTGC
AGTTCCTCATCCTATGCAATAAATGTATGTTGAGAGAGTGGCGCGGACCTGAAGCAGTAATGGCACATT
CCATAGTTGAGAACCTGTGATAGTGGGAGTATATCCACCAATGCGATTCATTTCGCTGTTGAAAGTTTG
GATCGTGATTGCCCGAATGCAATACTGCTTTTCTTGCTTATAACTGACTAACTGAGTGATAAATATATAA
ATTAAGTTGTCAGTTTAATTATATCTATACCAGGACTCACCTGTACATAACTACAACAAAGTAGATCACT
TATGCGTTGGAAACTGGACTACTATTTTAGTAATTCCCTTATCCCTGAACAAAGTTCTGATCCAATTCTTG
TACACTATGTCATGTGAATATTGAACTTTATTATTGTATTTATGTTCGTTGTGCATGATACATTCTGTTTTC
TACATGCAGGACGAAGAACTGGGTGCATCTCCCTTCGAGGCTGATGATGCTTTGATGCTTGGTGATGA
CGATGATGATGTCTCAGATGATGAAGATNAGATGATGATGATCATGAGGTAGTATTTCAAAGTTTCTTC
GATTGATCTCTTTGTTTTTCTTCAAGTTAGCGTGGCTTTAGTGGGCATGACTGAAAACTACATATTTTTGT
TGAAAATCTTCAGGTTCTACGTGGGTCTCTTCCTGACTGTGTCCCAGAGAGAGTGCATGATGTAAAACT
AGCAGATGCTGATGGTGGATCTAGTATTGCCTCGATAGCAAATGATAACCAGACACAACCCTCATCTGG
CTCCAGCATAAAAAATACTTTTAGTAGCAGGGGAGCAGGTTCTGTTGAACTTAGAACTCCAAGCACACT
TGGTTCTCGGGGCGCAATGTCGTTTGCTGCAGCTGCCATGGCTGGGCTTGCTTCTGTTGGTAGTCGTGG
TGTCAGAGGTAGCCAGGATAGGCGTGGCCTTCCACTTGGAACTAGTGCACATGAGCATTCCAACAAAT
TGATATTTACAGCTGGCGGCAAGCAGCTTAGCAAGCATTTGACTGTATATCAAGCTATGCAACAGCAAG
TAGTTCATGATGAGGATGATGAGGAAAGGTTGGGTGGTTCTGATTTACCCAATGATGGAAGCCGTCTC
TGGAGTGATATGTTCACTATAACATATCAAAAGGCTGATAATGAAGTGGATAGGGAATCAACCAGAGG
TTCATCTTTAGTGCTGAAATCGTCCAAATCAGATTTTTGCCGAGCTACATCTCAAGAACAATGCATTTCTC
TTCTTGATAGCATTTTGCAAGGAGAACTTCCTTGTGATATTGAGAAATCGACCCAAACTTACAATATCTT
AGCACTGTTGCGTGTATTGGAGGGATTAAATCAGCTATCTCCTCGTCTGAGACTACAGGCAACCTGTG A
TGATTTTATAGAGGGAAAAGTTGGTACCCTGGATGGGTTATATGGCACCGGAGCTAAGGTACCCTCAG
AGGAGTTTATCAGCAGTAAGTTGACACCAAAGCTTGCTCGGCAAATTCAGGATGTTCTTGCACTCTGTA
GTGGTAGTTTACCTTCTTGGTGTTATCAGATGACCAAAGCTTGCCCATTTCTGTTCCCTTTTGAAACAAG
AAGACAGCACTTCTACTCCACAGCTTTTGGGTTATCTAGGGCATTGAACCGTCTTCAGCAACAACAGGG
GGATAATAATAACTCTGCGACTGAAAGAGAAGTCCGGATTGGTAGATTGCAACGTCAGAAAGTTCGTG
TTTCTCGTAACCGGATCCTGGATTCTGCTGCCAAAGTAATGGAGATGTTCTCCAATCAGAAGGCTGTTCT
TGAAGTTGAATACTTTGGTGAAGTTGGAACTGGACTTGGTCCAACTTTGGAATTCTATACCCTCTTAAGT
CATGACCTGCAAAGGATTGGCTTAGGATTATGGAGATCTGATTCTGATTCTTTAGAAGCTAAAAAACAT
GATTCGATTTCACCTGCTGATAGCAGGAACTTGATACAAGCACCTCTTGGCTTGTTCCCTCGGCCTTGGC
CACCTAGTACTGCTTCTTCAGAGGGTAGTAAATTCTTCAAAGTTGTTGAGTATTTCCGCTTGGTTGGTCG
AATCATGGCAAAAGCATTGCAAGATGGAAGGCTTCTTGACTTGCCTTTGTCAACAGCATTTTATAAGCTT
CTACTTGGACAAGTAAGCATGAGAACCTGCTTGCAGTAGATCCATTCCAATAACCCCTTCCACCTTTTTG
TCAAGTCGTGGTGTTTTTTTTATTTTATCTACTGTCTTCTGTATTGACGCCATAATATTTTGCTTTGCTAGG
AACTTGATTTGTATGACATACTATCTTTTGATGCCGAGTTCGGTAAAATACTGCAAGAGTTGCAAGTTCT
TGTTGAGCGCAAGCGATTTCTGGAGTCCTGCTCTAATTATAGTCAACAAATAGAAGATTTGAGCTTCCG
TGGTGCTCCTATTGAAGACCTATGCTTAGATTTTACTCTTCCGGGCTATCCGGATTTTGTTCTGAAGGAA
GGTGAAGAAAATACAGTGGTATGTGATGGAGTAGATTAGGTTCTTGTGTTGTCATTACTTCAGCTTTTG
CTTCTAACTATTCATTGTTATTTTAACTTCCTGTAGGTCTGCATTTACAACTTAGAAGAGTACATTTCGTT
GGTAGTGGAGGCTACACTAAAGACTGGAATAATACGTCAAGTAGAAGCATTCAAAGCTGGATTTAATC
AGGTTTTCTCATTTTTCTAAGATACTTCTCATTGATATTTAGCTTTGCATTTCTCTTAAAACATTTTTATTTT
TCTAATTCAGGTATTTGACATATCATCACTACAAATATTTTCTCCTCAAGAGCTTGACTATCTCATTTGTG
GTCGACGGGAACTTTGGGAGGTAATGCCCTCTTAACTTTCTTTCTCCCTTCTATAATTAGTATCTTAACTT
GGTTCTGAGCAAATGCATGTAATGCAGCCGGAGACACTGGTCGAGCATATAAAGTTTGATCATGGTTA
TACCTCGAAGAGTCCAGCAATTGTCAATGTGAGTACATCCCTTATCTTTTAAAGAAGGCACATATCTTCA
CACAGCTTTTATTTCAGAACTTTGGAACTTCGGTTTAATGTTTGTGCTGTTGGTTTGCAGCTACTTGAGA
TCATGACGGAATTTACTCCGGAGCAACAACATGCTTTCTGCCAGTTTGTGACTGGTGCTCCTCGGCTTCC
ACCTGGTGGCTTAGCCTCCCTAAATCCGAAGCTGACTATCGTTAGGAAGGTAAGCCTGTTGTAGCAATG
CAGAATGACATCGTTTCTGTGTTCATGTTATTTAAGCTTTTGCATTTTGTATCTTGGCCAGCACTCCTCGA
CTGCGACGAATACTTCAAATGCAGCTGGAGCAGCAGAGTCTGCTGATGATGATCTGCCTAGCGTCATG
ACTTGTGCCAACTATCTTAAACTTCCGCCATACTCGACAAAGGTTTGGTTCTTTTGCTCGATGAATCTTTG
TTCTACCTTTTGGCATTGTCTTGCCTGGAAACTGACTTCTGCTATGGTTGTCGGGACGTTATTACAGGAA
GTTATGCACAAGAAGCTGCTTTATGCTATCAACGAAGGCCAGGGGTCGTTTGATCTTTCATAGTGGGTT
CAAAACTAACATACAGATGTTGGTGCACATGTAAATGCGCACCAGTTTTTATTCAGTTAGTTTGTTCATT
GTCGTCATGTATAACATAGGCTTTAAGTCGTTTCTTTTGTGAAAGGTTTAGAGCCTGGATCTTGTGGTGC
CAGTGCTTATAACATTCTCTCTTCATTCCTGGGCACTTGTATATATTCTCCAACTGATCTCTATAGTGACT
AAGAAGACATTCCTCTTTTGGTAGTCAGTTATATACTTCATCATCATACTCTCGTCTATTTTGAGTGACTT
GCGCTCGTGATTATTAGGTTGCTCTAATGAAAGCGATATCCTCAGTTCTTACTGTGCAATTAGTGCACAT
CTTTTGAATAACTAAATGCCTAGTGCCCTTACAATACGGGGCACATGTAATAATTCCTGCCAATTAGTCT
GCCTTTGTAGTACGAATTAAACCATTGGTGTGAACTCTCTAAAAAACGGTTATATTTGGTGAGTGGGGA
ATGGACAAAATATGAACATTTGAAATGTTGCTTGGATTTCAAATTGTGCCAATAGGAAAATTGTAACAC
CAAAGGGAGGACTTTTGTTATCTAGTGTGGTTGATTTGATTAGACAAACAATGTGGCCGTTCAATGTAT
TCTAATTCCACTATCACAACATGACATGCCAGATTTCATTGCTTGGAGCTATATGTAGAATGGTATGTTT
TCGGTCCGGTTTGCTTAATCTGTAGAGTGGGACCATTAGTATGAAATTAAACTGTGACATTTAATGGAA
TGGGACGAACTATGGCTAACCCTCTCTGGAGTAAGTTATGGAGGTTACCTTGCTCGGTAAATGTTAATA
TTTTTAACTCACGGACGTTACATGACACCCTTGTTGTGTAACGCTTGCAAACAAACATATGAAAATGTCA
CCAATTTGTCCCAAGATATAAAGCAT SEQ ID NO: 42: Barley UPL3 protein sequence > HORVU2Hr1G011040.15 protein
LRGSLPDCVPERVHDVKLADADGGSSIASIANDNQTQPSSGSSIKNTFSSRGAGSVELRTPSTLGSRGAMSF
AAAAMAGLASVGSRGVRGSQDRRGLPLGTSAHEHSNKLIFTAGGKQLSKHLTVYQAMQQQVVHDEDDEE
RLGGSDLPNDGSRLWSDMFTITYQKADNEVDRESTRGSSLVLKSSKSDFCRATSQEQCISLLDSILQGELPCDI
EKSTQTYNILALLRVLEGLNQLSPRLRLQATCDDFIEGKVGTLDGLYGTGAKVPSEEFISSKLTPKLARQIQDVL
ALCSGSLPSWCYQMTKACPFLFPFETRRQHFYSTAFGLSRALNRLQQQQGDNNNSATEREVRIGRLQRQK
VRVSRNRILDSAAKVMEMFSNQKAVLEVEYFGEVGTGLGPTLEFYTLLSHDLQRIGLGLWRSDSDSLEAKKH
DSISPADSRNLIQAPLGLFPRPWPPSTASSEGSKFFKVVEYFRLVGRIMAKALQDGRLLDLPLSTAFYKLLLGQ
ELDLYDILSFDAEFGKILQELQVLVERKRFLESCSNYSQQIEDLSFRGAPIEDLCLDFTLPGYPDFVLKEGEENTV
VCIYNLEEYISLVVEATLKTGIIRQVEAFKAGFNQRYLTYHHYKYFLLKSLTISFVVDGNFGSRRHWSSI -continued SEQ ID NO: 43: Cotton UPL3 genomic sequence > Gorai.008G035900 genomic
TAAAAAGCTTCACCCTTTTTATTTATTTATTCATTTTCACTTTAGGGTTTCAAGTTTCTCTCTTAACCTTCAT
CTCTTTAGGGCTCAAATTCTCCCCTAATTAATCATTGAATTCTATTTCATTCAAAACCAAGACAAAGGCGT
GGTTTCCCTGATTGTAAATTCTAGGGTTTTACATTTATCCGAAGCGTGGATTCCTTTGTTTTCGTTTTCTA
GGGTTTCGATAAGCTGTTGTTGAGATGCAACAAATAATCGGATCAGGAATCGTCTGATCTTGTGGTGGT
GACCGTCCGATAATCAGGGGCGTTGGTCCCCTTTGTATGGAAACTCGGAGCCGGAAGCGGGCGGAGG
CCTCCTCAGCTGCCCCTTCATCTTCTCCCTCCGGTCCCACCACTCGCTCTCATAAACGCGTTCGTCTCTCTT
CCTCCTCTGCCGCTGCCGCCGCCACCGTCGCTGTTACTCGCTCCCGTACTTCCCGCACATCACGTACTTCC
GCTGCCTTAATGGACCCCACTACAATCGAATCTTCTTCCGGTTCCCGCCGTGATCGCCGTTCCAGCAAAG
CTAACCAAACCACAACAAGTGACAATCCGAATCTTGCCTCTGATAGAGGAAAGGAAAAGGAACATGAT
CCTAGGATTCGCGATAGAGATAGAGACAGGGATAATAGAGACAACAATTCTAATCATCCTGAGAGAAA
TTTAGGATTAAATATGGACACCTCTGGAGGCGATGAGGATGATAATGATAGCGAAGGCGGTGTAGGG
ATTTTGCACCAGAATCTGACGTCAGCAAGCAGCGCGTTACAAGGCTTGTTGAGGAAGCTCGGTGCCGG
ACTTGATGATTTGCTTCCCTCATCGGCAATGGGTTCCGGGTCTTCATCTCATCAAAGTGGGAGGTTAAA
GAAGGTTCTGTCTGGATTGCGTGCTGATGGAGAGGAAGGGAGGCAAGTGGAGGCGCTGACCCAGCTG
TGTGAAATGCTTTCAATTGGTACTGAGGAATCGTTGAGCACGTTTTCTGTTGATTCCTTTGTTCCCGTGC
TCGTTGGATTGCTTAATCACGAGAGTAATCCTGATATCATGATACTTGCTGCAAGGGCGCTTACTCATTT
GTGTGATGTGTTGCCTTCTTCATGTGCTGCTGTTGTGCATTATGGTGCTGTTTCATGTTTTTGTGCTAGGT
TGCTCACTATAGAGTATATGGACTTGGCTGAACAGGTTGGCATTTTCGTTGCTTCCTAAATAATTGATTG
TTAGAAAATGAAATTGATCAAATATGTGGTTAAACTTAAACACCCTTGAGCTGATTGAGCGACATCTTG
CATTTCATTATGAACTATGGTGAACTGCAACTAGCTAATTCTACTAGAAGTTGGCCCCCCAACTGATAAA
CAGGGGATAGTTGAGCATTTTCCTGAAAGCCTATTTGACTTAAAATTTGCTTGTTTCTAACTAACTGTTA
AAAATTAATGTTGTGGGTATTCTTTATTGTTCTTAGTTATGGACTTGAATTAGAAAGTTGAAAACTGTAG
ATTTGCTCCCCTCCACTTTCTTATCTTTCTGGTTGAATTGCTGCAACAGTCTCTGCAAGCTCTGAAGAAGA
TATCTCAAGAACACCCAACTGCTTGTCTGCGAGCTGGTGCTCTCATGGCAGTGCTTTCATACTTGGATTT
CTTCTCCACTGGGGTTCAGGTGATTTAATTTGTGAACATTTTGAGTGTTAATCAGCATCTATGGAGTGGA
GAATTTTCTTGCTATTTAGATTCTTATTGTGTTTGTTTCCTATATTTGATCCCATATTCCAGCGAGTGGCA
CTATCTACTGCTGCAAATATGTGTAAGAAACTCCCTTCAGATGCAGCTGATTATGTCATGGAAGCTGTAC
CACTATTAACAAATCTTTTGCAGTATCATGATTCGAAGGTAACGTGAACATCATATTAGTGATGAGTCAT
TTGTGGTCAATTATGTTTCATCCTGAACACTTAGCTATCTTTCTAGGTGCTGGAGCATGCATCTGTTTGTT
TAACGCGCATTGCTGAAGCCTTTGCATCTTCCCCGGATAAATTAGATGAGCTTTGCAATTATGGACTGGT
TACTCAGGCTGCATCTCTCATTTCCATAAGTAATTCTGGAGGTGGACAGGCATCATTGAGTACACCAAC
ATATACGGTGAATTGATGGTGCTCCTTTGTTTATCTATTTGAATGCATTTTATGTACCATTTCATGACATT
TGGGTTTTTGAATTCAGGGCTTAATTCGGCTGCTCTCAACTTGTGCAAGTGGGTCTCCCTTGGGAGCAA
AAACTTTACTTCTGCTTGGGATCAGTGGCATACTTAAAGATATACTATCAGGTTCTGGTGTTTCGGCTAA
CTCATCTGTTTCACCAGCCTTAAGCAGACCGGCAGAGCAGGTAACAATTTTAATTCAAGCTGAAGAGTT
GGTAGTTATTATTGCTAGCTGTTTATTTAACTGTTTTACATGTGTGCGATGCTATATTAATACAAGTGGA
GCTGAGGAAATGGTATAACCTTTAAAGACAAAGTATCAACTCCAAGCTTTACTATCAATTTTGTGAACAT
TGCATGTCAGTTGTTTTTGTTTTGTGGTATCTTTTTTAGTTAAGGCTGAAGAGATTGTAGTCTTCATTG
CATGTTGTTTATATATACCTGTGTACATATGATACGTGTAAGGTTTGAATGTTATATTATTACTAGCAGT
GAGGAAAATGGTATAAATGTTAAGACACAAAGTTTAACCCTTTTTATTTGGTTAAAAGTTACTTGTTTTC
AATACTTCTATTTATTTCTTGCACTTTATACAGTCTATATTGACATACTAAATTAGTAATAGCTTATGCAT
GTAAGCCATATTTGTCTGATGGGTCTTGTAATTCTTATATGATTGTGTAGATTTTTGAGATTGTCAATCT
GGCAAATGAGCTTCTTCCTCCATTGCCACAAGGAACCATCTCCCTCCCTGCTAGCTCTAATATATTTGTG
AAAGGATCTATTTTGAAGAGGTCTCCTACTAGCAGCTCTGGGAAGCAAGAAGACACCAATCGAAATGC
TCTTGAGGTTTCACCCCGTGAGAAATTATTGAATGATCAACCTGAACTTCTTCAGCAGTTTGGAGTGGAT
CTCCTTCCTGTTCTCATTCAGGTAGCCTTTTCTTTGCAGATGGTAGTTTGGTTATCTCTTGGTTGTTGGTA
TTGTCTCTTATCTTTTATGGTATTTTCTTTTGTGTGTAGTATTATATAATTCCTTATCTTTTGTCTATCAGA
TCTATGGTTCCAGTGTCAATAGCCCTGTTCGCCACAAGTGTCTCTCAGTTATTGGAAAACTAATGTACTT
CAGCAGTGCAGAGATGATTCAGAATCTATTAAGTGTGACAAATATATCTAGGTATCCACCTTAAGTAAA
ATAGAGTCGTTAACATATTCATTGAATGATTGGTTATAGTGACTTATTATTTTGTTTGATCTTATAGCTTC
TTGGCTGGTGTTTTAGCATGGAAAGATCCATATGTCTTGGTTCCTTCCCTGCAAATTGCTGAGATCCTCA
TGGAAAAGCTTCCTGGAACTTTCTCCAAAATGTTTGTTCGAGAGGGCGTGGTTCATGCTGTGGACCAGC
TTGTTTTAATTGGTAATCAAAATACCACTCCTGTTCAAGCATCTTCACTTGAGAAAGATAATGAGTCTGT
ATCTGGAGCTTCATCACGTTCTAGGCGATATAGACGACGTAGTGGTAACTCTAATCTTGAAGGAAGTTC
TATGGAGGAGTCCAAGAATCCAGCATCTTTAAATATTGGCTCACCTACTAATTCAGTCGAAATTCCTACA
GCCAATTCCAATCTTCGTACTGCAGTAAGTGCATGTGCTAAAGCATTTAAAGATAAGTATTTCCCCTCTG
ATCCTGGGGCTGTTGAAGTTGGAGTAACAGATGATCTGTTACACTTAAAAAATCTTTGCATGAAATTGA
ATGCTGCTGTTAATGATCAAAAGACCAAGGCAAAAGGAAAATCTAAAGCTTCGGGGTCTCCATGGGTT
GATTTTTCTACTAGCAATGAAGAGTATTTGACTGGGGTGATTTCTGAGATGCTAGCAGAACTAAGCAAG
GGGGATGGTGTATCCACTTTTGAGTTTATTGGTAGTGGTGTTGTTGTGGCCTTGTTAAACTATTTTTCTT
GCGGGTACTTCTCCCAGGAGAGAATTTCAGATGTGAACCTGCCCAAGCTTCGTCAACAAGCCCTTAAGA
GATACAAATCATTTATCAGTGTTGCCCTTCCTTCTAGTGTTGATGAAGGAAGTATGGCTCCTATGACTGT
CCTGGTTCAGAAGCTTCAAAATGCTTTATCATCTTTAGAGCGTTTTCCTGTAGTTCTTAGCCATTCATCTA
GGTCATCTAGTGGGAGTGCACGCCTCTCTTCTGGTTTAGGTGCATTAGCTCAGCCTTTTAAGTTGCGGCT
CTGTCGAGCCCCAAGAGAGAAGTCTCTTCGTGACTATTCTTCGAATATTGTGTTGATTGACCCATTAGCA
AGTCTAGCAGCTGTTGAAGAATTTCTTTGGCCTCGAGTTCAACGAAGTGACACTTCTCAGAAACTCTCTG
TGACTGTTGGAAATTCTGAGTCTGGGAACACACCTAACCGGACTGATGTATCTTCTCCGTCTACCTCAAC
TCCTGCTTCTACCACCCGACGCCATTCTTCAAGGTCCAGATCATCTGTCAATATTGGAGATGTGGCCAGA
AAGGAGCAATCACAGGAGAAAAGCACTAGTTCATCAAAGGGAAAAGGTAAGGCTGTTTTGAAGCCTTC
TAAAGAGGAGCCAAGAGGACCTCAAACAAGAAATGCTGCTCGTAGAAGAGCTGCTCTGGATAAAGAT
GCTCCAATGAAACCTGTAAATGACGACTCTACTTCTGAGGTATGCTTTTTGATTATTAGATATGATTTTTC
ATTTGTTAATAAGGCAGTCATGTTCAATATGACTATGTCAGGACTTCCCTGTTTTTAGCTTGTGTTTCTTC
TCTGTTGCTTGCATGGAATTGTGCCTTTCTTTCTATTTCCTGTTGAATGATCATCATTTGACCCTTATTTGG
TTGGTTAGGATGAAGAATTGGATATGTCCCCTGTGGAGATTGATGATGCTTTGGTGATTGAAGATGAT
GATATTTCTGATGATGAAGATGATGAACATGAAGATGTAAGTTATATTGTGCCTGTAGAAATGTGCAGC
CCCTTGTTGATTGTAAACTCCTTTTAAATCTTACTATTGATTGATGGAAATGTTGTTCTTTTCCAGGTGCT
CAGGGATGATTCTCTTCCAGTTTGTACACCTGATAAAGTACATGATGTTAAGTTGAGTGATTCAGCTGA -continued AGATGGTTCTCCTGCTCCAGCTGCAAGTGATAGCCAAACTAATGCAGCTTCAGGATCTAGCAGCAGAGC
TGCTGCTATTAGGGGTTCAGACTCTGCTGATTTTAGGAGTGGCTATGGCTCAAGGGGTGCAATGTCGTT
TGCAGCTGCTGCCATGGCTGGGCTTGGATCTGCCAATGGTAGAGGTATTAGGGGAGGTAGAGATCGA
CAAGGAAGACCTCCTGGCAGTTCTAATGAGCCTCCAAAGTTGATATTCACTGCTGGTAATAAGCAGCTC
AACAGGCATTTGACCATCTATCAGGCCATTCAAAGACAGCTTGTGTTGGATGAGGATGATGATGAGAG
ATATGCTGGTAGTGATTTTACATCTAGTGATGGAAGAGGGGTGTGGAGTGATATCTACACAATAACAT
ATCAGAGGGCTGAGAGCCAAGCTGATCGATCATCACCAGGGGGATCAGGTTCTGCTACAGCATCTAAA
TCTGGTAAATCTGGTTCATCCAATTCCAGCTCTGATCCCCAACCTCATAGAATGTCTCTATTAGATAGCAT
ATTGCAAGGGGAACTTCCTTGTGATCTAGACAGATCCAATCCTACTTATACTATATTGGCACTGTTGCGC
GTGTTAGAGGGTCTGAATCAGCTTGCACCTCGTTTGAGAGCTCAGATTGTTTCTGATAATTTTGCTGAG
GGAAATGTTTTAACTCTGGGTGAGTTGAGCACCTCCGGTTCTAGAGTTCCTCATGAGGAATTTATTAAT
GGTAAGCTGACTCCAAAACTGGCGCGGCAAATTCAGGATGTTCTTGCTCTATGTAGTGGAAGCCTTCCT
TCCTGGTGTTACCAGTTGACAAAGGCATGCCCCTTCTTATTTCCTTTTGAGACACGAAGGCAGTACTTCT
ATTCAACTGCCTTTGGGTTGTCTCGTGCATTATATCGTCTGCAGCAGCATCAAGGTGCTGATGGCCATG
GGTCAACTAATGAAAGAGAGGTAAGGGTTGGGAGATTACAGAGGCAGAAAGTTCGTGTCTCCCGGAA
CCGCATTTTGGACTCTGCTGCAAAAGTGATGGAGATGTATTCCAGCCAAAAAACTGTGCTTGAAGTTGA
ATATTTTGGAGAAGTTGGCACCGGATTGGGTCCAACCTTGGAGTTTTATACGCTTTTAAGTCATGACTT
GCAAAAGGTTGGACTTGCAATGTGGAGGTCGAATTCTACATGGAACAAGTCAGTGATGGAAATTGATG
GAGATGGAGATAAAAATGGAAAAATTGCTGGTTCTGCTACTATTAACGGAGATATAGTCCAAGCTCCTC
TGGGGTTATTCCCCCGACCTTGGCCACCAAATGCTGATGCTTCTGAAGGTAGCCAATTTTTTAAAGTAAT
TGAACATTTCCGGCTGGTTGGGCGTGTTATGGCAAAAGCTCTTCAAGATGGACGGCTTTTAGATCTGCC
TCTCTCAATGGCATTTTATAAACTTGTGCTTGGTCAAGTAAGCTGACTGCATTTTTTGACTTATTGAACAT
GTTAAATCTACTTTAGCCTTGTATTTCACGTTTTCATACCGATAAAGTAATCCCTAGCATTGTCACAATGG
TCTTTTACCTGTTCTTGCTAAAGTTGACTTTATAAACCATTGCAGGAGCTTGATTTGCATGATATTCTGTC
TTTTGACGCCGAATTTGGCAAAATTCTGCAAGAATTGCATTTACTTGTTCGTCGAAAGCAATATCTAGAT
TCATTGGGTGGTGACAATAGTGATGCAATTCCTGACTTACGGTTCCGTGGAGCCTCAATAGAAGATCTC
TGTTTGGATTTCACGCTTCCAGGATATCCGGACTACATATTGAAGCTAGGGGATGAAACTGTATGTCTT
CAACTTCTCATTCTGTTACCCCCACCTCATTTTTTTGTCAAGATTTTTTAATGTAATGTTAAATATATCAGG
TGGATATCAACAACTTAGAGGAATACATATCTTTGGTGGTTGATGCAACTGTGAAGACTGGAATTATGC
ATCAAATGGAGGCATTTAGAGACGGTTTCAATCAGGTGAAGATGCTTTCTTTGTTCTGAGTTTCTTGACT
AATTACAAATTGATGTCCATCATGGATTTCCCTAATATATGCATGTAAGGAGCTGTTTTTGGGATTGATC
TCAATGTTAATATATCCGTTATATAACATGCAGGTTTTTGATATCTCATCACTGCAAATATTTACACCCCA
AGAGTTGGACTATTTGCTGTGTGGTCGTAGAGAGTTGTGGGAGGTAATTTGACACTTGAATTATGTGAT
CGTGTTGCCATCTTTGATCAGAACTGGTTTTGCACTTTGATTTTAACAATACTACTTTTAATTTTGCAGGC
TGAGACTCTTGCTGATCATATAAAATTCGATCATGGATATACTGCAAAGAGCCCTCCAATTGTTAATGTA
TGTTTGTTTCATACTACTCACATTTAAGTTTTTTGAGAGGCATTTGATCCGTAATGATGTTCTGTTTTGTG
ATTTCTTAGTTGCTTGAAATTATGGGAGAATTAACACCAGAGGAGCAGCGGGCCTTCTGTCAATTTGTT
ACTGGTGCACCCAGGCTTCCACCCGGTGGTCTGGCAGTGCTAAATCCAAGGCTGACAATTGTTAGAAA
GGTAATTTGAGTTAGAATTAAAAACCTTTTCTCAATATTTCTTCTTGATTACAATGATGTAGACATTTGTC
GTCTTGCATTGAAAATCTCATTAAGATGATTTTGGAAGTCAGGTGGAAATGGACATATTTATTGCAGGT
TATGGCTTCTTTATGTGCACTGGCTTCAATACTTTTAAAATTGCTACTAAAGATGGAATAAATTAATGAG
TGCTATGGCTAATGTTCTGATTCAGGCTAAATTATCGCTTTATTTATTTCTTGCTGTAAAATTATTGCTGT
TAAGATAATATTCCATTCACCTAGTCTAGTATCTAGGGCTATTCTTGTTTGGTATGTTGGTGGCTTGAAT
GCTAATCTGTCTGAAATCTAAATGCAGCATTCTTCGTCTGCGACTGCTGCTGCTGCTGCCAATGGAACTG
GACTCTCAGAATCAGCAGATGAGGACTTGCCTAGTGTCATGACTTGTGCTAATTACTTGAAGCTTCCTCC
ATATTCTACCAAGGTATGTGATTATTTTTTATTGTGAGGAAGGGGGTTAAATTATTCTTGTACTAATTTC
ATGGATATTAACAGGAAATTATGTATAAGAAATTGCTATATGCAATCAATGAAGGGCAAGGATCTTTTG
ATTTGTCATGAGTCCACCGCCACAAGGCTAACGAACAGAAGAGAGTTGTGTGGTGTTGTGTTGAGGCA
GTGTGTATATTTCTGAGCAGCACAATCCGAGGGTCAATTTTTCTCACCTGCTGCGAGTATTTTTGATGTT
CCAAAGTAGCATATTGATTTTGCTCAAATAATGGCATTTCTCTTCACTGCTGCTTCTCCGTTACTTCAAAC
TTTTCTCAAATCCTGGGTAGACACAAATCTGATTTTTTCCGCTTTAGTATTTCTAATATTTTCCCCAGTTGC
ATGCGACTTATATGCTAAAGCACAGAAGAATTTAGTAGGATGTTTTTTGTTAAAGCACTTCTGCATTCAG
CTGCTAGAGCTTTGTATATAAAATTAGGGAGGAAAATGAATAAAATAATGATGAAATTGTTATTCCTTT
TTCTTTTTCATCCTTTGTTTATATTTAGTCCTTTCGGTTTTCTAAATTGCTACGAGTTTTCCTATGAAAAATT
TGCAATTTTTGGGCTCGGTAAATTTTAGTTAACAAATAGAAATACTTTAGTTTGCTCAAAGTTGGTTTTG
CTACTTTCAGTTCTTTCATACTCTTTCTATTAATTATGTTCTTTTGTGAA SEQ ID NO: 44: Cotton UPL3 protein sequence > Gorai.008G035900.1_protein
METRSRKRAEASSAAPSSSPSGPTTRSHKRVRLSSSSAAAAATVAVTRSRTSRTSRTSRTSAALMDPTTIESSSGSR
RDRRSSKANQTTTSDNPNLASDRGKEKEHDPRIRDRDRDRDNRDNNSNHPERNLGLNMDTSGGDEDDN
DSEGGVGILHQNLTSASSALQGLLRKLGAGLDDLLPSSAMGSGSSSHQSGRLKKVLSGLRADGEEGRQVEAL
TQLCEMLSIGTEESLSTFSVDSFVPVLVGLLNHESNPDIMILAARALTHLCDVLPSSCAAVVHYGAVSCFCARL
LTIEYMDLAEQSLQALKKISQEHPTACLRAGALMAVLSYLDFFSTGVQRVALSTAANMCKKLPSDAADYVM
EAVPLLTNLLQYHDSKVLEHASVCLTRIAEAFASSPDKLDELCNYGLVTQAASLISISNSGGGQASLSTPTYTGL
IRLLSTCASGSPLGAKTLLLLGISGILKDILSGSGVSANSSVSPALSRPAEQIFEIVNLANELLPPLPQGTISLPASS
NIFVKGSILKRSPTSSSGKQEDTNRNALEVSPREKLLNDQPELLQQFGVDLLPVLIQIYGSSVNSPVRHKCLSVI
GKLMYFSSAEMIQNLLSVTNISSFLAGVLAWKDPYVLVPSLQIAEILMEKLPGTFSKMFVREGVVHAVDQLV
LIGNQNTTPVQASSLEKDNESVSGASSRSRRYRRRSGNSNLEGSSMEESKNPASLNIGSPTNSVEIPTANSNL
RTAVSACAKAFKDKYFPSDPGAVEVGVTDDLLHLKNLCMKLNAAVNDQKTKAKGKSKASGSPWVDFSTSN
EEYLTGVISEMLAELSKGDGVSTFEFIGSGVVVALLNYFSCGYFSQERISDVNLPKLRQQALKRYKSFISVALPS
SVDEGSMAPMTVLVQKLQNALSSLERFPVVLSHSSRSSSGSARLSSGLGALAQPFKLRLCRAPREKSLRDYSS
NIVLIDPLASLAAVEEFLWPRVQRSDTSQKLSVTVGNSESGNTPNRTDVSSPSTSTPASTTRRHSSRSRSSVNI
GDVARKEQSQEKSTSSSKGKGKAVLKPSKEEPRGPQTRNAARRRAALDKDAPMKPVNDDSTSEDEELDMS
PVEIDDALVIEDDDISDDEDDEHEDVLRDDSLPVCTPDKVHDVKLSDSAEDGSPAPAASDSQTNAASGSSSR
AAAIRGSDSADFRSGYGSRGAMSFAAAAMAGLGSANGRGIRGGRDRQGRPPGSSNEPPKLIFTAGNKQLN
RHLTIYQAIQRQLVLDEDDDERYAGSDFTSSDGRGVWSDIYTITYQRAESQADRSSPGGSGSATASKSGKSG
SSNSSSDPQPHRMSLLDSILQGELPCDLDRSNPTYTILALLRVLEGLNQLAPRLRAQIVSDNFAEGNVLTLGEL
STSGSRVPHEEFINGKLTPKLARQIQDVLALCSGSLPSWCYQLTKACPFLFPFETRRQYFYSTAFGLSRALYRL
QQHQGADGHGSTNEREVRVGRLQRQKVRVSRNRILDSAAKVMEMYSSQKTVLEVEYFGEVGTGLGPTLEF -continued

```
YTLLSHDLQKVGLAMWRSNSTWNKSVMEIDGDGDKNGKIAGSATINGDIVQAPLGLFPRPWPPNADASE
GSQFFKVIEHFRLVGRVMAKALQDGRLLDLPLSMAFYKLVLGQELDLHDILSFDAEFGKILQELHLLVRRKQY
LDSLGGDNSDAIPDLRFRGASIEDLCLDFTLPGYPDYILKLGDETVDINNLEEYISLVVDATVKTGIMHQMEAF
RDGFNQVFDISSLQIFTPQELDYLLCGRRELWEAETLADHIKFDHGYTAKSPPIVNLLEIMGELTPEEQRAFCQ
FVTGAPRLPPGGLAVLNPRLTIVRKHSSSATAAAAANGTGLSESADEDLPSVMTCANYLKLPPYSTKEIMYKK
LLYAINEGQGSFDLS*
```

SEQ ID NO: 45: *Triticum aestivum* UPL3 genomic sequence
TraesCS2A01G064700.1_genomic

```
ATGGAAACGCGCAGCCGCAAGCGGGCGNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNACCCCCGCACACCCCGCGCCCACCCGCGCCCGCCGCTCC
GTCGTCCTCTCCCCGCCCGCCCCGCAGCCCCCGATGGACTTCCCGGCCGACGGCGGCAAC
AACCCCCCGCCCCGCCGCCGCGGCGGCCGCGCCTCCAACGCCGACAAGGGCAAGGAGCAG
CAGGAGCCCTCGGAGAGCTCCCGCGTGCGCGAGGCCGAGCGGATGCTGGGCCTCAGCTTC
GACGGCATGGACGACGACGACGAGGGCCACGGGGCCTTCCCCCACGGCCTCACCTCCGCC
AGCAGCGCCCTGCAGGGGCTGCTCAGGAAGCTCGGCGCCGGCCTGGACGACATGCTGCCG
TCGTCCGCGCTCTCCGCCGCCGCCGCTGCTGCCTCCTCGTCGTCCATGTCTGGTCCGAAC
GGCACGCGGATGAAGAGCATGCTCGCGGGTCTCCGCGCCGACGGCGAGGAGGGGCGCCAG
GTGGAGGCGCTCACGCAGCTCTGCGAGATGCTGTCCATCGGCACCGAGGACACCCTCGCC
GGGTTCTCCGTGGACTCGTTCGTGCCTGTTCTGGTCGGGCTGCTCAACCATGAGAGCAAC
CCCGACATCATGCTGCTCGCCGCGCGGGCCCTGACCCACCTCTGTGACGTGCTTCCGTCG
TCCTGCTCTGCCGTTGTGCACTATGGCGCCGTCGCATGCTTCTGCGCCCGGCTTCTCACC
ATTGAATATATGGACCTTGCGGAGCAGGTGAGCACTGTTCTGTTGCATCGCTTGTTTGGT
TTATATATAGTACATGCTGCTTCTTTATCATGTTGCCTGATCCAGATCATGTCGCCCTGC
TTGTTTAGTGAACCATTGTTGTGTACTGTATTATGCATGATTATGCTGCCCATAGAGCCT
TAACCTACATTACATGAGTTTCCTTTTAGTGTTGCAGGTCATTTATAATATTTGAACTTG
CTCATGAGTAGTTTGCCTTTTGTGTAGCTGTGGTTTTTTCCCATTTTAGTGCTAAAATAA
ATATGGGTGAGAAGGTTACGAACATGATTTTTGTTGGCGTTGTGCCCATACTCGAGAAGT
TCCACTGTATGCTTTCTATGTTATGTTTCTGACTCAAGTTTCGGTGACCTGTACAGATGT
GGTAGTTGTAAGTTAGCCTCAGTTAATATTAAGTTTGAAATATGTGTATAATCAATTTTC
AAGGAACTATATATTTGAAATAGCTTGTTTGATTGTTCACTTGGCAAGTACCAAATATTG
CCTAGTTCAGTAGCTCACCATTTAATGATGTTACAAGAAATATCTAGAGAGTTAGGCAGA
AGGTGATCGGATCCCTTAGTAGCCTTGGGGCCTGCCTAGGGTCTAGGCACTGGTCGCTCT
GGGAGGAAGAAGCTGAGGATAGGAGACACATGAAAGAAAAAATGGTTAGATGAAAGCATG
TCCGAATGCACGTGATGCCTTAAAGCCTTAGGGAGCTTGTGGGCATGGAGATGTCTTCCC
TTCCTCTGGTGCCGCAGGAGGACTCGGGCTCCAAATCCTCACCAGCGAACTCAAATCCAT
CTAAGGACCTCATCTGCCCCTTAGAAGACTTTCTAGGCCTGATCATGGTGGTGCTCCTGC
CGAGCACCTGGGTGCCATTTAACACGGTTTTGCTGTGCCAAATCACCTATTTGTGCATGA
CTAAGCTAGCTATTTGAACATGTTTTTCATCTGAAATATTTCTAGCTCAGGGTCTGATTT
CACGCCTGTGTATGTGTATCCATCTGAAATACTAAGAAGTGGGTTGGAAATCAGATGCTA
AGATTCATGTAACTGGTTTCTGGCAGTGTTTCTTCTCTGCCTTCCCATCTTATATGGATA
TTATACTTCTGCTTTTCTTGGGTCTAATTCAAAACAATGTGAATTAACTTGATATCATCT
GTTTGAATTCCTTTGTAACCCTTTGTGCAATTGAATCTAGTTTGCTGCTCCACAATATGT
TATTGAGTAGTATCTACAACTATTAGGTTTAGCACCTAGGACATTTGAATTACTTTCTTA
GATTTTGATATTGTATTGCTTCTGTGGCACTTTAGATTAGCCACTTTCCTTGTTTTGTTT
TGTCGTTTAAAATATGCTGCAGGAAGAATCTATCATTGCTAGATCTTGATGTGGTACTAA
TATTTTCTTATGCCTTTTCTGGGTATTTTAGTCCTTACAAGCACTCAAGAAGATATCCCA
GGAGCATCCAACTGCCTGCTTGAGGGCTGGCGCGCTAATGGCAGTGCTATCATATCTTGA
CTTCTTCTCCACCGGTGTTCAAGTAATTTTTCTAAATACTTCTATGTTTTTCCAGCATTT
AGACATAACATTCTCAATACTTATGTTATTTTTTTGCACCATTTAGAAATTGGGACATAG
TAATTTGTCATATCACTATCTTTTTGTTGTACACATACTGTACTACATTTTTATTACTAC
TCACAGTTGTTTTTTTGGTGGAATGTATACAGAGAGTTGCGTTATCTACAGCTGCCAATA
TGTGTAGGAAGCTTCCTTCAGACGCCTCAGATTTTGTAATGGAAGCGGTTCCACTGCTAA
CAAATCTTCTGAACTACCATGATGCAAAAGTATGCTTGTTGTCTGTATTTGGATACCCTG
ATTATGCCATGATACCATCTATTCTTAGATGCTGATGATCTGTATCAATGTATTCCAGGT
GCTGGAACATGCTTCTGTTTGCCTGACTCGTATAGCAGAATCGTTTGCTTCATCCCCAGA
GAAATTGGATCAATTGTGCAATTATGGATTGGTTGCACAAGCTGCTAGCTTAATAGCTGT
TAGCAACTCAGCGGGACAAGCATCACTGAGTACATTAACATATACAGTATGCTTCTATTT
CACTTATCTACTGTATTATTTAGTATTTATGCAACTTTGCTAACTCTGGCTCATATATCC
TTGAAGGGAGTAATTCGTGTTCTGTCAATATGTGCAAGTGGATCTCCATTGGCAGCTAAA
ACACTCCTCCTCCATGGAATCAGCGGCACACTTAAAGATATCCTTTCAGGTTCTGGTTTG
GTTGCTGGTACAACTGTATCCCCCACTAGGCCAGCTGATCAGGTGATTATTGCTTTATGA
GGGCTATATCTATATTATAGCTACTTACTGTTTTATTTGAATGCCATCGGTTGATGACTC
TGTTCGGTTGTTGTTTTATCTGACTTAGCCGATGAAGCTTTTTGAGTGATACTTTTTTTT
CAATTTTAAATTCACTCAAGTGTGCGTTCAGTTCAGGTTTGTTTGGTAAACTGAAATTAA
TGTCACACAACAGAATATTCAAAATTTGGAAGAAAGTTGCATGCTGGATACTTTTTCTGT
GTATAATAATTTGCCAAATGTTTCCCGTGCTCGTGCTGTTTGTGCAGTCCTGCAAGCTAT
AACAGTGAGCAAACAATGTGGTAAATTGGATTAGGGGTTTGTCTTGGAACTCTTGGTTCA
TATACTTCTCTGTTTTCTACCCGATTTTCTTTCTCCAGTTATAATATGAAATTCACAATG
ATAGTATTGATCTTGATCAAGGTTTAGAGATGCACTAGACTGGCGGTAGGTGACCGCCTA
GATGACGCCCAGCTACTGTTTGTTAACCTTAATAATCTCGACATCATACCATATTACTTG
CTCCATTTTTCTTTTTAATTTATCAAAAGCCAAGAGTTTCCTGTAGTAGTTCTATGGTAG
TTTGCAGCTTGTTTTCATATCCTAATATTCTTTGTTGTGTCACACAGATGTATGAAATTG
TGAACCTTGCGGACGAATTGCTTCCTCCTCTACCTGCTGGAACCATTTCTTTACCAGCGC
```

-continued

ATTCCCATGTTTTTATGAAAGGCTCTTCTGTAAAGAAACCTGGTTCTAGCAAGCAAGGCG
AGTCTGGTTCAACAGATATTAAAGTCTCGGGTCGGGAGAAGTTATTGCGTGATCAGCCTG
AACTTCTCCAGCAATTTGGCATGGACATATTACCTACCATGACACAGGTCAGTCTCTTGG
TTTGCTGGCGTATCAGTTGATGTTGGTTGCTGACGATAACATTATTGAAATCCTGTTATC
TGAGACATTATTTGGATACACTCTATCCCTTGCAGGTGTATGGCTCCAGTGTAAATGGAC
CAATACGTCATAAATGCTTATCTGTCATTGCTAAATTAATGTATTACAGCTCAGCGGAAA
TGATCGAAATTCTCCATGGCACAACAAACATATCCAGGTGCTAATACGAAACTTCAGATG
CCATTCTTGCTTACTGTTATACATGTACTCGTGTACCTCTGGTTCCATCTAACCTGATAT
TGACCTTTGCAGCTTCTTAGCTGGCATCTTAGCTTGGAAAGATCCACATGTGTTGGTTCC
CGCTCTCCAGATAGCTGAAATTCTGATGGAAAAGCTCCCTGGGACATTTTCGAAGATGTT
TGTGAGGGAAGGTGTTGTTCATGCTGTAGAATCGCTTATATGCCAGGAAATCTCAAGTCC
AATGCTTTTTCAAGTACCACAGCAGGACAAGGATATTGATTCTGGTACATGTACATCTTC
ACGTTCAAGACGCAGCCGCCGGCGCAGCAGTGCTGGGAATACTGATAATAATTCCTTGGA
TGAACCAAAGGGTTCCCATACTACTATTGCCAATTCACCACCAAGCACGCTAGAAGGTCC
AAATACTAGAATTCGTGCTTCAGTTAGTGATCGTGCGAAGTCATTCAAAGATAAGTACTT
CCCCTCTGAACCCGGCTCAAGTGATATTGCAGTTACTGATGACCTTTTGAAGCTACGGGC
ACTCTGTGCAAAATTGAATGCCACTGCGGACACTGTTAAAACAAAAGCCAAAGGGAAATC
AAAGTCACTGGGAGGTGATGATTTTGATATCTTATGCAATGTCGAGGAACAGTTAGACGA
CATCATAGACAAAATATTGTCTGAGCTTAGCAATGGGGATGGGGTTTCCACGTTTGAGTT
TATTGGGAGTGGAGTTATCTCAGCATTGCTTAATTATTTGTCTTGTGGAACCTTTGGAAA
GGAAAAGGTGTCCGAAGCAAACCTACCCAAGTTGCGTCACCTGGCACTCAGGCGATATAA
AGCATTTATATATGTTGCCCTTCCAAATGATGCGGTAGGGAATCAAACTCCAATGGCATT
CTTAGTTCAAAAACTGCAAAGCGCGTTGTCTTCGCTGGAACGGTTCCCAGTTGTGATTAG
CCATTCTGGAAGGACGTCCAGTTTGGGAGGATCTCGTCCATCCTCTGGATTAAGTGCTCT
ATCTCAGCCCCTGAAGTTGCGCCTGTGTCGAGCAGCGGGTGAAAAAACGCTTAAGGATTA
TTCATCCAATATAGTTCTTATTGATCCCTTGGCAAGTTTAGCAGCCGTTGAAGATTTCCT
TTGGCCTAGAATCCAGCGTAGTGAGTCAATATCTTATCCTGCAGTATCATCTGGAAAGAA
TTCTGAATCTGTGGCACCTAGTGCAACAGCACCAGTGGCTTCGTCAACTCAATCTGTCCG
GCGGCCCTCAACTAGGTCGAAATCATTGGCTGATGCTGATTCTGCAACTAAGAAGGATAT
TCAGGAGGGGAGCGGAAACACATCCAAGGGAAAAGGCAAAGCTGTTGTTAAGTCGATGTC
CGATGAACCAAAAGGACCACATACTAGGACTGCAGCACGCAGGAAAGTTGCTTCACAGAA
AGATGCAGAAGTGAAGCCACCACACGGTCACAGTAGCTCAGAGGTTTGTTGTTCATTATG
GACTCATTTCTTAATAATCTATAGAATATATATTTCCTCCAGTACGTCTTGAATTTTTGC
TAGTTCCCCAAAATTTGATGCAGATGCTTGACTACATATTCTTTGTTTGGTAGTGCCTCC
CTGCAGTTACTCAGCTGCCAAGCTGATTTTCGTTATAACAACCGTCCTACTGTTTTTCGT
CGTCGTTTCATGATTATATCTGCTCTCCTTTCATTTAATAATTTGATGTGCAACTGTTAA
GGGGAATTGACATGATTAATACCGTTATGAAATTATTATTTAACACGAATTTCATTGTGG
AACCAATGTGTGAATTTCATAAAATTAGATCTACAGAGTACAATGCCTTTTGACCTGCAG
TTCGATATGGCATCTAGGGAGTACATATTGTCTCACCATGTCTACAATGCTTCAGTTGAT
GAAGACATTGTCTAACTAAAACCAATGATGTAGGGAAAGGTTGGTGCTCCCACCACTATC
TCGATCACTGAATGTGCCTAAAGGTTGTTGCAGTTCCTCATCCTATTCAATAATTATATG
TTGAGAGAGTGGCACGGACCTTAAGCAGCAATGGCACATTCCATAGTTGAGAACTTGTGA
TAGTGGGAGCATATTCACCAATGTGATTCATTTCACTGTTGAAAGTTTGCCCGAATGCAA
TACTGCTTTTCTTGCCTAACTGAGTGATAAATATATAAATTAAGTTGTCAGTTTAATTAT
ATCTATGTAATTAGCTGCAAGTACCCCTTACCAGTTCTCACCTGTATAACAAAATAGATC
ACTTATGCGTTGGAAACTGGATTACTATTTCACTAATTCCCTTATCCCTGAACAAAGTTC
TGATCCAATTCTTGTACACTATGTCATGTGATGTTAAACTTTATTATTGTATTTATGCTC
GTTGTGCATGATACATTCTGTTTCCTACATGCAGGACGAAGAACTGGGCGCATCTCCCTT
TGAGGCTGATGATGCTTTGATGCTTGGTGATGACGATGATGATGTTTCAGATGATGAAGA
TGATGACCATGAGGTAGTATTTCAAAAGTACTTCGGTTGATCTCTTTATTTTTCTGCAAG
TTAATGTGGCTTTAGTGGGCATGACTGAAAACTGCATATTTTTGTTGAAAATCCCCAGGT
TCTACGTGGGTCTCTTCCTGACTGTGTTCCAGAGAGTGTGCATGATGTAAAACTGGCAGA
TGCTGATGGGTCTAGTATTGCCTCAATAGCAAGTGATAACCAGACACAACCCTCATCTGG
CTCCAGCGTAAAACATACTTTTAGTAGCAGGGGAGCAGGTTCTGTTGAACTTAGAAATCC
AAGCACACTTGGTTCACGGGGCGCGATGTCGTTTGCTGCAGCTGCCATGGCTGGGCTTGC
TTCTGTTGGTAGTCGTGGTATCAGAGGTAGCCAGGATAGGCGTGGCCTTCCACTTGGAAC
TAGTGCACATGAACATTCGAACAAATTGATTTTTACAGCTGGCGGCAAGCAGCTTAGCAA
GCATTTGACTGTATATCAAGCTATGCAACAGCAAGTAGTTCATGATGAGGATGATGAGGA
AAGGCTAGGTGGTTCTGATTTACCCAATGATGGAAGCCGTCTCTGGAGTGATATGTTCAC
TATAACATATCAAAAGGCTGATAACGAAGTGGATAGGGAATCAACCAGAGGTTCATCTTT
AGTGCTGAAATCGTCCAAATCAGAACTTTGCAGAGCTACATCTCAAGAACAATGTACTTC
TCTTCTTGATAGCATTTTGCAAGGAGAACTTCCTTGTGATATTGAGAAATCGACCCAAAC
TTATAATATTTTAGCACTATTGCGTGTATTGGAGGGATTGAATCAGCTATCTCCTCGTCT
GAGACTACAGGCAACCTGTGATGATTTTATAGAGGGAAAAGTTGGTACCCTGGATGGGTT
ATATGGCACCGGAGCTAAGGTACCCTCAGAGGAGTTTATCAGCAGTAAGTTGACACCAAA
GCTTGCTCGGCAAATTCAGGATGTTCTTGCACTCTGCAGTGGTAGTTTACCTTCTTGGTG
TTATCAGATGACCAAAGCTTGTCCATTTCTGTTTCCTTTTGAAACAAGAAGACAACACTT
CTACTCCACAGCTTTTGGGTTATCTAGGGCATTGAATCGTCTTCAGCAACAACAGGGTGA
TAATAATAGCTCAGCGACTGAAAGAGAAGTCCGGATTGGTAGATTGCAACGCCAGAAAGT
TCGTGTTTCTCGTAACCGGATCCTGGATTCTGCTGCCAAAGTAATGGAGATGTTCTCCAA
TCAGAAGGCTGTTCTTGAAGTTGAATACTTTGGTGAAGTGGGAACTGGACTTGGTCCAAC
TTTGGAGTTCTACACCCTCTTAAGTCATGACCTGCAAAGGGTTGGCTTGGGATTATGGAG
ATCTGATTCTGATTCTTTAGAAGCTAAAAAACTTGATTCACATTCACCTGCTGATAGCAG
GAACTTGATACATGCACCTCTTGGCTTGTTCCCTCGGCCTTGGCCACCTAGTACTGCTTC
TTCAGAGGGTAGTAAATTCTTCAAAGTTGTTGAGTATTTCCGCTTAGTTGGTCGAATCAT
GGCAAAAGCATTGCAAGATGGAAGGCTTCTTGATTTGCCTTTGTCAACAGCATTTTATAA
GCTTCTACTTGGACAAGTAAGCATGAGAACCCGCTTGCAGTAGATCCATTCCAATATTCC
CTTCCACCTTCTTGTCAAGTCTTGGTATTTTTTTATTTCTTCTACTGTCTTCTGTATTG
ACGCCAAAATATTTTGCTTTACTAGGAACTTGATTTGTACGACATACTATCTTTTGATGC

TGAGTTTGGTAAAATACTTCAAGAGTTGCAAGTTCTTGTTGAACGCAAGCGATTTCTGGA
GTCCTGCTCTAATCATAGTCAACAAATAGAAGAATTGGGCTTTCGTGGTGCTCCTATTCA
AGACCTATGCTTAGATTTTACTCTTCCGGGCTATCCGGATTTTGTTCTGAAGGAAGGTGA
AGAAAATACAGTGGTATGTGATGGAGTAGATTAGGTTCTTATGTTGTCATCTAAGTGGTA
CTTCAGCTTTTGCTTCTAATTTTGTTGTTGACTATTCATTGTTATTGTTAACTTCCTGTA
GGTCTGCATTTACAACTTAGAAGAGTACATTTCGCTGGTAGTGGATGCTACACTTAAGAC
TGGAATAATGCGTCAAGTAGAAGCATTCAAAGCTGGATTTAATCAGGTTTTCTCATTTTT
CTAAGATATCTTATTTGCTGGCAATTATTGTTAATTAGCTATTGCATTTCTCTTATTATT
TTTCTAATTCAGGTATTTGATATATCATCACTCCAAATATTTTCTCCTCAAGAGCTTGAC
TATCTCATTTGTGGTCGACGGGAACTTTGGGAGGTAATGCCCTGTTAACTTTATTTCTCC
CTTCTATAATCATTATTTAACTTGTTCTGAGCAAATGCATGTAATGCAGCCGGAGACACT
GGTCGAACATATAAAGTTTGATCATGGTTATACCTCGAAGAGTCCAGCAATTGTCAATGT
GAGTACATCATCTTTAAAAAAGGGCACATCTCTTCACACAGCTTTATTTCAGATTTTTGG
AACTTCAGTTTAATGTTTGTGCTGTTGGTTTGCAGCTACTTGAGATCATGACGGAATTTA
CTCCGGAGCAACAACATGCATTCTGCCAGTTTGTGACTGGTGCTCCTCGGCTTCCACCTG
GTGGCTTAGCCTCCCTAAATCCTAAGCTGACTATAGTTAGGAAGGTAAGCCTGTTGTAGC
AATGCAGAATGACATCATTTCTGCGTTCATGTTATTTAAGCTTTTCCATTTTGTATCTTG
GCCAGCACTCTTCGACTGCGGCGAATACTTCAAATGCAGCTGGAGCAGCAGAGTCTGCAG
ATGATGATCTGCCTAGTGTCATGACTTGTGCCAACTATCTTAAACTTCCGCCATACTCGA
CAAAGGTTTGGTTCTTTTGGTTGATGAATTTTTTGTTCCACCTTTCCGTATCGTCTTGCC
TGGAAACTGACTTGTGCTATGGTCGTCGGAACATTGTTGCAGGAGGTTATGCACAAGAAG
CTGCTTTATGCTATCAACGAAGGCCAGGGGTCGTTTGATCTTTCATAG

SEQ ID NO: 46: *Triticum* aestivum UPL3 protein sequence
TraesCS2A01G064700.1_protein
METRSRKRAXXXXXXXXXXXXXXXXXXXXXXXXXXXXXXXXXXXTPAHPAPTRARRSVVLSPP
APQPPMDFPADGGNNPPPRRRGGRASNADKGKEQQEPSESSRVREAERMLGLSFDGMDDD
DEGHGAFPHGLTSASSALQGLLRKLGAGLDDMLPSSALSAAAAAASSSSMSGPNGTRMKS
MLAGLRADGEEGRQVEALTQLCEMLSIGTEDTLAGFSVDSFVPVLVGLLNHESNPDIMLL
AARALTHLCDVLPSSCSAVVHYGAVACFCARLLTIEYMDLAEQSLQALKKISQEHPTACL
RAGALMAVLSYLDFFSTGVQRVALSTAANMCRKLPSDASDFVMEAVPLLTNLLNYHDAKV
LEHASVCLTRIAESFASSPEKLDQLCNYGLVAQAASLIAVSNSAGQASLSTLTYTGVIRV
LSICASGSPLAAKTLLLHGISGTLKDILSGSGLVAGTTVSPTRPADQMYEIVNLADELLP
PLPAGTISLPAHSHVFMKGSSVKKPGSSKQGESGSTDIKVSGREKLLRDQPELLQQFGMD
ILPTMTQVYGSSVNGPIRHKCLSVIAKLMYYSSAEMIEILHGTTNISSFLAGILAWKDPH
VLVPALQIAEILMEKLPGTFSKMFVREGVVHAVESLICQEISSPMLFQVPQQDKDIDSGT
CTSSRSRRSRRRSSAGNTDNNSLDEPKGSHTTIANSPPSTLEGPNTRIRASVSDRAKSFK
DKYFPSEPGSSDIAVTDDLLKLRALCAKLNATADTVKTKAKGKSKSLGGDDFDILCNVEE
QLDDIIDKILSELSNGDGVSTFEFIGSGVISALLNYLSCGTFGKEKVSEANLPKLRHLAL
RRYKAFIYVALPNDAVGNQTPMAFLVQKLQSALSSLERFPVVISHSGRTSSLGGSRPSSG
LSALSQPLKLRLCRAAGEKTLKDYSSNIVLIDPLASLAAVEDFLWPRIQRSESISYPAVS
SGKNSESVAPSATAPVASSTQSVRRPSTRSKSLADADSATKKDIQEGSGNTSKGKGKAVV
KSMSDEPKGPHTRTAARRKVASQKDAEVKPPHGHSSSEDEELGASPFEADDALMLGDDDD
DVSDDEDDDHEVLRGSLPDCVPESVHDVKLADADGSSIASIASDNQTQPSSGSSVKHTFS
SRGAGSVELRNPSTLGSRGAMSFAAAAMAGLASVGSRGIRGSQDRRGLPLGTSAHEHSNK
LIFTAGGKQLSKHLTVYQAMQQQVVHDEDDEERLGGSDLPNDGSRLWSDMFTITYQKADN
EVDRESTRGSSLVLKSSKSELCRATSQEQCTSLLDSILQGELPCDIEKSTQTYNILALLR
VLEGLNQLSPRLRLQATCDDFIEGKVGTLDGLYGTGAKVPSEEFISSKLTPKLARQIQDV
LALCSGSLPSWCYQMTKACPFLFPFETRRQHFYSTAFGLSRALNRLQQQQGDNNSSATER
EVRIGRLQRQKVRVSRNRILDSAAKVMEMFSNQKAVLEVEYFGEVGTGLGPTLEFYTLLS
HDLQRVGLGLWRSDSDSLEAKKLDSHSPADSRNLIHAPLGLFPRPWPPSTASSEGSKFFK
VVEYFRLVGRIMAKALQDGRLLDLPLSTAFYKLLLGQELDLYDILSFDAEFGKILQELQV
LVERKRFLESCSNHSQQIEELGFRGAPIQDLCLDFTLPGYPDFVLKEGEENTVVCIYNLE
EYISLVVDATLKTGIMRQVEAFKAGFNQVFDISSLQIFSPQELDYLICGRRELWEPETLV
EHIKFDHGYTSKSPAIVNLLEIMTEFTPEQQHAFCQFVTGAPRLPPGGLASLNPKLTIVR
KHSSTAANTSNAAGAAESADDDLPSVMTCANYLKLPPYSTKEVMHKKLLYAINEGQGSFD
LS SEQ ID NO: 47: *Triticum aestivum* UPL3 genomic sequence
TraesCS21301G076900.1_genomic
ATGGACTTCCCGGCCGACGGCGGCGGCAACAACCCCCCGCCCCGCCGCCGCGGCGGCCGC
GCCTCCAACGCCGACAAGGGCAAGGAGCAGCAGGAGCCCTCGGAGAGCTCCCGCGTGCGC
GAGGCCGAGCGGATGCTGGGCCTCAGCTTCGACGGCATGGACGACGACGACGAGGGCCAC
GGGGCCTTCCCCCACGGCCTCACCTCCGCCAGCAGCGCCCTGCAGGGGCTGCTCAGGAAG
CTCGGCGCCGGCCTGGACGACATGCTGCCGTCGTCCGGGCTCTCGGCCGCCGCCGCGGCT
GCCTCCTCGTCGTCCATGTCTGGGCCGAACGGCGCGCGGATGAAGAGCATGCTCGCGGGT
CTCCGCGCCGACGGGGAGGAGGGGCGCCAGGTTGAGGCACTCACGCAGCTCTGCGAGATG
CTGTCCATCGGCACGGAGGACACCCTCGCGGGCTTCTCAGTGGACTCGTTCGTGCCTGTT
CTGGTCGGGCTGCTCAACCATGAGAGCAACCCCGACATCATGCTGCTCGCCGCGCGGGCC
CTGACCCACCTCTGCGACGTGCTTCCGTCGTCCTGCTCTGCCGTTGTGCACTATGGCGCC
GTGGCATGCTTCTGCGCCCGGCTTCTCACCATTGAATATATGGACCTTGCTGAGCAGGTG
AGCACTGCTCTGTTGCATCGCTTGCTTGGTTTATATATAGTACATGCTGCTTCTTTATCA
TGTTGCCTGATCCAGATCAATGCTTAGTGAACCATTCTTGTGTACTGTATTATGCATGAT
TATCCATAGAGCCTTAACCTACATTACACGAGTTTCCTTTTAGTGTTGCAGGTCATTTGG
ACTTGCTCATGAGTAGTTTGCCTTTTGTGTAGCTGTGGTTTTTTTCCCATTTTAGTGCTA
AAACAAACATGAGTGAGAAGGTTACAAACATGATTTTTGTTGGCGTTGTGCCCATACTTG
AGAAGTTCCACTGTATGCTTTCTATGTTATGTTTCTGACTCAAGTTTCAGTGACCTGTAC
AGATGTGGTAATTGTAAGTTAGCCTCAGTTAATATTAAGTTTGAAATATTGTGTATAATC
AATTTTGAAGGAACTATATATTTGAAATAGCTTGTTTGATTGTTCACTTGGCAAGTACCA -continued AATATTGCCTAGTTCAGTAGCTCACCATTTAATGATGTCACAAGAAATATCTAGAGAGTT
AGGCAGAAAGTGATACCTTAGTAGCCTTGGGGCCTGCCAAGGGTCTAGTCACTGGTCGCT
CTGGGAGGAAGAAGCTGAGGATAGGAGACACATGAAAGAAAAAATAGTTAGATGAAAGCA
TGTCCCAATGCACGTGATGCCTTAAAGCCTTAGGGAGCTTGTGGGCATGGAGATGTCTTC
CCTTCCTCTGCTGCCGCAGGAGGACTCGGGCTCCAAATCCTCACCAGCGAACGCAAATCC
ATCTAAGGACCTCATCTGCCCCTTAGAAGACTTTCTAGGCCTGATCATGGTGGTGCTCCT
GCCGAGCACCTGGGTGCCATTTAACATGGTTTTGCTGTGCCAAATCACCTATTTGTGCAT
GACTAAGCTAACTATTTGAACATGTTTTTCATCTGAAATATTTCTAGCTCAGGGTCTGAT
TTCACGCCTGTGTATGTGCTACTGTAATGATCCATCTGAAATACTAAGAAGTTGGTTGGA
AATCAGATGCTAAGATTCATGTAACCGGTTTCTGGCTATGTTTCTTCTCTGCCTTCCCAT
CTTATATGGATATTATACTTCTACTTTTCTTGGGTCTAATTCAAAACAATGTGAATTAAC
TTGATAGCATCTGTTTGAATTCCTTTGTAACCCTTTGTGCAATTGAATCTAGTTTGCTGC
TCCACAATATGTTATTGAGTAGTATCTACCACTATTAGCTTTATCACCTACGACATCTGA
ATTACTTTCTTAGATTTTGATATTGTATTGCTTCTGTGGTACTTTAGATTAGCCACTTTC
CTTGTTTTGTTTTGTCGTTTAAAATATGCTGCAGGAAGAATCTATCATTGATAGATCTTG
ATGTGGTACTAATATTTTCTTATGCCTTTTCTGGGTATTTTAGTCCTTACAAGCACTCAA
GAAGATATCCCAGGAGCATCCAACTGCCTGCTTGAGGGCTGGCGCGCTAATGGCAGTGCT
ATCGTATCTTGACTTCTTCTCCACCGGTGTTCAAGTAATTTTTCTAAATACTTTTATGTT
TTTCCAGCATTTAGACATAACATTCTCAATACTTGCGTTATTTTTTTGCACCATTTAGAA
ATTGGGACATACTAATTTGTAATATCACTTTATCTTTTTGTTGCACACATACTGTACTAC
ATTTTTATTACTACTCACAGTTGTTTTTTTGGTGGAATGTATACAGAGAGTTGCGTTATC
TACAGCTGCCAATATGTGTAGGAAGCTTCCTTCAGACGCCTCAGATTTTGTAATGGAAGC
GGTTCCACTGCTAACAAATCTTCTGAACTACCATGATGCAAAAGTATGCTTGTTGTCTGT
ATTTGGATACCCTGATTATGCCATGATACCATCTATTCTGAGATGCTGATTATCTGTATC
AATTTATTCCAGGTGCTGGAACATGCTTCTGTTTGCCTGACTCGTATAGCAGAATCGTTT
GCTTCATCCCCAGAGAAATTGGATCAATTGTGCAATTATGGATTGGTTGCACAAGCTGCT
AGCTTAATAGCTGTTAGCAACTCAGCGGGACAAGCATCACTGAGTACATTAACATATACA
GTATGCTTCTATTTCACTTATTTACTGTATTATTTAGTATTTACGCAACTTTGCTAACTC
TGGCTCATATATCCTTGAAGGGAGTAATTCGTGTTCTGTCAATATGTGCAAGTGGATCTT
CATTGGCAGCTAAAACACTCCTCCTCCATGGAATTAGCGGCACACTTAAAGATATCCTTT
CAGGTTCTGGTTTGGTTGCTGGTACAACTGTATCCCCCACTAGGCCAGCTGATCAGGTGA
TTATTGCTTTATGAGGGCTATATCTATATTATATATTACAGCTACTTACTGTTTTATTTG
AATGCCATCGGTTGATGACTCTGTTCGGTGGTTGTTTTATCTGACTTAGCCGATGAAGCT
TTTTGAGTGATACTTTTTTTTTTCAATCTTAAATTCACTCAAGTGTGCATTCAGTTCAGG
TTTGTTTGGTAAACTGAAATTAATATCACACAACAGAATATTCAAAATTTGGAAGAAAGT
TGCATGCTGGATACTTATTCTGTGTATAATAATTTGCCAAATGTTTCCCGTGCTCGTGCT
GTTTGTGCAGTCCTGCAAGCTATAACAGTGAGCAAACAATGTGGTAAATTGGATTAGGGT
TTGTCTTGGAACTCTTGGTTCATAGACCTCTCTGTTTTCTACCCGATTTTCTTTCTCCAG
TTATAATGAAATTCACAATGATAGTATTGATCTTGATCAAGGTTTAGAGATGCGCTAGAC
TGGCGGTAGGTGACCGCCTATATGACGCCCAGCCACTGTTTGTTAACCTTAATAATCTCG
ACATCATACCATATTACTTGCTCCATTTTTCTTTTTAATTTATCAAAAGCCAAGAGTTCC
CTGTAGTAGTTCTATGGTAGTTTGCAGCTTGTTTTCATATGCTAATGTTCTTTGTTGTGT
CACACAGATGTATGAAATTGTGAACCTTGCCGACGAATTGCTTCCTCCTCTACCTGCTGG
AACCATTTCTTTACCAGCGCATTCCCATGTTTTTATGAAAGGCTCTTCTGTAAAGAAACC
TGGTTCTAGCAAGCAAGGCGAGTCTGGTTCAACAGATATTAAAGTCTCGGGTCGGGAGAA
GTTATTGCGTGATCAGCCTGAACTTCTCCAGCAATTTGGCATGGACATATTACCTACCAT
GACACAGGTCAGTCCCATGGTTTGCTGGCGTATCAGTTGATGTTGGTTGCTGACGATAAC
ATTATTGAAATCCTGTTATCTGAGACATTATTTGGATACACTCTATCCCTTGCAGGTGTA
TGGCTCCAGTGTAAATGGACCAATACGTCATAAATGCTTATCTGTCATTGCTAAATTAAT
GTATTACAGCTCAGCGGAAATGATCGAAATTCTCCATGGCACAACAAACATATCCAGGTG
CTAATACGAAACTTCAGATGCCATTCTTGCTTACTGTTATACATGTACTCGTGTACCTCT
GGTTCCATCTAACCTGATATTGACCTTTGCAGCTTCTTAGCTGGCATCTTAGCTTGGAAA
GATCCACATGTGTTGGTTCCCGCTCTCCAGATAGCTGACATTCTGATGGAAAAGCTCCCT
GGGACATTTTCGAAGATGTTTGTGAGGGAAGGTGTTGTTCATGCTGTAGAATCGCTTATA
TGCCAGGAAATCTCTAGTCCAATGCTTTTTCAAGTACCACAGCAGGACAAGGATATTGAT
TCTGGTATATGTACATCTTCACGTTCAAGACGCAGCCGCCGGCGCAGCAGTGCTGGGAAT
ACTGATAATAATTCCTTGGATGAACCAAAGGGTTCCCATACTACTATTGCCAATTCACCA
CCAAGCACGCTAGAAGGTCCAAATACTAGTATTCGTGCTTCAGTTAGTGATCGTGCGAAG
TCATTCAAAGATAAGTACTTCCCCTCTGAACCCGGCTCAAGTGATATTGCAGTTACTGAT
GACCTTTTGAAGCTACGGGCACTCTGTGCAAAATTAAATGCCACTGCGGACACTGTTAAA
ACAAAAGCCAAGGGGAAATCAAAGTCACTGGGAGGTGATGATTTTGATATCTTATGCAAT
GTCGAGGAACAGTTAGACGACATCATAGACAAAATATTGTCTGAGCTTAGCAATGGGGAT
GGGGTTTCCACGTTTGAGTTTATTGGGAGTGGAGTTATCTCAGCATTGCTTAACTATTTG
TCTTGTGGAACCTTTGGAAAGGAAAAGGTGTCCGAAGCAAACCTACCCAAGTTGCGTCAC
CTGGCACTCAGGCGATATAAAGCATTTATATATGTTGCCCTTCCAAATGATGCGGTAGGG
AATCAAACTCCAATGGCATTCTTAGTTCAAAAACTGCAAAGCGCGTTGTCTTCGCTGGAA
CGGTTCCCAGTTGTGATTAGCCATTCTGGAAGGACGTCCAGTTTGGGAGGATCTCGTCCA
TCCTCTGGATTAAGTGCTCTATCCCAGCCCCTGAAGTTGCGCCTGTGTCGAGCAACAGGT
GAAAAAACGCTCAAGGATTATTCATCCAATATAGTTCTTATTGATCCCTTGGCAAGTTTA
GCAGCCGTTGAAGATTTCCTTTGGCCTAGAATCCAGCGTAGCGAGTCAATATCTTATCCT
GCAGTATCATCTGGAAAGAATTCTGAATCTGTGGCACCTAGTGCAACAGCACCAGTGGCT
TCGTCAACTCAATCTGTCCGGCGGCCCTCAACTAGGTCGAAATCATTGGCTGATGCTGAT
TCTGCAACTAAGAAGGATATTCAGGAGGGGAGCGGAAACACATCCAAGGGAAAAGGCAAA
GCTGTTGTTAAGTCGACGTCCGATGAACCAAAAGGACCACATACTAGGACTGCGGCACGC
AGAAAAGTTGCTTCACAGAAAGATGCAGAAGTGAAGCCACCACACAGTCACAGTAGCTCA
GAGGTTTGTTGTTCATTATGGACTCATTTCCTTAATAATCTATAGTGTATATATTTCCTC
TAGTACGTCTTGAATTTTTGCTAGTTCCCCAAAATTTGATACAGATGCTTGACTATATAT
TCTTTGTTTGGTAGTGCCTCCCTGCAGTTACCCAGCTGCCAAGCTGATTTTCGTTATAAC
AACCTTCCTACTGTTTTTCGTCGTCGTTTCATGATTATATCTGCTCTCCTTTCATTTAAT -continued AATTTGAGGTGCAACTGTTAAGGGGAATTGACATGATTAATACCGTTATGAAATTACTCC
CTCCGTCCCAAAATTCTTGTCTTAGATTTGTCCAGATATGGATGTATCTAATACTAAAAT
GTGACTTGATACATCCGTATTTAGACAAATCTAAGACAAGAATTTTGCGACGGAGGGAGT
ATTATTTAACATGAATTTCATTGTGGAACCAATGTGTGAATTTCATAAAATTAGATCTAC
AGAATACAATGCCTTTTGAACTGCAGTTTGATATGCCATCTAGGGAGTACATATTGTCTC
ACCATGTCTACAATGCTTCAGTTGATGAAGACATTGTCCAACTAAAACCAATGATGTAGG
GAAAGGTTGGTGCTCCCACCACTATCTCGATCACTGAATGTGCCTAAAGGTTGTTGCAGT
TCCTTATCCTATGCAATAATTATATGTTGAGAGAGTGGCACGGACCTCAAGCAGCAATGG
CACATTCCATAGTTGAGAACTTGTGATAGTGGGAGCATATTCACCAATGTGATGCATTTC
ACTGTTGAAAGTTTGCCCGAATGCAATACTGCTTTTCTTGCCTAACTGAGTGATGAATAT
ATAAATTAAGTTGTCAATTTAATTATATCTATGTAATTAGCTGCAAGTACCCCTTACCAG
TACTCACCTGTATAACAAAATAGATCACTTATGCGTTGGAAACTGGACTACTATTTCACT
AATTCCCTTATCCCTGAACAAAGTTCTGATCCAATTCTTGTACACTATGTCATGTGAATG
TTAAACTTTATTACTGTATTTATGCTCATTGTGCATGATACATTCTGTTTCCTACATGCA
GGACGAAGAACTGGGCGCATCTCCCTTTGAGGCTGATGATGCTTTGATGCTTGGTGATGA
CGATGATGATGTTTCAGATGATGAAGATGATGATCATGAGGTAGTATTTCAAAATTACTT
TGATTGCTCGCTTTGTTTCTCTGCAAGTTAATGTGGCTTTAGTGGGCATGACTGAAAACT
GCATATTTTTGTTGAAAATCCCCAGGTTCTACGTGGGTCTCTTCCTGACTGTGTTCCAGA
GAGTGTTCATGATGTAAAACTGGCAGATGCTGATGGATCTAGTATTGCCTCAATAGCAAG
TGATAACCAGGCACAACCCTCATCTGGCTCCAGCATAAAACATACTTTTAGTAGCAGGGG
AGCAGGTTCTGTTGAACTTAGAAATCCAAGCACACTTGGTTCGCGGGGCGCGATGTCGTT
TGCTGCAGCTGCCATGGCTGGGCTTGCTTCTGTTGGTAGTCGTGGTATCAGAGGTAGCCA
GGATAGGCGTGGCCTTCCACTTGGAACTAGTGCACATGAGCATTCGAACAAATTGATTTT
TACAGCTGGCGGCAAGCAGCTTAGCAAGCATTTGACCGTATATCAAGCTATGCAACAGCA
AGTAGTTCATGATGAGGATGATGAGGAAAGGCTAGGTGGTTCTGATTTACCCAATGATGG
AAGCCGTCTCTGGGGTGATATGTTCACTATAACATATCAAAAGGCTGATAACGAAGTGGA
TAGGGAATCAACCAGAGGTTCATCTTTAGTGCTGAAATCGTCCAAATCAGAACTTTGCAG
AGCTACATCTCAAGAACAATGTACTTCTCTTCTTGATAGCATTTTGCAAGGAGAACTTCC
TTGTGATATTGAGAAATCGACCCAAACTTATAATATTTTAGCACTATTGCGTGTATTGGA
GGGATTGAATCAGCTATCTCCTCGTCTGAGACTACAGGCAACCTGTGATGATTTTATAGA
GGGAAAAGTTGGTACCCTGGATGGGTTATATGGCACCGGAGCTAAGTTACCCTCAGAGGA
GTTTATCAGCAGTAAGTTGACACCAAAGCTTGCTCGGCAAATTCAGGATGTTCTTGCACT
CTGCAGTGGTAGTTTACCTTCTTGGTGTTATCAGATGACCAAAGCTTGTCCATTTCTGTT
TCCTTTTGAAACAAGAAGACAACACTTCTACTCCACAGCTTTTGGGTTATCTAGGGCATT
GAATCGTCTTCAGCAACAACAGGGTGATAATAATAGCTCAGCGACTGAAAGAGAAGTCCG
GATTGGTAGATTGCAACGCCAGAAAGTTCGTGTTTCTCGTAACCGGATCCTGGATTCTGC
TGCCAAAGTAATGGAGATGTTCTCCAATCAGAAGGCTGTTCTTGAAGTTGAATACTTTGG
TGAAGTGGGAACTGGACTTGGTCCAACTTTGGAGTTCTACACCCTCTTAAGTCATGACCT
GCAAAGGGTTGGCTTGGGATTATGGAGATCTGATTCTGATTCTTTAGAAGCTAAAAAACT
TGATTCGCATTCACCTGCTGATAGCAGGAACTTGGTACAAGCACCTCTTGGCTTGTTCCC
TCGGCCTTGGCCACCTAGTACTGCTTCTTCAGAGGGTAGTAAATTCTTCAAAGTTGTTGA
GTATTTCCGCTTAGTTGGTCGAATCATGGCAAAAGCATTGCAAGATGGAAGGCTTCTTGA
TTTGCCTTTGTCAACAGCATTTTATAAGCTTCTACTTGGACAGGTAAGCATGAAAACCCG
CTTGCAGTAGATCCATTCCAATATCCCCTTCCACCTTGTCAAGTCTTGGTATTTTTTTTA
TTTTCTCTACTGTCTTCTGTATTGATGCCAAAATATTTTGCTTTACTAGGAACTTGATTT
GTACGACATACTATCTTTTGATGCTGAGTTTGGTAAAATACTTCAAGAGTTGCAAGTTCT
TGTTGAACGCAAGCGATATCTGGAGTCCTGCTCTAGTCATAGTCAACAGATAGAAGAATT
GGGCTTTCGTGGTGCTCCTATTGAAGACCTATGCTTAGATTTTACTCTTCCGGGCTATCC
AGATTTTGTTCTGAAGGAAGGTGAAGAAAATACAGTGGTATGTGATGGAGTAGATTAGGT
TCTTATGTTGTCATTACTTCAGCTTTTGCTTCTAATATTGTTGTTGACTATTCATTGTTA
TTTTTAACTTCCTGTAGGTCTGCATTTACAACTTAGAAGAGTACATTTCGCTGGTAGTGG
ATGCTACACTTAAGGCTGGAATAATGCGCCAAGTAGAAGCATTCAAAGCTGGATTTAATC
AGGTTTTCTCATTTTTCTAAGATATCTTATTTGCTGGCAATTATTGTTAATTAGCTATTG
CATTTCTCTTAAAATATTTTTATTTTTCTATTTCAGGTATTTGATATATCATCACTCCAA
ATATTTTCTCCTCAAGAGCTTGACTATCTCATTTGTGGTCGACGGGAACTTTGGGAGGTA
ATGTCCTCTTAACTTTCTTCCTCCCTTCTATAATTATTATCTTAACTTGTTCTGAGCAAA
TGCATGTAATGCAGCCGGAGACGCTGGTCGAACATATAAAGTTTGATCATGGTTATACCT
CGAAGAGTCCAGCAATTGTCAATGTGAGTACATCCCTTATCTTTAAAAAGGGCACATCTC
TTCACACAGCTTTATTTCAGATTTTTGGAACTTGAGTTTATTGTTTGTGCTGTTGGTTTG
CAGCTACTTGAGATCATGACGGAATTTACTCCGGAGCAACAACATGCATTCTGCCAGTTT
GTGACTGGTGCTCCTCGGCTTCCACCTGGTGGCTTAGCCTCCCTAAATCCTAAGCTGACT
ATCGTTAGGAAGGTAAGCCTGTTGTAGCAATGCAGAATGACATCATTTCTGCGTTCATGT
TATTTAAGGCTTTTCCATTTTGTATCTTGGCCAGCACTCCTCGACTGCGGCGAATACTTC
AAATGCAGCTGGAGCAGCAGAGTCTGCAGATGACGATCTGCCTAGTGTCATGACTTGTGC
CAACTATCTTAAACTTCCGCCATACTCGACAAAGGTTTGGTTCTTTTGGTTGATGAATTT
TTGTTCCACCTTTCCGTATCGTCTTGCCTGGAAACTGACTTCTGCTATGGTCGTCGGAAC
GTTGTTGCAGGAGGTTATGCACAAGAAGCTGCTTTATGCTATCAACGAAGGCCAGGGGTC
GTTTGATCTTTCATAG SEQ ID NO: 48: *Triticum aestivum* UPL3 protein sequence
TraesCS2B01G076900.1_protein
MDFPADGGGNNPPPRRRGGRASNADKGKEQQEPSESSRVREAERMLGLSFDGMDDDDEGH
GAFPHGLTSASSALQGLLRKLGAGLDDMLPSSGLSAAAAAASSSSMSGPNGARMKSMLAG
LRADGEEGRQVEALTQLCEMLSIGTEDTLAGFSVDSFVPVLVGLLNHESNPDIMLLAARA
LTHLCDVLPSSCSAVVHYGAVACFCARLLTIEYMDLAEQSLQALKKISQEHPTACLRAGA
LMAVLSYLDFFSTGVQRVALSTAANMCRKLPSDASDFVMEAVPLLTNLLNYHDAKVLEHA
SVCLTRIAESFASSPEKLDQLCNYGLVAQAASLIAVSNSAGQASLSTLTYTGVIRVLSIC
ASGSSLAAKTLLLHGISGTLKDILSGSGLVAGTTVSPTRPADQNIQNLEESCMLDTYSVY
NNLPNVSRARAVCAVLQAITMYEIVNLADELLPPLPAGTISLPAHSHVFMKGSSVKKPGS -continued SKQGESGSTDIKVSGREKLLRDQPELLQQFGMDILPTMTQVYGSSVNGPIRHKCLSVIAK
LMYYSSAEMIEILHGTTNISSFLAGILAWKDPHVLVPALQIADILMEKLPGTFSKMFVRE
GVVHAVESLICQEISSPMLFQVPQQDKDIDSGICTSSRSRRSRRRSSAGNTDNNSLDEPK
GSHTTIANSPPSTLEGPNTSIRASVSDRAKSFKDKYFPSEPGSSDIAVTDDLLKLRALCA
KLNATADTVKTKAKGKSKSLGGDDFDILCNVEEQLDDIIDKILSELSNGDGVSTFEFIGS
GVISALLNYLSCGTFGKEKVSEANLPKLRHLALRRYKAFIYVALPNDAVGNQTPMAFLVQ
KLQSALSSLERFPVVISHSGRTSSLGGSRPSSGLSALSQPLKLRLCRATGEKTLKDYSSN
IVLIDPLASLAAVEDFLWPRIQRSESISYPAVSSGKNSESVAPSATAPVASSTQSVRRPS
TRSKSLADADSATKKDIQEGSGNTSKGKGKAVVKSTSDEPKGPHTRTAARRKVASQKDAE
VKPPHSHSSSEDEELGASPFEADDALMLGDDDDDVSDDEDDDHEVLRGSLPDCVPESVHD
VKLADADGSSIASIASDNQAQPSSGSSIKHTFSSRGAGSVELRNPSTLGSRGAMSFAAAA
MAGLASVGSRGIRGSQDRRGLPLGTSAHEHSNKLIFTAGGKQLSKHLTVYQAMQQQVVHD
EDDEERLGGSDLPNDGSRLWGDMFTITYQKADNEVDRESTRGSSLVLKSSKSELCRATSQ
EQCTSLLDSILQGELPCDIEKSTQTYNILALLRVLEGLNQLSPRLRLQATCDDFIEGKVG
TLDGLYGTGAKLPSEEFISSKLTPKLARQIQDVLALCSGSLPSWCYQMTKACPFLFPFET
RRQHFYSTAFGLSRALNRLQQQQGDNNSSATEREVRIGRLQRQKVRVSRNRILDSAAKVM
EMFSNQKAVLEVEYFGEVGTGLGPTLEFYTLLSHDLQRVGLGLWRSDSDSLEAKKLDSHS
PADSRNLVQAPLGLFPRPWPPSTASSEGSKFFKVVEYFRLVGRIMAKALQDGRLLDLPLS
TAFYKLLLGQELDLYDILSFDAEFGKILQELQVLVERKRYLESCSSHSQQIEELGFRGAP
IEDLCLDFTLPGYPDFVLKEGEENTVVCIYNLEEYISLVVDATLKAGIMRQVEAFKAGFN
QVFDISSLQIFSPQELDYLICGRRELWEPETLVEHIKFDHGYTSKSPAIVNLLEIMTEFT
PEQQHAFCQFVTGAPRLPPGGLASLNPKLTIVRKHSSTAANTSNAAGAAESADDDLPSVM
TCANYLKLPPYSTKEVMHKKLLYAINEGQGSFDLS SEQ ID NO: 49: *Triticum aestivum* UPL3 genomic sequence
TraesCS2D01G060300LC.1_genomic
GCCCGCCGCTCCGTCGTCCTCTCCCCGCCCGCCCCGCAGCCCCCGATGGACTTCCCGGCC
GACGGGAACAACAACCCCCCGCCCCGCCGCCGCGGCGGCCGCGCCTCCAACGCCGACAAG
GGCAAGGAGCAGCAGGAGCCCTCGGAGAGCTCCCGCGTGCGCGAGGCCGAGCGGATGCTG
GGCCTCAGCTTCGACGGCATGGACGACGACGACGAGGGCCACGGGGCCTTCCCCCACGGC
CTCACCTCCGCCAGCAGCGCCCTGCAGGGGCTGCTCAGGAAGCTCGGCGCCGGCCTGGAC
GACATGCTGCCGTCGTCCGCCCTCTCCGCCGCCGCCGCGGCTGCCTCCTCGTCGTCCATG
TCTGGGCCGAACGGCGCGCGGATGAAGAGCATGCTCGCGGGTCTCCGTGCCGACGGGGAG
GAGGGGCGCCAGGTGGAGGCGCTGACCCAGCTCTGTGAGATGCTGTCCATCGGCACCGAG
GACACCCTCGCCGGGTTCTCGGTGGACTCATTCGTGCCTGTTCTGGTCGGGCTGCTCAAC
CACGAGAGCAACCCTGACATCATGCTGCTCGCTGCGCGGGCCCTGACCCACCTCTGTGAC
GTGCTGCCGTCGTCCTGCTCTGCCGTTGTGCACTATGGCGCCGTGGCATGCTTCTGCGCC
CGGCTTCTCACCATTGAATATATGGACCTTGCGGAGCAGGTGAGCACTGTTCTGCTGCAT
CGCTTGTTTGGTTTATAGTACATGCTGCTTCTTTATCATGTTGCCTGATCCAGATCAATG
CTTAGTGAACCATTCTTGTGTACTGTATTATGCATGATTATGCTGTCCATAGAGCCTTAA
CCTACATTACATGAGTTTCCTTTTAGTGTTGCAGATCATTTATAGTATTTGGACTTGCTC
ATGAGTAGTTTGCCTTTTGTGTAGCTGTGTTTTTTTCCCATTTTAGTGCTAAAACAAATA
TGGATGAGAAGGTTAAGAACATGATTTTTGTTGGCGTTGTGCCCATACTCGAGAAGTTCC
ACTGTATGCTTTCTATGTTATGTTTCTGACTCAAGTTTCGGTGACCTGTACAGATGTGGT
AGTTGTAAGTTAGCCTCAGTTAATATTAAGTTTGAAATATTGTGTATAATCAGTTTTCAA
GGAACTATATATTTGAAATAGCTTGTTTGATTGTTCACTTGGCAAGTACCAAATATTGCC
TATTTCAGTAGCTCACCATTTAATGATGTTACAAGAAATATCTAGAGAGTTAGGCAGAAG
GTGATCCCTTAGCAGCCTTGGGGCCTGCCTAGGGTCTAGTCACTGGTCGCTCTGGGAGGA
AGAAGCTGAGGATAGGAGACACATGAAAGAAAAAATGGTTAGATGAAAGCATGTCCCAAT
GCACGTGATGCCTTAAAGCCTTAGGGAGCTTGTGGGCATGGAGATGTCTTCCCTTCCTCT
GGTGCCGCCGGAGGACTCGGGCTCCAAATCCTCACCAGCGAACTCAAATCCATCTAAGGA
CCTCATCTGCCCCTTAGAAGACTTTCTAGGCCTGATCATGGTGGTGTTCCTGCCGAGCAC
CTGGGTGCCATTTAACACGGTTTTGCTGTGTGCCAAATCACCTATTTGTGCATGACTAAG
CTAGCTATTTGAACATGTTTTTCATCTGAAATATTTCTAGCTCAGGGTCTGATTTCACGC
CTGTGTATGTGCTACTGTAATGATCCATCTGAAATACTAAGAAGTGGGTTGGAAATCAGA
TGCTAAGATTCATGTAACCGGTTTCTGGCTGTGTTTCTTCTCTGCCTTCCCATCTTATAT
GGATATTATACTTCTACTTCTCTTGGGTCTAATTCAAAACAATGTGAATTAACTTGATAT
CATCTGTTTGAATTCCTTTGTAACCCTTTGTGCAATTGAATCTAGTTTGCTGCTCCACAA
TATGTTATTGAGTAGTATCTACAACTATTAGGTTTAGCACCTAGGACATTTGAATTACTT
TCTTAGATTTTGATATTGTATTGCTTCTGTGGCACTTTAGATTAGCCACTTTCCTTGTTT
TGTTTTGTCGTTTAAAATATGCTGCAGGAAGAATCTATCATTGCTAGATCTTGATGTGTT
ACTAATATTTTCTTATGCCTTCTCTGTGTATTTTAGTCCTTACAAGCACTCAAGAAGATA
TCCCAGGAGCATCCAACTGCCTGCTTGAGGGCTGGCGCGCTAATGGCAGTGCTATCATAT
CTTGACTTCTTCTCCACCGGTGTTCAAGTAATTTTTCTAAATACTTCTATGTTTTTCCAG
CATTTAGACATAACATTCTCAATACTTACGTTATTTTTTTGCACCATTTAGAAATTGGGA
CATACTAATTTGTCATATCACTATCTTTTTGTTGTACACATACTGTACTACATTTTTATT
ACTACTCACAGTTGTTTTTTTGGTGGAATGTATACAGAGAGTTGCGTTATCTACAGCTGC
CAATATGTGTAGGAAGCTTCCTTCAGACGCCTCAGATTTTGTAATGGAAGCGGTTCCACT
GCTAACAAATCTTCTGAACTACCATGATGCAAAAGTATGCTTGTTGTCTGTATTTGGATA
CCATGATTATGCCATGATACCATCTATTCTTAGATGCTGATGATCTGTATCAATGTATTC
CAGGTGCTGGAACATGCTTCTGTTTGCCTGACTCGTATAGCAGAATCGTTTGCTTCATCC
CCAGAGAAATTAGATCAATTGTGCAATTATGGATTGGTTGCACAAGCTGCTAGCTTAATA
GCTGTTAGCAACTCAGCGGGACAAGCATCACTGAGTACATTAACATATACAGTATGCTTC
TATTTCACTTATCTACTGTATTATTTAGTAGTTACGCAACTTTGCTAACTCTGGCTCATA
TATCCTTGAAGGGAGTAATTCGTGTTCTGTCAATATGTGCAAGTGGATCTCCATTGGCAG
CTAAAACACTCCTCCTCCATGGAATTAGCGGCACACTTAAAGATATCCTTTCAGGTTCTG
GTTTGGTTGCTGGTACAACTGTATCCCCCACTAGGCCAGCTGATCAGGTGATTATTGCTT
TATGAGGGCTATATCTATATTATAGCTACTTACTGTTTTATTTGAATGCCATCGGTTGAT
GACTCTGTTCGGTTGTTGTTTTATCTGACTTAGCCGATGAAGCTTTTTGAGTGATACTTT -continued TTTTTTTCAAGTTTAAATTCACTCAAGTGTGCATTCAGTTCAGGCTTGTTTGGTAAACTG
AAATTAATATCACACAACAGAATATTCAAAATTTGGAAGAAAGTTGCATGCTGGATACTT
ATTCTGTGTATAATAATTTGCCAAATGTTTCCCGTGCTCGTGCTGTTTGTGCAGTCCTGC
AAGCTATAACAGTGAGCAAACAATGTGGTAAATTGGATTAGGGGTTTGTCTTGGAACTCT
TGGTTCATAGACTTCTCTGTTTTCTACCCGATTTTCTTTCTCCAGTTATAATATGAAATT
CACAATGATAGTATTGATCTTGATCAAGGTTTAGAGATGCGCTAGACTGGCGGTAGGTGA
CCACCTAGATGACGCCCAGCTACTGTTTGTTAACCTTAATAATCTCGACATCATACCATA
TTACTTGCTCCATTTTTCTTTTTAATTTATCAAAAGCCAAGAGTTTCCTGTAGTAGTTCT
ATGGTAGTTTGCAGCTTGTTTTCATATGCTAATATTCTTTGTTGTGTCACACAGATGTAT
GAAATTGTGAACCTTGCCGACGAATTGCTTCCTCCTCTACCTGCTGGAACCATTTCTTTA
CCAGCGCATTCCCATGTTTTTATGAAAGGCTCTTCTGTAAAGAAACCTGGTTCTAGCAAG
CAAGGCGAGTCTGGTTCAACAGATATTAAAGTCTCGGGTCGGGAGAAGTTATTACGTGAT
CAGCCTGAACTTCTCCAGCAATTTGGCATGGACATATTACCTACCATGACACAGGTCAGT
CTCTTGGTTTGCTGGCGTATCAGTTGATGTTGGTTGCTGACAATAACATTATTGAAATCC
TGTTATCTGAGACATTATTTGGATACACTCTATCCCTTGCAGGTGTATGGCTCCAGTGTA
AATGGACCAATACGTCATAAATGCTTATCTGTCATTGCTAAATTAATGTATTACAGCTCA
GCGGAAATGATCGAAATTCTCCATGGCACAACAAACATATCCAGGTGCTAATACGAAACT
TCAGATGCCATTCTTGCTTACTGTTATACATGTACTCGTGTACCTCTGGTTCCATCTAAC
CTGATATTGACCTTTGCAGCTTCTTAGCTGGCATCTTAGCTTGGAAAGATCCACATGTGT
TGGTTCCCGCTCTCCAGATAGCTGAAATTCTGATGGAAAAGCTCCCTGGGACATTTTCGA
AGATGTTTGTGAGGGAAGGTGTTGTTCATGCTGTAGAATCGCTTATATGCCAGGAAATCT
CAAGTCCAATGCTTTTTCAAGTACCACAGCAGGACAAGGATATTGATTCTGGTACATGTA
CATCTTCACGTTCAAGACGCAGCCGCCGGCGCAGCAGTGCTGGGAATACTGATAATAATT
CCTTGGATGAACCAAAGGGTTCCCATACTACTATTGCCAATTCACCACCAAGCACGCTAG
AAGGTCCAAATACTAGAATTCGTGCTTCAGTTAGTGATCGTGCGAAGTCATTCAAAGATA
AGTACTTCCCCTCTGAACCCGGCTCAAGTGATATTGCAGTTACTGATGACCTTTTGAAGC
TACGGGCACTCTGTGCAAAATTAAATGCCACTGCGGACACTGTTAAAACAAAAGCCAAAG
GGAAATCAAAGTCACTGGGAGGTGATGATTTTGATATCTTATGCAATGTCGAGGAACAGT
TAGACGATATCATAGATAAAATATTGTCTGAGCTTAGCAATGGGGATGGGGTTTCCACGT
TTGAGTTTATTGGGAGTGGAGTTATCTCAGCATTGCTTAATTATTTGTCTTGTGGAACCT
TTGGAAAGGAAAAGGTGTCCGAAGCAAACCTACCCAAGTTGCGTCACCTGGCACTCAGGC
GATATAAAGCATTTATATATGTTGCCCTTCCAAATGATGCGGTAGGGAATCAAACTCCAA
TGGCATTCTTAGTTCAAAAACTGCAAAGCGCGTTGTCTTCGCTGGAACGGTTCCCAGTTG
TGATTAGCCATTCTGGAAGGACGTCCAGTTTGGGAGGATCTCGTCCATCCTCTGGATTAA
GTGCTCTATCTCAGCCCCTGAAGTTGCGCCTGTGTCGAGCAGCGGGTGAAAAAATGCTTA
AGGATTATTCATCCAATATAGTTCTTATTGATCCCTTGGCAAGTTTAGCAGCCGTTGAAG
ATTTCCTTTGGTCTAGAATCCAGCGTAGCGAGTCAATATCTTATCCTGCAGTATCATCTG
GAAAGAATTCTGAATCTGTGGCACCTAGTGCAACAGCACCAGTGGCTTCGTCAACTCAAT
CTGTCCGGCGGCCCTCAACTAGGTCGAAATCATTGGCTGATGCTGATTCTGCAACTAAGA
AGGATATTCAGGAGGGGAGCGGAAACACATCCAAGGGAAAAGGCAAAGCTGTTGTTAAGT
CGACGTCCGATGAACCTAAAGGACCACATACTAGGACTGCAGCACGCAGAAAAGTTGCTT
CACAGAAAGATGCAGAAGTGAAGCCACCACACGGTCACAGTAGCTCAGAGGTTTGTTGTT
CATTATGGACTCATTTCCTTAATAATCTATAGAATATATATTTCCTCCAGTACGTCTTGA
ATTTTTGCTAGTTCCCCAAAATTTGATGCAAATGCTTGACTACATATTCTTTTTTTGGTA
GTGCCTCCCTGCAGTTACTCAGCTGCCAAGCTGATTTTCGTTATAACAACCGTCCTACTG
TTTTTCGTCGTCGTTTCATGATTATATCTGCTCTCCTTTCATTTAATAATTTGATGTGCA
ACTGTTAAGGGGAATTGACATGATTAATACTGTTATGAGATTATTATTTAACACAAATTT
CATTGTGGAACCAATGTGTGAATTTCATAAAATTAGATCTACAGAGTACAATGCCTTTTC
ACCTGCAGTTTGATATGGCATCTAGGGAGTACATATTGTCTCACCATGTCTACAATGCTT
CAGTTGATGAAGACATTGTCTTACTAAAACCAATGATGTAGGGAAAGGTTGGTGCTCCCA
CCACTATCTCGATCACTGAATGTGCCTAAAGGTTGTTGCAGTTCCTCATCCTATGCAATA
ATTATATGTTGAGAGAGTGGCACGGACCTCAAGCAGCAATGGCACATTCCATAGTTGAGA
ACTTGTGATAGTGGGAGCATATTCACCAATGTGATTCATTTCACTGTTGAAAGTTTGCCC
GAATGCAATACTGCTTTTCTTGCCTAACTGAGTGATAAATATATAAATAATAAATTAAGT
TGTCAAGTTAATTATATCTATGTAATTAGCTGCAAGTACCCCTTACCAGTACTCACCTGT
ATAACAAAATAGATCACTTATGCGTTGGAAACTGGACTACTATTTCACTAATTCCCTTAT
CCCTGAACAAAGTTCTGATCCAATTCTTGTACACCATGTCATGTGAATGTTAAACTTTAT
TATTGTATTTATGCTCGTTGTGCATGATACATTCTGTTTCCTACATGCAGGACGAAGAAC
TGGGCGCATCTCCCTTCGAGGCTGATGATGCTTTGATGCTTGGTGATGACGATGATGATG
TTTCAGATGATGAAGACGATGATCATGAGGTAGTATTTCAAAATTACTTCGATTGATCTC
TTTGTTTTCCTGCAAGTTAATGTGGCTTTAGTGGGCATGACTGAAAACTGCATATTTTTG
TTGAGAATCCCCAGGTTCTACGTGGGTCTCTTCCTGACTGTGTTCCAGAGAGTGTGCATG
ATGTAAAACTGGCAGATGCTGATGGATCTAGTATTGCCTCAATAGCAAGTGATAACCAGA
CACAACCCTCATCTGGCTCCAGCATAAAACATACTTTTAGTAGCAGGGGAGCAGGTTCTG
TTGAACTTAGAAATCCAAGCACACTTGGTTCGCGGGGCGCGATGTCGTTTGCTGCAGCTG
CCATGGCTGGGCTTGCTTCTGTTGGTAGTCGTGGTATCAGAGGTAGCCAGGATAGGCGTG
GCCTTCCACTTGGAACTAGTGCACATGAGCATTCGAACAAATTGATTTTTACAGCTGGCG
GCAAGCAGCTTAGCAAGCATTTGACCGTATATCAAGCTATGCAACAGCAAGTAGTTCATG
ATGAGGATGATGAGGAAAGGTTAGGTGGTTCTGATTTACCCAATGATGGAAGCCGTCTCT
GGAGTGATGTGTTCACTATAACATATCAAAAGGCTGATAACGAAGTGGATAGGGAATCAA
CCAGAGGTTCATCTTTAGTGCTGAAATCGTCCAAATCAGAACTTTGCAGAGCTACATCTC
AAGAACAATGTATTTCTCTTCTTGATAGCATTTTGCAAGGAGAACTTCCTTGTGATATTG
AGAAATCGACCCAAACTTATAATATTTTAGCACTATTGCGTGTATTGGAGGGATTGAATC
AGCTATCTCCTCGTCTGAGACTACAGGCAACCTGTGATGATTTTATAGAGGGAAAAGTTG
GTACCCTGGATGGGTTATATGGCACCGGAGCTAAGGTACCCTCAGAGGAGTTTATCAGCA
GTAAGTTGACACCAAAGCTTGCTCGGCAAATTCAGGATGTTCTTGCACTCTGCAGTGGTA
GTTTACCTTCTTGGTGTTATCAGATGACCAAAGCTTGTCCATTTCTGTTTCCTTTTGAAA
CAAGAAGACAACACTTCTACTCCACAGCTTTTGGGTTATCTAGGGCATTGAATCGTCTTC
AGCAACAACAGGGTGATAATAATAGCTCAGCGACTGAAAGAGAAGTCCGGATTGGTAGAT -continued TGCAACGCCAGAAAGTTCGTGTTTCTCGTAACCGGATCCTGGATTCTGCTGCCAAAGTAA
TGGAGATGTTCTCCAATCAGAAGGCTGTTCTTGAAGTTGAATACTTTGGTGAAGTGGGAA
CTGGACTTGGTCCAACTTTGGAGTTCTACACCCTCTTAAGTCATGACCTGCAAAGGGTTG
GCTTGGGATTATGGAGATCTGATTCTGATTCTTTAGAAGCTAAAAAAGTTGATTCGCATT
CACCTGCTGATAGCAGGAACTTGATACAAGCACCTCTTGGCTTGTTCCCTCGGCCTTGGC
CACCTAGTACTGCTTCTTCAGAGGGTAGTAAATTCTTCAAAGTTGTGGAGTATTTCCGCT
TAGTTGGTCGAATCATGGCAAAAGCATTGCAAGATGGAAGGCTTCTTGATTTGCCTTTGT
CAACAGCATTTTATAAGCTTCTACTTGGACAAGTAAGCATGAGAACCCGCTTGCAGTAGA
TCCATTCCAATATTCCCTTCCACCTTCTTGTCAAGTCTTGGTATTTTTTTTTTATTTTCT
CTACTGTCTTCTGTATTGACGCCAAAATATTTGCTTTACTAGGAACTTGATTTGTATGA
CATACTATCTTTTGATGCTGAGCTTGGTAAAATACTTCGAGAGTTGCAAGTTCTTGTTGA
ACGCAAGCGATTTCTGGAGTCCTGCTCTAATCATAGTCAACAAATAGAAGAATTGGGCTT
TCATGGTGCTCCTATTGAAGACCTATGCTTAGATTTTACTCTTCCGGGCTATCCGGATTT
TGTTCTGAAGGAAGGTGAAGAAAATACAGTGGTATGTGATGGAGTAGATTAGGTTCTTAT
GTCGTCATCACTTCAGCTTTTGCTTCTAATTTTGTTGTTGACTATTCATTGTTATTTTTA
ACTTCCTGTAGGTCTGCATTTACAACTTAGAAGAGTACATTTCGCTGGTAGTGGATGCTA
CACTTAAGACTGGAATAATGCGTCAAGTAGAAGCATTCAAAGCTGGATTTAATCAGGTTT
TCTCATTTTTCTAAGATATCTTATTTGCTGGCAATTATTGTTAATTAGCTATTGCATTTC
TCTTAATTTTTTTCTTCTAATTCAGGTATTTGATATATCATCACTCCAAATATTTTCTCC
TCAAGAGCTTGACTATCTCATTTGTGGTCGACGGGAACTTTGGGAGGTAATGCCCTGTTA
ACTTTATTTCTCCCTTCTATAATCATTATTTTAACTTGTTCTGAGCAAATGCATGTAATG
CAGCCGGAGACACTGGTCGAACATATAAAGTTTGATCATGGTTATACCTCGAAGAGTCCA
GCAATTGTCAATGTGAGTACATCATCTTTAAAAAAGGGCACATCTCTTCACACAGCTTTA
TTTCAGATTTTTGGAACTTCAGTTTAATGTTTGTGCTGTTGGTTTGCAGCTACTTGAGAT
CATGACAGAATTTACTCCGGAGCAACAACATGCATTCTGCCAGTTTGTGACTGGTGCTCC
TCGGCTTCCACCTGGTGGCTTAGCCTCCCTAAATCCTAAGCTGACTATCGTTAGGAAGGT
AAGCCTGTTTTAGCAATGCAGAATGACATCATTTCTGCGTTCATGTTATTTAAGCTTTTC
CATTTTGTATCTTGGCCAGCACTCCTCGACTGCGGCGAATACTTCAAATGCAGCTGGAGC
AGCAGAGTCTGCAGATGATGATCTGCCTAGTGTCATGACTTGTGCCAACTATCTTAAACT
TCCGCCATACTCGACAAAGGTTTGGTTCTTTTGGTTGATGAATTTTTGTTCCACCTTTCC
GTATCGTCTTGCCTGGAAACTGACTTCTGCTATGGTCGTCGGAACATTGTTGCAGGAGGT
TATGCACAAGAAGCTGCTTTATGCTATCAACGAAGGCCAGGGGTCGTTTGATCTTTCATA
G SEQ ID NO: 50: *Triticum aestivum* UPL3 protein sequence
TraesCS2D01G060300LC.1_protein
ARRSVVLSPPAPQPPMDFPADGNNNPPPRRRGGRASNADKGKEQQEPSESSRVREAERML
GLSFDGMDDDDEGHGAFPHGLTSASSALQGLLRKLGAGLDDMLPSSALSAAAAAASSSSM
SGPNGARMKSMLAGLRADGEEGRQVEALTQLCEMLSIGTEDTLAGFSVDSFVPVLVGLLN
HESNPDIMLLAARALTHLCDVLPSSCSAVVHYGAVACFCARLLTIEYMDLAEQSLQALKK
ISQEHPTACLRAGALMAVLSYLDFFSTGVQRVALSTAANMCRKLPSDASDFVMEAVPLLT
NLLNYHDAKVLEHASVCLTRIAESFASSPEKLDQLCNYGLVAQAASLIAVSNSAGQASLS
TLTYTGVIRVLSICASGSPLAAKTLLLHGISGTLKDILSGSGLVAGTTVSPTRPADQMYE
IVNLADELLPPLPAGTISLPAHSHVFMKGSSVKKPGSSKQGESGSTDIKVSGREKLLRDQ
PELLQQFGMDILPTMTQVYGSSVNGPIRHKCLSVIAKLMYYSSAEMIEILHGTTNISSFL
AGILAWKDPHVLVPALQIAEILMEKLPGTFSKMFVREGVVHAVESLICQEISSPMLFQVP
QQDKDIDSGTCTSSRSRRSRRRSSAGNTDNNSLDEPKGSHTTIANSPPSTLEGPNTRIRA
SVSDRAKSFKDKYFPSEPGSSDIAVTDDLLKLRALCAKLNATADTVKTKAKGKSKSLGGD
DFDILCNVEEQLDDIIDKILSELSNGDGVSTFEFIGSGVISALLNYLSCGTFGKEKVSEA
NLPKLRHLALRRYKAFIYVALPNDAVGNQTPMAFLVQKLQSALSSLERFPVVISHSGRTS
SLGGSRPSSGLSALSQPLKLRLCRAAGEKMLKDYSSNIVLIDPLASLAAVEDFLWSRIQR
SESISYPAVSSGKNSESVAPSATAPVASSTQSVRRPSTRSKSLADADSATKKDIQEGSGN
TSKGKGKAVVKSTSDEPKGPHTRTAARRKVASQKDAEVKPPHGHSSSEDEELGASPFEAD
DALMLGDDDDDVSDDEDDDHEVLRGSLPDCVPESVHDVKLADADGSSIASIASDNQTQPS
SGSSIKHTFSSRGAGSVELRNPSTLGSRGAMSFAAAAMAGLASVGSRGIRGSQDRRGLPL
GTSAHEHSNKLIFTAGGKQLSKHLTVYQAMQQQVVHDEDDEERLGGSDLPNDGSRLWSDV
FTITYQKADNEVDRESTRGSSLVLKSSKSELCRATSQEQCISLLDSILQGELPCDIEKST
QTYNILALLRVLEGLNQLSPRLRLQATCDDFlEGKVGTLDGLYGTGAKVPSEEFISSKLT
PKLARQIQDVLALCSGSLPSWCYQMTKACPFLFPFETRRQHFYSTAFGLSRALNRLQQQQ
GDNNSSATEREVRIGRLQRQKVRVSRNRILDSAAKVMEMFSNQKAVLEVEYFGEVGTGLG
PTLEFYTLLSHDLQRVGLGLWRSDSDSLEAKKVDSHSPADSRNLIQAPLGLFPRPWPPST
ASSEGSKFFKVVEYFRLVGRIMAKALQDGRLLDLPLSTAFYKLLLGQELDLYDILSFDAE
LGKILRELQVLVERKRFLESCSNHSQQIEELGFHGAPIEDLCLDFTLPGYPDFVLKEGEE
NTVVCIYNLEEYISLVVDATLKTGIMRQVEAFKAGFNQVFDISSLQIFSPQELDYLICGR
RELWEPETLVEHIKFDHGYTSKSPAIVNLLEIMTEFTPEQQHAFCQFVTGAPRLPPGGLA
SLNPKLTIVRKHSSTAANTSNAAGAAESADDDLPSVMTCANYLKLPPYSTKEVMHKKLLY
AINEGQGSFDLS Other UPL3 promoter homologues:
SEQ ID NO: 51: *B.Oleracea* promoter
ACAAAGGAAGAAACCCCTCCACACGAGTCTCTCTTATTCAGAGAGATTCCGATCGCATCTCAACTGATCC
AGAAACCGATCGGATTAAGCTCGCTCGAAACCCTAATTTGCTAGCGAGATCGTTAGGAGCTAGAGAGAAA
CAAACCTATTGATGAACGAATTCGAAATCAACGCAAAAGGGGCTACGAGATCGAAATCGAGAGAGGAAGG
AAGGAGGATCTTGATTTCTTTCGAGATTAGAAAACCCTAAATCGAGTAATGAGAGAAGAAAGGGATGAAA
AGGGCTTTTGCGCAAAATATATAGATTCAAGCGAAGCGAATACGATACCGTTTTCCTCCGTCCAGCTTTT
CCGACAAGAACTGACACGGGGATCCCCGCTACGTGTGATTCGTTTACTCCATTAAGCTTAATACGGTGTC
GTTTTACACTTTATCATGGGCTGGACAGATGGAAACAAAATAAGCCCAAGATATAAGGCTGGGCCCAACC
ATCAGCCATAGATATCTGCAAGCTTGCACGGGTTTAAGCCCCCACTATGATGGAGGTTCGCTTTCTTATA
CTTTCAACTCTACCTTCTCACTACGATCCATGGACTATATAACACATTACTCATTACAATTATATATATG -continued ATCTATGCAAAGATACAAATATATTCTTCTTTTATGATTGTAGTAAGGAAAAACTATGGTTTGTCGAGAA
AATAATTAGTCATTACAATTATATATATGATCTATGCAAAGATACAAATATATTCTTCTTTTATGATGGT
TTGTTAAGAAAATAAATATGATAATAAAATCTATCTATCTACTTATTTAAATGAATCTACTCAATGAAAT
GCAGGTGATCTATGCAAAGATACAAATTTATTCTTCTTTTTTTCTTTAGCCATCACACGCTAATTTAAAA
TCTAAATGTAGAAATTTTTGTTGTTTGGGTTTGAGTTTGTTAATCGGATGAAGACATATATAAATTATTG
TACATATTTTATAAAAAAAACATGACAGTATATAATACATTAGTTCTTTTATAAGTGTGCCCTTGTTTGG
AACTTACAGATTTTTTTAATATATATATATATATATACATATTAATTTAACCCGAAAAACAGAAATTATG
ATTCATTTATAAATCCAATATGAACATACCGAGGGAAAAAATCGTCGGTACGTCGTCGGAATAACGTTAT
TCCGACGACATACCGACGAAACAAGTCCTCGGAAATAACTCCTCGGAAATTCATTTTTTCTCGGAAATCC
CTCAGAAATTTCCGAAGGAATTCCGAGGAAATGAATTTCCGAGGAAACTCCGAGGACCACCAGTTCGTCG
GAAAGGTTCTCGGAATATATCGAGGGAGAACTTCTTCGGAATATTTCGATGGACTTTCCGATGGTCCAAT
CCTCGGAAGTTTCGATGAAATGTTCCTCGGAATTTTCATCGGGAATTTCCGAGAAACGGAGCCCTCAGAA
AATTCCGAGGAGGAAGGAGTCCCTCGGTATATTCCGACGACTTATTCTGAGGAAATGTTCGTCGGAAATT
TCCGAGGGTTCATTTCCTCGGAATTTCAAAAAAAAAATTAATTTTTTTTTAAAAATGAAAATTTTGAAAT
TTAAATTCGAAAATATAAAATTAAAATTAAAATTGTCTCCAACAAAGATATGCGATCATCCTTGTCCTTC
AACTGAGCCGTAAATATTTCTGGATCAACAAATGGCGGTGGTGCAGAAAAAGTAGGAACCGACCGAGAGC
GATGACCCAAACGTCCCTTCTTCTTTGGAACCGACTGAAATAGAAAATAGCCAAATTTAAATAATATAAA
AAGACGATAAAATAAAAATCAAGAAATAAATGAATTGAACTTTAAAAAAAAAAACTTAC SEQ ID NO: 52: *B.rapa* promoter
AAGCGTGCGGAGGCGACCTCAACTGCCCCATCTTCTTCTTCTTCCTCTCCTCCTCCTCCTCCTTCCTCAG
GTCCCACCACTCGCAGCAAACGCGCTCGCCTCTCGTCTCCCTCTTCATCTTCAGCCGCCGCTACTGCACC
TTCCTCCTCCACCCGCTCTCGTTCTTCTCGCTCTACCACCGCTACAGTCGCCGTTACTCCCATGGACACA
TCCACCGAGTCTTCTGGATTCCACCGCGGCGGAGGACGAGGTAACAGGGGAAACGATAATACTAACTCTG
ATAAGGGAAAAGAGAAGGAGCATGAGGTTAGGATTAGGGATAGAGAAAGAGACAGAGCTAGGCAACAGCT
CAACATGGACGCTGCAGCTGCTGCTGCCGCCGCCGCTGACGAGGACGACGACAATGATAGTGAGGATGGC
AACGGGGGATTCATGCATCCCAACATGAGCTCAGCCAGCAGTGCGTTACAAGGGTTGCTGAGGAAGCTTG
GAGCTGGACTTGATGACTTGCTTCCTTCTTCAGGTATTGGCTCAGGTTCGTCTTCTCACTTGAATGGGAG
GATGAAGAAGGTACTCGCTGGCTTGCGCTCTGAAGGAGAAGAGGGAAAGCAGGTCGAGGCTTTGACGCAG
CTGTGCGAGATGTTATCTATTGGGACCGAAGACTCCCTGAGCACCTTCTCTGTTGATTCCTTCGTCCCGG
TTCTTGTTGGTCTACTTAACCATGAGAGCAATCCGGATATTATGCTTCTTGCTGCCAGGGCTCTTACTCA
TCTGTGTGATGTTTTGCCGTCTTCTTGTGCTGCTGTTGTTCATTACGGGGCTGTTTCGTGCTTTGTCGCC
AGATTGTTGACAATAGAATACATGGACTTGGCCGAGCAGGTTCGATTTCCTAACAATTCTTGAATTTTTT
TGCTGAATATATATTGTGGAATGTTTTATGCTGCAGTTTCTACACGTACATATCCAATATTTTAGTTTAC
TTAGGACGAAATTTGAAATTTGATTTTATTCTTCATGTGATTTACAACAGTCTCTGCAAGCTCTCAAAAA
GATATCTCAGGAACACCCAACGGCCTGTTTGCGTGCTGGTGCTCTTATGGCAGTGCTATCATATCTGGAT
TTCTTCTCCACCGGTGTCCAGGTGGGTAATTTTGTAACTTTTCTTTAATGCTTTCCATACTCGTTTATCT
AATGCACTTTTTTTTTTACTTTTTGTAGCGTGTAGCAGTATCTACCGCTGCAAATATGTGCAAGAAGTTA
CCTTCTGATGCATCTGATTATGTTATGGAAGCTGTACCGGTACTGACAAACCTACTTCAGTATCATGATG
CGAAGGTAAACGATCCCTTTTTTTTTGCTATAATGTGGTATTATCTAGTTCTGCTCTTGCCCCAGTTTCC
TTCATAGTATGTTCGTACGGTGGCAGGTTTTGGAATATGCTTCTATCTGTTTGACTCGGATTGCCGAAGC
ATTTGCATCGTCCCCTGATAAATTAGATGAATTATGCAACCATGGCCTGGTGACTCAAGCTGCGACTCTT
ATATCCGCTAGCAACTCGGGAGGTGGGCAAGCATCTCTCGGTGTTTCAACATACACGGTATGAGTTAATT
CTTTTGTGTTTTCTATATTTCGTTATTCATAGGATGACATTTTCATCATATTTTCACAGGGATTAATCCG
ATTACTTTCCACCTGTGCGAGCGGTTCACCTCTTGGGTGCAGGACATTACTTCTTCTCGGTATTAGTAGC
ATTCTTAAGGATATTCTGTCGGGTTCCGGTGTCTCTGCTAATGCATCTATATCCCCAGCACTGAGCAGGC
CTGCAGATCAGGTACGGATTTACTTTTTGACATCACAGACTTTATTTTGTTCAATTCCTGATAAAGTCTA
TTCAGTAAAAAGTGTTTTGTTTAGGGGACACACCTTTAAATAGATCATCAACATAAATTGTGTGTTGAGT
GAGATGCTTAGGGGACACACCTTCAAATAGATCACTTGCATTTAAATGGATCACTTGCATTTAGGAGTTT
TGTCTATTCAGTTCAATGATAATCTTTTTTTTTTTGTAACACTCAGCTCAATGATAATCTATGTACATGT SEQ ID NO: 53: *Z.mays* promoter
ACAAAGGGAGCGGAGAAAGGCAGCGGCCGCCTCGCAGCGGCGCCGGTGGCGACGCGGCTATGAAGGGATA
GGCGAAAGAGGCGGGAACATCGGAGGTGTAGCGATCGGGGAGGGGGTGAGATCTGGCTTGGGTGGGGTTG
GGAATTTGAGGAAGGATGGGGATGGCTGCGCCTGCGCGGTGGTGACGCAGGAAGAGGCCGGAGGTTAGAG
GGAGGAGCTCGTGATTTGGGGGCCGGCTTTCATGCGGTATACGTGCTTCACACTGCGAGGGTGCTTCACA
CTGCGAGGGTGTTGCTGGGCTTCGCTAAACCCACGGCTTTTGCTAGGTCAGCGTCCGTGAATTGCTACGG
AAGGCTATCCATCAATCAGCTCAGCAAAAATGTCTCCATTCAACTGTAACGCATGCACGAATCAGCTCGA
TACAAAAATCTTACAACATATATGCACAGGGTATATATTTGTTTAAATATTTTTATTTTATTTTAAAAAA
TCTAAAAAATATATCAGGATAATTCTATTTCCAAATTTACTCGTTTGGCACACCTTTATTGTGTGGCCTT
GTATATCTTGTATTCCCCGTAACAACCTTTGGCCAACAGATTTTTTTAATTTGTTATCTATAGATGGATA
GGCCCTCTCATGTAAACCAAGTATCTAGGTCAAGTCAAGGTTGTTAGGTGGTTGTTGCATCTAATATAAG
TCTTGTGCACTAGTGTGAGCACGACGGTGGAGTCTGTAAATGAGGAGAATGTTGATTTAAATGGCGAGGC
CGTCGGCAAGCAAGATGTGGGCCGCTCAGTTGGCGATGGGTTGCGGCGCAGTGCAAGAGCCCGCCAACCA
AATGTGCATGTAACAGGCCCAAAACTAGATGTAATAGAGGCAGGTAGGCGTATAAGAGCGTGGGAGGGTG
AGCAGTGTTCGGCAAGAAAGAAGAAACATATGTAATCTACCTGCTACTCTGTGATCCACTAGCTACTCTG
TCTGAGAATTGGAGTTCCTCGGTTGCTCCTATCTCTTTTGATCCTGTCTACTTCTTCATCCCCTCTGTGT
GCTAATATTCTGGTATCAGATTCATCTCAGAAAGTTCGTCGCCCATCTGGAACTGTCGGCAGGATACAAC
TACTTCACATGTTTCTAGCAACATTAGAGTGCCATGGATCCTAACACCACACCTCGACGAGATGGAGAAG
AGGTTTTCGACCATGGAGTCGCGGCTGGAACGGAAGCTCATCGATCACACCGCGATGAAGGATGAGCGCA
CCAGCGCTCTAGAAGGCGCCGCTGAAGAGTTGGCGTTGTGGTGACCCAAGGTGGAGGCATACATGGATGA
TATCAAGTTGGAGCTGCGTCGGCTCACCAAGCACTGTGATCGCTCGGTGATGGAGGTGTCGGCATCGAAT
TTTGGTCTTCTCGGCATGCCTGATCCGCCGTCGATACGCTCTGCATCAGGCAAATTCTTCGACGGCCCAT
TCGGGCACCGTGATGATCAATTCATACGGGATCATGGTTTTAGGTCTATCAGGACCCTCCTCCCTGACCC
GACCAAGGGTACGCATCCAATACATCCTCCATCGACCAATATTCGTTTTCATGGTCCTTTTTATGATAGC
TACCTACATCGTTCACGTTTTGGGGATCCTGCATTTCGTACTAACGGCAAAATGCCCAAGTTGTTGTTCT
CCCTGTTTGATGGAGATAATCCAAGGCTTTGGAACATTCGATGTGAGACTTATTCCAAAATGTACTCAGT
TGAGCCCGACTCATGGGTCGAAATTGCCTCCATGCATTTATCATCACAGGTTGTGTGCTGATTAGTCGGT
TGAACGCAAGCACCATCGCTTGGGTTGGCCATTGCTTTATCGTCTGTTGCATGAGTGGTTTGGTCGAGAT -continued TAGTACCAAACCTTGCTTTGGGAATTATTCTGTATTCGCCAATCATCGGGTGTAGCAGAATATATTGAAT
GTTTTCCACTCTAGTTTATAAGCTCTCTACATATGTGTAACACCCTGAATTTGGGGTATAAAATTTCTGC
TTTAAATACCTACCAAATTTAGGTGTTACC SEQ ID NO: 54: Rice promoter
TTCCAGATCTTTCTCTGAAGCAGCTTTTCTGCGAGTAGCATTCCGTGTATTAGGTCCTTTTGGTTCTTCT
GAGTTTGGTTTTGCAACAGCCTTCCCCTTTCCCTTGGCAGTGTTTGTGCTTTCCTCCTGAGAATCCTTCT
TAGATGCACCACTACTTGCAGCAGATGATTTTGATCTTGTTGTTGGACGCCTGCCAGATGGAGCTGGTGC
AGCTGTGGATGACGCACCAGCTGCGGTGCCAGGTATGCCAGATTCAGAATTATTTCCTGATGGAACTGTA
GGCTTCGAAGCAGCCTCACTACGCTGAACTCTGGGCCAAAGAAACTCTTCAACAGCTGCTAGACTCGCAA
AGGGATCAATAAGCACAATATTTGACGAATAATCCCGAAGTGATTTTTCACCCTGACCTCGACAAAGGCG
CAACTTGAAGGGCTGAGCTAGAGCACTCAAACCTGAAGTCAAACGGGAGCCTCCAATACCTATTCTGCTG
GACTGGCTGAGCACAACAGGGAAGCGCTCCAATGAACACAAAGCACTTTGCAGTTTTTGGACCAAAAAAG
CCATAGGAGTCTCATTCCTTTCATGGTCAATAGAAAGGGCAACAGATATAAAAGACTTGTATCGCCTAAG
CGCCTGCTGACGAAGCTTTGGCAGGTTTGCCTCAGATACCCTCTCCTTTCCAAATGTCCCACAGGACAAA
TAGTCAAGCAATGCTGCAACAACTCCGCTTCTAATGAACTCAAATGTTGATACGCCGTTAGTTTTGCTAA
GCTCAGTAAGTATTTGTGTTATTATCAGCTCAAATTGTGCCTCCACATCATGTGAGATGTCAAAATGAGT
GGCACTTAACGCTTTTGATTTCCCTTTGGCTTTTGTCACGACATTCTCACTTGCAGAATTTAACTTTGCA
CAGAGTGTTCTCAGTTTAAGAAGATCGTCAGTAACTCCAAGATCTCTTGATTCATGGTCAGAAGGGAAGT
ATTTATCTTTGAACGACTTTGCACGATCACTAACTGCAAATCGAAGACTGGTGTTTTGAACTTCTGTAGA
GCATGGTGTTGAGCTGGCAATCCCAGGATTGGAAGTGTTTGATTCATCTAATGAGCTGTTTTCTGTTGGT
GCAGCAGCACCACGCCGGCGCTGGCGTCTAGAATGCGAGGGCATCACAGATTCATTGTCTTTATCATGTG
GCAATACCTGAGAAGGCACCATATCAGAGGATTCTGGACATATAAGCGACTCCACAGCATGAACGACACC
TTCCCTCACAAACAACTTAGAGAATGTCTCAGGAAGTTTTTCCATCATAATTTCTGCTATTTGAAGAGCA
GGAATCAACACTTGCGGATCTTTCCACGCAAGAATGCCTGCTAGGAAGCTGCAAATGGAAATTATGTAGC
TTAGCAAGGATCAGAAATGAAGGTGTGTCTACTTGCACAATACAAGAAATAAAAGCTTCCAATATACATA
TGCCAGTAAATCATTAGGTTGTGCCAAGGAGTGACTGGATCATTTCAGCAGGGCTGTAGCACATTAGTTT
TCCAGTTTTCCAGTGATTGATAAGCATTAGTTTTCAGCAGTCTTATTCTTCCAACATAAATATGCTTATC
AATAAAAACTTCCAACATAAATACAAGAAAAGAATAAGACTGAAGCAGAATCTTGTATTAGCACCTGGAT
ATGTTTGTTGTGCCAAGGAGGGACTGGATCATTTCAGCAGAGCTGTAGTACATTAGTTTTCCAATGATTG
ATAAGCATTTGTGGCGTATCGGTGCATTTACACTTGAGCCATACACCTGTCCAAGAACAGATGCCATTAA
GTACAGAAACCCTGACATATTCCCAAAAGTAGTAGTACTCCATCTGCCCCAAAATATAGCAACATCTGGC
TATGCACCTGGACAAAGTTGCTCTATTTTGGAAGGTAGTAGTTATGTTCACTGACAAGAAAGAGGATCTG
GGCACAAACCTGCGTCATTATGGGTAATAAGTCCATACCGAACTGCTTTAGAAGCTCAGGGTGCTCACGT
AATAGTCTCTCATGTCCTGACCT SEQ ID NO: 55: Barley promoter
CCATAGTTTTTCCTCTAGATCGTGTTTCTGCGGAGCTCGGGCGGAGCCCTGCTGAGACAAGATCATCACC
AACCTCCGGAGCGCCGTCACGCTGCCGGAGAACTCTTCTACCTCTCCGTCTCTCTTGCTGGATCAAGAAG
GCCGAGATCATCGTCGAGCTGTACGTGTGCTGAACGCGGAGGTGCCGTCCGTTCGGTACTAGATCGTGGG
ACTGATCGCGGGATTGTTCGCGGGGCGGATCGAGGGACGTGAGGATGTTCCACTACATCAACCGCGATCT
CTAATCGTTTCTGCTGTACGATCTACAAGGGTACGTAGATCACTCATCCCCTCTCGTAGATGGACATCAC
CATGATAGGTCTTCGTGCGCGTAGGAAAATTTTTGTTTCCCATGCGACGTTTCCCAACAGTAGGGATTTT
TTTTTTAAATTACTACGATCCCCAACACCACCAGCCCCGGAGGGCCACATGGGCCGAGCCAAGGTGGAAC
CAGCCACCTAGGTGGGCTGGTTCGGCCGGCCAAGGCCTGATGGCCAATTGGGCTGGGAACCCTAGGGCAA
AAGGTGGTCCACCTCCCAACTTGGGAGGCAAGCCACCTCCACCCTGGCCGCCGCCCCCTCTTGGGTCGTT
GCCCCTCCCATCTAGGGTGCGCCGCCCCTCCTAGGGTTTCCTAGGGTGGCCGGCCAACCCTCCCCCTCCT
CCTATATATACCAAGGGTTTTGGGGCTGCAACACACAAGTTTTCTTCCTTCCTTGGCACACCCCTGCTNG
TACCACCCAGCTCCACCGTCACCACTTCGTCGTGCTGCCGGAGCTCTCCCTCAACTTCTCCTCTCTCCTT
GCTGGATTAAGGTGAAGGAGACATCACCGGGCTGCACGTGTGTTGAATGCGGAGGGACCGTTGTTCGGCG
CTTAGATCAAAATCTTCCGCGATCTGAATCGCTGCGAGTACGACTCCATCACACGTGTTCATAGTAATGC
TTCCGCTTAGCGATCTACCCCTTGCTCGTTGCTAGCATCTCCTAGAAGATCTTGGTGTGACGTAGGTAAT
TTTTGAATTATTACTACGATCCCAATAGGAACAACAAGGTTGATTTAGAGGCCCTTCGTGATTGATGCCC
CCTCCGACAAGGCTCCAGATGGGATTACGACGGAAGAGAGATTTGCTGCGGCAAAAAAAGTGTTTCAGGT
GGCTCACCGGTGTTTTCTCAATATATAGGATTTATAGAAGTAGAGTTAGTTCAGGAGTGTCGGTAGGTGG
TCCCAATCCATCAGGACGCGGTCACTCCCTGGGCACGTCCTGTTGGCTTGGCACCACCCATGTGGCGTCT
GGTCTCCTCCAAAGCTTTCATTTCTTATTTTTGTCCAGAAAAAATCGTTAAAAACTTCCGTTGCATTTGG
ACTTCGTTTGATACTGATTTTCTGAAAAGCCAAAAAAACACAGAAAACAACAACTACATGTCCAGAAGGT
GATCAAGGCTAATGTGGACGGTGCTCTTTGAAAAGACCAGGGCTCGGGAGTTCTGGTCTTGTTCTTCGGA
ATAGCCATGGCGGATTCATTGCACATGCATGCCATTTTTTCCCGTAGCTGCCAATGTTGAGGTGACAGAG
CTCCTTGCGTGTATACGAGCCATTGTTCTTGCACAAGAACTACATGCCCAGAAGGTGATCGTAGAGACGG
GCTCGCAAGTGGTGGCAAGAAAAGTAGTATCTATTCAAAAAGATCTCTGAGCTAATGGGTAACTAGGTGA
GGAGATCAAAGTGTTGCTTGGAGCTTTTGATGAGTTTCGCGTTGTTTGGGGGCGACGGTCCATGAATAAA
GTCACGTATATTTTAGTTAGAAAAGGTTGTTGCAACTCCTTATGTAAAACTTGGCTCCATGTTCCATCGA
AGTGTATTCGCTCGGAGGTAGGAGACGAGGGGCCGTGAACTTTGAAATTTGAATAAATTGACAACATTTT
CTAAAATACAACAAAAACATTTACACGTTGAATTATTTTCTTACTTTTATTTTATTTAAAATATCAAAAA
TATTTATCATACACTATCTTTTAATAGGCTCATCCAACCGGCAAGATTGACACCCTTATAAGATTGTTGG
AGGTATACAAGGGTTTTATTTGTATTACTATTACAAGACATCCAACTACTCGACACACCTGTATGTTCAT
AGACTTACACATTGATTTCTCACTTACGAATGATGTCTATCACTATCACTTGATACAAGCCGACATACGA
AAAGAGTGGAGACGACCAATTCAGATGATTTTGGTGCGACTTCACTTGTTATCAAGGAGTTTCCTTGTTG
GTTTTTGGTTTATGTGTTCCTTACCTTAACTGTGCTATCTTACTCGCGG SEQ ID NO: 56: BnaA08g17010D_promoter (*B.napus*)
ACAAAGGAAGAAACCCCCCTACACGAGTCTCTCTTATTCAGAGAGATTCCGATCGCATCTCAACTGATCC
AGAAACCGATCGGATTAAGCTCGCTCGAAACCCTAATTTGCTAGCGAGATCGATCGGAGCTAGAGAGAAA
CAAACCTATTGACGAACGAATTCGAAATCAACAAGAAAGAGATCGAAATCGAGAGAGGGAGGATCTTGAT
TTCTTTCGAGATTAGAAAACCCTAAATCGAGTAATGAGAGAAGAAAGGGATGAAAAGGGCTTTTGCGCAA
GATATATATATTCAAGCGAACCGAATACGATACCGTTTTCCTCCGTCCAGCTTTTCGGACAACTGACACG
GGGATCCCCGCTACGTGTGATTCGTTTACTCCATTAAGCTTTATACGGCGTCGTTTTACACTTTATCATG GGCTGGACAGATGGAAACAAAATAAGCCCATGATATAAGACTGGGCCCAACCATCAGCTATGCACGGGTT
TAAGCCCCCACTATGGAGGGGTTCGCTTTCTTATACTTTCAAGTTTCAACTCTACCTTCTCACTACTATC
CATGGTATATATCAAAACACATTACAATTAGTCATATACAAAAACAAAATACAAATATATTCTTCTTTTA
TGATTGTAGTAAGGAAAAACTATGGTTTGTCAAGAAAATAAATATGATAATAAAATCTATCTATCTACTT
ATTTAATGAATCTACTCAATGAAATGCATGTGATCTATGCAAAGATACAAATTTATTCTTCTTTTTTTCT
TTAGCCATCACACGCTAATTTAAAAACTAAATGTAGAAATTTTGGTTGTTTGGGTTTGAGTTTGTTAATT
GGATGAAGANNNNNNNNNNNNNNNNNNNNNNTTTTGCCTAATATGTCTTGCAAAATAAGCAAAGATATTTAT
TCTCAACTAGGGTATTGTCCCTCTACTATATATTCTACCCGAGTACAAACCCATTCTACACATTCTTTTA
CCATTTACGCTGATGAAACATTACAAATGGTTTTAGCTGATGAAACTGTTAGTTCTATAATATTTGTATT
TTTTTTTTGAATTTTATAAAGTAGACTTTGAGCAAAATCATCTTTTCCTATTTTTGAATGTTTTTTTGTA
ACTTAGTTTCATTATTATTTTTGGTTTGTCTAAATAATGTATTTGTTTTCAAAAATTTCAATAAAATATT
TGAACTTTATATTCAACTTTTAAATAAAATATTTATAATTTAATTTAATAAAACCCCAAATATACTTAAA
CCTCCGATACTTTACTATTTAATTTACCAAATAAACTAAATAAAAATACAATAAAAGAAAAACACAATCT
CATAGTTTAAAAATGATGGCTAATCATATTGAACAAGACACACCGAAATCAAACCTGAAAAACATATGAA
TCTATAACATAATAAGTATAAACAATTAAATTTATCAAATTTTCAAAAGTTAAAAATATATGATTATGAA
AAACAAAATCATCCTTTTTTGAACAAGAAGAAAGCCCCCACGTTCTGTCTTGGATGGTATTACCAATATT
TCACATTCTTTATCTAATGGAAACGAAGAAACAACAACAAACATACATCGTGATATCAATCAAGAGGATA
ATGATTTTGTTAAAGGATGATGATTTTATTCATAGCCTTTGAATAAATTAATTTCCGTAAAAGTTATACC
TTATTTATCTATTTCATATATCATACTAACTCATAATTCTTTATTTCATCATATTTTAATGGTTTTCAAT
AGAAATGTGGTCCAAATTAAATTACCTTATCACAGTATGATCAATTTTGTTGCCACCGTGTGATCAAATT
ATGTTACAGCAATATTTGTATTATGTGATGTATTTTTGTCATTATTTGTATTAAAATTTTGATATATTAT
ATAATGGTGTAAAAAATTTTAATTACATTAAGTAAACAGAAAAAAAACACCCGCCCGGTCGGGCGGGACC
AGATCTAGTTACTATTCATTTATAAGTCCAATTTGAACAAAAGTTCCCAAGACAATTTATTACATTCTAG
GTAGATAGTTTCTAATG SEQ ID NO: 57: BnaC03g60060D_promoter (*B.napus*)
ACAAAGGAAGAAACCCCTCCACACGAGTCTCTCTTATTCAGAGAGATTCCGATCGCATCTCAACTGATCC
AGAAACCGATCGGATTAAGCTCGCTCGAAACCCTAATTTGCTAGCGAGATCGATAGGAGCTAGAGAGAAA
CAAAGCTATTGATGAACGAATTCGAAATCAACGCAAAAGGGGCTACGAGATCGAAATCGAGAGAGGAAGG
AAGGAGGATCTTGATTTCTTTCGAGATTAGAAAACCCTAAATCGAGTAATGAGAGAAGAAAGGGATGAAA
AGGGCTTTTGCGCAAAATATATAGATTCAAGCGAAGCGAATACGATACCGTTTTCCTCCGTCCAGCTTTT
CGGACAAGACTGACACGGGGATCCCCGCTACGTGTGATTCGTTTACTCCATTAAGCTTAATACGGTGTCG
TTTTACACTTTATCATGGGCTGGACAGATGGAAACAAAATAAGCCCAAGATATAAGGCTGGGCCCAACCA
TCAGCCATAGATATCTGCAAGCTTGCACGGGTTTAAGCCCCCACTATGATGGAGGTTCGCTTTCTTATAC
TTTCAACTCTACCTTCTCACTACGATCCATGGACTATATAACACATTAGTCATTACAATTATATATATGA
TCTATGCAAAGATACAAATATATTCTTCTTTTATGATTGTAGTAAGGAAAAACTATGGTTTGTTAAGAAA
ATAAATATGATAATAAAATCTATTTATCTACTTATTTAAATGAATCTACTCAACGAAATGCAGGTGATCT
ATGCAAAGATACAAATTTATTCTTCTTTTTTTCTTTAGCCATCACACGCTAATTTAAAATCTAAATGTAG
AAATTTTGGTTGTTTGGGTTTGAGTTTGTTAATCGGATGAAGACATATATAAATTATTGTACATATTTTA
TAAAAAAAACATGACAGTATATAATACATTAGTTTCTTTTATACGTGTGCCCTTGTTTGGAACTTACAGA
TTTTTTTAATATATATATATACATATTAATTTAACCCGAAAAACAGAAATTACGATTCATTTATAAATCC
AATTTGAACATACCAAAAGGGAAAAAATCGTCGGTACGTCGTCGGAATAACGTTATTCCGACGACGTACC
GACGATTTTTTCCCTTTTGGTATGTTCAAATTGGATTTATAAATGAATCGTAATTTCTGTTTTTCGGGTT
AAATTAATATGTATATATATATATATTAAAAAAATCTGTAAGTTCCAAACAAGGGCACACGTATAAAAGAAA
CTAATGTATTATATACTGTCATGTTTTTTTTATAAAATATGTACAATAATTTATATATGTCTTCATCCGA
TTAACAAACTCAAACCCAAACAACCAAAATTTCTACATTTAGATTTTAAATTAGCGTGTGATGGCTAAAG
AAAAAAAGAAGAATAAATTTGTATCTTTGCATAGATCACCTGCATTTCGTTGAGTAGATTCATTTAAATA
AGTAGATAAATAGATTTTATTATCATATTTATTTTCTTAACAAACCATAGTTTTTCCTTACTACAATCAT
AAAAGAAGAATATATTTGTATCTTTGCATAGATCATATATATAATTGTAATGACTAATGTGTTATATAGT
CCATGGATCGTAGTGAGAAGGTAGAGTTGAAAGTATAAGAAAGCGAACCTCCATCATAGTGGGGGCTTAA
ACCCGTGCAAGCTTGCAGATATCTATGGCTGATGGTTGGGCCCAGCCTTATATCTTGGGCTTATTTTGTT
TCCATCTGTCCAGCCCATGATAAAGTGTAAAACGACACCGTATTAAGCTTAATGGAGTAAACGAATCACA
CGTAGCGGGGATCCCCGTGTCAGTTCTTGTCCGAAAAGCTGGACGGAGGAAAACGGTATCGTATTCGCTT
CGCTTGAATCTATATATTTTGCGCAAAAGCCCTTTTCATCCCTTTCTTCTCTCATTACTCGATTTAGGGT
TTTCTAATCTCGAAAGAAATCAAGATCCTCCTTCCTTCCTCTCTCGATTTCGATCTCGTAGCCCCTTTTG
CGTTGATTTCG SEQ ID NO: 58: *T.aestivum* 2A promoter sequence (TGACv1_scaffold_114237_2AS 31791 to 32203 (-)
TGTTGCCGCCGTCGGCCGGGAAGTCCATCGGGGGCTGCGGGGCGGGCGGGGAGAGGACGA
CGGAGCGGCGGGCGCGGGTGGGCGCGGGGTGTGCGGGGGTGGGGGTCGGGCTAGGGTTAG
GGTTGGGGCGGGCGCGCTTGGAGGAGCGGGCCGAGGAGGAGGAGGTCGGGGTGGTGGAGG
AAGACGACGAGGCTTCCGCCCGCTTGCGGCTGCGCGTTTCCATACAAGGGGGAGGAGGGG
GAGGGGGGCGGCGGCCGCCTCGTCGGAGGCGGTGGCTGCGGCGCGGCGGCTAGGAGGCGG
TGGGCGTCGGGGGAGGAGGCATCGATGGGCGATCGGAGGAGATCTGGGTGGGGATTTTGT
TGATTGATTTGGGGAGGGGAGCAGGGAGGCGGTGCGGGTGGGGACTGCGGCTGCGGGGGC
GGCGACGCGAGATAAGAGAGAGAGAGAGAGAGACCCGAGGCCTTTGCCGGATGGAACGCGTG
AGCGTGAGGAGGGCCGCTTGGGCTTTTGCGGGGTTGTTCGGCTCTGCCCACGAGCACCGC
ACCGCACCGCACCGCCCTCCCTCGACCTAAGAAAAAGAAGAAGAAAACAAAATCTCCTCA
GAAAGGTCTCTCAAAAGATAAAATACTCCCTCCGAGTAATTCCGAATAAAGAAAGTATTT
GTTTAAATACATCCGTATCTAGATTATCTAGACATGTTTTGGCATTAGATGCATTCATAT
CTAGAAAAAATTATGACATGTAGGAGTAATTTGGAACGGAGGTAATAACATAAACCGAAA
ATTCAATGTACTGAGTTAACCGAAATTGTTTGTCTCTCTCTTCTAAAGAAAGAAAAATGC
TATCGAGGGACGTGGATAGCACAAGGTAAGATAAGGAACACGCAAGCCGGAAAAAATAGCA
AGGAAACTCCTTGGTAAGAGCTGAAGTCGCATCAAAATCGTCTGAATTGGTCGTCCTCAT
TCTTCCCTTGTGCGAGGTAAATTTGTTTTGGCATTGATACTCTGGCCATGCATGTCTAAC
TCTGACAATGTATATCTAGAGATTTGTGGCGAGGTTTTATCTGTGTGTATCTAGTAGATG
AATCCATTCATGATTCTACCAAAGGAAAGCTGTGCTCGTGATCTCCAACCTGAGGCGTCG
CCGGAGCTTTCGGCCAAGGGAGAACATATGAAAGTGCATTGTTTCTTCGATGGTATTCTC -continued GTGTTGATGACAATGGGTGCTAGTGAGGACTAGTGTAGATGACATGTGCTAAAGGTGTAA
TAGTTGGGGCTCCCTCGTATGTTGGTTTGTAGCAAGTGAGTAAATGTCTTCCCTTCATGA
TAAACCCAACAATCTATAGAGATGCAATAGTTGGATGTCTTTAACATCAATAAAACCCTC
TTATGCCCTCAACAACACAATAAGGATGTCAATCATTGCTAGTCTTGCTAGTTGAACAAG
CCTATTAAAAGATAATGTGTGATAAATATTTTTGGTATTTTCAGAATAAAATGAACATGA
AAATAAAACAATGTGTAAATATTTTTTAACACGGTACAGAGCATACGCTTATACATATGC
ATATACACCCAACCTTATGAACGCACGCACGCATATCCTGTCCATATGAGCACATCCGAG
AGACCAAGCTGACACATTATCTTAGATTGACGAAGTGCCACAGACGCCTTCATAGTTGAC
TGAAACGTCTCTCCCACTAAACGCACATCACCGAAAAGTGAAATAAATTCAGAAAATGCG
ATCACCAATGTCAAGTCTAGAACTTGAACTCTGGTGGTAGAGGATACCACTGACATCCTA
ACCATCCAACCATAGCTCCGTTCACATGTATAAATGTTGTTGGATTGTGATTCTAATGAT
GGAAACTGAACTGAGGTTCACGGGTTCACCAAGTGTAACTCTCAACGCATAAAACTGTGA
ATGTTAACTTTCTCATGTGTAAAAGTGCAATGGAAAACTCATGTTCATGTCAGACAAGTA
AAGTCATGAGAAGATATATAGACAGTACATCCATAACACCAAAGATCGAGACCTTCGCAT
GCATCTTCAGCTAAATAACTCTTTCATAGACCGACACACTCCTTATCACTTGCACGTTAA
CTATAAACACGGGTAATTATATTTAGCACAATGACATACTGTTAAGACTAGAGGATTATT
TATCCTCTACTAACCCTTAATCCTTAGTGGCCGGCAACAATTCTTGCAGGCCTTTTTCAT
TTTTTTTGTCACTATGGAAGATTATCTACAAGATTTGAACCTATCTAATGCATACCACTT
CCATTATTGGCTACCGTTCTAAACTGGAAAAGTGTAGTCAAATAACTAGAAAAAAATATG
CATCTATATACCTCTCCATCTCCTTCCTCGTTTTTCACCTCCAGCCACCATATCTGGATT
GTACGCTCCAGATCCAACGGCTCCAAGCACCCCAGTTCATCTCCACTCCTGCAGCCCATT
AGCCCTCACATAAGTATGTGTTGATTTGCAGATAACACGGAATCACACCGTGAAAGACCC
GCCAAACACTGCACTATAAAAAAGATAAAAACACACTCCATTATCTCCCCCACCCGCCAA
ACCAAATAGTCCCCCAGTTTCAATATAAGATGTATTTGTTTTCTGATGAAAAGTCAAATT
TCTTTAACTTTGATGAAGTTCAAAAATGGACATTCACAATGCTAAACAAATAAATAGAAA
AAACATTTCATGGTGAATCCAACGATACCAAATTGATTACAAGTAGGTCAAATAATGGGT
TTGACTTTTCAAAAAACTAATACACCTTACATTTTAAAACTGAAGGAGTAACAAAATTAT
GAAAAAAATCAACAACACCAACAACACAGCAAAGCGCGACCAACCCTTCTAGTATGTTGT
CTAACTAAGAGCTATACTTGAGTTGAGCTAAACTAGATTATTTATATTCTATCTTTTGAA
CAAAAATGCAGGAATGGAACCAAACACAGAATGAGGTTCCACTATAGTTGACCATTTCGT
TTAGGAACGAAGTGGAATGGAATGTCATGGTTCCATGGATAACCTCCGCCCCCTTAGCCG
CAATCCCCCCTTCGACGTCTCTTTTCATTTCTCCGCCGAGCGATTCACGTCATTTTCCCT
CTCTCGTAGATCCATGGCAGGAGGTGCTCAAGGACGTGGGGGCGCGGCGGTGAAAGCACA
AGTGCTCCCTGGGTGGTTTTGGTAATTAATGTCAACATATCTTTTGTTGGACTAATACTT SEQ ID NO: 59: *T.aestivum* 2B promoter sequence (TGACv1_scaffold_148309_2BS 21605 to 22261 (+))
GGAGACCTTTGATCCGCTATGGTCCAATGTTTATCCGGGAACAGTAGAGGATCCAAAATC
TGAACTACATCTACAACTGCAATGACGTCAAGGCTTTGTGGATGCTTCGAATGAAAAGAG
CACCATTTGCCAGGCTTGTCGAGACCTTCAGGAGCAGGGGGTTGCACAAGATAACATCAA
CACCAGTGTGGAAGAGCAAGTGGCCATGTTCCTCCATGTTGTTGGCCATAACCAAAGGTT
CAGGGTCATTCACAACACGTTCAGGAGATCAAATGGAGACCACCTCTAGGTACTTCAAGC
AGGTGCTTTTTGCTGTTGGGGAGCTTAGAGGAAAGATGATCAGGAGACCATCTGTCCGGA
CTCCACCCAAGATTCGCGGAAGCCCAAGATGGTATCCATATTTCAAGGTGAGCATTGATA
ATATACACTTTTCATGGCTTGATATGCTTGTATTGTTCAAGTTGAGCACTAACACAGGCT
TGTGATACCATTTTCAGGATTGCATTGGGGCAATAGATGGTACTCATGTCACTGCCAGAG
TTCTTAGGTCACAGTCTGCAGCATACAAGGGGAGGAAGCACTACACAAGCCAGAATGTGC
TTGTTGTTGTTGACTTTGATATGAAGTTCACATATGTGCTGGCTAGCTGGGAGGGGTCAG
CACATGATGCTAACATTCTCAATGACAACATGAGTCGACCTGATGGGATCAACATCCCCG
ACGGTAGGTTCTACCTTGAAGATGTTGGCTATGCATGTCCGGGTGTTGTTTCACCCTTCA
GGAAAACCAAGTACCATCTCAACGAGTTTTCTGGTAGGAACTATCCTAGGACAACACATG
CGTTGTTTAATCTCAGACACTCCAACCTTAGTGTAACTGTTGAGAGGGCATTTGGAGCTC
TGAAGAATAGATTTAAAATCTTGGATCAGAAGCCATTCCACCCATACTCCACTCAGGTTA
AGCTTGTTCTTGCTTGTTGCATTCTGCATAACTGGATCCTCCAGTGGGGCTTTGATGAAC
ACATGCCAGAGGAGGAAGAGGTCAAGCCTGACGATGTTGTTAGCTCCGGCCATGGTGTGG
AGGCATTTGACAATGACGCTTGGAAGAACAAAAGGTTGGAGTGGGCAGATGCAATGTGGC
TTAACAGAGGTCAGTGCCAGATTTGAAGAAGAGGAAGACGAAGAAGCAGCAGCACAAGAA
GAAGCAAAAGCAGAAGCAGAAGCAGAAGAAGAGGAAGATGAAGATCTGGTAGCAGCAACA
CCAATGAACTATCCCCTATTTAGCCAATGGCTTAATAATTTGTTCTGTCATTTGATAGTA
GTTAGGATGAATTGTCATTTGTTTAACTAGCTGACACTATATGTTCAGATTATGTGTGGT
AAGCTCATCACTAGTTAGAAATGGTGACAACACCTTATACGGGTTGCAACCAAACATCAT
GTCATATGTGCGTCCAATGCAATGCGGGCAACCAAACACCGGGCCAAAAATGGTTGTCTC
ATGCAACTAAGGTACATGCAGGCAACCAAACTATGTGCATCTGGAGTCTTTTTGTCTGCA
TCCCCTCAAACCGGCTCACTAGAGCCAGGCTCACCGGGCCAGACTCAATTGACAATGTAA
CCAAACACGCCCTTATATGTTCTCCCTTGGCCCGAAGCTCCGACGGCGTCTCATGCCGGA
AACCACGAGCACCGCTTTCCATCGGCAGAATCATGAATGGGTTCTCTACTGGATACACAC
GGATGAAGCCTCGCCATAAATCTCCAGATATACATACACACGGATGAAGCCTCGCCACAA
ATTTCGGTAACTCAGTATATTGAATTTTCATTTTTATGATATTACCTCCGTCCCAAACT
GCATCTTAAATTTGTCCGGATACAGATATATCTAACACTAAAACATGTCTAGATACGGGA
CATTCGTATATATCTACACAAATAGTAGTTTCTTGGTCCGGAATTGCTCGGAGGGAGTAT
TTTATCTTTTGAGAGACTTTTCTTGAGAAGATTTTTGTTTTCTTCTTCTTTTTCTTAGGT
CGAGGGAGGGCGGTGCGGGGCGGTGCTCTGCTCGTGGGCAGAGAGCCGAACAACCCCGCA
AAAGCCCAAGCGGCCCTCCTCGCGCTCACGCGTCCCATCCGGCCTCTCTCTCTCTCTCTT
ATCTCGCGTCGCCGCCCCCGCAGCCGCAGTCCCCACCGCCTCCCCTGCCCCCCAAATCAA
TCAACAAAATCCCCACCCAGATCTCCGCCGATCGCCCATCGATGCCCCCTCCCCCGCCGC
CCACCGCCTCCTAGCCGCCGCGCCGCACCCACCGCCTCCGACGAGGCGGCCGCCGCACCC
ACCGCCTCCGACGAGGCGGCCGCCGCCCCCTCCCCCTCCTCCCCCGTGTATGGAAACGCG
CAGCCGCAAGCGGGCGGAAGCCTCGTCGTCTTCCTCCACCACCCCGACCTCCTCCTCCTC -continued GGCCCGCTCCTCCAAGCGCGCCCGCCCCAACCCTAACCCTAGCCCCGCCCCCGCCGCGCC
CGCACACCCCGCGCCCCGCGCCCGCCGCTCCGTCCTCCTCTCCCCGCCCGCCCCGCAGCC
CCCGATG

SEQ ID NO: 60 *T.aestivum* 2B promoter sequence (TGACv1_scaffold_114237_2A5 30614 to 32233 (-))
TACAAAATCTGAGGCGTCTGAAGGAAGCTT
CCTACACATATTGGCAGCTGTAGATAACGCAACTCTCTGTATACATTCCACCAAAAAAAC
AACTGTGAGTAGTAATAAAAATGTAGTACAGTATGTGTACAACAAAAAGATAGTGATATG
ACAAATTAGTATGTCCCAATTTCTAAATGGTGCAAAAAAATAACGTAAGTATTGAGAATG
TTATGTCTAAATGCTGGAAAAACATAGAAGTATTTAGAAAAATTACTTGAACACCGGTGG
AGAAGAAGTCAAGATATGATAGCACTGCCATTAGCGCGCCAGCCCTCAAGCAGGCAGTTG
GATGCTCCTGGGATATCTTCTTGAGTGCTTGTAAGGACTAAAATACACAGAGAAGGCATA
AGAAAATATTAGTAACACATCAAGATCTAGCAATGATAGATTCTTCCTGCAGCATATTTT
AAACGACAAAACAAAACAAGGAAAGTGGCTAATCTAAAGTGCCACAGAAGCAATACAATA
TCAAAATCTAAGAAAGTAATTCAAATGTCCTAGGTGCTAAACCTAATAGTTGTAGATACT
ACTCAATAACATATTGTGGAGCAGCAAACTAGATTCAATTGCACAAAGGGTTACAAAGGA
ATTCAAACAGATGATATCAAGTTAATTCACATTGTTTTGAATTAGACCCAAGAGAAGTAG
AAGTATAATATCCATATAAGATGGGAAGGCAGAGAAGAAACACAGCCAGAAACCGGTTAC
ATGAATCTTAGCATCTGATTTCCAACCCACTTCTTAGTATTTCAGATGGATCATTACAGT
AGCACATACACAGGCGTGAAATCAGACCCTGAGCTAGAAATATTTCAGATGAAAAACATG
TTCAAATAGCTAGCTTAGTCATGCACAAATAGGTGATTTGGCACACAGCAAAACCGTGTT
AAATGGCACCCAGGTGCTCGGCAGGAACACCACCATGATCAGGCCTAGAAAGTCTTCTAA
GGGGCAGATGAGGTCCTTAGATGGATTTGAGTTCGCTGGTGAGGATTTGGAGCCCGAGTC
CTCCGGCGGCACCAGAGGAAGGGAAGACATCTCCATGCCCACAAGCTCCCTAAGGCTTTA
AGGCATCACGTGCATTGGGACATGCTTTCATCTAACCATTTTTTCTTTCATGTGTCTCCT
ATCCTCAGCTTCTTCCTCCCAGAGCGACCAGTGACTAGACCCTAGGCAGGCCCCAAGGCT
GCTAAGGGATCACCTTCTGCCTAACTCTCTAGATATTTCTTGTAACATCATTAAATGGTG
AGCTACTGAAATAGGCAATATTTGGTACTTGCCAAGTGAACAATCAAACAAGCTATTTCA
AATATATAGTTCCTTGAAAACTGATTATACACAATATTTCAAACTTAATATTAACTGAGG
CTAACTTACAACTACCACATCTGTACAGGTCACCGAAACTTGAGTCAGAAACATAACATA
GAAAGCATACAGTGGAACTTCTCGAGTATGGGCACAACGCCAACAAAAATCATGTTCTTA
ACCTTCTCATCCATATTTGTTTTAGCACTAAAATGGGAAAAAAACACAGCTACACAAAAG
GCAAACTACTCATGAGCAAGTCCAAATACTATAAATGATCTGCAACACTAAAAGGAAACT
CATGTAATGTAGGTTAAGGCTCTATGGACAGCATAATCATGCATAATACAGTACACAAGA
ATGGTTCACTAAGCATTGATCTGGATCAGGCAACATGATAAAGAAGCAGCATGTACTATA
AACCAAACAAGCGATGCAGCAGAACAGTGCTCACCTGCTCCGCAAGGTCCATATATTCAA
TGGTGAGAAGCCGGGCGCAGAAGCATGCCACGGCGCCATAGTGCACAACGGCAGAGCAGG
ACGACGGCAGCACGTCACAGAGGTGGGTCAGGGCCCGCGCAGCGAGCAGCATGATGTCAG
GGTTGCTCTCGTGGTTGAGCAGCCCGACCAGAACAGGCACGAATGAGTCCACCGAGAACC
CGGCGAGGGTGTCCTCGGTGCCGATGGACAGCATCTCACAGAGCTGGGTCAGCGCCTCCA
CCTGGCGCCCCTCCTCCCCGTCGGCACGGAGACCCGCGAGCATGCTCTTCATCCGCGCGC
CGTTCGGCCCAGACATGGACGACGAGGAGGCAGCCGCGGCGGCGGCGGAGAGGGCGGACG
ACGGCAGCATGTCGTCCAGGCCGGCGCCGAGCTTCCTGAGCAGCCCCTGCAGGGCGCTGC
TGGCGGAGGTGAGGCCGTGGGGGAAGGCCCCGTGGCCCTCGTCGTCGTCGTCCATGCCGT
CGAAGCTGAGGCCCAGCATCCGCTCGGCCTCGCGCACGCGGGAGCTCTCCGAGGGCTCCT
GCTGCTCCTTGCCCTTGTCGGCGTTGGAGGCGCGGCCGCCGCGGCGGCGGGGCGGGGGGT
TGTTGCCGCCGTCGGCCGGGAAGTCCAT

An Alignment of the Coriander (High Expresser) and Dimension (Low Expresser) BnC03 UPL3 Promoter Sequences (SEQ ID No: 2 to SEQ ID No: 1) Showing Extensive Segregating Variation

```
Dimension_BnC50          1 AGAGAGGCCTGGACGTTTGGGTCATCGCTCTCGGTCGGTTCCTACTTTTT
                             ||||||||||||||||||||||||||||||.|||||||||||||||||||
Coriander_BnC50          1 AGAGAGGCCTGGACGTTTGGGTCATCGCTCCCGGTCGGTTCCTACTTTTT

Dimension_BnC100        51 CTGCACCACCGCCATTTGTTGATCCAGAAATATTTACGGCTCAGTTGAAG
                             |||||||||||||||||||||||||||||.||||||||||||||||||||
Coriander_BnC100        51 CTGCACCACCGCCATTTGTTGATCCAGAAGTATTTACGGCTCAGTTGAAG

Dimension_BnC150       101 GACAAGGATGATCGCATATCTTTGTTGGAGACCCAGAAGACGGCTCAACA
                             |||||.||||||||||||||||||||||||||||||||||||||||||||
Coriander_BnC150       101 GACAAAGATGATCGCATATCTTTGTTGGAGACCCAGAAGACGGCTCAACA

Dimension_BnC200       151 GGCGGGCTATGAGGCACAGAAGAGGCTGAACCAGCAAATGATGAAAAGGA
                             ||||||||||||||||||||||||||||||||||||||||||||||||||
Coriander_BnC200       151 GGCGGGCTATGAGGCACAGAAGAGGCTGAACCAGCAAATGATGAAAAGGA

Dimension_BnC246       201 TGTACCCGAACGAGGTGTTCCCGAACGTGCAAGACCCGTAG----TTTTT
                             ||||.||||||||||||||||||||||||||||||||||||    |||||
Coriander_BnC250       201 TGTATCCGAACGAGGTGTTCCCGAACGTGCAAGACCCGTAGTTTTTTTTT

Dimension_BnC296       247 TTTTTCAAAAACTCGGAATGTTTATTTTTATTTGTACAACTTTGAATAT
                             ||||||||||||||||||||||||||||||||||||||||||||||||||
```

-continued

```
Coriander_BnC300        251 TTTTTCAAAAACTCGGAATGTTTTATTTTTATTTGTACAACTTTGAATAT

Dimension_BnC346        297 TATCTAATATGTTTTCAATTTTAATTTTAATTTTATATTTTCGAATTTAA
                            |||.||||||||||||||||||||||||||||||||||||||||||||||
Coriander_BnC350        301 TATTTAATATGTTTTCAATTTTAATTTTAATTTTATATTTTCGAATTTAA

Dimension_BnC394        347 ATTTCAAAATTTTCA--TTTTTAAAAAAAAATTAATTTTTTTTTTGAAAT
                            ||||.|||.||||.|  ||||||||||||||  |||||||||||||||
Coriander_BnC398        351 ATTTTAAATTTTTTATTTTTTTAAAAAAAAAT--ATTTTTTTTTTGAAAT

Dimension_BnC444        395 TCCGAGGAAATGAACCCTCGGAAATTTCCGACGAACATTTCCTCAGAATA
                            ||||||||||||||||||||||||||||||||||||||||||||||||||
Coriander_BnC448        399 TCCGAGGAAATGAACCCTCGGAAATTTCCGACGAACATTTCCTCAGAATA

Dimension_BnC494        445 AGTCGTCGGAATATACCGAGGGACTCCTTCCTCCTCGGAATTTTCTGAGG
                            |||||||||||||||||||||||||||||||||||||||||||||.||||
Coriander_BnC498        449 AGTCGTCGGAATATACCGAGGGACTCCTTCCTCCTCGGAATTTTCCGAGG

Dimension_BnC544        495 GCTCCGTTTCTCGGAAATTCCCGATGAAAATTCCGAGGAACATTTCATCG
                            ||||||||.|||||||||||||||||||||||||||||||||||||.|||
Coriander_BnC548        499 GCTCCGTTCCTCGGAAATTCCCGATGAAAATTCCGAGGAACATTTCGTCG

Dimension_BnC594        545 GAACTTCCGAGGATTGGACCATCGGAAAGTCCATCGAAATATTCCGAAGA
                            ||||||||||||||||||||||||||||||||||||||||||||.||.||
Coriander_BnC598        549 GAACTTCCGAGGATTGGACCATCGGAAAGTCCATCGAAATATTCTGAGGA

Dimension_BnC644        595 AGTTCTCCCTCGATATATTCCGAGAACCTTTCCGACGAACTGGTGGTCCT
                            ||||||||||.|.|||||||||||||||||||||||||||||||||||||
Coriander_BnC648        599 AGTTCTCCCTTGGTATATTCCGAGAACCTTTCCGACGAACTGGTGGTCCT

Dimension_BnC694        645 CGGAGTTTCCTCGGAAATTCATTTCCTCGGAATTCCTTCGGAAATTTCTG
                            |||||                ||||||||||||||||||||
Coriander_BnC675        649 CGGAG----------------TTTCCTCGGAATTCCTTCGGAA-------

Dimension_BnC744        695 AGGGATTTCCGAGAAAAAAATGAATTTCCGAGGAGTTATTTCCGAGGACTT
                                |||||||||.||||||||||||||||||||||||||||||||||||
Coriander_BnC721        676 ----ATTTCCGAGGAAAAATGAATTTCCGAGGAGTTATTTCCGAGGACTT

Dimension_BnC794        745 GTTTCGTCGGTATGTCGTCGGAATAACGTTATTCCGACGACGTACCGACG
                            ||||||||||||||||||||||||||||||||||||||||||||||||||
Coriander_BnC771        722 GTTTCGTCGGTATGTCGTCGGAATAACGTTATTCCGACGACGTACCGACG

Dimension_BnC842        795 ATTTTTTCCC--TCGGTATGTTCATATTGGATTTATAAATGAATCATAAT
                            ||||||||||  |.||||||||||.||||||||||||||||||||.||||
Coriander_BnC821        772 ATTTTTTCCCTTTGGTATGTTCAAATTGGATTTATAAATGAATCGTAAT

Dimension_BnC892        843 TTCTGTTTTTCGGGTTAAATTAATATGTATATATATATATATATATTAAA
                            ||||||||||||||||||||||||||      ||||||||||||||||
Coriander_BnC865        822 TTCTGTTTTTCGGGTTAAATTAATATG------TATATATATATATTAAA

Dimension_BnC941        893 AAAATCTGTAAGTTCCAAACAAGGGCACACTTATAAAAG-AACTAATGTA
                            ||||||||||||||||||||||||||||||.|||||||| ||||||||||
Coriander_BnC915        866 AAAATCTGTAAGTTCCAAACAAGGGCACACGTATAAAAGAAACTAATGTA

Dimension_BnC991        942 TTATATACTGTCATGTTTTTTTTATAAAATATGTACAATAATTTATATAT
                            ||||||||||||||||||||||||||||||||||||||||||||||||||
Coriander_BnC965        916 TTATATACTGTCATGTTTTTTTTATAAAATATGTACAATAATTTATATAT

Dimension_BnC1041       992 GTCTTCATCCGATTAACAAACTCAAACCCAAACAACAAAAATTTCTACAT
                            ||||||||||||||||||||||||||||||||||||.|||||||||||||
Coriander_BnC1015       966 GTCTTCATCCGATTAACAAACTCAAACCCAAACAACCAAAATTTCTACAT

Dimension_BnC1091      1042 TTAGATTTTAAATTAGCGTGTGATGGCTAAAGAAAAAAAGAAGAATAAAT
                            ||||||||||||||||||||||||||||||||||||||||||||||||||
Coriander_BnC1065      1016 TTAGATTTTAAATTAGCGTGTGATGGCTAAAGAAAAAAAGAAGAATAAAT

Dimension_BnC1141      1092 TTGTATCTTTGCATAGATCACCTGCATTTCATTGAGTAGATTCATTTAAA
                            ||||||||||||||||||||||||||||||.|||||||||||||||||||
Coriander_BnC1115      1066 TTGTATCTTTGCATAGATCACCTGCATTTCGTTGAGTAGATTCATTTAAA

Dimension_BnC1191      1142 TAAGTAGATAGATAGATTTTATTATCATATTTATTTTCTTAACAAACCAT
                            ||||||||||.|||||||||||||||||||||||||||||
Coriander_BnC1156      1116 TAAGTAGATAAATAGATTTTATTATCATATTTATTTTCTTA---------

Dimension_BnC1241      1192 CATAAAAGAAGAATATATTTGTATCTTTGCATAGATCATATATATAATTG

Coriander_BnC1156      1157 --------------------------------------------------
```

-continued

```
Dimension_BnC1291      1242 TAATGACTAATTATTTTCTCGACAAACCATAGTTTTTCCTTACTACAATC
                                                 |||||||||||||||||||||||||||||
Coriander_BnC1185      1157 ---------------------ACAAACCATAGTTTTTCCTTACTACAATC

Dimension_BnC1341      1292 ATAAAAGAAGAATATATTTGTATCTTTGCATAGATCATATATATAATTGT
                            ||||||||||||||||||||||||||||||||||||||||||||||||||
Coriander_BnC1235      1186 ATAAAAGAAGAATATATTTGTATCTTTGCATAGATCATATATATAATTGT

Dimension_BnC1391      1342 AATGAGTAATGTGTTATATAGTCCATGGATCGTAGTGAGAAGGTAGAGTT
                            |||||.||||||||||||||||||||||||||||||||||||||||||||
Coriander_BnC1285      1236 AATGACTAATGTGTTATATAGTCCATGGATCGTAGTGAGAAGGTAGAGTT

Dimension_BnC1441      1392 GAAAGTATAAGAAAGCGAACCTCCATCATAGTGGGGGCTTAAACCCGTGC
                            ||||||||||||||||||||||||||||||||||||||||||||||||||
Coriander_BnC1335      1286 GAAAGTATAAGAAAGCGAACCTCCATCATAGTGGGGGCTTAAACCCGTGC

Dimension_BnC1491      1442 AAGCTTGCAGATATCTATGGCTGATGGTTGGGCCCAGCCTTATATCTTGG
                            ||||||||||||||||||||||||||||||||||||||||||||||||||
Coriander_BnC1385      1336 AAGCTTGCAGATATCTATGGCTGATGGTTGGGCCCAGCCTTATATCTTGG

Dimension_BnC1541      1492 GCTTATTTTGTTTCCATCTGTCCAGCCCATGATAAAGTGTAAAACGACAC
                            ||||||||||||||||||||||||||||||||||||||||||||||||||
Coriander_BnC1435      1386 GCTTATTTTGTTTCCATCTGTCCAGCCCATGATAAAGTGTAAAACGACAC

Dimension_BnC1591      1542 CGTATTAAGCTTAATGGAGTAAACGAATCACACGTAGCGGGGATCCCCGT
                            ||||||||||||||||||||||||||||||||||||||||||||||||||
Coriander_BnC1485      1436 CGTATTAAGGTTAATGGAGTAAACGAATCACACGTAGCGGGGATCCCCGT

Dimension_BnC1641      1592 GTCAGTTCTTGTCGGAAAAGCTGGACGGAGGAAAACGGTATCGTATTCGC
                            |||||||||||||.||||||||||||||||||||||||||||||||||||
Coriander_BnC1535      1486 GTCAGTTCTTGTCCGAAAAGCTGGACGGAGGAAAACGGTATCGTATTCGC

Dimension_BnC1691      1642 TTCGCTTGAATCTATATATTTTGCGCAAAAGCCCTTTTCATCCCTTTCTT
                            ||||||||||||||||||||||||||||||||||||||||||||||||||
Coriander_BnC1585      1536 TTCGCTTGAATCTATATATTTTGCGCAAAAGCCCTTTTCATCCCTTTCTT

Dimension_BnC1741      1692 CTCTCATTACTCGATTTAGGGTTTTCTAATCTCGTAAGAAATCAAGATCC
                            ||||||||||||||||||||||||||||||||||||||||||||||||||
Coriander_BnC1635      1586 CTCTCATTACTCGATTTAGGGTTTTCTAATCTCGTAAGAAATCAAGATCC

Dimension_BnC1791      1742 TCCTTCCTTCCTCTCTCGATTTCGATCTCGTAGCCCCTTTTGCGTTGATT
                            ||||||||||||||||||||||||||||||||||||||||||||||||||
Coriander_BnC1685      1636 TCCTTCCTTCCTCTCTCGATTTCGATCTCGTAGCCCCTTTTGCGTTGATT

Dimension_BnC1841      1792 TCGAATTCGTTCATCAACAGGTTTGTTTCTCTCTAGCTCCTAACGATCTC
                            |||||||||||||||||.||.||||||||||||||||||||.||||||||
Coriander_BnC1735      1686 TCGAATTCGTTCATCAATAGCTTTGTTTCTCTCTAGCTCCTATCGATCTC

Dimension_BnC1891      1842 GCTAGCAAATTAGGGTTTCGAGCGAGCTTAATCCGATCGGTTTCTGGATC
                            ||||||||||||||||||||||||||||||||||||||||||||||||||
Coriander_BnC1785      1736 GCTAGCAAATTAGGGTTTCGAGCGAGCTTAATCCGATCGGTTTCTGGATC

Dimension_BnC1941      1892 AGTTGAGATGCGATCGGAATCTCTCTGAATAAGAGAGACTCGTGTGGAGG
                            ||||||||||||||||||||||||||||||||||||||||||||||||||
Coriander_BnC1835      1786 AGTTGAGATGCGATCGGAATCTCTCTGAATAAGAGAGACTCGTGTGGAGG

Dimension_BnC          1942 GGTTTCTTCCTTTGT 1956
                            |||||||||||||||
Coriander_BnC          1836 GGTTTCTTCCTTTGT 1850
```

The invention claimed is:

1. A method of increasing seed lipid content and/or seed protein content or reducing glucosinolate levels in a plant, the method comprising:

(A) reducing or eliminating expression of at least one endogenous ubiquitin protein ligase 3 (UPL3) gene which comprises a nucleic acid sequence encoding an endogenous ubiquitin protein ligase 3 (UPL3) polypeptide in a plant to create a genetically modified mutant plant, wherein said reducing or eliminating expression comprises introducing (i) at least one mutation into said nucleic acid sequence encoding said endogenous ULP3 polypeptide of the plant, and wherein said mutation is introduced using targeted genome modification selected from the group consisting of ZFNs, TALENs and CRISPR/Cas9, or (ii) a recombinant nucleic acid molecule comprising a synthetic expression cassette encoding an RNA inhibitory molecule that targets said nucleic acid sequence encoding said endogenous UPL3 polypeptide in said plant, and wherein said nucleic acid sequence encoding said endogenous UPL3 polypeptide has at least 90% nucleotide sequence identity to the nucleotide sequence selected from the group consisting of SEQ ID NO: 4, SEQ ID NO: 5, SEQ ID NO: 6 and SEQ ID NO: 7; and (B) measuring seed lipid content or seed protein content in said genetically modified mutant plant;

and wherein said reducing or eliminating expression of said at least one endogenous UPL3 gene encoding said endogenous UPL3 polypeptide in said genetically modified mutant plant results in increased seed lipid content and/or seed protein content or reduced glucosinolate levels as compared to a control plant of same species grown under similar growth conditions.

2. A method of increasing seed lipid content and/or seed protein content or reducing glucosinolate levels in a plant, the method comprising:

(A) reducing or eliminating expression of at least one endogenous ubiquitin protein ligase 3 (UPL3) gene in a plant to create a genetically modified mutant plant, wherein said reducing or eliminating expression comprises introducing at least one mutation into endogenous ULP3 gene promoter of said UPL3 gene, and wherein said mutation is introduced using targeted genome modification selected from the group consisting of ZFNs, TALENs and CRISPR/Cas9, and wherein said endogenous UPL3 gene promoter has at least 90% nucleotide sequence identity to the nucleotide sequence selected from the group consisting of SEQ ID NO: 1 and SEQ ID NO: 2; and (B) measuring seed lipid content or seed protein content in said genetically modified mutant plant;

and wherein said reducing or eliminating expression of said at least one endogenous UPL3 gene promoter in said genetically modified mutant plant results in increased seed lipid content and/or seed protein content or reduced glucosinolate levels as compared to a control plant of same species grown under similar growth conditions.

3. The method of claim 1 or claim 2, wherein the genetically modified mutant plant is a dicot plant.

4. The method of claim 1 or claim 2, wherein the genetically modified mutant plant is a *Brassica* oil seed crop, *Brassica juncea*, soybean, sunflower, linseed, cotton, hemp, oil palm, coconut, peanut, safflower, Camelina, olive, *Brassica oleracea*, maize, rice, wheat or barley.

5. The method of claim 1 or claim 2, wherein the genetically modified mutant plant is *Brassica napus.*

6. The method of claim 1, wherein said nucleic acid sequence has at least 95% nucleotide sequence identity to the nucleotide sequence selected from the group consisting of SEQ ID NO: 4, SEQ ID NO: 5, SEQ ID NO: 6 and SEQ ID NO: 7.

7. The method of claim 2, wherein said endogenous UPL3 gene promoter has at least 95% nucleotide sequence identity to the nucleotide sequence selected from the group consisting of SEQ ID NO: 1 and SEQ ID NO: 2.

8. A genetically modified mutant plant with increased seed lipid content and/or seed protein content or reduced glucosinolate levels comprising reduced or loss of expression of at least one endogenous ubiquitin protein ligase 3 (UPL3) gene which comprises a nucleic acid sequence encoding an endogenous ubiquitin protein ligase 3 (UPL3) polypeptide in said genetically modified mutant plant, wherein said reduced or loss of expression comprises introducing (i) at least one mutation into said nucleic acid sequence encoding said endogenous ULP3 polypeptide, and wherein said mutation is introduced using targeted genome modification selected from the group consisting of ZFNs, TALENs and CRISPR/Cas9, or (ii) a recombinant nucleic acid molecule comprising a synthetic expression cassette encoding an RNA inhibitory molecule that targets said nucleic acid sequence encoding said endogenous UPL3 polypeptide in said genetically modified mutant plant, wherein said nucleic acid sequence encoding said endogenous UPL3 polypeptide has at least 90% nucleotide sequence identity to the nucleotide sequence selected from the group consisting of SEQ ID NO: 4, SEQ ID NO: 5, SEQ ID NO: 6 and SEQ ID NO: 7, and wherein said reduced or loss of expression of said at least one endogenous UPL3 gene encoding said endogenous UPL3 polypeptide in said genetically modified mutant plant results in increased seed lipid content and/or seed protein content or reduced glucosinolate levels as compared to a control plant of same species grown under similar growth conditions.

9. A genetically modified mutant plant with increased seed lipid content and/or seed protein content or reduced glucosinolate levels comprising reduced or loss of expression of at least one endogenous ubiquitin protein ligase 3 (UPL3) gene in said genetically modified mutant plant, wherein said reduced or loss of expression comprises introducing at least one mutation into endogenous ULP3 gene promoter of said UPL3 gene, wherein said mutation is introduced using targeted genome modification selected from the group consisting of ZFNs, TALENs and CRISPR/Cas9, and wherein said endogenous UPL3 gene promoter has at least 90% nucleotide sequence identity to the nucleotide sequence selected from the group consisting of SEQ ID NO: 1 and SEQ ID NO: 2, and wherein said reduced or loss of expression of said at least one endogenous UPL3 gene promoter in said genetically modified mutant plant results in increased seed lipid content and/or seed protein content or reduced glucosinolate levels as compared to a control plant of same species grown under similar growth conditions.

10. The genetically modified mutant plant of claim 8 or claim 9, wherein the genetically modified mutant plant is a dicot plant.

11. The genetically modified mutant plant of claim 8 or claim 9, wherein the genetically modified mutant plant is a *Brassica* oil seed crop, *Brassica juncea*, soybean, sunflower, linseed, cotton, hemp, oil palm, coconut, peanut, safflower, Camelina, olive, *Brassica oleracea*, maize, rice, wheat or barley.

12. The genetically modified plant of claim 8 or claim 9, wherein the genetically modified mutant plant is *Brassica napus.*

13. A genetically modified mutant seed obtained from the genetically modified plant of claim 8, wherein the genetically modified mutant seed comprises said at least one mutation or said recombinant acid molecule.

14. A genetically modified mutant seed obtained from the genetically modified plant of claim 9, wherein the genetically modified mutant seed comprises said at least one mutation.

15. The genetically modified mutant plant of claim 8 wherein said nucleic acid sequence has at least 95% nucleotide sequence identity to the nucleotide sequence selected from the group consisting of SEQ ID NO: 4, SEQ ID NO: 5, SEQ ID NO: 6 and SEQ ID NO: 7.

16. The genetically modified mutant plant of claim 9 wherein said endogenous UPL3 gene promoter has at least 95% nucleotide sequence identity to the nucleotide sequence selected from the group consisting of SEQ ID NO: 1 and SEQ ID NO: 2.

* * * * *

SEQUENCE LISTING

```
<160> NUMBER OF SEQ ID NOS: 94

<210> SEQ ID NO 1
<211> LENGTH: 1850
<212> TYPE: DNA
<213> ORGANISM: Brassica napus

<400> SEQUENCE: 1

agagaggcct ggacgtttgg gtcatcgctc ccggtcggtt cctacttttt ctgcaccacc      60

gccatttgtt gatccagaag tatttacggc tcagttgaag gacaaagatg atcgcatatc     120
```

tttgttggag acccagaaga cggctcaaca ggcgggctat gaggcacaga agaggctgaa 180
ccagcaaatg atgaaaagga tgtatccgaa cgaggtgttc ccgaacgtgc aagacccgta 240
gttttttttt tttttcaaaa actcggaatg ttttattttt atttgtacaa ctttgaatat 300
tatttaatat gttttcaatt ttaattttaa ttttatattt tcgaatttaa attttaaatt 360
ttttattttt ttaaaaaaaa atattttttt tttgaaattc cgaggaaatg aaccctcgga 420
aatttccgac gaacatttcc tcagaataag tcgtcggaat ataccgaggg actccttcct 480
cctcggaatt ttccgagggc tccgttcctc ggaaattccc gatgaaaatt ccgaggaaca 540
tttcgtcgga acttccgagg attggaccat cggaaagtcc atcgaaatat tctgaggaag 600
ttctcccttg gtatattccg agaacctttc cgacgaactg gtggtcctcg gagtttcctc 660
ggaattcctt cggaaatttc cgaggaaaaa tgaatttccg aggagttatt tccgaggact 720
tgtttcgtcg gtatgtcgtc ggaataacgt tattccgacg acgtaccgac gatttttttcc 780 cttttggtat gttcaaattg gatttataaa tgaatcgtaa tttctgtttt tcgggttaaa 840
ttaatatgta tatatatata ttaaaaaaat ctgtaagttc caaacaaggg cacacgtata 900
aaagaaacta atgtattata tactgtcatg ttttttttat aaaatatgta caataattta 960
tatatgtctt catccgatta acaaactcaa acccaaacaa ccaaaatttc tacatttaga 1020
ttttaaatta gcgtgtgatg gctaaagaaa aaaagaagaa taaatttgta tctttgcata 1080
gatcacctgc atttcgttga gtagattcat ttaaataagt agataaatag attttattat 1140
catatttatt ttcttaacaa accatagttt ttccttacta caatcataaa agaagaatat 1200
atttgtatct ttgcatagat catatatata attgtaatga ctaatgtgtt atatagtcca 1260
tggatcgtag tgagaaggta gagttgaaag tataagaaag cgaacctcca tcatagtggg 1320
ggcttaaacc cgtgcaagct tgcagatatc tatggctgat ggttgggccc agccttatat 1380
cttgggctta ttttgtttcc atctgtccag cccatgataa agtgtaaaac gacaccgtat 1440
taagcttaat ggagtaaacg aatcacacgt agcggggatc cccgtgtcag ttcttgtccg 1500
aaaagctgga cggaggaaaa cggtatcgta ttcgcttcgc ttgaatctat atattttgcg 1560
caaaagccct tttcatccct ttcttctctc attactcgat ttagggtttt ctaatctcga 1620
aagaaatcaa gatcctcctt ccttcctctc tcgatttcga tctcgtagcc ccttttgcgt 1680
tgatttcgaa ttcgttcatc aatagctttg tttctctcta gctcctatcg atctcgctag 1740
caaattaggg tttcgagcga gcttaatccg atcggtttct ggatcagttg agatgcgatc 1800
ggaatctctc tgaataagag agactcgtgt ggaggggttt cttcctttgt 1850

<210> SEQ ID NO 2
<211> LENGTH: 1956
<212> TYPE: DNA
<213> ORGANISM: Brassica napus

<400> SEQUENCE: 2
agagaggcct ggacgtttgg gtcatcgctc tcggtcggtt cctacttttt ctgcaccacc 60
gccatttgtt gatccagaaa tatttacggc tcagttgaag gacaaggatg atcgcatatc 120
tttgttggag acccagaaga cggctcaaca ggcgggctat gaggcacaga agaggctgaa 180
ccagcaaatg atgaaaagga tgtacccgaa cgaggtgttc ccgaacgtgc aagacccgta 240
gttttttttt tcaaaaactc ggaatgtttt atttttattt gtacaacttt gaatattatc 300
taatatgttt tcaattttaa ttttaatttt atattttcga atttaaattt caaaattttc 360

-continued atttttaaaa aaaaattaat tttttttttg aaattccgag gaaatgaacc ctcggaaatt 420
tccgacgaac atttcctcag aataagtcgt cggaatatac cgagggactc cttcctcctc 480
ggaattttct gagggctccg tttctcggaa attcccgatg aaaattccga ggaacatttc 540
atcggaactt ccgaggattg gaccatcgga aagtccatcg aaatattccg aagaagttct 600
ccctcgatat attccgagaa cctttccgac gaactggtgg tcctcggagt ttcctcggaa 660
attcatttcc tcggaattcc ttcggaaatt tctgagggat ttccgagaaa aaatgaattt 720
ccgaggagtt atttccgagg acttgtttcg tcggtatgtc gtcggaataa cgttattccg 780
acgacgtacc gacgattttt tccctcggta tgttcatatt ggatttataa atgaatcata 840
atttctgttt ttcgggttaa attaatatgt atatatatat atatatatta aaaaaatctg 900
taagttccaa acaagggcac acttataaaa gaactaatgt attatatact gtcatgtttt 960
ttttataaaa tatgtacaat aatttatata tgtcttcatc cgattaacaa actcaaaccc 1020
aaacaacaaa aatttctaca tttagatttt aaattagcgt gtgatggcta aagaaaaaaa 1080
gaagaataaa tttgtatctt tgcatagatc acctgcattt cattgagtag attcatttaa 1140
ataagtagat agatagattt tattatcata tttattttct taacaaacca tcataaaaga 1200
agaatatatt tgtatctttg catagatcat atatataatt gtaatgacta attattttct 1260
cgacaaacca tagtttttcc ttactacaat cataaaagaa gaatatattt gtatctttgc 1320
atagatcata tatataattg taatgagtaa tgtgttatat agtccatgga tcgtagtgag 1380
aaggtagagt tgaaagtata agaaagcgaa cctccatcat agtgggggct taaacccgtg 1440
caagcttgca gatatctatg gctgatggtt gggcccagcc ttatatcttg ggcttatttt 1500
gtttccatct gtccagccca tgataaagtg taaaacgaca ccgtattaag cttaatggag 1560
taaacgaatc acacgtagcg gggatccccg tgtcagttct tgtcggaaaa gctggacgga 1620
ggaaaacggt atcgtattcg cttcgcttga atctatatat tttgcgcaaa agccctttc 1680 atccctttct tctctcatta ctcgatttag ggttttctaa tctcgaaaga aatcaagatc 1740
ctccttcctt cctctctcga tttcgatctc gtagcccctt ttgcgttgat ttcgaattcg 1800
ttcatcaaca ggtttgtttc tctctagctc ctaacgatct cgctagcaaa ttagggtttc 1860
gagcgagctt aatccgatcg gtttctggat cagttgagat gcgatcggaa tctctctgaa 1920
taagagagac tcgtgtggag gggtttcttc ctttgt 1956

<210> SEQ ID NO 3
<211> LENGTH: 2100
<212> TYPE: DNA
<213> ORGANISM: Glycine max

<400> SEQUENCE: 3
tgttatttcc aaaagcaaaa ctatgtccct ggtttatgtt tgaatattaa cttatgtttg 60
tgttttattt ccaaaaaaaa aaaaagaagt acagtcacaa tttatatttg aagttgctaa 120
actatactaa taagggagga aaactaggtt atttgaacat gaccggcccc ttgtcgacaa 180
caactgaaag ctcgataaat gatcatcact aaatcactat agtagcccga taacttctaa 240
aaaacattta gaaagtcacc tttcagtttt taaatgtgta aatattaatg attatgatga 300
tttttttttt aaaaattcta aacaagtcaa gtgcaaagat tatttatttc attcaggtta 360
agttaaaatg ggatttgtga ttgtgatttc ctaaagttag tgtgatccgt aatacatgtc 420
cagtattccg aaaagtacaa acaattactg atctaataaa caatatcctt aaaactttca 480
agactttatg gagacaaata gcaatcaaat gtacatgcaa aaaaaaaaaa aaacagaaat 540

```
atatccagga tttaagcatt ttcaatagga agactatgca ttgtatttgc acataaaagt    600

aggccgtaac aaaaagtcct atccccgctc ctctttcccc gatcgataag aatagaacat    660

ccaataatcc attaagggat ttctatcaac gttaattcta gctagaaacc tctgcatgag    720

aacactatct agtactctac tcgtgtcttt cattacatgt tcaagtgagc atgcaaagta    780

ggtgggggaa gtaataaacc agacaatcac caaccttttc catgagagag acatatatat    840

tagcaaagca aggaaccaaa gacttcaaat ttgcactctc agtgggaagg tctggtatat    900

aggcaactct ggggtacatt ggggcgtaat ttgttttaaa aatataacta ttattgaaaa    960

ttaaaataaa atgttgtagc tatttagagt atatagttaa aggtaaaaat atttagaaga   1020

aaaatgacaa ttattgcttt tataataatt atagatattg atagtgatat ataatagatt   1080

tatatagttt ttatttttta tttgtttttg aatattttat aaataaaaaa ttacaagtgt   1140

ttaaaatata cttctatcaa aaaaatcaaa ttaaaatgtg tatataaaca ttacatgatt   1200

attgtttcaa tttttagta ttttaagaat tattggtttg tgtgttataa gtattaattg   1260

ctactgactt ataagaatta agaactaaaa ttattgaaac aaagctgatt tggcagtatt   1320

tatttaaagc agttatagaa aaattgaaga aataatgtgt tgatttatca ttggcaatac   1380

attttttaa tttttttaa ttactcaatc caattatcta atccaacggc caattaatac   1440

cagccttatg tttaattgga ttatattgta aattagatta aactaaactc aatccaacca   1500

gttacatctt atatttttat ctaaaatttg tattataata cattttctat taaatacaat   1560

ttaataattt aactttattg tgcaagtgca acgtatatta atacaatgca ggtgtctatt   1620

gaaacgacga cgttgaggga tcgaagtgta cgcgccacat tgcgacagtg ccaccgagga   1680

gcgtagctag ttcagttccg tttgatgaac gaaaatgacc aatccaccga gcgaaattgt   1740

aattttcaac aataaaaaag gcaaagaaag ttacatatga aagcctgttt tgttctgtcc   1800

ctttttattc ttccctttct ttcttactta cccctttccc tggcttaggg ttttctgccc   1860

cccctgaatc ctcatcgcta ttcatgatta cactccttac aattctcact cagcgactcg   1920

ttcgaaatac gtgaaatccc cttatctcca atttctaggg tttcgattca ttcaactcac   1980

cacaaagatt ggatccatgg tagcgtgatt ggcgctcggt ggcgagcgag ttgataatta   2040

tcgggttggg tggattttgt atggaaactc ggagccggaa gcgggcggag gcttcctcag   2100
```

```
<210> SEQ ID NO 4
<211> LENGTH: 5682
<212> TYPE: DNA
<213> ORGANISM: Brassica napus

<400> SEQUENCE: 4

atggaaactc ggagccgcaa gcgtgcggag gcgacctcaa ctgccccatc ttcttcttct     60

tcgtctcctc ctcctcctcc ctcaggtccc accactcgca gcaaacgcgc tcgcctctcg    120

tctccctctt cctcttcagc cgccgccgct accaccgcta ctgcaccttc ctcctccacc    180

cgctctcgtt cttctcgctc tgccgctacc gctaccgcta cagccgccgt tactcccatg    240

gacacatcca ccgagtcttc tggattccgc cgcggcgggg gacgaggtaa caggggaaac    300

gataatacta attctgataa gggaaaggag aaggagcatg aggttaggat tagggataga    360

gaaagagacc gagccagaca gcagctcaac atggacgctg cagctgctgc cgccgccgct    420

gaagaggacg atgacaatga tagtgaggat ggcaacgggg gattcatgca tcccaacatg    480

agctcagcca gcagtgcgtt acaagggttg ctgaggaagc ttggagctgg acttgatgac    540
```

-continued

```
ttgcttcctt cttcaggtat tggctcaggt tcttcttccc atttaaatgg gaggatgaag    600
aagatactcg ctggcttgcg ctctgaagga aaagagggaa agcaagtcga ggctttgacc    660
cagctctgcg agatgttatc cattggcacc gaagactcct tgagcacctt ctctgttgat    720
tccttcgtcc ccgttcttgt tggtctactt aaccatgaga gcaatccgga tattatgctt    780
cttgctgcca gggctcttac ccatctgtgt gatgttttgc cctcttcttg tgctgctgtt    840
gttcattacg gggctgtttc atgctttgtc gccagattgc taaccattga atacatggac    900
ttggccgagc agtctctgca agctctcaaa aagatatctc aggaacaccc aacggcctgt    960
ttgcgagctg gtgctcttat ggcagtgcta tcatatctgg atttcttctc caccggtgtc   1020
cagcgtgtag cagtctctac cgctgcaaat atgtgcaaga agttaccttc tgatgcatct   1080
gattatgtta tggaagctgt accggtactg acaaacctac ttcagtatca tgatgcgaag   1140
gttttggaat atgcttctat ctgtttgact cggattgccg aagcatttgc atcgtcccct   1200
gataaattag atgaattatg caaccatggc ctggtgactc aagctgcgac tcttatatcc   1260
gctagcaact cgggaggtgg gcaagcatct cttggtgttt caacatacac gggattaatc   1320
cgattacttt ccacctgtgc gagcggttca cctcttgggt gcaggacatt acttcttctc   1380
ggtattagta gcattcttaa ggatattctg tcgggttctg gtgtctctgc taatgcatct   1440
atatccccag cactgagcag gcctgcagat cagatttttg agatagtcaa cctagcgaac   1500
gagctcctcc ctccattgcc agaaggaagt atctcccttc ctactagcgc aaacgcgtta   1560
gtgaaaggtt caggccaaaa aaattcttct ccaagtactt caggaaaaca agaagattct   1620
cccaaagttt cacctagaga aaaattactt agtgatcaac ccgaactttt gcagcaattt   1680
ggattggatc ttcttccagt tttagtgcag atctatggtt ctagtgtcaa tggtactatt   1740
cgtcataaat gtctctccgt tatcgcaaag ttgatgtatt tcagcactcc agaaatgatt   1800
caatctctaa ttggtgacac aaatatatcg agcttcttgg ctagtgtctt ggcatggaaa   1860
gatccacaag tcttggttcc tgctctacaa gttgcagaaa ttctgatgga aaaacttcct   1920
gaaactttct cgaaagtgtt tgtgagggaa ggggtggttc atgctgtaga tcaacttgtc   1980
ttggttggta aacctagtgc taatgcttct actgatcagg aaaatgactg tgtgcctgga   2040
tctgcacgat ctaggcgtta cagacggcga agtagtaatg ccaattctga tggaaatcag   2100
tcggaagagc ttaagaattc tgtgtcagct agcataggtg cgacccataa ttccatggaa   2160
tctcctacag cgagcttcat gctaagggaa acagttagct cctgtgcaaa agcattcaaa   2220
gacaagcact tcccgtctga tggtggggaa tttgatgttg gagttacaga tgatctcttg   2280
catctgaaga atctttgcac gaagctaact gctggtacaa atgatcataa agtgaaagga   2340
aaggggaaat ctaaagtctc tgggccatgc cttggcgatt tttctgctag caaagaagaa   2400
tacttgattg gtatcatctc cgagatactt ggcgagctaa gcaaagggga tggcgtctca   2460
acttttgagt ttattggcag tggtgtggta gcagcattgc ttaactattt ttcttatgga   2520
tacttttcca aagagaagat ctccgaggtt gatttgccca aacttcgcca ggatgggctc   2580
agaaggttca aagcttttct agaaattgca cttccttctg atggtaatga gggaaagatc   2640
cctcctatga ctgttttgat tcagaaactt caagatgctt tgtcttcact ggaacgcttt   2700
ccggtcgtcc ttagccatcc ctcaaggtca ctcagtggaa gtgctcgtct ctcatctgga   2760
ttgagtgctt tggcacatcc tttgaagttg cggttatgcc gtgcacctgg agagaaggct   2820
ctacgtgatt actcctccaa tattgttctc atagatccat tggcaagcat agcagcagtg   2880
gaggaatttc tctggccccg agttcaacgc agtgaatctg ggtgaaggc agcagcgcct    2940
```

-continued gctggaaaca ctgagccagg cacattacct agcggtgctg gtgtttcatc accatcctcg 3000
tcaactccag cttccaccac tcgtcattct tctagatcta gatcagcaat taaaataggc 3060
gatgcctcaa agaaagaacc tgtgcacgag aaaggtacca gctcatctaa aggtaaaggt 3120
gttatgaagc cggctcagcc ggataagggg cctcagacaa ggagcagtgc tcaaaggaaa 3180
gctgttcttg acaaagatac actaatgaaa ccagctagcg gagactccag ctctgaggac 3240
gaagaaatgg atatatcccc cgtcgacatg gatgatgctt tggtgattga agaggaagac 3300
atttctgacg acgatgatga tgatgatgag gaggatgtct tggatgacag tcttcccatg 3360
tgcacccctg ataaggttca tgatgtaaaa ttgggagacg cagtggatga tgagggagcc 3420
ggcctagcac ctagcggccg acagatgaat tcagctttgg caggaagtag tggaacagca 3480
actgcaaggg gatctaattc tactgatgct ggcattggga atctttatgg ttctaggggt 3540
gcactctcct tcgctgctgc ggcgatggca gggcttggag ctgccagtgg tagaggtatc 3600
agggggagta gagacctaca tggcgtaccc ctgaatcgaa gttctgatga gtcctctaag 3660
ttgatgttta ctgcgggagg aaagcaactt agtaggcata tgacgatata tcaggctgtg 3720
caacgacaac ttatgctaga cgaagatgat gatgacaggc tcggtggcag cgatttcatc 3780
tcgagtgatg gaagcagatt aaatgatata tatactatca tgtaccagat gccggacagc 3840
caagcgaata ggttgtctgc tggtggtgca agttctacca caccatctaa atccactaaa 3900
tctgctacta ctaatgcaag cgtagaagcc cagtcgtata gggcatctct tttggatagt 3960
atcgtacaag gaaagcttcc atgcgacctt gagaaggcaa attctacgta taatgttttg 4020
gcgttgttgc gtgtactaga gggtttaaat cagcttggcc ctcggttaag agcccaaacc 4080
atttctgatc gtttcgcaga gggtaaaatt acaagtctgg atgatctgaa tacaactgct 4140
gcaaaggttt ctcatgaaga attcatcaac agcaaactta cacccaaatt agctcgacag 4200
atccaggacg cgcttgcttt gtgcagtgga agtcttccct cttggtgcta ccagttgact 4260
acagcatgcc cgtttttgtt tccgtttcag acccggagac agtatttcta ttcaactgcc 4320
tttgggttgt cgcgtgcatt gaaccgcttg cagcagcagc aaggtgctga cggcagtggt 4380
tctacaaatg aacgagagat gagaataggg agattgcagc gccagaaagt gcgtgtatcc 4440
cgaaatagaa tattagattc tgctgcgaaa gttatggaga tgtattctag ccaaaaagct 4500
gtgcttgaag tagaatattt tggtgaagtt ggtactggtc taggccccac acttgagttt 4560
tacacactcc taagccatga tttgcaaaag gtttcccttg ggatgtggag atcaaattct 4620
ggtgacaagt tatctatgca aactgataga gatgagattc aagacggtaa atcagcagca 4680
gctagggaca gagatatagt tcaggcacca tttgggttgt tccctcggcc ctggccctca 4740
actgctgacg tatctgaagg tagtcggttt cataaagttg ttgaatattt ccgccttttta 4800
gggcgcgtga tggcaaaggc acttcaagat ggacggctaa tggacgtccc gttaagtaca 4860
gctttttata agctcattct tggtcaagag cttgatttgc atgatgttat attatttgat 4920
gctgaacttg gcaagacttt gcaagagctt cgtgttcttg ttggccgtaa gcactatctg 4980
gaagcagaag gtggtgacaa cagtagcgtg atttctgatt tatgtttacg tggatcccgt 5040
attgaagatc tttgcttgga cttcacccta cctggctatc ctgaatacat attgagacca 5100
ggagatgaca tgttgatatt aatagtcttg aggactatat atccctggtc gttgatgcca 5160
ctgtcaagag aggagttgcc cggcagattg aagccttcag atctggattc aatccaggtc 5220
tttgacataa aatctttaca agtattcacc ccttctgagc tggactactt gttatgtggt 5280

-continued cgtagagagt tgtgggaggc ggagactctt gttgaacata tcaagtttga tcacggttat 5340
actgcaaaaa gtccggcaat cattttctta ctggagatca tgggagagct tacagcagat 5400
caacagcgtg ctttctgcca gtttgtaact ggagctccta ggcttcctcc tggtggctta 5460
gctgttctca acccaaagct gacgattgtg agaaagctct catcaacctc aaatgcggct 5520
gccaatggga caggggcttc ggaaacagca gacgacgatc ttcccagcgt catgacttgc 5580
gccaactacc ttaagctccc tccttattct acaaaggaaa tcatgtacaa gaaactgctc 5640
tacgcgatca acgaagggca gggatcgttc gacctctcct ag 5682

<210> SEQ ID NO 5
<211> LENGTH: 5667
<212> TYPE: DNA
<213> ORGANISM: Brassica napus

<400> SEQUENCE: 5
atggaaactc ggagccgcaa gcgtgcggag gcgacctcaa ctgccccatc ttcttcttct 60
tcctctcctc ctcctcctcc ttcctcaggt cccaccactc gcagcaaacg cgctcgcctc 120
tcgtctccct cttcctcttc agccgccgct actgcacctt cctcctccac tcgctctcgt 180
tcttctcgct ctaccaccgc tacagccgcc gttactccca tggacacatc caccgagtct 240
tctggattcc gccgcggcgg aggacgaggt aacaggggaa acgataatac taactctgat 300
aagggaaagg agaaggagca tgaggttagg attagggata gagaaagaga cagagctaga 360
cagcagctca acatggacgc tgcagctgct gcagccgccg ccgctgatga ggacgacgac 420
aatgatagtg aggatggcaa cgggggattc atgcatccca acatgagctc agccagcagt 480
gcgttacaag ggttgcttag gaagcttgga gctggacttg atgacttgct tccttcttca 540
ggtattggct caggttcgtc ttctcacttg aatgggagga tgaagaaggt actcgctggc 600
ttgcgctctg aaggagaaga gggaaagcag gtcgaggctt tgacgcagct gtgcgagatg 660
ttatctattg ggaccgaaga ctccctgagc accttctctg ttgattcctt cgtcccggtt 720
cttgttggtc tacttaacca tgagagcaat ccggatatta tgcttcttgc tgccagggct 780
cttactcatc tgtgtgatgt tttgccgtct tcttgtgctg ctgttgttca ttacggggct 840
gtttcgtgct ttgtcgccag attgttgaca atagaataca tggacttggc cgagcagtct 900
ctgcaagctc tcaaaaagat atctcaggaa cacccaacgg cctgtttgcg tgctggtgct 960
cttatggcag tgctatcata tctggatttc ttctccaccg gtgtccagcg tgtagcagta 1020
tctaccgctg caaatatgtg caagaagtta ccttctgatg catctgatta tgttatggaa 1080
gctgtaccgg tactgacaaa cctacttcag tatcatgatg cgaaggtttt ggaatatgct 1140
tctatctgtt tgactcggat tgccgaagca tttgcatcgt cccctgataa attagatgaa 1200
ttatgcaacc atggcctggt gactcaagct gcgactctta tatccgctag caactcggga 1260
ggtgggcaag catctctcgg tgtttcaaca tacacgggat taatccgatt actttccacc 1320
tgtgcgagcg gttcacctct tgggtgcagg acattacttc ttctcggtat tagtagcatt 1380
cttaaggata ttctgtcggg ttccggtgtc tctgctaatg catctatatc cccagcactg 1440
agcaggcctg cagatcagat ttttgagata gtcaacctag cgaacgagct cctccctcca 1500
ctgccagaag gaagtatctc ccttcctact agcgcaaacg cgttagtgaa aggttcaggc 1560
caaaaaaagt cttctccaag tacttcagga aaacaagaag attctcccaa agtttcacct 1620
agagaaaaat tacttagtga tcaacccgaa cttctgcagc aatttggatt ggatcttctt 1680
ccagttttag tgcagatcta tggttctagt gtcaatggta ctattcgtca taaatgtctc 1740
tcagttatcg caaagttgat gtatttcagc actccagaaa tgattcaatc tctaattggt 1800
gacacaaata tatcgagctt cttggctagt gtcttggcat ggaaagatcc acaagtcttg 1860
gttcctgctc tacaagttgc agaaattctg atggaaaaac ttcctgaaac tttctcgaaa 1920
gtgtttgtga gggaaggggt ggttcatgct gtagatcaac ttgtcttggt tggtaaacct 1980
agttctcatg cttctactga tcaggaaaat gactgtgtgc ctggatctgc acgatctagg 2040
cgttatagac ggcgaagtag taacgccaat tctgatggaa atcagtcgga agagcttaag 2100
aattctgtgt cagctagtat aggtgcaaac cataattcca tggaatctcc tacagcgagc 2160
ttcatgctaa gggaaacagt tagctcctgt gcaaaagcat tcaaagacaa gcacttcccg 2220
tctgatggtg gggaatttga tgttggagtt acagatgatc tcttgcatct gaagaatctt 2280
tgcacgaagc taactgctgg tacaaatgat cataaagtga aaggaaaggg gaaatctaaa 2340
gcctctgggc catgcctcgg cgatttttct gctagcaaag aagaatactt gattggtatc 2400
atctccgaga tacttggcga gctaagcaaa ggagatggtg tctcaacttt tgagtttatt 2460
ggcagtggtg tggtagcagc attgcttaac tatttttctt atggatactt ttccaaagag 2520
aagatctccg aggttgattt gcccaaactt cgccaggatg ggctcagaag gttcacagct 2580
tttctagaaa ttgcacttcc ttctgatggt aatgagggaa agatccctcc tatgactgtt 2640
ttgattcaga aacttcaaga tgctttgtct tcactggaac gctttccggt cgtccttagc 2700
catccctcaa agtcactcag tggaagtgct cgtctctcat ctggattgag tgctttggca 2760
catcctttga agttgcggtt atgccgtgca cctggagaga aggcactacg tgattactcc 2820
tccaatattg ttctcataga tcctttggca agcatagcag cagtggagga atttctctgg 2880
ccccgagttc aacgcagtga atctggggtg aagccagcag cgcctgttgg aaacactgag 2940
ccaggcacat tacctagcgg tgctggtgtt tcatcaccat cctcgtcaac tccagcttcc 3000
accactcgtc attcttctag atctagatct gcaattaaaa taggcgatgc ctcaaagaaa 3060
gaacctgtgc acgagaaagg taccagctca tctaaaggta aaggtgttat gaagccggct 3120
cagccggata aggggcctca gacaaggagc agtgctcaaa ggaaagctgt tcttgacaaa 3180
gatacactaa tgaaaccagc tagcggagac tccagctctg aggacgaaga aatggatata 3240
tcccccgtcg acatggatga tgctttggtt attgaagagg aagacatttc tgacgacgat 3300
gaggatgatg atgatgagga tgtcttggat gacaatcttc ccatgtgcac ccctgataag 3360
gttcatgatg taaaattggg agacgcagtg gatgatgagg gagccggtct agcacctagc 3420
ggccgacaga tgaattcagc tttggcagga agtagtggaa cagcaactgc aaggggatct 3480
aattctactg atgctggcat tgggaatctt tatggttcta ggggtgcact ctccttcgct 3540
gctgcggcga tggcagggct tggagctgcc agtggtagag gtatcagggg aagtagagac 3600
ctacatgggc gtaccctgaa tcgaagttct gatgagtcct ctaagttgat gtttactgcg 3660
ggaggaaagc aacttagtag gcatatgacg atatatcagg ctgtgcaacg acaacttatg 3720
ctagacgaag atgatgatga caggctcggt ggcagcgatt tcatctccag tgatggaagc 3780
agattaaatg atatatatac tatcatgtac cagatgccgg acagccaagc gaataggttg 3840
tctgctggtg gtgcaagttc taccacacca tctaaatcca ccaaatctgc tactactaat 3900
gcaagcgtag aagctcagtc gtatagggca tctcttttgg atagtatcgt acaaggaaag 3960
cttccatgcg accttgagaa gtccaattct acgtataatg ttctggcgtt gttacgtgta 4020
ttagagggtt taaatcagct tggccctcgc ttaagagccc aaaccgtttc tgatcgtttt 4080
gcagagggta aaattacaag tctggatgat ctgaatacaa ctgctgcaaa ggtttctcat 4140
gaagaattca tcaacagcaa acttacaccc aaattagctc gacagatcca ggacgcgctt 4200
gctttgtgca gtggaagtct tccctcttgg tgctaccagt tgactacagc atgcccgttt 4260
ttgtttccgt ttcagacccg gagacagtat ttctattcaa ctgcctttgg gttgtcgcgt 4320
gcattgaacc gcttgcagca gcagcaaggt gctgacggca gtggttctac aaatgaacga 4380
gagatgagaa tagggagatt gcagcgccag aaagtgcgtg tatcccgaaa tagaatatta 4440
gattctgctg cgaaagttat ggagatgtat tctagccaaa aagctgtgct tgaagtagaa 4500
tattttggtg aagttggtac tggtctaggc cccacacttg agttttacac actcctaagc 4560
catgatttgc aaaaggtttc ccttgggatg tggagatcaa attctggtga caagttatct 4620
atgcaaactg atagagatga gattcaagac ggtaaatcag cagcagctag ggacagagat 4680
atagttcagg caccacttgg gttgttccct cggccctggc cctcaactgc tgacgtatct 4740
gaaggtagtc ggtttcataa agttgttgaa tatttccgcc ttttagggcg cgtgatggca 4800
aaggcacttc aagatggacg gctaatggac gtcccgttaa gtacagcttt ttataagctc 4860
attcttggtc aagagcttga tttgcatgat gttatattat ttgatgctga acttggcaag 4920
actttgcaag agcttcgtgt tcttgttggc cgtaagcact atctggaagc aggcggtggt 4980
gacaacagta gcgggatttc tgatttatgt ttgcgtggat cccgtattga agatctttgc 5040
ttggacttca ccctacctgg ctaccctgaa tacatattga gaccaggaga tgacattgtt 5100
gatattaata gtcttgagga ctatatatcc ctggtcgttg atgccactgt caagagagga 5160
gttgcccggc agattgaagc cttcagatct ggattcaatc aggtctttga cataaaatct 5220
ctacaaatat tcaccccttc tgagctggac tacttgttgt gtggtcgtag agagttgtgg 5280
gaggcggaga ctcttgttga acatatcaag tttgatcacg gttatactgc aaaaagtccg 5340
gcaatcattt tcttattgga gatcatggga gagctaacag cagatcaaca gcgggctttc 5400
tgccagttcg taactggagc tcctaggctt cctcctggtg gcttagctgt tctcaaccca 5460
aggctgacga ttgtgagaaa gctctcatca acctcaaatg ctgctgccaa tgggacaggg 5520
gcttcggaaa cagcagacga cgatcttccc agcgtcatga cttgcgccaa ctaccttaag 5580
ctccctcctt attctacaaa ggaaatcatg tacaagaaac tgctctacgc catcaacgaa 5640
gggcaggggt cgttcgacct atcctag 5667

<210> SEQ ID NO 6
<211> LENGTH: 7960
<212> TYPE: DNA
<213> ORGANISM: Brassica napus

<400> SEQUENCE: 6
atggaaactc ggagccgcaa gcgtgcggag gcgacctcaa ctgccccatc ttcttcttct 60
tcctctcctc ctcctcctcc ttcctcaggt cccaccactc gcagcaaacg cgctcgcctc 120
tcgtctccct cttcctcttc agccgccgct actgcacctt cctcctccac tcgctctcgt 180
tcttctcgct ctaccaccgc tacagccgcc gttactccca tggacacatc caccgagtct 240
tctggattcc gccgcggcgg aggacgaggt aacaggggaa acgataatac taactctgat 300
aagggaaagg agaaggagca tgaggttagg attagggata gagaaagaga cagagctaga 360
cagcagctca acatggacgc tgcagctgct gcagccgccg ccgctgatga ggacgacgac 420
aatgatagtg aggatggcaa cgggggattc atgcatccca acatgagctc agccagcagt 480
gcgttacaag ggttgcttag gaagcttgga gctggacttg atgacttgct tccttcttca 540

-continued

```
ggtattggct caggttcgtc ttctcacttg aatgggagga tgaagaaggt actcgctggc    600
ttgcgctctg aaggagaaga gggaaagcag gtcgaggctt tgacgcagct gtgcgagatg    660
ttatctattg ggaccgaaga ctccctgagc accttctctg ttgattcctt cgtcccggtt    720
cttgttggtc tacttaacca tgagagcaat ccggatatta tgcttcttgc tgccagggct    780
cttactcatc tgtgtgatgt tttgccgtct tcttgtgctg ctgttgttca ttacggggct    840
gtttcgtgct ttgtcgccag attgttgaca atagaataca tggacttggc cgagcaggtt    900
cgatttccta acaattcttg aattttttg ctgaatatat attgtggaat gttttatgct    960
gcagtttcta cacgtacata tccaatattt tagtttactt aggacgaaat ttgaaatttg   1020
attttattct tcatgtgatt tacaacagtc tctgcaagct ctcaaaaaga tatctcagga   1080
acacccaacg gcctgtttgc gtgctggtgc tcttatggca gtgctatcat atctggattt   1140
cttctccacc ggtgtccagg tgggtaattt tgtaactttt ctttaatgct ttccatactc   1200
gtttatctaa tgcacttttt tttttacttt ttgtagcgtg tagcagtatc taccgctgca   1260
aatatgtgca agaagttacc ttctgatgca tctgattatg ttatggaagc tgtaccggta   1320
ctgacaaacc tacttcagta tcatgatgcg aaggtaaacg atccctttt tttttgcta   1380
taatgtggta ttatctagtt ctgctcttgc cccagtttcc ttcatagtat gttcgtacgg   1440
tggcaggttt tggaatatgc ttctatctgt ttgactcgga ttgccgaagc atttgcatcg   1500
tcccctgata aattagatga attatgcaac catggcctgg tgactcaagc tgcgactctt   1560
atatccgcta gcaactcggg aggtgggcaa gcatctctcg gtgtttcaac atacacggta   1620
tgagttaatt cttttgtgtt ttctatattt cgttattcat aggatgacat tttcatcata   1680
ttttcacagg gattaatccg attactttcc acctgtgcga gcggttcacc tcttgggtgc   1740
aggacattac ttcttctcgg tattagtagc attcttaagg atattctgtc gggttccggt   1800
gtctctgcta atgcatctat atccccagca ctgagcaggc ctgcagatca ggtacggatt   1860
tactttttga catcacagac tttattttgt tcaattcctg ataaagtcta ttcagtaaaa   1920
agtgttttgt ttaggggaca cacctttaaa tagatcatca acataaattg tgtgttgagt   1980
gagatgctta ggggacacac cttcaaatag atcacttgca tttaaatgga tcacttgcat   2040
ttaggagttt tgtctattca gttcaatgat aatctttttt ttttgtaaca ctcagctcaa   2100
tgataatcta tgtacatgta ttttgagctt tatttatgtt gtaaccgatg gctcaacttt   2160
catatgcttg ttttctggta tggtgttaga agtggtatag ataaaagtgc ttagcgcttc   2220
atcagtgtgc tcggtcttgt ttatttaact ttttttatcc catgactcgc taattcttga   2280
atatattctt gaacatgatc atgtgaggtc ttttgtttcc gaattataac tcttgttttg   2340
catcttagat ttttgagata gtcaacctag cgaacgagct cctccctcca ctgccagaag   2400
gaagtatctc ccttcctact agcgcaaacg cgttagtgaa aggttcaggc caaaaaaagt   2460
cttctccaag tacttcagga aaacaagaag attctcccaa agtttcacct agagaaaaat   2520
tacttagtga tcaacccgaa cttctgcagc aatttggatt ggatcttctt ccagttttag   2580
tgcaggtaat tttttgttgc agttgctaca agttagtgtt catacaacct cctgtatgtc   2640
taattaccct tgttttcttt cctacagatc tatggttcta gtgtcaatgg tactattcgt   2700
cataaatgtc tctcagttat cgcaaagttg atgtatttca gcactccaga aatgattcaa   2760
tctctaattg gtgacacaaa tatatcgagg tatgctggtt atgttttaaa ttaggtatca   2820
catggcgcaa cttcttacat tatttttcct atgtagcttc ttggctagtg tcttggcatg   2880
```

-continued

```
gaaagatcca caagtcttgg ttcctgctct acaagttgca gaaattctga tggaaaaact   2940
tcctgaaact ttctcgaaag tgtttgtgag ggaaggggtg gttcatgctg tagatcaact   3000
tgtcttggtt ggtaaaccta gttctcatgc ttctactgat caggaaaatg actgtgtgcc   3060
tggatctgca cgatctaggc gttatagacg gcgaagtagt aacgccaatt ctgatggaaa   3120
tcagtcggaa gagcttaaga attctgtgtc agctagtata ggtgcaaacc ataattccat   3180
ggaatctcct acagcgagct tcatgctaag ggaaacagtt agctcctgtg caaaagcatt   3240
caaagacaag cacttcccgt ctgatggtgg ggaatttgat gttggagtta cagatgatct   3300
cttgcatctg aagaatcttt gcacgaagct aactgctggt acaaatgatc ataaagtgaa   3360
aggaaagggg aaatctaaag cctctgggcc atgcctcggc gatttttctg ctagcaaaga   3420
agaatacttg attggtatca tctccgagat acttggcgag ctaagcaaag gagatggtgt   3480
ctcaactttt gagtttattg gcagtggtgt ggtagcagca ttgcttaact atttttctta   3540
tggatacttt tccaaagaga agatctccga ggttgatttg cccaaacttc gccaggatgg   3600
gctcagaagg ttcacagctt ttctagaaat tgcacttcct tctgatggta atgagggaaa   3660
gatccctcct atgactgttt tgattcagaa acttcaagat gctttgtctt cactggaacg   3720
ctttccggtc gtccttagcc atccctcaaa gtcactcagt ggaagtgctc gtctctcatc   3780
tggattgagt gctttggcac atcctttgaa gttgcggtta tgccgtgcac ctggagagaa   3840
ggcactacgt gattactcct ccaatattgt tctcatagat cctttggcaa gcatagcagc   3900
agtggaggaa tttctctggc cccgagttca acgcagtgaa tctggggtga agccagcagc   3960
gcctgttgga aacactgagc caggcacatt acctagcggt gctggtgttt catcaccatc   4020
ctcgtcaact ccagcttcca ccactcgtca ttcttctaga tctagatctg caattaaaat   4080
aggcgatgcc tcaaagaaag aacctgtgca cgagaaaggt accagctcat ctaaaggtaa   4140
aggtgttatg aagccggctc agccggataa ggggcctcag acaaggagca gtgctcaaag   4200
gaaagctgtt cttgacaaag atacactaat gaaaccagct agcggagact ccagctctga   4260
ggtatgtcac tgtagaaagt tctggattac atggttgttt attgtgtaac attatattat   4320
gtttgtggtg tgatctgctt atgcagcact atcgtactta tattgcttgc aggacgaaga   4380
aatggatata tcccccgtcg acatggatga tgctttggtt attgaagagg aagacatttc   4440
tgacgacgat gaggatgatg atgatgagga tgtaagtatt ccctccccag tatgtacatt   4500
acagacgcaa ttatttctct tgctaacaac atgaaagatg atacttttcg caataatgct   4560
tgctagcttt ccgtattctt agataagttt accatattga gctcacctta tttggcacct   4620
ttccttttag aactgactaa agagaataat gaactttata ccacaatttc tcatattgat   4680
ctggtcttga attcaggtct tggatgacaa tcttcccatg tgcacccctg ataaggttca   4740
tgatgtaaaa ttgggagacg cagtggatga tgagggagcc ggtctagcac ctagcggccg   4800
acagatgaat tcagctttgg caggaagtag tggaacagca actgcaaggg gatctaattc   4860
tactgatgct ggcattggga atctttatgg ttctaggggt gcactctcct tcgctgctgc   4920
ggcgatggca gggcttggag ctgccagtgg tagaggtatc aggggaagta gagacctaca   4980
tgggcgtacc ctgaatcgaa gttctgatga gtcctctaag ttgatgttta ctgcgggagg   5040
aaagcaactt agtaggcata tgacgatata tcaggctgtg caacgacaac ttatgctaga   5100
cgaagatgat gatgacaggc tcggtggcag cgatttcatc tccagtgatg gaagcagatt   5160
aaatgatata tatactatca tgtaccagat gccggacagc caagcgaata ggttgtctgc   5220
tggtggtgca agttctacca caccatctaa atccaccaaa tctgctacta ctaatgcaag   5280
```

```
cgtagaagct cagtcgtata gggcatctct tttggatagt atcgtacaag gaaagcttcc   5340
atgcgacctt gagaagtcca attctacgta taatgttctg gcgttgttac gtgtattaga   5400
gggtttaaat cagcttggcc ctcgcttaag agcccaaacc gtttctgatc gttttgcaga   5460
gggtaaaatt acaagtctgg atgatctgaa tacaactgct gcaaaggttt ctcatgaaga   5520
attcatcaac agcaaactta cacccaaatt agctcgacag atccaggacg cgcttgcttt   5580
gtgcagtgga agtcttccct cttggtgcta ccagttgact acagcatgcc cgtttttgtt   5640
tccgtttcag acccggagac agtatttcta ttcaactgcc tttgggttgt cgcgtgcatt   5700
gaaccgcttg cagcagcagc aaggtgctga cggcagtggt tctacaaatg aacgagagat   5760
gagaataggg agattgcagc gccagaaagt gcgtgtatcc cgaaatagaa tattagattc   5820
tgctgcgaaa gttatggaga tgtattctag ccaaaaagct gtgcttgaag tagaatattt   5880
tggtgaagtt ggtactggtc taggccccac acttgagttt tacacactcc taagccatga   5940
tttgcaaaag gtttcccttg ggatgtggag atcaaattct ggtgacaagt tatctatgca   6000
aactgataga gatgagattc aagacggtaa atcagcagca gctagggaca gagatatagt   6060
tcaggcacca cttgggttgt tccctcggcc ctggccctca actgctgacg tatctgaagg   6120
tagtcggttt cataaagttg ttgaatattt ccgccttta gggcgcgtga tggcaaaggc    6180
acttcaagat ggacggctaa tggacgtccc gttaagtaca gctttttata agctcattct   6240
tggtcaagtg agtttttac tatcagtaac ttttttatt tagctaagag tggactagta     6300
gtttcgactt ctttacgttg ttcgtaattt cttactgctt ctttactcac ctgaacagga   6360
gcttgatttg catgatgtta tattatttga tgctgaactt ggcaagactt tgcaagagct   6420
tcgtgttctt gttggccgta agcactatct ggaagcaggc ggtggtgaca acagtagcgg   6480
gatttctgat ttatgtttgc gtggatcccg tattgaagat ctttgcttgg acttcaccct   6540
acctggctac cctgaataca tattgagacc aggagatgac attgtaccgt ctaataagct   6600
ttacatccga tatcttacta ttgttttagt tcttgtccat tgttgctgat gccgtgtact   6660
gttttctgtt ctattacagg ttgatattaa tagtcttgag gactatatat ccctggtcgt   6720
tgatgccact gtcaagagag gagttgcccg gcagattgaa gccttcagat ctggattcaa   6780
tcaggttagc agtttcacag actctccgct ttgtctctta cttttcctgt aggctttggc   6840
tttggctttg gctttggctt ctaaattaca taggagtggt ttcttttggt tcatacttta   6900
taatctttta aacaacaggt tgatgataat ttagtcttac ctttattatc tttacaagaa   6960
ttctctgttc ttacacatga ttaccaggtc tttgacataa aatctctaca aatattcacc   7020
ccttctgagc tggactactt gttgtgtggt cgtagagagt tgtgggaggt gagttttcat   7080
ctatttttg aatttccact acccatttga ctcgaatcga ctagataaaa ttttcttttc    7140
taaaaccttt cttttattgc aggcggagac tcttgttgaa catatcaagt ttgatcacgg   7200
ttatactgca aaaagtccgg caatcatttt cgtaagttac tttccgtact agtttgttaa   7260
aaaaccaatt ttcttttaca atcaagcttt ttgcttcttt attgttgatt cctttttgac   7320
tttgattttc accctggcgg tagttattgg agatcatggg agagctaaca gcagatcaac   7380
agcgggcttt ctgccagttc gtaactggag ctcctaggct tcctcctggt ggcttagctg   7440
ttctcaaccc aaggctgacg attgtgagaa aggtaagaaa cctttactta tatattcggt   7500
taaaaagcgt tttgtaatt gagccaagag gttctagtca tgttaaacta gacccaccaa    7560
gccatatatc agaatacatc tacacgtgac gcattgttgt gtttgcaaga cttgctaaga   7620
```

-continued

```
tgaattagct cttactcgat ttaagttgtg tatttgcttc caattgatgt gtttttggct   7680

tgatgcagct ctcatcaacc tcaaatgctg ctgccaatgg gacaggggct tcggaaacag   7740

cagacgacga tcttcccagc gtcatgactt gcgccaacta ccttaagctc cctccttatt   7800

ctacaaaggt aactcgtctc tcttttttta agtctacggt ttctgtgttt ggttggttgg   7860

ggtgagcctg aacacgagtt tgtacctgaa acaggaaatc atgtacaaga aactgctcta   7920

cgccatcaac gaagggcagg ggtcgttcga cctatcctag                          7960


<210> SEQ ID NO 7
<211> LENGTH: 7901
<212> TYPE: DNA
<213> ORGANISM: Brassica napus

<400> SEQUENCE: 7

atggaaactc ggagccgcaa gcgtgcggag gcgacctcaa ctgccccatc ttcttcttct     60

tcgtctcctc ctcctcctcc ctcaggtccc accactcgca gcaaacgcgc tcgcctctcg    120

tctccctctt cctcttcagc cgccgccgct accaccgcta ctgcaccttc ctcctccacc    180

cgctctcgtt cttctcgctc tgccgctacc gctaccgcta cagccgccgt tactcccatg    240

gacacatcca ccgagtcttc tggattccgc cgcggcgggg gacgaggtaa caggggaaac    300

gataatacta attctgataa gggaaaggag aaggagcatg aggttaggat tagggataga    360

gaaagagacc gagccagaca gcagctcaac atggacgctg cagctgctgc agccgccgcc    420

gctgaagagg acgatgacaa tgatagtgag gatggcaacg gggattcat gcatcccaac     480

atgagctcag ccagcagtgc gttacaaggg ttgctgagga agcttggagc tggacttgat    540

gacttgcttc cttcttcagg tattggctca ggttcttcct cccacttaaa tgggaggatg    600

aagaagatac tcgctggctt gcgctctgaa ggagaagagg gaaagcaggt cgaggctttg    660

acccagctct gcgagatgtt atccattggc accgaagact ccttgagcac cttctctgtt    720

gattccttcg tccccgttct tgttggtcta cttaaccatg agagcaatcc ggatattatg    780

cttcttgctg ccagggctct tacccatctg tgtgatgttt tgccctcttc ttgtgctgct    840

gttgttcatt acggggctgt ttcatgcttt gtcgccagat tgctaaccat tgaatacatg    900

gacttggccg agcaggttcg ctttcctagc aattcttgaa tttttttttt ttgaatataa    960

tacttatcta aaatctggat aaagtgtatg ttgtggaatg ttttatgctg cagtttctac   1020

acgtacatat ccaatatttt aatttactta ggacgaaatt tgaaatttga ttttattctt   1080

catgtgattt acaacagtct ctgcaagctc tcaaaaagat atctcaggaa cacccaacgg   1140

cctgtttgcg agctggtgct cttatggcag tgctatcata tctggatttc ttctccaccg   1200

gtgtccaggt gggtaatttt gtaacctttc ttttatgctt tccatactcg tttatctaat   1260

gcactttttt ttactttgac tttgtagcgt gtagcagtct ctaccgctgc aaatatgtgc   1320

aagaagttac cttctgatgc atctgattat gttatggaag ctgtaccggt actgacaaac   1380

ctacttcagt atcatgatgc gaaggtaaac gatccttttt ttttgctgta ctgtggtact   1440

atctagttct gctcttgccc cagtttcctt catagtatgt tcgtacggtg acaggttttg   1500

gaatatgctt ctatctgttt gactcggatt gccgaagcat ttgcatcgtc cctgataaa    1560

ttagatgaat tatgcaacca tggcctggtg actcaagctg cgactcttat atccgctagc   1620

aactcgggag gtgggcaagc atctcttggt gtttcaacat acacggtatg agttaattct   1680

ttcgtgtttt ctatatttcg ttattcatag gatgacattt tcatcatatt ttcacaggga   1740

ttaatccgat tactttccac ctgtgcgagc ggttcacctc ttgggtgcag gacattactt   1800
```

cttctcggta ttagtagcat tcttaaggat attctgtcgg gttctggtgt ctctgctaat 1860
gcatctatat ccccagcact gagcaggcct gcagatcagg tacggattta ctttttgaca 1920
tcacagactt tattttgttc atttcctgat aaaataaatg gtgtacaatg agatgcttag 1980
gggacacacc ttcaaataga tcacttgcat ttaggagatt tgtctattca gctcgatgat 2040
aatctatgta catgtatttt gagctttatt tatgttgtag ccgatggctc aagtttccta 2100
tgcttgtttt ctggtctggt gttagaagtg gtatagataa aagcgcttag cgcttcatca 2160
gtgtgctctg tcttgtttat ttaactttga tcccatgact ctctaattct tgaatatatt 2220
cttgaacatg atcatgtgag gtcctttgtt tccagaaagg ttccgaatta taactcttgt 2280
tttgcgtctt agatttttga gatagtcaac ctagcgaacg agctcctccc tccattgcca 2340
gaaggaagta tctcccttcc tactagcgca aacgcgttag tgaaaggttc aggccaaaaa 2400
aattcttctc caagtacttc aggaaaacaa gaagattctc ccaaagtttc acctagagaa 2460
aaattactta gtgatcaacc cgaacttttg cagcaatttg gattggatct tcttccagtt 2520
ttagtgcagg taatttttg ttgcggttgc tacaagttaa tgttcataca acctcctgta 2580
tgtctaatta cccttgtttt ctttccaaca gatctatggt tctagtgtca atggtactat 2640
tcgtcataaa tgtctctccg ttatcgcaaa gttgatgtat ttcagcactc cagaaatgat 2700
tcaatctcta attggtgaca caaatatatc gaggtatgct gtttatgttt taaattaggt 2760
atcacatggc gcaacttctt acattatttt tcctatgtag cttcttggct agtgtcttgg 2820
catggaaaga tccacaagtc ttggttcctg ctctacaagt tgcagaaatt ctgatggaaa 2880
aacttcctga aactttctcg aaagtgtttg tgagggaagg ggtggttcat gctgtagatc 2940
aacttgtctt ggttggtaaa cctagtgcta atgcttctac tgatcaggaa aatgactgtg 3000
tgcctggatc tgcacgatct aggcgttaca gacggcgaag tagtaatgcc aattctgatg 3060
gaaatcagtc ggaagagctt aagaattctg tgtcagctag cataggtgcg acccataatt 3120
ccatggaatc tcctacagcg agcttcatgc taagggaaac agttagctcc tgtgcaaaag 3180
cattcaaaga caagcacttc ccgtctgatg gtggggaatt tgatgttgga gttacagatg 3240
atctcttgca tctgaagaat ctttgcacga agctaactgc tggtacaaat gatcataaag 3300
tgaaaggaaa ggggaaatct aaagtctctg ggccatgcct tggcgatttt tctgctagca 3360
aagaagaata cttgattggt atcatctccg agatacttgg cgagctaagc aaaggggatg 3420
gcgtctcaac ttttgagttt attggcagtg gtgtggtagc agcattgctt aactattttt 3480
cttatggata cttttccaaa gagaagatct ccgaggttga tttgcccaaa cttcgccagg 3540
atgggctcag aaggttcaaa gcttttctag aaattgcact tccttctgat ggtaatgagg 3600
gaaagatccc tcctatgact gttttgattc agaaacttca agatgctttg tcttcactgg 3660
aacgctttcc ggtcgtcctt agccatccct caaggtcact cagtggaagt gctcgtctct 3720
catctggatt gagtgctttg gcacatcctt tgaagttgcg gttatgccgt gcacctggag 3780
agaaggctct acgtgattac tcctccaata ttgttctcat agatccattg gcaagcatag 3840
cagcagtgga ggaatttctc tggccccgag ttcaacgcag tgaatctggg gtgaaggcag 3900
cagcgcctgc tggaaacact gagccaggca cattacctag cggtgctggt gtttcatcac 3960
catcctcgtc aactccagct tccaccactc gtcattcttc tagatctaga tcagcaatta 4020
aaataggcga tgcctcaaag aaagaacctg tgcacgagaa aggtaccagc tcatctaaag 4080
gtaaaggtgt tatgaagccg gctcagccgg ataaggggcc tcagacaagg agcagtgctc 4140

-continued

```
aaaggaaagc tgttcttgac aaagatacac taatgaaacc agctagcgga gactccagct   4200
ctgaggtatg tcactgtagg aagttctgga ttacatggtt gtttattgtg taacattata   4260
ttatgtttgt ggtgtgatct gcttatgcag cactatctta cttatattgc ttgcaggacg   4320
aagaaatgga tatatccccc gtcgacatgg atgatgcttt ggtgattgaa gaggaagaca   4380
tttctgacga cgatgatgat gatgatgagg aggatgtaag tattccctcc ccagtatgta   4440
cattacagac gcaattattt ctcttgctaa caacatgaaa gatgatactt ctcgcaataa   4500
tgcttgctag ctttccgtat tcttagataa gtttaccata ttgagctgac cttatcggaa   4560
cctttccttt tagaactgac taaagagaat tatgaacttt ataccacaat ttctcatatt   4620
gatctggtct tgaattcagg tcttggatga cagtcttccc atgtgcaccc ctgataaggt   4680
tcatgatgta aaattgggag acgcagtgga tgatgaggga gccggcctag cacctagcgg   4740
ccgacagatg aattcagctt tggcaggaag tagtggaaca gcaactgcaa ggggatctaa   4800
ttctactgat gctggcattg ggaatcttta tggttctagg ggtgcactct ccttcgctgc   4860
tgcggcgatg gcagggcttg gagctgccag tggtagaggt atcagggga gtagagacct    4920
acatgggcgt accctgaatc gaagttctga tgagtcctct aagttgatgt ttactgcggg   4980
aggaaagcaa cttagtaggc atatgacgat atatcaggct gtgcaacgac aacttatgct   5040
agacgaagat gatgatgaca ggctcggtgg cagcgatttc atctcgagtg atggaagcag   5100
attaaatgat atatatacta tcatgtacca gatgccggac agccaagcga ataggttgtc   5160
tgctggtggt gcaagttcta ccacaccatc taaatccact aaatctgcta ctactaatgc   5220
aagcgtagaa gcccagtcgt atagggcatc tcttttggat agtatcgtac aaggaaagct   5280
tccatgcgac cttgagaagg caaattctac gtataatgtt ttggcgttgt tgcgtgtact   5340
agagggttta aatcagcttg gccctcggtt aagagcccaa accatttctg atcgtttcgc   5400
agagggtaaa attacaagtc tggatgatct gaatacaact gctgcaaagg tttctcatga   5460
agaattcatc aacagcaaac ttacacccaa attagctcga cagatccagg acgcgcttgc   5520
tttgtgcagt ggaagtcttc cctcttggtg ctaccagttg actacagcat gcccgttttt   5580
gtttccgttt cagacccgga gacagtattt ctattcaact gcctttgggt tgtcgcgtgc   5640
attgaaccgc ttgcagcagc agcaaggtgc tgacggcagt ggttctacaa atgaacgaga   5700
gatgagaata gggagattgc agcgccagaa agtgcgtgta tcccgaaata gaatattaga   5760
ttctgctgcg aaagttatgg agatgtattc tagccaaaaa gctgtgcttg aagtagaata   5820
ttttggtgaa gttggtactg gtctaggccc cacacttgag ttttacacac tcctaagcca   5880
tgatttgcaa aaggtttccc ttgggatgtg gagatcaaat tctggtgaca agttatctat   5940
gcaaactgat agagatgaga ttcaagacgg taaatcagca gcagctaggg acagagatat   6000
agttcaggca ccatttgggt tgttccctcg gccctggccc tcaactgctg acgtatctga   6060
aggtagtcgg tttcataaag ttgttgaata tttccgcctt ttagggcgcg tgatggcaaa   6120
ggcacttcaa gatggacggc taatggacgt cccgttaagt acagcttttt ataagctcat   6180
tcttggtcaa gtgagttttt ttactatcag taactttttt tatttagcta agagtggact   6240
agtagtttcg acacttcttt acgttgttcg taatttcttt ttcttttctc acctgaacag   6300
gagcttgatt tgcatgatgt tatattattt gatgctgaac ttggcaagac tttgcaagag   6360
cttcgtgttc ttgttggccg taagcactat ctggaagcag aaggtggtga caacagtagc   6420
gtgatttctg atttatgttt acgtggatcc cgtattgaag atctttgctt ggacttcacc   6480
ctacctggct atcctgaata catattgaga ccaggagatg acattgtacc gtctaataag   6540
```

ctttacatcc catatcttac tattctttta gttcttgtcc attgttgctg atgccgtgta 6600
ctgttttctg ttctattaca ggttgatatt aatagtcttg aggactatat atccctggtc 6660
gttgatgcca ctgtcaagag aggagttgcc cggcagattg aagccttcag atctggattc 6720
aatcaggtta gcagtttcac agactctccg ctttgtctct tacttttcct gttggcttct 6780
aaatcatatg gaaggagtgg tttcttttgg ttcattcttc ataatctttt aaacaacagg 6840
tttatattaa gtctttaatt tagtcttacc tttattatcc ttacaagacc tctctgttct 6900
tacacatgat taccaggtct ttgacataaa atctttacaa gtattcaccc cttctgagct 6960
ggactacttg ttatgtggtc gtagagagtt gtgggaggta atttgtaatt tttcaacttt 7020
cttttgaatt tccactaccc atttgacttg aatcaactag ataaaatttt catttctaaa 7080
acctttcttt tattgcaggc ggagactctt gttgaacata tcaagtttga tcacggttat 7140
actgcaaaaa gtccggcaat cattttcgta agttactttc ctcactagtt ttttaaaaaa 7200
ccaattttct tttacaatca agctttttgc ttctttattg ttgattcctt tttgactttg 7260
attttcaccc tggtggtagt tactggagat catgggagag cttacagcag atcaacagcg 7320
tgctttctgc cagtttgtaa ctggagctcc taggcttcct cctggtggct tagctgttct 7380
caacccaaag ctgacgattg tgagaaaggt aagaaacctt tacttatata ttcggttaaa 7440
aagcgttttt ttaattgagc caagaggttc ctagtcatgt taaactagac ccaccaagcc 7500
atatatcaaa atacatctac acgtgacgca tttgcttgca tttgcaagac ttgttaagag 7560
gaattagctc ttactcgatt taagttgtgt atttgctttc aattgatgtg tttttggctt 7620
gatgcagctc tcatcaacct caaatgcggc tgccaatggg acaggggctt cggaaacagc 7680
agacgacgat cttcccagcg tcatgacttg cgccaactac cttaagctcc ctccttattc 7740
tacaaaggta actcgtgtct ctcttttttt aagtctatgg tttctgtgtt tggttggttg 7800
gagtgagcct gaataggagt ttgtacctga aacaggaaat catgtacaag aaactgctct 7860
acgcgatcaa cgaagggcag ggatcgttcg acctctccta g 7901

<210> SEQ ID NO 8
<211> LENGTH: 8262
<212> TYPE: DNA
<213> ORGANISM: Arabidopsis thaliana

<400> SEQUENCE: 8
atggaaactc ggagccgcaa gcgggcggag gcgacctcag ctgccccatc ttcttcttct 60
tcttctcctc ctcctcctcc ctctgcctct ggtcccacca cccgcagcaa acgcgctcgt 120
ctttcttctt cttcttcttc ctcacttgcc cccactcctc cttcttcctc caccaccacc 180
cgctctcgtt cttctcgctc tgccgccgcc gctgctccca tggacacctc caccgactct 240
tctggatttc gccgaggcgg acgtggtaac aggggaaaca acaacgataa ttctgacaaa 300
ggtaaggaga aggaacatga cgttaggatt agggagcgtg aaagagaaag agaccgagcc 360
agagaacaac tcaacatgga tgctgccgcc gccgctgcta ggagcgctga cgaggatgac 420
gacaatgaca gtgaggatgg caacggcggt ttcatgcatc ctaacatgag ctctgcgagc 480
agtgctttac aaggcttgct caggaagctc ggtgctggat tggatgactt gcttccttct 540
tccggtatcg gctctgcttc ttcctcccac ttgaatggaa ggatgaagaa gattctctct 600
ggcttgcgcg ctgaaggaga agagggaaaa caggtcgagg ctttaaccca gctttgtgag 660
atgttatcca ttgggaccga agactcgctt agcaccttct ctgttgattc cttcgtccca 720
gttcttgtcg gtctacttaa ccatgaaagc aatcccgaca ttatgcttct tgctgccagg 780
gctcttaccc atctatgtga tgtcttgccg tcttcttgtg ctgctgttgt acattacggg 840
gcagtttcat gcttggtggc cagattgcta accatagaat acatggactt ggcggaacag 900
gttggctatc ataccaatac ttgaatcctc gatgctccag ctgctttttt aaaaattctt 960
cagggatcac acttgaaatt tgattcgtat ttatgtatgt gttttaaaac agtctctgca 1020
agctctcaaa aagatatctc aggagcaccc aactgcctgt ttgcgagctg gtgctcttat 1080
ggctgtgctc tcgtatctgg atttcttctc cactggtgtt caggtgggta aatttctaac 1140
ttctctttta tgctacactt actcgtgtat ctaatgcaca tgttacttgg cttcttgtag 1200
cgcgtagcac tatctactgc tgccaacatg tgcaagaaac taccttctga tgcatctgat 1260
tatgttatgg aagctgtacc tttgctgaca aacctacttc agtatcatga ttcgaaggta 1320
attgacctgc tttctgttat aatatggtac taatatctag ttccgctctt accccagtct 1380
cctccataat ctgttcgtat gatggtaggt tttggaatat gcttctatct gtctgactcg 1440
aattgctgaa gcatttgcac cgtatcccga gaaattagat gaattatgta accatggcct 1500
ggtgacgcaa gctgcgtctc ttatttccac gagcaattca ggaggtgggc aagcatctct 1560
tagtgtgtca acatacacgg taagcgtaaa atctttattg tgttttattt atccttatac 1620
acaagatgac attttcacca tattgtgcac aggggttaat ccgattactt tctacctgtg 1680
cgagcgggtc acctcttgga ttcaggacat tacttcttct tggtattagt agcattctta 1740
aggatattct gttgggttct ggggtctctg ctaatgcatc tgtatcccca gcactgagcc 1800
ggcctgcaga tcaggtaatt accttttctg tttaatacct gactgaaata agaatagctt 1860
aaatttaggg tacattctct atttcgggca tagtttccta cttgtttttg tattaccaag 1920
ttttacttag gtgtttgtat agtgtattga tcatagtcta tatacaggtc ttataatctg 1980
tacttatgtt ggagtactct tatgcctgtt ctgctcttat gttagatcta ggttttttat 2040
ctcatggtct ctaattctgg aatctataaa ttttgcttta tatattagat ttatgagata 2100
gtcaacctag cgaatgagct cctccctcca ttgccagaag gagttatctc tcttcctact 2160
agcacaaacg ctcttgtgaa aggttcatgc caaaagaaat ctagtccaag tacttcagga 2220
aaacaagaag atattctaaa aatttcacca agagaaaaat tacttggtga tcaacctgaa 2280
cttctgcagc agtttggatt ggatcttctt ccagttttag tgcaggtaat ttttctctgc 2340
gttggctaca agataatgct catactacct gctgttttgt ctaattattc ttgttttctt 2400
ttgcaacaga tctatggttc tagtgtcaat ggtacgattc gccataaatg tctctcagtc 2460
attggaaagt tgatgtattt cagcagttca gaaatgattc aatctctaat tggtgacaca 2520
aatatttcga ggtatgctgt ttacgatata aattaagttt gacacgacag tgtgtgcaac 2580
ttcttacatt tttttcttct tatgtagctt cttggctggt gtcttggcat ggaaagaccc 2640
acaggtcttg gttcctgctc tacaagttgc agagattttg atggaaaagc ttcctgaaac 2700
attctcgaaa gtgtttgtga gggaaggggt agtccatgct gtagatcaac ttgtcttggt 2760
tggtaaacca tcccatgcct cacctactga taaggacaat gactgtgtac ccggatctgc 2820
acgatctagg cgttatagac ggcgcagtag taatgccaat tccgatggaa accagtcgga 2880
agagcctaag aatcctgcgt cccttaccat aggggcaaac cataattccc ttgatactcc 2940
tacagctagc ttcatgctaa gggaaacagt tagttcctgc gccaaagcat tcaaagacaa 3000
gtacttcccg tctgatggtg gggatgttga tgttggagtt acagatgatc ttttacatct 3060
gaagaatctt tgcacgaagc taactgctgg tatagatgat cataaagtga aaggaaaggg 3120

```
aaaatctaaa gcctctgggc cattccttgg cgatttctct gctagcaagg aagagtactt   3180
gattggtgtc atttctgaga tacttggcga gataagtaaa ggggatggtg tctcaacttt   3240
tgagtttatt ggcagtggtg tggttgcagc attgcttaac tatttttctt gtggatactt   3300
ttccaaagag aagatctccg aacttaattt gcccaaactt cgccaggagg gactcagaag   3360
gtttaaagct tttctagaag tcgctcttcc ttttgatggt aatgagggaa aggtccctcc   3420
tatgacagtt ttgattcaga aacttcaaaa tgctttatcg tcactggagc gctttcctgt   3480
tgtccttagc catccctcaa ggtcactaag tggaagtgct cggctctcct cgggtttgag   3540
tgctttggca catcctttaa agttgcgatt atgccgagca tctggagaga aaacactacg   3600
tgattactcc tccaatattg tacttataga tccattggca agcttagcag cagtggagga   3660
atttctgtgg ccccgagttc aacggagtga atctgctctg aagccggcag cgcctattgg   3720
caatacagag ccaggcacgt tacctagcgg tgctggtgtt tcatcaccat cttcgtcaac   3780
tccagcttca accactcgtc gtcattcttc tagatctcga tcggcaatta acatcggtga   3840
tacttcaaag aaagatcctg tgcatgagaa aggtaccagc tcatcgaaag gaaaaggtaa   3900
aggcgttatg aaaccggctc aggcggataa ggggcctcaa acaaggagca atgctcaaaa   3960
gagagctgtt cttgacaaag atactcaaat gaaaccagct agcggagact ccagttctga   4020
ggcatgttac agtgctaagt tttgataac ataaatgttt tacttcgtta cttcgttact   4080
tcgttacatc atgatcttgt ggtgtgattt acttactcaa cacaatctta cttgtatgcc   4140
ttgcaggatg aggaattgga aatatcccca gtcgacattg atgatgcctt ggtgattgaa   4200
gaggatgaca tttctgatga tgaagatgat gataatgaag atgtaagttg tcctttggtt   4260
ttcttctccg cgattgttgt ttttgctaac accgtaatag atattgcatt tggcaataaa   4320
gcttgacagc tttcatattt tcgaattatc ttgccttgtt gagtctgttt tgttgataag   4380
ccgaactcac ttggaacctt ttctttttag aatagaccaa gtagatttac tagcttatgc   4440
ccctatttct catatttatc tcgctgctat caataacttt ggctttgtac cttacatgtg   4500
ctcttgattt tctttcaata ccttcacaat catatatact ttcatgtcca ggttttggat   4560
gacagtcttc ccatgtgcac gcctgataaa gtccatgatg tgaaattggc ggactcagtg   4620
gatgatgatg gtctagcaac cagcggccga caaatgaatc cagcttctgg aggcactagt   4680
ggagccgcag cagcaagggc atctgattct attgatactg gcattgggaa ttcctatggt   4740
tctagaggtg cactctcctt tgctgctgca gcgatggctg ggcttggagc tgccagtggt   4800
agaggtatca ggggaagtag ggacttgcat ggacgtaccc taaatcgaag ttcagatgag   4860
ccctctaagt tgatatttac tgcggcagga aaacaactta gtaggcattt gacgatttat   4920
caggctgtac agcgacaact tatgctagat gaagatgatg atgacaggtt tggtggcagt   4980
gatctagtct caagtgatgg aagcagattc aatgatattt acaccatcat gtaccagagg   5040
ccagacagcc aagtgaatag gttgtctgtt ggtggagcaa gttctaccac accgtcaaaa   5100
tccacgaaat ctgctactac caattccagt gtagaatctc agtcacatag ggcatctctt   5160
ttggatagta tcttacaagg ggagcttcca tgcgaccttg agaagtcgaa ttctacatat   5220
aatgttctgg cactgttacg tgtattagag ggtttaaatc agctttgccc tcgtttaaga   5280
gcccaaactc tttccgatcg ttttgcagag ggtaaaatta caagtctaga tgatctgagt   5340
acaactgctg ctaaggttcc tcttgatgaa tttgtcaata gcaaacttac acccaaattg   5400
gctcgacaaa tccaggatgc gcttgctttg tgcagtggaa gtcttccctc ttggtgctac   5460
```

```
cagttgacta gagcatgccc atttttgttt ccgtttcaaa cccggagaca gtatttctac   5520
tcgactgctt ttgggttgtc tcgtgcattg aatcgtttgc agcagcagca aggtgctgac   5580
ggcagtgggt ctacaaatga acgagagatg agaataggga gattgcagcg ccagaaagtc   5640
cgtgtatccc gaaataggat attagattct gctgcaaaag ttatggagat gtattctagc   5700
cagaaagctg tgcttgaagt agaatatttt ggtgaagttg gtactggtct aggccctacc   5760
cttgagtttt acacacttct aagccatgat ctgcaaaagg cttccctagg gatgtggaga   5820
tcaagttctg gtgacaaggt atctatgcaa attggtagag atgagattga agacggaaaa   5880
ccatctgcag ctaacagaga tatagttctg gcaccacttg gattgtttcc tcggccttgg   5940
ccctcaacag ctgacatatc tgaaggtggt cagtttcata aagtcattga atatttccgc   6000
cttttagggc gtgtgatggc caaagcactt caagatggac ggctattgga cgtcccattg   6060
agtacagcgt tttataaact tattcttggt caagtgagtt tttttttac tactagtgtt    6120
tgtttagtta aaagtgaaat agtggtttct actttttcac ttctgtcggc ctttgctaat   6180
aagttcgtcc tctttcattg actaagcagg agcttgattt gcatgatatt gtattatttg   6240
acgctgaact tggcaagacc ttgcaagagc tgcgtgttgt tgttgcccgc aagcactatc   6300
tggagggagt aggtggtgac aatagcagca cgatttctga tttatgttta cgtggatgcc   6360
gaatagaaga tctctccttg gaattcacgc tacctggcta tcctgagtac atcctgagat   6420
caggagatga aattgtactg tcttagctta caccccacct cttactattc ttttagaaca   6480
tgtccatgat tgctgatgac gtgctgtttt gttacaggtt gatattacta atcttgagga   6540
gtatatatcc cttgtcgttg atgctactgt caagagagga gtcactcggc agatcgaagc   6600
cttcagatct ggattcaatc aggttaacag tctcgcagac tttctgtctc tttctttgtc   6660
tattgccttt ggcttctaaa cataatatag aaaattctgt agattagaga cttgcatttt   6720
ttctttttag ggcggacctt aaacttttac cttcatttgt taacttacaa aacctttctg   6780
tttctgcaca taattatcag gtgtttgaca taacatctct acaaatattc accccttctg   6840
agctggacta tttgctgtgt ggtcgtagag agttgtggga ggtgaatttt tcacttttca   6900
atttccataa ccaagagact tgaatccctt agatgtaaga aaatatcatt tctaaaactt   6960
tcttttcttg caggtggaga ctcttgctga acatatcaaa tttgatcatg ggtataatgc   7020
caaaagtccg gcaatcatta acgtatgtta tccatcaagt tgttagatat catatcttta   7080
tttattctta cctttccttt tgtttctgaa ccgttgatta ctttctgatt ctgattttca   7140
ccccaccctg tagttactgg agatcatggg agaacttaca gcagatcagc agagggcttt   7200
ctgccaattt gtaactggag ctcctaggct tcctcctggt ggcttagctg ttctgaaccc   7260
aaagcttacg attgtgagaa aggtaaaaaa actttaaatc atttgcaagt catttttgta   7320
atttagccac caaggatatg ttagaaggca tctatgtgtg ggcaagggct tttgctcttt   7380
ttttctaaga gcagacacgt attgtggtgt ttgtttgcat tggcaagagt tattcagatg   7440
aattatgtct tactgtcgtg aagttgttaa ttattggttt tgcatgggat tctaaaattg   7500
catgtgtctt tggctggtgc agcactcatc gacctcaagt gcagcagcca acggagcagg   7560
ggcttcggag acagcagatg atgatttgcc cagtgtcatg acttgcgcaa actaccttaa   7620
actccctcct tattctacaa aggtgagtca tgtcttctat tcttcttgag tccatgttag   7680
tgtggttgtt ggtgagcctg aggagttgta tgttattgaa acaggaaatc atgtacaaga   7740
aactgctcta cgccatcaac gaagggcaag gatcgttcga cctctcataa gcaacatatg   7800
gctgtgtttc ttcctcccct ctcttgtaca ttacatcgga agactggttt tgatttctct   7860
```

gctttttggg gtttttatga tctgacaaag ccgaagatac cccaaaatcc aggtgactac 7920
tgttgttctc ccggagactt tgtaatggag gggatatagg gttgtgactt gtgatgtaaa 7980
ttttgtcttt gcaggctctg cagaaggcgc cgccattatt gtgtagataa agaaagatga 8040
taggcttatc ttttccttcc tttttttttt tttcttcttc ttcttcgttt cttagattcc 8100
ctctatgtaa aagatcgatc atttcatttg gtcggtcaaa actatggaaa ctcaagttcg 8160
atccgtctca gaaaactaga atatggacgg cactttgaat atgtttaaca atgagttaca 8220
tatatagttt agcttcatta tataagctct cttattacat ca 8262

<210> SEQ ID NO 9
<211> LENGTH: 5667
<212> TYPE: DNA
<213> ORGANISM: Arabidopsis thaliana

<400> SEQUENCE: 9
atggaaactc ggagccgcaa gcgggcggag gcgacctcag ctgccccatc ttcttcttct 60
tcttctcctc ctcctcctcc ctctgcctct ggtcccacca cccgcagcaa acgcgctcgt 120
ctttcttctt cttcttcttc ctcacttgcc cccactcctc cttcttcctc caccaccacc 180
cgctctcgtt cttctcgctc tgccgccgcc gctgctccca tggacacctc caccgactct 240
tctggatttc gccgaggcgg acgtggtaac aggggaaaca acaacgataa ttctgacaaa 300
ggtaaggaga aggaacatga cgttaggatt agggagcgtg aaagagaaag agaccgagcc 360
agagaacaac tcaacatgga tgctgccgcc gccgctgcta ggagcgctga cgaggatgac 420
gacaatgaca gtgaggatgg caacggcggt ttcatgcatc ctaacatgag ctctgcgagc 480
agtgctttac aaggcttgct caggaagctc ggtgctggat tggatgactt gcttccttct 540
tccggtatcg gctctgcttc ttcctcccac ttgaatggaa ggatgaagaa gattctctct 600
ggcttgcgcg ctgaaggaga agagggaaaa caggtcgagg ctttaaccca gctttgtgag 660
atgttatcca ttgggaccga agactcgctt agcaccttct ctgttgattc cttcgtccca 720
gttcttgtcg gtctacttaa ccatgaaagc aatcccgaca ttatgcttct tgctgccagg 780
gctcttaccc atctatgtga tgtcttgccg tcttcttgtg ctgctgttgt acattacggg 840
gcagtttcat gcttggtggc cagattgcta accatagaat acatggactt ggcggaacag 900
tctctgcaag ctctcaaaaa gatatctcag gagcacccaa ctgcctgttt gcgagctggt 960
gctcttatgg ctgtgctctc gtatctggat ttcttctcca ctggtgttca gcgcgtagca 1020
ctatctactg ctgccaacat gtgcaagaaa ctaccttctg atgcatctga ttatgttatg 1080
gaagctgtac ctttgctgac aaacctactt cagtatcatg attcgaaggt tttggaatat 1140
gcttctatct gtctgactcg aattgctgaa gcatttgcac cgtatcccga gaaattagat 1200
gaattatgta accatggcct ggtgacgcaa gctgcgtctc ttatttccac gagcaattca 1260
ggaggtgggc aagcatctct tagtgtgtca acatacacgg ggttaatccg attactttct 1320
acctgtgcga gcgggtcacc tcttggattc aggacattac ttcttcttgg tattagtagc 1380
attcttaagg atattctgtt gggttctggg gtctctgcta atgcatctgt atccccagca 1440
ctgagccggc ctgcagatca gatttatgag atagtcaacc tagcgaatga gctcctccct 1500
ccattgccag aaggagttat ctctcttcct actagcacaa acgctcttgt gaaaggttca 1560
tgccaaaaga aatctagtcc aagtacttca ggaaaacaag aagatattct aaaaatttca 1620
ccaagagaaa aattacttgg tgatcaacct gaacttctgc agcagtttgg attggatctt 1680

-continued

```
cttccagttt tagtgcagat ctatggttct agtgtcaatg gtacgattcg ccataaatgt   1740
ctctcagtca ttggaaagtt gatgtatttc agcagttcag aaatgattca atctctaatt   1800
ggtgacacaa atatttcgag cttcttggct ggtgtcttgg catggaaaga cccacaggtc   1860
ttggttcctg ctctacaagt tgcagagatt ttgatggaaa agcttcctga aacattctcg   1920
aaagtgtttg tgagggaagg ggtagtccat gctgtagatc aacttgtctt ggttggtaaa   1980
ccatcccatg cctcacctac tgataaggac aatgactgtg tacccggatc tgcacgatct   2040
aggcgttata gacggcgcag tagtaatgcc aattccgatg gaaaccagtc ggaagagcct   2100
aagaatcctg cgtcccttac catagggga aaccataatt cccttgatac tcctacagct   2160
agcttcatgc taagggaaac agttagttcc tgcgccaaag cattcaaaga caagtacttc   2220
ccgtctgatg gtggggatgt tgatgttgga gttacagatg atcttttaca tctgaagaat   2280
ctttgcacga agctaactgc tggtatagat gatcataaag tgaaaggaaa gggaaaatct   2340
aaagcctctg ggccattcct tggcgatttc tctgctagca aggaagagta cttgattggt   2400
gtcatttctg agatacttgg cgagataagt aaaggggatg gtgtctcaac ttttgagttt   2460
attggcagtg gtgtggttgc agcattgctt aactattttt cttgtggata cttttccaaa   2520
gagaagatct ccgaacttaa tttgcccaaa cttcgccagg agggactcag aaggtttaaa   2580
gcttttctag aagtcgctct tccttttgat ggtaatgagg gaaaggtccc tcctatgaca   2640
gttttgattc agaaacttca aaatgcttta tcgtcactgg agcgctttcc tgttgtcctt   2700
agccatccct caaggtcact aagtggaagt gctcggctct cctcgggttt gagtgctttg   2760
gcacatcctt taaagttgcg attatgccga gcatctggag agaaaacact acgtgattac   2820
tcctccaata ttgtacttat agatccattg gcaagcttag cagcagtgga ggaatttctg   2880
tggccccgag ttcaacggag tgaatctgct ctgaagccgg cagcgcctat tggcaataca   2940
gagccaggca cgttacctag cggtgctggt gtttcatcac catcttcgtc aactccagct   3000
tcaaccactc gtcgtcattc ttctagatct cgatcggcaa ttaacatcgg tgatacttca   3060
aagaaagatc ctgtgcatga gaaaggtacc agctcatcga aaggaaaagg taaaggcgtt   3120
atgaaaccgg ctcaggcgga taaggggcct caaacaagga gcaatgctca aaagagagct   3180
gttcttgaca aagatactca aatgaaacca gctagcggag actccagttc tgaggatgag   3240
gaattggaaa tatccccagt cgacattgat gatgccttgg tgattgaaga ggatgacatt   3300
tctgatgatg aagatgatga taatgaagat gttttggatg acagtcttcc catgtgcacg   3360
cctgataaag tccatgatgt gaaattggcg gactcagtgg atgatgatgg tctagcaacc   3420
agcggccgac aaatgaatcc agcttctgga ggcactagtg gagccgcagc agcaagggca   3480
tctgattcta ttgatactgg cattgggaat tcctatggtt ctagaggtgc actctccttt   3540
gctgctgcag cgatggctgg gcttggagct gccagtggta gaggtatcag gggaagtagg   3600
gacttgcatg gacgtaccct aaatcgaagt tcagatgagc cctctaagtt gatatttact   3660
gcggcaggaa aacaacttag taggcatttg acgatttatc aggctgtaca gcgacaactt   3720
atgctagatg aagatgatga tgacaggttt ggtggcagtg atctagtctc aagtgatgga   3780
agcagattca atgatattta caccatcatg taccagaggc cagacagcca agtgaatagg   3840
ttgtctgttg gtggagcaag ttctaccaca ccgtcaaaat ccacgaaatc tgctactacc   3900
aattccagtg tagaatctca gtcacatagg gcatctcttt tggatagtat cttacaaggg   3960
gagcttccat gcgaccttga gaagtcgaat tctacatata atgttctggc actgttacgt   4020
gtattagagg gtttaaatca gctttgccct cgtttaagag cccaaactct ttccgatcgt   4080
```

tttgcagagg gtaaaattac aagtctagat gatctgagta caactgctgc taaggttcct 4140
cttgatgaat ttgtcaatag caaacttaca cccaaattgg ctcgacaaat ccaggatgcg 4200
cttgctttgt gcagtggaag tcttccctct tggtgctacc agttgactag agcatgccca 4260
tttttgtttc cgtttcaaac ccggagacag tatttctact cgactgcttt tgggttgtct 4320
cgtgcattga atcgtttgca gcagcagcaa ggtgctgacg gcagtgggtc tacaaatgaa 4380
cgagagatga gaatagggag attgcagcgc cagaaagtcc gtgtatcccg aaataggata 4440
ttagattctg ctgcaaaagt tatggagatg tattctagcc agaaagctgt gcttgaagta 4500
gaatattttg gtgaagttgg tactggtcta ggccctaccc ttgagtttta cacacttcta 4560
agccatgatc tgcaaaaggc ttccctaggg atgtggagat caagttctgg tgacaaggta 4620
tctatgcaaa ttggtagaga tgagattgaa gacggaaaac catctgcagc taacagagat 4680
atagttctgg caccacttgg attgtttcct cggccttggc cctcaacagc tgacatatct 4740
gaaggtggtc agtttcataa agtcattgaa tatttccgcc ttttagggcg tgtgatggcc 4800
aaagcacttc aagatggacg gctattggac gtcccattga gtacagcgtt ttataaactt 4860
attcttggtc aagagcttga tttgcatgat attgtattat ttgacgctga acttggcaag 4920
accttgcaag agctgcgtgt tgttgttgcc cgcaagcact atctggaggg agtaggtggt 4980
gacaatagca gcacgatttc tgatttatgt ttacgtggat gccgaataga agatctctcc 5040
ttggaattca cgctacctgg ctatcctgag tacatcctga gatcaggaga tgaaattgtt 5100
gatattacta atcttgagga gtatatatcc cttgtcgttg atgctactgt caagagagga 5160
gtcactcggc agatcgaagc cttcagatct ggattcaatc aggtgtttga cataacatct 5220
ctacaaatat tcaccccttc tgagctggac tatttgctgt gtggtcgtag agagttgtgg 5280
gaggtggaga ctcttgctga acatatcaaa tttgatcatg ggtataatgc caaaagtccg 5340
gcaatcatta acttactgga gatcatggga gaacttacag cagatcagca gagggctttc 5400
tgccaatttg taactggagc tcctaggctt cctcctggtg gcttagctgt tctgaaccca 5460
aagcttacga ttgtgagaaa gcactcatcg acctcaagtg cagcagccaa cggagcaggg 5520
gcttcggaga cagcagatga tgatttgccc agtgtcatga cttgcgcaaa ctaccttaaa 5580
ctccctcctt attctacaaa ggaaatcatg tacaagaaac tgctctacgc catcaacgaa 5640
gggcaaggat cgttcgacct ctcataa 5667

<210> SEQ ID NO 10
<211> LENGTH: 10093
<212> TYPE: DNA
<213> ORGANISM: Glycine max

<400> SEQUENCE: 10
atggaaactc ggagccggaa gcgggcggag gcttcctcag ctgccccttc atccccttcc 60
tctggtccca ccactcgttc cagcaagcgt gcacgcctct cttcttcttc ctccgcttcc 120
gccgccgctg ccgccgcatc cgtttcttcc gtgaacactc gctcccgttc atcccggact 180
aaggaaccct tgccccctaa gaatcctcct cccatggact ctgccaatga atcctctggc 240
tcccgccgcg atcgccgcaa caaagacaac tccgacaagg ggaaggagaa agagcatgat 300
gttaggatta gggacaggga tgctgacaga gggctggcat tgaacatgga tggtggcgga 360
gacgatgatg acaatgacag cgaaggcggt gtgggggatt ttgcatcaaa acttgacctc 420
tgcgagtagt gcacttcagg ggcttcttcg gaaacttggt gctggtttgg atgatctgct 480

```
tccatcatcg gctatgggtt ctgcgtcttc ctctcaccag agtgggaggc tgaaaaagat    540
cctcttcgga ttgcgggcgg atggcgaaga agggcggcag gttgaagcat tgacacagct    600
ctgtgagatg ctttcgattg ggactgaaga gtcacttagt acattctctg ttgattcgtt    660
tgttcccgtg cttgtggggt tgttgaatca cgagagcaac cctgacatca tgcttcttgc    720
tgccagagca ttgacccatc tctgtgatgt gctcccttca tcttgtgctg ctgttgtgca    780
ttatggtgcc gtgtcaatct tttgtgcgag gttgctcacc atagaataca tggacctggc    840
tgagcaggtt gttccttggt tcatgactat tgtggaatta atgaaaatgg tgctagaaag    900
ttataaaata aatatttgtg tttcagtgtt gaaccctggt gctgcctaat tgtttttaaa    960
actatatatt tcgatgtttc tgggtcaaat tttcagttgt agaagaatta tgcctttttt   1020
ttttaatcta agacttagca ttttgaaaat gaaattcata tagtttgatt actgtatttg   1080
atggcatgaa cagtcccttc aagctctgaa gaagatatct caggagcatc ccactgcctg   1140
cctacgagca ggtgctctta tggccgtgct ttcctatttg gacttctttt caacaggagt   1200
tcaggtaaat tgtcagtgaa gtacctacat ttagaggatg attgcatccc actggtcctt   1260
ttggacagtc ataaatcatt tggccacagg tgccattagt gagcaagtgt atgttgacat   1320
tattctttgt ttcagcgggt tgcattgtct actgctgcaa atatgtgcaa aaagcttcct   1380
tcagatgcag ctgattttgt gatggaagct gttcctcttc tgacaaacct tcttcagtac   1440
catgattcca aggtaaggtc atgttttgtt gcaagtcttg tcacataatg gaaactgtat   1500
ttttcctttt gcatccataa acttgccttt taaggaagtt tagcttgaga agagggaaat   1560
tttgatccct atatcccatg gtataaaata tttatctata gcttcacctt atgcattttc   1620
aatttttgta ggttctggag cacgcctctg tttgtttgac tcgaatagct gaagcttttg   1680
cgtcatctcc agacaaatta gatgaattgt gcaaccatgg acttgtaaca caagctgcct   1740
ccctcatttc taacagcagt tctgggggtg gtcaggcttc tctcagcacg ccgacatata   1800
ctgtaagtgc aatttttact tttagttaga tgcattttgc ctatagtttg gtccttgacc   1860
tgggtatatg cagggtttaa tccgacttct ttcaacttgt gcgagtggat ctcctcttgg   1920
agctaaaacc ttactacttc ttggaattag tggtattctt aaagatattc tatctggttc   1980
tggagtttct tctaaggcct ctgtttctcc tgcattaagt aggccgccag aacaggtata   2040
gtataacatc agaacttttc ttttggtcat tcatgtgtag ttttatctcg taatgttcat   2100
taaacagaca ctgaccttaa atccatcatt attctaattc ttggtttcaa atatatagat   2160
atttgagatt gtaaacctca cgaatgagct tctgcctcca ttgccacatg gaacaatttc   2220
tctccctatc atctccaaca tgtttttgaa agggcccatt gtaaagaagt ctcctgctgg   2280
tagctctgga aaacaagaag acacaaatgg aaatgttcct gagatatcgg ctcgtgagaa   2340
actattaaat gatcagcctg aactacttaa gcaatttgcg atggatctcc ttccagtttt   2400
aatacaggtt gatatttgtg catcaattgc ttaaactttg cttgataaat ttgttaaatt   2460
gaaaaaaatg ttctgataaa ttgctccttt gcttccttat ttgtcttctt tggttaattg   2520
atgatattgg cttgctgttg atatagatat atggttctag tgtcaatggt cctgttcggc   2580
acaaatgcct ttctgtcatt ggaaaattga tgtatttcag cacagcagag atgatccagt   2640
ctttgttgag tgtgacaaat atatcaaggt atgttgaaat ttaattgagt tgatattgct   2700
tgataccctc actgatttta tgggtttaga aaatttatgc attgttgctt tgatcatata   2760
gtttcttagc tggcgtctta gcatggaaag atccacatgt tttgcttcct gccttgaaaa   2820
ttgctgaaat tcttatggaa aagcttcctg ggacattctc caagatgttc attagagaag   2880
```

```
gtgttgtgca tgcagtggac caacttattt taactggaaa ttcgaccaat atctctacac   2940
aggcatcttc tgccgagaag gataatgatt ctatatctgg agcatcatct cgctctaggc   3000
gttatcggcg acgcagtggg aattccaatc ctgatggaaa tcctttggac gatttgaaaa   3060
ctccagtttc agtaaatgtt ggttcacctc ctaattctgt ggatatgcca acagtaaatt   3120
ccagtattcg gttatctgtt agtacagctg ccaaagcttt taaagataag tattttcctt   3180
cagatcctgg ggctgctgaa gtgggtatta ctgatgatct tttgcatctg aaaaatcttt   3240
gcatgaagtt aaatgctggt gctgatgaac aaaggaccaa tggaaagggg aaatctaaaa   3300
cttctggatt tggtctggaa gagtatttaa ttgggatcat agctgacatg ctaaaggaac   3360
ttggcaaagg agatggggta tctacttttg aattcattgg tagtggtgtt gttgcagctc   3420
tgttgaatta tttttcttgt gggtatttct ctaaagatcg accattagaa acccaccttc   3480
ccaagcttcg ccaacaagca cttacaaggt ttaagttatt tatagctgtt gcactacctt   3540
ctactactga agatgggact gtggctccta tgactgtctt ggtccagaag cttcaaaatg   3600
ccttgtcctc cttggagcgt ttccctgttg tgctgagtca ttcatctagg tcatctagtg   3660
ggagtgcacg cctctcctct ggactaagtg cattatctca gcccttcaag ttgcggcttt   3720
gtcgagccca gggtgaaagg tcacttaggg attattcatc caatgttgta ctggttgatc   3780
cattagcaag tttagcagca attgaggaat ttgtttggcc tcgtatccaa cgaagtgaat   3840
tgggtcagaa gtccactgta cctgctggga attctgaatc tgggacaact cctacaggag   3900
ctggtgtatc ctctccaact acccatcgcc attctactag atccagatca tctgttaata   3960
taggtgatac atctagaaag gaaataagtc aagataaaag cacaagctct tccaagggta   4020
agggaaaagc tgtattaaag cctgcacaag aggaggcaag aggacctcag accagaaatg   4080
ctactcgcag aagagaagct cttgataaag atgctcaaat aaagcctgta aacggtgact   4140
ctacttctga ggtatactga tggaaaccga gttaggggca gatatgacag ttatctgtag   4200
aaaataactg ctttagaaat caattctgta taagaaactc aaataactgt cttagaaaac   4260
agtactgtat tagaaactgc aggatggtag ttatgtgtag aaaataactg ctggtagtta   4320
tgtattagga gtatatgtct gttagtatgt ggtgtaattg ggcagtgtaa agtcattttt   4380
aagtttgtgg atagagaata ctctgtagga gacttctgtc tctgggacag ctagtgctgt   4440
tttttgtata tgataggaga ctttagtctc taggacggca ggtgtattgc tgtatttgta   4500
tgtgatagga gacttttgtc tctgggacag caagtgtatt gctgtattgt gtgatttcag   4560
tgttctatat attttaggta aatgctaggg ctctggttga ggaagtaaaa agagggatgc   4620
gtaaaaatgt actcctccta tgatttccaa aaaaaaactt ttcttttta attccttaac   4680
cagtgcctgg cactggttag caagacccta tattttatta ctttatcatt tggtgttcta   4740
tcatatactg tgaaatccta gcgatgactt tacaatgctt caactttttt cttctgttaa   4800
tttataactt ccttctggct atgtatgacc tgactatgaa tgctctgttt tcatgttggc   4860
ttataaagtg aaatacgaag agaatacttg ataatgccaa tataagatgt aaagatgcat   4920
tattacattt ttcattgcaa gcttgaaaag acatcttaca tttctctgta tctgtaactt   4980
tggacatgct ggattttgtt gtctgtagat ccttaaaatg ttacctctgc catttagttt   5040
tataaatggt ttttgattat aattatctat ttaagatatc atctctaata tgagaaacac   5100
tgcctaggtt ttctttggat tatgttgaac agttgctttt ttgcaccatt gatttcttta   5160
catacattaa aattaagctg ttgtaaggtt tccctgcaaa agtgttgatt tactaaaaaa   5220
```

-continued ttgaggcaga gctagcactg agaggataac ttatctattt tgcgttgaag taacattgct 5280
gtaagtaata gtgtatttgg atgtaatcag atggatactt tgtatatgct gatcctcatc 5340
cttctttcat taagtgcatg tgtcagaatt tttagtatgg taccactcaa aaagtcaaaa 5400
tcgattccta ttttcagttt agcttagttt ttaattattt tcttataaca ttaaacttgt 5460
ctgtcatgaa gttgtagttt gtatgactct cattggggaa tattttagat tatttgtggg 5520
cgggttacat attttttccg tttaggtgaa gctttcttgt tttgtttttt gttgcttttg 5580
attatggcag tgtttacatg catgttgttt agctaggttc ttgtggttgt taaactggtg 5640
gaagcatctt tgagtataaa tttttttttt tggaaggcgt ctttgagtat aaatattagt 5700
catttgtttt tcctgctatg ctttggacta aatcatgaac ctaatccaag tatcttgaag 5760
tagtcatttg tttttccttt tcttttttta cccttctagt gacattttcc aatgtctaca 5820
ttgtaggatg aagatttgga tatatcccct gttgagattg atgaggcatt ggtgattgaa 5880
gatgatgata tttctgatga tgaagatgat gaccatgatg atgtatgtta tctactgttt 5940
cttcttcttt ggctaggatt ttcttacttc cttggtgatg agtatctcat ttaagtaatt 6000
actgtgtttc tgtctttttt tttttttgc ttttctgaca tcatttcctt ttttaacatg 6060
gcttttaaat atgttaaaat ctgtgtgcat ctttattttt ttatttccag tgctggtgtc 6120
cttcaatctt gtttacaatt ttttcaaaat gagttgctgc tgtctttcta tcatttcttt 6180
gttttctatt tttcttttct gggtataatg atgcaatgaa gttttggttt atgaccttat 6240
gcaaactatc cataatccaa gtctctgacc aatagctcaa tcctggtgtt ttatttccaa 6300
atttttaatt ttagctacca tcattattgt taaccaagat tgaacattat aattaaattc 6360
agttgtatct attaaaattt ttgtgcttgt tttgtttttt ctgatgcaca ggtactgagg 6420
gatgattctc ttcctgtttg ttcacctgac aaagtacatg atgtgaaatt gggcgacata 6480
gtggaggaga gtaatgttgc tcctgcaact agtgatggtg gccagactaa tgctgcctca 6540
ggttctagta gcaaagctgg tacagtcagg ggatcagact ctgctgattt taggagtggc 6600
tatacctcaa gctcaagagg tgcaatgtca tttgctgctg ctgctatggc tggacttgga 6660
tctgccaata gcagaggtat caggggtgga agagatcgac tagggcgtcc attgtttggt 6720
agttctaatg atcctccaaa gttgatattt actgctggtg ggaagcagct taataggcat 6780
ttgactattt atcaggcaat tcaaaggcag cttgtgctag atgaagatga tgaggagaga 6840
tttgctggca gtagtgacta tgtatccagt gatggaagca ggttgtgggg tgatatttat 6900
actataactt atcagagggc agagaaccag acagatagga ctccccctgg aggttcaacc 6960
tctaatgctt caaaatctgg caaatctggg tctgtattga attctagttc tgaagacaag 7020
ctaaatcaga catctgtatt agatagtatt ttgcagggag aattgccctg tgaactggag 7080
aaatctaatc ctacatacaa tatattggca ttattgcggg tgcttgaggg tttgaaccaa 7140
cttgcatctc gtttgagggc ccaagtggtt actgatagct ttgcagaggg aaaaattttg 7200
gatttagttg agctaagttt taccagtggt gctagggttc ctacagagga atttataagc 7260
agcaaactta ctccaaaatt agctaggcaa atacaagatg cccttgcctt atgtagtggg 7320
agtcttccct catggtgtta ccagttatct aaagcgtgcc ctttttttgtt tccttttgag 7380
acccggcgac agtattttta ttcaactgcc tttgggttat ctcgtgcatt gtatcgcctt 7440
cagcagcagc agggtgctga tggtcatgga tcaacaaatg aaagagaggt cagggttggg 7500
agattgcagc gtcaaaaggt tcgtgtctct cgaaatcgca ttttggattc tgctgctaag 7560
gtgatggagt tgtattctag tcaaaaggct gtacttgaag tagaatattt tggtgaagtt 7620

-continued

```
ggcaccggtc tgggtcccac tctggagttc tacacacttc tcagtcatga cttacaaaaa   7680
gttgtacttc aaatgtggag atcaggttct tcagagaaat atcaaatgga aattgatgga   7740
gatgaaaaga aaatgaaaaa tagtgaaggc tcttttgttg gagatggaga actcgttcaa   7800
gctcctcttg ggctgtttcc tcgaccttgg cctgcaaatg ctgatgcatc agagggtacc   7860
caaattttca aagtgattga atatttccga ttattaggcc gtgtaatggc taaagctctt   7920
caagatggac gcttattgga tttaccattg tcagtggcat tttataagct tgttcttggt   7980
caagtaagtt atgaaatgtt gatgtcttgt ctgatttcat gtgtatctta aggttgattt   8040
ttagtctcta tatatttagc ctttgatata ttgcaggagc ttgatttgca tgacattctt   8100
ttcattgatg ctgaacttgg gaaaactttg caagagttaa atgcccttgt ttgccggaaa   8160
tgttttatag aatctattgg tggtagctac actgatacct ttgctaattt gcattttcgt   8220
ggggccccaa tagaagatct ctgcttggac ttcacacttc ctggttatcc agagtacatc   8280
ttgaaacctg gagatgaaat tgtatgtatt cagtctgttt tttttacctg gtttttgttt   8340
tggttctgat tctgtctgta ataaaaattg ctttgaactt actgtcaaac tttcaggttg   8400
acatcaataa tctagaggag tacatatcca tggtggttga ggcaacggtt aagactggaa   8460
tcatgcgtca aatggaagct tttagagcag ggtttaatca ggttatatgt tgtctcaata   8520
aattcatgta actttgtctt tgactgtgca tcttgtttgg tgatgctgag tataaaaaat   8580
atcatgtatt ttttaactga ttaatggttc attctttttg gtattccttt tctagtttct   8640
ctcaaacaat tttattgaaa actaaacttg actggggttt aatttgaaaa tattgagtat   8700
ggatttttca gcttttagat tcttaagggg cattgttttc tactaaaaat tgttactttt   8760
ggttatgtct tgagcagtga actgtatata tatcctgaat ctcggatgta tcaattaaga   8820
aattactaaa tgtttgtttc tgacttttac ttatgtttgc taccaacctt gtatcccccct  8880
tcccctgcag atgaagaatg gaagttagaa aatacacatt ttttttgtat tgatgtcaaa   8940
tattcagtta tttaatgtca aaattttaca agtgaaatga gctactagcc taacttatat   9000
ggaagagatg ggctgggcaa tagtttgaac ttggaacaac tagttggata atttgttcat   9060
ttgcttgagt ccaaaaacta aacatttgtc actttcccac ttgttcttgt caattcaggt   9120
ttttgacatc tcatctttac aaatttttttc tccccaagaa ctggattact tgctttgcgg  9180
ccggagagaa ttgtggaagg tattcttttt tatacaaaag tattactgct gcttacaaca   9240
atcttttaga tgttaccatg gataatgtag ttataatttt ttttctccta tctgcagact   9300
gagacactag ctgatcatat aaaatttgac catggttata ctgccaagag ccctgccata   9360
gttaatgtat gtttttttat tcctgtagaa ggacaattgt gtttttggaa atttaggctt   9420
gttatatttg gtgctgaacc tgtatgatgc tattttcagt tactcgaaat tatgggagaa   9480
ttcacaccag agcagcagcg tgccttctgt caatttgtta ctggtgcacc taggctgcct   9540
cctggtggac tggcagttct aaatccaaaa ttaacgattg tgaggaaggt attgaaaaat   9600
atttttgatc acttgcaacc tgtgttattc attcatgcct tcatgcaatt ttgtacttga   9660
tatcttgaat gttaaagttt tttgggggggc gaggatctat ttgaacttcg gtagcaagat  9720
gtgtctggat ttactgcctg acatatgttg ctccactatt cctttacctc ttgaaggggg   9780
gttttcaaaa tgcaatgtta gtaagtgatt acatttacat gtctgggtgc agctttcgtc   9840
aagtgcagct aatgcttcat ctaacgggaa tgggccttca gaattagcag atgatgactt   9900
gccaagtgtg atgacgtgtg caaattacct gaagcttcct ccttattcta ccaaggtaga   9960
```

acactgcaaa gcattgttgg ttatatgatc atgcatgtca aagtgtcttt tgatctttga 10020
tttccatttt aaaacaggaa attatgtaca agaagctact ctatgcaatc agtgaaggcc 10080
agggatcctt tga 10093

<210> SEQ ID NO 11
<211> LENGTH: 3294
<212> TYPE: DNA
<213> ORGANISM: Brassica napus

<400> SEQUENCE: 11
atggataact tcttgccctt ttcctcttct aacgcaaact ctgtccaaga actctccatg 60
gatcttaaca agaatcgctc gcacttctcc atggcgcagc ctcagcactt gttgccgcct 120
tactcgtacg ttgcatgtcc ggcacttgat cagacgggga ccatgaatca tcagcctctt 180
cactcatcgg atgcttttcc tcagatcccg gttgtacaaa ccggaggtga attcggctat 240
ttggtttgta agcccggtgt gaggcaggaa cgaggtggat ttcttgatcc acactccact 300
aagatggcta ggatcaacag gaagaaggcg atgctaagat caagaaacaa ctctaaccct 360
aattctagtt cgaatgagtt ggttgattca aggagacaag tggctcttac catgaaaaat 420
aatgccgaga ttgctgctag aaaagatttt tatcgattct cctcattcga taacaaggta 480
tgtatttctt tggcccaaaa taatggaata tatgcgattc tacattcata acatgataat 540
gtttttgaat tttttgttga ctgtacgtag aaacttaggg ttttgttggt gaagcacttg 600
aagaacagcg atgttgggtc acttggaagg attgttctac caaaggtgtg taaattctta 660
catttctcgt attctttatg gtataattaa tgttaaaaca attttgtaga ggtaaaaaca 720
ctaaatatgt tggggatgga ttgatgaaag attatcaact acgtaactac gaattttaaa 780
acctcaattt catgagaaag ttttttaaaa gtaatataat ttctgatttg gctattacca 840
tttaaaaaga tattatcact gcgaccacat attctctcat tatgcaattt cacacatttt 900
cctccattca aaccatcgtt gtttaaccaa tgagaagttt agtctctaaa acacatggaa 960
aacaagaggg attttttttt gataaaccag aggaaaatta aacatgaaaa caaaatgtga 1020
aatatataat tgtttaatca atacggagta ttttcgttca ttccttttgg tgtgagcttt 1080
tatgttatac agtactatag tatttttttt agtttagcaa gaatatggtg attaaaaatc 1140
tagtttaaat ttggtttatc tatattttaa atttgaagga ctaaaagtca aagttttgga 1200
atgagcacca aaaatgaaat acagtatgaa aaaaaatcga aatagattga tcatagctcc 1260
ttcaatctaa tattccgtgt aaaaacttac taaccaatga ataaaaaaca cgagaagtaa 1320
acgattttct agttgtagtt agctaaaatg gttaataaag tggttaaaat gactttattt 1380
tgaaacgggg ttgaaaaaaa gtcgtatata tatatatata ttcctttcct aattaattgc 1440
ctcttaaatg gcattcctcg aaatcattaa ggaaaagtag aaaacaaaca aaaagccatt 1500
atggattaat tggggcagtt tactagtttt attatagaaa aatcatatca aatcatcccc 1560
tttatctatc ttagtaagaa aataattagt ttatttgcac ccaaaaaaata attagtttat 1620 taaaaagtaa ctaagtaaat catgggtttg gagcgcagag agaagcagaa ggaaatcttc 1680
cggagctatc tgataaagaa ggaatggtat tagagatgag agatgttgac tctgtgcagt 1740
cttggtcttt caaatacaag tgaagtctcg tttcctttct cttatatatt gatagaaaac 1800
atttttatgt tccatttttt aatctaccaa tagtttaaca aaccttataa gttctttagt 1860
gattttttgt tagtggtatg ttttatagct tggaatttgt tatatcggtt tcaatttaat 1920
atttttggaa cgagagaact tataaggctt gcattaatgt gaaacgcagg tactggtcca 1980

```
ataacaagag cagaatgtat gtcctcgaaa acacaggtaa ttaaggaact actttgttct   2040

ttcaacaagt atagtttttt ttttaattct tttatgttga aaattaaagg agaatttgtg   2100

aagaaaaatg gagtattgat gggagactat ctaacaatct acgaggacga aagcaagaat   2160

ctcgtgagct ctcttattaa ctctcttttc ttattttatt ttggaaaaga caaaatgtta   2220

aataatgatt gattagtagt ccaaaattgg aaatttgaaa gtgtgtcatt gaatttagtt   2280

tgttcagcat ccagacaaaa aaaattaatt gcatttttat gatttttaaa tgaagatttt   2340

aattgatgtt tctgctatat ttgatcataa atataacatt ctactatctt attacatctt   2400

tgaaatagta gtcaagtatt tggtgatgtt ttatcctttc caaaaaatag ttattttgag   2460

cagccaattt atttggtttt gaatacatgc attgtaccaa ccgaacagtt tttcagaatt   2520

tggttttcta tttgagttat tattttatgt atatatataa atatataaaa aatgatattg   2580

aagtcaattt tgactagtat ggtttgaact aaaaaaagaa aagttagtag tcttaatatt   2640

tctgtttatc ttcacagaat atttttatca aaattaattt aatattaatg ctaaaaaaaa   2700

tttttacata tgtaaaaatc aatactgaaa gtatatagtt aaagtcctat acatgacttg   2760

ttgaaattta attgaataat gttttggtca acaacataga acttattaga gttttttttt   2820

tttttggtaa aagaacttat tagagttttt tcatgcttat atttggtttg gttattaaat   2880

aattttctaa catttatttc tcctaattga ccaaaatgat caactgcttt tttttttttt   2940

tgaacaaccc aaaatgatca actgctaaaa catcttatat atgtgtatat ttgtttggct   3000

tcattacagt acttctccat cagaaagcac ccacacaaac aaaatgatgg aagagaggat   3060

gagtcgatgg aagttatcga gatgaacttc tatgaagata taatgtttga ttacatacca   3120

aatgatgaag acgattccat tgcaatgctc ctcggaaatc taaacgagca ctatccctac   3180

ccaaatgatc ttatggatct cactgtcaat cttgatcagc atcagcaagc cacctcctcg   3240

tcgccacctg ctgatcacat gagctcgaac gatttcttat ggtgatgtga tgga         3294
```

<210> SEQ ID NO 12
<211> LENGTH: 3704
<212> TYPE: DNA
<213> ORGANISM: Brassica napus

<400> SEQUENCE: 12

```
atggataact tcttgccctt ttcctcttct aacgcaaact ttgtccaaga actctcaatg     60

gatcttaaca acaatcgctc acgcttatca acgttcccta cttatgatca tcatcatcag    120

gcgcagcctc actcgttgca accctactca tatgttgcat gtcctgtgga tcagacggcg    180

gctatgaatc ctcagatccc ggttacacaa accggaagtg agttcggttc tctggtttgt    240

aatcccggtt tcggacaagc aagaggtgga tttcttgatc cacacacggc taagatggcc    300

aggatcaaca gaaagaaagc gatgataaga tcaagaaaca attctagccc taactctagt    360

tcgaatgagc tggttggttc aaggagacaa gtggttctta ccatgaaaaa taatgccgag    420

atagcagcaa ggaaagatct ctatcgatat ccctcattcg ataacaaggt ttgttccaaa    480

tattagatat tttcgatttt atatatatat aaaacttgat caaacgtttt ggattttgtg    540

gttgactgta gaagcttagg gttttgttgg tgaaacactt gaagaacagc gatgttggat    600

cacttgggag gatcgttcta ccaaaggtgt gtaaattctt acaattcttt tatccatcgt    660

tttcgttaag gtgtaaagat aaaataaatt ttataggtaa aacattaata tgaaatagtt    720

aactttaata tgaaatagtt atcaatcacg taactacgaa atttgaaacc tcaattccat    780
```

```
ggaaaagttt tagaaaagta atatggtttc aggatttggc tggccccttt ttcaaagaag    840
gtttgtggaa caaaagtaca taagtcattg cggccacaaa ctctcattaa gaaatttcac    900
tgagattttt tctaacattt cattccattt ttaaaatata gtagtagtat atttagcgat    960
ttcgtggttt aaccaattac aagttcagtc tctaaaaaca acacggaaaa caaggggaat   1020
gtgaaacatg acaacaaaat gtagaatgta gtaaagttgt ttatagtatt tgtgtttgtt   1080
caagtacgaa ttttatgac atttttatag atttttagtt taggaagaat atggattgtt    1140
tgtaaattct aactaagctg atttatttaa agatatctgg agtttgaagg attaacaaat   1200
tcttcaagtt ttggagtgaa aaaatctaaa tagattcaat atagtttcct ttttgtaacc   1260
aataaggaaa agacatgagt gatagaacat gagaaataat caattttatt ctactactag   1320
ataaagtgaa actgtttata tgaatttatt ccaaaatgat gctgaagaaa aataaagtcg   1380
tctatttgcc tttcctaatt aattgactct taaatggtat acctcgaaat cattatggga   1440
aagtatcaag aaacaaaaaa aaacaatttg gaaaagaggt tcaacgatat ttacttgata   1500
ctgactgaaa caaattataa ttgtctgtta tctgtcttaa ttaaaacagt aagaaagtca   1560
tttttcgata agaaaagtca ttaaataatc ccttaaataa gtcatggctt tggaacgcag   1620
agagaagctg aagggaatct tccggagcta tctactaaag aaggaatgat agtagacatg   1680
agagatgcgg actctatgca gaattggtct ttcaaataca agttaagtct cgttttcatc   1740
tcttatatga actcaattat attcacaaaa gcaatttatt aatcgtttta ttttaccaat   1800
gggttataac aatcttttaa gctcactttt tgatgatttc aagttagaat ttttatcaat   1860
gtcaatttaa tgtcatactt aaaaaagctt gtatcactgt gaacataggt tctggtccaa   1920
taacaagagc agaatgtatg tccttgaaaa cacaggtaat taaggagcta ctatattctt   1980
tttaaagtat actacttatt taaactattt tattataata cgtttttcct tttgtcttaa   2040
aaattaaagg acaatttgtg actgaaaaaa gagttgagat tggagatttt ttaacaatct   2100
acgaggacga aagcaagaat ctcgtgagct ctcttattaa ctctcttttc ttgttttatt   2160
ttaaaaaaga caaaactcta aaataaacta ataatgattg attagcagtc cgaaattgga   2220
aatttaaaaa gtgagccatt aaattgtgtt tgttaagcat ctagacaaaa acttattgcc   2280
tttttgacct tttctgtcga tgatagctgt ccgtataagg aaggtactat aagaatttca   2340
aaccttagtt ttaatatact actgaaaatc gattctttat tcttttcttt tttttgctaa   2400
actgaaaatt aaagacatga tatattcttt caaaaaaaga tgtgaaatat atgagggtga   2460
ctagtattaa tttaaatttt atgtttaata aaatgcttct tctatttact catattttta   2520
ttctactatt ttgctaagta gggagtgatg taatatgttt ttctctagaa aagttgttct   2580
ttttatcagc caatttgttt ggtttgacta cataaactct ttgttgacaa aaaaaaagcc   2640
tacataaact cttccaaatt aacaaactgt ttttaggatt tgatttcata tcagaaataa   2700
tttcttttag aaaaatatta tttttattta tctaaatttt ttcaattttg aagataattt   2760
atttctccat tattttcgac aaagttcaaa tttaataaaa atatttagta tactattttc   2820
tagttatcct cacaaaatac tttttattag cataataata taatgtgcaa aatttagttc   2880
atacgtactt gaattttata actaagacaa attgttttgt aattagaaac ctgtaaatga   2940
catattggca tttaactgag taggagtagt gttttggttc aaaaacatgg aacttattta   3000
ctactctaca gtttttcata ggttatttaa ttttcctttg gatattaaat aatctaatat   3060
ttataatatt taaatctcct aactttttca gttgttaatc atttataaat tcagccaatt   3120
gctaagacac cttaaagcat gattaacctc ggttttttag ccgggattct taactcatga   3180
```

tttgacattt ttttatatat tttttggtta agaaacagtt tttttatctc ttatttaaga 3240
gacggttctt agctattctt agttaaaatc taaaaaaagt taagaatcgt ctcttatcca 3300
aaattaagaa ccccagttaa aagactggag ttaatcatgg tcttatatat gcatgttttg 3360
tttgtttggt cttactgcag tacttctcca taagaaagca cgcagacaaa ccaaatgaag 3420
gaagagaaga tgagtcgatg gaagccaacg acatgaactt ctacgaagat attgcgtttg 3480
atttcatacc aaaagatgaa gacgaagatt ctattgcaat gctcatcgga aatctaaatg 3540
atcactatcc caacccaaac aatcgtatgg acctcccaat cgatcttcat cagcatcatc 3600
aagccacctc attgccacct gcggattaca tgaccaatcc tcagtatggt ggttcctcca 3660
atgatctcat gagctttaac gacttcgtat ggtgatgcga ttga 3704

<210> SEQ ID NO 13
<211> LENGTH: 3676
<212> TYPE: DNA
<213> ORGANISM: Brassica napus

<400> SEQUENCE: 13
atggataact tcttgccctt ttcctcttct aacgcaaact ctgtcgaaga actctcaatg 60
gatcttaaca acaatcgctc acgcttatca acgttcccta cttatgatca tcatcatcag 120
gcgcagcatc actcgttgca accctactca tacgttgcat gtcctgtgga tcagacggcg 180
gctatgaatc ctcagatctc ggttatacaa accggaagtg agttcggttc tctggtttgt 240
aatcccggtt tcagacaagc aagaggtgga ttccttgatc cacacacggc taagatggcc 300
aggatcaaca gaaagaaagc gatgataaga tcaagaaaca attctagccc taactctagt 360
tcgaatgagc tggttggttc aaggagacaa gtggttctta ccatgaaaaa taatgccgag 420
attgcagcaa ggaaagatct ctatcgatat tcctcattcg ataacaaggt ttgttccaca 480
tattagatat tttagatttt atatatatat aaaacttgat caaacgtttt ggattttgtg 540
gttgactgta gaagcttagg gttttgctgg tgaaacactt gaagaacagc gatgttggat 600
cacttgggag gatcgttcta ccaaaggtgt gtaaattctt acaattcttt tatccatcgt 660
tttcgttaag gtataaagat aaaataaatt tttttttttt tttggtaact ctggtatctg 720
ggcagccaca ttcccaacta tctccgtagg gggtccagcg ccccaacgga agggatgtta 780
aatccgttgt ggccggggct cgaactcgtg atggcggaca cctcagccga ggttcctata 840
ccaccagacc acgaggcccg gttagataaa ataaatttta taggtaaaac attaatatga 900
aatagttaac tttaatatga aatagttatc agtcacgtaa ctacgaaatt tgaaacctca 960
attccatgga aattttttag aaaagtaata tggtttcagg atttggctgg cccctttttc 1020
aaagaaggtt tgtggaacaa aagtacataa gtcattgcgg ccacaaactc tcattaagaa 1080
atttcacaga gatttatttc taacatttca ttccacattt aaaatatagt agtagtatat 1140
ttagcgattt cattgtttaa ccaattacaa gttcagtctc taaaaacaac acggaaaaca 1200
aggggaatat gaaagatgac aacaaaatgt agaatgtagt aaagttgttt atagtatttg 1260
tgtttgttca agtacgaatt tttatgacat ttttatagtt ttttagttta ggaagaatat 1320
ggattgtttg taaattctaa ctaaactgat ttatttaaag atatctggag tttgaaggat 1380
tacaaattct tcaagttttg gagtgaaaaa atgtaaatag attcaatata gtttcctttt 1440
agtaaccaat aatgaaaaaa catgagtgaa agaacatgag aaataatcaa ttttattcta 1500
ctagataaag tgaaactgtt taaatgaatt tattccaaaa tgatgctgaa gaaaaataaa 1560

-continued

```
gtcgtctatt tgcctttcct aattaattgc ctcttaaatg gtatacctcg aaatcattat   1620
gggaaagtat caagaaacaa aaaaaaaaca atttggaaaa aaggttcaac gatattactt   1680
gatagttata ttgaaacaaa ttataattgt gtctcttatc tgtcttaatt aaaacagtaa   1740
aaaagtcatt tttcgataag aaaagtcatt aaataatccc ttaaataagt catggctttg   1800
gaacgcagag agaagctgaa gggaatcttc cggagctatc tactaaagaa ggaatgatag   1860
tagagatgag agatgcggac tctatgcaga attggtcttt caaatacaag ttaagtgtcg   1920
ttttcatctc ttatatgaac tcaattatat tcacaaaagc aatttcttaa tcgttttatt   1980
ttaccaatgg ggttatacta acaatctttt aagctcactt tttgatgaat tcaagttaga   2040
atttttatca atgtcaattt aatgttatac ttaaaaaagc ttgcatcact gtgaacatag   2100
gttctggtcc aataacaaga gcagaatgta tgtccttgaa aacacaggta attaaggagc   2160
tactacattc ttttaaaagt atactactta tttaaactat tttattataa tatgtttttc   2220
cttttgtctt aaaaattaaa ggagaatttg tggctgaaaa aagagttgag attggagatt   2280
ttttaacaat ctacgaggac gaaagcaaga atctcgtgag ctctcttatt aactctcttt   2340
tcttgtttta ttttgaaaaa gacaaaactc ttaaataaac aaataatgat tgattagcag   2400
tccgaaattg gaaatttaaa aagtgagtca ttaaattgtg tttgttaagc atccagacaa   2460
atatttattg cctttttgac cttttctgtc gatgatagct gtccgtatga ggaaggtact   2520
ataagaattt caaaccctag ttttaatata ctactgaaaa tcgattcttt attcttttct   2580
ttttttgcta aactgaaaat taaagacatg atatattttt tcaaaaaaga cgtgaaatat   2640
atgagggtga ctagtattaa tttaaatttt atgtttaata aaatgcttct tctatttact   2700
catattttta ttctttgcta agtagggaat gatgtaatat gtttttctct aaaaagttgt   2760
tctttttaac agccaatttg tttggtttga ctacataaac tctatgttga cacaaaaaaa   2820
gcctacataa actctaccaa attaacaaac tgtttttagg atttggtttc atatcagaaa   2880
taatttcttt tagaaaaata ctatttttat ttatctaaat tttgtcaatt ttgaagataa   2940
tttatttccc cattattttc gaccaagtga aaatttaata aaaaaattta gtatactatt   3000
ttcaagttat cctcacaaaa tactttttat tagcataata taatgtgcga aatttagttc   3060
atacgtactt gaattttata actaagacaa attattttgt aattagaaac ctgtaaatgt   3120
catgttggca tttaactgag taggagtagt gttttggttc aaaaacatgg aacttattta   3180
ctactctaca gtttttcata ggttatttaa ttttcgtttg gatattaaat aatctaatat   3240
ttataacatt taaatctcct aactttgtca gttgttaatt atttataaat tcagccaatt   3300
gctaagacac cttatatatg catgttttgt ttgtttggtc gtactacagt acttctccat   3360
aagaaagcac gcagacaaac caaatgaagg aagagaagat gagtcgatgg aagccaacga   3420
catgaacttc tacgaagata ttgcgtttga tttcatacca aaagatgaag acgaagattc   3480
tattgcaatg ctcatcggaa atctaaatga tcactatccc aacccaaaca atcttatgga   3540
cctcccaatc gatcttcatc agcatcatca agccacctcc tcgttgccac ctgtggatta   3600
catgaccaat cctcagtata gtggttcctc caatgatcac atgagcttta acgacttcgt   3660
atggtgatgc gattga                                                   3676
```

<210> SEQ ID NO 14
<211> LENGTH: 4144
<212> TYPE: DNA
<213> ORGANISM: Brassica napus

<400> SEQUENCE: 14

-continued

```
atggataact tcttgccctt ttcctcttct aacgcaaact ctgtccaaga actctccatg     60
gatcttaaca agaatcgctc gcacttctcc atggcgcagc ctcagcactt gttgccgcct    120
tactcgtacg ttgcatgtcc ggtacttgat cagacggggg ccatgaatca tcagcctctt    180
cactcatcgg atgcttttcc tcagatcccg gttgtgcaaa ccggaggtga attcggctat    240
ttggtttgta agcccggtgt gaggcaggaa agaggtggat ttcttgatcc acactcgact    300
aagatggcta ggatcaacag gaagaaggcg atgataagat caagaaacaa ctctaacctt    360
aattctagtt cgaatgagtt ggttgattca aggagacaag tggctcttac catgaaaaat    420
aatgccgaga ttgctgctag aaaagatttt tatcgattct cctcattcga taacaaggtt    480
tgtatttctt tggtccaaaa taatggaata tatgcgattc tacatacaca acatgataat    540
gtttttgaaa tttttgttaa ctgtacgtag aaacttaggg ttttgttggt gaagcacttg    600
aagaacagcg atgttgggtc acttgggagg attgttctac caaaggtgtg taaattttta    660
caattctcgt attctttatg gtataattaa tgttaaaaca attttgtaga ggtaaaaaca    720
ctaatatgtt ggggatggat tgatgaaaga ttatcaatta cgtaactacg aattttaaaa    780
cctcaattca tgagaaagtt ttttaaaagt aatataattt caggatttgg ctattaccat    840
ttaaaaagat attatcactg cgaccacata ttctctcatt atgcaatttc acacattttc    900
ctccattcaa accatcgttg tttaaccaat gagaagttta ttctctaaaa cacatggaag    960
acaagaggga ttttttttatg atcaaccaga ggaaaattaa acatgaaaac aaaatgtgaa   1020
atatataatt gtttaatcaa tacggagtat tttcgttcat tccttctggt ttgagctttt   1080
atgttataca gtactagtat ttttttagtt tagcaagaat atggtgatta aaaatctagt   1140
ttaaatttgg tttatatata tcttaaattt gaaggactaa aagtcaaagt tttggaatga   1200
gcaccaaaaa tgaaatacag tatgaaaaaa aaatcaaaat agattgatca tagctccttc   1260
aatctaatat tccgtgtaag aacttagtaa ccaatgaata aaaaacatga gaagtaaacg   1320
attttctagt tttagttagc taaaatggtt aataacgtgg ttaaaatgac tttattttga   1380
aacggggttg aaaaaaagtc gtatatattc ctttcctaat taattgcctc ttaaatggca   1440
ttcctcgaaa tcattaagga aaagtaaaaa acaaacaaaa agccattatg gattaattgg   1500
ggtagtttac tagttttatt atagaaaaat catatcaaat catccccttt atctatctta   1560
ataagaaaat aattagttag gaatcgccac tcgctagcta ggaatgcccg ttattttcat   1620
agatttctta gctttattgg ttgttctatt ccggtctggt tacctagacc gcctcaagtt   1680
tgagtaatag aataactgtt tgttgcaaaa aaaaataaaa taataattag tttattaaaa   1740
agtaattaag taaatcatgg gtttggagcg cagagagaag cagaaggaaa tcttccggag   1800
ctatctgata aagaaggaat ggtattacag atgagagatg ttgactctgt gcagtcttgg   1860
tctttcaaat acaagttaag tctcgtttcc tttctcatat atatattgat agaaaacatt   1920
ttatgttcca ttttttaatc taccaatagt ttaacaaatt aaccttataa gttctttagg   1980
gctttttttgt tagtggtatg ttttatagct tggaatttgt tatatcggtt tcaatttaat   2040
atttttggaa cgagagaact gataaggctt gcattaatgt gaaacacagg tactggtcca   2100
ataacaagag cagaatgtat gtcctcgaaa acacaggtaa ttaagaaact acattgttct   2160
ttcaacaagt atagtttctt ttaaaaaaat tcttttatgt tgaaaattaa aggagaattt   2220
gtgaagaaaa atggagtatt gatgggagac tatctaacaa tctacgagga cgaaagcaag   2280
aatctcgtga gctctcttat taactctctt ttcttatttt attttggaaa aggcaaaatg   2340
```

-continued

```
ttaaataatg attgattagt agtccaaaat tggaaatttg aaagtgtgtc attgaattta   2400
gtttgttcag catccagaca aaaaaaatta attgcatttt tatgattttt aaatgaagat   2460
tttaattgat gtttctgcta tatttgatca taaatataac attctactat cttattacat   2520
ctttgaaata gtagtcaagt atttggtgat gttttatcct ttccaaaaaa tatttatttt   2580
gagcagccaa tttatttggt tttgaatata catgcattgt accaaccgat cagtttttca   2640
gaatttggtt ttctatttga gttattattt tatgtatata tatatatata aatatataaa   2700
aaatgatatt gaagttagat tttgactagt atggtttgtc gaccaagttg gaactgaaaa   2760
aagaaaagtt agtagtctaa tatttctgtt tatcttcaca gaatattttt atcagaatta   2820
attttatatt aatgctaaaa aaaatttaca tatgtaaaaa tcaatactga aagtatctta   2880
tatattaaaa cagaagtcac aactttgatt catatgtgat ttttaaaaac atggacttaa   2940
tggacctatt actaaaaagc catattacat ttaatctcta atcttatcat ttaaattttt   3000
ggcataccag aaatttttat tgggctatca ataattgaat ttaaacaata gaagatccat   3060
tggatttata gatagtataa attaaatata tataatttaa tgttataata ctatacctcc   3120
atatgttaat tatttaaata tttgtcgatg ttaactttta aaattataaa aaaaaaattt   3180
aaataacaaa aatcatatta tctacaatga ttaatcttta ctcccataaa ccaatgaaaa   3240
caaattttaa actatatagt ttattttaaa aattaaacaa aaactaaatg tttaattatt   3300
tactcgataa tataaatcta tgaagcgaaa agtttaattt tttaaaaact ttctaaattt   3360
gtgaaatgtt acaatatctt tgaatacgac aataaaacaa tattttacta atatttatat   3420
atatagttac gattttaata atgaaataat aatccgaaaa tatatatata gaagaagata   3480
gaaatacatg tgaaagtttg aaacaatcta ttcaatgaaa aaaatatacc gtaaacttat   3540
tatgtttaaa aattgataga cacatatata ttataatata taccaattta gaattgaaaa   3600
taaaatgttt atataaaaat aaatgaaaac aaaaacccgc gaatcgagat ctagtattag   3660
ttaaagtcat atacatgact tgttgaaatt taattgaata atgttttggt caacaacata   3720
gaacttatta gatttttttc atgcttatat ttggtttggt tattaaataa ttttctaaca   3780
tttatttctc ctaattgacc aaaaagatca actgctaaaa catcttatat atgtgtatat   3840
ttgtttggtt ttattacagt acttctccat cagaaagcac ccacacaaac aaaatgatgg   3900
aagagaggat gagtcaatgg aagtcatcga gatgaacttc tatgaagata taatgtttga   3960
ttacatacca aatggtgaag acgattccat tgcaatgctc ctcggaaatc taaacgagca   4020
ctatccctac ccaaatgata ttatggatct cactgtcgat cttgatcagc atcagcaagc   4080
cacctcctcg tcgccacctg ctgatcacat gagctcgaac gatttcttat ggtgatgtga   4140
tgga                                                                4144
```

<210> SEQ ID NO 15
<211> LENGTH: 3010
<212> TYPE: DNA
<213> ORGANISM: Arabidopsis thaliana

<400> SEQUENCE: 15

```
gatctctctc cctctctctc tctctctctc cgggaaaaat ggataacttc ttaccctttc     60
cctcttctaa cgcaaactct gtccaagaac tctctatgga tcctaacaac aatcgctcgc    120
acttcacaac agtccctact tatgatcatc atcaggctca gcctcatcac ttcttgcctc    180
cgttttcata cccggtggag cagatggcgg cggtgatgaa tcctcagccg gtttacttat    240
cggagtgtta tcctcagatc ccggttacgc aaaccggaag tgaattcggt tctctggttg    300
```

```
gtaatccttg tttgtggcaa gagagaggtg gttttcttga tccgcgtatg acgaagatgg    360
caaggatcaa caggaaaaac gccatgatga gatcaagaaa caactctagc cctaattcta    420
gtccaagtga gttggttgat tcaaagagac agctgatgat gcttaacttg aaaaataacg    480
tgcagatctc cgacaagaaa gatagctacc aacagtccac atttgataac aaggtttggt    540
ttttattcgt cccaattttt gaatatgtac gatttctta tttatttttt ggttttcatg    600
ttattatatg aatatataca attttgggtg tataaaactt tatgatacaa tttttaatta    660
tttttatttt gttttggttg ttgcttgtag aagcttaggg ttttgtgtga gaaggaattg    720
aagaacagcg atgttgggtc actcgggagg atagttctac caaaggtatg tgaattctta    780
aaattctttt taatttctcg aaccaatact tggtaaaaaa ttctgtttgt tttcatgatt    840
tttcttcttt ttctgttatt gtataatgat aaatgaaatg cattgatgaa aatgataatc    900
atcaatcacg tacgtcattg aaaatttaaa acacaatccc ataaaaaaat tcttagaaga    960
ataaagttat tttatgagga ttagacttcc gtcattttat acaagagatt tgtggaacac   1020
aagcacaaaa atcgttgcgg ccacatatta tctcattatt caatttcact gagtttttct   1080
tgcacatttc attttacttt caaattttac ataatatgtt tatctaactg ttttctgttt   1140
aaccaataaa aagttttaag tctttaaaat aagtatccac acgaaaacaa gatgaataag   1200
aaacatgaga agaaaatgtg gactgaagta aagttagttt aatcaaattt tgtttggttt   1260
ctgtacgaac ttttatgttt ttgatttttt atttatttag caagtagtat atgaattaat   1320
ttaatttttt atagttttaa acttgatttt tttaaagata gcttataatt attgaatata   1380
tggaatgcta cttcttcctt caatgttgtt atttgtattt gttaaatttg aaattgggtt   1440
gaagaaaatg aaaggtcgtt tatatgcctt tcctaattaa ttgtccattg aatggtttac   1500
cactttacct cgaaaaagtg aataaataaa aatcattagg gaaaaagatt ctacatatct   1560
tggggtttta tcaaactttt aatcaatttt attttaatga tatcgttctt atttttctta   1620
gcaagacact aatacgtgaa tcatggcttt ggaatgcaga gagatgcaga agcaaatctt   1680
ccgaagctat ctgataaaga aggaatcgtt gtacagatga gagatgtttt ctctatgcag   1740
tcttggtctt tcaaatacaa gtaaataatt cgctttctaa tccatttttc atttcccaat   1800
taacacaact ttaattttat gctcaactgt tagtcccttt ttgtgttacc ggttctcata   1860
cttagtttta aattttgatt ttttttttat caattgggaa cagtattata attagaagac   1920
taaatgctcg tattaatgac ataggttttg gtccaataac aagagcagaa tgtatgtcct   1980
cgagaacaca ggtaaattaa ggagctccaa tattatttca aaagtacaaa atcttatgta   2040
aaactacttt taaataaata tgatttacct tttccttttt ttttgtggtg ataactaaag   2100
gagaatttgt gaagcaaaat ggagctgaga taggagactt tttaacaata tacgaggacg   2160
aaagcaagaa tctcgtgagc tctctattta cttcatttcc ctatttaatt ttgtaaaaag   2220
acatgaaaaa gttaaaaaaa aaatgattaa ttagtagtcc aaaattggaa atttaaaaag   2280
tggtctttga attgagtttg ttaagcatcc agacaaaagt tttaaaacct ttttctgtca   2340
atgataactg ttcttatatg gtaggtatta ataacttgtg ggcctagggg gaagtaaata   2400
ctatggagaa aattttataa taattgaaat ttggttaatt tagagtttat aatatggttt   2460
gatttggttt ggttaggact tatgacttat gtgtctgtgt gtgatcgctt gttcttatta   2520
cagtacttcg ccatgaatgg aaattcggga aaacaaaatg aaggaagaga aaatgagtcg   2580
agggaaagga accactacga agaggcaatg cttgattaca taccaagaga cgaagaggaa   2640
```

gcttccattg caatgctcat cggaaatcta aacgatcact atcccatccc taacgatctc 2700
atggacctca ccactgacct tcagcaccat caagccacgt cctcatcaat gccacctgag 2760
gatcacgcgt acgtgggttc atccgatgat caggtgagct ttaacgactt tgagtggtgg 2820
tgatatggtg gtggaagttc tcaagttcat aaccccccttt atgaaaatag accttaagat 2880
atacaaaaga gattaaaaga aaaaaaagtt agtatatttc atcatatctc tcattgaaga 2940
tgagatttat atctataatt gtttaatagt gtttttatta cttttctatc aatatattaa 3000
agttttaatt 3010

<210> SEQ ID NO 16
<211> LENGTH: 1092
<212> TYPE: DNA
<213> ORGANISM: Arabidopsis thaliana

<400> SEQUENCE: 16
atggataact tcttaccctt tccctcttct aacgcaaact ctgtccaaga actctctatg 60
gatcctaaca acaatcgctc gcacttcaca acagtcccta cttatgatca tcatcaggct 120
cagcctcatc acttcttgcc tccgttttca tacccggtgg agcagatggc ggcggtgatg 180
aatcctcagc cggtttactt atcggagtgt tatcctcaga tcccggttac gcaaaccgga 240
agtgaattcg gttctctggt tggtaatcct tgtttgtggc aagagagagg tggttttctt 300
gatccgcgta tgacgaagat ggcaaggatc aacaggaaaa acgccatgat gagatcaaga 360
aacaactcta gccctaattc tagtccaagt gagttggttg attcaaagag acagctgatg 420
atgcttaact tgaaaaataa cgtgcagatc tccgacaaga aagatagcta ccaacagtcc 480
acatttgata acaagaagct tagggttttg tgtgagaagg aattgaagaa cagcgatgtt 540
gggtcactcg ggaggatagt tctaccaaag agagatgcag aagcaaatct tccgaagcta 600
tctgataaag aaggaatcgt tgtacagatg agagatgttt tctctatgca gtcttggtct 660
ttcaaataca agttttggtc caataacaag agcagaatgt atgtcctcga gaacacagga 720
gaatttgtga agcaaaatgg agctgagata ggagactttt taacaatata cgaggacgaa 780
agcaagaatc tctacttcgc catgaatgga aattcgggaa aacaaaatga aggaagagaa 840
aatgagtcga gggaaaggaa ccactacgaa gaggcaatgc ttgattacat accaagagac 900
gaagaggaag cttccattgc aatgctcatc ggaaatctaa acgatcacta tcccatccct 960
aacgatctca tggacctcac cactgacctt cagcaccatc aagccacgtc ctcatcaatg 1020
ccacctgagg atcacgcgta cgtgggttca tccgatgatc aggtgagctt taacgacttt 1080
gagtggtggt ga 1092

<210> SEQ ID NO 17
<211> LENGTH: 9159
<212> TYPE: DNA
<213> ORGANISM: Brassica rapa

<400> SEQUENCE: 17
aatgtgtttg atatatacca tggatagtag tgagaaggta gagttcaaag tataagaaag 60
cgaacccctc catagtgggg gcttaaaccc gtgcaagctt gcatatatct atagctgatg 120
gttgggccca aacttatatc ttgggcttat tttgtttcca tctgtccagc ccatgataaa 180
gtgtaaaacg acaccgtata aagcttaatg gagtaaacga atcacacgta gcggggatcc 240
ccgtgtcagt tcttgtccga aaagctggac ggaggaaaac ggcatcgtat tcgcttcgct 300
tgaatatata tattttgcgc aaaagccctt ttcatccctt tcttctctca ttactcgatt 360
tagggttttc taatctcgaa agaaatcaag atcctccttc ctccctctct cgatttcgat 420
ctctttcgtg ttgatttcga attcgttcgt caataggttt gtttctctct agctccgatc 480
gatctcgcta gcaaattagg gtttcgagcg agcttaatcc gatcggtttc tggatcagtt 540
gagatgcgat cggaatctct ctgaataaga gagactcgtg tggggggttt cttcctttgt 600
atggaaactc ggagccgcaa gcgtgcggag gcgacctcaa ctgccccatc ttcttcttct 660
tcctctcctc ctcctcctcc ttcctcaggt cccaccactc gcagcaaacg cgctcgcctc 720
tcgtctccct cttcatcttc agccgccgct actgcacctt cctcctccac ccgctctcgt 780
tcttctcgct ctaccaccgc tacagtcgcc gttactccca tggacacatc caccgagtct 840
tctggattcc accgcggcgg aggacgaggt aacaggggaa acgataatac taactctgat 900
aagggaaaag agaaggagca tgaggttagg attagggata gagaaagaga cagagctagg 960
caacagctca acatggacgc tgcagctgct gctgccgccg ccgctgacga ggacgacgac 1020
aatgatagtg aggatggcaa cgggggattc atgcatccca acatgagctc agccagcagt 1080
gcgttacaag ggttgctgag gaagcttgga gctggacttg atgacttgct tccttcttca 1140
ggtattggct caggttcgtc ttctcacttg aatgggagga tgaagaaggt actcgctggc 1200
ttgcgctctg aaggagaaga gggaaagcag gtcgaggctt tgacgcagct gtgcgagatg 1260
ttatctattg ggaccgaaga ctccctgagc accttctctg ttgattcctt cgtcccggtt 1320
cttgttggtc tacttaacca tgagagcaat ccggatatta tgcttcttgc tgccagggct 1380
cttactcatc tgtgtgatgt tttgccgtct tcttgtgctg ctgttgttca ttacggggct 1440
gtttcgtgct ttgtcgccag attgttgaca atagaataca tggacttggc cgagcaggtt 1500
cgatttccta acaattcttg aatttttttg ctgaatatat attgtggaat gttttatgct 1560
gcagtttcta cacgtacata tccaatattt tagtttactt aggacgaaat ttgaaatttg 1620
attttattct tcatgtgatt tacaacagtc tctgcaagct ctcaaaaaga tatctcagga 1680
acacccaacg gcctgtttgc gtgctggtgc tcttatggca gtgctatcat atctggattt 1740
cttctccacc ggtgtccagg tgggtaattt tgtaactttt ctttaatgct ttccatactc 1800
gtttatctaa tgcacttttt tttttacttt ttgtagcgtg tagcagtatc taccgctgca 1860
aatatgtgca agaagttacc ttctgatgca tctgattatg ttatggaagc tgtaccggta 1920
ctgacaaacc tacttcagta tcatgatgcg aaggtaaacg atcccttttt ttttgctata 1980
atgtggtatt atctagttct gctcttgccc cagtttcctt catagtatgt tcgtacggtg 2040
gcaggttttg gaatatgctt ctatctgttt gactcggatt gccgaagcat ttgcatcgtc 2100
ccctgataaa ttagatgaat tatgcaacca tggcctggtg actcaagctg cgactcttat 2160
atccgctagc aactcgggag gtgggcaagc atctctcggt gtttcaacat acacggtatg 2220
agttaattct tttgtgtttt ctatatttcg ttattcatag gatgacattt tcatcatatt 2280
ttcacaggga ttaatccgat tactttccac ctgtgcgagc ggttcacctc ttgggtgcag 2340
gacattactt cttctcggta ttagtagcat tcttaaggat attctgtcgg gttccggtgt 2400
ctctgctaat gcatctatat ccccagcact gagcaggcct gcagatcagg tacggattta 2460
ctttttgaca tcacagactt tattttgttc aattcctgat aaagtctatt cagtaaaaag 2520
tgttttgttt aggggacaca cctttaaata gatcatcaac ataaattgtg tgttgagtga 2580
gatgcttagg ggacacacct tcaaatagat cacttgcatt taaatggatc acttgcattt 2640
aggagttttg tctattcagt tcaatgataa tctttttttt tttgtaacac tcagctcaat 2700

-continued

```
gataatctat gtacatgtat tttgagcttt atttatgttg taaccgatgg ctcaactttc   2760
atatgcttgt tttctggtat ggtgttagaa gtggtataga taaaagtgct tagcgcttca   2820
tcagtgtgct cggtcttgtt tatttaactt tttttatccc atgactcgct aattcttgaa   2880
tatattcttg aacatgatca tgtgaggtct tttgtttccg aattataact cttgttttgc   2940
atcttagatt tttgagatag tcaacctagc gaacgagctc ctccctccac tgccagaagg   3000
aagtatctcc cttcctacta gcgcaaacgc gttagtgaaa ggttcaggcc aaaaaaagtc   3060
ttctccaagt acttcaggaa aacaagaaga ttctcccaaa gtttcaccta gagaaaaatt   3120
acttagtgat caacccgaac ttctgcagca atttggattg gatcttcttc cagttttagt   3180
gcaggtaatt ttttgttgca gttgctacaa gttagtgttc atacaacctc ctgtatgtct   3240
aattaccctt gttttctttc ctacagatct atggttctag tgtcaatggt actattcgtc   3300
ataaatgtct ctcagttatc gcaaagttga tgtatttcag cactccagaa atgattcaat   3360
ctctaattgg tgacacaaat atatcgaggt atgctggtta tgttttaaat taggtatcac   3420
atggcgcaac ttcttacatt atttttccta tgtagcttct tggctagtgt cttggcatgg   3480
aaagatccac aagtcttggt tcctgctcta caagttgcag aaattctgat ggaaaaactt   3540
cctgaaactt tctcgaaagt gtttgtgagg gaaggggtgg ttcatgctgt agatcaactt   3600
gtcttggttg gtaaacctag ttctcatgct tctactgatc aggaaaatga ctgtgtgcct   3660
ggatctgcac gatctaggcg ttatagacgg cgaagtagta acgccaattc tgatggaaat   3720
cagtcggaag agcttaagaa ttctgtgtca gctagtatag gtgcaaacca taattccatg   3780
gaatctccta cagcgagctt catgctaagg gaaacagtta gctcctgtgc aaaagcattc   3840
aaagacaagc acttcccgtc tgatggtggg gaatttgatg ttggagttac agatgatctc   3900
ttgcatctga agaatctttg cacgaagcta actgctggta caaatgatca taaagtgaaa   3960
ggaaagggga aatctaaagc ctctgggcca tgcctcggcg atttttctgc tagcaaagaa   4020
gaatacttga ttggtatcat ctccgagata cttggcgagc taagcaaagg agatggtgtc   4080
tcaacttttg agtttattgg cagtggtgtg gtagcagcat tgcttaacta tttttcttat   4140
ggatactttt ccaaagagaa gatctccgag gttgatttgc ccaaacttcg ccaggatggg   4200
ctcagaaggt tcacagcttt tctagaaatt gcacttcctt ctgatggtaa tgagggaaag   4260
atccctccta tgactgtttt gattcagaaa cttcaagatg ctttgtcttc actggaacgc   4320
tttccggtcg tccttagcca tccctcaaag tcactcagtg gaagtgctcg tctctcatct   4380
ggattgagtg ctttggcaca tcctttgaag ttgcggttat gccgtgcacc tggagagaag   4440
gcactacgtg attactcctc caatattgtt ctcatagatc ctttggcaag catagcagca   4500
gtggaggaat ttctctggcc ccgagttcaa cgcagtgaat ctggggtgaa gccagcagcg   4560
cctgttggaa acactgagcc aggcacatta cctagcggtg ctggtgtttc atcaccatcc   4620
tcgtcaactc cagcttccac cactcgtcat tcttctagat ctagatctgc aattaaaata   4680
ggcgatgcct caaagaaaga acctgtgcac gagaaaggta ccagctcatc taaaggtaaa   4740
ggtgttatga agccggctca gccggataag gggcctcaga caaggagcag tgctcaaagg   4800
aaagctgttc ttgacaaaga tacactaatg aaaccagcta gcggagactc cagctctgag   4860
gtatgtcact gtagaaagtt ctggattaca tggttgttta ttgtgtaaca ttatattatg   4920
tttgtggtgt gatctgctta tgcagcacta tcgtacttat attgcttgca ggacgaagaa   4980
atggatatat cccccgtcga catggatgat gctttggtta ttgaagagga agacatttct   5040
gacgacgatg aggatgatga tgatgaggat gtaagtattc cctccccagt atgtacatta   5100
```

cagacgcaat tatttctctt gctaacaaca tgaaagatga tacttttcgc aataatgctt 5160
gctagctttc cgtattctta gataagttta ccatattgag ctcaccttat ttggcacctt 5220 tcctttaga actgactaaa gagaataatg aactttatac cacaatttct catattgatc 5280
tggtcttgaa ttcaggtctt ggatgacaat cttcccatgt gcacccctga taaggttcat 5340
gatgtaaaat tgggagacgc agtggatgat gagggagccg gtctagcacc tagcggccga 5400
cagatgaatt cagctttggc aggaagtagt ggaacagcaa ctgcaagggg atctaattct 5460
actgatgctg gcattgggaa tctttatggt tctaggggtg cactctcctt cgctgctgcg 5520
gcgatggcag ggcttggagc tgccagtggt agaggtatca ggggaagtag agacctacat 5580
gggcgtaccc tgaatcgaag ttctgatgag tcctctaagt tgatgtttac tgcgggagga 5640
aagcaactta gtaggcatat gacgatatat caggctgtgc aacgacaact tatgctagac 5700
gaagatgatg atgacaggct cggtggcagc gatttcatct ccagtgatgg aagcagatta 5760
aatgatatat atactatcat gtaccagatg ccggacagcc aagcgaatag gttgtctgct 5820
ggtggtgcaa gttctaccac accatctaaa tccaccaaat ctgctactac taatgcaagc 5880
gtagaagctc agtcgtatag ggcatctctt ttggatagta tcgtacaagg aaagcttcca 5940
tgcgaccttg agaagtccaa ttctacgtat aatgttctgg cgttgttacg tgtattagag 6000
ggtttaaatc agcttggccc tcgcttaaga gcccaaaccg tttctgatcg ttttgcagag 6060
ggtaaaatta caagtctgga tgatctgaat acaactgctg caaaggtttc tcatgaagaa 6120
ttcatcaaca gcaaacttac acccaaatta gctcgacaga tccaggacgc gcttgctttg 6180
tgcagtggaa gtcttccctc ttggtgctac cagttgacta cagcatgccc gtttttgttt 6240
ccgtttcaga cccggagaca gtatttctat tcaactgcct ttgggttgtc gcgtgcattg 6300
aaccgcttgc agcagcagca aggtgctgac ggcagtggtt ctacaaatga acgagagatg 6360
agaataggga gattgcagcg ccagaaagtg cgtgtatccc gaaatagaat attagattct 6420
gctgcgaaag ttatggagat gtattctagc caaaaagctg tgcttgaagt agaatatttt 6480
ggtgaagttg gtactggtct aggcccgaca cttgagtttt acacactcct aagccatgat 6540
ttgcaaaagg tttcccttgg gatgtggaga tcaaattctg gtgacaagtt atctatgcaa 6600
actgatagag atgagattca agacggtaaa tcagcagcag ctagggacag agatatagtt 6660
caggcaccac ttgggttgtt ccctcggccc tggccctcaa ctgctgacgt atctgaaggt 6720
agtcggtttc ataaagttgt tgaatatttc cgccttttag ggcgcgtgat ggcaaaggca 6780
cttcaagatg gacggctaat ggacgtcccg ttaagtacag ctttttataa gctcattctt 6840
ggtcaagtga gtttttttact atcagtaact ttttttattt agctaagagt ggactagtag 6900
tttcgacttc tttacgttgt tcgtaatttc ttactgcttc tttactcacc tgaacaggag 6960
cttgatttgc atgatgttat attatttgat gctgaacttg gcaagacttt gcaagagctt 7020
cgtgttcttg ttggccgtaa gcactatctg gaagcaggcg gtggtgacaa cagtagcggg 7080
atttctgatt tatgtttgcg tggatcccgt attgaagatc tttgcttgga cttcacccta 7140
cctggctacc ctgaatacat attgagacca ggagatgaca ttgtaccgtc taataagctt 7200
tacatccgat atcttactat tgttttagtt cttgtccatt gttgctgatg ccgtgtactg 7260
ttttctgttc tattacaggt tgatattaat agtcttgagg actatatatc cctggtcgtt 7320
gatgccactg tcaagagagg agttgcccgg cagattgaag ccttcagatc tggattcaat 7380
caggttagca gtttcacaga ctctccgctt tgtctcttac ttttcctgta ggctttggct 7440

```
ttggctttgg ctttggcttc taaattacat aggagtggtt tcttttggtt catactttat   7500

aatcttttaa acaacaggtt gatgataatt tagtcttacc tttattatct ttacaagaat   7560

tctctgttct tacacatgat taccaggtct ttgacataaa atctctacaa atattcaccc   7620

cttctgagct ggactacttg ttgtgtggtc gtagagagtt gtgagaggtg agttttcatc   7680

tatttttga atttccacta cccatttgac tcgaatcgac tagataaaat tttcttttct   7740

aaaacctttc ttttattgca ggcggagact cttgttgaac atatcaagtt tgatcacggt   7800

tatactgcaa aaagtccggc aatcattttc gtaagttact ttccgtacta gtttgttaaa   7860

aaaccaattt tcttttacaa tcaagctttt tgcttcttta ttgttgattc ctttttgact   7920

ttgattttca ccctggcggt agttattgga gatcatggga gagctaacag cagatcaaca   7980

gcgggctttc tgctagttcg taactggagc tcctaggctt cctcctggtg gcttagctgt   8040

tctcaaccca aggctgacga ttgtgagaaa ggtaagaaac ctttacttat atattcggtt   8100

aaaaagcgtt tttgtaattg agccaagagg ttctagtcat gttaaactag acccaccaag   8160

ccatatatca gaatacatct acacgtgacg cattgttgtg tttgcaagac ttgctaagat   8220

gaattagctc ttactcgatt taagttgtgt atttgcttcc aattgatgtg tttttggctt   8280

gatgcagctc tcatcaacct caaatgctgc tgccaatggg acaggggctt cggaaacagc   8340

agacgacgat cttcccagcg tcatgacttg cgccaactac cttaagctcc ctccttattc   8400

tacaaaggta actcgtctct cttttttaa gtctacggtt tctgtgtttg gttggttggg   8460

gtgagcctga acacgagttt gtacctgaaa caggaaatca tgtacaagaa actgctctac   8520

gccatcaacg aagggcaggg gtcgttcgac ctatcctagg catctctctc tgttgtggct   8580

gcggctagaa accaccaacc ctctctcttc tttgtacatt ttatatcgga agactctgat   8640

tttgcacttt gaatgttatt tctgttaaac catgaattat taaaattagg ttcaatattt   8700

ttcatgtgca agtaacatat taatacatgg aggataaaaa taaaatcaaa agacaaactt   8760

gaataatttt ggttgccttt aaaattcgtt tgaaaattcc gaagcaatta tatatagtgt   8820

gaataaaagt cgtcagctga aggaataaag gtacaaaggt acaaaggttt aggtgttgta   8880

tgatccaaaa ttctgttttt ttttaaagac gggctctatc agtcacagca gttgactgta   8940

agatatcaaa ggaataagaa acagttgttc gtttgtagtt ttctggagat tgaacaagag   9000

aactcgtctt cgtttcatca gttttctttt tgataaaagt caattcgaca tagatatctc   9060

tagacacgag aaacaaaagc ataaatagga aaacattaca attataaaag agcgttacga   9120

gtacagagtc caaactaggc acaagaaacc taccatatg                          9159
```

<210> SEQ ID NO 18
<211> LENGTH: 80
<212> TYPE: DNA
<213> ORGANISM: Brassica napus

<400> SEQUENCE: 18

```
tcataaaaga agaatatatt tgtatctttg catagatcat atatatattg taatgactaa   60

ttattttctc gacaaaccat                                                80
```

<210> SEQ ID NO 19
<211> LENGTH: 1888
<212> TYPE: PRT
<213> ORGANISM: Brassica napus

<400> SEQUENCE: 19

Met Glu Thr Arg Ser Arg Lys Arg Ala Glu Ala Thr Ser Ala Ala Pro

-continued

```
1               5                   10                  15

Ser Ser Ser Ser Ser Ser Pro Pro Pro Pro Pro Ser Ala Ser Gly Pro
            20                  25                  30

Thr Thr Arg Ser Lys Arg Ala Arg Leu Ser Ser Ser Ser Ser Ser Ser
        35                  40                  45

Leu Ala Pro Thr Pro Pro Ser Ser Ser Thr Thr Thr Arg Ser Arg Ser
    50                  55                  60

Ser Arg Ser Ala Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
            100                 105                 110

Arg Glu Arg Glu Arg Asp Arg Ala Arg Glu Gln Leu Asn Met Asp Ala
        115                 120                 125

Ala Ala Ala Ala Ala Arg Ser Ala Asp Glu Asp Asp Asp Asn Asp Ser
    130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser Ser His Leu Asn
            180                 185                 190

Gly Arg Met Lys Lys Ile Leu Ser Gly Leu Arg Ala Glu Gly Glu Glu
        195                 200                 205

Gly Lys Gln Val Glu Ala Leu Thr Gln Leu Cys Glu Met Leu Ser Ile
    210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255

Leu Ala Ala Arg Ala Leu Thr His Leu Cys Asp Val Leu Pro Ser Ser
            260                 265                 270

Cys Ala Ala Val Val His Tyr Gly Ala Val Ser Cys Leu Val Ala Arg
        275                 280                 285

Leu Leu Thr Ile Glu Tyr Met Asp Leu Ala Glu Gln Ser Leu Gln Ala
    290                 295                 300

Leu Lys Lys Ile Ser Gln Glu His Pro Thr Ala Cys Leu Arg Ala Gly
305                 310                 315                 320

Ala Leu Met Ala Val Leu Ser Tyr Leu Asp Phe Phe Ser Thr Gly Val
                325                 330                 335

Gln Arg Val Ala Leu Ser Thr Ala Ala Asn Met Cys Lys Lys Leu Pro
            340                 345                 350

Ser Asp Ala Ser Asp Tyr Val Met Glu Ala Val Pro Leu Leu Thr Asn
        355                 360                 365

Leu Leu Gln Tyr His Asp Ser Lys Val Leu Glu Tyr Ala Ser Ile Cys
    370                 375                 380

Leu Thr Arg Ile Ala Glu Ala Phe Ala Pro Tyr Pro Glu Lys Leu Asp
385                 390                 395                 400

Glu Leu Cys Asn His Gly Leu Val Thr Gln Ala Ala Ser Leu Ile Ser
                405                 410                 415

Thr Ser Asn Ser Gly Gly Gly Gln Ala Ser Leu Ser Val Ser Thr Tyr
            420                 425                 430
```

-continued

```
Thr Gly Leu Ile Arg Leu Leu Ser Thr Cys Ala Ser Gly Ser Pro Leu
        435                 440                 445

Gly Phe Arg Thr Leu Leu Leu Leu Gly Ile Ser Ser Ile Leu Lys Asp
    450                 455                 460

Ile Leu Leu Gly Ser Gly Val Ser Ala Asn Ala Ser Val Ser Pro Ala
465                 470                 475                 480

Leu Ser Arg Pro Ala Asp Gln Ile Tyr Glu Ile Val Asn Leu Ala Asn
                485                 490                 495

Glu Leu Leu Pro Pro Leu Pro Glu Gly Val Ile Ser Leu Pro Thr Ser
            500                 505                 510

Thr Asn Ala Leu Val Lys Gly Ser Cys Gln Lys Lys Ser Ser Pro Ser
        515                 520                 525

Thr Ser Gly Lys Gln Glu Asp Ile Leu Lys Ile Ser Pro Arg Glu Lys
    530                 535                 540

Leu Leu Gly Asp Gln Pro Glu Leu Leu Gln Gln Phe Gly Leu Asp Leu
545                 550                 555                 560

Leu Pro Val Leu Val Gln Ile Tyr Gly Ser Ser Val Asn Gly Thr Ile
                565                 570                 575

Arg His Lys Cys Leu Ser Val Ile Gly Lys Leu Met Tyr Phe Ser Ser
            580                 585                 590

Ser Glu Met Ile Gln Ser Leu Ile Gly Asp Thr Asn Ile Ser Ser Phe
        595                 600                 605

Leu Ala Gly Val Leu Ala Trp Lys Asp Pro Gln Val Leu Val Pro Ala
    610                 615                 620

Leu Gln Val Ala Glu Ile Leu Met Glu Lys Leu Pro Glu Thr Phe Ser
625                 630                 635                 640

Lys Val Phe Val Arg Glu Gly Val Val His Ala Val Asp Gln Leu Val
                645                 650                 655

Leu Val Gly Lys Pro Ser His Ala Ser Pro Thr Asp Lys Asp Asn Asp
            660                 665                 670

Cys Val Pro Gly Ser Ala Arg Ser Arg Arg Tyr Arg Arg Arg Ser Ser
        675                 680                 685

Asn Ala Asn Ser Asp Gly Asn Gln Ser Glu Glu Pro Lys Asn Pro Ala
    690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
                725                 730                 735

Asp Lys Tyr Phe Pro Ser Asp Gly Gly Asp Val Asp Val Gly Val Thr
            740                 745                 750

Asp Asp Leu Leu His Leu Lys Asn Leu Cys Thr Lys Leu Thr Ala Gly
        755                 760                 765

Ile Asp Asp His Lys Val Lys Gly Lys Gly Lys Ser Lys Ala Ser Gly
    770                 775                 780

Pro Phe Leu Gly Asp Phe Ser Ala Ser Lys Glu Glu Tyr Leu Ile Gly
785                 790                 795                 800

Val Ile Ser Glu Ile Leu Gly Glu Ile Ser Lys Gly Asp Gly Val Ser
                805                 810                 815

Thr Phe Glu Phe Ile Gly Ser Gly Val Val Ala Ala Leu Leu Asn Tyr
            820                 825                 830

Phe Ser Cys Gly Tyr Phe Ser Lys Glu Lys Ile Ser Glu Leu Asn Leu
        835                 840                 845
```

-continued

```
Pro Lys Leu Arg Gln Glu Gly Leu Arg Arg Phe Lys Ala Phe Leu Glu
    850                 855                 860

Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
                885                 890                 895

Pro Val Val Leu Ser His Pro Ser Arg Ser Leu Ser Gly Ser Ala Arg
            900                 905                 910

Leu Ser Ser Gly Leu Ser Ala Leu Ala His Pro Leu Lys Leu Arg Leu
        915                 920                 925

Cys Arg Ala Ser Gly Glu Lys Thr Leu Arg Asp Tyr Ser Ser Asn Ile
    930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Ala Pro
                965                 970                 975

Ile Gly Asn Thr Glu Pro Gly Thr Leu Pro Ser Gly Ala Gly Val Ser
            980                 985                 990

Ser Pro Ser Ser Ser Thr Pro Ala  Ser Thr Thr Arg Arg  His Ser Ser
        995                 1000                1005

Arg Ser  Arg Ser Ala Ile Asn  Ile Gly Asp Thr Ser  Lys Lys Asp
    1010                1015                1020

Pro Val  His Glu Lys Gly Thr  Ser Ser Ser Lys Gly  Lys Gly Lys
    1025                1030                1035

Gly Val  Met Lys Pro Ala Gln  Ala Asp Lys Gly Pro  Gln Thr Arg
    1040                1045                1050

Ser Asn  Ala Gln Lys Arg Ala  Val Leu Asp Lys Asp  Thr Gln Met
    1055                1060                1065

Lys Pro  Ala Ser Gly Asp Ser  Ser Ser Glu Asp Glu  Glu Leu Glu
    1070                1075                1080

Ile Ser  Pro Val Asp Ile Asp  Asp Ala Leu Val Ile  Glu Glu Asp
    1085                1090                1095

Asp Ile  Ser Asp Asp Glu Asp  Asp Asp Asn Glu Asp  Val Leu Asp
    1100                1105                1110

Asp Ser  Leu Pro Met Cys Thr  Pro Asp Lys Val His  Asp Val Lys
    1115                1120                1125

Leu Ala  Asp Ser Val Asp Asp  Asp Gly Leu Ala Thr  Ser Gly Arg
    1130                1135                1140

Gln Met  Asn Pro Ala Ser Gly  Gly Thr Ser Gly Ala  Ala Ala Ala
    1145                1150                1155

Arg Ala  Ser Asp Ser Ile Asp  Thr Gly Ile Gly Asn  Ser Tyr Gly
    1160                1165                1170

Ser Arg  Gly Ala Leu Ser Phe  Ala Ala Ala Ala Met  Ala Gly Leu
    1175                1180                1185

Gly Ala  Ala Ser Gly Arg Gly  Ile Arg Gly Ser Arg  Asp Leu His
    1190                1195                1200

Gly Arg  Thr Leu Asn Arg Ser  Ser Asp Glu Pro Ser  Lys Leu Ile
    1205                1210                1215

Phe Thr  Ala Ala Gly Lys Gln  Leu Ser Arg His Leu  Thr Ile Tyr
    1220                1225                1230

Gln Ala  Val Gln Arg Gln Leu  Met Leu Asp Glu Asp  Asp Asp Asp
    1235                1240                1245

Arg Phe  Gly Gly Ser Asp Leu  Val Ser Ser Asp Gly  Ser Arg Phe
```

```
    1250                1255                1260

Asn Asp  Ile Tyr Thr Ile Met  Tyr Gln Arg Pro Asp  Ser Gln Val
    1265                1270                1275

Asn Arg  Leu Ser Val Gly Gly  Ala Ser Ser Thr Thr  Pro Ser Lys
    1280                1285                1290

Ser Thr  Lys Ser Ala Thr Thr  Asn Ser Ser Val Glu  Ser Gln Ser
    1295                1300                1305

His Arg  Ala Ser Leu Leu Asp  Ser Ile Leu Gln Gly  Glu Leu Pro
    1310                1315                1320

Cys Asp  Leu Glu Lys Ser Asn  Ser Thr Tyr Asn Val  Leu Ala Leu
    1325                1330                1335

Leu Arg  Val Leu Glu Gly Leu  Asn Gln Leu Cys Pro  Arg Leu Arg
    1340                1345                1350

Ala Gln  Thr Leu Ser Asp Arg  Phe Ala Glu Gly Lys  Ile Thr Ser
    1355                1360                1365

Leu Asp  Asp Leu Ser Thr Thr  Ala Ala Lys Val Pro  Leu Asp Glu
    1370                1375                1380

Phe Val  Asn Ser Lys Leu Thr  Pro Lys Leu Ala Arg  Gln Ile Gln
    1385                1390                1395

Asp Ala  Leu Ala Leu Cys Ser  Gly Ser Leu Pro Ser  Trp Cys Tyr
    1400                1405                1410

Gln Leu  Thr Arg Ala Cys Pro  Phe Leu Phe Pro Phe  Gln Thr Arg
    1415                1420                1425

Arg Gln  Tyr Phe Tyr Ser Thr  Ala Phe Gly Leu Ser  Arg Ala Leu
    1430                1435                1440

Asn Arg  Leu Gln Gln Gln Gln  Gly Ala Asp Gly Ser  Gly Ser Thr
    1445                1450                1455

Asn Glu  Arg Glu Met Arg Ile  Gly Arg Leu Gln Arg  Gln Lys Val
    1460                1465                1470

Arg Val  Ser Arg Asn Arg Ile  Leu Asp Ser Ala Ala  Lys Val Met
    1475                1480                1485

Glu Met  Tyr Ser Ser Gln Lys  Ala Val Leu Glu Val  Glu Tyr Phe
    1490                1495                1500

Gly Glu  Val Gly Thr Gly Leu  Gly Pro Thr Leu Glu  Phe Tyr Thr
    1505                1510                1515

Leu Leu  Ser His Asp Leu Gln  Lys Ala Ser Leu Gly  Met Trp Arg
    1520                1525                1530

Ser Ser  Ser Gly Asp Lys Val  Ser Met Gln Ile Gly  Arg Asp Glu
    1535                1540                1545

Ile Glu  Asp Gly Lys Pro Ser  Ala Ala Asn Arg Asp  Ile Val Leu
    1550                1555                1560

Ala Pro  Leu Gly Leu Phe Pro  Arg Pro Trp Pro Ser  Thr Ala Asp
    1565                1570                1575

Ile Ser  Glu Gly Gly Gln Phe  His Lys Val Ile Glu  Tyr Phe Arg
    1580                1585                1590

Leu Leu  Gly Arg Val Met Ala  Lys Ala Leu Gln Asp  Gly Arg Leu
    1595                1600                1605

Leu Asp  Val Pro Leu Ser Thr  Ala Phe Tyr Lys Leu  Ile Leu Gly
    1610                1615                1620

Gln Glu  Leu Asp Leu His Asp  Ile Val Leu Phe Asp  Ala Glu Leu
    1625                1630                1635

Gly Lys  Thr Leu Gln Glu Leu  Arg Val Val Val Ala  Arg Lys His
    1640                1645                1650
```

Tyr Leu Glu Gly Val Gly Gly Asp Asn Ser Ser Thr Ile Ser Asp
1655 1660 1665

Leu Cys Leu Arg Gly Cys Arg Ile Glu Asp Leu Ser Leu Glu Phe
1670 1675 1680

Thr Leu Pro Gly Tyr Pro Glu Tyr Ile Leu Arg Ser Gly Asp Glu
1685 1690 1695

Ile Val Asp Ile Thr Asn Leu Glu Glu Tyr Ile Ser Leu Val Val
1700 1705 1710

Asp Ala Thr Val Lys Arg Gly Val Thr Arg Gln Ile Glu Ala Phe
1715 1720 1725

Arg Ser Gly Phe Asn Gln Val Phe Asp Ile Thr Ser Leu Gln Ile
1730 1735 1740

Phe Thr Pro Ser Glu Leu Asp Tyr Leu Leu Cys Gly Arg Arg Glu
1745 1750 1755

Leu Trp Glu Val Glu Thr Leu Ala Glu His Ile Lys Phe Asp His
1760 1765 1770

Gly Tyr Asn Ala Lys Ser Pro Ala Ile Ile Asn Leu Leu Glu Ile
1775 1780 1785

Met Gly Glu Leu Thr Ala Asp Gln Gln Arg Ala Phe Cys Gln Phe
1790 1795 1800

Val Thr Gly Ala Pro Arg Leu Pro Pro Gly Gly Leu Ala Val Leu
1805 1810 1815

Asn Pro Lys Leu Thr Ile Val Arg Lys His Ser Ser Thr Ser Ser
1820 1825 1830

Ala Ala Ala Asn Gly Ala Gly Ala Ser Glu Thr Ala Asp Asp Asp
1835 1840 1845

Leu Pro Ser Val Met Thr Cys Ala Asn Tyr Leu Lys Leu Pro Pro
1850 1855 1860

Tyr Ser Thr Lys Glu Ile Met Tyr Lys Lys Leu Leu Tyr Ala Ile
1865 1870 1875

Asn Glu Gly Gln Gly Ser Phe Asp Leu Ser
1880 1885

<210> SEQ ID NO 20
<211> LENGTH: 1955
<212> TYPE: DNA
<213> ORGANISM: Brassica napus

<400> SEQUENCE: 20
agagaggcct ggacgtttgg gtcatcgctc tcggtcggtt cctacttttt ctgcaccacc 60
gccatttgtt gatccagaaa tatttacggc tcagttgaag gacaaggatg atcgcatatc 120
tttgttggag acccagaaga cggctcaaca ggcgggctat gaggcacaga agaggctgaa 180
ccagcaaatg atgaaaagga tgtacccgaa cgaggtgttc ccgaacgtgc aagacccgta 240
gttttttttt tcaaaaactc ggaatgtttt atttttattt gtacaacttt gaatattatc 300
taatatgttt tcaattttaa ttttaatttt atattttcga atttaaattt caaaattttc 360
atttttaaaa aaaaattaat tttttttttg aaattccgag gaaatgaacc ctcggaaatt 420
tccgacgaac atttcctcag aataagtcgt cggaatatac cgagggactc cttcctcctc 480
ggaattttct gagggctccg tttctcggaa attcccgatg aaaattccga ggaacatttc 540
atcggaactt ccgaggattg gaccatcgga aagtccatcg aaatattccg aagaagttct 600
ccctcgatat attccgagaa cctttccgac gaactggtgg tcctcggagt ttcctcggaa 660

```
attcatttcc tcggaattcc ttcggaaatt tctgagggat ttccgagaaa aaatgaattt    720

ccgaggagtt atttccgagg acttgtttcg tcggtatgtc gtcggaataa cgttatccga    780

cgacgtaccg acgatttttt ccctcggtat gttcatattg gatttataaa tgaatcataa    840

tttctgtttt tcgggttaaa ttaatatgta tatatatata tatatattaa aaaaatctgt    900

aagttccaaa caagggcaca cttataaaag aactaatgta ttatatactg tcatgttttt    960

tttataaaat atgtacaata atttatatat gtcttcatcc gattaacaaa ctcaaaccca   1020

aacaacaaaa atttctacat ttagatttta aattagcgtg tgatggctaa agaaaaaaag   1080

aagaataaat ttgtatcttt gcatagatca cctgcatttc attgagtaga ttcatttaaa   1140

taagtagata gatagatttt attatcatat ttattttctt aacaaaccat cataaaagaa   1200

gaatatattt gtatctttgc atagatcata tatataattg taatgactaa ttattttctc   1260

gacaaaccat agtttttcct tactacaatc ataaaagaag aatatatttg tatctttgca   1320

tagatcatat atataattgt aatgagtaat gtgttatata gtccatggat cgtagtgaga   1380

aggtagagtt gaaagtataa gaaagcgaac ctccatcata gtgggggctt aaacccgtgc   1440

aagcttgcag atatctatgg ctgatggttg ggcccagcct tatatcttgg gcttattttg   1500

tttccatctg tccagcccat gataaagtgt aaaacgacac cgtattaagc ttaatggagt   1560

aaacgaatca cacgtagcgg ggatccccgt gtcagttctt gtcggaaaag ctggacggag   1620

gaaaacggta tcgtattcgc ttcgcttgaa tctatatatt ttgcgcaaaa gccctttca   1680

tccctttctt ctctcattac tcgatttagg gttttctaat ctcgaaagaa atcaagatcc   1740

tccttccttc ctctctcgat ttcgatctcg tagccccttt tgcgttgatt tcgaattcgt   1800

tcatcaacag gtttgtttct ctctagctcc taacgatctc gctagcaaat tagggtttcg   1860

agcgagctta atccgatcgg tttctggatc agttgagatg cgatcggaat ctctctgaat   1920

aagagagact cgtgtggagg ggtttcttcc tttgt                              1955


<210> SEQ ID NO 21
<211> LENGTH: 1888
<212> TYPE: PRT
<213> ORGANISM: Brassica napus

<400> SEQUENCE: 21

Met Glu Thr Arg Ser Arg Lys Arg Ala Glu Ala Thr Ser Thr Ala Pro
1               5                   10                  15

Ser Ser Ser Ser Ser Ser Pro Pro Pro Pro Pro Ser Ser Gly Pro Thr
            20                  25                  30

Thr Arg Ser Lys Arg Ala Arg Leu Ser Ser Pro Ser Ser Ser Ser Ala
        35                  40                  45

Ala Ala Thr Ala Pro Ser Ser Ser Thr Arg Ser Arg Ser Ser Arg Ser
    50                  55                  60

Thr Thr Ala Thr Ala Ala Val Thr Pro Met Asp Thr Ser Thr Glu Ser
65                  70                  75                  80

Ser Gly Phe Arg Arg Gly Gly Gly Arg Gly Asn Arg Gly Asn Asp Asn
                85                  90                  95

Thr Asn Ser Asp Lys Gly Lys Glu Lys Glu His Glu Val Arg Ile Arg
            100                 105                 110

Asp Arg Glu Arg Asp Arg Ala Arg Gln Gln Leu Asn Met Asp Ala Ala
        115                 120                 125

Ala Ala Ala Ala Ala Ala Ala Asp Glu Asp Asp Asp Asn Asp Ser Glu
    130                 135                 140
```

-continued

```
Asp Gly Asn Gly Gly Phe Met His Pro Asn Met Ser Ser Ala Ser Ser
145                 150                 155                 160

Ala Leu Gln Gly Leu Leu Arg Lys Leu Gly Ala Gly Leu Asp Asp Leu
                165                 170                 175

Leu Pro Ser Ser Gly Ile Gly Ser Gly Ser Ser Ser His Leu Asn Gly
            180                 185                 190

Arg Met Lys Lys Val Leu Ala Gly Leu Arg Ser Glu Gly Glu Glu Gly
        195                 200                 205

Lys Gln Val Glu Ala Leu Thr Gln Leu Cys Glu Met Leu Ser Ile Gly
    210                 215                 220

Thr Glu Asp Ser Leu Ser Thr Phe Ser Val Asp Ser Phe Val Pro Val
225                 230                 235                 240

Leu Val Gly Leu Leu Asn His Glu Ser Asn Pro Asp Ile Met Leu Leu
                245                 250                 255

Ala Ala Arg Ala Leu Thr His Leu Cys Asp Val Leu Pro Ser Ser Cys
            260                 265                 270

Ala Ala Val Val His Tyr Gly Ala Val Ser Cys Phe Val Ala Arg Leu
        275                 280                 285

Leu Thr Ile Glu Tyr Met Asp Leu Ala Glu Gln Ser Leu Gln Ala Leu
    290                 295                 300

Lys Lys Ile Ser Gln Glu His Pro Thr Ala Cys Leu Arg Ala Gly Ala
305                 310                 315                 320

Leu Met Ala Val Leu Ser Tyr Leu Asp Phe Phe Ser Thr Gly Val Gln
                325                 330                 335

Arg Val Ala Val Ser Thr Ala Ala Asn Met Cys Lys Lys Leu Pro Ser
            340                 345                 350

Asp Ala Ser Asp Tyr Val Met Glu Ala Val Pro Val Leu Thr Asn Leu
        355                 360                 365

Leu Gln Tyr His Asp Ala Lys Val Leu Glu Tyr Ala Ser Ile Cys Leu
    370                 375                 380

Thr Arg Ile Ala Glu Ala Phe Ala Ser Ser Pro Asp Lys Leu Asp Glu
385                 390                 395                 400

Leu Cys Asn His Gly Leu Val Thr Gln Ala Ala Thr Leu Ile Ser Ala
                405                 410                 415

Ser Asn Ser Gly Gly Gly Gln Ala Ser Leu Gly Val Ser Thr Tyr Thr
            420                 425                 430

Gly Leu Ile Arg Leu Leu Ser Thr Cys Ala Ser Gly Ser Pro Leu Gly
        435                 440                 445

Cys Arg Thr Leu Leu Leu Leu Gly Ile Ser Ser Ile Leu Lys Asp Ile
    450                 455                 460

Leu Ser Gly Ser Gly Val Ser Ala Asn Ala Ser Ile Ser Pro Ala Leu
465                 470                 475                 480

Ser Arg Pro Ala Asp Gln Ile Phe Glu Ile Val Asn Leu Ala Asn Glu
                485                 490                 495

Leu Leu Pro Pro Leu Pro Glu Gly Ser Ile Ser Leu Pro Thr Ser Ala
            500                 505                 510

Asn Ala Leu Val Lys Gly Ser Gly Gln Lys Lys Ser Ser Pro Ser Thr
        515                 520                 525

Ser Gly Lys Gln Glu Asp Ser Pro Lys Val Ser Pro Arg Glu Lys Leu
    530                 535                 540

Leu Ser Asp Gln Pro Glu Leu Leu Gln Gln Phe Gly Leu Asp Leu Leu
545                 550                 555                 560

Pro Val Leu Val Gln Ile Tyr Gly Ser Ser Val Asn Gly Thr Ile Arg
```

```
                565                 570                 575

His Lys Cys Leu Ser Val Ile Ala Lys Leu Met Tyr Phe Ser Thr Pro
            580                 585                 590

Glu Met Ile Gln Ser Leu Ile Gly Asp Thr Asn Ile Ser Ser Phe Leu
        595                 600                 605

Ala Ser Val Leu Ala Trp Lys Asp Pro Gln Val Leu Val Pro Ala Leu
    610                 615                 620

Gln Val Ala Glu Ile Leu Met Glu Lys Leu Pro Glu Thr Phe Ser Lys
625                 630                 635                 640

Val Phe Val Arg Glu Gly Val Val His Ala Val Asp Gln Leu Val Leu
                645                 650                 655

Val Gly Lys Pro Ser Ser His Ala Ser Thr Asp Gln Glu Asn Asp Cys
            660                 665                 670

Val Pro Gly Ser Ala Arg Ser Arg Arg Tyr Arg Arg Arg Ser Ser Asn
        675                 680                 685

Ala Asn Ser Asp Gly Asn Gln Ser Glu Glu Leu Lys Asn Ser Val Ser
    690                 695                 700

Ala Ser Ile Gly Ala Asn His Asn Ser Met Glu Ser Pro Thr Ala Ser
705                 710                 715                 720

Phe Met Leu Arg Glu Thr Val Ser Ser Cys Ala Lys Ala Phe Lys Asp
                725                 730                 735

Lys His Phe Pro Ser Asp Gly Gly Glu Phe Asp Val Gly Val Thr Asp
            740                 745                 750

Asp Leu Leu His Leu Lys Asn Leu Cys Thr Lys Leu Thr Ala Gly Thr
        755                 760                 765

Asn Asp His Lys Val Lys Gly Lys Gly Lys Ser Lys Ala Ser Gly Pro
    770                 775                 780

Cys Leu Gly Asp Phe Ser Ala Ser Lys Glu Glu Tyr Leu Ile Gly Ile
785                 790                 795                 800

Ile Ser Glu Ile Leu Gly Glu Leu Ser Lys Gly Asp Gly Val Ser Thr
                805                 810                 815

Phe Glu Phe Ile Gly Ser Gly Val Val Ala Ala Leu Leu Asn Tyr Phe
            820                 825                 830

Ser Tyr Gly Tyr Phe Ser Lys Glu Lys Ile Ser Glu Val Asp Leu Pro
        835                 840                 845

Lys Leu Arg Gln Asp Gly Leu Arg Arg Phe Thr Ala Phe Leu Glu Ile
    850                 855                 860

Ala Leu Pro Ser Asp Gly Asn Glu Gly Lys Ile Pro Pro Met Thr Val
865                 870                 875                 880

Leu Ile Gln Lys Leu Gln Asp Ala Leu Ser Ser Leu Glu Arg Phe Pro
                885                 890                 895

Val Val Leu Ser His Pro Ser Lys Ser Leu Ser Gly Ser Ala Arg Leu
            900                 905                 910

Ser Ser Gly Leu Ser Ala Leu Ala His Pro Leu Lys Leu Arg Leu Cys
        915                 920                 925

Arg Ala Pro Gly Glu Lys Ala Leu Arg Asp Tyr Ser Ser Asn Ile Val
    930                 935                 940

Leu Ile Asp Pro Leu Ala Ser Ile Ala Ala Val Glu Glu Phe Leu Trp
945                 950                 955                 960

Pro Arg Val Gln Arg Ser Glu Ser Gly Val Lys Pro Ala Ala Pro Val
                965                 970                 975

Gly Asn Thr Glu Pro Gly Thr Leu Pro Ser Gly Ala Gly Val Ser Ser
            980                 985                 990
```

```
Pro Ser Ser Ser Thr Pro Ala Ser  Thr Thr Arg His Ser  Ser Arg Ser
        995                 1000                 1005

Arg Ser  Ala Ile Lys Ile Gly  Asp Ala Ser Lys Lys  Glu Pro Val
    1010                 1015                 1020

His Glu  Lys Gly Thr Ser Ser  Ser Lys Gly Lys Gly  Val Met Lys
    1025                 1030                 1035

Pro Ala  Gln Pro Asp Lys Gly  Pro Gln Thr Arg Ser  Ser Ala Gln
    1040                 1045                 1050

Arg Lys  Ala Val Leu Asp Lys  Asp Thr Leu Met Lys  Pro Ala Ser
    1055                 1060                 1065

Gly Asp  Ser Ser Ser Glu Asp  Glu Glu Met Asp Ile  Ser Pro Val
    1070                 1075                 1080

Asp Met  Asp Asp Ala Leu Val  Ile Glu Glu Glu Asp  Ile Ser Asp
    1085                 1090                 1095

Asp Asp  Glu Asp Asp Asp Asp  Glu Asp Val Leu Asp  Asp Asn Leu
    1100                 1105                 1110

Pro Met  Cys Thr Pro Asp Lys  Val His Asp Val Lys  Leu Gly Asp
    1115                 1120                 1125

Ala Val  Asp Asp Glu Gly Ala  Gly Leu Ala Pro Ser  Gly Arg Gln
    1130                 1135                 1140

Met Asn  Ser Ala Leu Ala Gly  Ser Ser Gly Thr Ala  Thr Ala Arg
    1145                 1150                 1155

Gly Ser  Asn Ser Thr Asp Ala  Gly Ile Gly Asn Leu  Tyr Gly Ser
    1160                 1165                 1170

Arg Gly  Ala Leu Ser Phe Ala  Ala Ala Ala Met Ala  Gly Leu Gly
    1175                 1180                 1185

Ala Ala  Ser Gly Arg Gly Ile  Arg Gly Ser Arg Asp  Leu His Gly
    1190                 1195                 1200

Arg Thr  Leu Asn Arg Ser Ser  Asp Glu Ser Ser Lys  Leu Met Phe
    1205                 1210                 1215

Thr Ala  Gly Gly Lys Gln Leu  Ser Arg His Met Thr  Ile Tyr Gln
    1220                 1225                 1230

Ala Val  Gln Arg Gln Leu Met  Leu Asp Glu Asp Asp  Asp Asp Arg
    1235                 1240                 1245

Leu Gly  Gly Ser Asp Phe Ile  Ser Ser Asp Gly Ser  Arg Leu Asn
    1250                 1255                 1260

Asp Ile  Tyr Thr Ile Met Tyr  Gln Met Pro Asp Ser  Gln Ala Asn
    1265                 1270                 1275

Arg Leu  Ser Ala Gly Gly Ala  Ser Ser Thr Thr Pro  Ser Lys Ser
    1280                 1285                 1290

Thr Lys  Ser Ala Thr Thr Asn  Ala Ser Val Glu Ala  Gln Ser Tyr
    1295                 1300                 1305

Arg Ala  Ser Leu Leu Asp Ser  Ile Val Gln Gly Lys  Leu Pro Cys
    1310                 1315                 1320

Asp Leu  Glu Lys Ser Asn Ser  Thr Tyr Asn Val Leu  Ala Leu Leu
    1325                 1330                 1335

Arg Val  Leu Glu Gly Leu Asn  Gln Leu Gly Pro Arg  Leu Arg Ala
    1340                 1345                 1350

Gln Thr  Val Ser Asp Arg Phe  Ala Glu Gly Lys Ile  Thr Ser Leu
    1355                 1360                 1365

Asp Asp  Leu Asn Thr Thr Ala  Ala Lys Val Ser His  Glu Glu Phe
    1370                 1375                 1380
```

-continued

```
Ile Asn Ser Lys Leu Thr Pro Lys Leu Ala Arg Gln Ile Gln Asp
    1385                1390                1395

Ala Leu Ala Leu Cys Ser Gly Ser Leu Pro Ser Trp Cys Tyr Gln
    1400                1405                1410

Leu Thr Thr Ala Cys Pro Phe Leu Phe Pro Phe Gln Thr Arg Arg
    1415                1420                1425

Gln Tyr Phe Tyr Ser Thr Ala Phe Gly Leu Ser Arg Ala Leu Asn
    1430                1435                1440

Arg Leu Gln Gln Gln Gln Gly Ala Asp Gly Ser Gly Ser Thr Asn
    1445                1450                1455

Glu Arg Glu Met Arg Ile Gly Arg Leu Gln Arg Gln Lys Val Arg
    1460                1465                1470

Val Ser Arg Asn Arg Ile Leu Asp Ser Ala Ala Lys Val Met Glu
    1475                1480                1485

Met Tyr Ser Ser Gln Lys Ala Val Leu Glu Val Glu Tyr Phe Gly
    1490                1495                1500

Glu Val Gly Thr Gly Leu Gly Pro Thr Leu Glu Phe Tyr Thr Leu
    1505                1510                1515

Leu Ser His Asp Leu Gln Lys Val Ser Leu Gly Met Trp Arg Ser
    1520                1525                1530

Asn Ser Gly Asp Lys Leu Ser Met Gln Thr Asp Arg Asp Glu Ile
    1535                1540                1545

Gln Asp Gly Lys Ser Ala Ala Ala Arg Asp Arg Asp Ile Val Gln
    1550                1555                1560

Ala Pro Leu Gly Leu Phe Pro Arg Pro Trp Pro Ser Thr Ala Asp
    1565                1570                1575

Val Ser Glu Gly Ser Arg Phe His Lys Val Val Glu Tyr Phe Arg
    1580                1585                1590

Leu Leu Gly Arg Val Met Ala Lys Ala Leu Gln Asp Gly Arg Leu
    1595                1600                1605

Met Asp Val Pro Leu Ser Thr Ala Phe Tyr Lys Leu Ile Leu Gly
    1610                1615                1620

Gln Glu Leu Asp Leu His Asp Val Ile Leu Phe Asp Ala Glu Leu
    1625                1630                1635

Gly Lys Thr Leu Gln Glu Leu Arg Val Leu Val Gly Arg Lys His
    1640                1645                1650

Tyr Leu Glu Ala Gly Gly Gly Asp Asn Ser Ser Gly Ile Ser Asp
    1655                1660                1665

Leu Cys Leu Arg Gly Ser Arg Ile Glu Asp Leu Cys Leu Asp Phe
    1670                1675                1680

Thr Leu Pro Gly Tyr Pro Glu Tyr Ile Leu Arg Pro Gly Asp Asp
    1685                1690                1695

Ile Val Asp Ile Asn Ser Leu Glu Asp Tyr Ile Ser Leu Val Val
    1700                1705                1710

Asp Ala Thr Val Lys Arg Gly Val Ala Arg Gln Ile Glu Ala Phe
    1715                1720                1725

Arg Ser Gly Phe Asn Gln Val Phe Asp Ile Lys Ser Leu Gln Ile
    1730                1735                1740

Phe Thr Pro Ser Glu Leu Asp Tyr Leu Leu Cys Gly Arg Arg Glu
    1745                1750                1755

Leu Trp Glu Ala Glu Thr Leu Val Glu His Ile Lys Phe Asp His
    1760                1765                1770

Gly Tyr Thr Ala Lys Ser Pro Ala Ile Ile Phe Leu Leu Glu Ile
```

```
    1775                1780                1785

Met Gly  Glu Leu Thr Ala Asp  Gln Gln Arg Ala Phe  Cys Gln Phe
    1790                1795                1800

Val Thr  Gly Ala Pro Arg Leu  Pro Pro Gly Gly Leu  Ala Val Leu
    1805                1810                1815

Asn Pro  Arg Leu Thr Ile Val  Arg Lys Leu Ser Ser  Thr Ser Asn
    1820                1825                1830

Ala Ala  Ala Asn Gly Thr Gly  Ala Ser Glu Thr Ala  Asp Asp Asp
    1835                1840                1845

Leu Pro  Ser Val Met Thr Cys  Ala Asn Tyr Leu Lys  Leu Pro Pro
    1850                1855                1860

Tyr Ser  Thr Lys Glu Ile Met  Tyr Lys Lys Leu Leu  Tyr Ala Ile
    1865                1870                1875

Asn Glu  Gly Gln Gly Ser Phe  Asp Leu Ser
    1880                1885


<210> SEQ ID NO 22
<211> LENGTH: 1888
<212> TYPE: PRT
<213> ORGANISM: Brassica napus

<400> SEQUENCE: 22

Met Glu Thr Arg Ser Arg Lys Arg Ala Glu Ala Thr Ser Ala Ala Pro
1               5                   10                  15

Ser Ser Ser Ser Ser Ser Pro Pro Pro Pro Pro Ser Ala Ser Gly Pro
            20                  25                  30

Thr Thr Arg Ser Lys Arg Ala Arg Leu Ser Ser Ser Ser Ser Ser Ser
        35                  40                  45

Leu Ala Pro Thr Pro Pro Ser Ser Ser Thr Thr Thr Arg Ser Arg Ser
    50                  55                  60

Ser Arg Ser Ala Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
            100                 105                 110

Arg Glu Arg Glu Arg Asp Arg Ala Arg Glu Gln Leu Asn Met Asp Ala
        115                 120                 125

Ala Ala Ala Ala Ala Arg Ser Ala Asp Glu Asp Asp Asp Asn Asp Ser
    130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser Ser His Leu Asn
            180                 185                 190

Gly Arg Met Lys Lys Ile Leu Ser Gly Leu Arg Ala Glu Gly Glu Glu
        195                 200                 205

Gly Lys Gln Val Glu Ala Leu Thr Gln Leu Cys Glu Met Leu Ser Ile
    210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255
```

-continued

```
Leu Ala Ala Arg Ala Leu Thr His Leu Cys Asp Val Leu Pro Ser Ser
            260                 265                 270

Cys Ala Ala Val Val His Tyr Gly Ala Val Ser Cys Leu Val Ala Arg
        275                 280                 285

Leu Leu Thr Ile Glu Tyr Met Asp Leu Ala Glu Gln Ser Leu Gln Ala
    290                 295                 300

Leu Lys Lys Ile Ser Gln Glu His Pro Thr Ala Cys Leu Arg Ala Gly
305                 310                 315                 320

Ala Leu Met Ala Val Leu Ser Tyr Leu Asp Phe Phe Ser Thr Gly Val
                325                 330                 335

Gln Arg Val Ala Leu Ser Thr Ala Ala Asn Met Cys Lys Lys Leu Pro
            340                 345                 350

Ser Asp Ala Ser Asp Tyr Val Met Glu Ala Val Pro Leu Leu Thr Asn
        355                 360                 365

Leu Leu Gln Tyr His Asp Ser Lys Val Leu Glu Tyr Ala Ser Ile Cys
    370                 375                 380

Leu Thr Arg Ile Ala Glu Ala Phe Ala Pro Tyr Pro Glu Lys Leu Asp
385                 390                 395                 400

Glu Leu Cys Asn His Gly Leu Val Thr Gln Ala Ala Ser Leu Ile Ser
                405                 410                 415

Thr Ser Asn Ser Gly Gly Gly Gln Ala Ser Leu Ser Val Ser Thr Tyr
            420                 425                 430

Thr Gly Leu Ile Arg Leu Leu Ser Thr Cys Ala Ser Gly Ser Pro Leu
        435                 440                 445

Gly Phe Arg Thr Leu Leu Leu Leu Gly Ile Ser Ser Ile Leu Lys Asp
    450                 455                 460

Ile Leu Leu Gly Ser Gly Val Ser Ala Asn Ala Ser Val Ser Pro Ala
465                 470                 475                 480

Leu Ser Arg Pro Ala Asp Gln Ile Tyr Glu Ile Val Asn Leu Ala Asn
                485                 490                 495

Glu Leu Leu Pro Pro Leu Pro Glu Gly Val Ile Ser Leu Pro Thr Ser
            500                 505                 510

Thr Asn Ala Leu Val Lys Gly Ser Cys Gln Lys Lys Ser Ser Pro Ser
        515                 520                 525

Thr Ser Gly Lys Gln Glu Asp Ile Leu Lys Ile Ser Pro Arg Glu Lys
    530                 535                 540

Leu Leu Gly Asp Gln Pro Glu Leu Leu Gln Gln Phe Gly Leu Asp Leu
545                 550                 555                 560

Leu Pro Val Leu Val Gln Ile Tyr Gly Ser Ser Val Asn Gly Thr Ile
                565                 570                 575

Arg His Lys Cys Leu Ser Val Ile Gly Lys Leu Met Tyr Phe Ser Ser
            580                 585                 590

Ser Glu Met Ile Gln Ser Leu Ile Gly Asp Thr Asn Ile Ser Ser Phe
        595                 600                 605

Leu Ala Gly Val Leu Ala Trp Lys Asp Pro Gln Val Leu Val Pro Ala
    610                 615                 620

Leu Gln Val Ala Glu Ile Leu Met Glu Lys Leu Pro Glu Thr Phe Ser
625                 630                 635                 640

Lys Val Phe Val Arg Glu Gly Val Val His Ala Val Asp Gln Leu Val
                645                 650                 655

Leu Val Gly Lys Pro Ser His Ala Ser Pro Thr Asp Lys Asp Asn Asp
            660                 665                 670

Cys Val Pro Gly Ser Ala Arg Ser Arg Arg Tyr Arg Arg Arg Ser Ser
```

-continued

```
        675                 680                 685

Asn Ala Asn Ser Asp Gly Asn Gln Ser Glu Glu Pro Lys Asn Pro Ala
    690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
                725                 730                 735

Asp Lys Tyr Phe Pro Ser Asp Gly Gly Asp Val Asp Val Gly Val Thr
            740                 745                 750

Asp Asp Leu Leu His Leu Lys Asn Leu Cys Thr Lys Leu Thr Ala Gly
        755                 760                 765

Ile Asp Asp His Lys Val Lys Gly Lys Gly Lys Ser Lys Ala Ser Gly
    770                 775                 780

Pro Phe Leu Gly Asp Phe Ser Ala Ser Lys Glu Glu Tyr Leu Ile Gly
785                 790                 795                 800

Val Ile Ser Glu Ile Leu Gly Glu Ile Ser Lys Gly Asp Gly Val Ser
                805                 810                 815

Thr Phe Glu Phe Ile Gly Ser Gly Val Val Ala Ala Leu Leu Asn Tyr
            820                 825                 830

Phe Ser Cys Gly Tyr Phe Ser Lys Glu Lys Ile Ser Glu Leu Asn Leu
        835                 840                 845

Pro Lys Leu Arg Gln Glu Gly Leu Arg Arg Phe Lys Ala Phe Leu Glu
    850                 855                 860

Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
                885                 890                 895

Pro Val Val Leu Ser His Pro Ser Arg Ser Leu Ser Gly Ser Ala Arg
            900                 905                 910

Leu Ser Ser Gly Leu Ser Ala Leu Ala His Pro Leu Lys Leu Arg Leu
        915                 920                 925

Cys Arg Ala Ser Gly Glu Lys Thr Leu Arg Asp Tyr Ser Ser Asn Ile
    930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Ala Pro
                965                 970                 975

Ile Gly Asn Thr Glu Pro Gly Thr Leu Pro Ser Gly Ala Gly Val Ser
            980                 985                 990

Ser Pro Ser Ser Ser Thr Pro Ala  Ser Thr Thr Arg Arg  His Ser Ser
        995                 1000                 1005

Arg Ser  Arg Ser Ala Ile Asn  Ile Gly Asp Thr Ser  Lys Lys Asp
    1010                 1015                 1020

Pro Val  His Glu Lys Gly Thr  Ser Ser Ser Lys Gly  Lys Gly Lys
    1025                 1030                 1035

Gly Val  Met Lys Pro Ala Gln  Ala Asp Lys Gly Pro  Gln Thr Arg
    1040                 1045                 1050

Ser Asn  Ala Gln Lys Arg Ala  Val Leu Asp Lys Asp  Thr Gln Met
    1055                 1060                 1065

Lys Pro  Ala Ser Gly Asp Ser  Ser Ser Glu Asp Glu  Glu Leu Glu
    1070                 1075                 1080

Ile Ser  Pro Val Asp Ile Asp  Asp Ala Leu Val Ile  Glu Glu Asp
    1085                 1090                 1095
```

```
Asp Ile  Ser Asp Asp Glu Asp  Asp Asp Asn Glu Asp  Val Leu Asp
    1100                 1105                 1110

Asp Ser  Leu Pro Met Cys Thr  Pro Asp Lys Val His  Asp Val Lys
    1115                 1120                 1125

Leu Ala  Asp Ser Val Asp Asp  Asp Gly Leu Ala Thr  Ser Gly Arg
    1130                 1135                 1140

Gln Met  Asn Pro Ala Ser Gly  Gly Thr Ser Gly Ala  Ala Ala Ala
    1145                 1150                 1155

Arg Ala  Ser Asp Ser Ile Asp  Thr Gly Ile Gly Asn  Ser Tyr Gly
    1160                 1165                 1170

Ser Arg  Gly Ala Leu Ser Phe  Ala Ala Ala Ala Met  Ala Gly Leu
    1175                 1180                 1185

Gly Ala  Ala Ser Gly Arg Gly  Ile Arg Gly Ser Arg  Asp Leu His
    1190                 1195                 1200

Gly Arg  Thr Leu Asn Arg Ser  Ser Asp Glu Pro Ser  Lys Leu Ile
    1205                 1210                 1215

Phe Thr  Ala Ala Gly Lys Gln  Leu Ser Arg His Leu  Thr Ile Tyr
    1220                 1225                 1230

Gln Ala  Val Gln Arg Gln Leu  Met Leu Asp Glu Asp  Asp Asp Asp
    1235                 1240                 1245

Arg Phe  Gly Gly Ser Asp Leu  Val Ser Ser Asp Gly  Ser Arg Phe
    1250                 1255                 1260

Asn Asp  Ile Tyr Thr Ile Met  Tyr Gln Arg Pro Asp  Ser Gln Val
    1265                 1270                 1275

Asn Arg  Leu Ser Val Gly Gly  Ala Ser Ser Thr Thr  Pro Ser Lys
    1280                 1285                 1290

Ser Thr  Lys Ser Ala Thr Thr  Asn Ser Ser Val Glu  Ser Gln Ser
    1295                 1300                 1305

His Arg  Ala Ser Leu Leu Asp  Ser Ile Leu Gln Gly  Glu Leu Pro
    1310                 1315                 1320

Cys Asp  Leu Glu Lys Ser Asn  Ser Thr Tyr Asn Val  Leu Ala Leu
    1325                 1330                 1335

Leu Arg  Val Leu Glu Gly Leu  Asn Gln Leu Cys Pro  Arg Leu Arg
    1340                 1345                 1350

Ala Gln  Thr Leu Ser Asp Arg  Phe Ala Glu Gly Lys  Ile Thr Ser
    1355                 1360                 1365

Leu Asp  Asp Leu Ser Thr Thr  Ala Ala Lys Val Pro  Leu Asp Glu
    1370                 1375                 1380

Phe Val  Asn Ser Lys Leu Thr  Pro Lys Leu Ala Arg  Gln Ile Gln
    1385                 1390                 1395

Asp Ala  Leu Ala Leu Cys Ser  Gly Ser Leu Pro Ser  Trp Cys Tyr
    1400                 1405                 1410

Gln Leu  Thr Arg Ala Cys Pro  Phe Leu Phe Pro Phe  Gln Thr Arg
    1415                 1420                 1425

Arg Gln  Tyr Phe Tyr Ser Thr  Ala Phe Gly Leu Ser  Arg Ala Leu
    1430                 1435                 1440

Asn Arg  Leu Gln Gln Gln Gln  Gly Ala Asp Gly Ser  Gly Ser Thr
    1445                 1450                 1455

Asn Glu  Arg Glu Met Arg Ile  Gly Arg Leu Gln Arg  Gln Lys Val
    1460                 1465                 1470

Arg Val  Ser Arg Asn Arg Ile  Leu Asp Ser Ala Ala  Lys Val Met
    1475                 1480                 1485
```

```
Glu Met  Tyr Ser Ser Gln Lys  Ala Val Leu Glu Val  Glu Tyr Phe
    1490                 1495                 1500

Gly Glu  Val Gly Thr Gly Leu  Gly Pro Thr Leu Glu  Phe Tyr Thr
    1505                 1510                 1515

Leu Leu  Ser His Asp Leu Gln  Lys Ala Ser Leu Gly  Met Trp Arg
    1520                 1525                 1530

Ser Ser  Ser Gly Asp Lys Val  Ser Met Gln Ile Gly  Arg Asp Glu
    1535                 1540                 1545

Ile Glu  Asp Gly Lys Pro Ser  Ala Ala Asn Arg Asp  Ile Val Leu
    1550                 1555                 1560

Ala Pro  Leu Gly Leu Phe Pro  Arg Pro Trp Pro Ser  Thr Ala Asp
    1565                 1570                 1575

Ile Ser  Glu Gly Gly Gln Phe  His Lys Val Ile Glu  Tyr Phe Arg
    1580                 1585                 1590

Leu Leu  Gly Arg Val Met Ala  Lys Ala Leu Gln Asp  Gly Arg Leu
    1595                 1600                 1605

Leu Asp  Val Pro Leu Ser Thr  Ala Phe Tyr Lys Leu  Ile Leu Gly
    1610                 1615                 1620

Gln Glu  Leu Asp Leu His Asp  Ile Val Leu Phe Asp  Ala Glu Leu
    1625                 1630                 1635

Gly Lys  Thr Leu Gln Glu Leu  Arg Val Val Val Ala  Arg Lys His
    1640                 1645                 1650

Tyr Leu  Glu Gly Val Gly Gly  Asp Asn Ser Ser Thr  Ile Ser Asp
    1655                 1660                 1665

Leu Cys  Leu Arg Gly Cys Arg  Ile Glu Asp Leu Ser  Leu Glu Phe
    1670                 1675                 1680

Thr Leu  Pro Gly Tyr Pro Glu  Tyr Ile Leu Arg Ser  Gly Asp Glu
    1685                 1690                 1695

Ile Val  Asp Ile Thr Asn Leu  Glu Glu Tyr Ile Ser  Leu Val Val
    1700                 1705                 1710

Asp Ala  Thr Val Lys Arg Gly  Val Thr Arg Gln Ile  Glu Ala Phe
    1715                 1720                 1725

Arg Ser  Gly Phe Asn Gln Val  Phe Asp Ile Thr Ser  Leu Gln Ile
    1730                 1735                 1740

Phe Thr  Pro Ser Glu Leu Asp  Tyr Leu Leu Cys Gly  Arg Arg Glu
    1745                 1750                 1755

Leu Trp  Glu Val Glu Thr Leu  Ala Glu His Ile Lys  Phe Asp His
    1760                 1765                 1770

Gly Tyr  Asn Ala Lys Ser Pro  Ala Ile Ile Asn Leu  Leu Glu Ile
    1775                 1780                 1785

Met Gly  Glu Leu Thr Ala Asp  Gln Gln Arg Ala Phe  Cys Gln Phe
    1790                 1795                 1800

Val Thr  Gly Ala Pro Arg Leu  Pro Pro Gly Gly Leu  Ala Val Leu
    1805                 1810                 1815

Asn Pro  Lys Leu Thr Ile Val  Arg Lys His Ser Ser  Thr Ser Ser
    1820                 1825                 1830

Ala Ala  Ala Asn Gly Ala Gly  Ala Ser Glu Thr Ala  Asp Asp Asp
    1835                 1840                 1845

Leu Pro  Ser Val Met Thr Cys  Ala Asn Tyr Leu Lys  Leu Pro Pro
    1850                 1855                 1860

Tyr Ser  Thr Lys Glu Ile Met  Tyr Lys Lys Leu Leu  Tyr Ala Ile
    1865                 1870                 1875

Asn Glu  Gly Gln Gly Ser Phe  Asp Leu Ser
```

```
    1880                1885


<210> SEQ ID NO 23
<211> LENGTH: 349
<212> TYPE: PRT
<213> ORGANISM: Brassica napus

<400> SEQUENCE: 23

Met Asp Asn Phe Leu Pro Phe Ser Ser Ser Asn Ala Asn Ser Val Gln
1               5                   10                  15

Glu Leu Ser Met Asp Leu Asn Lys Asn Arg Ser His Phe Ser Met Ala
            20                  25                  30

Gln Pro Gln His Leu Leu Pro Pro Tyr Ser Tyr Val Ala Cys Pro Ala
        35                  40                  45

Leu Asp Gln Thr Gly Thr Met Asn His Gln Pro Leu His Ser Ser Asp
    50                  55                  60

Ala Phe Pro Gln Ile Pro Val Val Gln Thr Gly Gly Glu Phe Gly Tyr
65                  70                  75                  80

Leu Val Cys Lys Pro Gly Val Arg Gln Glu Arg Gly Gly Phe Leu Asp
                85                  90                  95

Pro His Ser Thr Lys Met Ala Arg Ile Asn Arg Lys Lys Ala Met Leu
            100                 105                 110

Arg Ser Arg Asn Asn Ser Asn Pro Asn Ser Ser Ser Asn Glu Leu Val
        115                 120                 125

Asp Ser Arg Arg Gln Val Ala Leu Thr Met Lys Asn Asn Ala Glu Ile
    130                 135                 140

Ala Ala Arg Lys Asp Phe Tyr Arg Phe Ser Ser Phe Asp Asn Lys Lys
145                 150                 155                 160

Leu Arg Val Leu Leu Val Lys His Leu Lys Asn Ser Asp Val Gly Ser
                165                 170                 175

Leu Gly Arg Ile Val Leu Pro Lys Arg Glu Ala Glu Gly Asn Leu Pro
            180                 185                 190

Glu Leu Ser Asp Lys Glu Gly Met Val Leu Glu Met Arg Asp Val Asp
        195                 200                 205

Ser Val Gln Ser Trp Ser Phe Lys Tyr Lys Tyr Trp Ser Asn Asn Lys
    210                 215                 220

Ser Arg Met Tyr Val Leu Glu Asn Thr Gly Glu Phe Val Lys Lys Asn
225                 230                 235                 240

Gly Val Leu Met Gly Asp Tyr Leu Thr Ile Tyr Glu Asp Glu Ser Lys
                245                 250                 255

Asn Leu Tyr Phe Ser Ile Arg Lys His Pro His Lys Gln Asn Asp Gly
            260                 265                 270

Arg Glu Asp Glu Ser Met Glu Val Ile Glu Met Asn Phe Tyr Glu Asp
        275                 280                 285

Ile Met Phe Asp Tyr Ile Pro Asn Asp Glu Asp Asp Ser Ile Ala Met
    290                 295                 300

Leu Leu Gly Asn Leu Asn Glu His Tyr Pro Tyr Pro Asn Asp Leu Met
305                 310                 315                 320

Asp Leu Thr Val Asn Leu Asp Gln His Gln Gln Ala Thr Ser Ser Ser
                325                 330                 335

Pro Pro Ala Asp His Met Ser Ser Asn Asp Phe Leu Trp
            340                 345


<210> SEQ ID NO 24
<211> LENGTH: 359
```

<212> TYPE: PRT
<213> ORGANISM: Brassica napus

<400> SEQUENCE: 24

```
Met Asp Asn Phe Leu Pro Phe Ser Ser Ser Asn Ala Asn Phe Val Gln
1               5                   10                  15

Glu Leu Ser Met Asp Leu Asn Asn Asn Arg Ser Arg Leu Ser Thr Phe
            20                  25                  30

Pro Thr Tyr Asp His His His Gln Ala Gln Pro His Ser Leu Gln Pro
        35                  40                  45

Tyr Ser Tyr Val Ala Cys Pro Val Asp Gln Thr Ala Ala Met Asn Pro
    50                  55                  60

Gln Ile Pro Val Thr Gln Thr Gly Ser Glu Phe Gly Ser Leu Val Cys
65                  70                  75                  80

Asn Pro Gly Phe Gly Gln Ala Arg Gly Gly Phe Leu Asp Pro His Thr
                85                  90                  95

Ala Lys Met Ala Arg Ile Asn Arg Lys Lys Ala Met Ile Arg Ser Arg
            100                 105                 110

Asn Asn Ser Ser Pro Asn Ser Ser Ser Asn Glu Leu Val Gly Ser Arg
        115                 120                 125

Arg Gln Val Val Leu Thr Met Lys Asn Asn Ala Glu Ile Ala Ala Arg
    130                 135                 140

Lys Asp Leu Tyr Arg Tyr Pro Ser Phe Asp Asn Lys Lys Leu Arg Val
145                 150                 155                 160

Leu Leu Val Lys His Leu Lys Asn Ser Asp Val Gly Ser Leu Gly Arg
                165                 170                 175

Ile Val Leu Pro Lys Arg Glu Ala Glu Gly Asn Leu Pro Glu Leu Ser
            180                 185                 190

Thr Lys Glu Gly Met Ile Val Asp Met Arg Asp Ala Asp Ser Met Gln
        195                 200                 205

Asn Trp Ser Phe Lys Tyr Lys Phe Trp Ser Asn Asn Lys Ser Arg Met
    210                 215                 220

Tyr Val Leu Glu Asn Thr Gly Gln Phe Val Thr Glu Lys Arg Val Glu
225                 230                 235                 240

Ile Gly Asp Phe Leu Thr Ile Tyr Glu Asp Glu Ser Lys Asn Leu Tyr
                245                 250                 255

Phe Ser Ile Arg Lys His Ala Asp Lys Pro Asn Glu Gly Arg Glu Asp
            260                 265                 270

Glu Ser Met Glu Ala Asn Asp Met Asn Phe Tyr Glu Asp Ile Ala Phe
        275                 280                 285

Asp Phe Ile Pro Lys Asp Glu Asp Glu Asp Ser Ile Ala Met Leu Ile
    290                 295                 300

Gly Asn Leu Asn Asp His Tyr Pro Asn Pro Asn Asn Arg Met Asp Leu
305                 310                 315                 320

Pro Ile Asp Leu His Gln His His Gln Ala Thr Ser Leu Pro Pro Ala
                325                 330                 335

Asp Tyr Met Thr Asn Pro Gln Tyr Gly Gly Ser Ser Asn Asp Leu Met
            340                 345                 350

Ser Phe Asn Asp Phe Val Trp
        355
```

<210> SEQ ID NO 25
<211> LENGTH: 360
<212> TYPE: PRT
<213> ORGANISM: Brassica napus

<400> SEQUENCE: 25

Met Asp Asn Phe Leu Pro Phe Ser Ser Ser Asn Ala Asn Ser Val Glu
1               5                   10                  15

Glu Leu Ser Met Asp Leu Asn Asn Asn Arg Ser Arg Leu Ser Thr Phe
            20                  25                  30

Pro Thr Tyr Asp His His His Gln Ala Gln His His Ser Leu Gln Pro
        35                  40                  45

Tyr Ser Tyr Val Ala Cys Pro Val Asp Gln Thr Ala Ala Met Asn Pro
    50                  55                  60

Gln Ile Ser Val Ile Gln Thr Gly Ser Glu Phe Gly Ser Leu Val Cys
65                  70                  75                  80

Asn Pro Gly Phe Arg Gln Ala Arg Gly Gly Phe Leu Asp Pro His Thr
                85                  90                  95

Ala Lys Met Ala Arg Ile Asn Arg Lys Lys Ala Met Ile Arg Ser Arg
            100                 105                 110

Asn Asn Ser Ser Pro Asn Ser Ser Ser Asn Glu Leu Val Gly Ser Arg
        115                 120                 125

Arg Gln Val Val Leu Thr Met Lys Asn Asn Ala Glu Ile Ala Ala Arg
    130                 135                 140

Lys Asp Leu Tyr Arg Tyr Ser Ser Phe Asp Asn Lys Lys Leu Arg Val
145                 150                 155                 160

Leu Leu Val Lys His Leu Lys Asn Ser Asp Val Gly Ser Leu Gly Arg
                165                 170                 175

Ile Val Leu Pro Lys Arg Glu Ala Glu Gly Asn Leu Pro Glu Leu Ser
            180                 185                 190

Thr Lys Glu Gly Met Ile Val Glu Met Arg Asp Ala Asp Ser Met Gln
        195                 200                 205

Asn Trp Ser Phe Lys Tyr Lys Phe Trp Ser Asn Asn Lys Ser Arg Met
    210                 215                 220

Tyr Val Leu Glu Asn Thr Gly Glu Phe Val Ala Glu Lys Arg Val Glu
225                 230                 235                 240

Ile Gly Asp Phe Leu Thr Ile Tyr Glu Asp Glu Ser Lys Asn Leu Tyr
                245                 250                 255

Phe Ser Ile Arg Lys His Ala Asp Lys Pro Asn Glu Gly Arg Glu Asp
            260                 265                 270

Glu Ser Met Glu Ala Asn Asp Met Asn Phe Tyr Glu Asp Ile Ala Phe
        275                 280                 285

Asp Phe Ile Pro Lys Asp Glu Asp Glu Asp Ser Ile Ala Met Leu Ile
    290                 295                 300

Gly Asn Leu Asn Asp His Tyr Pro Asn Pro Asn Asn Leu Met Asp Leu
305                 310                 315                 320

Pro Ile Asp Leu His Gln His His Gln Ala Thr Ser Ser Leu Pro Pro
                325                 330                 335

Val Asp Tyr Met Thr Asn Pro Gln Tyr Ser Gly Ser Ser Asn Asp His
            340                 345                 350

Met Ser Phe Asn Asp Phe Val Trp
        355                 360

<210> SEQ ID NO 26
<211> LENGTH: 349
<212> TYPE: PRT
<213> ORGANISM: Brassica napus

<400> SEQUENCE: 26

```
Met Asp Asn Phe Leu Pro Phe Ser Ser Ser Asn Ala Asn Ser Val Gln
1               5                   10                  15

Glu Leu Ser Met Asp Leu Asn Lys Asn Arg Ser His Phe Ser Met Ala
            20                  25                  30

Gln Pro Gln His Leu Leu Pro Pro Tyr Ser Tyr Val Ala Cys Pro Val
        35                  40                  45

Leu Asp Gln Thr Gly Ala Met Asn His Gln Pro Leu His Ser Ser Asp
    50                  55                  60

Ala Phe Pro Gln Ile Pro Val Val Gln Thr Gly Gly Glu Phe Gly Tyr
65                  70                  75                  80

Leu Val Cys Lys Pro Gly Val Arg Gln Glu Arg Gly Gly Phe Leu Asp
                85                  90                  95

Pro His Ser Thr Lys Met Ala Arg Ile Asn Arg Lys Lys Ala Met Ile
            100                 105                 110

Arg Ser Arg Asn Asn Ser Asn Leu Asn Ser Ser Ser Asn Glu Leu Val
        115                 120                 125

Asp Ser Arg Arg Gln Val Ala Leu Thr Met Lys Asn Asn Ala Glu Ile
    130                 135                 140

Ala Ala Arg Lys Asp Phe Tyr Arg Phe Ser Ser Phe Asp Asn Lys Lys
145                 150                 155                 160

Leu Arg Val Leu Leu Val Lys His Leu Lys Asn Ser Asp Val Gly Ser
                165                 170                 175

Leu Gly Arg Ile Val Leu Pro Lys Arg Glu Ala Glu Gly Asn Leu Pro
            180                 185                 190

Glu Leu Ser Asp Lys Glu Gly Met Val Leu Gln Met Arg Asp Val Asp
        195                 200                 205

Ser Val Gln Ser Trp Ser Phe Lys Tyr Lys Tyr Trp Ser Asn Asn Lys
    210                 215                 220

Ser Arg Met Tyr Val Leu Glu Asn Thr Gly Glu Phe Val Lys Lys Asn
225                 230                 235                 240

Gly Val Leu Met Gly Asp Tyr Leu Thr Ile Tyr Glu Asp Glu Ser Lys
                245                 250                 255

Asn Leu Tyr Phe Ser Ile Arg Lys His Pro His Lys Gln Asn Asp Gly
            260                 265                 270

Arg Glu Asp Glu Ser Met Glu Val Ile Glu Met Asn Phe Tyr Glu Asp
        275                 280                 285

Ile Met Phe Asp Tyr Ile Pro Asn Gly Glu Asp Asp Ser Ile Ala Met
    290                 295                 300

Leu Leu Gly Asn Leu Asn Glu His Tyr Pro Tyr Pro Asn Asp Ile Met
305                 310                 315                 320

Asp Leu Thr Val Asp Leu Asp Gln His Gln Gln Ala Thr Ser Ser Ser
                325                 330                 335

Pro Pro Ala Asp His Met Ser Ser Asn Asp Phe Leu Trp
            340                 345
```

<210> SEQ ID NO 27
<211> LENGTH: 1888
<212> TYPE: PRT
<213> ORGANISM: Arabidopsis thaliana

<400> SEQUENCE: 27

```
Met Glu Thr Arg Ser Arg Lys Arg Ala Glu Ala Thr Ser Ala Ala Pro
1               5                   10                  15

Ser Ser Ser Ser Ser Ser Pro Pro Pro Pro Pro Ser Ala Ser Gly Pro
```

```
            20                  25                  30

Thr Thr Arg Ser Lys Arg Ala Arg Leu Ser Ser Ser Ser Ser Ser Ser
        35                  40                  45

Leu Ala Pro Thr Pro Pro Ser Ser Ser Thr Thr Thr Arg Ser Arg Ser
    50                  55                  60

Ser Arg Ser Ala Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
            100                 105                 110

Arg Glu Arg Glu Arg Asp Arg Ala Arg Glu Gln Leu Asn Met Asp Ala
        115                 120                 125

Ala Ala Ala Ala Ala Arg Ser Ala Asp Glu Asp Asp Asp Asn Asp Ser
    130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser Ser His Leu Asn
            180                 185                 190

Gly Arg Met Lys Lys Ile Leu Ser Gly Leu Arg Ala Glu Gly Glu Glu
        195                 200                 205

Gly Lys Gln Val Glu Ala Leu Thr Gln Leu Cys Glu Met Leu Ser Ile
    210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255

Leu Ala Ala Arg Ala Leu Thr His Leu Cys Asp Val Leu Pro Ser Ser
            260                 265                 270

Cys Ala Ala Val Val His Tyr Gly Ala Val Ser Cys Leu Val Ala Arg
        275                 280                 285

Leu Leu Thr Ile Glu Tyr Met Asp Leu Ala Glu Gln Ser Leu Gln Ala
    290                 295                 300

Leu Lys Lys Ile Ser Gln Glu His Pro Thr Ala Cys Leu Arg Ala Gly
305                 310                 315                 320

Ala Leu Met Ala Val Leu Ser Tyr Leu Asp Phe Phe Ser Thr Gly Val
                325                 330                 335

Gln Arg Val Ala Leu Ser Thr Ala Ala Asn Met Cys Lys Lys Leu Pro
            340                 345                 350

Ser Asp Ala Ser Asp Tyr Val Met Glu Ala Val Pro Leu Leu Thr Asn
        355                 360                 365

Leu Leu Gln Tyr His Asp Ser Lys Val Leu Glu Tyr Ala Ser Ile Cys
    370                 375                 380

Leu Thr Arg Ile Ala Glu Ala Phe Ala Pro Tyr Pro Glu Lys Leu Asp
385                 390                 395                 400

Glu Leu Cys Asn His Gly Leu Val Thr Gln Ala Ala Ser Leu Ile Ser
                405                 410                 415

Thr Ser Asn Ser Gly Gly Gly Gln Ala Ser Leu Ser Val Ser Thr Tyr
            420                 425                 430

Thr Gly Leu Ile Arg Leu Leu Ser Thr Cys Ala Ser Gly Ser Pro Leu
        435                 440                 445
```

```
Gly Phe Arg Thr Leu Leu Leu Leu Gly Ile Ser Ser Ile Leu Lys Asp
    450                 455                 460

Ile Leu Leu Gly Ser Gly Val Ser Ala Asn Ala Ser Val Ser Pro Ala
465                 470                 475                 480

Leu Ser Arg Pro Ala Asp Gln Ile Tyr Glu Ile Val Asn Leu Ala Asn
                485                 490                 495

Glu Leu Leu Pro Pro Leu Pro Glu Gly Val Ile Ser Leu Pro Thr Ser
            500                 505                 510

Thr Asn Ala Leu Val Lys Gly Ser Cys Gln Lys Lys Ser Ser Pro Ser
        515                 520                 525

Thr Ser Gly Lys Gln Glu Asp Ile Leu Lys Ile Ser Pro Arg Glu Lys
    530                 535                 540

Leu Leu Gly Asp Gln Pro Glu Leu Leu Gln Gln Phe Gly Leu Asp Leu
545                 550                 555                 560

Leu Pro Val Leu Val Gln Ile Tyr Gly Ser Ser Val Asn Gly Thr Ile
                565                 570                 575

Arg His Lys Cys Leu Ser Val Ile Gly Lys Leu Met Tyr Phe Ser Ser
            580                 585                 590

Ser Glu Met Ile Gln Ser Leu Ile Gly Asp Thr Asn Ile Ser Ser Phe
        595                 600                 605

Leu Ala Gly Val Leu Ala Trp Lys Asp Pro Gln Val Leu Val Pro Ala
    610                 615                 620

Leu Gln Val Ala Glu Ile Leu Met Glu Lys Leu Pro Glu Thr Phe Ser
625                 630                 635                 640

Lys Val Phe Val Arg Glu Gly Val Val His Ala Val Asp Gln Leu Val
                645                 650                 655

Leu Val Gly Lys Pro Ser His Ala Ser Pro Thr Asp Lys Asp Asn Asp
            660                 665                 670

Cys Val Pro Gly Ser Ala Arg Ser Arg Arg Tyr Arg Arg Arg Ser Ser
        675                 680                 685

Asn Ala Asn Ser Asp Gly Asn Gln Ser Glu Glu Pro Lys Asn Pro Ala
    690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
                725                 730                 735

Asp Lys Tyr Phe Pro Ser Asp Gly Gly Asp Val Asp Val Gly Val Thr
            740                 745                 750

Asp Asp Leu Leu His Leu Lys Asn Leu Cys Thr Lys Leu Thr Ala Gly
        755                 760                 765

Ile Asp Asp His Lys Val Lys Gly Lys Gly Lys Ser Lys Ala Ser Gly
    770                 775                 780

Pro Phe Leu Gly Asp Phe Ser Ala Ser Lys Glu Glu Tyr Leu Ile Gly
785                 790                 795                 800

Val Ile Ser Glu Ile Leu Gly Glu Ile Ser Lys Gly Asp Gly Val Ser
                805                 810                 815

Thr Phe Glu Phe Ile Gly Ser Gly Val Val Ala Ala Leu Leu Asn Tyr
            820                 825                 830

Phe Ser Cys Gly Tyr Phe Ser Lys Glu Lys Ile Ser Glu Leu Asn Leu
        835                 840                 845

Pro Lys Leu Arg Gln Glu Gly Leu Arg Arg Phe Lys Ala Phe Leu Glu
    850                 855                 860
```

-continued

```
Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
                885                 890                 895

Pro Val Val Leu Ser His Pro Ser Arg Ser Leu Ser Gly Ser Ala Arg
            900                 905                 910

Leu Ser Ser Gly Leu Ser Ala Leu Ala His Pro Leu Lys Leu Arg Leu
        915                 920                 925

Cys Arg Ala Ser Gly Glu Lys Thr Leu Arg Asp Tyr Ser Ser Asn Ile
    930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Ala Pro
                965                 970                 975

Ile Gly Asn Thr Glu Pro Gly Thr Leu Pro Ser Gly Ala Gly Val Ser
            980                 985                 990

Ser Pro Ser Ser Ser Thr Pro Ala  Ser Thr Thr Arg Arg  His Ser Ser
        995                 1000                1005

Arg Ser  Arg Ser Ala Ile Asn  Ile Gly Asp Thr Ser  Lys Lys Asp
    1010                1015                1020

Pro Val  His Glu Lys Gly Thr  Ser Ser Ser Lys Gly  Lys Gly Lys
    1025                1030                1035

Gly Val  Met Lys Pro Ala Gln  Ala Asp Lys Gly Pro  Gln Thr Arg
    1040                1045                1050

Ser Asn  Ala Gln Lys Arg Ala  Val Leu Asp Lys Asp  Thr Gln Met
    1055                1060                1065

Lys Pro  Ala Ser Gly Asp Ser  Ser Ser Glu Asp Glu  Glu Leu Glu
    1070                1075                1080

Ile Ser  Pro Val Asp Ile Asp  Asp Ala Leu Val Ile  Glu Glu Asp
    1085                1090                1095

Asp Ile  Ser Asp Asp Glu Asp  Asp Asp Asn Glu Asp  Val Leu Asp
    1100                1105                1110

Asp Ser  Leu Pro Met Cys Thr  Pro Asp Lys Val His  Asp Val Lys
    1115                1120                1125

Leu Ala  Asp Ser Val Asp Asp  Asp Gly Leu Ala Thr  Ser Gly Arg
    1130                1135                1140

Gln Met  Asn Pro Ala Ser Gly  Gly Thr Ser Gly Ala  Ala Ala Ala
    1145                1150                1155

Arg Ala  Ser Asp Ser Ile Asp  Thr Gly Ile Gly Asn  Ser Tyr Gly
    1160                1165                1170

Ser Arg  Gly Ala Leu Ser Phe  Ala Ala Ala Ala Met  Ala Gly Leu
    1175                1180                1185

Gly Ala  Ala Ser Gly Arg Gly  Ile Arg Gly Ser Arg  Asp Leu His
    1190                1195                1200

Gly Arg  Thr Leu Asn Arg Ser  Ser Asp Glu Pro Ser  Lys Leu Ile
    1205                1210                1215

Phe Thr  Ala Ala Gly Lys Gln  Leu Ser Arg His Leu  Thr Ile Tyr
    1220                1225                1230

Gln Ala  Val Gln Arg Gln Leu  Met Leu Asp Glu Asp  Asp Asp Asp
    1235                1240                1245

Arg Phe  Gly Gly Ser Asp Leu  Val Ser Ser Asp Gly  Ser Arg Phe
    1250                1255                1260

Asn Asp  Ile Tyr Thr Ile Met  Tyr Gln Arg Pro Asp  Ser Gln Val
```

```
    1265                1270                1275

Asn Arg Leu Ser Val Gly Gly Ala Ser Ser Thr Thr Pro Ser Lys
    1280                1285                1290

Ser Thr Lys Ser Ala Thr Thr Asn Ser Ser Val Glu Ser Gln Ser
    1295                1300                1305

His Arg Ala Ser Leu Leu Asp Ser Ile Leu Gln Gly Glu Leu Pro
    1310                1315                1320

Cys Asp Leu Glu Lys Ser Asn Ser Thr Tyr Asn Val Leu Ala Leu
    1325                1330                1335

Leu Arg Val Leu Glu Gly Leu Asn Gln Leu Cys Pro Arg Leu Arg
    1340                1345                1350

Ala Gln Thr Leu Ser Asp Arg Phe Ala Glu Gly Lys Ile Thr Ser
    1355                1360                1365

Leu Asp Asp Leu Ser Thr Thr Ala Ala Lys Val Pro Leu Asp Glu
    1370                1375                1380

Phe Val Asn Ser Lys Leu Thr Pro Lys Leu Ala Arg Gln Ile Gln
    1385                1390                1395

Asp Ala Leu Ala Leu Cys Ser Gly Ser Leu Pro Ser Trp Cys Tyr
    1400                1405                1410

Gln Leu Thr Arg Ala Cys Pro Phe Leu Phe Pro Phe Gln Thr Arg
    1415                1420                1425

Arg Gln Tyr Phe Tyr Ser Thr Ala Phe Gly Leu Ser Arg Ala Leu
    1430                1435                1440

Asn Arg Leu Gln Gln Gln Gln Gly Ala Asp Gly Ser Gly Ser Thr
    1445                1450                1455

Asn Glu Arg Glu Met Arg Ile Gly Arg Leu Gln Arg Gln Lys Val
    1460                1465                1470

Arg Val Ser Arg Asn Arg Ile Leu Asp Ser Ala Ala Lys Val Met
    1475                1480                1485

Glu Met Tyr Ser Ser Gln Lys Ala Val Leu Glu Val Glu Tyr Phe
    1490                1495                1500

Gly Glu Val Gly Thr Gly Leu Gly Pro Thr Leu Glu Phe Tyr Thr
    1505                1510                1515

Leu Leu Ser His Asp Leu Gln Lys Ala Ser Leu Gly Met Trp Arg
    1520                1525                1530

Ser Ser Ser Gly Asp Lys Val Ser Met Gln Ile Gly Arg Asp Glu
    1535                1540                1545

Ile Glu Asp Gly Lys Pro Ser Ala Ala Asn Arg Asp Ile Val Leu
    1550                1555                1560

Ala Pro Leu Gly Leu Phe Pro Arg Pro Trp Pro Ser Thr Ala Asp
    1565                1570                1575

Ile Ser Glu Gly Gly Gln Phe His Lys Val Ile Glu Tyr Phe Arg
    1580                1585                1590

Leu Leu Gly Arg Val Met Ala Lys Ala Leu Gln Asp Gly Arg Leu
    1595                1600                1605

Leu Asp Val Pro Leu Ser Thr Ala Phe Tyr Lys Leu Ile Leu Gly
    1610                1615                1620

Gln Glu Leu Asp Leu His Asp Ile Val Leu Phe Asp Ala Glu Leu
    1625                1630                1635

Gly Lys Thr Leu Gln Glu Leu Arg Val Val Val Ala Arg Lys His
    1640                1645                1650

Tyr Leu Glu Gly Val Gly Gly Asp Asn Ser Ser Thr Ile Ser Asp
    1655                1660                1665
```

Leu Cys Leu Arg Gly Cys Arg Ile Glu Asp Leu Ser Leu Glu Phe
1670 1675 1680

Thr Leu Pro Gly Tyr Pro Glu Tyr Ile Leu Arg Ser Gly Asp Glu
1685 1690 1695

Ile Val Asp Ile Thr Asn Leu Glu Glu Tyr Ile Ser Leu Val Val
1700 1705 1710

Asp Ala Thr Val Lys Arg Gly Val Thr Arg Gln Ile Glu Ala Phe
1715 1720 1725

Arg Ser Gly Phe Asn Gln Val Phe Asp Ile Thr Ser Leu Gln Ile
1730 1735 1740

Phe Thr Pro Ser Glu Leu Asp Tyr Leu Leu Cys Gly Arg Arg Glu
1745 1750 1755

Leu Trp Glu Val Glu Thr Leu Ala Glu His Ile Lys Phe Asp His
1760 1765 1770

Gly Tyr Asn Ala Lys Ser Pro Ala Ile Ile Asn Leu Leu Glu Ile
1775 1780 1785

Met Gly Glu Leu Thr Ala Asp Gln Gln Arg Ala Phe Cys Gln Phe
1790 1795 1800

Val Thr Gly Ala Pro Arg Leu Pro Pro Gly Gly Leu Ala Val Leu
1805 1810 1815

Asn Pro Lys Leu Thr Ile Val Arg Lys His Ser Ser Thr Ser Ser
1820 1825 1830

Ala Ala Ala Asn Gly Ala Gly Ala Ser Glu Thr Ala Asp Asp Asp
1835 1840 1845

Leu Pro Ser Val Met Thr Cys Ala Asn Tyr Leu Lys Leu Pro Pro
1850 1855 1860

Tyr Ser Thr Lys Glu Ile Met Tyr Lys Lys Leu Leu Tyr Ala Ile
1865 1870 1875

Asn Glu Gly Gln Gly Ser Phe Asp Leu Ser
1880 1885

<210> SEQ ID NO 28
<211> LENGTH: 1872
<212> TYPE: PRT
<213> ORGANISM: Glycine max

<400> SEQUENCE: 28

Met Glu Thr Arg Ser Arg Lys Arg Ala Glu Ala Ser Ser Ala Ala Pro
1 5 10 15

Ser Ser Pro Ser Ser Gly Pro Thr Thr Arg Ser Ser Lys Arg Ala Arg
20 25 30

Leu Ser Ser Ser Ser Ser Ala Ser Ala Ala Val Asn Thr Arg Ser Arg
35 40 45

Ala Ser Asn Thr Lys Glu Pro Leu Pro Pro Lys Asn Pro Pro Pro Pro
50 55 60

Leu Pro Pro Met Asp Ser Ala Asn Glu Ser Ser Gly Ser Arg Arg Asp
65 70 75 80

Arg Arg Asn Asn Lys Glu Asn Ser Ser Asp Lys Gly Lys Glu Lys Glu
85 90 95

His Asp Val Arg Ile Arg Asp Arg Asp Ala Ala Leu Asn Met Asp Gly
100 105 110

Ser Gly Gly Asp Glu Asp Asp Asp Asn Asp Asn Asp Ser Glu Gly Gly
115 120 125

Val Gly Ile Leu His Gln Asn Leu Thr Ser Ala Ser Ser Ala Leu Gln

-continued

```
    130                 135                 140

Gly Leu Leu Arg Lys Leu Gly Ala Gly Leu Asp Asp Leu Leu Pro Ser
145                 150                 155                 160

Ser Ala Met Gly Ser Ala Ser Ser Ser His Gln Ser Gly Arg Leu Lys
                165                 170                 175

Lys Ile Leu Phe Gly Leu Arg Ala Asp Gly Glu Glu Gly Arg Gln Val
            180                 185                 190

Glu Ala Leu Thr Gln Leu Cys Glu Met Leu Ser Ile Gly Thr Glu Glu
        195                 200                 205

Ser Leu Ser Thr Phe Ser Val Asp Ser Phe Val Pro Val Leu Val Gly
    210                 215                 220

Leu Leu Asn His Glu Ser Asn Pro Asp Ile Met Leu Leu Ala Ala Arg
225                 230                 235                 240

Ala Leu Thr His Leu Cys Asp Val Leu Pro Ser Ser Cys Ala Ala Val
                245                 250                 255

Val His Tyr Gly Ala Val Ser Ile Phe Cys Ala Arg Leu Leu Thr Ile
            260                 265                 270

Glu Tyr Met Asp Leu Ala Glu Gln Ser Leu Gln Ala Leu Lys Lys Ile
        275                 280                 285

Ser Leu Glu His Pro Thr Ala Cys Leu Arg Ala Gly Ala Leu Met Ala
    290                 295                 300

Val Leu Ser Tyr Leu Asp Phe Phe Ser Thr Gly Val Gln Arg Val Ala
305                 310                 315                 320

Leu Ser Thr Ala Ala Asn Met Cys Lys Lys Leu Pro Ser Asp Ala Ala
                325                 330                 335

Asp Phe Val Met Glu Ala Val Pro Leu Leu Thr Asn Leu Leu Gln Tyr
            340                 345                 350

His Asp Ser Lys Val Leu Glu His Ala Ser Val Cys Leu Thr Arg Ile
        355                 360                 365

Ala Glu Ala Phe Ala Ser Ser Pro Asp Lys Leu Asp Glu Leu Cys Asn
    370                 375                 380

His Gly Leu Val Thr Gln Ala Thr Ser Leu Ile Ser Asn Ser Ser Ser
385                 390                 395                 400

Gly Gly Gly Gln Ala Ser Leu Ser Thr Pro Thr Tyr Thr Gly Leu Ile
                405                 410                 415

Arg Leu Leu Ser Thr Cys Ala Ser Gly Ser Pro Leu Gly Ala Lys Thr
            420                 425                 430

Leu Leu Leu Leu Gly Ile Ser Gly Ile Leu Lys Asp Ile Leu Ser Gly
        435                 440                 445

Ser Gly Val Ser Ser Asn Ala Ser Val Ser Pro Ala Leu Ser Arg Pro
    450                 455                 460

Pro Glu Gln Ile Phe Glu Ile Val Asn Leu Ala Asn Glu Leu Leu Pro
465                 470                 475                 480

Pro Leu Pro His Gly Thr Ile Ser Leu Pro Ile Ile Ser Asn Met Phe
                485                 490                 495

Leu Lys Gly Pro Ile Val Lys Lys Ser Pro Ser Gly Ser Ser Gly Lys
            500                 505                 510

Gln Glu Asp Thr Asn Gly Asn Val Pro Glu Ile Ser Ala Arg Glu Lys
        515                 520                 525

Leu Leu Asn Asp Gln Pro Glu Leu Leu Lys Gln Phe Ala Met Asp Leu
    530                 535                 540

Leu Pro Val Leu Ile Gln Ile Tyr Gly Ser Ser Val Asn Gly Pro Val
545                 550                 555                 560
```

-continued

Arg His Lys Cys Leu Ser Val Ile Gly Lys Leu Met Tyr Phe Ser Thr
565 570 575

Ala Glu Met Ile Gln Ser Leu Leu Ser Val Thr Asn Ile Ser Ser Phe
580 585 590

Leu Ala Gly Val Leu Ala Trp Lys Asp Pro His Val Leu Leu Pro Ala
595 600 605

Leu Lys Ile Ala Glu Ile Leu Met Glu Lys Leu Pro Gly Thr Phe Ser
610 615 620

Lys Met Phe Ile Arg Glu Gly Val Val His Ala Val Asp Gln Leu Ile
625 630 635 640

Leu Ala Ser Asn Ser Thr Asn Ile Ser Thr Gln Ala Ser Pro Ala Glu
645 650 655

Lys Asp Asn Asp Ser Ile Ser Gly Ala Ser Ser Arg Ser Arg Arg Tyr
660 665 670

Arg Arg Arg Ser Gly Asn Ser Asn Pro Asp Gly Asn Pro Leu Asp Asp
675 680 685

Leu Lys Thr Pro Val Ser Val Asn Val Gly Ser Pro Pro Ser Ser Val
690 695 700

Asp Met Pro Thr Leu Asn Ser Ser Ile Arg Leu Ser Val Ser Thr Ala
705 710 715 720

Ala Lys Ala Phe Lys Asp Lys Tyr Phe Pro Ser Asp Pro Gly Ala Ala
725 730 735

Glu Val Gly Ile Thr Asp Asp Leu Leu His Leu Lys Asn Leu Cys Met
740 745 750

Lys Leu Asn Ala Gly Asp Asp Glu Gln Arg Thr Asn Gly Lys Gly Glu
755 760 765

Ser Lys Thr Ser Gly Phe Gly Pro Glu Glu Tyr Leu Ile Gly Ile Ile
770 775 780

Ala Asn Met Leu Lys Glu Leu Gly Lys Gly Asp Gly Val Ser Thr Phe
785 790 795 800

Glu Phe Ile Gly Ser Gly Val Val Ala Ala Leu Leu Asn Tyr Phe Ser
805 810 815

Cys Gly Tyr Phe Ser Lys Asp Arg Pro Leu Glu Ala His Leu Pro Lys
820 825 830

Leu Arg Gln Gln Ala Leu Thr Arg Phe Lys Leu Phe Ile Ala Val Ala
835 840 845

Leu Pro Ser Thr Ile Glu Val Gly Thr Val Ala Pro Met Thr Val Leu
850 855 860

Val Gln Lys Leu Gln Asn Ala Leu Ser Ser Leu Glu Arg Phe Pro Val
865 870 875 880

Val Leu Ser His Ser Ser Arg Ser Ser Ser Gly Ser Ala Arg Leu Ser
885 890 895

Ser Gly Leu Ser Ala Leu Ser Gln Pro Phe Lys Leu Arg Leu Cys Arg
900 905 910

Ala Gln Gly Glu Lys Ser Leu Arg Asp Tyr Ser Ser Asn Val Val Leu
915 920 925

Val Asp Pro Leu Ala Ser Leu Ala Ala Ile Glu Glu Phe Val Trp Pro
930 935 940

Arg Ile Gln Arg Ser Glu Ser Gly Gln Lys Ser Thr Val Ala Thr Gly
945 950 955 960

Asn Ser Glu Ser Gly Thr Thr Pro Ala Gly Ala Gly Val Ser Ser Pro
965 970 975

-continued

```
Thr Thr Arg Arg His Ser Thr Arg Ser Arg Ser Ser Val Asn Ile Gly
            980                 985                 990

Asp Thr Ser Arg Lys Glu Ile Thr  Gln Asp Lys Ser Thr  Ser Ser Ser
        995                 1000                 1005

Lys Gly  Lys Gly Lys Val Val  Leu Lys Pro Ala Gln  Glu Glu Ala
    1010                 1015                 1020

Arg Gly  Pro Gln Thr Arg Asn  Ala Thr Arg Arg Arg  Ala Ala Leu
    1025                 1030                 1035

Asp Lys  Asp Ala Gln Met Lys  Pro Val Asn Ala Asp  Ser Thr Ser
    1040                 1045                 1050

Glu Asp  Glu Asp Leu Asp Ile  Ser Pro Val Glu Ile  Asp Glu Ala
    1055                 1060                 1065

Leu Val  Ile Glu Asp Asp Asp  Ile Ser Asp Asp Glu  Asp Asp Asp
    1070                 1075                 1080

His Glu  Asp Val Leu Arg Asp  Asp Ser Leu Pro Val  Cys Ser Pro
    1085                 1090                 1095

Asp Lys  Val His Asp Val Lys  Leu Gly Asp Leu Ala  Glu Glu Ser
    1100                 1105                 1110

Asn Val  Ala Pro Ala Thr Ser  Asp Gly Gln Ala Asn  Ala Ala Ser
    1115                 1120                 1125

Gly Ser  Ser Ser Lys Ala Gly  Thr Val Arg Gly Ser  Asp Ser Thr
    1130                 1135                 1140

Asp Phe  Arg Ser Gly Tyr Asn  Ser Ser Ser Arg Gly  Ala Met Ser
    1145                 1150                 1155

Phe Ala  Ala Ala Ala Met Ala  Gly Leu Gly Ser Ala  Asn Ser Arg
    1160                 1165                 1170

Gly Ile  Arg Gly Gly Arg Asp  Arg Leu Gly Arg Pro  Leu Phe Gly
    1175                 1180                 1185

Ser Ser  Asn Asp Pro Pro Lys  Leu Ile Phe Thr Ala  Gly Gly Lys
    1190                 1195                 1200

Gln Leu  Asn Arg His Leu Thr  Ile Tyr Gln Ala Ile  Gln Arg Gln
    1205                 1210                 1215

Leu Val  Leu Asp Asp Asp Glu  Arg Phe Ala Gly Ser  Ser Asp Tyr
    1220                 1225                 1230

Val Ser  Ser Asp Gly Ser Arg  Leu Trp Gly Asp Ile  Tyr Thr Ile
    1235                 1240                 1245

Thr Tyr  His Arg Ala Glu Asn  Gln Thr Asp Arg Thr  Pro Pro Gly
    1250                 1255                 1260

Gly Ser  Thr Ser Asn Ala Ser  Lys Ser Cys Lys Ser  Gly Ser Val
    1265                 1270                 1275

Ser Asn  Ser Ser Ser Glu Ala  Lys Leu His Gln Thr  Ser Val Leu
    1280                 1285                 1290

Asp Ser  Ile Leu Gln Gly Glu  Leu Pro Cys Glu Leu  Glu Lys Ser
    1295                 1300                 1305

Asn Pro  Thr Tyr Asn Ile Leu  Ala Leu Leu Arg Val  Leu Glu Gly
    1310                 1315                 1320

Leu Asn  Gln Leu Ala Ser Arg  Leu Arg Ala Gln Val  Val Thr Asp
    1325                 1330                 1335

Ser Phe  Ala Glu Gly Lys Ile  Leu Asp Leu Asp Glu  Leu Ser Val
    1340                 1345                 1350

Thr Ser  Gly Ala Arg Val Pro  Thr Glu Glu Phe Ile  Ser Ser Lys
    1355                 1360                 1365

Leu Thr  Pro Lys Leu Ala Arg  Gln Ile Gln Asp Ala  Leu Ala Leu
```

1370 1375 1380

Cys Ser Gly Ser Leu Pro Ser Trp Cys Tyr Gln Leu Ser Lys Ala
1385 1390 1395

Cys Pro Phe Leu Phe Pro Phe Glu Thr Arg Arg Gln Tyr Phe Tyr
1400 1405 1410

Ser Thr Ala Phe Gly Leu Ser Arg Ala Leu Tyr Arg Leu Gln Gln
1415 1420 1425

Gln Gln Gly Ala Asp Gly His Gly Ser Thr Asn Glu Arg Glu Val
1430 1435 1440

Arg Val Gly Arg Leu Gln Arg Gln Lys Val Arg Val Ser Arg Asn
1445 1450 1455

Arg Ile Leu Asp Ser Ala Ala Lys Val Met Glu Leu Tyr Ser Ser
1460 1465 1470

Gln Lys Ala Val Leu Glu Val Glu Tyr Phe Gly Glu Val Gly Thr
1475 1480 1485

Gly Leu Gly Pro Thr Leu Glu Phe Tyr Thr Leu Leu Ser His Asp
1490 1495 1500

Leu Gln Lys Ile Ile Leu Glu Met Trp Arg Ser Gly Ser Ser Glu
1505 1510 1515

Lys Tyr Gln Met Lys Ile Asp Gly Asp Glu Lys Lys Met Lys Arg
1520 1525 1530

Ser Glu Gly Ser Phe Val Gly Asp Gly Glu Leu Val Gln Ala Pro
1535 1540 1545

Leu Gly Leu Phe Pro Arg Pro Trp Ser Ala Asn Ala Asp Ala Ser
1550 1555 1560

Glu Gly Thr Gln Phe Phe Lys Val Ile Glu Tyr Phe Arg Leu Leu
1565 1570 1575

Gly Arg Val Met Ala Lys Ala Leu Gln Asp Gly Arg Leu Leu Asp
1580 1585 1590

Leu Pro Met Ser Val Ala Phe Tyr Lys Leu Val Leu Gly Gln Glu
1595 1600 1605

Leu Asp Leu His Asp Ile Leu Phe Ile Asp Ala Glu Leu Gly Lys
1610 1615 1620

Thr Leu Gln Glu Leu Asn Ala Leu Val Cys Arg Lys His Tyr Ile
1625 1630 1635

Gln Ser Thr Gly Gly Ser Tyr Thr Asp Thr Phe Ala Asn Leu His
1640 1645 1650

Phe Arg Gly Ala Pro Ile Glu Asp Leu Cys Leu Asp Phe Thr Leu
1655 1660 1665

Pro Gly Tyr Pro Glu Tyr Ile Leu Lys Pro Gly Asp Glu Ile Val
1670 1675 1680

Asp Ile Asn Asn Leu Glu Glu Tyr Ile Ser Met Val Val Glu Ala
1685 1690 1695

Thr Val Lys Thr Gly Ile Met Arg Gln Met Glu Ala Phe Arg Ala
1700 1705 1710

Gly Phe Asn Gln Val Phe Asp Ile Ser Ser Leu Gln Ile Phe Ser
1715 1720 1725

Pro Gln Glu Leu Asp Tyr Leu Leu Cys Gly Arg Arg Glu Leu Trp
1730 1735 1740

Lys Thr Glu Thr Leu Ala Asp His Ile Lys Phe Asp His Gly Tyr
1745 1750 1755

Thr Ala Lys Ser Pro Ala Ile Val Asn Leu Leu Gly Ile Met Gly
1760 1765 1770

Glu Phe Thr Pro Glu Gln Gln Arg Ala Phe Cys Gln Phe Val Thr
1775 1780 1785

Gly Ala Pro Arg Leu Pro Pro Gly Gly Leu Ala Val Leu Asn Pro
1790 1795 1800

Lys Leu Thr Ile Val Arg Lys Leu Ser Ser Ser Ala Ala Asn Ala
1805 1810 1815

Ser Ser Asn Gly Asn Gly Pro Ser Glu Leu Ala Asp Asp Asp Leu
1820 1825 1830

Pro Ser Val Met Thr Cys Ala Asn Tyr Leu Lys Leu Pro Pro Tyr
1835 1840 1845

Ser Thr Lys Glu Ile Met Tyr Lys Lys Leu Leu Tyr Ala Ile Ser
1850 1855 1860

Glu Gly Gln Gly Ser Phe Asp Leu Ser
1865 1870

<210> SEQ ID NO 29
<211> LENGTH: 426
<212> TYPE: PRT
<213> ORGANISM: Brassica napus

<400> SEQUENCE: 29

Met Arg Ile Gly Arg Leu Gln Arg Gln Lys Val Arg Val Ser Arg Asn
1 5 10 15

Arg Ile Leu Asp Ser Ala Ala Lys Val Met Glu Met Tyr Ser Ser Gln
20 25 30

Lys Ala Val Leu Glu Val Glu Tyr Phe Gly Glu Val Gly Thr Gly Leu
35 40 45

Gly Pro Thr Leu Glu Phe Tyr Thr Leu Leu Ser His Asp Leu Gln Lys
50 55 60

Ala Ser Leu Gly Met Trp Arg Ser Ser Ser Gly Asp Lys Val Ser Met
65 70 75 80

Gln Ile Gly Arg Asp Glu Ile Glu Asp Gly Lys Pro Ser Ala Ala Asn
85 90 95

Arg Asp Ile Val Leu Ala Pro Leu Gly Leu Phe Pro Arg Pro Trp Pro
100 105 110

Ser Thr Ala Asp Ile Ser Glu Gly Gly Gln Phe His Lys Val Ile Glu
115 120 125

Tyr Phe Arg Leu Leu Gly Arg Val Met Ala Lys Ala Leu Gln Asp Gly
130 135 140

Arg Leu Leu Asp Val Pro Leu Ser Thr Ala Phe Tyr Lys Leu Ile Leu
145 150 155 160

Gly Gln Glu Leu Asp Leu His Asp Ile Val Leu Phe Asp Ala Glu Leu
165 170 175

Gly Lys Thr Leu Gln Glu Leu Arg Val Val Val Ala Arg Lys His Tyr
180 185 190

Leu Glu Gly Val Gly Gly Asp Asn Ser Ser Thr Ile Ser Asp Leu Cys
195 200 205

Leu Arg Gly Cys Arg Ile Glu Asp Leu Ser Leu Glu Phe Thr Leu Pro
210 215 220

Gly Tyr Pro Glu Tyr Ile Leu Arg Ser Gly Asp Glu Ile Val Asp Ile
225 230 235 240

Thr Asn Leu Glu Glu Tyr Ile Ser Leu Val Val Asp Ala Thr Val Lys
245 250 255

Arg Gly Val Thr Arg Gln Ile Glu Ala Phe Arg Ser Gly Phe Asn Gln

```
            260                 265                 270

Val Phe Asp Ile Thr Ser Leu Gln Ile Phe Thr Pro Ser Glu Leu Asp
        275                 280                 285

Tyr Leu Leu Cys Gly Arg Arg Glu Leu Trp Glu Val Glu Thr Leu Ala
    290                 295                 300

Glu His Ile Lys Phe Asp His Gly Tyr Asn Ala Lys Ser Pro Ala Ile
305                 310                 315                 320

Ile Asn Leu Leu Glu Ile Met Gly Glu Leu Thr Ala Asp Gln Gln Arg
                325                 330                 335

Ala Phe Cys Gln Phe Val Thr Gly Ala Pro Arg Leu Pro Pro Gly Gly
            340                 345                 350

Leu Ala Val Leu Asn Pro Lys Leu Thr Ile Val Arg Lys His Ser Ser
        355                 360                 365

Thr Ser Ser Ala Ala Ala Asn Gly Ala Gly Ala Ser Glu Thr Ala Asp
    370                 375                 380

Asp Asp Leu Pro Ser Val Met Thr Cys Ala Asn Tyr Leu Lys Leu Pro
385                 390                 395                 400

Pro Tyr Ser Thr Lys Glu Ile Met Tyr Lys Lys Leu Leu Tyr Ala Ile
                405                 410                 415

Asn Glu Gly Gln Gly Ser Phe Asp Leu Ser
            420                 425
```

<210> SEQ ID NO 30
<211> LENGTH: 56
<212> TYPE: PRT
<213> ORGANISM: Brassica napus

<400> SEQUENCE: 30

```
Arg Gly Asn Asn Asn Asp Asn Ser Asp Lys Gly Lys Glu Lys Glu His
1               5                   10                  15

Asp Val Arg Ile Arg Glu Arg Glu Arg Glu Arg Asp Arg Ala Arg Glu
            20                  25                  30

Gln Leu Asn Met Asp Ala Ala Ala Ala Ala Ala Arg Ser Ala Asp Glu
        35                  40                  45

Asp Asp Asp Asn Asp Ser Glu Asp
    50                  55
```

<210> SEQ ID NO 31
<211> LENGTH: 300
<212> TYPE: PRT
<213> ORGANISM: Brassica napus

<400> SEQUENCE: 31

```
Leu Asn Gly Arg Met Lys Lys Ile Leu Ser Gly Leu Arg Ala Glu Gly
1               5                   10                  15

Glu Glu Gly Lys Gln Val Glu Ala Leu Thr Gln Leu Cys Glu Met Leu
            20                  25                  30

Ser Ile Gly Thr Glu Asp Ser Leu Ser Thr Phe Ser Val Asp Ser Phe
        35                  40                  45

Val Pro Val Leu Val Gly Leu Leu Asn His Glu Ser Asn Pro Asp Ile
    50                  55                  60

Met Leu Leu Ala Ala Arg Ala Leu Thr His Leu Cys Asp Val Leu Pro
65                  70                  75                  80

Ser Ser Cys Ala Ala Val Val His Tyr Gly Ala Val Ser Cys Leu Val
                85                  90                  95

Ala Arg Leu Leu Thr Ile Glu Tyr Met Asp Leu Ala Glu Gln Ser Leu
```

```
            100                 105                 110

Gln Ala Leu Lys Lys Ile Ser Gln Glu His Pro Thr Ala Cys Leu Arg
        115                 120                 125

Ala Gly Ala Leu Met Ala Val Leu Ser Tyr Leu Asp Phe Phe Ser Thr
    130                 135                 140

Gly Val Gln Arg Val Ala Leu Ser Thr Ala Ala Asn Met Cys Lys Lys
145                 150                 155                 160

Leu Pro Ser Asp Ala Ser Asp Tyr Val Met Glu Ala Val Pro Leu Leu
                165                 170                 175

Thr Asn Leu Leu Gln Tyr His Asp Ser Lys Val Leu Glu Tyr Ala Ser
            180                 185                 190

Ile Cys Leu Thr Arg Ile Ala Glu Ala Phe Ala Pro Tyr Pro Glu Lys
        195                 200                 205

Leu Asp Glu Leu Cys Asn His Gly Leu Val Thr Gln Ala Ala Ser Leu
    210                 215                 220

Ile Ser Thr Ser Asn Ser Gly Gly Gly Gln Ala Ser Leu Ser Val Ser
225                 230                 235                 240

Thr Tyr Thr Gly Leu Ile Arg Leu Leu Ser Thr Cys Ala Ser Gly Ser
                245                 250                 255

Pro Leu Gly Phe Arg Thr Leu Leu Leu Leu Gly Ile Ser Ser Ile Leu
            260                 265                 270

Lys Asp Ile Leu Leu Gly Ser Gly Val Ser Ala Asn Ala Ser Val Ser
        275                 280                 285

Pro Ala Leu Ser Arg Pro Ala Asp Gln Ile Tyr Glu
    290                 295                 300


<210> SEQ ID NO 32
<211> LENGTH: 125
<212> TYPE: PRT
<213> ORGANISM: Brassica napus

<400> SEQUENCE: 32

Gly Lys Gln Glu Asp Ile Leu Lys Ile Ser Pro Arg Glu Lys Leu Leu
1               5                   10                  15

Gly Asp Gln Pro Glu Leu Leu Gln Gln Phe Gly Leu Asp Leu Leu Pro
            20                  25                  30

Val Leu Val Gln Ile Tyr Gly Ser Ser Val Asn Gly Thr Ile Arg His
        35                  40                  45

Lys Cys Leu Ser Val Ile Gly Lys Leu Met Tyr Phe Ser Ser Ser Glu
    50                  55                  60

Met Ile Gln Ser Leu Ile Gly Asp Thr Asn Ile Ser Ser Phe Leu Ala
65                  70                  75                  80

Gly Val Leu Ala Trp Lys Asp Pro Gln Val Leu Val Pro Ala Leu Gln
                85                  90                  95

Val Ala Glu Ile Leu Met Glu Lys Leu Pro Glu Thr Phe Ser Lys Val
            100                 105                 110

Phe Val Arg Glu Gly Val Val His Ala Val Asp Gln Leu
        115                 120                 125


<210> SEQ ID NO 33
<211> LENGTH: 9098
<212> TYPE: DNA
<213> ORGANISM: Brassica oleracea

<400> SEQUENCE: 33

atatagtcca tggatcgtag tgagaaggta gagttgaaag tataagaaag cgaacctcca      60
```

-continued tcatagtggg ggcttaaacc cgtgcaagct tgcagatatc tatggctgat ggttgggccc 120
agccttatat cttgggctta ttttgtttcc atctgtccag cccatgataa agtgtaaaac 180
gacaccgtat taagcttaat ggagtaaacg aatcacacgt agcggggatc cccgtgtcag 240
ttcttgtcgg aaaagctgga cggaggaaaa cggtatcgta ttcgcttcgc ttgaatctat 300
atattttgcg caaaagccct tttcatccct ttcttctctc attactcgat ttagggtttt 360
ctaatctcga aagaaatcaa gatcctcctt ccttcctctc tcgatttcga tctcgtagcc 420
ccttttgcgt tgatttcgaa ttcgttcatc aataggtttg tttctctcta gctcctaacg 480
atctcgctag caaattaggg tttcgagcga gcttaatccg atcggtttct ggatcagttg 540
agatgcgatc ggaatctctc tgaataagag agactcgtgt ggaggggttt cttcctttgt 600
atggaaactc ggagccgcaa gcgtgcggag gcgacctcaa ctgccccatc ttcttcttct 660
tcgtctcctc ctcctcctcc ctcaggtccc accactcgca gcaaacgcgc tcgcctctcg 720
tctccctctt cctcttcagc cgccgccgct accaccgcta ctgcaccttc ctcctccacc 780
cgctctcgtt cttctcgctc tgccgctacc gctaccgcta cagccgccgt tactcccatg 840
gacacatcca ccgagtcttc tggattccgc cgcggcgggg gacgaggtaa caggggaaac 900
gataatacta attctgataa gggaaaggag aaggagcatg aggttaggat tagggataga 960
gaaagagacc gagccagaca gcagctcaac atggacgctg cagctgctgc cgccgccgct 1020
gaagaggacg atgacaatga tagtgaggat ggcaacgggg gattcatgca tcccaacatg 1080
agctcagcca gcagtgcgtt acaagggttg ctgaggaagc ttggagctgg acttgatgac 1140
ttgcttcctt cttcaggtat tggctcaggt tcttcttccc atttaaatgg gaggatgaag 1200
aagatactcg ctggcttgcg ctctgaagga gaagagggaa agcaggtcga ggctttgacc 1260
cagctctgcg agatgttatc cattggcacc gaagactcct tgagcacctt ctctgttgat 1320
tccttcgtcc ccgttcttgt tggtctactt aaccatgaga gcaatccgga tattatgctt 1380
cttgctgcca gggctcttac ccatctgtgt gatgttttgc cctcttcttg tgctgctgtt 1440
gttcattacg gggctgtttc atgctttgtc gccagattgc taaccattga atacatggac 1500
ttggccgagc aggttcgctt tcctagcaat tcttgatttt tttttttttg aatataatac 1560
ttatctaaaa tctggataaa gtgtatgttg tggaatgttt tatgctgcag tttctacacg 1620
tacatatcca atattttaat ttacttagga cgaaatttga aatttgattt tattcttcat 1680
gtgatttaca acagtctctg caagctctca aaaagatatc tcaggaacac ccaacggcct 1740
gtttgcgagc tggtgctctt atggcagtgc tatcatatct ggatttcttc tccaccggtg 1800
tccaggtggg taattttgta acctttcttt tatgctttcc atactcgttt atctaatgca 1860
ctttttttta ctttgacttt gtagcgtgta gcagtctcta ccgctgcaaa tatgtgcaag 1920
aagttacctt ctgatgcatc tgattatgtt atggaagctg taccggtact gacaaaccta 1980
cttcagtatc atgatgcgaa ggtaaacgat cctttttttt tgctgtactg tggtactatc 2040
tagttctgct cttgccccag tttccttcat agtatgttcg tacggtgaca ggttttggaa 2100
tatgcttcta tctgtttgac tcggattgcc gaagcatttg catcgtcccc tgataaatta 2160
gatgaattat gcaaccatgg cctggtgact caagctgcga ctcttatatc cgctagcaac 2220
tcgggaggtg ggcaagcatc tcttggtgtt tcaacataca cggtatgagt taattctttt 2280
gtgttttcta tatttcgtta ttcataggat gacattttca tcatattttc acagggatta 2340
atccgattac tttccacctg tgcgagcggt tcacctcttg ggtgcaggac attacttctt 2400

-continued

```
ctcggtatta gtagcattct taaggatatt ctgtcgggtt ctggtgtctc tgctaatgca   2460
tctatatccc cagcactgag caggcctgca gatcaggtac ggatttactt tttgacatca   2520
cagactttat tttgttcatt tcctgataaa ataaatggtg tacaatgaga tgcttagggg   2580
acacaccttc aaatagatca cttgcattta ggagatttgt ctattcagct cgatgataat   2640
ctatgtacat gtattttgag ctttatttat gttgtagccg atggctcaag tttcctatgc   2700
ttgttttctg gtctggtgtt ggaagtggta tagataaaag cgcttagcgc ttcatcagtg   2760
tgctctgtct tgtttattta actttgatcc catgactctc taattcttga atatattctt   2820
gaacatgatc atgtgaggtc ctttgtttcc agaaaggttc cgaattataa ctcttgtttt   2880
gcatcttaga tttttgagat agtcaaccta gcgaacgagc tcctccctcc attgccagaa   2940
ggaagtatct cccttcctac tagcgcaaac gcgttagtga aaggttcagg ccaaaaaaat   3000
tcttctccaa gtacttcagg aaaacaagaa gattctccca aagtttcacc tagagaaaaa   3060
ttactttgtg atcaacccga acttttgcag caatttggat tggatcttct tccagtttta   3120
gtgcaggtaa tttttttgttg cggttgctac aagttaatgt tcatacaacc tcctgtatgt   3180
ctaattaccc ttgttttctt tccaacagat ctatggttct agtgtcaatg gtactattcg   3240
tcataaatgt ctctccgtta tcgcaaagtt gatgtatttc agcactccag aaatgattca   3300
atctctaatt ggtgacacaa atatatcgag gtatgctgtt tatgttttaa attaggtatc   3360
acatggcgca acttcttaca ttatttttcc tatgtagctt cttggctagt gtcttggcat   3420
ggaaagatcc acaagtcttg gttcctgctc tacaagttgc agaaattctg atggaaaaac   3480
ttcctgaaac tttctcgaaa gtgtttgtga gggaaggggt ggttcatgct gtagatcaac   3540
ttgtcttggt tggtaaacct agtgctaatg cttctactga tcaggaaaat gactgtgtgc   3600
ctggatctgc acgatctagg cgttacagac ggcgaagtag taatgccaat tctgatggaa   3660
atcagtcgga agagcttaag aattctgtgt cagctagcat aggtgcgacc cataattcca   3720
tggaatctcc tacagcgagc ttcatgctaa gggaaacagt tagctcctgt gcaaaagcat   3780
tcaaagacaa gcacttcccg tctgatggtg gggaatttga tgttggagtt acagatgatc   3840
tcttgcatct gaagaatctt tgcacgaagc taactgctgg tacaaatgat cataaagtga   3900
aaggaaaggg gaaatctaaa gtctctgggc catgccttgg cgatttttct gctagcaaag   3960
aagaatactt gattggtatc atctccgaga tacttggcga gctaagcaaa ggggatggcg   4020
tctcaacttt tgagtttatt ggcagtggtg tggtagcagc attgcttaac tatttttctt   4080
atggatactt ttccaaagag aagatctccg aggttgattt gcccaaactt cgccaggatg   4140
ggctcagaag gttcaaagct tttctagaaa ttgcacttcc ttctgatggt aatgagggaa   4200
agatccctcc tatgactgtt ttgattcaga aacttcaaga tgctttgtct tcactggaac   4260
gctttccggt cgtccttagc catccctcaa ggtcactcag tggaagtgct cgtctctcat   4320
ctgggttgag tgctttggca catcctttga agttgcggtt atgccgtgca cctggagaga   4380
aggctctacg tgattactcc tccaatattg ttctcataga tccattggca agcatagcag   4440
cagtggagga atttctctgg ccccgagttc aacgcagtga atctggggtg aaggcagcag   4500
cgcctgctgg aaacactgag ccaggcacat tacctagcgg tgctggtgtt tcatcaccat   4560
cctcgtcaac tccagcttcc accactcgtc attcttctag atctagatca gcaattaaaa   4620
taggcgatgc ctcaaagaaa gaacctgtgc acgagaaagg taccagctca tctaaaggta   4680
aaggtgttat gaagccggct cagccggata aggggcctca gacaaggagc agtgctcaaa   4740
ggaaagctgt tcttgacaaa gatacactaa tgaaaccagc tagcggagac tccagctctg   4800
```

aggtatgtca ctgtaggaag ttctggatta catggttgtt tattgtgtaa cattatatta 4860
tgtttgtggt gtgatctgct tatgcagcac tatcttactt atattgcttg caggacgaag 4920
aaatggatat atccccgtc gacatggatg atgctttggt gattgaagag gaagacattt 4980
ctgacgacga tgatgatgat gatgaggagg atgtaagtat tccctcccca gtatgtacat 5040
tacagacgca attatttctc ttgctaacaa catgaaagat gatacttctc gcaataatgc 5100
ttgctagctt tccgtattct tagataagtt taccatattg agctgacctt atcggaacct 5160
ttccttttag aactgactaa agagaattat gaactttata ccacaatttc tcatattgat 5220
ctggtcttga attcaggtct tggatgacag tcttcccatg tgcacccctg ataaggttca 5280
tgatgtaaaa ttgggagacg cagtggatga tgagggagcc ggcctagcac ctagcggccg 5340
acagatgaat tcagctttgg caggaagtag tggaacagca actgcaaggg gatctaattc 5400
tactgatgct ggcattggga atctttatgg ttctaggggt gcactctcct tcgctgctgc 5460
ggcgatggca gggcttggag ctgccagtgg tagaggtatc agggggagta gagacctaca 5520
tgggcgtacc ctgaatcgaa gttctgatga gtcctctaag ttgatgttta ctgcgggagg 5580
aaagcaactt agtaggcata tgacgatata tcaggctgtg caacgacaac ttatgctaga 5640
cgaagatgat gatgacaggc tcggtggcag cgatttcatc tcgagtgatg gaagcagatt 5700
aaatgatata tatactatca tgtaccagat gccggacagc caagcgaata ggttgtctgc 5760
tggtggtgca agttctacca caccatctaa atccactaaa tctgctacta ctaatgcaag 5820
cgtagaagcc cagtcgtata gggcatctct tttggatagt atcgtacaag gaaagcttcc 5880
atgcgacctt gagaaggcaa attctacgta taatgttttg gcgttgttgc gtgtactaga 5940
gggtttaaat cagcttggcc ctcggttaag agcccaaacc atttctgatc gtttcgcaga 6000
gggtaaaatt acaagtctag atgatctgaa tacaactgct gcaaaggttt ctcatgaaga 6060
attcatcaac agcaaactta cacccaaatt agctcgacag atccaggacg cgcttgcttt 6120
gtgcagtgga agtcttccct cttggtgcta ccagttgact acagcatgcc cgtttttgtt 6180
tccgtttcag acccggagac agtatttcta ttcaactgcc tttgggttgt cgcgtgcatt 6240
gaaccgcttg cagcagcagc aaggtgctga cggcagtggt tctacaaatg aacgagagat 6300
gagaataggg agattgcagc gccagaaagt gcgggtatcc cgaaatagaa tattagattc 6360
tgctgcgaaa gttatggaga tgtattctag ccaaaaagct gtgcttgaag tagaatattt 6420
tggtgaagtt ggtactggtc taggccccac acttgagttt tacacactcc taagccatga 6480
tttgcaaaag gtttcccttg ggatgtggag atcaaattct ggtgacaagt tatctatgca 6540
aactgataga gatgagattc aagacggtaa atctgcagca gctagggaca gagatatagt 6600
tcaggcacca cttgggttgt tccctcggcc ctggccctca actgctgacg tatctgaagg 6660
tagtcggttt cataaagttg ttgaatattt ccgcctttta gggcgcgtga tggcaaaggc 6720
acttcaagat ggacggctaa tggacgtccc gttaagtaca gctttttata agctcattct 6780
tggtcaagtg agtttttac tatcagtaac tttttttatt tagctaagag tggactagta 6840
gtttcgacac ttctttacgt tgttcgtaat ttctttttct tttctcacct gaacaggagc 6900
ttgatttgca tgatgttata atatttgata ctgaacttgg caagactttg caagagcttc 6960
gtgttcttgt tggccgtaag cactatctgg aagcagaagg tggtgacaac agtagcgtga 7020
tttctgattt atgtttacgt ggatcccgta ttgaagatct ttgcttggac ttcaccctac 7080
ctggctatcc tgaatacata ttgagaccag gagatgacat tgtaccgtct aataagcttt 7140
acatcccata tcttactatt cttttagttc ttgtccattg ttgctgatgc cgtgtactgt 7200
tttctgttct attacaggtt gatattaata gtcttgagga ctatatatcc ctggtcgttg 7260
atgccactgt caagagagga gttgcccggc agattgaagc cttcagatct ggattcaatc 7320
aggttagcag tttcacagac tctccgcttt gtctctttct tttcctgttg gcttctaaat 7380
catatggaag gagtggtttc ttttggttca tacttcataa tcttttaaac aacaggttta 7440
tattaagtct ttaatttagt cttaccttta ttatccttac aagacctctc tgttcttaca 7500
catgattacc aggtctttga cataaaatct ttacaagtat tcaccccttc tgagctggac 7560
tacttgttat gtggtcgtag agagttgtgg gaggtaattt ttcaactttc ttttgaattt 7620
ccactaccca tttgacttga atcaactaga taaaattttc atttctaaaa cctttctttt 7680
attgcaggcg gagactcttg ttgaacatat caagtttgat cacggttata ctgcaaaaag 7740
tccggcaatc attttcgtaa gttactttcc ttgctagttt tttaaaaaac caattttctt 7800
ttacaatcaa gctttttgct tatttattgt tgattccttt ttgactttga ttttcaccct 7860
ggtggtagtt actggagatc atgggagagc ttacagcaga tcaacagcgt gctttctgcc 7920
agtttgtaac tggagctcct aggcttcctc ctggtggctt agctgttctc aacccaaagc 7980
tgacgattgt gagaaaggta agaaaccttt acttatatat tcggttaaaa agcgtttttt 8040
taattgagcc aagaggttcc tagtcatgtt aaactagacc cacgaagcca tatatcaaaa 8100
tacatctaca cgtgacgcat tgtggtgttt gcttgcattt gcaagacttg ttaagaggaa 8160
ttagctctta ctcgatttaa gttgtgtatt tgctttcaat tgatgtgttt ttggcttggt 8220
gcagctctca tcaacctcaa atgcggctgc caatgggaca ggggcttcgg aaacagcaga 8280
cgacgatctt cccagcgtca tgacttgcgc caactacctt aagctccctc cttattctac 8340
aaaggtaact cgtgtctctc ttttttaag tctatggttt ctgtgtttgg ttggttggag 8400
tgagcctgaa taggagtttg tacctgaaac aggaaatcat gtacaagaaa ctgctctacg 8460
cgatcaacga agggcaggga tcgttcgacc tctcctaggc gtctctctct gttgtcgctg 8520
cggctagaaa ccaccaaccc tctctcttct ttgtacattt tacatcggaa gactctgatt 8580
ttgcactttg aatgttattt ctattaaacc atgaattatt aaaattaggt tcaatatttt 8640
tcatgtgcaa gtaatatatt aaaacatgga ggataaaaat aaaatcaaaa gacaaacttg 8700
aataattttg gttgcctttg aaattcgttt gaaaattccg aagcaattgg atagtggtga 8760
ataaaagctg tcagctgaaa gaaataaaaa aggtacaaag gtttaggtgt tgtatgatcc 8820
aaaattctgt tttttataaa gacaggatct atcagtcaca gcagttgact gttaagatat 8880
caaaggaatc aagaaataat tgttcgtttc tggagattga acagaagacg ttttcatcag 8940
ttttcttttt gataaaagtt aattggacat agatatctct agacacgaga aacaaaagca 9000
taaataggaa aacattacaa ttaaaaagag cgttacgagt acagagttca agctagacac 9060
aagaaaccta ccatatggtg gtattgacta ttaatata 9098

<210> SEQ ID NO 34
<211> LENGTH: 1893
<212> TYPE: PRT
<213> ORGANISM: Brassica oleracea

<400> SEQUENCE: 34

Met Glu Thr Arg Ser Arg Lys Arg Ala Glu Ala Thr Ser Thr Ala Pro
1 5 10 15

Ser Ser Ser Ser Ser Ser Pro Pro Pro Pro Pro Ser Gly Pro Thr Thr
20 25 30

-continued

```
Arg Ser Lys Arg Ala Arg Leu Ser Ser Pro Ser Ser Ser Ser Ala Ala
        35                  40                  45

Ala Ala Thr Thr Ala Thr Ala Pro Ser Ser Ser Thr Arg Ser Arg Ser
    50                  55                  60

Ser Arg Ser Ala Ala Thr Ala Thr Ala Thr Ala Ala Val Thr Pro Met
65                  70                  75                  80

Asp Thr Ser Thr Glu Ser Ser Gly Phe Arg Arg Gly Gly Gly Arg Gly
                85                  90                  95

Asn Arg Gly Asn Asp Asn Thr Asn Ser Asp Lys Gly Lys Glu Lys Glu
            100                 105                 110

His Glu Val Arg Ile Arg Asp Arg Glu Arg Asp Arg Ala Arg Gln Gln
        115                 120                 125

Leu Asn Met Asp Ala Ala Ala Ala Ala Ala Ala Ala Glu Glu Asp Asp
    130                 135                 140

Asp Asn Asp Ser Glu Asp Gly Asn Gly Gly Phe Met His Pro Asn Met
145                 150                 155                 160

Ser Ser Ala Ser Ser Ala Leu Gln Gly Leu Leu Arg Lys Leu Gly Ala
                165                 170                 175

Gly Leu Asp Asp Leu Leu Pro Ser Ser Gly Ile Gly Ser Gly Ser Ser
            180                 185                 190

Ser His Leu Asn Gly Arg Met Lys Lys Ile Leu Ala Gly Leu Arg Ser
        195                 200                 205

Glu Gly Glu Glu Gly Lys Gln Val Glu Ala Leu Thr Gln Leu Cys Glu
    210                 215                 220

Met Leu Ser Ile Gly Thr Glu Asp Ser Leu Ser Thr Phe Ser Val Asp
225                 230                 235                 240

Ser Phe Val Pro Val Leu Val Gly Leu Leu Asn His Glu Ser Asn Pro
                245                 250                 255

Asp Ile Met Leu Leu Ala Ala Arg Ala Leu Thr His Leu Cys Asp Val
            260                 265                 270

Leu Pro Ser Ser Cys Ala Ala Val Val His Tyr Gly Ala Val Ser Cys
        275                 280                 285

Phe Val Ala Arg Leu Leu Thr Ile Glu Tyr Met Asp Leu Ala Glu Gln
    290                 295                 300

Ser Leu Gln Ala Leu Lys Lys Ile Ser Gln Glu His Pro Thr Ala Cys
305                 310                 315                 320

Leu Arg Ala Gly Ala Leu Met Ala Val Leu Ser Tyr Leu Asp Phe Phe
                325                 330                 335

Ser Thr Gly Val Gln Arg Val Ala Val Ser Thr Ala Ala Asn Met Cys
            340                 345                 350

Lys Lys Leu Pro Ser Asp Ala Ser Asp Tyr Val Met Glu Ala Val Pro
        355                 360                 365

Val Leu Thr Asn Leu Leu Gln Tyr His Asp Ala Lys Val Leu Glu Tyr
    370                 375                 380

Ala Ser Ile Cys Leu Thr Arg Ile Ala Glu Ala Phe Ala Ser Ser Pro
385                 390                 395                 400

Asp Lys Leu Asp Glu Leu Cys Asn His Gly Leu Val Thr Gln Ala Ala
                405                 410                 415

Thr Leu Ile Ser Ala Ser Asn Ser Gly Gly Gly Gln Ala Ser Leu Gly
            420                 425                 430

Val Ser Thr Tyr Thr Gly Leu Ile Arg Leu Leu Ser Thr Cys Ala Ser
        435                 440                 445
```

-continued

```
Gly Ser Pro Leu Gly Cys Arg Thr Leu Leu Leu Leu Gly Ile Ser Ser
    450                 455                 460

Ile Leu Lys Asp Ile Leu Ser Gly Ser Gly Val Ser Ala Asn Ala Ser
465                 470                 475                 480

Ile Ser Pro Ala Leu Ser Arg Pro Ala Asp Gln Ile Phe Glu Ile Val
                485                 490                 495

Asn Leu Ala Asn Glu Leu Leu Pro Pro Leu Pro Glu Gly Ser Ile Ser
            500                 505                 510

Leu Pro Thr Ser Ala Asn Ala Leu Val Lys Gly Ser Gly Gln Lys Asn
        515                 520                 525

Ser Ser Pro Ser Thr Ser Gly Lys Gln Glu Asp Ser Pro Lys Val Ser
    530                 535                 540

Pro Arg Glu Lys Leu Leu Cys Asp Gln Pro Glu Leu Leu Gln Gln Phe
545                 550                 555                 560

Gly Leu Asp Leu Leu Pro Val Leu Val Gln Ile Tyr Gly Ser Ser Val
                565                 570                 575

Asn Gly Thr Ile Arg His Lys Cys Leu Ser Val Ile Ala Lys Leu Met
            580                 585                 590

Tyr Phe Ser Thr Pro Glu Met Ile Gln Ser Leu Ile Gly Asp Thr Asn
        595                 600                 605

Ile Ser Ser Phe Leu Ala Ser Val Leu Ala Trp Lys Asp Pro Gln Val
    610                 615                 620

Leu Val Pro Ala Leu Gln Val Ala Glu Ile Leu Met Glu Lys Leu Pro
625                 630                 635                 640

Glu Thr Phe Ser Lys Val Phe Val Arg Glu Gly Val Val His Ala Val
                645                 650                 655

Asp Gln Leu Val Leu Val Gly Lys Pro Ser Ala Asn Ala Ser Thr Asp
            660                 665                 670

Gln Glu Asn Asp Cys Val Pro Gly Ser Ala Arg Ser Arg Arg Tyr Arg
        675                 680                 685

Arg Arg Ser Ser Asn Ala Asn Ser Asp Gly Asn Gln Ser Glu Glu Leu
    690                 695                 700

Lys Asn Ser Val Ser Ala Ser Ile Gly Ala Thr His Asn Ser Met Glu
705                 710                 715                 720

Ser Pro Thr Ala Ser Phe Met Leu Arg Glu Thr Val Ser Ser Cys Ala
                725                 730                 735

Lys Ala Phe Lys Asp Lys His Phe Pro Ser Asp Gly Gly Glu Phe Asp
            740                 745                 750

Val Gly Val Thr Asp Asp Leu Leu His Leu Lys Asn Leu Cys Thr Lys
        755                 760                 765

Leu Thr Ala Gly Thr Asn Asp His Lys Val Lys Gly Lys Gly Lys Ser
    770                 775                 780

Lys Val Ser Gly Pro Cys Leu Gly Asp Phe Ser Ala Ser Lys Glu Glu
785                 790                 795                 800

Tyr Leu Ile Gly Ile Ile Ser Glu Ile Leu Gly Glu Leu Ser Lys Gly
                805                 810                 815

Asp Gly Val Ser Thr Phe Glu Phe Ile Gly Ser Gly Val Val Ala Ala
            820                 825                 830

Leu Leu Asn Tyr Phe Ser Tyr Gly Tyr Phe Ser Lys Glu Lys Ile Ser
        835                 840                 845

Glu Val Asp Leu Pro Lys Leu Arg Gln Asp Gly Leu Arg Arg Phe Lys
    850                 855                 860

Ala Phe Leu Glu Ile Ala Leu Pro Ser Asp Gly Asn Glu Gly Lys Ile
```

-continued

```
865                 870                 875                 880

Pro Pro Met Thr Val Leu Ile Gln Lys Leu Gln Asp Ala Leu Ser Ser
                885                 890                 895

Leu Glu Arg Phe Pro Val Val Leu Ser His Pro Ser Arg Ser Leu Ser
            900                 905                 910

Gly Ser Ala Arg Leu Ser Ser Gly Leu Ser Ala Leu Ala His Pro Leu
        915                 920                 925

Lys Leu Arg Leu Cys Arg Ala Pro Gly Glu Lys Ala Leu Arg Asp Tyr
    930                 935                 940

Ser Ser Asn Ile Val Leu Ile Asp Pro Leu Ala Ser Ile Ala Ala Val
945                 950                 955                 960

Glu Glu Phe Leu Trp Pro Arg Val Gln Arg Ser Glu Ser Gly Val Lys
                965                 970                 975

Ala Ala Ala Pro Ala Gly Asn Thr Glu Pro Gly Thr Leu Pro Ser Gly
            980                 985                 990

Ala Gly Val Ser Ser Pro Ser Ser  Ser Thr Pro Ala Ser  Thr Thr Arg
        995                 1000                1005

His Ser  Ser Arg Ser Arg Ser  Ala Ile Lys Ile Gly  Asp Ala Ser
    1010                1015                1020

Lys Lys  Glu Pro Val His Glu  Lys Gly Thr Ser Ser  Ser Lys Gly
    1025                1030                1035

Lys Gly  Val Met Lys Pro Ala  Gln Pro Asp Lys Gly  Pro Gln Thr
    1040                1045                1050

Arg Ser  Ser Ala Gln Arg Lys  Ala Val Leu Asp Lys  Asp Thr Leu
    1055                1060                1065

Met Lys  Pro Ala Ser Gly Asp  Ser Ser Ser Glu Asp  Glu Glu Met
    1070                1075                1080

Asp Ile  Ser Pro Val Asp Met  Asp Asp Ala Leu Val  Ile Glu Glu
    1085                1090                1095

Glu Asp  Ile Ser Asp Asp Asp  Asp Asp Asp Asp Glu  Glu Asp Val
    1100                1105                1110

Leu Asp  Asp Ser Leu Pro Met  Cys Thr Pro Asp Lys  Val His Asp
    1115                1120                1125

Val Lys  Leu Gly Asp Ala Val  Asp Asp Glu Gly Ala  Gly Leu Ala
    1130                1135                1140

Pro Ser  Gly Arg Gln Met Asn  Ser Ala Leu Ala Gly  Ser Ser Gly
    1145                1150                1155

Thr Ala  Thr Ala Arg Gly Ser  Asn Ser Thr Asp Ala  Gly Ile Gly
    1160                1165                1170

Asn Leu  Tyr Gly Ser Arg Gly  Ala Leu Ser Phe Ala  Ala Ala Ala
    1175                1180                1185

Met Ala  Gly Leu Gly Ala Ala  Ser Gly Arg Gly Ile  Arg Gly Ser
    1190                1195                1200

Arg Asp  Leu His Gly Arg Thr  Leu Asn Arg Ser Ser  Asp Glu Ser
    1205                1210                1215

Ser Lys  Leu Met Phe Thr Ala  Gly Gly Lys Gln Leu  Ser Arg His
    1220                1225                1230

Met Thr  Ile Tyr Gln Ala Val  Gln Arg Gln Leu Met  Leu Asp Glu
    1235                1240                1245

Asp Asp  Asp Asp Arg Leu Gly  Gly Ser Asp Phe Ile  Ser Ser Asp
    1250                1255                1260

Gly Ser  Arg Leu Asn Asp Ile  Tyr Thr Ile Met Tyr  Gln Met Pro
    1265                1270                1275
```

-continued

```
Asp Ser  Gln Ala Asn Arg Leu  Ser Ala Gly Gly Ala  Ser Ser Thr
    1280                 1285                 1290

Thr Pro  Ser Lys Ser Thr Lys  Ser Ala Thr Thr Asn  Ala Ser Val
    1295                 1300                 1305

Glu Ala  Gln Ser Tyr Arg Ala  Ser Leu Leu Asp Ser  Ile Val Gln
    1310                 1315                 1320

Gly Lys  Leu Pro Cys Asp Leu  Glu Lys Ala Asn Ser  Thr Tyr Asn
    1325                 1330                 1335

Val Leu  Ala Leu Leu Arg Val  Leu Glu Gly Leu Asn  Gln Leu Gly
    1340                 1345                 1350

Pro Arg  Leu Arg Ala Gln Thr  Ile Ser Asp Arg Phe  Ala Glu Gly
    1355                 1360                 1365

Lys Ile  Thr Ser Leu Asp Asp  Leu Asn Thr Thr Ala  Ala Lys Val
    1370                 1375                 1380

Ser His  Glu Glu Phe Ile Asn  Ser Lys Leu Thr Pro  Lys Leu Ala
    1385                 1390                 1395

Arg Gln  Ile Gln Asp Ala Leu  Ala Leu Cys Ser Gly  Ser Leu Pro
    1400                 1405                 1410

Ser Trp  Cys Tyr Gln Leu Thr  Thr Ala Cys Pro Phe  Leu Phe Pro
    1415                 1420                 1425

Phe Gln  Thr Arg Arg Gln Tyr  Phe Tyr Ser Thr Ala  Phe Gly Leu
    1430                 1435                 1440

Ser Arg  Ala Leu Asn Arg Leu  Gln Gln Gln Gln Gly  Ala Asp Gly
    1445                 1450                 1455

Ser Gly  Ser Thr Asn Glu Arg  Glu Met Arg Ile Gly  Arg Leu Gln
    1460                 1465                 1470

Arg Gln  Lys Val Arg Val Ser  Arg Asn Arg Ile Leu  Asp Ser Ala
    1475                 1480                 1485

Ala Lys  Val Met Glu Met Tyr  Ser Ser Gln Lys Ala  Val Leu Glu
    1490                 1495                 1500

Val Glu  Tyr Phe Gly Glu Val  Gly Thr Gly Leu Gly  Pro Thr Leu
    1505                 1510                 1515

Glu Phe  Tyr Thr Leu Leu Ser  His Asp Leu Gln Lys  Val Ser Leu
    1520                 1525                 1530

Gly Met  Trp Arg Ser Asn Ser  Gly Asp Lys Leu Ser  Met Gln Thr
    1535                 1540                 1545

Asp Arg  Asp Glu Ile Gln Asp  Gly Lys Ser Ala Ala  Ala Arg Asp
    1550                 1555                 1560

Arg Asp  Ile Val Gln Ala Pro  Leu Gly Leu Phe Pro  Arg Pro Trp
    1565                 1570                 1575

Pro Ser  Thr Ala Asp Val Ser  Glu Gly Ser Arg Phe  His Lys Val
    1580                 1585                 1590

Val Glu  Tyr Phe Arg Leu Leu  Gly Arg Val Met Ala  Lys Ala Leu
    1595                 1600                 1605

Gln Asp  Gly Arg Leu Met Asp  Val Pro Leu Ser Thr  Ala Phe Tyr
    1610                 1615                 1620

Lys Leu  Ile Leu Gly Gln Glu  Leu Asp Leu His Asp  Val Ile Ile
    1625                 1630                 1635

Phe Asp  Thr Glu Leu Gly Lys  Thr Leu Gln Glu Leu  Arg Val Leu
    1640                 1645                 1650

Val Gly  Arg Lys His Tyr Leu  Glu Ala Glu Gly Gly  Asp Asn Ser
    1655                 1660                 1665
```

```
Ser Val  Ile Ser Asp Leu Cys  Leu Arg Gly Ser Arg  Ile Glu Asp
    1670                 1675                 1680

Leu Cys  Leu Asp Phe Thr Leu  Pro Gly Tyr Pro Glu  Tyr Ile Leu
    1685                 1690                 1695

Arg Pro  Gly Asp Asp Ile Val  Asp Ile Asn Ser Leu  Glu Asp Tyr
    1700                 1705                 1710

Ile Ser  Leu Val Val Asp Ala  Thr Val Lys Arg Gly  Val Ala Arg
    1715                 1720                 1725

Gln Ile  Glu Ala Phe Arg Ser  Gly Phe Asn Gln Val  Phe Asp Ile
    1730                 1735                 1740

Lys Ser  Leu Gln Val Phe Thr  Pro Ser Glu Leu Asp  Tyr Leu Leu
    1745                 1750                 1755

Cys Gly  Arg Arg Glu Leu Trp  Glu Ala Glu Thr Leu  Val Glu His
    1760                 1765                 1770

Ile Lys  Phe Asp His Gly Tyr  Thr Ala Lys Ser Pro  Ala Ile Ile
    1775                 1780                 1785

Phe Leu  Leu Glu Ile Met Gly  Glu Leu Thr Ala Asp  Gln Gln Arg
    1790                 1795                 1800

Ala Phe  Cys Gln Phe Val Thr  Gly Ala Pro Arg Leu  Pro Pro Gly
    1805                 1810                 1815

Gly Leu  Ala Val Leu Asn Pro  Lys Leu Thr Ile Val  Arg Lys Leu
    1820                 1825                 1830

Ser Ser  Thr Ser Asn Ala Ala  Ala Asn Gly Thr Gly  Ala Ser Glu
    1835                 1840                 1845

Thr Ala  Asp Asp Asp Leu Pro  Ser Val Met Thr Cys  Ala Asn Tyr
    1850                 1855                 1860

Leu Lys  Leu Pro Pro Tyr Ser  Thr Lys Glu Ile Met  Tyr Lys Lys
    1865                 1870                 1875

Leu Leu  Tyr Ala Ile Asn Glu  Gly Gln Gly Ser Phe  Asp Leu Ser
    1880                 1885                 1890
```

<210> SEQ ID NO 35
<211> LENGTH: 9159
<212> TYPE: DNA
<213> ORGANISM: Brassica rapa

<400> SEQUENCE: 35

```
aatgtgtttg atatatacca tggatagtag tgagaaggta gagttcaaag tataagaaag     60

cgaacccctc catagtgggg gcttaaaccc gtgcaagctt gcatatatct atagctgatg    120

gttgggccca aacttatatc ttgggcttat tttgtttcca tctgtccagc ccatgataaa    180

gtgtaaaacg acaccgtata aagcttaatg gagtaaacga atcacacgta gcggggatcc    240

ccgtgtcagt tcttgtccga aaagctggac ggaggaaaac ggcatcgtat tcgcttcgct    300

tgaatatata tattttgcgc aaaagccctt ttcatccctt tcttctctca ttactcgatt    360

tagggttttc taatctcgaa agaaatcaag atcctccttc ctccctctct cgatttcgat    420

ctctttcgtg ttgatttcga attcgttcgt caataggttt gtttctctct agctccgatc    480

gatctcgcta gcaaattagg gtttcgagcg agcttaatcc gatcggtttc tggatcagtt    540

gagatgcgat cggaatctct ctgaataaga gagactcgtg tggggggttt cttcctttgt    600

atggaaactc ggagccgcaa gcgtgcggag gcgacctcaa ctgccccatc ttcttcttct    660

tcctctcctc ctcctcctcc ttcctcaggt cccaccactc gcagcaaacg cgctcgcctc    720

tcgtctccct cttcatcttc agccgccgct actgcacctt cctcctccac ccgctctcgt    780
```

-continued

```
tcttctcgct ctaccaccgc tacagtcgcc gttactccca tggacacatc caccgagtct    840
tctggattcc accgcggcgg aggacgaggt aacaggggaa acgataatac taactctgat    900
aagggaaaag agaaggagca tgaggttagg attagggata gagaaagaga cagagctagg    960
caacagctca acatggacgc tgcagctgct gctgccgccg ccgctgacga ggacgacgac   1020
aatgatagtg aggatggcaa cgggggattc atgcatccca acatgagctc agccagcagt   1080
gcgttacaag ggttgctgag gaagcttgga gctggacttg atgacttgct tccttcttca   1140
ggtattggct caggttcgtc ttctcacttg aatgggagga tgaagaaggt actcgctggc   1200
ttgcgctctg aaggagaaga gggaaagcag gtcgaggctt tgacgcagct gtgcgagatg   1260
ttatctattg ggaccgaaga ctccctgagc accttctctg ttgattcctt cgtcccggtt   1320
cttgttggtc tacttaacca tgagagcaat ccggatatta tgcttcttgc tgccagggct   1380
cttactcatc tgtgtgatgt tttgccgtct tcttgtgctg ctgttgttca ttacggggct   1440
gtttcgtgct ttgtcgccag attgttgaca atagaataca tggacttggc cgagcaggtt   1500
cgatttccta acaattcttg aatttttttg ctgaatatat attgtggaat gttttatgct   1560
gcagtttcta cacgtacata tccaatattt tagtttactt aggacgaaat ttgaaatttg   1620
attttattct tcatgtgatt tacaacagtc tctgcaagct ctcaaaaaga tatctcagga   1680
acacccaacg gcctgtttgc gtgctggtgc tcttatggca gtgctatcat atctggattt   1740
cttctccacc ggtgtccagg tgggtaattt tgtaactttt ctttaatgct ttccatactc   1800
gtttatctaa tgcacttttt tttttacttt ttgtagcgtg tagcagtatc taccgctgca   1860
aatatgtgca agaagttacc ttctgatgca tctgattatg ttatggaagc tgtaccggta   1920
ctgacaaacc tacttcagta tcatgatgcg aaggtaaacg atcccttttt ttttgctata   1980
atgtggtatt atctagttct gctcttgccc cagtttcctt catagtatgt tcgtacggtg   2040
gcaggttttg gaatatgctt ctatctgttt gactcggatt gccgaagcat ttgcatcgtc   2100
ccctgataaa ttagatgaat tatgcaacca tggcctggtg actcaagctg cgactcttat   2160
atccgctagc aactcgggag gtgggcaagc atctctcggt gtttcaacat acacggtatg   2220
agttaattct tttgtgtttt ctatatttcg ttattcatag gatgacattt tcatcatatt   2280
ttcacaggga ttaatccgat tactttccac ctgtgcgagc ggttcacctc ttgggtgcag   2340
gacattactt cttctcggta ttagtagcat tcttaaggat attctgtcgg gttccggtgt   2400
ctctgctaat gcatctatat ccccagcact gagcaggcct gcagatcagg tacggattta   2460
ctttttgaca tcacagactt tattttgttc aattcctgat aaagtctatt cagtaaaaag   2520
tgttttgttt aggggacaca cctttaaata gatcatcaac ataaattgtg tgttgagtga   2580
gatgcttagg ggacacacct tcaaatagat cacttgcatt taaatggatc acttgcattt   2640
aggagttttg tctattcagt tcaatgataa tctttttttt tttgtaacac tcagctcaat   2700
gataatctat gtacatgtat tttgagcttt atttatgttg taaccgatgg ctcaactttc   2760
atatgcttgt tttctggtat ggtgttagaa gtggtataga taaaagtgct tagcgcttca   2820
tcagtgtgct cggtcttgtt tatttaactt tttttatccc atgactcgct aattcttgaa   2880
tatattcttg aacatgatca tgtgaggtct tttgtttccg aattataact cttgttttgc   2940
atcttagatt tttgagatag tcaacctagc gaacgagctc ctccctccac tgccagaagg   3000
aagtatctcc cttcctacta gcgcaaacgc gttagtgaaa ggttcaggcc aaaaaaagtc   3060
ttctccaagt acttcaggaa aacaagaaga ttctcccaaa gtttcaccta gagaaaaatt   3120
acttagtgat caacccgaac ttctgcagca atttggattg gatcttcttc cagttttagt   3180
```

```
gcaggtaatt ttttgttgca gttgctacaa gttagtgttc atacaacctc ctgtatgtct   3240
aattaccctt gttttctttc ctacagatct atggttctag tgtcaatggt actattcgtc   3300
ataaatgtct ctcagttatc gcaaagttga tgtatttcag cactccagaa atgattcaat   3360
ctctaattgg tgacacaaat atatcgaggt atgctggtta tgttttaaat taggtatcac   3420
atggcgcaac ttcttacatt atttttccta tgtagcttct tggctagtgt cttggcatgg   3480
aaagatccac aagtcttggt tcctgctcta caagttgcag aaattctgat ggaaaaactt   3540
cctgaaactt tctcgaaagt gtttgtgagg gaaggggtgg ttcatgctgt agatcaactt   3600
gtcttggttg gtaaacctag ttctcatgct tctactgatc aggaaaatga ctgtgtgcct   3660
ggatctgcac gatctaggcg ttatagacgg cgaagtagta acgccaattc tgatggaaat   3720
cagtcggaag agcttaagaa ttctgtgtca gctagtatag gtgcaaacca taattccatg   3780
gaatctccta cagcgagctt catgctaagg gaaacagtta gctcctgtgc aaaagcattc   3840
aaagacaagc acttcccgtc tgatggtggg gaatttgatg ttggagttac agatgatctc   3900
ttgcatctga agaatctttg cacgaagcta actgctggta caaatgatca taaagtgaaa   3960
ggaaagggga aatctaaagc ctctgggcca tgcctcggcg atttttctgc tagcaaagaa   4020
gaatacttga ttggtatcat ctccgagata cttggcgagc taagcaaagg agatggtgtc   4080
tcaactttg agtttattgg cagtggtgtg gtagcagcat tgcttaacta tttttcttat    4140
ggatactttt ccaaagagaa gatctccgag gttgatttgc ccaaacttcg ccaggatggg   4200
ctcagaaggt tcacagcttt tctagaaatt gcacttcctt ctgatggtaa tgagggaaag   4260
atccctccta tgactgtttt gattcagaaa cttcaagatg ctttgtcttc actggaacgc   4320
tttccggtcg tccttagcca tccctcaaag tcactcagtg gaagtgctcg tctctcatct   4380
ggattgagtg ctttggcaca tcctttgaag ttgcggttat gccgtgcacc tggagagaag   4440
gcactacgtg attactcctc caatattgtt ctcatagatc ctttggcaag catagcagca   4500
gtggaggaat ttctctggcc ccgagttcaa cgcagtgaat ctggggtgaa gccagcagcg   4560
cctgttggaa acactgagcc aggcacatta cctagcggtg ctggtgtttc atcaccatcc   4620
tcgtcaactc cagcttccac cactcgtcat tcttctagat ctagatctgc aattaaaata   4680
ggcgatgcct caaagaaaga acctgtgcac gagaaaggta ccagctcatc taaaggtaaa   4740
ggtgttatga agccggctca gccggataag gggcctcaga caaggagcag tgctcaaagg   4800
aaagctgttc ttgacaaaga tacactaatg aaaccagcta gcggagactc cagctctgag   4860
gtatgtcact gtagaaagtt ctggattaca tggttgttta ttgtgtaaca ttatattatg   4920
tttgtggtgt gatctgctta tgcagcacta tcgtacttat attgcttgca ggacgaagaa   4980
atggatatat cccccgtcga catggatgat gctttggtta ttgaagagga agacatttct   5040
gacgacgatg aggatgatga tgatgaggat gtaagtattc cctccccagt atgtacatta   5100
cagacgcaat tatttctctt gctaacaaca tgaaagatga tacttttcgc aataatgctt   5160
gctagctttc cgtattctta gataagttta ccatattgag ctcaccttat ttggcacctt   5220
tcctttaga actgactaaa gagaataatg aactttatac cacaatttct catattgatc    5280
tggtcttgaa ttcaggtctt ggatgacaat cttcccatgt gcacccctga taaggttcat   5340
gatgtaaaat tgggagacgc agtggatgat gagggagccg gtctagcacc tagcggccga   5400
cagatgaatt cagctttggc aggaagtagt ggaacagcaa ctgcaagggg atctaattct   5460
actgatgctg gcattgggaa tctttatggt tctaggggtg cactctcctt cgctgctgcg   5520
```

-continued

```
gcgatggcag ggcttggagc tgccagtggt agaggtatca ggggaagtag agacctacat   5580
gggcgtaccc tgaatcgaag ttctgatgag tcctctaagt tgatgtttac tgcgggagga   5640
aagcaactta gtaggcatat gacgatatat caggctgtgc aacgacaact tatgctagac   5700
gaagatgatg atgacaggct cggtggcagc gatttcatct ccagtgatgg aagcagatta   5760
aatgatatat atactatcat gtaccagatg ccggacagcc aagcgaatag gttgtctgct   5820
ggtggtgcaa gttctaccac accatctaaa tccaccaaat ctgctactac taatgcaagc   5880
gtagaagctc agtcgtatag ggcatctctt ttggatagta tcgtacaagg aaagcttcca   5940
tgcgaccttg agaagtccaa ttctacgtat aatgttctgg cgttgttacg tgtattagag   6000
ggtttaaatc agcttggccc tcgcttaaga gcccaaaccg tttctgatcg ttttgcagag   6060
ggtaaaatta caagtctgga tgatctgaat acaactgctg caaaggtttc tcatgaagaa   6120
ttcatcaaca gcaaacttac acccaaatta gctcgacaga tccaggacgc gcttgctttg   6180
tgcagtggaa gtcttccctc ttggtgctac cagttgacta cagcatgccc gtttttgttt   6240
ccgtttcaga cccggagaca gtatttctat tcaactgcct ttgggttgtc gcgtgcattg   6300
aaccgcttgc agcagcagca aggtgctgac ggcagtggtt ctacaaatga acgagagatg   6360
agaataggga gattgcagcg ccagaaagtg cgtgtatccc gaaatagaat attagattct   6420
gctgcgaaag ttatggagat gtattctagc caaaaagctg tgcttgaagt agaatatttt   6480
ggtgaagttg gtactggtct aggcccgaca cttgagtttt acacactcct aagccatgat   6540
ttgcaaaagg tttcccttgg gatgtggaga tcaaattctg gtgacaagtt atctatgcaa   6600
actgatagag atgagattca agacggtaaa tcagcagcag ctagggacag agatatagtt   6660
caggcaccac ttgggttgtt ccctcggccc tggccctcaa ctgctgacgt atctgaaggt   6720
agtcggtttc ataaagttgt tgaatatttc cgccttttag ggcgcgtgat ggcaaaggca   6780
cttcaagatg gacggctaat ggacgtcccg ttaagtacag ctttttataa gctcattctt   6840
ggtcaagtga gtttttttact atcagtaact ttttttattt agctaagagt ggactagtag   6900
tttcgacttc tttacgttgt tcgtaatttc ttactgcttc tttactcacc tgaacaggag   6960
cttgatttgc atgatgttat attatttgat gctgaacttg gcaagacttt gcaagagctt   7020
cgtgttcttg ttggccgtaa gcactatctg gaagcaggcg gtggtgacaa cagtagcggg   7080
atttctgatt tatgtttgcg tggatcccgt attgaagatc tttgcttgga cttcacccta   7140
cctggctacc ctgaatacat attgagacca ggagatgaca ttgtaccgtc taataagctt   7200
tacatccgat atcttactat tgttttagtt cttgtccatt gttgctgatg ccgtgtactg   7260
ttttctgttc tattacaggt tgatattaat agtcttgagg actatatatc cctggtcgtt   7320
gatgccactg tcaagagagg agttgcccgg cagattgaag ccttcagatc tggattcaat   7380
caggttagca gtttcacaga ctctccgctt tgtctcttac ttttcctgta ggctttggct   7440
ttggctttgg ctttggcttc taaattacat aggagtggtt tcttttggtt catactttat   7500
aatcttttaa acaacaggtt gatgataatt tagtcttacc tttattatct ttacaagaat   7560
tctctgttct tacacatgat taccaggtct ttgacataaa atctctacaa atattcaccc   7620
cttctgagct ggactacttg ttgtgtggtc gtagagagtt gtgggaggtg agttttcatc   7680
tattttttga atttccacta cccatttgac tcgaatcgac tagataaaat tttcttttct   7740
aaaacctttc ttttattgca ggcggagact cttgttgaac atatcaagtt tgatcacggt   7800
tatactgcaa aaagtccggc aatcattttc gtaagttact ttccgtacta gtttgttaaa   7860
aaaccaattt tcttttacaa tcaagctttt tgcttcttta ttgttgattc ctttttgact   7920
```

```
ttgattttca ccctggcggt agttattgga gatcatggga gagctaacag cagatcaaca   7980

gcgggctttc tgccagttcg taactggagc tcctaggctt cctcctggtg gcttagctgt   8040

tctcaaccca aggctgacga ttgtgagaaa ggtaagaaac ctttacttat atattcggtt   8100

aaaaagcgtt tttgtaattg agccaagagg ttctagtcat gttaaactag acccaccaag   8160

ccatatatca gaatacatct acacgtgacg cattgttgtg tttgcaagac ttgctaagat   8220

gaattagctc ttactcgatt taagttgtgt atttgcttcc aattgatgtg tttttggctt   8280

gatgcagctc tcatcaacct caaatgctgc tgccaatggg acaggggctt cggaaacagc   8340

agacgacgat cttcccagcg tcatgacttg cgccaactac cttaagctcc ctccttattc   8400

tacaaaggta actcgtctct ctttttttaa gtctacggtt tctgtgtttg gttggttggg   8460

gtgagcctga acacgagttt gtacctgaaa caggaaatca tgtacaagaa actgctctac   8520

gccatcaacg aagggcaggg gtcgttcgac ctatcctagg catctctctc tgttgtggct   8580

gcggctagaa accaccaacc ctctctcttc tttgtacatt ttatatcgga agactctgat   8640

tttgcacttt gaatgttatt tctgttaaac catgaattat taaaattagg ttcaatattt   8700

ttcatgtgca agtaacatat taatacatgg aggataaaaa taaaatcaaa agacaaactt   8760

gaataatttt ggttgccttt aaaattcgtt tgaaaattcc gaagcaatta tatatagtgt   8820

gaataaaagt cgtcagctga aggaataaag gtacaaaggt acaaaggttt aggtgttgta   8880

tgatccaaaa ttctgttttt ttttaaagac gggctctatc agtcacagca gttgactgta   8940

agatatcaaa ggaataagaa acagttgttc gtttgtagtt ttctggagat tgaacaagag   9000

aactcgtctt cgtttcatca gttttctttt tgataaaagt caattcgaca tagatatctc   9060

tagacacgag aaacaaaagc ataaatagga aaacattaca attataaaag agcgttacga   9120

gtacagagtc caaactaggc acaagaaacc taccatatg                          9159
```

<210> SEQ ID NO 36
<211> LENGTH: 1888
<212> TYPE: PRT
<213> ORGANISM: Brassica napus

<400> SEQUENCE: 36

```
Met Glu Thr Arg Ser Arg Lys Arg Ala Glu Ala Thr Ser Thr Ala Pro
1               5                   10                  15

Ser Ser Ser Ser Ser Ser Pro Pro Pro Pro Pro Ser Ser Gly Pro Thr
            20                  25                  30

Thr Arg Ser Lys Arg Ala Arg Leu Ser Ser Pro Ser Ser Ser Ser Ala
        35                  40                  45

Ala Ala Thr Ala Pro Ser Ser Ser Thr Arg Ser Arg Ser Ser Arg Ser
    50                  55                  60

Thr Thr Ala Thr Val Ala Val Thr Pro Met Asp Thr Ser Thr Glu Ser
65                  70                  75                  80

Ser Gly Phe His Arg Gly Gly Gly Arg Gly Asn Arg Gly Asn Asp Asn
                85                  90                  95

Thr Asn Ser Asp Lys Gly Lys Glu Lys Glu His Glu Val Arg Ile Arg
            100                 105                 110

Asp Arg Glu Arg Asp Arg Ala Arg Gln Gln Leu Asn Met Asp Ala Ala
        115                 120                 125

Ala Ala Ala Ala Ala Ala Ala Asp Glu Asp Asp Asp Asn Asp Ser Glu
    130                 135                 140

Asp Gly Asn Gly Gly Phe Met His Pro Asn Met Ser Ser Ala Ser Ser
```

-continued

```
145                 150                 155                 160

Ala Leu Gln Gly Leu Leu Arg Lys Leu Gly Ala Gly Leu Asp Asp Leu
                165                 170                 175

Leu Pro Ser Ser Gly Ile Gly Ser Gly Ser Ser Ser His Leu Asn Gly
            180                 185                 190

Arg Met Lys Lys Val Leu Ala Gly Leu Arg Ser Glu Gly Glu Glu Gly
        195                 200                 205

Lys Gln Val Glu Ala Leu Thr Gln Leu Cys Glu Met Leu Ser Ile Gly
    210                 215                 220

Thr Glu Asp Ser Leu Ser Thr Phe Ser Val Asp Ser Phe Val Pro Val
225                 230                 235                 240

Leu Val Gly Leu Leu Asn His Glu Ser Asn Pro Asp Ile Met Leu Leu
                245                 250                 255

Ala Ala Arg Ala Leu Thr His Leu Cys Asp Val Leu Pro Ser Ser Cys
            260                 265                 270

Ala Ala Val Val His Tyr Gly Ala Val Ser Cys Phe Val Ala Arg Leu
        275                 280                 285

Leu Thr Ile Glu Tyr Met Asp Leu Ala Glu Gln Ser Leu Gln Ala Leu
    290                 295                 300

Lys Lys Ile Ser Gln Glu His Pro Thr Ala Cys Leu Arg Ala Gly Ala
305                 310                 315                 320

Leu Met Ala Val Leu Ser Tyr Leu Asp Phe Phe Ser Thr Gly Val Gln
                325                 330                 335

Arg Val Ala Val Ser Thr Ala Ala Asn Met Cys Lys Lys Leu Pro Ser
            340                 345                 350

Asp Ala Ser Asp Tyr Val Met Glu Ala Val Pro Val Leu Thr Asn Leu
        355                 360                 365

Leu Gln Tyr His Asp Ala Lys Val Leu Glu Tyr Ala Ser Ile Cys Leu
    370                 375                 380

Thr Arg Ile Ala Glu Ala Phe Ala Ser Ser Pro Asp Lys Leu Asp Glu
385                 390                 395                 400

Leu Cys Asn His Gly Leu Val Thr Gln Ala Ala Thr Leu Ile Ser Ala
                405                 410                 415

Ser Asn Ser Gly Gly Gly Gln Ala Ser Leu Gly Val Ser Thr Tyr Thr
            420                 425                 430

Gly Leu Ile Arg Leu Leu Ser Thr Cys Ala Ser Gly Ser Pro Leu Gly
        435                 440                 445

Cys Arg Thr Leu Leu Leu Leu Gly Ile Ser Ser Ile Leu Lys Asp Ile
    450                 455                 460

Leu Ser Gly Ser Gly Val Ser Ala Asn Ala Ser Ile Ser Pro Ala Leu
465                 470                 475                 480

Ser Arg Pro Ala Asp Gln Ile Phe Glu Ile Val Asn Leu Ala Asn Glu
                485                 490                 495

Leu Leu Pro Pro Leu Pro Glu Gly Ser Ile Ser Leu Pro Thr Ser Ala
            500                 505                 510

Asn Ala Leu Val Lys Gly Ser Gly Gln Lys Lys Ser Ser Pro Ser Thr
        515                 520                 525

Ser Gly Lys Gln Glu Asp Ser Pro Lys Val Ser Pro Arg Glu Lys Leu
    530                 535                 540

Leu Ser Asp Gln Pro Glu Leu Leu Gln Gln Phe Gly Leu Asp Leu Leu
545                 550                 555                 560

Pro Val Leu Val Gln Ile Tyr Gly Ser Ser Val Asn Gly Thr Ile Arg
                565                 570                 575
```

-continued

```
His Lys Cys Leu Ser Val Ile Ala Lys Leu Met Tyr Phe Ser Thr Pro
            580                 585                 590

Glu Met Ile Gln Ser Leu Ile Gly Asp Thr Asn Ile Ser Ser Phe Leu
        595                 600                 605

Ala Ser Val Leu Ala Trp Lys Asp Pro Gln Val Leu Val Pro Ala Leu
    610                 615                 620

Gln Val Ala Glu Ile Leu Met Glu Lys Leu Pro Glu Thr Phe Ser Lys
625                 630                 635                 640

Val Phe Val Arg Glu Gly Val Val His Ala Val Asp Gln Leu Val Leu
                645                 650                 655

Val Gly Lys Pro Ser Ser His Ala Ser Thr Asp Gln Glu Asn Asp Cys
            660                 665                 670

Val Pro Gly Ser Ala Arg Ser Arg Arg Tyr Arg Arg Arg Ser Ser Asn
        675                 680                 685

Ala Asn Ser Asp Gly Asn Gln Ser Glu Glu Leu Lys Asn Ser Val Ser
    690                 695                 700

Ala Ser Ile Gly Ala Asn His Asn Ser Met Glu Ser Pro Thr Ala Ser
705                 710                 715                 720

Phe Met Leu Arg Glu Thr Val Ser Ser Cys Ala Lys Ala Phe Lys Asp
                725                 730                 735

Lys His Phe Pro Ser Asp Gly Gly Glu Phe Asp Val Gly Val Thr Asp
            740                 745                 750

Asp Leu Leu His Leu Lys Asn Leu Cys Thr Lys Leu Thr Ala Gly Thr
        755                 760                 765

Asn Asp His Lys Val Lys Gly Lys Gly Lys Ser Lys Ala Ser Gly Pro
    770                 775                 780

Cys Leu Gly Asp Phe Ser Ala Ser Lys Glu Glu Tyr Leu Ile Gly Ile
785                 790                 795                 800

Ile Ser Glu Ile Leu Gly Glu Leu Ser Lys Gly Asp Gly Val Ser Thr
                805                 810                 815

Phe Glu Phe Ile Gly Ser Gly Val Val Ala Ala Leu Leu Asn Tyr Phe
            820                 825                 830

Ser Tyr Gly Tyr Phe Ser Lys Glu Lys Ile Ser Glu Val Asp Leu Pro
        835                 840                 845

Lys Leu Arg Gln Asp Gly Leu Arg Arg Phe Thr Ala Phe Leu Glu Ile
    850                 855                 860

Ala Leu Pro Ser Asp Gly Asn Glu Gly Lys Ile Pro Pro Met Thr Val
865                 870                 875                 880

Leu Ile Gln Lys Leu Gln Asp Ala Leu Ser Ser Leu Glu Arg Phe Pro
                885                 890                 895

Val Val Leu Ser His Pro Ser Lys Ser Leu Ser Gly Ser Ala Arg Leu
            900                 905                 910

Ser Ser Gly Leu Ser Ala Leu Ala His Pro Leu Lys Leu Arg Leu Cys
        915                 920                 925

Arg Ala Pro Gly Glu Lys Ala Leu Arg Asp Tyr Ser Ser Asn Ile Val
    930                 935                 940

Leu Ile Asp Pro Leu Ala Ser Ile Ala Ala Val Glu Glu Phe Leu Trp
945                 950                 955                 960

Pro Arg Val Gln Arg Ser Glu Ser Gly Val Lys Pro Ala Ala Pro Val
                965                 970                 975

Gly Asn Thr Glu Pro Gly Thr Leu Pro Ser Gly Ala Gly Val Ser Ser
            980                 985                 990
```

```
Pro Ser Ser Ser Thr Pro Ala Ser  Thr Thr Arg His Ser  Ser Arg Ser
        995                 1000                 1005

Arg Ser  Ala Ile Lys Ile Gly  Asp Ala Ser Lys Lys  Glu Pro Val
    1010                 1015                 1020

His Glu  Lys Gly Thr Ser Ser  Ser Lys Gly Lys Gly  Val Met Lys
    1025                 1030                 1035

Pro Ala  Gln Pro Asp Lys Gly  Pro Gln Thr Arg Ser  Ser Ala Gln
    1040                 1045                 1050

Arg Lys  Ala Val Leu Asp Lys  Asp Thr Leu Met Lys  Pro Ala Ser
    1055                 1060                 1065

Gly Asp  Ser Ser Ser Glu Asp  Glu Glu Met Asp Ile  Ser Pro Val
    1070                 1075                 1080

Asp Met  Asp Asp Ala Leu Val  Ile Glu Glu Glu Asp  Ile Ser Asp
    1085                 1090                 1095

Asp Asp  Glu Asp Asp Asp Asp  Glu Asp Val Leu Asp  Asp Asn Leu
    1100                 1105                 1110

Pro Met  Cys Thr Pro Asp Lys  Val His Asp Val Lys  Leu Gly Asp
    1115                 1120                 1125

Ala Val  Asp Asp Glu Gly Ala  Gly Leu Ala Pro Ser  Gly Arg Gln
    1130                 1135                 1140

Met Asn  Ser Ala Leu Ala Gly  Ser Ser Gly Thr Ala  Thr Ala Arg
    1145                 1150                 1155

Gly Ser  Asn Ser Thr Asp Ala  Gly Ile Gly Asn Leu  Tyr Gly Ser
    1160                 1165                 1170

Arg Gly  Ala Leu Ser Phe Ala  Ala Ala Ala Met Ala  Gly Leu Gly
    1175                 1180                 1185

Ala Ala  Ser Gly Arg Gly Ile  Arg Gly Ser Arg Asp  Leu His Gly
    1190                 1195                 1200

Arg Thr  Leu Asn Arg Ser Ser  Asp Glu Ser Ser Lys  Leu Met Phe
    1205                 1210                 1215

Thr Ala  Gly Gly Lys Gln Leu  Ser Arg His Met Thr  Ile Tyr Gln
    1220                 1225                 1230

Ala Val  Gln Arg Gln Leu Met  Leu Asp Glu Asp Asp  Asp Asp Arg
    1235                 1240                 1245

Leu Gly  Gly Ser Asp Phe Ile  Ser Ser Asp Gly Ser  Arg Leu Asn
    1250                 1255                 1260

Asp Ile  Tyr Thr Ile Met Tyr  Gln Met Pro Asp Ser  Gln Ala Asn
    1265                 1270                 1275

Arg Leu  Ser Ala Gly Gly Ala  Ser Ser Thr Thr Pro  Ser Lys Ser
    1280                 1285                 1290

Thr Lys  Ser Ala Thr Thr Asn  Ala Ser Val Glu Ala  Gln Ser Tyr
    1295                 1300                 1305

Arg Ala  Ser Leu Leu Asp Ser  Ile Val Gln Gly Lys  Leu Pro Cys
    1310                 1315                 1320

Asp Leu  Glu Lys Ser Asn Ser  Thr Tyr Asn Val Leu  Ala Leu Leu
    1325                 1330                 1335

Arg Val  Leu Glu Gly Leu Asn  Gln Leu Gly Pro Arg  Leu Arg Ala
    1340                 1345                 1350

Gln Thr  Val Ser Asp Arg Phe  Ala Glu Gly Lys Ile  Thr Ser Leu
    1355                 1360                 1365

Asp Asp  Leu Asn Thr Thr Ala  Ala Lys Val Ser His  Glu Glu Phe
    1370                 1375                 1380

Ile Asn  Ser Lys Leu Thr Pro  Lys Leu Ala Arg Gln  Ile Gln Asp
```

```
    1385                1390                1395

Ala Leu  Ala Leu Cys Ser Gly  Ser Leu Pro Ser Trp  Cys Tyr Gln
    1400                1405                1410

Leu Thr  Thr Ala Cys Pro Phe  Leu Phe Pro Phe Gln  Thr Arg Arg
    1415                1420                1425

Gln Tyr  Phe Tyr Ser Thr Ala  Phe Gly Leu Ser Arg  Ala Leu Asn
    1430                1435                1440

Arg Leu  Gln Gln Gln Gln Gly  Ala Asp Gly Ser Gly  Ser Thr Asn
    1445                1450                1455

Glu Arg  Glu Met Arg Ile Gly  Arg Leu Gln Arg Gln  Lys Val Arg
    1460                1465                1470

Val Ser  Arg Asn Arg Ile Leu  Asp Ser Ala Ala Lys  Val Met Glu
    1475                1480                1485

Met Tyr  Ser Ser Gln Lys Ala  Val Leu Glu Val Glu  Tyr Phe Gly
    1490                1495                1500

Glu Val  Gly Thr Gly Leu Gly  Pro Thr Leu Glu Phe  Tyr Thr Leu
    1505                1510                1515

Leu Ser  His Asp Leu Gln Lys  Val Ser Leu Gly Met  Trp Arg Ser
    1520                1525                1530

Asn Ser  Gly Asp Lys Leu Ser  Met Gln Thr Asp Arg  Asp Glu Ile
    1535                1540                1545

Gln Asp  Gly Lys Ser Ala Ala  Ala Arg Asp Arg Asp  Ile Val Gln
    1550                1555                1560

Ala Pro  Leu Gly Leu Phe Pro  Arg Pro Trp Pro Ser  Thr Ala Asp
    1565                1570                1575

Val Ser  Glu Gly Ser Arg Phe  His Lys Val Val Glu  Tyr Phe Arg
    1580                1585                1590

Leu Leu  Gly Arg Val Met Ala  Lys Ala Leu Gln Asp  Gly Arg Leu
    1595                1600                1605

Met Asp  Val Pro Leu Ser Thr  Ala Phe Tyr Lys Leu  Ile Leu Gly
    1610                1615                1620

Gln Glu  Leu Asp Leu His Asp  Val Ile Leu Phe Asp  Ala Glu Leu
    1625                1630                1635

Gly Lys  Thr Leu Gln Glu Leu  Arg Val Leu Val Gly  Arg Lys His
    1640                1645                1650

Tyr Leu  Glu Ala Gly Gly Gly  Asp Asn Ser Ser Gly  Ile Ser Asp
    1655                1660                1665

Leu Cys  Leu Arg Gly Ser Arg  Ile Glu Asp Leu Cys  Leu Asp Phe
    1670                1675                1680

Thr Leu  Pro Gly Tyr Pro Glu  Tyr Ile Leu Arg Pro  Gly Asp Asp
    1685                1690                1695

Ile Val  Asp Ile Asn Ser Leu  Glu Asp Tyr Ile Ser  Leu Val Val
    1700                1705                1710

Asp Ala  Thr Val Lys Arg Gly  Val Ala Arg Gln Ile  Glu Ala Phe
    1715                1720                1725

Arg Ser  Gly Phe Asn Gln Val  Phe Asp Ile Lys Ser  Leu Gln Ile
    1730                1735                1740

Phe Thr  Pro Ser Glu Leu Asp  Tyr Leu Leu Cys Gly  Arg Arg Glu
    1745                1750                1755

Leu Trp  Glu Ala Glu Thr Leu  Val Glu His Ile Lys  Phe Asp His
    1760                1765                1770

Gly Tyr  Thr Ala Lys Ser Pro  Ala Ile Ile Phe Leu  Leu Glu Ile
    1775                1780                1785
```

```
Met Gly  Glu Leu Thr Ala Asp  Gln Gln Arg Ala Phe  Cys Gln Phe
    1790                 1795                 1800

Val Thr  Gly Ala Pro Arg Leu  Pro Pro Gly Gly Leu  Ala Val Leu
    1805                 1810                 1815

Asn Pro  Arg Leu Thr Ile Val  Arg Lys Leu Ser Ser  Thr Ser Asn
    1820                 1825                 1830

Ala Ala  Ala Asn Gly Thr Gly  Ala Ser Glu Thr Ala  Asp Asp Asp
    1835                 1840                 1845

Leu Pro  Ser Val Met Thr Cys  Ala Asn Tyr Leu Lys  Leu Pro Pro
    1850                 1855                 1860

Tyr Ser  Thr Lys Glu Ile Met  Tyr Lys Lys Leu Leu  Tyr Ala Ile
    1865                 1870                 1875

Asn Glu  Gly Gln Gly Ser Phe  Asp Leu Ser
    1880                 1885
```

<210> SEQ ID NO 37
<211> LENGTH: 20755
<212> TYPE: DNA
<213> ORGANISM: Zea mays

<400> SEQUENCE: 37

```
ttatacgcct acctgcctct attacatcta gttttgggcc tgttacatgc acatttggtt     60
ggcgggctct tgcactgcgc cgcaacccat cgccaactga gcggcccaca tcttgcttgc    120
cgacggcctc gccatttaaa tcaacattct cctcatttac agactccacc gtcgtgctca    180
cactagtgca caagacttat attagatgca acaaccacct aacaaccttg acttgaccta    240
gatacttggt ttacatgaga gggcctatcc atctatagat aacaaattaa aaaaatctgt    300
tggccaaagg ttgttacggg gaatacaaga tatacaaggc cacacaataa aggtgtgcca    360
aacgagtaaa tttggaaata gaattatcct gatatatttt ttagattttt taaaataaaa    420
taaaaatatt taaacaaata tataccctgt gcatatatgt tgtaagattt ttgtatcgag    480
ctgattcgtg catgcgttac agttgaatgg agacattttt gctgagctga ttgatggata    540
gccttccgta gcaattcacg gacgctgacc tagcaaaagc cgtgggttta gcgaagccca    600
gcaacaccct cgcagtgtga agcaccctcg cagtgtgaag cacgtatacc gcatgaaagc    660
cggcccccaa atcacgagct cctccctcta acctccggcc tcttcctgcg tcaccaccgc    720
gcaggcgcag ccatccccat ccttcctcaa attcccaacc ccacccaagc cagatctcac    780
cccctccccg atcgctacac ctccgatgtt cccgcctctt tcgcctatcc cttcatagcc    840
gcgtcgccac cggcgccgct gcgaggcggc cgctgccttt ctccgctccc tttgtatgga    900
aacgcgcagc cgcaagcggg cggaggcctc ttcttcttcc gcgacctcct cctcccgctc    960
ctccaagcgc tcgcgacaca accctaaccc taatcctccc gccggcccct cccccgcccc   1020
caaactcgtc ccgttgccac cacgcacccg ccgctcgacc gctgtcaatc ccctcccccc   1080
gatggattcc tcgggcgaca acaactccaa tcccgtcccg ccgccgcggc gccgcggtcg   1140
cccctccaac acagataagg gtaaggagca gcagcagccg gagccgtctc acagctcccg   1200
agtgcgcgag gccgagcgcc tgctgggtct aggtttcgag ggcattgatg atgatgaaga   1260
ttcagggttc ggggctgggg ccatccccca cagcctgact tccgcgagca ccgcgctcca   1320
gggtcttctt aggaagcttg gtgctggcct ggacgatata ctgccatcgt cggcactgtc   1380
agctgcagct gcagccgcgt catcgtcatc agcatccggg cagctgagtg ggaggttgaa   1440
gaatattctt gcaggtttgc gtgctgatgg ggaggatgga aggcaggtcg aggcgttaac   1500
```

acaactctgt gagatgctgt ccattggcac agaagagtct cttggggcat tctcggtgga 1560
ctcatttgta cctgtcctgg tcggtctgct caatcatgag agcaacccag acatcatgtt 1620
gctcgcagca cgagccctaa ctcacctctg tgatgtgctg ccgtcttctt gttctgcagt 1680
tgtgcattat ggtgctgtgc cttgcttttg tgcccggctt ctcaccattg aatacatgga 1740
cttggcggag caggtatgct ttacattaac acattgcttt caaaatgctg cttgtttgtc 1800
attttgctgc atccctttca ttgatttgtg aacatggttt tatcttgtgt gcttcatatg 1860
ctggtgccta cacattgcct agccttccat ttgttcctaa atagtttgga attgctaatg 1920
gtcagatatt agttcatgtt tcctatatga gtgatataag gcaaagacaa ggagttaagg 1980
aacacaactt tgttcatggt acaccttgtt ctggagaaat gcaacaatta ccttttttatt 2040
ttctgtttac acattaccct gtcttgaatg ctacatagtt tctactgatt agttcagttt 2100
atgactatat ggtcttactt attctctgat acatttggca aaggtaaaac ttcagggcca 2160
acataggcca tgctctcccc cgatcatttt agcaactctg cagaatatct gacagtattt 2220
tgagctatat tgctaatgaa acatgtaaat atgcttttgg aaacactgaa tttatcttca 2280
aatcacaacc ctctttgcct cctaacatcg gctgcaagct ctgccactgg tttttgatag 2340
aacatttttt ctgctttcta ttgttgtttg gatctctaga aataatatct tcacgtttga 2400
aatactatgc atacagataa tagacgcata cgtgtaccat ctctttgtat ttgtatgcat 2460
gctcttgatg gtggcctaac atatatgcta cgttttttta tttagtcatt gcaagctctt 2520
aaaaaaatat ccctggagca tccaactgcg tgcttgcgag ctggtgcact aatggcagtc 2580
ctatcatacc ttgacttttt ctccacaggt gttcaggtaa tcactctctg cctattatag 2640
acttttgcat cacaaaatac tttgtttgtt tcagctcatt tatctcatag cttattctta 2700
tgcattactt gtcattatat tgtgacagat gaactgtatt atttattctt gttatttatt 2760
tttattacta actgttgttt ttgttgatgg aatgttttca gagagttgca ttatctacag 2820
ctgctaatat gtgtaggaaa cttccttctg atgcatcaga ttttgtaatg gaagcggttc 2880
cacttcttac taatctactg aactaccatg attcaaaagt acaattgcca ttccaaatgc 2940
tgatatcctc tatgatacca tttatgtttc agatgctgat attccgtttt gcttattcca 3000
ggtactggag catgcttctg tctgccttac ccgtattgcg gaatcttttt caccatttcc 3060
agaaaaattg gatgagttgt gcagtcatgg attggttgca caagctgcta gcttagtgtc 3120
tgttagcaac tcagcaggac aggcatcctt gagtacatca acatatacgg tacgctccat 3180
tttggctttt tgggtacaat tatttgtttt acgtttgtga agtttatgcc atgtttttat 3240
agggtgtgat tcgtcttctc tcaatatgcg caagtggatc acctctggca gctaaaacac 3300
ttctccttct tggaattagt ggcatactta aagatatcct ttcaggctct gggttggttg 3360
ctggcacgac tgtgtcccct gctttaacaa gaccagctga tcaggtgatt ttgtcttttc 3420
ataggcactt caaggctctt tgggtatcat gtgtgcttga tgtctacatt tgttgtttat 3480
cttaacaagc taaggccccg tttggcactg ctccacttca caaaaacaag cgcaacttca 3540
tgaacttcaa aatatagcag cccagctttg aagttgcaga gtttttgaag agtttggctt 3600
gtagaccagc tttagtttca taaaaaatat aataaaaaaa aacttgtttc ttcttccttt 3660
ggccgtggcg gccagaggcg cacgtgcgcg acttgggaag acagacacaa cgctgcgatg 3720
gcctggcgtg gctctggcgg cccagcgcgc tgcacgcagc ctggcggcac gttgtcggcc 3780
gatgcggccc tgctcgctag cgcaggtggt ggcacgcgcg ctgccagagt ttggttcagg 3840

-continued

```
cgtggctctg gcagcggcac atggcctggc ggtgcggctg ccggtcggca cggccctgct   3900
cgctggcgta actgtgtgcg gcctgagttc ccttgagaac agaacgaaag aaaacatttc   3960
gtgagggatt gcgtaactga tggcaaaggt gggtaatttc accccaactt aatgagggag   4020
ttaaaaatac ccattcgtga agtatacttt tggttgtttc atggatttgg tgaagttagg   4080
gtcaacttca cctttttgg tgaagctggg agtgtttggc tagagtttta taaagctaag   4140
ctagattttg tgaagtgaag cagtcccaaa cattccctaa gtgtaaatta atggagctag   4200
gcttactcta tgcttcagat agtacttcaa ccattgattc caatttccaa gcctcaggat   4260
atcatctcta ttaaggcccc ctttggcacg gctctggctc tagcttcttg cagccccttg   4320
gaaggagccc tgccaaacag ccatctaaaa cacagctcct ggcaaggagc cagggccaga   4380
aaaatggttt ctcccagctc cttacaaact tgatacaaat tattacaaaa ctgccactgg   4440
acctgttttg accaaacctt ttccaaaacg gcttcaactg gcccaaatta taaaggcagc   4500
acaattaatc ccatacactt cccaacctta caagcccctt aatacagccc atctctgcct   4560
tcattctcca tacatatctg aaagtcttcc atgttctctc tcttctacca cttcgtggcg   4620
cagtgagggg ggcttacttc taggagcgcc taacatgtgc tatataacat ctttacgcac   4680
aatgacatag gaacaagtgt cgtcaaagaa aacaaataat atttgtgtat attaaaacat   4740
tttttgatga atttgatgaa atgaaaccaa atcgtcccat aacatgtttt tctcataatg   4800
cattttgttt tttaatcgcc accaataata tactttgagc ttgtagtcaa tgttcgttta   4860
tggtatgaca ttgtttttct ttaatgtgag catactcata ctactttcca tgtcgagcat   4920
ttgtgaacat gatgttatcc tatgttctat tcatgatagc acaatttata tttgtgatga   4980
attgtcatct atgttaaatt ttaatgggta ctgtaacttg taaagctact gactttttgg   5040
tagtaataga ttatcaccac acaattccat atgcaaatga tgccattatg tgtttttttgg  5100
tattacacag atgaatgaga ttgtgaagct tgcagatgag ttacttcctt ctctgcctgt   5160
tgggaccatt tctttaccag tgtattctgg tgttcacatg aaaggttgtt ctgtaaagaa   5220
atccacttct agtaagcagg gtgaacatgg ttcaacagca aatgaactat caggtcggga   5280
gaagttattg cgtgatcagc ctgaacttct gcagcaattt ggcatggacc tgttacctac   5340
catgacacag gtcagtcttg tcttattaat gttctctttg atgttgttaa tggtaatgct   5400
gatgtggtat tacgggacat tgttgctatc atgttggtgt gatacttaag gacttcaata   5460
ccttgaacag gtgtatggct ctagtgtaag tggaccaata cggcacaggt gcttatctgt   5520
cattgggaaa ttaatgtact atagctcagc tgagatgatc cagtctctcc ttagcacaac   5580
aaacatttcc aggtgcttaa cacaatatat ttcatcgagt tatctcatgt tattagaaac   5640
tatcttatca catgaattcc aaatatttgt ttcaagctat taacttctat atcaaccatt   5700
gcagcttttt ggctggcatt ttagcttgga aagatccaca agtgttgatc cctgctcttc   5760
agatagcaga agttttaatg gaaaaacttc cagagatttt tttgaagatg tttgtgaggg   5820
aaggcgttgt tcatgctgtt gagtcactta tatgcccaga attatctggt caggtgactc   5880
ctcatgtgga ttccattaca tcttcacata ataggcgcaa ccgccgtaga aataatgctg   5940
tgaacactgg aaataacttg cctgatggac caaaaggttc caattctatg attgccaatt   6000
cacccccaag catggctgaa gttccaaata atagtcttcg tgctttagtt agtaatcatg   6060
caaagtcatt taaggataaa tatttccctt ccgagcctgg ctcaagtgac attgcagtta   6120
ccgatgacct tcttaaactg agggcacttt gtgcaaaact gaatacaaca gctgacacta   6180
tcaaaacaaa agctaaagga aaatcaaagg tagtgtctga caatagtttt gatgtcttgt   6240
```

```
gcaatattga ggagcaattg gatgatataa tagctgaaat gttgtctgag cttagcaagg   6300
gtgatggtgt ttcgacattt gagttcatcg gaagtggagt tgttacggct ttgctaacct   6360
atctgtcatg tggaacattt gggagggaaa aggtgtctga ggcaaacata ccaaatttgc   6420
gtcatcaggc agtcagacga tacaaaacat ttatatcttt tgcacttcca aatgataaag   6480
atgggaataa aactcctatg gcattcctag tccataaact gcaaagtgcc ctatcttcgt   6540
tggaacgttt cccagttgtg ctcagccatt ctggaagggc atcgactttg ggaggatccc   6600
gcctgacaac aggtttagga tctctgtcgc agcccatcaa attgcgtctt tgtcgagcgc   6660
ctggtgagaa gtcacttaag gatttttcgt ccaatgttgt tcttattgac tcattagcta   6720
gtctggcagc tgttgaagat tttctttggc ctagagtcca gcgcactgaa ccagtattga   6780
agcctccaat gtcatctgca aataattctg gatctggagc agcaagctcc acagcttgtg   6840
cgccttcaat tccatcagaa actcaatctg tccgtcgcac atcgttaaga tcaaagtcat   6900
cagctgccac cagtggtgca attaagaagg attatcagga gggaagcata aacacctcaa   6960
agggaaaagg aaaagctgtt cttaaattga gtttggatga acctaaaggc ccacatacta   7020
ggaatgctgc gcgcagaaaa gctacttcag agaaagatgt tgaactgaag ccatcacatg   7080
gtcacatcac ttcagaggtt agatactcgt gcattcaatc ttatttgtta tttgcataat   7140
atatgcgaaa tggcctctag cctagtggtt aaaggcttcc gaatagcacc tccaagtctc   7200
gggttcgatt cccctcaggg gcgaattttc cggcttcctg tgcgccaccc tccggttgga   7260
ccgctgtaga ggggacggtt gacgtcggct cgttagtgat ggggaggggg ggggcagagt   7320
ttggggattt tctcggccga gaccattgtt ttagtctatc ttgatataat accgggatgg   7380
cggtcattcc ttccctggct gagttttttt tatttgcata atatatcaat tgagccctcc   7440
taagtgagct ccgttgggaa gtttagcttt aatttctggc tctaggacac attgattgca   7500
aatgtttttt taacaatgcc ttttgtttac tcagctgaca aatgttatca tagtaatgat   7560
acaacagtaa tgcagctgat ttattttgcc ttaagtgtat ctagtttgat cagtactttg   7620
ttttagtatg taagcaatgg atttcaaagg gatgttcttc atagacatga tgtacagatt   7680
gtataactat aaaaggaggg gggggcagtg ctgcaggctc cgacatgagg agtctgggga   7740
agggataaac cgaggcaacc cttctcccat aaatacggag agacactgct ttgaacccac   7800
aacctggtga ctccgggaga caattcacac cactgacgta cagattgtat aactataagt   7860
ctataatatc ataaatgtat aacaatgaaa atgcactgaa ctgtgacatt tctgtgtatc   7920
atgcatttat aatattatat ctgagatagg atataaaaac tgaagcattt tttataagag   7980
caacaaagat taaagtagaa atatgcctgt ttcactaata ttttataatt tagtcatatt   8040
atgtaatgac ctgactacgc tttcgtaact tagtatactg gactatattg tggatactca   8100
caaatatgaa atatcagtgt aatcttttac tctaaacaag gttcagctag gcgctaggcg   8160
gaatctaggc ggtgacccat tgcctagcgc ctagtcggga gtactcggtc ttaggcgctt   8220
ctaggcgctt ttctaggcgt tttggcaata tagccataaa ttatatatat atattatgta   8280
tataactata tatacgtata taactactat atatgactat atgagtcaca gtaagtataa   8340
aaagaaggcc agtagacata tctgattcct agctgagctt actcttgcat gttcctagct   8400
cctgcaaggc tgcaacatat tttgacagct agtagttagt aaattagtca atagacagct   8460
agctgttcat aaaaaaaata gaaaacacta aattgtgact tatctggatg atttcagcag   8520
cctcccattc atgagcagtt gagcacactg cacaccatat cagcagctgg taattacaac   8580
```

```
acaagtggat aggacagtaa tacaagtgca gaacacaatt tataaataaa ggacaacaca   8640
agcttccaac acaagtgact tcttctgact cctctccaac cctagataca ttcacttcct   8700
ctctaagttc tagctcacga acagtcttct cctccctctt cctttttgca gcctctattg   8760
ctttcttgca cttctcttta gcctctagag cctgcggtgt tgcagacgtg catttcttca   8820
cattctttcc aacatgggca agatgctcct tcaacctata aatccctccc ctcatctcct   8880
tgtcacagaa cttacacttc accttgtctt tgttgttagc atcaacaaga acaccatatt   8940
cccatccaac atcatctgaa tttcttttta ggagattcgc tctagctgct tcagtttcag   9000
aaggtgcagc tgcagtttct gatgacatcc ttaatccttt gatttctttc acttgtacac   9060
tgcacagggg aggaaagcag tttcagcagg ggaggaaagc aggggagggg gatgagcagg   9120
gaggggagca gccgacgggg gaggagaact caccggcggg ggagcaggga ggggagcagc   9180
cggcggggga gcagcaggag gggatgagcg ccggcggggg agcaatttcc gtgaccgtgt   9240
gggagggaga ctgagcggct gcacagcgcg cgcgctaaaa attgccgcgc gctcgcctgc   9300
gcgcccgcct aggcgcctgc gcgccgccta ggcgcggctg agcgctgcct agtcgctgcg   9360
gccgcctaga cgccgcacag agccctaggc tacgcggcag cctatcgact agcgcctagg   9420
cgcgcctaat cgccgcctag tcggcgcctt gccgaacact gactctaaat aaaagatatt   9480
gttgtatttt gattttaaat atctaagtga agttttcagg ggaaacaact ttatgaatta   9540
ttatttggaa tagtacgtgc atgttctttt ataagtttga tatctgaatt ttagaaatta   9600
aaaagtttga aagccctgca acatatattt atattattat acctgcagga tgaagatctt   9660
gatgcttctc ctgttgagat tgatgatgct ttaattcttg atgatgatga cgaggatgtc   9720
ccagatgatg aagatgatga tcatgaggcg gtaattattt tttaaatctt gcttattact   9780
acaaaggttt gtattgaggg gacatgattt ggaactcagt agattttgtt gaaatgatca   9840
ggttctccga ggttctcttc cttcctgtgt tcctgagaga gtgcatgatg tgaaattagg   9900
agatgctgat gattctagtg ttgcctcatt ggcaaatgat aaccaggcac agccctcatc   9960
tggttctagt acaaaaaata cttctagcag ggattggac actgctgaat ttagaagtcc   10020
agccacattt ggttcacgag gtgcaatgtc gtttgctgca gctgcaatgg ctggattaac   10080
tccagtaggt ggtcgtggaa ttagaggtag ccgagatcgg aatggccttc cattgggtgc   10140
tcgtgcaact gagcattaca acaaattgat atttacagct gctgggaagc agctgaacaa   10200
acatttgact gtatatcaag ctgttcaaag acaagtagtt catgccgagg atgatgaaga   10260
tcgattcggt ggatctgatt tacctgatga tggtaaccac ttctgggatg atataagggg   10320
tgatgtgttc actataacgt atcagaaggc tgataacaca gcggagaagg ggtctgttgg   10380
aggttcagct tcagtgccaa aatcttccaa atcagattct tgcagaactt tgtctgaaaa   10440
acagtgtact tctcttcttg atagtatttt gcaaggagag cttccctgtg atttagagaa   10500
atcaaaccaa acctacaata tcttatcact attacatgtg ttggagggtt tgaatcagtt   10560
atcacctcgt ctgagactgc agtcagcctg tgatgatttt gctgaaggaa aagttgctac   10620
attaaatggg ctatacgatg ttggagctaa ggtaccctca aaggagttta tcaacagtaa   10680
gatgacccca aaacttgctc ggcaaattca ggatgttctt gcactgtgta gtggcagttt   10740
accatcttgg tgttatcagc tgacgaaagc ttgtcctttt ctgtttcctt tcgaaacacg   10800
aaggcaatac ttctattcca cagcttttgg gttgtctcgt gcacttcatc gtcttcagca   10860
acaaccgggc aatgataata acactgcttt tgaaagagaa gtcaggattg gtagattgca   10920
acgccagaaa gtccgtgttt ctcgtaaccg tatcttggat tctgcagcta aagttatgga   10980
```

```
gatgttctct aatcaaaagg ctgtcctaga agttgaatac tttggtgaag ttggaactgg  11040
tcttggtcca actttggagt tttatactct cttaagccgt gagctgcaaa gggttgactt  11100
aggattgtgg agatctcatt cttcagataa ttctgggatg caaattgatg cgaatgctga  11160
tgatttaata agaagtaaaa atcatgaatc agaatcactt actgagagca ggaacatagt  11220
acaatcacct cttggattat ttcctcagcc ttggccacct actgctgctg catcagaagg  11280
tagcaaattc ttcaaagttg tcgagtattt ccgcttagtt ggtcgagtga tggcaaaagc  11340
attgcaagat ggaaggcttc tcgatttgcc tttgtcgaca gcattttaca aacttttgct  11400
tggacaagta agcatgaggg cctccttgag ctagttttat cttatgttgt cttctaaaac  11460
cttcctcttt tcggttggca cttaactttc tgtgcctttt ccttattaat ttaccaaatt  11520
tgctttaata ggaacttgat ttatatgata tattatcttt tgataccgag ttcggaaaga  11580
cattgcaaga attgcaaatt ctcgttgcac gtaaacaatt tttggactcc tgctctagtg  11640
agagccaaaa gatagatcta tgtttccgtg gtgctcccgt tgaagattta tatttggact  11700
tcactcttcc gggctatcct gaatatgttc tcaaggaagg tggagagaat gcagaggtaa  11760
gttatatgat accctagttt gtttttttct tctagtgttg ctgcagatga ctcattgtta  11820
tcctgtctta taggtcaaca tttgtaactt agaagagtat atttctttgg ttgtggatgc  11880
tactgttaag accggcataa tgcggcaagt agaggcattt aaggcaggat tcaatcaggt  11940
cttctttctt attttgtgat ttgtgggcaa tttctattaa taattgatcc tagaactaac  12000
tagcacattt atttatttat tcagaaaaaa atactcattg tatatttctc acttcaggtg  12060
tttgacatat catcactgca aatattttct cctcaagaac ttgattatct gatttgtggt  12120
cgctgtgaac tttgggaggt attgcttttg tggtcattct tgatgttgta cttcctctgt  12180
cccagaatga taagcatagt ttgtatagga aaaagtcaaa tttagaattt tatttcccag  12240
aaattgcttg tattatacta gtttatgtgg ctttgtgtcc cgctgccata ggtcaatgtt  12300
agctattgaa agctagttgc tctagtctac tgcttccctt tttttcgggc cgggggggg  12360
ggtattctcc ctcctttgca cttcaccttt tttctctctt aatgaaatga tacacaattc  12420
tcttttgtgt tcgagaattc tttttacaaa ctttggccaa caattaatca aattatatac  12480
atgttttgga caaacttgca tcaatagatt catattcaga gtgcatttga gatgagatta  12540
attgtttagc aaacataaac atattgtacg agaaattaat ggtcaatttt tttaatagat  12600
tatgtgagtt attgtactca gtctaagtgt tatggaccct ggtcccgccc atgtaactcc  12660
ttttccaata tatgcaacgt agcccaccct gattggagtt aacatggtat caagcttggt  12720
cttttctctc cctcccttcc ctagccgcca cctcctggcc gccatcacta ccgtcgggtc  12780
gctattgtcg tctgcgcctc catctcctcc ctagcgcctt tcttgctcat cggccaccca  12840
tatttattaa ggcggtgtta ataaccatgg ggccaccacc ttcactttag ctttctaggc  12900
gcgactggtg gccttgttgg ccctacggtt ggcgccttgc ccaccggtgc tttagtcccg  12960
gtcacctcga ttgctgcccc agtcgctccc gtcgcccttg cctttgctgt ggccatctat  13020
ggcatgggtg ccgccagcca gggcccagac ctagctgact ctggcctagc ttatctttcg  13080
gtcgcgttac ttccccctga tgtcgctttc gctcactcca ccttggccat agccccccatt  13140
gctgccaaga cggtgtttgc tgctgctcgg gatcgggaac atgttgctgc ccttgcttag  13200
gggcacaaac gcaccacgac ggatgcactc gctcgatagc agaccaatgc tgagggtcac  13260
ctgctcggct cctcctgcat cgagaccctc ccagcgctct agtggtcgcc cctttgtcgg  13320
```

agtacgaggt cgagatcatc accaacctct atgccgaggt ggcgtgtgtc cagaacattt 13380
gctctatgat tctcgtcatc cttgatacaa cttcctccaa ctacgccttc tggcgggcga 13440
tcttgtctac actctccatc actacgcctt ggactaccac gtcctcacca acactgtctc 13500
cctcactaac ctatcctggc ggcagatgga tagtgtggtc ctctcgtgga tccccaggac 13560
cgccatcgtt gcgctgcatg acgtggtttg cgagcgtggt ggcactatcc gtcttggacg 13620
tcgtcgagta gttccttggc aatcgtgagg cttgcactct ctaccttgat gtcgcctttc 13680
agacttttgt ctaggggaac ctctttgtca ctgagtactt ttgtcagagg aagggcatgc 13740
cagcctccct ctatgacctt ggggagcccg tctcccatag catgctcatc ctcaacctcc 13800
tgcatggcct tcacctccac acttcgatca cttcctcagt cccgttccac aaggtcaagg 13860
tcaacaacga cctcatttcc gaggagctca ccaaggggct gctaccaccc tctacaactc 13920
caccactggg gggccagcgc atgcaccctc ttctactact atcttgggag gatcgtcgtt 13980
gactcgttgc gctcgtctgt tcatcaaatc tcaagcattg cacatcctcc ccacttgcct 14040
tggtctgagg ggaggggtct agggtggcgg tcgacgaaag ggcggtcgtg gtggtggcca 14100
tggggacact ccttggcctt ccatctacaa cctgtggact gatcgcatct ccatgtggcc 14160
tggtccttct ccgagagtcc cttctcagcg tatcactcca ccgtagccag ctcacttgac 14220
attgctcggt ctggggtatc accttggcca tcctacgcca ttagcacctg agtcaccact 14280
tctgtcaccg ccaccccacc tcgctttgtc ctggaacccg tggccaggtg ggtgggatca 14340
acagtctctt gctagctcct tcaacacgat gaccttgact cctcccactg tcacctacta 14400
ggtggctgat tcctggtgcc tcctatcaca ccactttgga cgcgagtatg ctatattctt 14460
atccacctct tcgtctactc ctaccattgt gggtaacgag aacattctct cggtcacctc 14520
tgtcagtgat tcggttcttc ctaggccctt tcaccttcac aatgttcttg ttgccccaca 14580
tatcctttaa tattttatcc gttcacctat tgagcatcgg taattcttgt tccatagatt 14640
ttgatccttt tggcttgtct gtgaaggatc ttgctaccta gagtcttctt gcttgttttg 14700
atagatctag gcccctgtac acccatgcag gcctgcgtct acctccccac atactggttt 14760
cgctacatca tcacattcgt cctcgctaca gtcgcctgct ttgactactt ccactatttg 14820
tagtacttgg catcgtcgac ttgtccatcc caaccttgta gcgtagtcca agctatgtag 14880
tactttagta atttcttgta gtaggggcac ccttgagcat ctatgccagt tgtgtaagtt 14940
aggtcgtcat tttcgacttc ctttctctag cttctcacag catacgctgt gatttgtgga 15000
cctctcctgt taccaatgtt ttgggatata aatattattt ggtgattctt gatgattgct 15060
atcattgttt gtggattttt ccattgagtt taaagtctga cacctttacg actctgctcg 15120
gttacttcgc ttgggtttac actcagtttg gttgcactat gaagatcgtc cagtgtgaca 15180
atggtcgtga gtttgataac ttctctcgat cctttacctc aattggagtc tagcttcgaa 15240
tgtcttgccc ctacacttcc catcagagtg gtaaggctga gtgtatgatt tgcaccacga 15300
ataatgtaat gtgttccttg atatttcaat catctgtttc cgctcgctag tgggatggga 15360
gcctccacac tgctacctac ctccttaatt gtcttcctac aacgacaact cttatgtcat 15420
gccccccacc ccactttgct cgaatggcaa ggcttagcgc atgaattaat gtcatgtttt 15480
tcttgctatt ttactatttt aggcatccgt tccttctcct tactggtctg agagcctcca 15540
caccaccacc tacctcttta attgttttcc tattacgacg actcgtgccc ccacttccca 15600
ctttgctctt tttgtcaaca ctccaatgac catcttcgtg ttttgggtat gtgtgccacc 15660
ctaacctttc caccactact ctccatcttg ttctttgttc tgctcgctgt gtctttctcg 15720

```
ggtactcatc tgatcacaaa gggtactggt gtcttggcct caccactcct cgccatttga  15780
tctctcatca cgtcatattc gttgggatgg atgtcccctt ctcaactaac acctagccca  15840
ccaccgcctc ccctttcgag ttgtattttc ttcatgatcc tgactccgtg gtgccctttg  15900
tccaaccact gtttttctag ttgctgtttt cctctccact gtttcagccg gtggcccctg  15960
tgtgcccatg gtggatcata cgcccttgaa ttccttccgg gttgcaccgt tgcccctcgt  16020
cgacccgtgt gtcacctcgt caacccatgt tgggtcccta ggccccggtg gccccacttt  16080
tgacattgcc ttcgttgcta gggccctctt tattgccctc gcctgtgccc tcgccttgtt  16140
gctatgccca acctgtgcat ttctatcagc gacatgcccg agtgggtaca ccgcctcgct  16200
cttgcgacga gccgacaatg tatcacccct tcatcgtgac tctcaccaca tccacttgat  16260
ggcgaattgc caggccactg gggtccttag ccctgttgat tgcctcatcc tctccgtgac  16320
ctcctcattg tcggtttctc atgtgtcgtc ttgcgttgat tgcacccttt ctaatactca  16380
ttggcgccac gctatgaaga aagagtacct gactatcctt gccaaccaca cctgggttct  16440
ggtattctgg tgccccatct ttcgtgcgac aatgtggtga ttgacaagtg ggtctggaca  16500
cataagcggc aggcggctgg ctcgctgggc tactcagtgt cgtgctgttg actacgatga  16560
gacgttaatt ctcgttgtga agcctgctac cgaccgtgcc atcctcactt tggccctctc  16620
ccatttttgg ccaattcatc acttggatgt caaaaatgct tttctgcatg ggactctcac  16680
ttagacttgt ctactgctgt cagcctacta gctttgttga tcatgcacac cccgatatgg  16740
tatgcaagct caacaaagta tgcaaactca acaagtccct ctatggttcg aggcaagccc  16800
cacgtttggt acaaccgctt caccatatat ctgctctctt tgttttgttg aggccaagtc  16860
agacacattt ctgttcatct atcggtgtgg tagtgacact gtatacctac tcctatatgt  16920
tgatgacatc gtgctcacta cctcctttct catgcactag atcaccaccg ctcttcagca  16980
tgagttcacc atgaaggatt taggccccct tcactttatg gggattgctg ttgagcatcg  17040
ctttgatggc ctctttttc agcagcgacg atacaccctg gacatcctcg agcgtgctgg  17100
cattctggat tgcaagcctt gtgtggcgtc agtggacatg taggccaagc tctctggcgt  17160
cagtgctcca gtcagtggcc ccatcaccta ccatagcctc atcggtgctc ttcaccatct  17220
caccttcacc agacctgaca tcgtgtatgc catccaacaa gtatgtcttt atatgcatga  17280
tccctgtgac ctgtacttgg gtgtggtcaa gtggaatcct tattgttgac tatggtctcc  17340
tcctttggcg ctccttcatc catgagctaa tcatctatac tgacgccgat gggccgagtg  17400
tcctggacac ctgtcggtat acctcggcga acctcatctc ctggtcctcc aagcggtagc  17460
cagtggtctc ccgttccagt gctgacgttg agtactggct gttgctaatg gggtggctga  17520
ggcgagcaag ctgcaccaac ttctccagta gcttcacaac ccactcacca tgagtaccct  17580
ggtctactac gacaacgtca gcatcgtcta cctctctgtc aacccttttc aacaccaccg  17640
tattgaccgt tttactattg gggacgtccg cgtatgtttc aacgagctcg tagtttgatg  17700
acaccttcac taagggtttt cccttgttct tggagtttcg gttgttgggg caggagacag  17760
aaccggtcct caactaccaa ttgtactcac cactcaccaa gattcctaat gcagagtaac  17820
cgactaggag gtgcgaaggc ctatggcaga aggggcaagc cacggaggcc gaccccaact  17880
tcggtccttc ctaacaatcg cgaaggctac ttgactacgc agggaccttg gccaaacctc  17940
gacgagggac aaacacgttc agcgagggca ggcgggggct aggacgcgtc gaagaccccc  18000
gaagcaccga acgaagaccc aactgctacc agccgatgtt gaccgaggcg agatcgctcc  18060
```

-continued

```
tctttggtag gccgtcgtga ggcagttttt ctctaaggcc cccacgcaga ggccataaga  18120
cgaggaatgt tggattccgc caagcggcgg ctcagttgtg ggcgtagact cgcctactcc  18180
acacgtcagc ctttgatgtg ggtgagaaag atggtgtaat atggaatgta gccaggggac  18240
ctgtaattac cccgttgcac acctgttgca cggtatatct atggcatgta gtaggtaacc  18300
aagggcatta cgatatttta ggccttgggc ccttggccgc cctatagata gccccatcct  18360
gtagctggat gggacacact tgacaagaca tttgtgctcc cagccaattg ttttgtcgtg  18420
ccacctgtaa caccactctc gagtgcttgg gcacactgtt ctaagtccca acatcggtcc  18480
agtctcaaca tctttcacga ctagagtttc atctgcgggg gtgggggtag ggtgttaga  18540
ttcttgtgcg ttattgtact caatttatgt gttatgggcc ttggcccagc ccatgtaacc  18600
catgcaacac agtttaccct aatttgggtt aggtttccaa caattttgtt tgacttttcc  18660
attatcaaaa cacacttagg ccttgtttgt ttacgtcgga ttgcacccgg aaacgttcca  18720
gctaatcaaa gtttatataa attagagaag caatccggct aggaatcgtt ccgacccacc  18780
aatccgacac aaacgaacaa gaccttaata tttcacgatg aatactcaat ttaagtgtta  18840
tgggccttgg cccagcccat gtaacccatg caacacagtt caccctaatt tgggttaggt  18900
ttccaacaat tttgtttgac ttttccatta tcaaaacaca cttaatattt cacgatgaat  18960
gtagttgttt tggcttattc tgaacaattt cacatcatgc agccggaaac actgcctgaa  19020
catataaaat tcgaccatgg ttatacctct aagagtcctg caattattaa tgtaagtttc  19080
cctgcttctt tgtaattcat ttgtaggttt cgtaagttta tttggatgtt tctaatgttg  19140
tgttttgcag tttcttgaga tcatggcaga atttactcct gagcagcaac atgctttctg  19200
ccagtttgtg accggtgctc ctcggcttcc acctgggggt ttggctgctc taaatcctaa  19260
gttgaccatt gttaggaagg taaattggct atctttgttc ttatttctac tttatggttg  19320
acatgcctgc ccacattgtt gaagttttga attcttaaat tccagcactc ttctgtggca  19380
aataataatt caaatgcaac tggagcgaca gagtctgcag atgatgattt gcctagtgtc  19440
atgacttgcg ccaactatct taaactacca ccatactcca ccaaggtatg cttctttctg  19500
ctttttggct aactgtggtt atatctcctg tattgtctta taaattgagg attcagaaac  19560
ccagtcacca aagaattact tcatatagcc ttatcgtaac aggtaactgg acaaattttc  19620
aactaaggac gtggaaacta aaatttaatg tgggcagcac cttccagcca ctcattagtt  19680
agaattatta tttcgttagt ttaaatcaaa tagcatattc cacattgctt gaacccttta  19740
tattgacgca tgctggtttt ttttctggaa ggaaatattt acagtgctac tcgtgctagt  19800
gtgtggcttg ttatctctgt ctgaattttg ttgaaaactt cttgcaggct atcatgctaa  19860
agaaactgct ttatgcgatc aacgaaggcc aagggtcatt tgatctttcg tgaatctcaa  19920
cactaacata ggtattggtc cacctagaaa tctgcgtcat tgttacccag agttagtttc  19980
tacctcattc atgtatgaca taggttaaac tcagctctcc ggagtcccac cgaaggtttg  20040
gagcccgtac ctttgggtgt ggatgtctat actctctttt cttcttggtt gtatattctt  20100
gcggatcttt atagtgaata atagtaataa attgttttgc gcttcttact atgctaatca  20160
tcagtgcccc acccgaagcg tcagtcgtac aaattttgct cgatggtttc gctgcccacg  20220
aatcggatgg atgggggccc atgaacaagg gcacgggatt tccggggcta tctgaaatag  20280
tgacgggcat gcaaacacac ctaaggttca cggcctgctt ttggtcgaca cagtgccacg  20340
cgaccgtgct ggatcttatc actggcctgt ccgaggcatc tgaggatgtc aagttgtcaa  20400
ccgaggcgcc tatgtgggca cgggactgat cactttcact cgggtcacag cgttcggttc  20460
```

aagagcattg ggcacagtca cacacttctt caggtcttgg cgcttcagcc acaaccccaa 20520
ggatgacgat agatgggcac aagacacagc cgtgccggcc acgacagttg cacagatccc 20580
ctcgtctcgt ttgcaggtac cagcgaaatt gctaacgtgc gatgcgaccc gctgcgaaaa 20640
cgacggatca cgtatcagcg gtcgttgtca tatatgatca gtcggccgtg ccttggcact 20700
gcacaagcca ataaaactcc gccagaactg aggaaagatg gaaccgtcca ggagt 20755

<210> SEQ ID NO 38
<211> LENGTH: 1559
<212> TYPE: PRT
<213> ORGANISM: Zea mays

<400> SEQUENCE: 38

Met Glu Cys Phe Gln Arg Val Ala Leu Ser Thr Ala Ala Asn Met Cys
1               5                   10                  15

Arg Lys Leu Pro Ser Asp Ala Ser Asp Phe Val Met Glu Ala Val Pro
            20                  25                  30

Leu Leu Thr Asn Leu Leu Asn Tyr His Asp Ser Lys Val Leu Glu His
        35                  40                  45

Ala Ser Val Cys Leu Thr Arg Ile Ala Glu Ser Phe Ser Pro Phe Pro
    50                  55                  60

Glu Lys Leu Asp Glu Leu Cys Ser His Gly Leu Val Ala Gln Ala Ala
65                  70                  75                  80

Ser Leu Val Ser Val Ser Asn Ser Ala Gly Gln Ala Ser Leu Ser Thr
                85                  90                  95

Ser Thr Tyr Thr Gly Val Ile Arg Leu Leu Ser Ile Cys Ala Ser Gly
            100                 105                 110

Ser Pro Leu Ala Ala Lys Thr Leu Leu Leu Gly Ile Ser Gly Ile
        115                 120                 125

Leu Lys Asp Ile Leu Ser Gly Ser Gly Leu Val Ala Gly Thr Thr Val
    130                 135                 140

Ser Pro Ala Leu Thr Arg Pro Ala Asp Gln Met Asn Glu Ile Val Lys
145                 150                 155                 160

Leu Ala Asp Glu Leu Leu Pro Ser Leu Pro Val Gly Thr Ile Ser Leu
                165                 170                 175

Pro Val Tyr Ser Gly Val His Met Lys Gly Cys Ser Val Lys Lys Ser
            180                 185                 190

Thr Ser Ser Lys Gln Gly Glu His Gly Ser Thr Ala Asn Glu Leu Ser
        195                 200                 205

Gly Arg Glu Lys Leu Leu Arg Asp Gln Pro Glu Leu Leu Gln Gln Phe
    210                 215                 220

Gly Met Asp Leu Leu Pro Thr Met Thr Gln Val Tyr Gly Ser Ser Val
225                 230                 235                 240

Ser Gly Pro Ile Arg His Arg Cys Leu Ser Val Ile Gly Lys Leu Met
                245                 250                 255

Tyr Tyr Ser Ser Ala Glu Met Ile Gln Ser Leu Leu Ser Thr Thr Asn
            260                 265                 270

Ile Ser Ser Phe Leu Ala Gly Ile Leu Ala Trp Lys Asp Pro Gln Val
        275                 280                 285

Leu Ile Pro Ala Leu Gln Ile Ala Glu Val Leu Met Glu Lys Leu Pro
    290                 295                 300

Glu Ile Phe Leu Lys Met Phe Val Arg Glu Gly Val Val His Ala Val
305                 310                 315                 320

```
Glu Ser Leu Ile Cys Pro Glu Leu Ser Gly Gln Val Thr Pro His Val
                325                 330                 335

Asp Ser Ile Thr Ser Ser His Asn Arg Arg Asn Arg Arg Arg Asn Asn
            340                 345                 350

Ala Val Asn Thr Gly Asn Asn Leu Pro Asp Gly Pro Lys Gly Ser Asn
        355                 360                 365

Ser Met Ile Ala Asn Ser Pro Pro Ser Met Ala Glu Val Pro Asn Asn
    370                 375                 380

Ser Leu Arg Ala Leu Val Ser Asn His Ala Lys Ser Phe Lys Asp Lys
385                 390                 395                 400

Tyr Phe Pro Ser Glu Pro Gly Ser Ser Asp Ile Ala Val Thr Asp Asp
                405                 410                 415

Leu Leu Lys Leu Arg Ala Leu Cys Ala Lys Leu Asn Thr Thr Ala Asp
            420                 425                 430

Thr Ile Lys Thr Lys Ala Lys Gly Lys Ser Lys Val Val Ser Asp Asn
        435                 440                 445

Ser Phe Asp Val Leu Cys Asn Ile Glu Glu Gln Leu Asp Asp Ile Ile
    450                 455                 460

Ala Glu Met Leu Ser Glu Leu Ser Lys Gly Asp Gly Val Ser Thr Phe
465                 470                 475                 480

Glu Phe Ile Gly Ser Gly Val Val Thr Ala Leu Leu Thr Tyr Leu Ser
                485                 490                 495

Cys Gly Thr Phe Gly Arg Glu Lys Val Ser Glu Ala Asn Ile Pro Asn
            500                 505                 510

Leu Arg His Gln Ala Val Arg Arg Tyr Lys Thr Phe Ile Ser Phe Ala
        515                 520                 525

Leu Pro Asn Asp Lys Asp Gly Asn Lys Thr Pro Met Ala Phe Leu Val
    530                 535                 540

His Lys Leu Gln Ser Ala Leu Ser Ser Leu Glu Arg Phe Pro Val Val
545                 550                 555                 560

Leu Ser His Ser Gly Arg Ala Ser Thr Leu Gly Gly Ser Arg Leu Thr
                565                 570                 575

Thr Gly Leu Gly Ser Leu Ser Gln Pro Ile Lys Leu Arg Leu Cys Arg
            580                 585                 590

Ala Pro Gly Glu Lys Ser Leu Lys Asp Phe Ser Ser Asn Val Val Leu
        595                 600                 605

Ile Asp Ser Leu Ala Ser Leu Ala Ala Val Glu Asp Phe Leu Trp Pro
    610                 615                 620

Arg Val Gln Arg Thr Glu Pro Val Leu Lys Pro Pro Met Ser Ser Ala
625                 630                 635                 640

Asn Asn Ser Gly Ser Gly Ala Ala Ser Ser Thr Ala Cys Ala Pro Ser
                645                 650                 655

Ile Pro Ser Glu Thr Gln Ser Val Arg Arg Thr Ser Leu Arg Ser Lys
            660                 665                 670

Ser Ser Ala Ala Thr Ser Gly Ala Ile Lys Lys Asp Tyr Gln Glu Gly
        675                 680                 685

Ser Ile Asn Thr Ser Lys Gly Lys Gly Lys Ala Val Leu Lys Leu Ser
    690                 695                 700

Leu Asp Glu Pro Lys Gly Pro His Thr Arg Asn Ala Ala Arg Arg Lys
705                 710                 715                 720

Ala Thr Ser Glu Lys Asp Val Glu Leu Lys Pro Ser His Gly His Ile
                725                 730                 735

Thr Ser Glu Asp Glu Asp Leu Asp Ala Ser Pro Val Glu Ile Asp Asp
```

-continued

```
            740                 745                 750

Ala Leu Ile Leu Asp Asp Asp Asp Glu Asp Val Pro Asp Asp Glu Asp
        755                 760                 765

Asp Asp His Glu Ala Val Leu Arg Gly Ser Leu Pro Ser Cys Val Pro
    770                 775                 780

Glu Arg Val His Asp Val Lys Leu Gly Asp Ala Asp Asp Ser Ser Val
785                 790                 795                 800

Ala Ser Leu Ala Asn Asp Asn Gln Ala Gln Pro Ser Ser Gly Ser Ser
                805                 810                 815

Thr Lys Asn Thr Ser Ser Arg Gly Leu Asp Thr Ala Glu Phe Arg Ser
            820                 825                 830

Pro Ala Thr Phe Gly Ser Arg Gly Ala Met Ser Phe Ala Ala Ala Ala
        835                 840                 845

Met Ala Gly Leu Thr Pro Val Gly Gly Arg Gly Ile Arg Gly Ser Arg
    850                 855                 860

Asp Arg Asn Gly Leu Pro Leu Gly Ala Arg Ala Thr Glu His Tyr Asn
865                 870                 875                 880

Lys Leu Ile Phe Thr Ala Ala Gly Lys Gln Leu Asn Lys His Leu Thr
                885                 890                 895

Val Tyr Gln Ala Val Gln Arg Gln Val Val His Ala Glu Asp Asp Glu
            900                 905                 910

Asp Arg Phe Gly Gly Ser Asp Leu Pro Asp Asp Gly Asn His Phe Trp
        915                 920                 925

Asp Asp Ile Arg Gly Asp Val Phe Thr Ile Thr Tyr Gln Lys Ala Asp
    930                 935                 940

Asn Thr Ala Glu Lys Gly Ser Val Gly Gly Ser Ala Ser Val Pro Lys
945                 950                 955                 960

Ser Ser Lys Ser Asp Ser Cys Arg Thr Leu Ser Glu Lys Gln Cys Thr
                965                 970                 975

Ser Leu Leu Asp Ser Ile Leu Gln Gly Glu Leu Pro Cys Asp Leu Glu
            980                 985                 990

Lys Ser Asn Gln Thr Tyr Asn Ile  Leu Ser Leu Leu His  Val Leu Glu
        995                 1000                1005

Gly Leu  Asn Gln Leu Ser Pro  Arg Leu Arg Leu Gln  Ser Ala Cys
    1010                1015                1020

Asp Asp  Phe Ala Glu Gly Lys  Val Ala Thr Leu Asn  Gly Leu Tyr
    1025                1030                1035

Asp Val  Gly Ala Lys Val Pro  Ser Lys Glu Phe Ile  Asn Ser Lys
    1040                1045                1050

Met Thr  Pro Lys Leu Ala Arg  Gln Ile Gln Asp Val  Leu Ala Leu
    1055                1060                1065

Cys Ser  Gly Ser Leu Pro Ser  Trp Cys Tyr Gln Leu  Thr Lys Ala
    1070                1075                1080

Cys Pro  Phe Leu Phe Pro Phe  Glu Thr Arg Arg Gln  Tyr Phe Tyr
    1085                1090                1095

Ser Thr  Ala Phe Gly Leu Ser  Arg Ala Leu His Arg  Leu Gln Gln
    1100                1105                1110

Gln Pro  Gly Asn Asp Asn Asn  Thr Ala Phe Glu Arg  Glu Val Arg
    1115                1120                1125

Ile Gly  Arg Leu Gln Arg Gln  Lys Val Arg Val Ser  Arg Asn Arg
    1130                1135                1140

Ile Leu  Asp Ser Ala Ala Lys  Val Met Glu Met Phe  Ser Asn Gln
    1145                1150                1155
```

```
Lys Ala  Val Leu Glu Val Glu  Tyr Phe Gly Glu Val  Gly Thr Gly
    1160                 1165                 1170

Leu Gly  Pro Thr Leu Glu Phe  Tyr Thr Leu Leu Ser  Arg Glu Leu
    1175                 1180                 1185

Gln Arg  Val Asp Leu Gly Leu  Trp Arg Ser His Ser  Ser Asp Asn
    1190                 1195                 1200

Ser Gly  Met Gln Ile Asp Ala  Asn Ala Asp Asp Leu  Ile Arg Ser
    1205                 1210                 1215

Lys Asn  His Glu Ser Glu Ser  Leu Thr Glu Ser Arg  Asn Ile Val
    1220                 1225                 1230

Gln Ser  Pro Leu Gly Leu Phe  Pro Gln Pro Trp Pro  Pro Thr Ala
    1235                 1240                 1245

Ala Ala  Ser Glu Gly Ser Lys  Phe Phe Lys Val Val  Glu Tyr Phe
    1250                 1255                 1260

Arg Leu  Val Gly Arg Val Met  Ala Lys Ala Leu Gln  Asp Gly Arg
    1265                 1270                 1275

Leu Leu  Asp Leu Pro Leu Ser  Thr Ala Phe Tyr Lys  Leu Leu Leu
    1280                 1285                 1290

Gly Gln  Glu Leu Asp Leu Tyr  Asp Ile Leu Ser Phe  Asp Thr Glu
    1295                 1300                 1305

Phe Gly  Lys Thr Leu Gln Glu  Leu Gln Ile Leu Val  Ala Arg Lys
    1310                 1315                 1320

Gln Phe  Leu Asp Ser Cys Ser  Ser Glu Ser Gln Lys  Ile Asp Leu
    1325                 1330                 1335

Cys Phe  Arg Gly Ala Pro Val  Glu Asp Leu Tyr Leu  Asp Phe Thr
    1340                 1345                 1350

Leu Pro  Gly Tyr Pro Glu Tyr  Val Leu Lys Glu Gly  Gly Glu Asn
    1355                 1360                 1365

Ala Glu  Val Asn Ile Cys Asn  Leu Glu Glu Tyr Ile  Ser Leu Val
    1370                 1375                 1380

Val Asp  Ala Thr Val Lys Thr  Gly Ile Met Arg Gln  Val Glu Ala
    1385                 1390                 1395

Phe Lys  Ala Gly Phe Asn Gln  Val Phe Asp Ile Ser  Ser Leu Gln
    1400                 1405                 1410

Ile Phe  Ser Pro Gln Glu Leu  Asp Tyr Leu Ile Cys  Gly Arg Cys
    1415                 1420                 1425

Glu Leu  Trp Glu Pro Glu Thr  Leu Pro Glu His Ile  Lys Phe Asp
    1430                 1435                 1440

His Gly  Tyr Thr Ser Lys Ser  Pro Ala Ile Ile Asn  Phe Leu Glu
    1445                 1450                 1455

Ile Met  Ala Glu Phe Thr Pro  Glu Gln Gln His Ala  Phe Cys Gln
    1460                 1465                 1470

Phe Val  Thr Gly Ala Pro Arg  Leu Pro Pro Gly Gly  Leu Ala Ala
    1475                 1480                 1485

Leu Asn  Pro Lys Leu Thr Ile  Val Arg Lys His Ser  Ser Val Ala
    1490                 1495                 1500

Asn Asn  Asn Ser Asn Ala Thr  Gly Ala Thr Glu Ser  Ala Asp Asp
    1505                 1510                 1515

Asp Leu  Pro Ser Val Met Thr  Cys Ala Asn Tyr Leu  Lys Leu Pro
    1520                 1525                 1530

Pro Tyr  Ser Thr Lys Ala Ile  Met Leu Lys Lys Leu  Leu Tyr Ala
    1535                 1540                 1545
```

Ile Asn Glu Gly Gln Gly Ser Phe Asp Leu Ser
1550 1555

<210> SEQ ID NO 39
<211> LENGTH: 6343
<212> TYPE: DNA
<213> ORGANISM: Oryza sativa

<400> SEQUENCE: 39
gtcctgtggg acatttggaa aggagagggt atctgaggca aacctgccaa agcttcgtca 60
gcaggcgctt aggcgataca agtcttttat atctgttgcc ctttctattg accatgaaag 120
gaatgagact cctatggctt ttttggtcca aaaactgcaa agtgctttgt gttcattgga 180
gcgcttccct gttgtgctca gccagtccag cagaataggt attggaggct cccgtttgac 240
ttcaggtttg agtgctctag ctcagccctt caagttgcgc ctttgtcgag gtcagggtga 300
aaaatcactt cgggattatt cgtcaaatat tgtgcttatt gatccctttg cgagtctagc 360
agctgttgaa gagtttcttt ggcccagagt tcagcgtagt gaggctgctt cgaagcctac 420
agttccatca ggaaataatt ctgaatctgg catacctggc accgcagctg gtgcgtcatc 480
cacagctgca ccagctccat ctggcaggcg tccaacaaca agatcaaaat catctgctgc 540
aagtagtggt gcatctaaga aggattctca ggaggaaagc acaaacactg ccaagggaaa 600
ggggaaggct gttgcaaaac caaactcaga agaaccaaaa ggacctaata cacggaatgc 660
tactcgcaga aaagctgctt cagagaaaga tctggaaatg aagcgagcac atggtgacag 720
cagctctgag gtatttcttt catttctctg aatgaacatg aaaaattcta atagagatta 780
cgaatgcagt tgtcagtttt atttagctct atacaagatt ctagtgcatg ttaattctat 840
gttgagaggc atatagacat aataattgtc caacaagtat taaattaaag ataatgtaca 900
atctcctttt tgtataccaa gatttgacct cagcgcctta taaactactt cctccgtttc 960
acaatgtaag actttctagc attgcccaca ttcatataga tgttaataaa tctagacata 1020
tctatatgaa tgtgaacaat gctagaaagt cttacaatat gaaacggagg gagtacattt 1080
tcatttttct tttataatat ttcatgttgg tttcatagca aacctatgtg gttttccacc 1140
tagctattag tttgcgctag atgtggccat ttaatttata gagtaaacaa atcataacaa 1200
ttctgtatct gatacccatg ttcgacatag agttcagtct ccgattgcca ttcccaacag 1260
agttgtatgt gaaacaaggt atattatatt ttactgatga ggacaattat tgttaaaaaa 1320
gatgacttga agttccaatg cattttttata tgagaaacta gctgtgtgta tgcatactat 1380
ctgctaatta ttggatatga cttgcatgga ctgggagcaa tgcaagtagt aaatttgtgt 1440
ttttgtgcat gcaggatgag gagcttgaca catctcctat tgaaattgat gacgctttaa 1500
tgattgatga tgatgacatg tcagaggatg aagaagatga tcatgaggta atgtttacca 1560
ctttccaaaa tttattgtgc ttctaatttt gtattgttgc aacctgcact aatttgtagg 1620
tttatatata agtttgttca catggcattt tagagctagc ttgaccttat ttaagtttcg 1680
gcatacacca atgataagca taagtttggt ctaaccagct atcgagtctt ttcggcttga 1740
tattcaaata taagcttttc ttccacagag aagatgtatt ataaatgaag tggggtggtg 1800
cgcttatgct agggctcaca agtcacaatg ggattttatg caaacaacat gttgtgcttg 1860
ttgatatata agctgtaagc ttttatttga taggcctgcc tgtaagatca gcatattata 1920
tcatatgcca ataaagctct tagtttttca ttattacaga tattatttgc tctggtctgt 1980
aaataaataa ctgtactact atttatcagg ttctccaaga tggctctctt cctatttgtg 2040

-continued

```
ttcaagatgg ggtgcatgac gtgaaattgg gtgacactga tgactctaac attggttcag   2100
caagtgatag ccaagtgcag ccctcatctg gttccagcac taggaacatc atgagcaggg   2160
gagtagatcc aaataccttt ggttcacgag gtgcaatgtc atttgttgct gcgacaatgg   2220
ctgggctggc ttctgttggt ggtcgggggg ttagaggtag tcgcgatcga cgtggcctgt   2280
cacttggagg tagcataaat gagcacaata aactgatatt tatggctggg gggaagcagc   2340
tcagcaaaca tctgactgtg tatcaagctc tccaacgtca gctgatgttt gaagaggatg   2400
atgatgagaa gtttaatgga tctgatttgt caaatgatgg aaatcgattt tggggtgatg   2460
tgttcacgat aacataccag aaggctgata gccaggctga gaaggtatcc caaggtggtt   2520
ccacctcgtt gaactcaaaa tcagatcctt caagatctat atctgaattg aaaggtgttt   2580
ctctccttga tagcatctta caggcagaac tcccatgtga tctagagaga acaaactcaa   2640
cttacaacat tttagcacta ttgcgtgtat tagaggggct caatcagttg tcccctcgtt   2700
taagagtaca tgctgcttct gatgattttg ctgagggaaa aatcaccaca ctggatgagc   2760
tatatagaac tggagccaag gtaccgtcag aagagtttgt taatagtaag ttgacaccaa   2820
agcttgctcg gcaaatgcag gatgttcttg ccctctgtag tggcagttta ccttcttggt   2880
gttaccagat gaccaaagcc tgccctttct tgtttccctt tgaaacaagg agacagtact   2940
tttactccac agcatttggg ttgtcccgtg ctttgaatcg acttcagcaa caacagggtg   3000
acaaccaaaa tgctggtggc gaaagggaga tccgatttgg aaggctacaa cgtcaaaaag   3060
ttcgtgtttc ccgtaaccgt attctggatt ctgctgctaa agttatggag atgttctcca   3120
gtcagagagc tgttcttgag gtagaatact ttggtgaagt tggaacaggg cttgggccca   3180
ctttggagtt ctatactctc ttaagccatg aactccagag tgttcgcctt ggattatgga   3240
gatctagttc tccatctgat acgggaatgc aaattgatag gagcgcaagt cccgacgatg   3300
acttggcagc caaagaactc agctcagatt tacctgacaa tggcagccac ttgatacaag   3360
ctccctttgg attgtttcct cggccttggc cacttaccgt tgatgcttca gaaggcagta   3420
gattttctaa ggtcatcgaa catttccgct tggttgggcg agtgatggca aaagttttgc   3480
aagatggaag acttttagat ttgcctctat caacagcact ttataagctt atacttggac   3540
aagtaagtga tatactctta ctggattaat atcagttttt ccttttgtta catttgtttt   3600
attgaagtta gtctgaacaa atgaactgta tgtgccagga gctggactta tttgacataa   3660
tctcatttga tgctgaattc ggaaagacat tgcaagaact gcaaattctt gttgaacgga   3720
agaggttcct tgaatccact tatggcatga atcagctaga agtcacggac ttgcgtttcc   3780
gtggcactcc tatcgaagat ttgtgtttag attttactct tccaggttat cctgattata   3840
ttcttaaaga aggcgaggaa aacacaattg taagtgatga aacccatctt agttttgtgt   3900
ttgtcccagt gactagtgtc tgcatttgct cctttttgtg gtaataaata gtattactct   3960
gttttgcagg taaatattta caacttggaa gagtatgtta ctttggtagt ggatgctaca   4020
gttaaatcag ggataatgag gcaagtcgaa gcatttagat caggatttaa ccaggtgcaa   4080
cgtcattttc tctctcttgt aatcatttta ttagctgttt ttttttgttt actgtaattg   4140
ttcatgttta cctttctgtt ttaggtcttt gacatctcat ccctgaaaat attttcacct   4200
gaagagcttg actatctaat atgtggtcgc cgagaaattt gggaggtaat gctctctctc   4260
tctctctcac acacacacac acacacacgc acacagtttt agtttgttac atttcactga   4320
ataaacctgt gctgcagcct gattcattgg tggataatat aaaatttgat catgggtata   4380
ctgctaaaag tcctgcaatt gtaaatgtaa gtgcgctata tgcatttcaa tatctgaatt   4440
```

ggccttctgt aagtttagtt acttaattgc tctacatgtt tgtagctact cgagatcatg 4500
gctgaattca ccccagagca acaacatgca ttctgccagt ttgtaactgg tgctcctcgg 4560
cttccgcctg gtggtttagc tgcccttaat cccaagctta ctatagttag gaaggtaaca 4620
ttcttggtat atcttattag catgttataa cgtatgaata ttgtcgcctc attttgggtg 4680
atataacttt gttgttgctt ttgatcatta gcacccctca agtgcggtga atacttcaaa 4740
tatcgctgga gttacagagt ctgcagatga tgatctgcca agtgttatga catgtgctaa 4800
ttatcttaaa ttgcctccat actccacaaa agtacggttt ctttctctgg tacatggtga 4860
atttttcgtt ttctcttgta catgtgctaa ttatcttaac tggctttatg cttttgcttt 4920
ttgcaggaag tgatgcgcaa gaaattgctt tatgcgatcc tagaaggccg tggatcattt 4980
gatctatcat gagttgatga taactaacat acagggctca ccattgaatg ccctatcaat 5040
tttatccaga attagtttct ttgttgcccg tgtgacataa taggttgagg ctaccagccg 5100
ctgtggacaa agcttgaagg acagagtctc ccttcagaca caggtgctga actggagtat 5160
ttctcatgtt aaatactccc atatatataa gctgatacat aaatagataa tgtagtattg 5220
gtttttgcag tgaaatcaag ttccatatat gtggcgtggg cagcctcgcg agcaccgaga 5280
agaggagctc tatcctttgc cgtacatgta aataaagaaa aaaaaagaag gggcaatagt 5340
agtttacata tttgtcgaaa gaaggattga ttcgttggtg aaaccctttg ctgtgtatct 5400
ggaatgttat tactttgcta ttattatgtt gttaaccatc atgtgtacat gtgtgatcga 5460
taatatcgta ctgtttttgt actaataaat gtggtgtagt gctagtacat agacggtatt 5520
gtcttgcccc cccccccccc ccccccaagg agcgaaaagc aaagattttg ctcaaagacg 5580
acatcagtta gctccgaatc atttatatag ctccgaatca tttagctcca aatcatttat 5640
atagctccga atcatttata gtaaatctaa tagacaattc atatgtataa tagttaactt 5700
atgtactaca tcattaataa ttagttctat tatacacata taatgggctt gtttggttta 5760
ataccatctt attgccttat ccaatagtac ccaatgttag tcactaataa aattttggta 5820
gggcaaaaat tggttccgaa tcaaacaagc ccaatgtttc ctttctaatc cacacaaatt 5880
tgcagttcgt tctcttcttt cttatctact taaaagccat aatttacttt gcaagaacta 5940
cctccccagt atgtggcatg tgaaatgttc aaatcagttt caactctatt tgctactaca 6000
gtagtatctt gcaacacatt cctactagtg tatttatttt cgtttatagt ttccagaagc 6060
tatgtcctct ttgattcaaa ggaaagttaa agtaattttt ggaggaattc attcctatgg 6120
gatttttccc ctagatgatc ctttttcaaa ggaatgaata aaattgaatc ctatgaaatc 6180
ttatggaata ctcatgccat acaagttttg gaggaaattt aacatgaggt aaaacctcat 6240
ggaaactttc ctttaaatct ttctctcttc tgtaattctt gtattttttt atacggtcga 6300
aacaaacggt cgttcctatg tttcgtaatc ctacgattta aag 6343

<210> SEQ ID NO 40
<211> LENGTH: 819
<212> TYPE: PRT
<213> ORGANISM: Oryza sativa

<400> SEQUENCE: 40

Met Lys Arg Ala His Gly Asp Ser Ser Ser Glu Asp Glu Glu Leu Asp
1 5 10 15

Thr Ser Pro Ile Glu Ile Asp Asp Ala Leu Met Ile Asp Asp Asp Asp
20 25 30

```
Met Ser Glu Asp Glu Glu Asp Asp His Glu Val Leu Gln Asp Gly Ser
        35                  40                  45

Leu Pro Ile Cys Val Gln Asp Gly Val His Asp Val Lys Leu Gly Asp
    50                  55                  60

Thr Asp Asp Ser Asn Ile Gly Ser Ala Ser Asp Ser Gln Val Gln Pro
65                  70                  75                  80

Ser Ser Gly Ser Ser Thr Arg Asn Ile Met Ser Arg Gly Val Asp Pro
                85                  90                  95

Asn Thr Phe Gly Ser Arg Gly Ala Met Ser Phe Val Ala Ala Thr Met
            100                 105                 110

Ala Gly Leu Ala Ser Val Gly Gly Arg Gly Val Arg Gly Ser Arg Asp
        115                 120                 125

Arg Arg Gly Leu Ser Leu Gly Gly Ser Ile Asn Glu His Asn Lys Leu
    130                 135                 140

Ile Phe Met Ala Gly Gly Lys Gln Leu Ser Lys His Leu Thr Val Tyr
145                 150                 155                 160

Gln Ala Leu Gln Arg Gln Leu Met Phe Glu Glu Asp Asp Asp Glu Lys
                165                 170                 175

Phe Asn Gly Ser Asp Leu Ser Asn Asp Gly Asn Arg Phe Trp Gly Asp
            180                 185                 190

Val Phe Thr Ile Thr Tyr Gln Lys Ala Asp Ser Gln Ala Glu Lys Val
        195                 200                 205

Ser Gln Gly Gly Ser Thr Ser Leu Asn Ser Lys Ser Asp Pro Ser Arg
    210                 215                 220

Ser Ile Ser Glu Leu Lys Gly Val Ser Leu Leu Asp Ser Ile Leu Gln
225                 230                 235                 240

Ala Glu Leu Pro Cys Asp Leu Glu Arg Thr Asn Ser Thr Tyr Asn Ile
                245                 250                 255

Leu Ala Leu Leu Arg Val Leu Glu Gly Leu Asn Gln Leu Ser Pro Arg
            260                 265                 270

Leu Arg Val His Ala Ala Ser Asp Asp Phe Ala Glu Gly Lys Ile Thr
        275                 280                 285

Thr Leu Asp Glu Leu Tyr Arg Thr Gly Ala Lys Val Pro Ser Glu Glu
    290                 295                 300

Phe Val Asn Ser Lys Leu Thr Pro Lys Leu Ala Arg Gln Met Gln Asp
305                 310                 315                 320

Val Leu Ala Leu Cys Ser Gly Ser Leu Pro Ser Trp Cys Tyr Gln Met
                325                 330                 335

Thr Lys Ala Cys Pro Phe Leu Phe Pro Phe Glu Thr Arg Arg Gln Tyr
            340                 345                 350

Phe Tyr Ser Thr Ala Phe Gly Leu Ser Arg Ala Leu Asn Arg Leu Gln
        355                 360                 365

Gln Gln Gln Gly Asp Asn Gln Asn Ala Gly Gly Glu Arg Glu Ile Arg
    370                 375                 380

Phe Gly Arg Leu Gln Arg Gln Lys Val Arg Val Ser Arg Asn Arg Ile
385                 390                 395                 400

Leu Asp Ser Ala Ala Lys Val Met Glu Met Phe Ser Ser Gln Arg Ala
                405                 410                 415

Val Leu Glu Val Glu Tyr Phe Gly Glu Val Gly Thr Gly Leu Gly Pro
            420                 425                 430

Thr Leu Glu Phe Tyr Thr Leu Leu Ser His Glu Leu Gln Ser Val Arg
        435                 440                 445

Leu Gly Leu Trp Arg Ser Ser Ser Pro Ser Asp Thr Gly Met Gln Ile
```

```
    450                 455                 460

Asp Arg Ser Ala Ser Pro Asp Asp Asp Leu Ala Ala Lys Glu Leu Ser
465                 470                 475                 480

Ser Asp Leu Pro Asp Asn Gly Ser His Leu Ile Gln Ala Pro Phe Gly
                485                 490                 495

Leu Phe Pro Arg Pro Trp Pro Leu Thr Val Asp Ala Ser Glu Gly Ser
            500                 505                 510

Arg Phe Ser Lys Val Ile Glu His Phe Arg Leu Val Gly Arg Val Met
        515                 520                 525

Ala Lys Val Leu Gln Asp Gly Arg Leu Leu Asp Leu Pro Leu Ser Thr
    530                 535                 540

Ala Leu Tyr Lys Leu Ile Leu Gly Gln Glu Leu Asp Leu Phe Asp Ile
545                 550                 555                 560

Ile Ser Phe Asp Ala Glu Phe Gly Lys Thr Leu Gln Glu Leu Gln Ile
                565                 570                 575

Leu Val Glu Arg Lys Arg Phe Leu Glu Ser Thr Tyr Gly Met Asn Gln
            580                 585                 590

Leu Glu Val Thr Asp Leu Arg Phe Arg Gly Thr Pro Ile Glu Asp Leu
        595                 600                 605

Cys Leu Asp Phe Thr Leu Pro Gly Tyr Pro Asp Tyr Ile Leu Lys Glu
    610                 615                 620

Gly Glu Glu Asn Thr Ile Val Asn Ile Tyr Asn Leu Glu Glu Tyr Val
625                 630                 635                 640

Thr Leu Val Val Asp Ala Thr Val Lys Ser Gly Ile Met Arg Gln Val
                645                 650                 655

Glu Ala Phe Arg Ser Gly Phe Asn Gln Val Phe Asp Ile Ser Ser Leu
            660                 665                 670

Lys Ile Phe Ser Pro Glu Glu Leu Asp Tyr Leu Ile Cys Gly Arg Arg
        675                 680                 685

Glu Ile Trp Glu Pro Asp Ser Leu Val Asp Asn Ile Lys Phe Asp His
    690                 695                 700

Gly Tyr Thr Ala Lys Ser Pro Ala Ile Val Asn Leu Leu Glu Ile Met
705                 710                 715                 720

Ala Glu Phe Thr Pro Glu Gln Gln His Ala Phe Cys Gln Phe Val Thr
                725                 730                 735

Gly Ala Pro Arg Leu Pro Pro Gly Gly Leu Ala Ala Leu Asn Pro Lys
            740                 745                 750

Leu Thr Ile Val Arg Lys His Pro Ser Ser Ala Val Asn Thr Ser Asn
        755                 760                 765

Ile Ala Gly Val Thr Glu Ser Ala Asp Asp Asp Leu Pro Ser Val Met
    770                 775                 780

Thr Cys Ala Asn Tyr Leu Lys Leu Pro Pro Tyr Ser Thr Lys Glu Val
785                 790                 795                 800

Met Arg Lys Lys Leu Leu Tyr Ala Ile Leu Glu Gly Arg Gly Ser Phe
                805                 810                 815

Asp Leu Ser


<210> SEQ ID NO 41
<211> LENGTH: 11157
<212> TYPE: DNA
<213> ORGANISM: Hordeum vulgare
<220> FEATURE:
<221> NAME/KEY: misc_feature
<222> LOCATION: (51)..(898)
<223> OTHER INFORMATION: n is a, c, g, or t
```

<220> FEATURE:
<221> NAME/KEY: misc_feature
<222> LOCATION: (7121)..(7121)
<223> OTHER INFORMATION: n is a, c, g, or t

<400> SEQUENCE: 41
ttgttggttt ttggtttatg tgttccttac cttaactgtg ctatcttact nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnncg 900
cggatgaaga gcatgctcgc gggcctccgc gccgacgggg aggagggccg ccaggtggag 960
gcgctgacgc agctcggcga gatgctgtcc attggcaccg aggacaccct cgccggcttc 1020
tcggttgact ccttcgtgcc tgttctggtc gggctgctca accatgagag caacccccgac 1080 atcatgctgc tcgcagcccg ggccctgacc cacctctgcg acgtgctccc gtcatcctgc 1140
tccgccgttg tgcactatgg tgcagtggca tgcttctgcg cccggcttct caccattgag 1200
tacatggacc ttgcggagca ggtgagcact gttctgttgc atcgtttgtt ctgtttatag 1260
tatatgctgc ttctatatca tgttgcctga tccagatcaa tgcttattga accatttttt 1320
ttactgtatt atgcatgatt atgccttaac ccacggtaga tgagtttcct tcaagtgttg 1380
cagctcattt gtaatatttg gacttgctgg tgagtagtgt gccttttgtg tagctgtgtt 1440
tttttctctc cccattttag ttctaaaatg aatatgggtg agaaggttaa atacttccta 1500
gttcagtacc tcaccattta acgatattac aagaaatatc tagagggtta ggctgaaggt 1560
gaatccttag cagcctaggg tcctgcctag gatctagtca ctgcccgctc tgggagggaa 1620
gaagctaagg ataggagaca catgaaagaa aaaatggttg gatgaaaaaa ggcctgatag 1680
tcacctcaag gatgttggct gaagccttag ggagcttgtc ggcatggaga ggtcttccct 1740
tcctctgctg ccgcaggagg actcggactc caaatcctca ccagcgaact caaatccatc 1800
taaggacctc atcggcccct tagaagactt tctaggcctg atcatggtgt cctcctgccg 1860
agcacatagg tgctgtttaa cacggttttg ctgtgccaga tcacctattg ctgcatgact 1920
aagctagcta tttgaacatg tttttcatct gtaatattca gggtctaata tcatgcctgt 1980
gtatgtggta ctgtaacgat ccatctgaaa tactaagaag tgggttggaa atcagatgct 2040
aagattcatg tatccggttt ctggctgtgt tttctctctg ccttcctatc ttatggatat 2100
tatacttcta cttttcttgg gtctaattca aaacaatgtg aattaacttg atatcatcag 2160

-continued

```
tttgaattcc tttgtaacca tttgtgctat tgaatctaat ttgccgctcc gaatatgtta   2220
ttgagtagta tctaccacta tcagctttat cacctaggac acttgaatta ctttgttaga   2280
ttttggtatt ttattgcttc tgtggcactt tagattagcc attttcctta ttttgtgctg   2340
tcgtttaaaa tatgctgcac aaagaatctg tcattgctag gatttgcata tttgtatgaa   2400
tggtcttgat gtggtgctaa catttcttat gccttttctg ggtattttag tcattgcaag   2460
cacttaagaa gatatcccag gagcatccaa ctgcctgctt gagggctggc gcgctaatgg   2520
cagtgctatc atatcttgac ttcttctcca ccggtgttca agtaattttg ctaaatactt   2580
ttatgttttg ccagcattta gacgtaacat tctcaatacg aacttattct ttttgcagca   2640
tttagaactt gggacataat aatttgtcat atcactttat ctttttgttg tacacatgta   2700
ctacattttt attattactc acagttgttt ttttggttaa atgtatacag agagttgcgt   2760
tatctacagc cgctaatata tgtaggaagc ttccttcaga tgcctcagat tttgtaatgg   2820
aagcggttcc actgctaaca aatcttctga actaccatga cgcaaaagta tgcttgttgt   2880
ttgtatttgg atacccttat catgccatga tatcatctat tcttagatgc tgttgttctg   2940
tatcgattta tttcaggtgc tggaacatgc ttccgtttgc ctgactcgta tagcagaatc   3000
atttgcttca tcttcagaga aactggatca gttgtgcaat catggattgg ttgcacaagc   3060
tgctagctta atagctgtta gcaactcagc gggacaagca tcactgagta cattaacata   3120
cacagtatgc ttctatttca ctttgtattg ctactactgt agtatttacg caaatttgct   3180
aactctggct catatatcct tgaagggagt aattcgtgtt ctgtcaatat gtgcaagtgg   3240
atctccattg gcagctaaaa cgctcctcct ccatggaatt agcggcacac tcaaagatat   3300
cctttcaggt tctggtttgg ttgctggtac aactgtatcc cccactaggc cagctgatca   3360
ggtgattatt attgctttat gaaggctata tcgagctaga ttatagctac ttaccgtttt   3420
atttgaatgc catcggttga tgactctgtt cggttgttgt tttatctgac ttagctgatg   3480
aagctttttg agtgatattt tgtttttcag ttttagattc actcaagtgt gcatacaatt   3540
cagttttgtt tggcaaactg aaattaatat cacacaacag aaatttcaaa atttggaaga   3600
aagttgcatg ctagatactt attctgtggt ttgtgtagtc cagtaaaaat ttaaatgttt   3660
gtaagaaagt tcagaacatg tattgtgaac agtatataat aatttgccaa acgtttcccg   3720
tgctcctggt ctttgtgcgg tgctgcaagc tataacagtg agcaaacaat gtggtagata   3780
gaattaggga tttgacttga actctctgtt taactgctca tagacctctc tgttgtctac   3840
ctgattttct ccttccagtc gtaatatgaa attcacaatg atgttattga ctttgatcaa   3900
ggtttagaga tgcgctagac tggcggtagg tgacccacat agatggcgct ctgccactgt   3960
ttgttaacct taataatctt gacatcatac ctatattact tgttccattt tctttttaaa   4020
tcaaagccaa gagtttctta tagtagttct atggtaattt gcagcttgtt ttcatatgct   4080
aatattcttt gttgtgtcac acagatgtat gaaattgtga acctcgccaa cgaattgctt   4140
cctcctctac ctgctggaac catttcttta ccagcgcatt cccatgtttt tatgaaaggc   4200
tcttctgtaa agaaacctgg ttctagcaag caaggcgagt ctggttcaac agatattaaa   4260
gtctcaggcc gggagaagtt actgcatgat cagcctgaac ttctccagca atttggcatg   4320
gatatattgc ctaccatgac acaggtcagt cccttggttt gctgatgtat cagttgatgt   4380
tgattgctga tgataaacat tattgaaata ctgttatctg atacattgtt tggatacgct   4440
ctatcccttg caggtgtatg gctccagtgt aaatggacca atacgtcata aatgcttatc   4500
tgttattgct aaattaatgt attacagctc agcggaaatg attgaaattc tccatggcac   4560
```

-continued

```
aacaaacata tccaggtgct aatacgaaac ttcagatgcc attccggctt actgttgtac   4620
atatacttgt gtacctctgg ttccatctaa cctgatattc acctttgcag cttcttagct   4680
ggcatcttag cttggaaaga tccacatgtg ttggttcctg ctcttcagat agctgaaatt   4740
ctgatggaaa agctccctgg aacattttcg aagatgtttg tgagggaagg tgttgttcat   4800
gctgtagagt cgcttatatg ccaggaaatc tcaagtccaa tgctttttca agtaccacca   4860
caggataagg atattgattc tggtacatgt acatcttcac gttcaagacg cagccgccga   4920
cgcagcagtg ctgggaatac tgataataat tccttggatg aaccaaagag ttcccatact   4980
actattgcca attcactacc aagcacgcta gaaagtccaa atactagtat tcgtgcttca   5040
gttagtgatc gcgcaaagtt attcaaagat aagtacttcc cctctgaacc cggctcaagt   5100
gatattgcag ttactgatga ccttttgaag ctacgggcac tctgtgcaaa attaaatgcc   5160
actgcagaca ctgttaaaac aaaagctaaa gggaaatcaa agtcactggg aggtgatgat   5220
tttgatatct tatgcaatgt tgaggaacag ttagacgaca tcatagctaa aatattgtct   5280
gaacttagca atggggatgg ggtttccacg tttgagttta ttgggagtgg agttatctca   5340
gcgttgctta attatttgtc ctgtggaacc tttggaaagg aaaaggtgtc cgaagcaaac   5400
ctacccaagt tgcgtcacct ggcactcagg cgatataaaa catttatata tgttgccctt   5460
ccaaatgatg cggcagggaa tcaaactcca atggcattct tagttcaaaa actgcaaagt   5520
gcgctgtctt cactggaacg gttccctgtt gtgattagcc attctggaag gacgtccagt   5580
ttgggaggat ctcgtccatc ctctggatta agtgctctat cccagcccct gaagctgcgc   5640
ctgtgtcgag caccgggtga aaagacactc aaggattatt catccaatat agttcttatt   5700
gatcccttgg caagtctagc agcagttgaa gatttccttt ggcctagaat ccagcgtagc   5760
gagtcaatat cttatcctgc agtgtcatct ggaaagaatt ctgaatctgg ggtgcctagt   5820
gcaacagcac cagtggcttc gtcaactcaa tctgttcggc ggccctcgac taggtcgaaa   5880
tcattggctg atgctgattc tgcaactaag aaggatattc aggaggggag tggaaacaca   5940
tccaagggaa aaggcaaagc tgttgttaaa tcgacgtcgg atgaaccaaa aggaccacat   6000
actaggactg cagcacgcag aaaagttgct ttagagaaag acgcagaagt gaagccagcg   6060
cacggtcaca gtagctcaga ggtttgttgt tcattatgga ctcatttcct taataatcta   6120
tagaatatat atttcctcta gtacgtcttg aatttttgct agttccccaa aatttgatga   6180
agatgcttga ctacatatgc tttgtttggt agtgcctctc cacagttact cagctgccaa   6240
gctgattttc gttatacaac tgtcctactg ttttcgtcga cgtttcatga ttatatctgc   6300
cctccttcat tagtaatttg atgtgcatct gttaagggaa atatacatga ttaataccat   6360
tatgaaatta ttatttaaca caaatttcat tgtgaaacca atgtgtgaat ttcataaaat   6420
tagatctaca gactacaatg ccttttgacc tgcagtttga tatggcatct agggggcaca   6480
tattgtctcg ccatgtctac aatgctttgg tagatgaaga cattgtctaa ctaaaatcaa   6540
tggtttaggt aaaggttggt gctcccacta tctcgaccat tgaatgtgcc taaatgttgt   6600
tgcagttcct catcctatgc aataaatgta tgttgagaga gtggcgcgga cctgaagcag   6660
taatggcaca ttccatagtt gagaacctgt gatagtggga gtatatccac caatgcgatt   6720
catttcgctg ttgaaagttt ggatcgtgat tgcccgaatg caatactgct tttcttgctt   6780
ataactgact aactgagtga taaatatata aattaagttg tcagtttaat tatatctata   6840
ccaggactca cctgtacata actacaacaa agtagatcac ttatgcgttg gaaactggac   6900
```

```
tactatttta gtaattccct tatccctgaa caaagttctg atccaattct tgtacactat   6960
gtcatgtgaa tattgaactt tattattgta tttatgttcg ttgtgcatga tacattctgt   7020
tttctacatg caggacgaag aactgggtgc atctcccttc gaggctgatg atgctttgat   7080
gcttggtgat gacgatgatg atgtctcaga tgatgaagat nagatgatga tgatcatgag   7140
gtagtatttc aaagtttctt cgattgatct ctttgttttt cttcaagtta gcgtggcttt   7200
agtgggcatg actgaaaact acatattttt gttgaaaatc ttcaggttct acgtgggtct   7260
cttcctgact gtgtcccaga gagagtgcat gatgtaaaac tagcagatgc tgatggtgga   7320
tctagtattg cctcgatagc aaatgataac cagacacaac cctcatctgg ctccagcata   7380
aaaaatactt ttagtagcag gggagcaggt tctgttgaac ttagaactcc aagcacactt   7440
ggttctcggg gcgcaatgtc gtttgctgca gctgccatgg ctgggcttgc ttctgttggt   7500
agtcgtggtg tcagaggtag ccaggatagg cgtggccttc cacttggaac tagtgcacat   7560
gagcattcca acaaattgat atttacagct ggcggcaagc agcttagcaa gcatttgact   7620
gtatatcaag ctatgcaaca gcaagtagtt catgatgagg atgatgagga aaggttgggt   7680
ggttctgatt tacccaatga tggaagccgt ctctggagtg atatgttcac tataacatat   7740
caaaaggctg ataatgaagt ggatagggaa tcaaccagag gttcatcttt agtgctgaaa   7800
tcgtccaaat cagatttttg ccgagctaca tctcaagaac aatgcatttc tcttcttgat   7860
agcattttgc aaggagaact tccttgtgat attgagaaat cgacccaaac ttacaatatc   7920
ttagcactgt tgcgtgtatt ggagggatta aatcagctat ctcctcgtct gagactacag   7980
gcaacctgtg atgattttat agagggaaaa gttggtaccc tggatgggtt atatggcacc   8040
ggagctaagg taccctcaga ggagtttatc agcagtaagt tgacaccaaa gcttgctcgg   8100
caaattcagg atgttcttgc actctgtagt ggtagtttac cttcttggtg ttatcagatg   8160
accaaagctt gcccatttct gttccctttt gaaacaagaa gacagcactt ctactccaca   8220
gcttttgggt tatctagggc attgaaccgt cttcagcaac aacaggggga taataataac   8280
tctgcgactg aaagagaagt ccggattggt agattgcaac gtcagaaagt tcgtgtttct   8340
cgtaaccgga tcctggattc tgctgccaaa gtaatggaga tgttctccaa tcagaaggct   8400
gttcttgaag ttgaatactt tggtgaagtt ggaactggac ttggtccaac tttggaattc   8460
tataccctct taagtcatga cctgcaaagg attggcttag gattatggag atctgattct   8520
gattctttag aagctaaaaa acatgattcg atttcacctg ctgatagcag gaacttgata   8580
caagcacctc ttggcttgtt ccctcggcct tggccaccta gtactgcttc ttcagagggt   8640
agtaaattct tcaaagttgt tgagtatttc cgcttggttg gtcgaatcat ggcaaaagca   8700
ttgcaagatg gaaggcttct tgacttgcct ttgtcaacag cattttataa gcttctactt   8760
ggacaagtaa gcatgagaac ctgcttgcag tagatccatt ccaataaccc cttccacctt   8820
tttgtcaagt cgtggtgttt tttttatttt atctactgtc ttctgtattg acgccataat   8880
attttgcttt gctaggaact tgatttgtat gacatactat cttttgatgc cgagttcggt   8940
aaaatactgc aagagttgca agttcttgtt gagcgcaagc gatttctgga gtcctgctct   9000
aattatagtc aacaaataga agatttgagc ttccgtggtg ctcctattga agacctatgc   9060
ttagatttta ctcttccggg ctatccggat tttgttctga aggaaggtga agaaaataca   9120
gtggtatgtg atggagtaga ttaggttctt gtgttgtcat tacttcagct tttgcttcta   9180
actattcatt gttattttaa cttcctgtag gtctgcattt acaacttaga agagtacatt   9240
tcgttggtag tggaggctac actaaagact ggaataatac gtcaagtaga agcattcaaa   9300
```

-continued

```
gctggattta atcaggtttt ctcatttttc taagatactt ctcattgata tttagctttg   9360
catttctctt aaaacatttt tatttttcta attcaggtat ttgacatatc atcactacaa   9420
atattttctc ctcaagagct tgactatctc atttgtggtc gacgggaact ttgggaggta   9480
atgccctctt aactttcttt ctcccttcta taattagtat cttaacttgg ttctgagcaa   9540
atgcatgtaa tgcagccgga gacactggtc gagcatataa agtttgatca tggttatacc   9600
tcgaagagtc cagcaattgt caatgtgagt acatccctta tcttttaaag aaggcacata   9660
tcttcacaca gcttttattt cagaactttg gaacttcggt ttaatgtttg tgctgttggt   9720
ttgcagctac ttgagatcat gacggaattt actccggagc aacaacatgc tttctgccag   9780
tttgtgactg gtgctcctcg gcttccacct ggtggcttag cctccctaaa tccgaagctg   9840
actatcgtta ggaaggtaag cctgttgtag caatgcagaa tgacatcgtt tctgtgttca   9900
tgttatttaa gcttttgcat tttgtatctt ggccagcact cctcgactgc gacgaatact   9960
tcaaatgcag ctggagcagc agagtctgct gatgatgatc tgcctagcgt catgacttgt  10020
gccaactatc ttaaacttcc gccatactcg acaaaggttt ggttcttttg ctcgatgaat  10080
ctttgttcta ccttttggca ttgtcttgcc tggaaactga cttctgctat ggttgtcggg  10140
acgttattac aggaagttat gcacaagaag ctgctttatg ctatcaacga aggccagggg  10200
tcgtttgatc tttcatagtg ggttcaaaac taacatacag atgttggtgc acatgtaaat  10260
gcgcaccagt ttttattcag ttagtttgtt cattgtcgtc atgtataaca taggctttaa  10320
gtcgtttctt ttgtgaaagg tttagagcct ggatcttgtg gtgccagtgc ttataacatt  10380
ctctcttcat tcctgggcac ttgtatatat tctccaactg atctctatag tgactaagaa  10440
gacattcctc ttttggtagt cagttatata cttcatcatc atactctcgt ctattttgag  10500
tgacttgcgc tcgtgattat taggttgctc taatgaaagc gatatcctca gttcttactg  10560
tgcaattagt gcacatcttt tgaataacta aatgcctagt gcccttacaa tacggggcac  10620
atgtaataat tcctgccaat tagtctgcct ttgtagtacg aattaaacca ttggtgtgaa  10680
ctctctaaaa aacggttata tttggtgagt ggggaatgga caaaatatga acatttgaaa  10740
tgttgcttgg atttcaaatt gtgccaatag gaaaattgta acaccaaagg gaggactttt  10800
gttatctagt gtggttgatt tgattagaca aacaatgtgg ccgttcaatg tattctaatt  10860
ccactatcac aacatgacat gccagatttc attgcttgga gctatatgta gaatggtatg  10920
ttttcggtcc ggtttgctta atctgtagag tgggaccatt agtatgaaat taaactgtga  10980
catttaatgg aatgggacga actatggcta accctctctg gagtaagtta tggaggttac  11040
cttgctcggt aaatgttaat atttttaact cacggacgtt acatgacacc cttgttgtgt  11100
aacgcttgca aacaaacata tgaaaatgtc accaatttgt cccaagatat aaagcat     11157
```

```
<210> SEQ ID NO 42
<211> LENGTH: 652
<212> TYPE: PRT
<213> ORGANISM: Hordeum vulgare

<400> SEQUENCE: 42

Leu Arg Gly Ser Leu Pro Asp Cys Val Pro Glu Arg Val His Asp Val
1               5                   10                  15

Lys Leu Ala Asp Ala Asp Gly Gly Ser Ser Ile Ala Ser Ile Ala Asn
            20                  25                  30

Asp Asn Gln Thr Gln Pro Ser Ser Gly Ser Ser Ile Lys Asn Thr Phe
        35                  40                  45
```

-continued

Ser Ser Arg Gly Ala Gly Ser Val Glu Leu Arg Thr Pro Ser Thr Leu
    50                  55                  60

Gly Ser Arg Gly Ala Met Ser Phe Ala Ala Ala Ala Met Ala Gly Leu
65                  70                  75                  80

Ala Ser Val Gly Ser Arg Gly Val Arg Gly Ser Gln Asp Arg Arg Gly
                85                  90                  95

Leu Pro Leu Gly Thr Ser Ala His Glu His Ser Asn Lys Leu Ile Phe
            100                 105                 110

Thr Ala Gly Gly Lys Gln Leu Ser Lys His Leu Thr Val Tyr Gln Ala
        115                 120                 125

Met Gln Gln Gln Val Val His Asp Glu Asp Asp Glu Glu Arg Leu Gly
    130                 135                 140

Gly Ser Asp Leu Pro Asn Asp Gly Ser Arg Leu Trp Ser Asp Met Phe
145                 150                 155                 160

Thr Ile Thr Tyr Gln Lys Ala Asp Asn Glu Val Asp Arg Glu Ser Thr
                165                 170                 175

Arg Gly Ser Ser Leu Val Leu Lys Ser Ser Lys Ser Asp Phe Cys Arg
            180                 185                 190

Ala Thr Ser Gln Glu Gln Cys Ile Ser Leu Leu Asp Ser Ile Leu Gln
        195                 200                 205

Gly Glu Leu Pro Cys Asp Ile Glu Lys Ser Thr Gln Thr Tyr Asn Ile
    210                 215                 220

Leu Ala Leu Leu Arg Val Leu Glu Gly Leu Asn Gln Leu Ser Pro Arg
225                 230                 235                 240

Leu Arg Leu Gln Ala Thr Cys Asp Asp Phe Ile Glu Gly Lys Val Gly
                245                 250                 255

Thr Leu Asp Gly Leu Tyr Gly Thr Gly Ala Lys Val Pro Ser Glu Glu
            260                 265                 270

Phe Ile Ser Ser Lys Leu Thr Pro Lys Leu Ala Arg Gln Ile Gln Asp
        275                 280                 285

Val Leu Ala Leu Cys Ser Gly Ser Leu Pro Ser Trp Cys Tyr Gln Met
    290                 295                 300

Thr Lys Ala Cys Pro Phe Leu Phe Pro Phe Glu Thr Arg Arg Gln His
305                 310                 315                 320

Phe Tyr Ser Thr Ala Phe Gly Leu Ser Arg Ala Leu Asn Arg Leu Gln
                325                 330                 335

Gln Gln Gln Gly Asp Asn Asn Asn Ser Ala Thr Glu Arg Glu Val Arg
            340                 345                 350

Ile Gly Arg Leu Gln Arg Gln Lys Val Arg Val Ser Arg Asn Arg Ile
        355                 360                 365

Leu Asp Ser Ala Ala Lys Val Met Glu Met Phe Ser Asn Gln Lys Ala
    370                 375                 380

Val Leu Glu Val Glu Tyr Phe Gly Glu Val Gly Thr Gly Leu Gly Pro
385                 390                 395                 400

Thr Leu Glu Phe Tyr Thr Leu Leu Ser His Asp Leu Gln Arg Ile Gly
                405                 410                 415

Leu Gly Leu Trp Arg Ser Asp Ser Asp Ser Leu Glu Ala Lys Lys His
            420                 425                 430

Asp Ser Ile Ser Pro Ala Asp Ser Arg Asn Leu Ile Gln Ala Pro Leu
        435                 440                 445

Gly Leu Phe Pro Arg Pro Trp Pro Pro Ser Thr Ala Ser Ser Glu Gly
    450                 455                 460

-continued

```
Ser Lys Phe Phe Lys Val Val Glu Tyr Phe Arg Leu Val Gly Arg Ile
465                 470                 475                 480

Met Ala Lys Ala Leu Gln Asp Gly Arg Leu Leu Asp Leu Pro Leu Ser
                485                 490                 495

Thr Ala Phe Tyr Lys Leu Leu Leu Gly Gln Glu Leu Asp Leu Tyr Asp
            500                 505                 510

Ile Leu Ser Phe Asp Ala Glu Phe Gly Lys Ile Leu Gln Glu Leu Gln
        515                 520                 525

Val Leu Val Glu Arg Lys Arg Phe Leu Glu Ser Cys Ser Asn Tyr Ser
    530                 535                 540

Gln Gln Ile Glu Asp Leu Ser Phe Arg Gly Ala Pro Ile Glu Asp Leu
545                 550                 555                 560

Cys Leu Asp Phe Thr Leu Pro Gly Tyr Pro Asp Phe Val Leu Lys Glu
                565                 570                 575

Gly Glu Glu Asn Thr Val Val Cys Ile Tyr Asn Leu Glu Glu Tyr Ile
            580                 585                 590

Ser Leu Val Val Glu Ala Thr Leu Lys Thr Gly Ile Ile Arg Gln Val
        595                 600                 605

Glu Ala Phe Lys Ala Gly Phe Asn Gln Arg Tyr Leu Thr Tyr His His
    610                 615                 620

Tyr Lys Tyr Phe Leu Leu Lys Ser Leu Thr Ile Ser Phe Val Val Asp
625                 630                 635                 640

Gly Asn Phe Gly Ser Arg Arg His Trp Ser Ser Ile
                645                 650
```

<210> SEQ ID NO 43
<211> LENGTH: 9256
<212> TYPE: DNA
<213> ORGANISM: Gossypium hirsutum

<400> SEQUENCE: 43

```
taaaaagctt caccctttttt atttatttat tcattttcac tttagggttt caagtttctc     60

tcttaacctt catctcttta gggctcaaat tctcccctaa ttaatcattg aattctattt    120

cattcaaaac caagacaaag gcgtggtttc cctgattgta aattctaggg ttttacattt    180

atccgaagcg tggattcctt tgttttcgtt ttctagggtt tcgataagct gttgttgaga    240

tgcaacaaat aatcggatca ggaatcgtct gatcttgtgg tggtgaccgt ccgataatca    300

ggggcgttgg tcccctttgt atggaaactc ggagccggaa gcgggcggag gcctcctcag    360

ctgcccttc atcttctccc tccggtccca ccactcgctc tcataaacgc gttcgtctct    420

cttcctcctc tgccgctgcc gccgccaccg tcgctgttac tcgctcccgt acttcccgca    480

catcacgtac ttccgctgcc ttaatggacc ccactacaat cgaatcttct tccggttccc    540

gccgtgatcg ccgttccagc aaagctaacc aaaccacaac aagtgacaat ccgaatcttg    600

cctctgatag aggaaaggaa aaggaacatg atcctaggat tcgcgataga gatagagaca    660

gggataatag agacaacaat tctaatcatc ctgagagaaa tttaggatta aatatggaca    720

cctctggagg cgatgaggat gataatgata gcgaaggcgg tgtagggatt ttgcaccaga    780

atctgacgtc agcaagcagc gcgttacaag gcttgttgag gaagctcggt gccggacttg    840

atgatttgct tccctcatcg gcaatgggtt ccgggtcttc atctcatcaa agtgggaggt    900

taaagaaggt tctgtctgga ttgcgtgctg atggagagga agggaggcaa gtggaggcgc    960

tgacccagct gtgtgaaatg ctttcaattg gtactgagga atcgttgagc acgttttctg   1020

ttgattcctt tgttcccgtg ctcgttggat tgcttaatca cgagagtaat cctgatatca   1080
```

-continued

```
tgatacttgc tgcaagggcg cttactcatt tgtgtgatgt gttgccttct tcatgtgctg   1140
ctgttgtgca ttatggtgct gtttcatgtt tttgtgctag gttgctcact atagagtata   1200
tggacttggc tgaacaggtt ggcattttcg ttgcttccta aataattgat tgttagaaaa   1260
tgaaattgat caaatatgtg gttaaactta aacacccttg agctgattga gcgacatctt   1320
gcatttcatt atgaactatg gtgaactgca actagctaat tctactagaa gttggccccc   1380
caactgataa acaggggata gttgagcatt ttcctgaaag cctatttgac ttaaaatttg   1440
cttgtttcta actaactgtt aaaaattaat gttgtgggta ttctttattg ttcttagtta   1500
tggacttgaa ttagaaagtt gaaaactgta gatttgctcc cctccacttt cttatctttc   1560
tggttgaatt gctgcaacag tctctgcaag ctctgaagaa gatatctcaa gaacacccaa   1620
ctgcttgtct gcgagctggt gctctcatgg cagtgctttc atacttggat ttcttctcca   1680
ctggggttca ggtgatttaa tttgtgaaca ttttgagtgt taatcagcat ctatggagtg   1740
gagaattttc ttgctattta gattcttatt gtgtttgttt cctatatttg atcccatatt   1800
ccagcgagtg gcactatcta ctgctgcaaa tatgtgtaag aaactccctt cagatgcagc   1860
tgattatgtc atggaagctg taccactatt aacaaatctt ttgcagtatc atgattcgaa   1920
ggtaacgtga acatcatatt agtgatgagt catttgtggt caattatgtt tcatcctgaa   1980
cacttagcta tctttctagg tgctggagca tgcatctgtt tgtttaacgc gcattgctga   2040
agcctttgca tcttccccgg ataaattaga tgagctttgc aattatggac tggttactca   2100
ggctgcatct ctcatttcca taagtaattc tggaggtgga caggcatcat tgagtacacc   2160
aacatatacg gtgaattgat ggtgctcctt tgtttatcta tttgaatgca ttttatgtac   2220
catttcatga catttgggtt tttgaattca gggcttaatt cggctgctct caacttgtgc   2280
aagtgggtct cccttgggag caaaaacttt acttctgctt gggatcagtg gcatacttaa   2340
agatatacta tcaggttctg gtgtttcggc taactcatct gtttcaccag ccttaagcag   2400
accggcagag caggtaacaa ttttaattca agctgaagag ttggtagtta ttattgctag   2460
ctgtttattt aactgtttta catgtgtgcg atgctatatt aatacaagtg gagctgagga   2520
aatggtataa cctttaaaga caaagtatca actccaagct ttactatcaa ttttgtgaac   2580
attgcatgtc agttgttttt tgttttgtgg tatctttttt tagttaaggc tgaagagatt   2640
gtagtcttca ttgcatgttg tttatatata cctgtgtaca tatgatacgt gtaaggtttg   2700
aatgttatat tattactagc agtgaggaaa atggtataaa tgttaagaca caaagtttaa   2760
cccttttttat ttggttaaaa gttacttgtt ttcaatactt ctatttattt cttgcacttt   2820
atacagtcta tattgacata ctaaattagt aatagcttat gcatgtaagc catatttgtc   2880
tgatgggtct tgtaattctt atatgattgt gtagattttt gagattgtca atctggcaaa   2940
tgagcttctt cctccattgc cacaaggaac catctccctc cctgctagct ctaatatatt   3000
tgtgaaagga tctattttga agaggtctcc tactagcagc tctgggaagc aagaagacac   3060
caatcgaaat gctcttgagg tttcaccccg tgagaaatta ttgaatgatc aacctgaact   3120
tcttcagcag tttggagtgg atctccttcc tgttctcatt caggtagcct tttctttgca   3180
gatggtagtt tggttatctc ttggttgttg gtattgtctc ttatctttta tggtattttc   3240
tttttgtgtg tagtattata taattcctta tcttttgtct atcagatcta tggttccagt   3300
gtcaatagcc ctgttcgcca caagtgtctc tcagttattg gaaaactaat gtacttcagc   3360
agtgcagaga tgattcagaa tctattaagt gtgacaaata tatctaggta tccaccttaa   3420
```

```
gtaaaataga gtcgttaaca tattcattga atgattggtt atagtgactt attattttgt   3480
ttgatcttat agcttcttgg ctggtgtttt agcatggaaa gatccatatg tcttggttcc   3540
ttccctgcaa attgctgaga tcctcatgga aaagcttcct ggaactttct ccaaaatgtt   3600
tgttcgagag ggcgtggttc atgctgtgga ccagcttgtt ttaattggta atcaaaatac   3660
cactcctgtt caagcatctt cacttgagaa agataatgag tctgtatctg gagcttcatc   3720
acgttctagg cgatatagac gacgtagtgg taactctaat cttgaaggaa gttctatgga   3780
ggagtccaag aatccagcat ctttaaatat tggctcacct actaattcag tcgaaattcc   3840
tacagccaat tccaatcttc gtactgcagt aagtgcatgt gctaaagcat ttaaagataa   3900
gtatttcccc tctgatcctg gggctgttga agttggagta acagatgatc tgttacactt   3960
aaaaaatctt tgcatgaaat tgaatgctgc tgttaatgat caaaagacca aggcaaaagg   4020
aaaatctaaa gcttcggggt ctccatgggt tgatttttct actagcaatg aagagtattt   4080
gactggggtg atttctgaga tgctagcaga actaagcaag gggggatggtg tatccacttt   4140
tgagtttatt ggtagtggtg ttgttgtggc cttgttaaac tatttttctt gcgggtactt   4200
ctcccaggag agaatttcag atgtgaacct gcccaagctt cgtcaacaag cccttaagag   4260
atacaaatca tttatcagtg ttgcccttcc ttctagtgtt gatgaaggaa gtatggctcc   4320
tatgactgtc ctggttcaga agcttcaaaa tgctttatca tctttagagc gttttcctgt   4380
agttcttagc cattcatcta ggtcatctag tgggagtgca cgcctctctt ctggtttagg   4440
tgcattagct cagcctttta agttgcggct ctgtcgagcc ccaagagaga agtctcttcg   4500
tgactattct tcgaatattg tgttgattga cccattagca agtctagcag ctgttgaaga   4560
atttctttgg cctcgagttc aacgaagtga cacttctcag aaactctctg tgactgttgg   4620
aaattctgag tctgggaaca cacctaaccg gactgatgta tcttctccgt ctacctcaac   4680
tcctgcttct accacccgac gccattcttc aaggtccaga tcatctgtca atattggaga   4740
tgtggccaga aaggagcaat cacaggagaa aagcactagt tcatcaaagg gaaaaggtaa   4800
ggctgttttg aagccttcta aagaggagcc aagaggacct caaacaagaa atgctgctcg   4860
tagaagagct gctctggata aagatgctcc aatgaaacct gtaaatgacg actctacttc   4920
tgaggtatgc tttttgatta ttagatatga tttttcattt gttaataagg cagtcatgtt   4980
caatatgact atgtcaggac ttccctgttt ttagcttgtg tttcttctct gttgcttgca   5040
tggaattgtg cctttctttc tatttcctgt tgaatgatca tcatttgacc cttatttggt   5100
tggttaggat gaagaattgg atatgtcccc tgtggagatt gatgatgctt tggtgattga   5160
agatgatgat atttctgatg atgaagatga tgaacatgaa gatgtaagtt atattgtgcc   5220
tgtagaaatg tgcagcccct tgttgattgt aaactccttt taaatcttac tattgattga   5280
tggaaatgtt gttcttttcc aggtgctcag ggatgattct cttccagttt gtacacctga   5340
taaagtacat gatgttaagt tgagtgattc agctgaagat ggttctcctg ctccagctgc   5400
aagtgatagc caaactaatg cagcttcagg atctagcagc agagctgctg ctattagggg   5460
ttcagactct gctgatttta ggagtggcta tggctcaagg ggtgcaatgt cgtttgcagc   5520
tgctgccatg gctgggcttg gatctgccaa tggtagaggt attaggggag gtagagatcg   5580
acaaggaaga cctcctggca gttctaatga gcctccaaag ttgatattca ctgctggtaa   5640
taagcagctc aacaggcatt tgaccatcta tcaggccatt caaagacagc ttgtgttgga   5700
tgaggatgat gatgagagat atgctggtag tgattttaca tctagtgatg gaagaggggt   5760
gtggagtgat atctacacaa taacatatca gagggctgag agccaagctg atcgatcatc   5820
```

accaggggga tcaggttctg ctacagcatc taaatctggt aaatctggtt catccaattc 5880
cagctctgat ccccaacctc atagaatgtc tctattagat agcatattgc aaggggaact 5940
tccttgtgat ctagacagat ccaatcctac ttatactata ttggcactgt tgcgcgtgtt 6000
agagggtctg aatcagcttg cacctcgttt gagagctcag attgtttctg ataattttgc 6060
tgagggaaat gttttaactc tgggtgagtt gagcacctcc ggttctagag ttcctcatga 6120
ggaatttatt aatggtaagc tgactccaaa actggcgcgg caaattcagg atgttcttgc 6180
tctatgtagt ggaagccttc cttcctggtg ttaccagttg acaaaggcat gcccctttctt 6240
atttcctttt gagacacgaa ggcagtactt ctattcaact gcctttgggt tgtctcgtgc 6300
attatatcgt ctgcagcagc atcaaggtgc tgatggccat gggtcaacta atgaaagaga 6360
ggtaagggtt gggagattac agaggcagaa agttcgtgtc tcccggaacc gcattttgga 6420
ctctgctgca aaagtgatgg agatgtattc cagccaaaaa actgtgcttg aagttgaata 6480
ttttggagaa gttggcaccg gattgggtcc aaccttggag ttttatacgc ttttaagtca 6540
tgacttgcaa aaggttggac ttgcaatgtg gaggtcgaat tctacatgga acaagtcagt 6600
gatggaaatt gatggagatg gagataaaaa tggaaaaatt gctggttctg ctactattaa 6660
cggagatata gtccaagctc ctctggggtt attcccccga ccttggccac caaatgctga 6720
tgcttctgaa ggtagccaat tttttaaagt aattgaacat ttccggctgg ttgggcgtgt 6780
tatggcaaaa gctcttcaag atggacggct tttagatctg cctctctcaa tggcatttta 6840
taaacttgtg cttggtcaag taagctgact gcatttttttg acttattgaa catgttaaat 6900
ctactttagc cttgtatttc acgttttcat accgataaag taatccctag cattgtcaca 6960
atggtctttt acctgttctt gctaaagttg actttataaa ccattgcagg agcttgattt 7020
gcatgatatt ctgtcttttg acgccgaatt tggcaaaatt ctgcaagaat tgcatttact 7080
tgttcgtcga aagcaatatc tagattcatt gggtggtgac aatagtgatg caattcctga 7140
cttacggttc cgtggagcct caatagaaga tctctgtttg gatttcacgc ttccaggata 7200
tccggactac atattgaagc taggggatga aactgtatgt cttcaacttc tcattctgtt 7260
acccccacct cattttttttg tcaagatttt ttaatgtaat gttaaatata tcaggtggat 7320
atcaacaact tagaggaata catatctttg gtggttgatg caactgtgaa gactggaatt 7380
atgcatcaaa tggaggcatt tagagacggt ttcaatcagg tgaagatgct ttctttgttc 7440
tgagtttctt gactaattac aaattgatgt ccatcatgga tttccctaat atatgcatgt 7500
aaggagctgt ttttgggatt gatctcaatg ttaatatatc cgttatataa catgcaggtt 7560
tttgatatct catcactgca aatatttaca ccccaagagt tggactattt gctgtgtggt 7620
cgtagagagt tgtgggaggt aatttgacac ttgaattatg tgatcgtgtt gccatctttg 7680
atcagaactg gttttgcact ttgattttaa caatactact tttaattttg caggctgaga 7740
ctcttgctga tcatataaaa ttcgatcatg gatatactgc aaagagccct ccaattgtta 7800
atgtatgttt gtttcatact actcacattt aagtttttttg agaggcattt gatccgtaat 7860
gatgttctgt tttgtgattt cttagttgct tgaaattatg ggagaattaa caccagagga 7920
gcagcgggcc ttctgtcaat ttgttactgg tgcacccagg cttccacccg gtggtctggc 7980
agtgctaaat ccaaggctga caattgttag aaaggtaatt tgagttagaa ttaaaaacct 8040
tttctcaata tttcttcttg attacaatga tgtagacatt tgtcgtcttg cattgaaaat 8100
ctcattaaga tgattttgga agtcaggtgg aaatggacat atttattgca ggttatggct 8160

-continued tctttatgtg cactggcttc aatactttta aaattgctac taaagatgga ataaattaat 8220
gagtgctatg gctaatgttc tgattcaggc taaattatcg ctttatttat ttcttgctgt 8280
aaaattattg ctgttaagat aatattccat tcacctagtc tagtatctag ggctattctt 8340
gtttggtatg ttggtggctt gaatgctaat ctgtctgaaa tctaaatgca gcattcttcg 8400
tctgcgactg ctgctgctgc tgccaatgga actggactct cagaatcagc agatgaggac 8460
ttgcctagtg tcatgacttg tgctaattac ttgaagcttc ctccatattc taccaaggta 8520
tgtgattatt ttttattgtg aggaaggggg ttaaattatt cttgtactaa tttcatggat 8580
attaacagga aattatgtat aagaaattgc tatatgcaat caatgaaggg caaggatctt 8640
ttgatttgtc atgagtccac cgccacaagg ctaacgaaca gaagagagtt gtgtggtgtt 8700
gtgttgaggc agtgtgtata tttctgagca gcacaatccg agggtcaatt tttctcacct 8760
gctgcgagta tttttgatgt tccaaagtag catattgatt ttgctcaaat aatggcattt 8820
ctcttcactg ctgcttctcc gttacttcaa acttttctca aatcctgggt agacacaaat 8880
ctgatttttt ccgctttagt atttctaata ttttccccag ttgcatgcga cttatatgct 8940
aaagcacaga agaatttagt aggatgtttt ttgttaaagc acttctgcat tcagctgcta 9000
gagctttgta tataaaatta gggaggaaaa tgaataaaat aatgatgaaa ttgttattcc 9060
tttttctttt tcatcctttg tttatattta gtcctttcgg ttttctaaat tgctacgagt 9120
tttcctatga aaaatttgca atttttgggc tcggtaaatt ttagttaaca aatagaaata 9180
ctttagtttg ctcaaagttg gttttgctac tttcagttct ttcatactct ttctattaat 9240
tatgttcttt tgtgaa 9256

<210> SEQ ID NO 44
<211> LENGTH: 1904
<212> TYPE: PRT
<213> ORGANISM: Gossypium hirsutum

<400> SEQUENCE: 44

Met Glu Thr Arg Ser Arg Lys Arg Ala Glu Ala Ser Ser Ala Ala Pro
1 5 10 15

Ser Ser Ser Pro Ser Gly Pro Thr Thr Arg Ser His Lys Arg Val Arg
20 25 30

Leu Ser Ser Ser Ser Ala Ala Ala Ala Ala Thr Val Ala Val Thr Arg
35 40 45

Ser Arg Thr Ser Arg Thr Ser Arg Thr Ser Ala Ala Leu Met Asp Pro
50 55 60

Thr Thr Ile Glu Ser Ser Ser Gly Ser Arg Arg Asp Arg Arg Ser Ser
65 70 75 80

Lys Ala Asn Gln Thr Thr Thr Ser Asp Asn Pro Asn Leu Ala Ser Asp
85 90 95

Arg Gly Lys Glu Lys Glu His Asp Pro Arg Ile Arg Asp Arg Asp Arg
100 105 110

Asp Arg Asp Asn Arg Asp Asn Asn Ser Asn His Pro Glu Arg Asn Leu
115 120 125

Gly Leu Asn Met Asp Thr Ser Gly Gly Asp Glu Asp Asp Asn Asp Ser
130 135 140

Glu Gly Gly Val Gly Ile Leu His Gln Asn Leu Thr Ser Ala Ser Ser
145 150 155 160

Ala Leu Gln Gly Leu Leu Arg Lys Leu Gly Ala Gly Leu Asp Asp Leu
165 170 175

-continued

```
Leu Pro Ser Ser Ala Met Gly Ser Gly Ser Ser Ser His Gln Ser Gly
            180                 185                 190

Arg Leu Lys Lys Val Leu Ser Gly Leu Arg Ala Asp Gly Glu Glu Gly
        195                 200                 205

Arg Gln Val Glu Ala Leu Thr Gln Leu Cys Glu Met Leu Ser Ile Gly
    210                 215                 220

Thr Glu Glu Ser Leu Ser Thr Phe Ser Val Asp Ser Phe Val Pro Val
225                 230                 235                 240

Leu Val Gly Leu Leu Asn His Glu Ser Asn Pro Asp Ile Met Ile Leu
                245                 250                 255

Ala Ala Arg Ala Leu Thr His Leu Cys Asp Val Leu Pro Ser Ser Cys
            260                 265                 270

Ala Ala Val Val His Tyr Gly Ala Val Ser Cys Phe Cys Ala Arg Leu
        275                 280                 285

Leu Thr Ile Glu Tyr Met Asp Leu Ala Glu Gln Ser Leu Gln Ala Leu
    290                 295                 300

Lys Lys Ile Ser Gln Glu His Pro Thr Ala Cys Leu Arg Ala Gly Ala
305                 310                 315                 320

Leu Met Ala Val Leu Ser Tyr Leu Asp Phe Phe Ser Thr Gly Val Gln
                325                 330                 335

Arg Val Ala Leu Ser Thr Ala Ala Asn Met Cys Lys Lys Leu Pro Ser
            340                 345                 350

Asp Ala Ala Asp Tyr Val Met Glu Ala Val Pro Leu Leu Thr Asn Leu
        355                 360                 365

Leu Gln Tyr His Asp Ser Lys Val Leu Glu His Ala Ser Val Cys Leu
    370                 375                 380

Thr Arg Ile Ala Glu Ala Phe Ala Ser Ser Pro Asp Lys Leu Asp Glu
385                 390                 395                 400

Leu Cys Asn Tyr Gly Leu Val Thr Gln Ala Ala Ser Leu Ile Ser Ile
                405                 410                 415

Ser Asn Ser Gly Gly Gly Gln Ala Ser Leu Ser Thr Pro Thr Tyr Thr
            420                 425                 430

Gly Leu Ile Arg Leu Leu Ser Thr Cys Ala Ser Gly Ser Pro Leu Gly
        435                 440                 445

Ala Lys Thr Leu Leu Leu Leu Gly Ile Ser Gly Ile Leu Lys Asp Ile
    450                 455                 460

Leu Ser Gly Ser Gly Val Ser Ala Asn Ser Ser Val Ser Pro Ala Leu
465                 470                 475                 480

Ser Arg Pro Ala Glu Gln Ile Phe Glu Ile Val Asn Leu Ala Asn Glu
                485                 490                 495

Leu Leu Pro Pro Leu Pro Gln Gly Thr Ile Ser Leu Pro Ala Ser Ser
            500                 505                 510

Asn Ile Phe Val Lys Gly Ser Ile Leu Lys Arg Ser Pro Thr Ser Ser
        515                 520                 525

Ser Gly Lys Gln Glu Asp Thr Asn Arg Asn Ala Leu Glu Val Ser Pro
    530                 535                 540

Arg Glu Lys Leu Leu Asn Asp Gln Pro Glu Leu Leu Gln Gln Phe Gly
545                 550                 555                 560

Val Asp Leu Leu Pro Val Leu Ile Gln Ile Tyr Gly Ser Ser Val Asn
                565                 570                 575

Ser Pro Val Arg His Lys Cys Leu Ser Val Ile Gly Lys Leu Met Tyr
            580                 585                 590

Phe Ser Ser Ala Glu Met Ile Gln Asn Leu Leu Ser Val Thr Asn Ile
```

```
        595                 600                 605

Ser Ser Phe Leu Ala Gly Val Leu Ala Trp Lys Asp Pro Tyr Val Leu
    610                 615                 620

Val Pro Ser Leu Gln Ile Ala Glu Ile Leu Met Glu Lys Leu Pro Gly
625                 630                 635                 640

Thr Phe Ser Lys Met Phe Val Arg Glu Gly Val Val His Ala Val Asp
                645                 650                 655

Gln Leu Val Leu Ile Gly Asn Gln Asn Thr Thr Pro Val Gln Ala Ser
            660                 665                 670

Ser Leu Glu Lys Asp Asn Glu Ser Val Ser Gly Ala Ser Ser Arg Ser
        675                 680                 685

Arg Arg Tyr Arg Arg Arg Ser Gly Asn Ser Asn Leu Glu Gly Ser Ser
    690                 695                 700

Met Glu Glu Ser Lys Asn Pro Ala Ser Leu Asn Ile Gly Ser Pro Thr
705                 710                 715                 720

Asn Ser Val Glu Ile Pro Thr Ala Asn Ser Asn Leu Arg Thr Ala Val
                725                 730                 735

Ser Ala Cys Ala Lys Ala Phe Lys Asp Lys Tyr Phe Pro Ser Asp Pro
            740                 745                 750

Gly Ala Val Glu Val Gly Val Thr Asp Asp Leu Leu His Leu Lys Asn
        755                 760                 765

Leu Cys Met Lys Leu Asn Ala Ala Val Asn Asp Gln Lys Thr Lys Ala
    770                 775                 780

Lys Gly Lys Ser Lys Ala Ser Gly Ser Pro Trp Val Asp Phe Ser Thr
785                 790                 795                 800

Ser Asn Glu Glu Tyr Leu Thr Gly Val Ile Ser Glu Met Leu Ala Glu
                805                 810                 815

Leu Ser Lys Gly Asp Gly Val Ser Thr Phe Glu Phe Ile Gly Ser Gly
            820                 825                 830

Val Val Val Ala Leu Leu Asn Tyr Phe Ser Cys Gly Tyr Phe Ser Gln
        835                 840                 845

Glu Arg Ile Ser Asp Val Asn Leu Pro Lys Leu Arg Gln Gln Ala Leu
    850                 855                 860

Lys Arg Tyr Lys Ser Phe Ile Ser Val Ala Leu Pro Ser Ser Val Asp
865                 870                 875                 880

Glu Gly Ser Met Ala Pro Met Thr Val Leu Val Gln Lys Leu Gln Asn
                885                 890                 895

Ala Leu Ser Ser Leu Glu Arg Phe Pro Val Val Leu Ser His Ser Ser
            900                 905                 910

Arg Ser Ser Ser Gly Ser Ala Arg Leu Ser Ser Gly Leu Gly Ala Leu
        915                 920                 925

Ala Gln Pro Phe Lys Leu Arg Leu Cys Arg Ala Pro Arg Glu Lys Ser
    930                 935                 940

Leu Arg Asp Tyr Ser Ser Asn Ile Val Leu Ile Asp Pro Leu Ala Ser
945                 950                 955                 960

Leu Ala Ala Val Glu Glu Phe Leu Trp Pro Arg Val Gln Arg Ser Asp
                965                 970                 975

Thr Ser Gln Lys Leu Ser Val Thr Val Gly Asn Ser Glu Ser Gly Asn
            980                 985                 990

Thr Pro Asn Arg Thr Asp Val Ser  Ser Pro Ser Thr Ser  Thr Pro Ala
        995                 1000                1005

Ser Thr  Thr Arg Arg His Ser  Ser Arg Ser Arg Ser  Ser Val Asn
    1010                1015                1020
```

Ile Gly Asp Val Ala Arg Lys Glu Gln Ser Gln Glu Lys Ser Thr
1025 1030 1035

Ser Ser Ser Lys Gly Lys Gly Lys Ala Val Leu Lys Pro Ser Lys
1040 1045 1050

Glu Glu Pro Arg Gly Pro Gln Thr Arg Asn Ala Ala Arg Arg Arg
1055 1060 1065

Ala Ala Leu Asp Lys Asp Ala Pro Met Lys Pro Val Asn Asp Asp
1070 1075 1080

Ser Thr Ser Glu Asp Glu Glu Leu Asp Met Ser Pro Val Glu Ile
1085 1090 1095

Asp Asp Ala Leu Val Ile Glu Asp Asp Asp Ile Ser Asp Asp Glu
1100 1105 1110

Asp Asp Glu His Glu Asp Val Leu Arg Asp Asp Ser Leu Pro Val
1115 1120 1125

Cys Thr Pro Asp Lys Val His Asp Val Lys Leu Ser Asp Ser Ala
1130 1135 1140

Glu Asp Gly Ser Pro Ala Pro Ala Ala Ser Asp Ser Gln Thr Asn
1145 1150 1155

Ala Ala Ser Gly Ser Ser Ser Arg Ala Ala Ala Ile Arg Gly Ser
1160 1165 1170

Asp Ser Ala Asp Phe Arg Ser Gly Tyr Gly Ser Arg Gly Ala Met
1175 1180 1185

Ser Phe Ala Ala Ala Ala Met Ala Gly Leu Gly Ser Ala Asn Gly
1190 1195 1200

Arg Gly Ile Arg Gly Gly Arg Asp Arg Gln Gly Arg Pro Pro Gly
1205 1210 1215

Ser Ser Asn Glu Pro Pro Lys Leu Ile Phe Thr Ala Gly Asn Lys
1220 1225 1230

Gln Leu Asn Arg His Leu Thr Ile Tyr Gln Ala Ile Gln Arg Gln
1235 1240 1245

Leu Val Leu Asp Glu Asp Asp Asp Glu Arg Tyr Ala Gly Ser Asp
1250 1255 1260

Phe Thr Ser Ser Asp Gly Arg Gly Val Trp Ser Asp Ile Tyr Thr
1265 1270 1275

Ile Thr Tyr Gln Arg Ala Glu Ser Gln Ala Asp Arg Ser Ser Pro
1280 1285 1290

Gly Gly Ser Gly Ser Ala Thr Ala Ser Lys Ser Gly Lys Ser Gly
1295 1300 1305

Ser Ser Asn Ser Ser Ser Asp Pro Gln Pro His Arg Met Ser Leu
1310 1315 1320

Leu Asp Ser Ile Leu Gln Gly Glu Leu Pro Cys Asp Leu Asp Arg
1325 1330 1335

Ser Asn Pro Thr Tyr Thr Ile Leu Ala Leu Leu Arg Val Leu Glu
1340 1345 1350

Gly Leu Asn Gln Leu Ala Pro Arg Leu Arg Ala Gln Ile Val Ser
1355 1360 1365

Asp Asn Phe Ala Glu Gly Asn Val Leu Thr Leu Gly Glu Leu Ser
1370 1375 1380

Thr Ser Gly Ser Arg Val Pro His Glu Glu Phe Ile Asn Gly Lys
1385 1390 1395

Leu Thr Pro Lys Leu Ala Arg Gln Ile Gln Asp Val Leu Ala Leu
1400 1405 1410

-continued

```
Cys Ser Gly Ser Leu Pro Ser Trp Cys Tyr Gln Leu Thr Lys Ala
    1415                1420                1425

Cys Pro Phe Leu Phe Pro Phe Glu Thr Arg Arg Gln Tyr Phe Tyr
    1430                1435                1440

Ser Thr Ala Phe Gly Leu Ser Arg Ala Leu Tyr Arg Leu Gln Gln
    1445                1450                1455

His Gln Gly Ala Asp Gly His Gly Ser Thr Asn Glu Arg Glu Val
    1460                1465                1470

Arg Val Gly Arg Leu Gln Arg Gln Lys Val Arg Val Ser Arg Asn
    1475                1480                1485

Arg Ile Leu Asp Ser Ala Ala Lys Val Met Glu Met Tyr Ser Ser
    1490                1495                1500

Gln Lys Thr Val Leu Glu Val Glu Tyr Phe Gly Glu Val Gly Thr
    1505                1510                1515

Gly Leu Gly Pro Thr Leu Glu Phe Tyr Thr Leu Leu Ser His Asp
    1520                1525                1530

Leu Gln Lys Val Gly Leu Ala Met Trp Arg Ser Asn Ser Thr Trp
    1535                1540                1545

Asn Lys Ser Val Met Glu Ile Asp Gly Asp Gly Asp Lys Asn Gly
    1550                1555                1560

Lys Ile Ala Gly Ser Ala Thr Ile Asn Gly Asp Ile Val Gln Ala
    1565                1570                1575

Pro Leu Gly Leu Phe Pro Arg Pro Trp Pro Pro Asn Ala Asp Ala
    1580                1585                1590

Ser Glu Gly Ser Gln Phe Phe Lys Val Ile Glu His Phe Arg Leu
    1595                1600                1605

Val Gly Arg Val Met Ala Lys Ala Leu Gln Asp Gly Arg Leu Leu
    1610                1615                1620

Asp Leu Pro Leu Ser Met Ala Phe Tyr Lys Leu Val Leu Gly Gln
    1625                1630                1635

Glu Leu Asp Leu His Asp Ile Leu Ser Phe Asp Ala Glu Phe Gly
    1640                1645                1650

Lys Ile Leu Gln Glu Leu His Leu Leu Val Arg Arg Lys Gln Tyr
    1655                1660                1665

Leu Asp Ser Leu Gly Gly Asp Asn Ser Asp Ala Ile Pro Asp Leu
    1670                1675                1680

Arg Phe Arg Gly Ala Ser Ile Glu Asp Leu Cys Leu Asp Phe Thr
    1685                1690                1695

Leu Pro Gly Tyr Pro Asp Tyr Ile Leu Lys Leu Gly Asp Glu Thr
    1700                1705                1710

Val Asp Ile Asn Asn Leu Glu Glu Tyr Ile Ser Leu Val Val Asp
    1715                1720                1725

Ala Thr Val Lys Thr Gly Ile Met His Gln Met Glu Ala Phe Arg
    1730                1735                1740

Asp Gly Phe Asn Gln Val Phe Asp Ile Ser Ser Leu Gln Ile Phe
    1745                1750                1755

Thr Pro Gln Glu Leu Asp Tyr Leu Leu Cys Gly Arg Arg Glu Leu
    1760                1765                1770

Trp Glu Ala Glu Thr Leu Ala Asp His Ile Lys Phe Asp His Gly
    1775                1780                1785

Tyr Thr Ala Lys Ser Pro Pro Ile Val Asn Leu Leu Glu Ile Met
    1790                1795                1800

Gly Glu Leu Thr Pro Glu Glu Gln Arg Ala Phe Cys Gln Phe Val
```

```
    1805                1810                1815

Thr Gly  Ala Pro Arg Leu Pro  Pro Gly Gly Leu Ala  Val Leu Asn
    1820                1825                1830

Pro Arg  Leu Thr Ile Val Arg  Lys His Ser Ser Ser  Ala Thr Ala
    1835                1840                1845

Ala Ala  Ala Ala Asn Gly Thr  Gly Leu Ser Glu Ser  Ala Asp Glu
    1850                1855                1860

Asp Leu  Pro Ser Val Met Thr  Cys Ala Asn Tyr Leu  Lys Leu Pro
    1865                1870                1875

Pro Tyr  Ser Thr Lys Glu Ile  Met Tyr Lys Lys Leu  Leu Tyr Ala
    1880                1885                1890

Ile Asn  Glu Gly Gln Gly Ser  Phe Asp Leu Ser
    1895                1900


<210> SEQ ID NO 45
<211> LENGTH: 10248
<212> TYPE: DNA
<213> ORGANISM: Triticum aestivum
<220> FEATURE:
<221> NAME/KEY: misc_feature
<222> LOCATION: (28)..(381)
<223> OTHER INFORMATION: n is a, c, g, or t

<400> SEQUENCE: 45

atggaaacgc gcagccgcaa gcgggcgnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnnnnnnn     360

nnnnnnnnnn nnnnnnnnnn nacccccgca caccccgcgc ccacccgcgc ccgccgctcc     420

gtcgtcctct ccccgcccgc cccgcagccc ccgatggact tcccggccga cggcggcaac     480

aacccccccgc cccgccgccg cggcggccgc gcctccaacg ccgacaaggg caaggagcag     540

caggagccct cggagagctc ccgcgtgcgc gaggccgagc ggatgctggg cctcagcttc     600

gacggcatgg acgacgacga cgagggccac ggggccttcc cccacggcct cacctccgcc     660

agcagcgccc tgcaggggct gctcaggaag ctcggcgccg gcctggacga catgctgccg     720

tcgtccgcgc tctccgccgc cgccgctgct gcctcctcgt cgtccatgtc tggtccgaac     780

ggcacgcgga tgaagagcat gctcgcgggt ctccgcgccg acggcgagga ggggcgccag     840

gtggaggcgc tcacgcagct ctgcgagatg ctgtccatcg gcaccgagga caccctcgcc     900

gggttctccg tggactcgtt cgtgcctgtt ctggtcgggc tgctcaacca tgagagcaac     960

cccgacatca tgctgctcgc cgcgcgggcc ctgacccacc tctgtgacgt gcttccgtcg    1020

tcctgctctg ccgttgtgca ctatggcgcc gtcgcatgct tctgcgcccg gcttctcacc    1080

attgaatata tggaccttgc ggagcaggtg agcactgttc tgttgcatcg cttgtttggt    1140

ttatatatag tacatgctgc ttctttatca tgttgcctga tccagatcat gtcgccctgc    1200

ttgtttagtg aaccattgtt gtgtactgta ttatgcatga ttatgctgcc catagagcct    1260

taacctacat tacatgagtt tccttttagt gttgcaggtc atttataata tttgaacttg    1320

ctcatgagta gtttgccttt tgtgtagctg tggtttttttc ccattttagt gctaaaataa    1380

atatgggtga gaaggttacg aacatgattt ttgttggcgt tgtgcccata ctcgagaagt    1440
```

-continued

```
tccactgtat gctttctatg ttatgtttct gactcaagtt tcggtgacct gtacagatgt   1500
ggtagttgta agttagcctc agttaatatt aagtttgaaa tatgtgtata atcaattttc   1560
aaggaactat atatttgaaa tagcttgttt gattgttcac ttggcaagta ccaaatattg   1620
cctagttcag tagctcacca tttaatgatg ttacaagaaa tatctagaga gttaggcaga   1680
aggtgatcgg atcccttagt agccttgggg cctgcctagg gtctaggcac tggtcgctct   1740
gggaggaaga agctgaggat aggagacaca tgaaagaaaa aatggttaga tgaaagcatg   1800
tccgaatgca cgtgatgcct taaagcctta gggagcttgt gggcatggag atgtcttccc   1860
ttcctctggt gccgcaggag gactcgggct ccaaatcctc accagcgaac tcaaatccat   1920
ctaaggacct catctgcccc ttagaagact ttctaggcct gatcatggtg gtgctcctgc   1980
cgagcacctg ggtgccattt aacacggttt tgctgtgcca aatcacctat ttgtgcatga   2040
ctaagctagc tatttgaaca tgtttttcat ctgaaatatt tctagctcag ggtctgattt   2100
cacgcctgtg tatgtgtatc catctgaaat actaagaagt gggttggaaa tcagatgcta   2160
agattcatgt aactggtttc tggcagtgtt tcttctctgc cttcccatct tatatggata   2220
ttatacttct gcttttcttg ggtctaattc aaaacaatgt gaattaactt gatatcatct   2280
gtttgaattc ctttgtaacc ctttgtgcaa ttgaatctag tttgctgctc cacaatatgt   2340
tattgagtag tatctacaac tattaggttt agcacctagg acatttgaat tactttctta   2400
gattttgata ttgtattgct tctgtggcac tttagattag ccactttcct tgttttgttt   2460
tgtcgtttaa aatatgctgc aggaagaatc tatcattgct agatcttgat gtggtactaa   2520
tattttctta tgccttttct gggtatttta gtccttacaa gcactcaaga agatatccca   2580
ggagcatcca actgcctgct tgagggctgg cgcgctaatg gcagtgctat catatcttga   2640
cttcttctcc accggtgttc aagtaatttt tctaaatact tctatgtttt tccagcattt   2700
agacataaca ttctcaatac ttatgttatt tttttgcacc atttagaaat tgggacatag   2760
taatttgtca tatcactatc tttttgttgt acacatactg tactacattt ttattactac   2820
tcacagttgt ttttttggtg gaatgtatac agagagttgc gttatctaca gctgccaata   2880
tgtgtaggaa gcttccttca gacgcctcag attttgtaat ggaagcggtt ccactgctaa   2940
caaatcttct gaactaccat gatgcaaaag tatgcttgtt gtctgtattt ggataccctg   3000
attatgccat gataccatct attcttagat gctgatgatc tgtatcaatg tattccaggt   3060
gctggaacat gcttctgttt gcctgactcg tatagcagaa tcgtttgctt catccccaga   3120
gaaattggat caattgtgca attatggatt ggttgcacaa gctgctagct taatagctgt   3180
tagcaactca gcgggacaag catcactgag tacattaaca tatacagtat gcttctattt   3240
cacttatcta ctgtattatt tagtatttat gcaactttgc taactctggc tcatatatcc   3300
ttgaagggag taattcgtgt tctgtcaata tgtgcaagtg gatctccatt ggcagctaaa   3360
acactcctcc tccatggaat cagcggcaca cttaaagata tcctttcagg ttctggtttg   3420
gttgctggta caactgtatc ccccactagg ccagctgatc aggtgattat tgctttatga   3480
gggctatatc tatattatag ctacttactg ttttatttga atgccatcgg ttgatgactc   3540
tgttcggttg ttgttttatc tgacttagcc gatgaagctt tttgagtgat acttttttttt   3600
caattttaaa ttcactcaag tgtgcgttca gttcaggttt gtttggtaaa ctgaaattaa   3660
tgtcacacaa cagaatattc aaaatttgga agaaagttgc atgctggata ctttttctgt   3720
gtataataat ttgccaaatg tttcccgtgc tcgtgctgtt tgtgcagtcc tgcaagctat   3780
```

-continued

```
aacagtgagc aaacaatgtg gtaaattgga ttaggggttt gtcttggaac tcttggttca   3840
tatacttctc tgttttctac ccgattttct ttctccagtt ataatatgaa attcacaatg   3900
atagtattga tcttgatcaa ggtttagaga tgcactagac tggcggtagg tgaccgccta   3960
gatgacgccc agctactgtt tgttaacctt aataatctcg acatcatacc atattacttg   4020
ctccattttt ctttttaatt tatcaaaagc caagagtttc ctgtagtagt tctatggtag   4080
tttgcagctt gttttcatat cctaatattc tttgttgtgt cacacagatg tatgaaattg   4140
tgaaccttgc ggacgaattg cttcctcctc tacctgctgg aaccatttct ttaccagcgc   4200
attcccatgt ttttatgaaa ggctcttctg taaagaaacc tggttctagc aagcaaggcg   4260
agtctggttc aacagatatt aaagtctcgg gtcgggagaa gttattgcgt gatcagcctg   4320
aacttctcca gcaatttggc atggacatat tacctaccat gacacaggtc agtctcttgg   4380
tttgctggcg tatcagttga tgttggttgc tgacgataac attattgaaa tcctgttatc   4440
tgagacatta tttggataca ctctatccct tgcaggtgta tggctccagt gtaaatggac   4500
caatacgtca taaatgctta tctgtcattg ctaaattaat gtattacagc tcagcggaaa   4560
tgatcgaaat tctccatggc acaacaaaca tatccaggtg ctaatacgaa acttcagatg   4620
ccattcttgc ttactgttat acatgtactc gtgtacctct ggttccatct aacctgatat   4680
tgacctttgc agcttcttag ctggcatctt agcttggaaa gatccacatg tgttggttcc   4740
cgctctccag atagctgaaa ttctgatgga aaagctccct gggacatttt cgaagatgtt   4800
tgtgagggaa ggtgttgttc atgctgtaga atcgcttata tgccaggaaa tctcaagtcc   4860
aatgcttttt caagtaccac agcaggacaa ggatattgat tctggtacat gtacatcttc   4920
acgttcaaga cgcagccgcc ggcgcagcag tgctgggaat actgataata attccttgga   4980
tgaaccaaag ggttcccata ctactattgc caattcacca ccaagcacgc tagaaggtcc   5040
aaatactaga attcgtgctt cagttagtga tcgtgcgaag tcattcaaag ataagtactt   5100
cccctctgaa cccggctcaa gtgatattgc agttactgat gaccttttga agctacgggc   5160
actctgtgca aaattgaatg ccactgcgga cactgttaaa acaaaagcca aagggaaatc   5220
aaagtcactg ggaggtgatg attttgatat cttatgcaat gtcgaggaac agttagacga   5280
catcatagac aaaatattgt ctgagcttag caatggggat ggggtttcca cgtttgagtt   5340
tattgggagt ggagttatct cagcattgct taattatttg tcttgtggaa cctttggaaa   5400
ggaaaaggtg tccgaagcaa acctacccaa gttgcgtcac ctggcactca ggcgatataa   5460
agcatttata tatgttgccc ttccaaatga tgcggtaggg aatcaaactc caatggcatt   5520
cttagttcaa aaactgcaaa gcgcgttgtc ttcgctggaa cggttcccag ttgtgattag   5580
ccattctgga aggacgtcca gtttgggagg atctcgtcca tcctctggat taagtgctct   5640
atctcagccc ctgaagttgc gcctgtgtcg agcagcgggt gaaaaaacgc ttaaggatta   5700
ttcatccaat atagttctta ttgatccctt ggcaagttta gcagccgttg aagatttcct   5760
ttggcctaga atccagcgta gtgagtcaat atcttatcct gcagtatcat ctggaaagaa   5820
ttctgaatct gtggcaccta gtgcaacagc accagtggct tcgtcaactc aatctgtccg   5880
gcggccctca actaggtcga aatcattggc tgatgctgat tctgcaacta agaaggatat   5940
tcaggagggg agcggaaaca catccaaggg aaaaggcaaa gctgttgtta agtcgatgtc   6000
cgatgaacca aaaggaccac atactaggac tgcagcacgc aggaaagttg cttcacagaa   6060
agatgcagaa gtgaagccac cacacggtca cagtagctca gaggtttgtt gttcattatg   6120
gactcatttc ttaataatct atagaatata tatttcctcc agtacgtctt gaatttttgc   6180
```

```
tagttcccca aaatttgatg cagatgcttg actacatatt ctttgtttgg tagtgcctcc   6240
ctgcagttac tcagctgcca agctgatttt cgttataaca accgtcctac tgtttttcgt   6300
cgtcgtttca tgattatatc tgctctcctt tcatttaata atttgatgtg caactgttaa   6360
ggggaattga catgattaat accgttatga aattattatt taacacgaat ttcattgtgg   6420
aaccaatgtg tgaatttcat aaaattagat ctacagagta caatgccttt tgacctgcag   6480
ttcgatatgg catctaggga gtacatattg tctcaccatg tctacaatgc ttcagttgat   6540
gaagacattg tctaactaaa accaatgatg tagggaaagg ttggtgctcc caccactatc   6600
tcgatcactg aatgtgccta aaggttgttg cagttcctca tcctattcaa taattatatg   6660
ttgagagagt ggcacggacc ttaagcagca atggcacatt ccatagttga gaacttgtga   6720
tagtgggagc atattcacca atgtgattca tttcactgtt gaaagtttgc ccgaatgcaa   6780
tactgctttt cttgcctaac tgagtgataa atatataaat taagttgtca gtttaattat   6840
atctatgtaa ttagctgcaa gtaccctta ccagttctca cctgtataac aaaatagatc   6900
acttatgcgt tggaaactgg attactattt cactaattcc cttatccctg aacaaagttc   6960
tgatccaatt cttgtacact atgtcatgtg atgttaaact ttattattgt atttatgctc   7020
gttgtgcatg atacattctg tttcctacat gcaggacgaa gaactgggcg catctccctt   7080
tgaggctgat gatgctttga tgcttggtga tgacgatgat gatgtttcag atgatgaaga   7140
tgatgaccat gaggtagtat ttcaaaagta cttcggttga tctctttatt tttctgcaag   7200
ttaatgtggc tttagtgggc atgactgaaa actgcatatt tttgttgaaa atccccaggt   7260
tctacgtggg tctcttcctg actgtgttcc agagagtgtg catgatgtaa aactggcaga   7320
tgctgatggg tctagtattg cctcaatagc aagtgataac cagacacaac cctcatctgg   7380
ctccagcgta aaacatactt ttagtagcag gggagcaggt tctgttgaac ttagaaatcc   7440
aagcacactt ggttcacggg gcgcgatgtc gtttgctgca gctgccatgg ctgggcttgc   7500
ttctgttggt agtcgtggta tcagaggtag ccaggatagg cgtggccttc cacttggaac   7560
tagtgcacat gaacattcga acaaattgat ttttacagct ggcggcaagc agcttagcaa   7620
gcatttgact gtatatcaag ctatgcaaca gcaagtagtt catgatgagg atgatgagga   7680
aaggctaggt ggttctgatt tacccaatga tggaagccgt ctctggagtg atatgttcac   7740
tataacatat caaaaggctg ataacgaagt ggatagggaa tcaaccagag gttcatcttt   7800
agtgctgaaa tcgtccaaat cagaactttg cagagctaca tctcaagaac aatgtacttc   7860
tcttcttgat agcattttgc aaggagaact tccttgtgat attgagaaat cgacccaaac   7920
ttataatatt ttagcactat tgcgtgtatt ggagggattg aatcagctat ctcctcgtct   7980
gagactacag gcaacctgtg atgattttat agagggaaaa gttggtaccc tggatgggtt   8040
atatggcacc ggagctaagg taccctcaga ggagtttatc agcagtaagt tgacaccaaa   8100
gcttgctcgg caaattcagg atgttcttgc actctgcagt ggtagtttac cttcttggtg   8160
ttatcagatg accaaagctt gtccatttct gtttcctttt gaaacaagaa gacaacactt   8220
ctactccaca gcttttgggt tatctagggc attgaatcgt cttcagcaac aacagggtga   8280
taataatagc tcagcgactg aaagagaagt ccggattggt agattgcaac gccagaaagt   8340
tcgtgtttct cgtaaccgga tcctggattc tgctgccaaa gtaatggaga tgttctccaa   8400
tcagaaggct gttcttgaag ttgaatactt tggtgaagtg ggaactggac ttggtccaac   8460
tttggagttc tacaccctct taagtcatga cctgcaaagg gttggcttgg gattatggag   8520
```

```
atctgattct gattctttag aagctaaaaa acttgattca cattcacctg ctgatagcag   8580

gaacttgata catgcacctc ttggcttgtt ccctcggcct tggccaccta gtactgcttc   8640

ttcagagggt agtaaattct tcaaagttgt tgagtatttc cgcttagttg gtcgaatcat   8700

ggcaaaagca ttgcaagatg gaaggcttct tgatttgcct ttgtcaacag cattttataa   8760

gcttctactt ggacaagtaa gcatgagaac ccgcttgcag tagatccatt ccaatattcc   8820

cttccacctt cttgtcaagt cttggtattt tttttatttc ttctactgtc ttctgtattg   8880

acgccaaaat attttgcttt actaggaact tgatttgtac gacatactat cttttgatgc   8940

tgagtttggt aaaatacttc aagagttgca agttcttgtt gaacgcaagc gatttctgga   9000

gtcctgctct aatcatagtc aacaaataga agaattgggc tttcgtggtg ctcctattca   9060

agacctatgc ttagatttta ctcttccggg ctatccggat tttgttctga aggaaggtga   9120

agaaaataca gtggtatgtg atggagtaga ttaggttctt atgttgtcat ctaagtggta   9180

cttcagcttt tgcttctaat tttgttgttg actattcatt gttattgtta acttcctgta   9240

ggtctgcatt tacaacttag aagagtacat ttcgctggta gtggatgcta cacttaagac   9300

tggaataatg cgtcaagtag aagcattcaa agctggattt aatcaggttt tctcattttt   9360

ctaagatatc ttatttgctg gcaattattg ttaattagct attgcatttc tcttattatt   9420

tttctaattc aggtatttga tatatcatca ctccaaatat tttctcctca agagcttgac   9480

tatctcattt gtggtcgacg ggaactttgg gaggtaatgc cctgttaact ttatttctcc   9540

cttctataat cattatttaa cttgttctga gcaaatgcat gtaatgcagc cggagacact   9600

ggtcgaacat ataaagtttg atcatggtta tacctcgaag agtccagcaa ttgtcaatgt   9660

gagtacatca tctttaaaaa agggcacatc tcttcacaca gctttatttc agatttttgg   9720

aacttcagtt taatgtttgt gctgttggtt tgcagctact tgagatcatg acggaattta   9780

ctccggagca acaacatgca ttctgccagt ttgtgactgg tgctcctcgg cttccacctg   9840

gtggcttagc ctccctaaat cctaagctga ctatagttag gaaggtaagc ctgttgtagc   9900

aatgcagaat gacatcattt ctgcgttcat gttatttaag cttttccatt ttgtatcttg   9960

gccagcactc ttcgactgcg gcgaatactt caaatgcagc tggagcagca gagtctgcag  10020

atgatgatct gcctagtgtc atgacttgtg ccaactatct taaacttccg ccatactcga  10080

caaaggtttg gttcttttgg ttgatgaatt ttttgttcca cctttccgta tcgtcttgcc  10140

tggaaactga cttgtgctat ggtcgtcgga acattgttgc aggaggttat gcacaagaag  10200

ctgctttatg ctatcaacga aggccagggg tcgtttgatc tttcatag              10248
```

```
<210> SEQ ID NO 46
<211> LENGTH: 1862
<212> TYPE: PRT
<213> ORGANISM: Triticum aestivum
<220> FEATURE:
<221> NAME/KEY: misc_feature
<222> LOCATION: (10)..(41)
<223> OTHER INFORMATION: Xaa can be any naturally occurring amino acid

<400> SEQUENCE: 46

Met Glu Thr Arg Ser Arg Lys Arg Ala Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Thr Pro Ala His Pro Ala Pro
        35                  40                  45
```

-continued

```
Thr Arg Ala Arg Arg Ser Val Val Leu Ser Pro Pro Ala Pro Gln Pro
    50                  55                  60

Pro Met Asp Phe Pro Ala Asp Gly Gly Asn Asn Pro Pro Pro Arg Arg
65                  70                  75                  80

Arg Gly Gly Arg Ala Ser Asn Ala Asp Lys Gly Lys Glu Gln Gln Glu
                85                  90                  95

Pro Ser Glu Ser Ser Arg Val Arg Glu Ala Glu Arg Met Leu Gly Leu
            100                 105                 110

Ser Phe Asp Gly Met Asp Asp Asp Asp Glu Gly His Gly Ala Phe Pro
        115                 120                 125

His Gly Leu Thr Ser Ala Ser Ser Ala Leu Gln Gly Leu Leu Arg Lys
    130                 135                 140

Leu Gly Ala Gly Leu Asp Asp Met Leu Pro Ser Ser Ala Leu Ser Ala
145                 150                 155                 160

Ala Ala Ala Ala Ala Ser Ser Ser Ser Met Ser Gly Pro Asn Gly Thr
                165                 170                 175

Arg Met Lys Ser Met Leu Ala Gly Leu Arg Ala Asp Gly Glu Glu Gly
            180                 185                 190

Arg Gln Val Glu Ala Leu Thr Gln Leu Cys Glu Met Leu Ser Ile Gly
        195                 200                 205

Thr Glu Asp Thr Leu Ala Gly Phe Ser Val Asp Ser Phe Val Pro Val
    210                 215                 220

Leu Val Gly Leu Leu Asn His Glu Ser Asn Pro Asp Ile Met Leu Leu
225                 230                 235                 240

Ala Ala Arg Ala Leu Thr His Leu Cys Asp Val Leu Pro Ser Ser Cys
                245                 250                 255

Ser Ala Val Val His Tyr Gly Ala Val Ala Cys Phe Cys Ala Arg Leu
            260                 265                 270

Leu Thr Ile Glu Tyr Met Asp Leu Ala Glu Gln Ser Leu Gln Ala Leu
        275                 280                 285

Lys Lys Ile Ser Gln Glu His Pro Thr Ala Cys Leu Arg Ala Gly Ala
    290                 295                 300

Leu Met Ala Val Leu Ser Tyr Leu Asp Phe Phe Ser Thr Gly Val Gln
305                 310                 315                 320

Arg Val Ala Leu Ser Thr Ala Ala Asn Met Cys Arg Lys Leu Pro Ser
                325                 330                 335

Asp Ala Ser Asp Phe Val Met Glu Ala Val Pro Leu Leu Thr Asn Leu
            340                 345                 350

Leu Asn Tyr His Asp Ala Lys Val Leu Glu His Ala Ser Val Cys Leu
        355                 360                 365

Thr Arg Ile Ala Glu Ser Phe Ala Ser Ser Pro Glu Lys Leu Asp Gln
    370                 375                 380

Leu Cys Asn Tyr Gly Leu Val Ala Gln Ala Ala Ser Leu Ile Ala Val
385                 390                 395                 400

Ser Asn Ser Ala Gly Gln Ala Ser Leu Ser Thr Leu Thr Tyr Thr Gly
                405                 410                 415

Val Ile Arg Val Leu Ser Ile Cys Ala Ser Gly Ser Pro Leu Ala Ala
            420                 425                 430

Lys Thr Leu Leu Leu His Gly Ile Ser Gly Thr Leu Lys Asp Ile Leu
        435                 440                 445

Ser Gly Ser Gly Leu Val Ala Gly Thr Thr Val Ser Pro Thr Arg Pro
    450                 455                 460

Ala Asp Gln Met Tyr Glu Ile Val Asn Leu Ala Asp Glu Leu Leu Pro
```

```
465                 470                 475                 480

Pro Leu Pro Ala Gly Thr Ile Ser Leu Pro Ala His Ser His Val Phe
                485                 490                 495

Met Lys Gly Ser Ser Val Lys Lys Pro Gly Ser Ser Lys Gln Gly Glu
            500                 505                 510

Ser Gly Ser Thr Asp Ile Lys Val Ser Gly Arg Glu Lys Leu Leu Arg
        515                 520                 525

Asp Gln Pro Glu Leu Leu Gln Gln Phe Gly Met Asp Ile Leu Pro Thr
    530                 535                 540

Met Thr Gln Val Tyr Gly Ser Ser Val Asn Gly Pro Ile Arg His Lys
545                 550                 555                 560

Cys Leu Ser Val Ile Ala Lys Leu Met Tyr Tyr Ser Ser Ala Glu Met
                565                 570                 575

Ile Glu Ile Leu His Gly Thr Thr Asn Ile Ser Ser Phe Leu Ala Gly
            580                 585                 590

Ile Leu Ala Trp Lys Asp Pro His Val Leu Val Pro Ala Leu Gln Ile
        595                 600                 605

Ala Glu Ile Leu Met Glu Lys Leu Pro Gly Thr Phe Ser Lys Met Phe
    610                 615                 620

Val Arg Glu Gly Val Val His Ala Val Glu Ser Leu Ile Cys Gln Glu
625                 630                 635                 640

Ile Ser Ser Pro Met Leu Phe Gln Val Pro Gln Gln Asp Lys Asp Ile
                645                 650                 655

Asp Ser Gly Thr Cys Thr Ser Ser Arg Ser Arg Arg Ser Arg Arg Arg
            660                 665                 670

Ser Ser Ala Gly Asn Thr Asp Asn Asn Ser Leu Asp Glu Pro Lys Gly
        675                 680                 685

Ser His Thr Thr Ile Ala Asn Ser Pro Pro Ser Thr Leu Glu Gly Pro
    690                 695                 700

Asn Thr Arg Ile Arg Ala Ser Val Ser Asp Arg Ala Lys Ser Phe Lys
705                 710                 715                 720

Asp Lys Tyr Phe Pro Ser Glu Pro Gly Ser Ser Asp Ile Ala Val Thr
                725                 730                 735

Asp Asp Leu Leu Lys Leu Arg Ala Leu Cys Ala Lys Leu Asn Ala Thr
            740                 745                 750

Ala Asp Thr Val Lys Thr Lys Ala Lys Gly Lys Ser Lys Ser Leu Gly
        755                 760                 765

Gly Asp Asp Phe Asp Ile Leu Cys Asn Val Glu Glu Gln Leu Asp Asp
    770                 775                 780

Ile Ile Asp Lys Ile Leu Ser Glu Leu Ser Asn Gly Asp Gly Val Ser
785                 790                 795                 800

Thr Phe Glu Phe Ile Gly Ser Gly Val Ile Ser Ala Leu Leu Asn Tyr
                805                 810                 815

Leu Ser Cys Gly Thr Phe Gly Lys Glu Lys Val Ser Glu Ala Asn Leu
            820                 825                 830

Pro Lys Leu Arg His Leu Ala Leu Arg Arg Tyr Lys Ala Phe Ile Tyr
        835                 840                 845

Val Ala Leu Pro Asn Asp Ala Val Gly Asn Gln Thr Pro Met Ala Phe
    850                 855                 860

Leu Val Gln Lys Leu Gln Ser Ala Leu Ser Ser Leu Glu Arg Phe Pro
865                 870                 875                 880

Val Val Ile Ser His Ser Gly Arg Thr Ser Ser Leu Gly Gly Ser Arg
                885                 890                 895
```

-continued

```
Pro Ser Ser Gly Leu Ser Ala Leu Ser Gln Pro Leu Lys Leu Arg Leu
            900                 905                 910

Cys Arg Ala Ala Gly Glu Lys Thr Leu Lys Asp Tyr Ser Ser Asn Ile
        915                 920                 925

Val Leu Ile Asp Pro Leu Ala Ser Leu Ala Ala Val Glu Asp Phe Leu
    930                 935                 940

Trp Pro Arg Ile Gln Arg Ser Glu Ser Ile Ser Tyr Pro Ala Val Ser
945                 950                 955                 960

Ser Gly Lys Asn Ser Glu Ser Val Ala Pro Ser Ala Thr Ala Pro Val
                965                 970                 975

Ala Ser Ser Thr Gln Ser Val Arg Arg Pro Ser Thr Arg Ser Lys Ser
            980                 985                 990

Leu Ala Asp Ala Asp Ser Ala Thr  Lys Lys Asp Ile Gln  Glu Gly Ser
        995                 1000                1005

Gly Asn  Thr Ser Lys Gly Lys  Gly Lys Ala Val Val  Lys Ser Met
    1010                 1015                 1020

Ser Asp  Glu Pro Lys Gly Pro  His Thr Arg Thr Ala  Ala Arg Arg
    1025                 1030                 1035

Lys Val  Ala Ser Gln Lys Asp  Ala Glu Val Lys Pro  Pro His Gly
    1040                 1045                 1050

His Ser  Ser Ser Glu Asp Glu  Glu Leu Gly Ala Ser  Pro Phe Glu
    1055                 1060                 1065

Ala Asp  Asp Ala Leu Met Leu  Gly Asp Asp Asp Asp  Asp Val Ser
    1070                 1075                 1080

Asp Asp  Glu Asp Asp Asp His  Glu Val Leu Arg Gly  Ser Leu Pro
    1085                 1090                 1095

Asp Cys  Val Pro Glu Ser Val  His Asp Val Lys Leu  Ala Asp Ala
    1100                 1105                 1110

Asp Gly  Ser Ser Ile Ala Ser  Ile Ala Ser Asp Asn  Gln Thr Gln
    1115                 1120                 1125

Pro Ser  Ser Gly Ser Ser Val  Lys His Thr Phe Ser  Ser Arg Gly
    1130                 1135                 1140

Ala Gly  Ser Val Glu Leu Arg  Asn Pro Ser Thr Leu  Gly Ser Arg
    1145                 1150                 1155

Gly Ala  Met Ser Phe Ala Ala  Ala Ala Met Ala Gly  Leu Ala Ser
    1160                 1165                 1170

Val Gly  Ser Arg Gly Ile Arg  Gly Ser Gln Asp Arg  Arg Gly Leu
    1175                 1180                 1185

Pro Leu  Gly Thr Ser Ala His  Glu His Ser Asn Lys  Leu Ile Phe
    1190                 1195                 1200

Thr Ala  Gly Gly Lys Gln Leu  Ser Lys His Leu Thr  Val Tyr Gln
    1205                 1210                 1215

Ala Met  Gln Gln Gln Val Val  His Asp Glu Asp Asp  Glu Glu Arg
    1220                 1225                 1230

Leu Gly  Gly Ser Asp Leu Pro  Asn Asp Gly Ser Arg  Leu Trp Ser
    1235                 1240                 1245

Asp Met  Phe Thr Ile Thr Tyr  Gln Lys Ala Asp Asn  Glu Val Asp
    1250                 1255                 1260

Arg Glu  Ser Thr Arg Gly Ser  Ser Leu Val Leu Lys  Ser Ser Lys
    1265                 1270                 1275

Ser Glu  Leu Cys Arg Ala Thr  Ser Gln Glu Gln Cys  Thr Ser Leu
    1280                 1285                 1290
```

-continued

```
Leu Asp  Ser Ile Leu Gln Gly  Glu Leu Pro Cys Asp  Ile Glu Lys
    1295                 1300                 1305

Ser Thr  Gln Thr Tyr Asn Ile  Leu Ala Leu Leu Arg  Val Leu Glu
    1310                 1315                 1320

Gly Leu  Asn Gln Leu Ser Pro  Arg Leu Arg Leu Gln  Ala Thr Cys
    1325                 1330                 1335

Asp Asp  Phe Ile Glu Gly Lys  Val Gly Thr Leu Asp  Gly Leu Tyr
    1340                 1345                 1350

Gly Thr  Gly Ala Lys Val Pro  Ser Glu Glu Phe Ile  Ser Ser Lys
    1355                 1360                 1365

Leu Thr  Pro Lys Leu Ala Arg  Gln Ile Gln Asp Val  Leu Ala Leu
    1370                 1375                 1380

Cys Ser  Gly Ser Leu Pro Ser  Trp Cys Tyr Gln Met  Thr Lys Ala
    1385                 1390                 1395

Cys Pro  Phe Leu Phe Pro Phe  Glu Thr Arg Arg Gln  His Phe Tyr
    1400                 1405                 1410

Ser Thr  Ala Phe Gly Leu Ser  Arg Ala Leu Asn Arg  Leu Gln Gln
    1415                 1420                 1425

Gln Gln  Gly Asp Asn Asn Ser  Ser Ala Thr Glu Arg  Glu Val Arg
    1430                 1435                 1440

Ile Gly  Arg Leu Gln Arg Gln  Lys Val Arg Val Ser  Arg Asn Arg
    1445                 1450                 1455

Ile Leu  Asp Ser Ala Ala Lys  Val Met Glu Met Phe  Ser Asn Gln
    1460                 1465                 1470

Lys Ala  Val Leu Glu Val Glu  Tyr Phe Gly Glu Val  Gly Thr Gly
    1475                 1480                 1485

Leu Gly  Pro Thr Leu Glu Phe  Tyr Thr Leu Leu Ser  His Asp Leu
    1490                 1495                 1500

Gln Arg  Val Gly Leu Gly Leu  Trp Arg Ser Asp Ser  Asp Ser Leu
    1505                 1510                 1515

Glu Ala  Lys Lys Leu Asp Ser  His Ser Pro Ala Asp  Ser Arg Asn
    1520                 1525                 1530

Leu Ile  His Ala Pro Leu Gly  Leu Phe Pro Arg Pro  Trp Pro Pro
    1535                 1540                 1545

Ser Thr  Ala Ser Ser Glu Gly  Ser Lys Phe Phe Lys  Val Val Glu
    1550                 1555                 1560

Tyr Phe  Arg Leu Val Gly Arg  Ile Met Ala Lys Ala  Leu Gln Asp
    1565                 1570                 1575

Gly Arg  Leu Leu Asp Leu Pro  Leu Ser Thr Ala Phe  Tyr Lys Leu
    1580                 1585                 1590

Leu Leu  Gly Gln Glu Leu Asp  Leu Tyr Asp Ile Leu  Ser Phe Asp
    1595                 1600                 1605

Ala Glu  Phe Gly Lys Ile Leu  Gln Glu Leu Gln Val  Leu Val Glu
    1610                 1615                 1620

Arg Lys  Arg Phe Leu Glu Ser  Cys Ser Asn His Ser  Gln Gln Ile
    1625                 1630                 1635

Glu Glu  Leu Gly Phe Arg Gly  Ala Pro Ile Gln Asp  Leu Cys Leu
    1640                 1645                 1650

Asp Phe  Thr Leu Pro Gly Tyr  Pro Asp Phe Val Leu  Lys Glu Gly
    1655                 1660                 1665

Glu Glu  Asn Thr Val Val Cys  Ile Tyr Asn Leu Glu  Glu Tyr Ile
    1670                 1675                 1680

Ser Leu  Val Val Asp Ala Thr  Leu Lys Thr Gly Ile  Met Arg Gln
```

```
1685                1690                1695

Val Glu  Ala Phe Lys Ala Gly  Phe Asn Gln Val Phe  Asp Ile Ser
    1700                1705                1710

Ser Leu  Gln Ile Phe Ser Pro  Gln Glu Leu Asp Tyr  Leu Ile Cys
    1715                1720                1725

Gly Arg  Arg Glu Leu Trp Glu  Pro Glu Thr Leu Val  Glu His Ile
    1730                1735                1740

Lys Phe  Asp His Gly Tyr Thr  Ser Lys Ser Pro Ala  Ile Val Asn
    1745                1750                1755

Leu Leu  Glu Ile Met Thr Glu  Phe Thr Pro Glu Gln  Gln His Ala
    1760                1765                1770

Phe Cys  Gln Phe Val Thr Gly  Ala Pro Arg Leu Pro  Pro Gly Gly
    1775                1780                1785

Leu Ala  Ser Leu Asn Pro Lys  Leu Thr Ile Val Arg  Lys His Ser
    1790                1795                1800

Ser Thr  Ala Ala Asn Thr Ser  Asn Ala Ala Gly Ala  Ala Glu Ser
    1805                1810                1815

Ala Asp  Asp Asp Leu Pro Ser  Val Met Thr Cys Ala  Asn Tyr Leu
    1820                1825                1830

Lys Leu  Pro Pro Tyr Ser Thr  Lys Glu Val Met His  Lys Lys Leu
    1835                1840                1845

Leu Tyr  Ala Ile Asn Glu Gly  Gln Gly Ser Phe Asp  Leu Ser
    1850                1855                1860
```

<210> SEQ ID NO 47
<211> LENGTH: 9916
<212> TYPE: DNA
<213> ORGANISM: Triticum aestivum

<400> SEQUENCE: 47

```
atggacttcc cggccgacgg cggcggcaac aaccccccgc cccgccgccg cggcggccgc     60
gcctccaacg ccgacaaggg caaggagcag caggagccct cggagagctc ccgcgtgcgc    120
gaggccgagc ggatgctggg cctcagcttc gacggcatgg acgacgacga cgagggccac    180
ggggccttcc cccacggcct cacctccgcc agcagcgccc tgcaggggct gctcaggaag    240
ctcggcgccg gcctggacga catgctgccg tcgtccgggc tctcggccgc cgccgcggct    300
gcctcctcgt cgtccatgtc tgggccgaac ggcgcgcgga tgaagagcat gctcgcgggt    360
ctccgcgccg acggggagga ggggcgccag gttgaggcac tcacgcagct ctgcgagatg    420
ctgtccatcg gcacggagga caccctcgcg ggcttctcag tggactcgtt cgtgcctgtt    480
ctggtcgggc tgctcaacca tgagagcaac cccgacatca tgctgctcgc cgcgcgggcc    540
ctgacccacc tctgcgacgt gcttccgtcg tcctgctctg ccgttgtgca ctatggcgcc    600
gtggcatgct tctgcgcccg gcttctcacc attgaatata tggaccttgc tgagcaggtg    660
agcactgctc tgttgcatcg cttgcttggt ttatatatag tacatgctgc ttctttatca    720
tgttgcctga tccagatcaa tgcttagtga accattcttg tgtactgtat tatgcatgat    780
tatccataga gccttaacct acattacacg agtttccttt tagtgttgca ggtcatttgg    840
acttgctcat gagtagtttg ccttttgtgt agctgtggtt tttttcccat tttagtgcta    900
aaacaaacat gagtgagaag gttacaaaca tgatttttgt tggcgttgtg cccatacttg    960
agaagttcca ctgtatgctt tctatgttat gtttctgact caagtttcag tgacctgtac   1020
agatgtggta attgtaagtt agcctcagtt aatattaagt ttgaaatatt gtgtataatc   1080
```

```
aattttgaag gaactatata tttgaaatag cttgtttgat tgttcacttg gcaagtacca   1140
aatattgcct agttcagtag ctcaccattt aatgatgtca caagaaatat ctagagagtt   1200
aggcagaaag tgatacctta gtagccttgg ggcctgccaa gggtctagtc actggtcgct   1260
ctgggaggaa gaagctgagg ataggagaca catgaaagaa aaaatagtta gatgaaagca   1320
tgtcccaatg cacgtgatgc cttaaagcct tagggagctt gtgggcatgg agatgtcttc   1380
ccttcctctg ctgccgcagg aggactcggg ctccaaatcc tcaccagcga acgcaaatcc   1440
atctaaggac ctcatctgcc ccttagaaga ctttctaggc ctgatcatgg tggtgctcct   1500
gccgagcacc tgggtgccat ttaacatggt tttgctgtgc caaatcacct atttgtgcat   1560
gactaagcta actatttgaa catgtttttc atctgaaata tttctagctc agggtctgat   1620
ttcacgcctg tgtatgtgct actgtaatga tccatctgaa atactaagaa gttggttgga   1680
aatcagatgc taagattcat gtaaccggtt tctggctatg tttcttctct gccttcccat   1740
cttatatgga tattatactt ctacttttct tgggtctaat tcaaaacaat gtgaattaac   1800
ttgatagcat ctgtttgaat tcctttgtaa ccctttgtgc aattgaatct agtttgctgc   1860
tccacaatat gttattgagt agtatctacc actattagct ttatcaccta cgacatctga   1920
attactttct tagattttga tattgtattg cttctgtggt actttagatt agccactttc   1980
cttgttttgt tttgtcgttt aaaatatgct gcaggaagaa tctatcattg atagatcttg   2040
atgtggtact aatattttct tatgcctttt ctgggtattt tagtccttac aagcactcaa   2100
gaagatatcc caggagcatc caactgcctg cttgagggct ggcgcgctaa tggcagtgct   2160
atcgtatctt gacttcttct ccaccggtgt tcaagtaatt tttctaaata cttttatgtt   2220
tttccagcat ttagacataa cattctcaat acttgcgtta ttttttgca ccatttagaa   2280
attgggacat actaatttgt aatatcactt tatctttttg ttgcacacat actgtactac   2340
atttttatta ctactcacag ttgttttttt ggtggaatgt atacagagag ttgcgttatc   2400
tacagctgcc aatatgtgta ggaagcttcc ttcagacgcc tcagattttg taatggaagc   2460
ggttccactg ctaacaaatc ttctgaacta ccatgatgca aaagtatgct tgttgtctgt   2520
atttggatac cctgattatg ccatgatacc atctattctg agatgctgat tatctgtatc   2580
aatttattcc aggtgctgga acatgcttct gtttgcctga ctcgtatagc agaatcgttt   2640
gcttcatccc cagagaaatt ggatcaattg tgcaattatg gattggttgc acaagctgct   2700
agcttaatag ctgttagcaa ctcagcggga caagcatcac tgagtacatt aacatataca   2760
gtatgcttct atttcactta tttactgtat tatttagtat ttacgcaact ttgctaactc   2820
tggctcatat atccttgaag ggagtaattc gtgttctgtc aatatgtgca agtggatctt   2880
cattggcagc taaaacactc ctcctccatg gaattagcgg cacacttaaa gatatccttt   2940
caggttctgg tttggttgct ggtacaactg tatcccccac taggccagct gatcaggtga   3000
ttattgcttt atgagggcta tatctatatt atatattaca gctacttact gttttatttg   3060
aatgccatcg gttgatgact ctgttcggtg gttgttttat ctgacttagc cgatgaagct   3120
ttttgagtga tacttttttt tttcaatctt aaattcactc aagtgtgcat tcagttcagg   3180
tttgtttggt aaactgaaat taatatcaca caacagaata ttcaaaattt ggaagaaagt   3240
tgcatgctgg atacttattc tgtgtataat aatttgccaa atgtttcccg tgctcgtgct   3300
gtttgtgcag tcctgcaagc tataacagtg agcaaacaat gtggtaaatt ggattagggt   3360
ttgtcttgga actcttggtt catagacctc tctgttttct acccgatttt ctttctccag   3420
ttataatgaa attcacaatg atagtattga tcttgatcaa ggtttagaga tgcgctagac   3480
```

```
tggcggtagg tgaccgccta tatgacgccc agccactgtt tgttaacctt aataatctcg   3540
acatcatacc atattacttg ctccattttt ctttttaatt tatcaaaagc caagagttcc   3600
ctgtagtagt tctatggtag tttgcagctt gttttcatat gctaatgttc tttgttgtgt   3660
cacacagatg tatgaaattg tgaaccttgc cgacgaattg cttcctcctc tacctgctgg   3720
aaccatttct ttaccagcgc attcccatgt ttttatgaaa ggctcttctg taaagaaacc   3780
tggttctagc aagcaaggcg agtctggttc aacagatatt aaagtctcgg gtcgggagaa   3840
gttattgcgt gatcagcctg aacttctcca gcaatttggc atggacatat tacctaccat   3900
gacacaggtc agtcccatgg tttgctggcg tatcagttga tgttggttgc tgacgataac   3960
attattgaaa tcctgttatc tgagacatta tttggataca ctctatccct tgcaggtgta   4020
tggctccagt gtaaatggac caatacgtca taaatgctta tctgtcattg ctaaattaat   4080
gtattacagc tcagcggaaa tgatcgaaat tctccatggc acaacaaaca tatccaggtg   4140
ctaatacgaa acttcagatg ccattcttgc ttactgttat acatgtactc gtgtacctct   4200
ggttccatct aacctgatat tgacctttgc agcttcttag ctggcatctt agcttggaaa   4260
gatccacatg tgttggttcc cgctctccag atagctgaca ttctgatgga aaagctccct   4320
gggacatttt cgaagatgtt tgtgagggaa ggtgttgttc atgctgtaga atcgcttata   4380
tgccaggaaa tctctagtcc aatgcttttt caagtaccac agcaggacaa ggatattgat   4440
tctggtatat gtacatcttc acgttcaaga cgcagccgcc ggcgcagcag tgctgggaat   4500
actgataata attccttgga tgaaccaaag ggttcccata ctactattgc caattcacca   4560
ccaagcacgc tagaaggtcc aaatactagt attcgtgctt cagttagtga tcgtgcgaag   4620
tcattcaaag ataagtactt cccctctgaa cccggctcaa gtgatattgc agttactgat   4680
gaccttttga agctacgggc actctgtgca aaattaaatg ccactgcgga cactgttaaa   4740
acaaaagcca aggggaaatc aaagtcactg ggaggtgatg attttgatat cttatgcaat   4800
gtcgaggaac agttagacga catcatagac aaaatattgt ctgagcttag caatggggat   4860
ggggtttcca cgtttgagtt tattgggagt ggagttatct cagcattgct taactatttg   4920
tcttgtggaa cctttggaaa ggaaaaggtg tccgaagcaa acctacccaa gttgcgtcac   4980
ctggcactca ggcgatataa agcatttata tatgttgccc ttccaaatga tgcggtaggg   5040
aatcaaactc caatggcatt cttagttcaa aaactgcaaa gcgcgttgtc ttcgctggaa   5100
cggttcccag ttgtgattag ccattctgga aggacgtcca gtttgggagg atctcgtcca   5160
tcctctggat taagtgctct atcccagccc ctgaagttgc gcctgtgtcg agcaacaggt   5220
gaaaaaacgc tcaaggatta ttcatccaat atagttctta ttgatccctt ggcaagttta   5280
gcagccgttg aagatttcct ttggcctaga atccagcgta gcgagtcaat atcttatcct   5340
gcagtatcat ctggaaagaa ttctgaatct gtggcaccta gtgcaacagc accagtggct   5400
tcgtcaactc aatctgtccg gcggccctca actaggtcga aatcattggc tgatgctgat   5460
tctgcaacta agaaggatat tcaggagggg agcggaaaca catccaaggg aaaaggcaaa   5520
gctgttgtta agtcgacgtc cgatgaacca aaaggaccac atactaggac tgcggcacgc   5580
agaaaagttg cttcacagaa agatgcagaa gtgaagccac cacacagtca cagtagctca   5640
gaggtttgtt gttcattatg gactcatttc cttaataatc tatagtgtat atatttcctc   5700
tagtacgtct tgaatttttg ctagttcccc aaaatttgat acagatgctt gactatatat   5760
tctttgtttg gtagtgcctc cctgcagtta cccagctgcc aagctgattt tcgttataac   5820
```

-continued

```
aaccttccta ctgtttttcg tcgtcgtttc atgattatat ctgctctcct ttcatttaat   5880
aatttgaggt gcaactgtta aggggaattg acatgattaa taccgttatg aaattactcc   5940
ctccgtccca aaattcttgt cttagatttg tccagatatg gatgtatcta atactaaaat   6000
gtgacttgat acatccgtat ttagacaaat ctaagacaag aattttgcga cggagggagt   6060
attatttaac atgaatttca ttgtggaacc aatgtgtgaa tttcataaaa ttagatctac   6120
agaatacaat gccttttgaa ctgcagtttg atatgccatc tagggagtac atattgtctc   6180
accatgtcta caatgcttca gttgatgaag acattgtcca actaaaacca atgatgtagg   6240
gaaaggttgg tgctcccacc actatctcga tcactgaatg tgcctaaagg ttgttgcagt   6300
tccttatcct atgcaataat tatatgttga gagagtggca cggacctcaa gcagcaatgg   6360
cacattccat agttgagaac ttgtgatagt gggagcatat tcaccaatgt gatgcatttc   6420
actgttgaaa gtttgcccga atgcaatact gcttttcttg cctaactgag tgatgaatat   6480
ataaattaag ttgtcaattt aattatatct atgtaattag ctgcaagtac cccttaccag   6540
tactcacctg tataacaaaa tagatcactt atgcgttgga aactggacta ctatttcact   6600
aattccctta tccctgaaca aagttctgat ccaattcttg tacactatgt catgtgaatg   6660
ttaaacttta ttactgtatt tatgctcatt gtgcatgata cattctgttt cctacatgca   6720
ggacgaagaa ctgggcgcat ctccctttga ggctgatgat gctttgatgc ttggtgatga   6780
cgatgatgat gtttcagatg atgaagatga tgatcatgag gtagtatttc aaaattactt   6840
tgattgctcg ctttgtttct ctgcaagtta atgtggcttt agtgggcatg actgaaaact   6900
gcatattttt gttgaaaatc cccaggttct acgtgggtct cttcctgact gtgttccaga   6960
gagtgttcat gatgtaaaac tggcagatgc tgatggatct agtattgcct caatagcaag   7020
tgataaccag gcacaaccct catctggctc cagcataaaa catactttta gtagcagggg   7080
agcaggttct gttgaactta gaaatccaag cacacttggt tcgcggggcg cgatgtcgtt   7140
tgctgcagct gccatggctg ggcttgcttc tgttggtagt cgtggtatca gaggtagcca   7200
ggataggcgt ggccttccac ttggaactag tgcacatgag cattcgaaca aattgatttt   7260
tacagctggc ggcaagcagc ttagcaagca tttgaccgta tatcaagcta tgcaacagca   7320
agtagttcat gatgaggatg atgaggaaag gctaggtggt tctgatttac ccaatgatgg   7380
aagccgtctc tggggtgata tgttcactat aacatatcaa aaggctgata acgaagtgga   7440
tagggaatca accagaggtt catctttagt gctgaaatcg tccaaatcag aactttgcag   7500
agctacatct caagaacaat gtacttctct tcttgatagc attttgcaag gagaacttcc   7560
ttgtgatatt gagaaatcga cccaaactta taatatttta gcactattgc gtgtattgga   7620
gggattgaat cagctatctc ctcgtctgag actacaggca acctgtgatg attttataga   7680
gggaaaagtt ggtaccctgg atgggttata tggcaccgga gctaagttac cctcagagga   7740
gtttatcagc agtaagttga caccaaagct tgctcggcaa attcaggatg ttcttgcact   7800
ctgcagtggt agtttacctt cttggtgtta tcagatgacc aaagcttgtc catttctgtt   7860
tccttttgaa acaagaagac aacacttcta ctccacagct tttgggttat ctagggcatt   7920
gaatcgtctt cagcaacaac agggtgataa taatagctca gcgactgaaa gagaagtccg   7980
gattggtaga ttgcaacgcc agaaagttcg tgtttctcgt aaccggatcc tggattctgc   8040
tgccaaagta atggagatgt tctccaatca gaaggctgtt cttgaagttg aatactttgg   8100
tgaagtggga actggacttg gtccaacttt ggagttctac accctcttaa gtcatgacct   8160
gcaaagggtt ggcttgggat tatggagatc tgattctgat tctttagaag ctaaaaaact   8220
```

-continued

```
tgattcgcat tcacctgctg atagcaggaa cttggtacaa gcacctcttg gcttgttccc   8280

tcggccttgg ccacctagta ctgcttcttc agagggtagt aaattcttca aagttgttga   8340

gtatttccgc ttagttggtc gaatcatggc aaaagcattg caagatggaa ggcttcttga   8400

tttgcctttg tcaacagcat tttataagct tctacttgga caggtaagca tgaaaacccg   8460

cttgcagtag atccattcca atatcccctt ccaccttgtc aagtcttggt attttttta   8520

ttttctctac tgtcttctgt attgatgcca aaatatttg ctttactagg aacttgattt   8580

gtacgacata ctatcttttg atgctgagtt tggtaaaata cttcaagagt tgcaagttct   8640

tgttgaacgc aagcgatatc tggagtcctg ctctagtcat agtcaacaga tagaagaatt   8700

gggctttcgt ggtgctccta ttgaagacct atgcttagat tttactcttc cgggctatcc   8760

agattttgtt ctgaaggaag gtgaagaaaa tacagtggta tgtgatggag tagattaggt   8820

tcttatgttg tcattacttc agcttttgct tctaatattg ttgttgacta ttcattgtta   8880

tttttaactt cctgtaggtc tgcatttaca acttagaaga gtacatttcg ctggtagtgg   8940

atgctacact taaggctgga ataatgcgcc aagtagaagc attcaaagct ggatttaatc   9000

aggttttctc atttttctaa gatatcttat ttgctggcaa ttattgttaa ttagctattg   9060

catttctctt aaaatatttt tatttttcta tttcaggtat ttgatatatc atcactccaa   9120

atattttctc ctcaagagct tgactatctc atttgtggtc gacgggaact ttgggaggta   9180

atgtcctctt aactttcttc ctcccttcta taattattat cttaacttgt tctgagcaaa   9240

tgcatgtaat gcagccggag acgctggtcg aacatataaa gtttgatcat ggttatacct   9300

cgaagagtcc agcaattgtc aatgtgagta catcccttat ctttaaaaag ggcacatctc   9360

ttcacacagc tttatttcag atttttggaa cttgagttta ttgtttgtgc tgttggtttg   9420

cagctacttg agatcatgac ggaatttact ccggagcaac aacatgcatt ctgccagttt   9480

gtgactggtg ctcctcggct tccacctggt ggcttagcct ccctaaatcc taagctgact   9540

atcgttagga aggtaagcct gttgtagcaa tgcagaatga catcatttct gcgttcatgt   9600

tatttaaggc ttttccattt tgtatcttgg ccagcactcc tcgactgcgg cgaatacttc   9660

aaatgcagct ggagcagcag agtctgcaga tgacgatctg cctagtgtca tgacttgtgc   9720

caactatctt aaacttccgc catactcgac aaaggtttgg ttcttttggt tgatgaattt   9780

ttgttccacc tttccgtatc gtcttgcctg gaaactgact tctgctatgg tcgtcggaac   9840

gttgttgcag gaggttatgc acaagaagct gctttatgct atcaacgaag gccaggggtc   9900

gtttgatctt tcatag                                                   9916
```

<210> SEQ ID NO 48
<211> LENGTH: 1835
<212> TYPE: PRT
<213> ORGANISM: Triticum aestivum

<400> SEQUENCE: 48

```
Met Asp Phe Pro Ala Asp Gly Gly Gly Asn Asn Pro Pro Pro Arg Arg
1               5                   10                  15

Arg Gly Gly Arg Ala Ser Asn Ala Asp Lys Gly Lys Glu Gln Gln Glu
            20                  25                  30

Pro Ser Glu Ser Ser Arg Val Arg Glu Ala Glu Arg Met Leu Gly Leu
        35                  40                  45

Ser Phe Asp Gly Met Asp Asp Asp Asp Glu Gly His Gly Ala Phe Pro
    50                  55                  60
```

-continued

```
His Gly Leu Thr Ser Ala Ser Ser Ala Leu Gln Gly Leu Leu Arg Lys
65                  70                  75                  80

Leu Gly Ala Gly Leu Asp Asp Met Leu Pro Ser Ser Gly Leu Ser Ala
                85                  90                  95

Ala Ala Ala Ala Ala Ser Ser Ser Ser Met Ser Gly Pro Asn Gly Ala
            100                 105                 110

Arg Met Lys Ser Met Leu Ala Gly Leu Arg Ala Asp Gly Glu Glu Gly
        115                 120                 125

Arg Gln Val Glu Ala Leu Thr Gln Leu Cys Glu Met Leu Ser Ile Gly
    130                 135                 140

Thr Glu Asp Thr Leu Ala Gly Phe Ser Val Asp Ser Phe Val Pro Val
145                 150                 155                 160

Leu Val Gly Leu Leu Asn His Glu Ser Asn Pro Asp Ile Met Leu Leu
                165                 170                 175

Ala Ala Arg Ala Leu Thr His Leu Cys Asp Val Leu Pro Ser Ser Cys
            180                 185                 190

Ser Ala Val Val His Tyr Gly Ala Val Ala Cys Phe Cys Ala Arg Leu
        195                 200                 205

Leu Thr Ile Glu Tyr Met Asp Leu Ala Glu Gln Ser Leu Gln Ala Leu
    210                 215                 220

Lys Lys Ile Ser Gln Glu His Pro Thr Ala Cys Leu Arg Ala Gly Ala
225                 230                 235                 240

Leu Met Ala Val Leu Ser Tyr Leu Asp Phe Phe Ser Thr Gly Val Gln
                245                 250                 255

Arg Val Ala Leu Ser Thr Ala Ala Asn Met Cys Arg Lys Leu Pro Ser
            260                 265                 270

Asp Ala Ser Asp Phe Val Met Glu Ala Val Pro Leu Leu Thr Asn Leu
        275                 280                 285

Leu Asn Tyr His Asp Ala Lys Val Leu Glu His Ala Ser Val Cys Leu
    290                 295                 300

Thr Arg Ile Ala Glu Ser Phe Ala Ser Ser Pro Glu Lys Leu Asp Gln
305                 310                 315                 320

Leu Cys Asn Tyr Gly Leu Val Ala Gln Ala Ala Ser Leu Ile Ala Val
                325                 330                 335

Ser Asn Ser Ala Gly Gln Ala Ser Leu Ser Thr Leu Thr Tyr Thr Gly
            340                 345                 350

Val Ile Arg Val Leu Ser Ile Cys Ala Ser Gly Ser Ser Leu Ala Ala
        355                 360                 365

Lys Thr Leu Leu Leu His Gly Ile Ser Gly Thr Leu Lys Asp Ile Leu
    370                 375                 380

Ser Gly Ser Gly Leu Val Ala Gly Thr Thr Val Ser Pro Thr Arg Pro
385                 390                 395                 400

Ala Asp Gln Asn Ile Gln Asn Leu Glu Glu Ser Cys Met Leu Asp Thr
                405                 410                 415

Tyr Ser Val Tyr Asn Asn Leu Pro Asn Val Ser Arg Ala Arg Ala Val
            420                 425                 430

Cys Ala Val Leu Gln Ala Ile Thr Met Tyr Glu Ile Val Asn Leu Ala
        435                 440                 445

Asp Glu Leu Leu Pro Pro Leu Pro Ala Gly Thr Ile Ser Leu Pro Ala
    450                 455                 460

His Ser His Val Phe Met Lys Gly Ser Ser Val Lys Lys Pro Gly Ser
465                 470                 475                 480

Ser Lys Gln Gly Glu Ser Gly Ser Thr Asp Ile Lys Val Ser Gly Arg
```

```
                485                 490                 495

Glu Lys Leu Leu Arg Asp Gln Pro Glu Leu Leu Gln Gln Phe Gly Met
            500                 505                 510

Asp Ile Leu Pro Thr Met Thr Gln Val Tyr Gly Ser Ser Val Asn Gly
        515                 520                 525

Pro Ile Arg His Lys Cys Leu Ser Val Ile Ala Lys Leu Met Tyr Tyr
    530                 535                 540

Ser Ser Ala Glu Met Ile Glu Ile Leu His Gly Thr Thr Asn Ile Ser
545                 550                 555                 560

Ser Phe Leu Ala Gly Ile Leu Ala Trp Lys Asp Pro His Val Leu Val
                565                 570                 575

Pro Ala Leu Gln Ile Ala Asp Ile Leu Met Glu Lys Leu Pro Gly Thr
            580                 585                 590

Phe Ser Lys Met Phe Val Arg Glu Gly Val Val His Ala Val Glu Ser
        595                 600                 605

Leu Ile Cys Gln Glu Ile Ser Ser Pro Met Leu Phe Gln Val Pro Gln
    610                 615                 620

Gln Asp Lys Asp Ile Asp Ser Gly Ile Cys Thr Ser Ser Arg Ser Arg
625                 630                 635                 640

Arg Ser Arg Arg Arg Ser Ser Ala Gly Asn Thr Asp Asn Asn Ser Leu
                645                 650                 655

Asp Glu Pro Lys Gly Ser His Thr Thr Ile Ala Asn Ser Pro Pro Ser
            660                 665                 670

Thr Leu Glu Gly Pro Asn Thr Ser Ile Arg Ala Ser Val Ser Asp Arg
        675                 680                 685

Ala Lys Ser Phe Lys Asp Lys Tyr Phe Pro Ser Glu Pro Gly Ser Ser
    690                 695                 700

Asp Ile Ala Val Thr Asp Asp Leu Leu Lys Leu Arg Ala Leu Cys Ala
705                 710                 715                 720

Lys Leu Asn Ala Thr Ala Asp Thr Val Lys Thr Lys Ala Lys Gly Lys
                725                 730                 735

Ser Lys Ser Leu Gly Gly Asp Asp Phe Asp Ile Leu Cys Asn Val Glu
            740                 745                 750

Glu Gln Leu Asp Asp Ile Ile Asp Lys Ile Leu Ser Glu Leu Ser Asn
        755                 760                 765

Gly Asp Gly Val Ser Thr Phe Glu Phe Ile Gly Ser Gly Val Ile Ser
    770                 775                 780

Ala Leu Leu Asn Tyr Leu Ser Cys Gly Thr Phe Gly Lys Glu Lys Val
785                 790                 795                 800

Ser Glu Ala Asn Leu Pro Lys Leu Arg His Leu Ala Leu Arg Arg Tyr
                805                 810                 815

Lys Ala Phe Ile Tyr Val Ala Leu Pro Asn Asp Ala Val Gly Asn Gln
            820                 825                 830

Thr Pro Met Ala Phe Leu Val Gln Lys Leu Gln Ser Ala Leu Ser Ser
        835                 840                 845

Leu Glu Arg Phe Pro Val Val Ile Ser His Ser Gly Arg Thr Ser Ser
    850                 855                 860

Leu Gly Gly Ser Arg Pro Ser Ser Gly Leu Ser Ala Leu Ser Gln Pro
865                 870                 875                 880

Leu Lys Leu Arg Leu Cys Arg Ala Thr Gly Glu Lys Thr Leu Lys Asp
                885                 890                 895

Tyr Ser Ser Asn Ile Val Leu Ile Asp Pro Leu Ala Ser Leu Ala Ala
            900                 905                 910
```

```
Val Glu Asp Phe Leu Trp Pro Arg Ile Gln Arg Ser Glu Ser Ile Ser
        915                 920                 925

Tyr Pro Ala Val Ser Ser Gly Lys Asn Ser Glu Ser Val Ala Pro Ser
    930                 935                 940

Ala Thr Ala Pro Val Ala Ser Ser Thr Gln Ser Val Arg Arg Pro Ser
945                 950                 955                 960

Thr Arg Ser Lys Ser Leu Ala Asp Ala Asp Ser Ala Thr Lys Lys Asp
                965                 970                 975

Ile Gln Glu Gly Ser Gly Asn Thr Ser Lys Gly Lys Gly Lys Ala Val
            980                 985                 990

Val Lys Ser Thr Ser Asp Glu Pro  Lys Gly Pro His Thr  Arg Thr Ala
        995                 1000                1005

Ala Arg  Arg Lys Val Ala Ser  Gln Lys Asp Ala Glu  Val Lys Pro
    1010                 1015                 1020

Pro His  Ser His Ser Ser Ser  Glu Asp Glu Glu Leu  Gly Ala Ser
    1025                 1030                 1035

Pro Phe  Glu Ala Asp Asp Ala  Leu Met Leu Gly Asp  Asp Asp Asp
    1040                 1045                 1050

Asp Val  Ser Asp Asp Glu Asp  Asp Asp His Glu Val  Leu Arg Gly
    1055                 1060                 1065

Ser Leu  Pro Asp Cys Val Pro  Glu Ser Val His Asp  Val Lys Leu
    1070                 1075                 1080

Ala Asp  Ala Asp Gly Ser Ser  Ile Ala Ser Ile Ala  Ser Asp Asn
    1085                 1090                 1095

Gln Ala  Gln Pro Ser Ser Gly  Ser Ser Ile Lys His  Thr Phe Ser
    1100                 1105                 1110

Ser Arg  Gly Ala Gly Ser Val  Glu Leu Arg Asn Pro  Ser Thr Leu
    1115                 1120                 1125

Gly Ser  Arg Gly Ala Met Ser  Phe Ala Ala Ala Ala  Met Ala Gly
    1130                 1135                 1140

Leu Ala  Ser Val Gly Ser Arg  Gly Ile Arg Gly Ser  Gln Asp Arg
    1145                 1150                 1155

Arg Gly  Leu Pro Leu Gly Thr  Ser Ala His Glu His  Ser Asn Lys
    1160                 1165                 1170

Leu Ile  Phe Thr Ala Gly Gly  Lys Gln Leu Ser Lys  His Leu Thr
    1175                 1180                 1185

Val Tyr  Gln Ala Met Gln Gln  Gln Val Val His Asp  Glu Asp Asp
    1190                 1195                 1200

Glu Glu  Arg Leu Gly Gly Ser  Asp Leu Pro Asn Asp  Gly Ser Arg
    1205                 1210                 1215

Leu Trp  Gly Asp Met Phe Thr  Ile Thr Tyr Gln Lys  Ala Asp Asn
    1220                 1225                 1230

Glu Val  Asp Arg Glu Ser Thr  Arg Gly Ser Ser Leu  Val Leu Lys
    1235                 1240                 1245

Ser Ser  Lys Ser Glu Leu Cys  Arg Ala Thr Ser Gln  Glu Gln Cys
    1250                 1255                 1260

Thr Ser  Leu Leu Asp Ser Ile  Leu Gln Gly Glu Leu  Pro Cys Asp
    1265                 1270                 1275

Ile Glu  Lys Ser Thr Gln Thr  Tyr Asn Ile Leu Ala  Leu Leu Arg
    1280                 1285                 1290

Val Leu  Glu Gly Leu Asn Gln  Leu Ser Pro Arg Leu  Arg Leu Gln
    1295                 1300                 1305
```

-continued

```
Ala Thr  Cys Asp Asp Phe Ile  Glu Gly Lys Val Gly  Thr Leu Asp
    1310                 1315                 1320

Gly Leu  Tyr Gly Thr Gly Ala  Lys Leu Pro Ser Glu  Glu Phe Ile
    1325                 1330                 1335

Ser Ser  Lys Leu Thr Pro Lys  Leu Ala Arg Gln Ile  Gln Asp Val
    1340                 1345                 1350

Leu Ala  Leu Cys Ser Gly Ser  Leu Pro Ser Trp Cys  Tyr Gln Met
    1355                 1360                 1365

Thr Lys  Ala Cys Pro Phe Leu  Phe Pro Phe Glu Thr  Arg Arg Gln
    1370                 1375                 1380

His Phe  Tyr Ser Thr Ala Phe  Gly Leu Ser Arg Ala  Leu Asn Arg
    1385                 1390                 1395

Leu Gln  Gln Gln Gln Gly Asp  Asn Asn Ser Ser Ala  Thr Glu Arg
    1400                 1405                 1410

Glu Val  Arg Ile Gly Arg Leu  Gln Arg Gln Lys Val  Arg Val Ser
    1415                 1420                 1425

Arg Asn  Arg Ile Leu Asp Ser  Ala Ala Lys Val Met  Glu Met Phe
    1430                 1435                 1440

Ser Asn  Gln Lys Ala Val Leu  Glu Val Glu Tyr Phe  Gly Glu Val
    1445                 1450                 1455

Gly Thr  Gly Leu Gly Pro Thr  Leu Glu Phe Tyr Thr  Leu Leu Ser
    1460                 1465                 1470

His Asp  Leu Gln Arg Val Gly  Leu Gly Leu Trp Arg  Ser Asp Ser
    1475                 1480                 1485

Asp Ser  Leu Glu Ala Lys Lys  Leu Asp Ser His Ser  Pro Ala Asp
    1490                 1495                 1500

Ser Arg  Asn Leu Val Gln Ala  Pro Leu Gly Leu Phe  Pro Arg Pro
    1505                 1510                 1515

Trp Pro  Pro Ser Thr Ala Ser  Ser Glu Gly Ser Lys  Phe Phe Lys
    1520                 1525                 1530

Val Val  Glu Tyr Phe Arg Leu  Val Gly Arg Ile Met  Ala Lys Ala
    1535                 1540                 1545

Leu Gln  Asp Gly Arg Leu Leu  Asp Leu Pro Leu Ser  Thr Ala Phe
    1550                 1555                 1560

Tyr Lys  Leu Leu Leu Gly Gln  Glu Leu Asp Leu Tyr  Asp Ile Leu
    1565                 1570                 1575

Ser Phe  Asp Ala Glu Phe Gly  Lys Ile Leu Gln Glu  Leu Gln Val
    1580                 1585                 1590

Leu Val  Glu Arg Lys Arg Tyr  Leu Glu Ser Cys Ser  Ser His Ser
    1595                 1600                 1605

Gln Gln  Ile Glu Glu Leu Gly  Phe Arg Gly Ala Pro  Ile Glu Asp
    1610                 1615                 1620

Leu Cys  Leu Asp Phe Thr Leu  Pro Gly Tyr Pro Asp  Phe Val Leu
    1625                 1630                 1635

Lys Glu  Gly Glu Glu Asn Thr  Val Val Cys Ile Tyr  Asn Leu Glu
    1640                 1645                 1650

Glu Tyr  Ile Ser Leu Val Val  Asp Ala Thr Leu Lys  Ala Gly Ile
    1655                 1660                 1665

Met Arg  Gln Val Glu Ala Phe  Lys Ala Gly Phe Asn  Gln Val Phe
    1670                 1675                 1680

Asp Ile  Ser Ser Leu Gln Ile  Phe Ser Pro Gln Glu  Leu Asp Tyr
    1685                 1690                 1695

Leu Ile  Cys Gly Arg Arg Glu  Leu Trp Glu Pro Glu  Thr Leu Val
```

```
    1700                1705                1710

Glu His  Ile Lys Phe Asp His  Gly Tyr Thr Ser Lys  Ser Pro Ala
    1715                1720                1725

Ile Val  Asn Leu Leu Glu Ile  Met Thr Glu Phe Thr  Pro Glu Gln
    1730                1735                1740

Gln His  Ala Phe Cys Gln Phe  Val Thr Gly Ala Pro  Arg Leu Pro
    1745                1750                1755

Pro Gly  Gly Leu Ala Ser Leu  Asn Pro Lys Leu Thr  Ile Val Arg
    1760                1765                1770

Lys His  Ser Ser Thr Ala Ala  Asn Thr Ser Asn Ala  Ala Gly Ala
    1775                1780                1785

Ala Glu  Ser Ala Asp Asp Asp  Leu Pro Ser Val Met  Thr Cys Ala
    1790                1795                1800

Asn Tyr  Leu Lys Leu Pro Pro  Tyr Ser Thr Lys Glu  Val Met His
    1805                1810                1815

Lys Lys  Leu Leu Tyr Ala Ile  Asn Glu Gly Gln Gly  Ser Phe Asp
    1820                1825                1830

Leu Ser
    1835


<210> SEQ ID NO 49
<211> LENGTH: 9841
<212> TYPE: DNA
<213> ORGANISM: Triticum aestivum

<400> SEQUENCE: 49

gcccgccgct ccgtcgtcct ctccccgccc gccccgcagc ccccgatgga cttcccggcc     60

gacgggaaca acaacccccc gccccgccgc cgcggcggcc gcgcctccaa cgccgacaag    120

ggcaaggagc agcaggagcc ctcggagagc tcccgcgtgc gcgaggccga gcggatgctg    180

ggcctcagct tcgacggcat ggacgacgac gacgagggcc acggggcctt cccccacggc    240

ctcacctccg ccagcagcgc cctgcagggg ctgctcagga agctcggcgc cggcctggac    300

gacatgctgc cgtcgtccgc cctctccgcc gccgccgcgg ctgcctcctc gtcgtccatg    360

tctgggccga acggcgcgcg gatgaagagc atgctcgcgg gtctccgtgc cgacggggag    420

gaggggcgcc aggtggaggc gctgacccag ctctgtgaga tgctgtccat cggcaccgag    480

gacaccctcg ccgggttctc ggtggactca ttcgtgcctg ttctggtcgg gctgctcaac    540

cacgagagca accctgacat catgctgctc gctgcgcggg ccctgaccca cctctgtgac    600

gtgctgccgt cgtcctgctc tgccgttgtg cactatggcg ccgtggcatg cttctgcgcc    660

cggcttctca ccattgaata tatggacctt gcggagcagg tgagcactgt tctgctgcat    720

cgcttgtttg gtttatagta catgctgctt ctttatcatg ttgcctgatc cagatcaatg    780

cttagtgaac cattcttgtg tactgtatta tgcatgatta tgctgtccat agagccttaa    840

cctacattac atgagtttcc ttttagtgtt gcagatcatt tatagtattt ggacttgctc    900

atgagtagtt tgccttttgt gtagctgtgt ttttttccca ttttagtgct aaaacaaata    960

tggatgagaa ggttaagaac atgatttttg ttggcgttgt gcccatactc gagaagttcc   1020

actgtatgct ttctatgtta tgtttctgac tcaagtttcg gtgacctgta cagatgtggt   1080

agttgtaagt tagcctcagt taatattaag tttgaaatat tgtgtataat cagttttcaa   1140

ggaactatat atttgaaata gcttgtttga ttgttcactt ggcaagtacc aaatattgcc   1200

tatttcagta gctcaccatt taatgatgtt acaagaaata tctagagagt taggcagaag   1260
```

-continued

```
gtgatccctt agcagccttg gggcctgcct agggtctagt cactggtcgc tctgggagga   1320
agaagctgag gataggagac acatgaaaga aaaaatggtt agatgaaagc atgtcccaat   1380
gcacgtgatg ccttaaagcc ttagggagct tgtgggcatg gagatgtctt cccttcctct   1440
ggtgccgccg gaggactcgg gctccaaatc ctcaccagcg aactcaaatc catctaagga   1500
cctcatctgc cccttagaag actttctagg cctgatcatg gtggtgttcc tgccgagcac   1560
ctgggtgcca tttaacacgg ttttgctgtg tgccaaatca cctatttgtg catgactaag   1620
ctagctattt gaacatgttt ttcatctgaa atatttctag ctcagggtct gatttcacgc   1680
ctgtgtatgt gctactgtaa tgatccatct gaaatactaa gaagtgggtt ggaaatcaga   1740
tgctaagatt catgtaaccg gtttctggct gtgtttcttc tctgccttcc catcttatat   1800
ggatattata cttctacttc tcttgggtct aattcaaaac aatgtgaatt aacttgatat   1860
catctgtttg aattcctttg taaccctttg tgcaattgaa tctagtttgc tgctccacaa   1920
tatgttattg agtagtatct acaactatta ggtttagcac ctaggacatt tgaattactt   1980
tcttagattt tgatattgta ttgcttctgt ggcactttag attagccact ttccttgttt   2040
tgttttgtcg tttaaaatat gctgcaggaa gaatctatca ttgctagatc ttgatgtgtt   2100
actaatattt tcttatgcct tctctgtgta ttttagtcct tacaagcact caagaagata   2160
tcccaggagc atccaactgc ctgcttgagg gctggcgcgc taatggcagt gctatcatat   2220
cttgacttct tctccaccgg tgttcaagta atttttctaa atacttctat gtttttccag   2280
catttagaca taacattctc aatacttacg ttattttttt gcaccattta gaaattggga   2340
catactaatt tgtcatatca ctatcttttt gttgtacaca tactgtacta catttttatt   2400
actactcaca gttgtttttt tggtggaatg tatacagaga gttgcgttat ctacagctgc   2460
caatatgtgt aggaagcttc cttcagacgc ctcagatttt gtaatggaag cggttccact   2520
gctaacaaat cttctgaact accatgatgc aaaagtatgc ttgttgtctg tatttggata   2580
ccatgattat gccatgatac catctattct tagatgctga tgatctgtat caatgtattc   2640
caggtgctgg aacatgcttc tgtttgcctg actcgtatag cagaatcgtt tgcttcatcc   2700
ccagagaaat tagatcaatt gtgcaattat ggattggttg cacaagctgc tagcttaata   2760
gctgttagca actcagcggg acaagcatca ctgagtacat taacatatac agtatgcttc   2820
tatttcactt atctactgta ttatttagta gttacgcaac tttgctaact ctggctcata   2880
tatccttgaa gggagtaatt cgtgttctgt caatatgtgc aagtggatct ccattggcag   2940
ctaaaacact cctcctccat ggaattagcg gcacacttaa agatatcctt tcaggttctg   3000
gtttggttgc tggtacaact gtatccccca ctaggccagc tgatcaggtg attattgctt   3060
tatgagggct atatctatat tatagctact tactgtttta tttgaatgcc atcggttgat   3120
gactctgttc ggttgttgtt ttatctgact tagccgatga agctttttga gtgatacttt   3180
tttttttcaa gtttaaattc actcaagtgt gcattcagtt caggcttgtt tggtaaactg   3240
aaattaatat cacacaacag aatattcaaa atttggaaga aagttgcatg ctggatactt   3300
attctgtgta taataatttg ccaaatgttt cccgtgctcg tgctgtttgt gcagtcctgc   3360
aagctataac agtgagcaaa caatgtggta aattggatta ggggtttgtc ttggaactct   3420
tggttcatag acttctctgt tttctacccg attttctttc tccagttata atatgaaatt   3480
cacaatgata gtattgatct tgatcaaggt ttagagatgc gctagactgg cggtaggtga   3540
ccacctagat gacgcccagc tactgtttgt taaccttaat aatctcgaca tcataccata   3600
ttacttgctc catttttctt tttaatttat caaaagccaa gagtttcctg tagtagttct   3660
```

atggtagttt gcagcttgtt ttcatatgct aatattcttt gttgtgtcac acagatgtat 3720
gaaattgtga accttgccga cgaattgctt cctcctctac ctgctggaac catttcttta 3780
ccagcgcatt cccatgtttt tatgaaaggc tcttctgtaa agaaacctgg ttctagcaag 3840
caaggcgagt ctggttcaac agatattaaa gtctcgggtc gggagaagtt attacgtgat 3900
cagcctgaac ttctccagca atttggcatg gacatattac ctaccatgac acaggtcagt 3960
ctcttggttt gctggcgtat cagttgatgt tggttgctga caataacatt attgaaatcc 4020
tgttatctga gacattattt ggatacactc tatcccttgc aggtgtatgg ctccagtgta 4080
aatggaccaa tacgtcataa atgcttatct gtcattgcta aattaatgta ttacagctca 4140
gcggaaatga tcgaaattct ccatggcaca acaaacatat ccaggtgcta atacgaaact 4200
tcagatgcca ttcttgctta ctgttataca tgtactcgtg tacctctggt tccatctaac 4260
ctgatattga cctttgcagc ttcttagctg gcatcttagc ttggaaagat ccacatgtgt 4320
tggttcccgc tctccagata gctgaaattc tgatggaaaa gctccctggg acattttcga 4380
agatgtttgt gagggaaggt gttgttcatg ctgtagaatc gcttatatgc caggaaatct 4440
caagtccaat gctttttcaa gtaccacagc aggacaagga tattgattct ggtacatgta 4500
catcttcacg ttcaagacgc agccgccggc gcagcagtgc tgggaatact gataataatt 4560
ccttggatga accaaagggt tcccatacta ctattgccaa ttcaccacca agcacgctag 4620
aaggtccaaa tactagaatt cgtgcttcag ttagtgatcg tgcgaagtca ttcaaagata 4680
agtacttccc ctctgaaccc ggctcaagtg atattgcagt tactgatgac cttttgaagc 4740
tacgggcact ctgtgcaaaa ttaaatgcca ctgcggacac tgttaaaaca aaagccaaag 4800
ggaaatcaaa gtcactggga ggtgatgatt ttgatatctt atgcaatgtc gaggaacagt 4860
tagacgatat catagataaa atattgtctg agcttagcaa tggggatggg gtttccacgt 4920
ttgagtttat tgggagtgga gttatctcag cattgcttaa ttatttgtct tgtggaacct 4980
ttggaaagga aaaggtgtcc gaagcaaacc tacccaagtt gcgtcacctg gcactcaggc 5040
gatataaagc atttatatat gttgcccttc caaatgatgc ggtagggaat caaactccaa 5100
tggcattctt agttcaaaaa ctgcaaagcg cgttgtcttc gctggaacgg ttcccagttg 5160
tgattagcca ttctggaagg acgtccagtt tgggaggatc tcgtccatcc tctggattaa 5220
gtgctctatc tcagcccctg aagttgcgcc tgtgtcgagc agcgggtgaa aaaatgctta 5280
aggattattc atccaatata gttcttattg atcccttggc aagtttagca gccgttgaag 5340
atttcctttg gtctagaatc cagcgtagcg agtcaatatc ttatcctgca gtatcatctg 5400
gaaagaattc tgaatctgtg gcacctagtg caacagcacc agtggcttcg tcaactcaat 5460
ctgtccggcg gccctcaact aggtcgaaat cattggctga tgctgattct gcaactaaga 5520
aggatattca ggaggggagc ggaaacacat ccaagggaaa aggcaaagct gttgttaagt 5580
cgacgtccga tgaacctaaa ggaccacata ctaggactgc agcacgcaga aaagttgctt 5640
cacagaaaga tgcagaagtg aagccaccac acggtcacag tagctcagag gtttgttgtt 5700
cattatggac tcatttcctt aataatctat agaatatata tttcctccag tacgtcttga 5760
atttttgcta gttccccaaa atttgatgca aatgcttgac tacatattct ttttttggta 5820
gtgcctccct gcagttactc agctgccaag ctgattttcg ttataacaac cgtcctactg 5880
tttttcgtcg tcgtttcatg attatatctg ctctcctttc atttaataat ttgatgtgca 5940
actgttaagg ggaattgaca tgattaatac tgttatgaga ttattattta acacaaattt 6000

-continued

```
cattgtggaa ccaatgtgtg aatttcataa aattagatct acagagtaca atgccttttc   6060
acctgcagtt tgatatggca tctagggagt acatattgtc tcaccatgtc tacaatgctt   6120
cagttgatga agacattgtc ttactaaaac caatgatgta gggaaaggtt ggtgctccca   6180
ccactatctc gatcactgaa tgtgcctaaa ggttgttgca gttcctcatc ctatgcaata   6240
attatatgtt gagagagtgg cacggacctc aagcagcaat ggcacattcc atagttgaga   6300
acttgtgata gtgggagcat attcaccaat gtgattcatt tcactgttga aagtttgccc   6360
gaatgcaata ctgcttttct tgcctaactg agtgataaat atataaataa taaattaagt   6420
tgtcaagtta attatatcta tgtaattagc tgcaagtacc ccttaccagt actcacctgt   6480
ataacaaaat agatcactta tgcgttggaa actggactac tatttcacta attcccttat   6540
ccctgaacaa agttctgatc caattcttgt acaccatgtc atgtgaatgt taaactttat   6600
tattgtattt atgctcgttg tgcatgatac attctgtttc ctacatgcag gacgaagaac   6660
tgggcgcatc tcccttcgag gctgatgatg ctttgatgct tggtgatgac gatgatgatg   6720
tttcagatga tgaagacgat gatcatgagg tagtatttca aaattacttc gattgatctc   6780
tttgttttcc tgcaagttaa tgtggcttta gtgggcatga ctgaaaactg catatttttg   6840
ttgagaatcc ccaggttcta cgtgggtctc ttcctgactg tgttccagag agtgtgcatg   6900
atgtaaaact ggcagatgct gatggatcta gtattgcctc aatagcaagt gataaccaga   6960
cacaaccctc atctggctcc agcataaaac atacttttag tagcagggga gcaggttctg   7020
ttgaacttag aaatccaagc acacttggtt cgcggggcgc gatgtcgttt gctgcagctg   7080
ccatggctgg gcttgcttct gttggtagtc gtggtatcag aggtagccag gataggcgtg   7140
gccttccact tggaactagt gcacatgagc attcgaacaa attgattttt acagctggcg   7200
gcaagcagct tagcaagcat ttgaccgtat atcaagctat gcaacagcaa gtagttcatg   7260
atgaggatga tgaggaaagg ttaggtggtt ctgatttacc caatgatgga agccgtctct   7320
ggagtgatgt gttcactata acatatcaaa aggctgataa cgaagtggat agggaatcaa   7380
ccagaggttc atctttagtg ctgaaatcgt ccaaatcaga actttgcaga gctacatctc   7440
aagaacaatg tatttctctt cttgatagca ttttgcaagg agaacttcct tgtgatattg   7500
agaaatcgac ccaaacttat aatattttag cactattgcg tgtattggag ggattgaatc   7560
agctatctcc tcgtctgaga ctacaggcaa cctgtgatga ttttatagag ggaaaagttg   7620
gtaccctgga tgggttatat ggcaccggag ctaaggtacc ctcagaggag tttatcagca   7680
gtaagttgac accaaagctt gctcggcaaa ttcaggatgt tcttgcactc tgcagtggta   7740
gtttaccttc ttggtgttat cagatgacca aagcttgtcc atttctgttt ccttttgaaa   7800
caagaagaca acacttctac tccacagctt ttgggttatc tagggcattg aatcgtcttc   7860
agcaacaaca gggtgataat aatagctcag cgactgaaag agaagtccgg attggtagat   7920
tgcaacgcca gaaagttcgt gtttctcgta accggatcct ggattctgct gccaaagtaa   7980
tggagatgtt ctccaatcag aaggctgttc ttgaagttga atactttggt gaagtgggaa   8040
ctggacttgg tccaactttg gagttctaca ccctcttaag tcatgacctg caaagggttg   8100
gcttgggatt atggagatct gattctgatt ctttagaagc taaaaaagtt gattcgcatt   8160
cacctgctga tagcaggaac ttgatacaag cacctcttgg cttgttccct cggccttggc   8220
cacctagtac tgcttcttca gagggtagta aattcttcaa agttgtggag tatttccgct   8280
tagttggtcg aatcatggca aaagcattgc aagatggaag gcttcttgat ttgcctttgt   8340
caacagcatt ttataagctt ctacttggac aagtaagcat gagaacccgc ttgcagtaga   8400
```

```
tccattccaa tattcccttc caccttcttg tcaagtcttg gtattttttt tttattttct   8460

ctactgtctt ctgtattgac gccaaaatat tttgctttac taggaacttg atttgtatga   8520

catactatct tttgatgctg agcttggtaa aatacttcga gagttgcaag ttcttgttga   8580

acgcaagcga tttctggagt cctgctctaa tcatagtcaa caaatagaag aattgggctt   8640

tcatggtgct cctattgaag acctatgctt agattttact cttccgggct atccggattt   8700

tgttctgaag gaaggtgaag aaaatacagt ggtatgtgat ggagtagatt aggttcttat   8760

gtcgtcatca cttcagcttt tgcttctaat tttgttgttg actattcatt gttattttta   8820

acttcctgta ggtctgcatt tacaacttag aagagtacat ttcgctggta gtggatgcta   8880

cacttaagac tggaataatg cgtcaagtag aagcattcaa agctggattt aatcaggttt   8940

tctcattttt ctaagatatc ttatttgctg gcaattattg ttaattagct attgcatttc   9000

tcttaatttt tttcttctaa ttcaggtatt tgatatatca tcactccaaa tattttctcc   9060

tcaagagctt gactatctca tttgtggtcg acgggaactt tgggaggtaa tgccctgtta   9120

actttatttc tcccttctat aatcattatt ttaacttgtt ctgagcaaat gcatgtaatg   9180

cagccggaga cactggtcga acatataaag tttgatcatg gttatacctc gaagagtcca   9240

gcaattgtca atgtgagtac atcatcttta aaaaagggca catctcttca cacagcttta   9300

tttcagattt ttggaacttc agtttaatgt ttgtgctgtt ggtttgcagc tacttgagat   9360

catgacagaa tttactccgg agcaacaaca tgcattctgc cagtttgtga ctggtgctcc   9420

tcggcttcca cctggtggct tagcctccct aaatcctaag ctgactatcg ttaggaaggt   9480

aagcctgttt tagcaatgca gaatgacatc atttctgcgt tcatgttatt taagcttttc   9540

cattttgtat cttggccagc actcctcgac tgcggcgaat acttcaaatg cagctggagc   9600

agcagagtct gcagatgatg atctgcctag tgtcatgact tgtgccaact atcttaaact   9660

tccgccatac tcgacaaagg tttggttctt ttggttgatg aatttttgtt ccacctttcc   9720

gtatcgtctt gcctggaaac tgacttctgc tatggtcgtc ggaacattgt tgcaggaggt   9780

tatgcacaag aagctgcttt atgctatcaa cgaaggccag gggtcgtttg atctttcata   9840

g                                                                   9841
```

<210> SEQ ID NO 50
<211> LENGTH: 1812
<212> TYPE: PRT
<213> ORGANISM: Triticum aestivum

<400> SEQUENCE: 50

```
Ala Arg Arg Ser Val Val Leu Ser Pro Pro Ala Pro Gln Pro Pro Met
1               5                   10                  15

Asp Phe Pro Ala Asp Gly Asn Asn Asn Pro Pro Pro Arg Arg Arg Gly
            20                  25                  30

Gly Arg Ala Ser Asn Ala Asp Lys Gly Lys Glu Gln Gln Glu Pro Ser
        35                  40                  45

Glu Ser Ser Arg Val Arg Glu Ala Glu Arg Met Leu Gly Leu Ser Phe
    50                  55                  60

Asp Gly Met Asp Asp Asp Asp Glu Gly His Gly Ala Phe Pro His Gly
65                  70                  75                  80

Leu Thr Ser Ala Ser Ser Ala Leu Gln Gly Leu Leu Arg Lys Leu Gly
                85                  90                  95

Ala Gly Leu Asp Asp Met Leu Pro Ser Ser Ala Leu Ser Ala Ala Ala
            100                 105                 110
```

-continued

```
Ala Ala Ala Ser Ser Ser Ser Met Ser Gly Pro Asn Gly Ala Arg Met
        115                 120                 125

Lys Ser Met Leu Ala Gly Leu Arg Ala Asp Gly Glu Glu Gly Arg Gln
    130                 135                 140

Val Glu Ala Leu Thr Gln Leu Cys Glu Met Leu Ser Ile Gly Thr Glu
145                 150                 155                 160

Asp Thr Leu Ala Gly Phe Ser Val Asp Ser Phe Val Pro Val Leu Val
                165                 170                 175

Gly Leu Leu Asn His Glu Ser Asn Pro Asp Ile Met Leu Leu Ala Ala
            180                 185                 190

Arg Ala Leu Thr His Leu Cys Asp Val Leu Pro Ser Ser Cys Ser Ala
        195                 200                 205

Val Val His Tyr Gly Ala Val Ala Cys Phe Cys Ala Arg Leu Leu Thr
    210                 215                 220

Ile Glu Tyr Met Asp Leu Ala Glu Gln Ser Leu Gln Ala Leu Lys Lys
225                 230                 235                 240

Ile Ser Gln Glu His Pro Thr Ala Cys Leu Arg Ala Gly Ala Leu Met
                245                 250                 255

Ala Val Leu Ser Tyr Leu Asp Phe Phe Ser Thr Gly Val Gln Arg Val
            260                 265                 270

Ala Leu Ser Thr Ala Ala Asn Met Cys Arg Lys Leu Pro Ser Asp Ala
        275                 280                 285

Ser Asp Phe Val Met Glu Ala Val Pro Leu Leu Thr Asn Leu Leu Asn
    290                 295                 300

Tyr His Asp Ala Lys Val Leu Glu His Ala Ser Val Cys Leu Thr Arg
305                 310                 315                 320

Ile Ala Glu Ser Phe Ala Ser Ser Pro Glu Lys Leu Asp Gln Leu Cys
                325                 330                 335

Asn Tyr Gly Leu Val Ala Gln Ala Ala Ser Leu Ile Ala Val Ser Asn
            340                 345                 350

Ser Ala Gly Gln Ala Ser Leu Ser Thr Leu Thr Tyr Thr Gly Val Ile
        355                 360                 365

Arg Val Leu Ser Ile Cys Ala Ser Gly Ser Pro Leu Ala Ala Lys Thr
    370                 375                 380

Leu Leu Leu His Gly Ile Ser Gly Thr Leu Lys Asp Ile Leu Ser Gly
385                 390                 395                 400

Ser Gly Leu Val Ala Gly Thr Thr Val Ser Pro Thr Arg Pro Ala Asp
                405                 410                 415

Gln Met Tyr Glu Ile Val Asn Leu Ala Asp Glu Leu Leu Pro Pro Leu
            420                 425                 430

Pro Ala Gly Thr Ile Ser Leu Pro Ala His Ser His Val Phe Met Lys
        435                 440                 445

Gly Ser Ser Val Lys Lys Pro Gly Ser Ser Lys Gln Gly Glu Ser Gly
    450                 455                 460

Ser Thr Asp Ile Lys Val Ser Gly Arg Glu Lys Leu Leu Arg Asp Gln
465                 470                 475                 480

Pro Glu Leu Leu Gln Gln Phe Gly Met Asp Ile Leu Pro Thr Met Thr
                485                 490                 495

Gln Val Tyr Gly Ser Ser Val Asn Gly Pro Ile Arg His Lys Cys Leu
            500                 505                 510

Ser Val Ile Ala Lys Leu Met Tyr Tyr Ser Ser Ala Glu Met Ile Glu
        515                 520                 525
```

-continued

```
Ile Leu His Gly Thr Thr Asn Ile Ser Ser Phe Leu Ala Gly Ile Leu
    530                 535                 540

Ala Trp Lys Asp Pro His Val Leu Val Pro Ala Leu Gln Ile Ala Glu
545                 550                 555                 560

Ile Leu Met Glu Lys Leu Pro Gly Thr Phe Ser Lys Met Phe Val Arg
                565                 570                 575

Glu Gly Val Val His Ala Val Glu Ser Leu Ile Cys Gln Glu Ile Ser
            580                 585                 590

Ser Pro Met Leu Phe Gln Val Pro Gln Gln Asp Lys Asp Ile Asp Ser
        595                 600                 605

Gly Thr Cys Thr Ser Ser Arg Ser Arg Arg Ser Arg Arg Arg Ser Ser
    610                 615                 620

Ala Gly Asn Thr Asp Asn Asn Ser Leu Asp Glu Pro Lys Gly Ser His
625                 630                 635                 640

Thr Thr Ile Ala Asn Ser Pro Pro Ser Thr Leu Glu Gly Pro Asn Thr
                645                 650                 655

Arg Ile Arg Ala Ser Val Ser Asp Arg Ala Lys Ser Phe Lys Asp Lys
            660                 665                 670

Tyr Phe Pro Ser Glu Pro Gly Ser Ser Asp Ile Ala Val Thr Asp Asp
        675                 680                 685

Leu Leu Lys Leu Arg Ala Leu Cys Ala Lys Leu Asn Ala Thr Ala Asp
    690                 695                 700

Thr Val Lys Thr Lys Ala Lys Gly Lys Ser Lys Ser Leu Gly Gly Asp
705                 710                 715                 720

Asp Phe Asp Ile Leu Cys Asn Val Glu Glu Gln Leu Asp Asp Ile Ile
                725                 730                 735

Asp Lys Ile Leu Ser Glu Leu Ser Asn Gly Asp Gly Val Ser Thr Phe
            740                 745                 750

Glu Phe Ile Gly Ser Gly Val Ile Ser Ala Leu Leu Asn Tyr Leu Ser
        755                 760                 765

Cys Gly Thr Phe Gly Lys Glu Lys Val Ser Glu Ala Asn Leu Pro Lys
    770                 775                 780

Leu Arg His Leu Ala Leu Arg Arg Tyr Lys Ala Phe Ile Tyr Val Ala
785                 790                 795                 800

Leu Pro Asn Asp Ala Val Gly Asn Gln Thr Pro Met Ala Phe Leu Val
                805                 810                 815

Gln Lys Leu Gln Ser Ala Leu Ser Ser Leu Glu Arg Phe Pro Val Val
            820                 825                 830

Ile Ser His Ser Gly Arg Thr Ser Ser Leu Gly Gly Ser Arg Pro Ser
        835                 840                 845

Ser Gly Leu Ser Ala Leu Ser Gln Pro Leu Lys Leu Arg Leu Cys Arg
    850                 855                 860

Ala Ala Gly Glu Lys Met Leu Lys Asp Tyr Ser Ser Asn Ile Val Leu
865                 870                 875                 880

Ile Asp Pro Leu Ala Ser Leu Ala Ala Val Glu Asp Phe Leu Trp Ser
                885                 890                 895

Arg Ile Gln Arg Ser Glu Ser Ile Ser Tyr Pro Ala Val Ser Ser Gly
            900                 905                 910

Lys Asn Ser Glu Ser Val Ala Pro Ser Ala Thr Ala Pro Val Ala Ser
        915                 920                 925

Ser Thr Gln Ser Val Arg Arg Pro Ser Thr Arg Ser Lys Ser Leu Ala
    930                 935                 940

Asp Ala Asp Ser Ala Thr Lys Lys Asp Ile Gln Glu Gly Ser Gly Asn
```

-continued

```
945                 950                 955                 960

Thr Ser Lys Gly Lys Gly Lys Ala Val Val Lys Ser Thr Ser Asp Glu
                965                 970                 975

Pro Lys Gly Pro His Thr Arg Thr Ala Ala Arg Arg Lys Val Ala Ser
            980                 985                 990

Gln Lys Asp Ala Glu Val Lys Pro  Pro His Gly His Ser  Ser Ser Glu
        995                 1000                1005

Asp Glu  Glu Leu Gly Ala Ser  Pro Phe Glu Ala Asp  Asp Ala Leu
    1010                 1015                 1020

Met Leu  Gly Asp Asp Asp Asp  Asp Val Ser Asp Asp  Glu Asp Asp
    1025                 1030                 1035

Asp His  Glu Val Leu Arg Gly  Ser Leu Pro Asp Cys  Val Pro Glu
    1040                 1045                 1050

Ser Val  His Asp Val Lys Leu  Ala Asp Ala Asp Gly  Ser Ser Ile
    1055                 1060                 1065

Ala Ser  Ile Ala Ser Asp Asn  Gln Thr Gln Pro Ser  Ser Gly Ser
    1070                 1075                 1080

Ser Ile  Lys His Thr Phe Ser  Ser Arg Gly Ala Gly  Ser Val Glu
    1085                 1090                 1095

Leu Arg  Asn Pro Ser Thr Leu  Gly Ser Arg Gly Ala  Met Ser Phe
    1100                 1105                 1110

Ala Ala  Ala Ala Met Ala Gly  Leu Ala Ser Val Gly  Ser Arg Gly
    1115                 1120                 1125

Ile Arg  Gly Ser Gln Asp Arg  Arg Gly Leu Pro Leu  Gly Thr Ser
    1130                 1135                 1140

Ala His  Glu His Ser Asn Lys  Leu Ile Phe Thr Ala  Gly Gly Lys
    1145                 1150                 1155

Gln Leu  Ser Lys His Leu Thr  Val Tyr Gln Ala Met  Gln Gln Gln
    1160                 1165                 1170

Val Val  His Asp Glu Asp Asp  Glu Glu Arg Leu Gly  Gly Ser Asp
    1175                 1180                 1185

Leu Pro  Asn Asp Gly Ser Arg  Leu Trp Ser Asp Val  Phe Thr Ile
    1190                 1195                 1200

Thr Tyr  Gln Lys Ala Asp Asn  Glu Val Asp Arg Glu  Ser Thr Arg
    1205                 1210                 1215

Gly Ser  Ser Leu Val Leu Lys  Ser Ser Lys Ser Glu  Leu Cys Arg
    1220                 1225                 1230

Ala Thr  Ser Gln Glu Gln Cys  Ile Ser Leu Leu Asp  Ser Ile Leu
    1235                 1240                 1245

Gln Gly  Glu Leu Pro Cys Asp  Ile Glu Lys Ser Thr  Gln Thr Tyr
    1250                 1255                 1260

Asn Ile  Leu Ala Leu Leu Arg  Val Leu Glu Gly Leu  Asn Gln Leu
    1265                 1270                 1275

Ser Pro  Arg Leu Arg Leu Gln  Ala Thr Cys Asp Asp  Phe Ile Glu
    1280                 1285                 1290

Gly Lys  Val Gly Thr Leu Asp  Gly Leu Tyr Gly Thr  Gly Ala Lys
    1295                 1300                 1305

Val Pro  Ser Glu Glu Phe Ile  Ser Ser Lys Leu Thr  Pro Lys Leu
    1310                 1315                 1320

Ala Arg  Gln Ile Gln Asp Val  Leu Ala Leu Cys Ser  Gly Ser Leu
    1325                 1330                 1335

Pro Ser  Trp Cys Tyr Gln Met  Thr Lys Ala Cys Pro  Phe Leu Phe
    1340                 1345                 1350
```

Pro Phe Glu Thr Arg Arg Gln His Phe Tyr Ser Thr Ala Phe Gly
1355 1360 1365

Leu Ser Arg Ala Leu Asn Arg Leu Gln Gln Gln Gln Gly Asp Asn
1370 1375 1380

Asn Ser Ser Ala Thr Glu Arg Glu Val Arg Ile Gly Arg Leu Gln
1385 1390 1395

Arg Gln Lys Val Arg Val Ser Arg Asn Arg Ile Leu Asp Ser Ala
1400 1405 1410

Ala Lys Val Met Glu Met Phe Ser Asn Gln Lys Ala Val Leu Glu
1415 1420 1425

Val Glu Tyr Phe Gly Glu Val Gly Thr Gly Leu Gly Pro Thr Leu
1430 1435 1440

Glu Phe Tyr Thr Leu Leu Ser His Asp Leu Gln Arg Val Gly Leu
1445 1450 1455

Gly Leu Trp Arg Ser Asp Ser Asp Ser Leu Glu Ala Lys Lys Val
1460 1465 1470

Asp Ser His Ser Pro Ala Asp Ser Arg Asn Leu Ile Gln Ala Pro
1475 1480 1485

Leu Gly Leu Phe Pro Arg Pro Trp Pro Pro Ser Thr Ala Ser Ser
1490 1495 1500

Glu Gly Ser Lys Phe Phe Lys Val Val Glu Tyr Phe Arg Leu Val
1505 1510 1515

Gly Arg Ile Met Ala Lys Ala Leu Gln Asp Gly Arg Leu Leu Asp
1520 1525 1530

Leu Pro Leu Ser Thr Ala Phe Tyr Lys Leu Leu Leu Gly Gln Glu
1535 1540 1545

Leu Asp Leu Tyr Asp Ile Leu Ser Phe Asp Ala Glu Leu Gly Lys
1550 1555 1560

Ile Leu Arg Glu Leu Gln Val Leu Val Glu Arg Lys Arg Phe Leu
1565 1570 1575

Glu Ser Cys Ser Asn His Ser Gln Gln Ile Glu Glu Leu Gly Phe
1580 1585 1590

His Gly Ala Pro Ile Glu Asp Leu Cys Leu Asp Phe Thr Leu Pro
1595 1600 1605

Gly Tyr Pro Asp Phe Val Leu Lys Glu Gly Glu Glu Asn Thr Val
1610 1615 1620

Val Cys Ile Tyr Asn Leu Glu Glu Tyr Ile Ser Leu Val Val Asp
1625 1630 1635

Ala Thr Leu Lys Thr Gly Ile Met Arg Gln Val Glu Ala Phe Lys
1640 1645 1650

Ala Gly Phe Asn Gln Val Phe Asp Ile Ser Ser Leu Gln Ile Phe
1655 1660 1665

Ser Pro Gln Glu Leu Asp Tyr Leu Ile Cys Gly Arg Arg Glu Leu
1670 1675 1680

Trp Glu Pro Glu Thr Leu Val Glu His Ile Lys Phe Asp His Gly
1685 1690 1695

Tyr Thr Ser Lys Ser Pro Ala Ile Val Asn Leu Leu Glu Ile Met
1700 1705 1710

Thr Glu Phe Thr Pro Glu Gln Gln His Ala Phe Cys Gln Phe Val
1715 1720 1725

Thr Gly Ala Pro Arg Leu Pro Pro Gly Gly Leu Ala Ser Leu Asn
1730 1735 1740

Pro Lys Leu Thr Ile Val Arg Lys His Ser Ser Thr Ala Ala Asn
    1745                1750                1755

Thr Ser Asn Ala Ala Gly Ala Ala Glu Ser Ala Asp Asp Asp Leu
    1760                1765                1770

Pro Ser Val Met Thr Cys Ala Asn Tyr Leu Lys Leu Pro Pro Tyr
    1775                1780                1785

Ser Thr Lys Glu Val Met His Lys Lys Leu Leu Tyr Ala Ile Asn
    1790                1795                1800

Glu Gly Gln Gly Ser Phe Asp Leu Ser
    1805                1810

<210> SEQ ID NO 51
<211> LENGTH: 1880
<212> TYPE: DNA
<213> ORGANISM: Brassica oleracea

<400> SEQUENCE: 51
acaaaggaag aaacccctcc acacgagtct ctcttattca gagagattcc gatcgcatct 60
caactgatcc agaaaccgat cggattaagc tcgctcgaaa ccctaatttg ctagcgagat 120
cgttaggagc tagagagaaa caaacctatt gatgaacgaa ttcgaaatca acgcaaaagg 180
ggctacgaga tcgaaatcga gagaggaagg aaggaggatc ttgatttctt tcgagattag 240
aaaaccctaa atcgagtaat gagagaagaa agggatgaaa agggcttttg cgcaaaatat 300
atagattcaa gcgaagcgaa tacgataccg ttttcctccg tccagctttt ccgacaagaa 360
ctgacacggg gatccccgct acgtgtgatt cgtttactcc attaagctta atacggtgtc 420
gttttacact ttatcatggg ctggacagat ggaaacaaaa taagcccaag atataaggct 480
gggcccaacc atcagccata gatatctgca agcttgcacg ggtttaagcc cccactatga 540
tggaggttcg ctttcttata ctttcaactc taccttctca ctacgatcca tggactatat 600
aacacattac tcattacaat tatatatatg atctatgcaa agatacaaat atattcttct 660
tttatgattg tagtaaggaa aaactatggt ttgtcgagaa aataattagt cattacaatt 720
atatatatga tctatgcaaa gatacaaata tattcttctt ttatgatggt ttgttaagaa 780
aataaatatg ataataaaat ctatctatct acttatttaa atgaatctac tcaatgaaat 840
gcaggtgatc tatgcaaaga tacaaattta ttcttctttt tttctttagc catcacacgc 900
taatttaaaa tctaaatgta gaaatttttg ttgtttgggt ttgagtttgt taatcggatg 960
aagacatata taaattattg tacatatttt ataaaaaaaa catgacagta tataatacat 1020
tagttctttt ataagtgtgc ccttgtttgg aacttacaga tttttttaat atatatatat 1080
atatatacat attaatttaa cccgaaaaac agaaattatg attcatttat aaatccaata 1140
tgaacatacc gagggaaaaa atcgtcggta cgtcgtcgga ataacgttat tccgacgaca 1200
taccgacgaa acaagtcctc ggaaataact cctcggaaat tcattttttc tcggaaatcc 1260
ctcagaaatt tccgaaggaa ttccgaggaa atgaatttcc gaggaaactc cgaggaccac 1320
cagttcgtcg gaaaggttct cggaatatat cgagggagaa cttcttcgga atatttcgat 1380
ggactttccg atggtccaat cctcggaagt ttcgatgaaa tgttcctcgg aattttcatc 1440
gggaatttcc gagaaacgga gccctcagaa aattccgagg aggaaggagt ccctcggtat 1500
attccgacga cttattctga ggaaatgttc gtcggaaatt tccgagggtt catttcctcg 1560
gaatttcaaa aaaaaaatta attttttttt aaaaatgaaa attttgaaat ttaaattcga 1620
aaatataaaa ttaaaattaa aattgtctcc aacaaagata tgcgatcatc cttgtccttc 1680

-continued

```
aactgagccg taaatatttc tggatcaaca aatggcggtg gtgcagaaaa agtaggaacc   1740

gaccgagagc gatgacccaa acgtcccttc ttctttggaa ccgactgaaa tagaaaatag   1800

ccaaatttaa ataatataaa aagacgataa aataaaaatc aagaaataaa tgaattgaac   1860

tttaaaaaaa aaaaacttac                                               1880
```

<210> SEQ ID NO 52
<211> LENGTH: 2100
<212> TYPE: DNA
<213> ORGANISM: Brassica rapa

<400> SEQUENCE: 52

```
aagcgtgcgg aggcgacctc aactgcccca tcttcttctt cttcctctcc tcctcctcct     60

ccttcctcag gtcccaccac tcgcagcaaa cgcgctcgcc tctcgtctcc ctcttcatct    120

tcagccgccg ctactgcacc ttcctcctcc acccgctctc gttcttctcg ctctaccacc    180

gctacagtcg ccgttactcc catggacaca tccaccgagt cttctggatt ccaccgcggc    240

ggaggacgag gtaacagggg aaacgataat actaactctg ataagggaaa agagaaggag    300

catgaggtta ggattaggga tagagaaaga gacagagcta ggcaacagct caacatggac    360

gctgcagctg ctgctgccgc cgccgctgac gaggacgacg acaatgatag tgaggatggc    420

aacgggggat tcatgcatcc caacatgagc tcagccagca gtgcgttaca agggttgctg    480

aggaagcttg gagctggact tgatgacttg cttccttctt caggtattgg ctcaggttcg    540

tcttctcact tgaatgggag gatgaagaag gtactcgctg gcttgcgctc tgaaggagaa    600

gagggaaagc aggtcgaggc tttgacgcag ctgtgcgaga tgttatctat tgggaccgaa    660

gactccctga gcaccttctc tgttgattcc ttcgtcccgg ttcttgttgg tctacttaac    720

catgagagca atccggatat tatgcttctt gctgccaggg ctcttactca tctgtgtgat    780

gttttgccgt cttcttgtgc tgctgttgtt cattacgggg ctgtttcgtg ctttgtcgcc    840

agattgttga caatagaata catggacttg gccgagcagg ttcgatttcc taacaattct    900

tgaatttttt tgctgaatat atattgtgga atgttttatg ctgcagtttc tacacgtaca    960

tatccaatat tttagtttac ttaggacgaa atttgaaatt tgattttatt cttcatgtga   1020

tttacaacag tctctgcaag ctctcaaaaa gatatctcag gaacacccaa cggcctgttt   1080

gcgtgctggt gctcttatgg cagtgctatc atatctggat ttcttctcca ccggtgtcca   1140

ggtgggtaat tttgtaactt ttctttaatg ctttccatac tcgtttatct aatgcacttt   1200

tttttttact ttttgtagcg tgtagcagta tctaccgctg caaatatgtg caagaagtta   1260

ccttctgatg catctgatta tgttatggaa gctgtaccgg tactgacaaa cctacttcag   1320

tatcatgatg cgaaggtaaa cgatcccttt ttttttgcta taatgtggta ttatctagtt   1380

ctgctcttgc cccagtttcc ttcatagtat gttcgtacgg tggcaggttt tggaatatgc   1440

ttctatctgt ttgactcgga ttgccgaagc atttgcatcg tcccctgata aattagatga   1500

attatgcaac catggcctgg tgactcaagc tgcgactctt atatccgcta gcaactcggg   1560

aggtgggcaa gcatctctcg gtgtttcaac atacacggta tgagttaatt cttttgtgtt   1620

ttctatattt cgttattcat aggatgacat tttcatcata ttttcacagg gattaatccg   1680

attactttcc acctgtgcga gcggttcacc tcttgggtgc aggacattac ttcttctcgg   1740

tattagtagc attcttaagg atattctgtc gggttccggt gtctctgcta atgcatctat   1800

atccccagca ctgagcaggc ctgcagatca ggtacggatt tactttttga catcacagac   1860

tttattttgt tcaattcctg ataaagtcta ttcagtaaaa agtgttttgt ttaggggaca   1920
```

caccttttaaa tagatcatca acataaattg tgtgttgagt gagatgctta ggggacacac 1980
cttcaaatag atcacttgca tttaaatgga tcacttgcat ttaggagttt tgtctattca 2040
gttcaatgat aatctttttt tttttgtaac actcagctca atgataatct atgtacatgt 2100

<210> SEQ ID NO 53
<211> LENGTH: 2060
<212> TYPE: DNA
<213> ORGANISM: Zea mays

<400> SEQUENCE: 53
acaaagggag cggagaaagg cagcggccgc ctcgcagcgg cgccggtggc gacgcggcta 60
tgaagggata ggcgaaagag gcgggaacat cggaggtgta gcgatcgggg agggggtgag 120
atctggcttg ggtggggttg ggaatttgag gaaggatggg gatggctgcg cctgcgcggt 180
ggtgacgcag gaagaggccg gaggttagag ggaggagctc gtgatttggg ggccggcttt 240
catgcggtat acgtgcttca cactgcgagg gtgcttcaca ctgcgagggt gttgctgggc 300
ttcgctaaac ccacggcttt tgctaggtca gcgtccgtga attgctacgg aaggctatcc 360
atcaatcagc tcagcaaaaa tgtctccatt caactgtaac gcatgcacga atcagctcga 420
tacaaaaatc ttacaacata tatgcacagg gtatatattt gtttaaatat ttttattttta 480 ttttaaaaaa tctaaaaaat atatcaggat aattctattt ccaaatttac tcgtttggca 540
cacctttatt gtgtggcctt gtatatcttg tattccccgt aacaaccttt ggccaacaga 600 ttttttttaat ttgttatcta tagatggata ggccctctca tgtaaaccaa gtatctaggt 660
caagtcaagg ttgttaggtg gttgttgcat ctaatataag tcttgtgcac tagtgtgagc 720
acgacggtgg agtctgtaaa tgaggagaat gttgatttaa atggcgaggc cgtcggcaag 780
caagatgtgg gccgctcagt tggcgatggg ttgcggcgca gtgcaagagc ccgccaacca 840
aatgtgcatg taacaggccc aaaactagat gtaatagagg caggtaggcg tataagagcg 900
tgggagggtg agcagtgttc ggcaagaaag aagaaacata tgtaatctac ctgctactct 960
gtgatccact agctactctg tctgagaatt ggagttcctc ggttgctcct atctcttttg 1020
atcctgtcta cttcttcatc ccctctgtgt gctaatattc tggtatcaga ttcatctcag 1080
aaagttcgtc gcccatctgg aactgtcggc aggatacaac tacttcacat gtttctagca 1140
acattagagt gccatggatc ctaacaccac acctcgacga gatggagaag aggttttcga 1200
ccatggagtc gcggctggaa cggaagctca tcgatcacac cgcgatgaag gatgagcgca 1260
ccagcgctct agaaggcgcc gctgaagagt tggcgttgtg gtgacccaag gtggaggcat 1320
acatggatga tatcaagttg gagctgcgtc ggctcaccaa gcactgtgat cgctcggtga 1380
tggaggtgtc ggcatcgaat tttggtcttc tcggcatgcc tgatccgccg tcgatacgct 1440
ctgcatcagg caaattcttc gacggcccat tcgggcaccg tgatgatcaa ttcatacggg 1500
atcatggttt taggtctatc aggaccctcc tccctgaccc gaccaagggt acgcatccaa 1560
tacatcctcc atcgaccaat attcgttttc atggtccttt ttatgatagc tacctacatc 1620
gttcacgttt tggggatcct gcatttcgta ctaacggcaa aatgcccaag ttgttgttct 1680
ccctgtttga tggagataat ccaaggcttt ggaacattcg atgtgagact tattccaaaa 1740
tgtactcagt tgagcccgac tcatgggtcg aaattgcctc catgcattta tcatcacagg 1800
ttgtgtgctg attagtcggt tgaacgcaag caccatcgct tgggttggcc attgctttat 1860
cgtctgttgc atgagtggtt tggtcgagat tagtaccaaa ccttgctttg ggaattattc 1920

```
tgtattcgcc aatcatcggg tgtagcagaa tatattgaat gttttccact ctagtttata   1980

agctctctac atatgtgtaa caccctgaat ttggggtata aaatttctgc tttaaatacc   2040

taccaaattt aggtgttacc                                               2060
```

<210> SEQ ID NO 54
<211> LENGTH: 2053
<212> TYPE: DNA
<213> ORGANISM: Oryza sativa

<400> SEQUENCE: 54

```
ttccagatct ttctctgaag cagcttttct gcgagtagca ttccgtgtat taggtccttt     60

tggttcttct gagtttggtt ttgcaacagc cttccccttt cccttggcag tgtttgtgct    120

ttcctcctga gaatccttct tagatgcacc actacttgca gcagatgatt ttgatcttgt    180

tgttggacgc ctgccagatg gagctggtgc agctgtggat gacgcaccag ctgcggtgcc    240

aggtatgcca gattcagaat tatttcctga tggaactgta ggcttcgaag cagcctcact    300

acgctgaact ctgggccaaa gaaactcttc aacagctgct agactcgcaa agggatcaat    360

aagcacaata tttgacgaat aatcccgaag tgatttttca ccctgacctc gacaaaggcg    420

caacttgaag ggctgagcta gagcactcaa acctgaagtc aaacgggagc ctccaatacc    480

tattctgctg gactggctga gcacaacagg gaagcgctcc aatgaacaca aagcactttg    540

cagtttttgg accaaaaaag ccataggagt ctcattcctt tcatggtcaa tagaaagggc    600

aacagatata aaagacttgt atcgcctaag cgcctgctga cgaagctttg gcaggtttgc    660

ctcagatacc ctctcctttc caaatgtccc acaggacaaa tagtcaagca atgctgcaac    720

aactccgctt ctaatgaact caaatgttga tacgccgtta gttttgctaa gctcagtaag    780

tatttgtgtt attatcagct caaattgtgc ctccacatca tgtgagatgt caaaatgagt    840

ggcacttaac gcttttgatt tccctttggc ttttgtcacg acattctcac ttgcagaatt    900

taactttgca cagagtgttc tcagtttaag aagatcgtca gtaactccaa gatctcttga    960

ttcatggtca gaagggaagt atttatcttt gaacgacttt gcacgatcac taactgcaaa   1020

tcgaagactg gtgttttgaa cttctgtaga gcatggtgtt gagctggcaa tcccaggatt   1080

ggaagtgttt gattcatcta atgagctgtt ttctgttggt gcagcagcac cacgccggcg   1140

ctggcgtcta gaatgcgagg gcatcacaga ttcattgtct ttatcatgtg gcaatacctg   1200

agaaggcacc atatcagagg attctggaca tataagcgac tccacagcat gaacgacacc   1260

ttccctcaca aacaacttag agaatgtctc aggaagtttt tccatcataa tttctgctat   1320

ttgaagagca ggaatcaaca cttgcggatc tttccacgca agaatgcctg ctaggaagct   1380

gcaaatggaa attatgtagc ttagcaagga tcagaaatga aggtgtgtct acttgcacaa   1440

tacaagaaat aaaagcttcc aatatacata tgccagtaaa tcattaggtt gtgccaagga   1500

gtgactggat catttcagca gggctgtagc acattagttt tccagttttc cagtgattga   1560

taagcattag ttttcagcag tcttattctt ccaacataaa tatgcttatc aataaaaact   1620

tccaacataa atacaagaaa agaataagac tgaagcagaa tcttgtatta gcacctggat   1680

atgtttgttg tgccaaggag ggactggatc atttcagcag agctgtagta cattagtttt   1740

ccaatgattg ataagcattt gtggcgtatc ggtgcattta cacttgagcc atacacctgt   1800

ccaagaacag atgccattaa gtacagaaac cctgacatat tcccaaaagt agtagtactc   1860

catctgcccc aaaatatagc aacatctggc tatgcacctg gacaaagttg ctctattttg   1920

gaaggtagta gttatgttca ctgacaagaa agaggatctg ggcacaaacc tgcgtcatta   1980
```

tgggtaataa gtccataccg aactgcttta gaagctcagg gtgctcacgt aatagtctct 2040
catgtcctga cct 2053

<210> SEQ ID NO 55
<211> LENGTH: 2359
<212> TYPE: DNA
<213> ORGANISM: Hordeum vulgare
<220> FEATURE:
<221> NAME/KEY: misc_feature
<222> LOCATION: (769)..(769)
<223> OTHER INFORMATION: n is a, c, g, or t

<400> SEQUENCE: 55
ccatagtttt tcctctagat cgtgtttctg cggagctcgg gcggagccct gctgagacaa 60
gatcatcacc aacctccgga gcgccgtcac gctgccggag aactcttcta cctctccgtc 120
tctcttgctg gatcaagaag gccgagatca tcgtcgagct gtacgtgtgc tgaacgcgga 180
ggtgccgtcc gttcggtact agatcgtggg actgatcgcg ggattgttcg cggggcggat 240
cgagggacgt gaggatgttc cactacatca accgcgatct ctaatcgttt ctgctgtacg 300
atctacaagg gtacgtagat cactcatccc ctctcgtaga tggacatcac catgataggt 360
cttcgtgcgc gtaggaaaat ttttgtttcc catgcgacgt ttcccaacag tagggatttt 420
ttttttaaat tactacgatc cccaacacca ccagccccgg agggccacat gggccgagcc 480
aaggtggaac cagccaccta ggtgggctgg ttcggccggc caaggcctga tggccaattg 540
ggctgggaac cctagggcaa aaggtggtcc acctcccaac ttgggaggca agccacctcc 600
accctggccg ccgccccctc ttgggtcgtt gcccctccca tctagggtgc gccgcccctc 660
ctagggtttc ctagggtggc cggccaaccc tccccctcct cctatatata ccaagggttt 720
tggggctgca acacacaagt tttcttcctt ccttggcaca cccctgctng taccacccag 780
ctccaccgtc accacttcgt cgtgctgccg gagctctccc tcaacttctc ctctctcctt 840
gctggattaa ggtgaaggag acatcaccgg gctgcacgtg tgttgaatgc ggagggaccg 900
ttgttcggcg cttagatcaa aatcttccgc gatctgaatc gctgcgagta cgactccatc 960
acacgtgttc atagtaatgc ttccgcttag cgatctaccc cttgctcgtt gctagcatct 1020
cctagaagat cttggtgtga cgtaggtaat ttttgaatta ttactacgat cccaatagga 1080
acaacaaggt tgatttagag gcccttcgtg attgatgccc cctccgacaa ggctccagat 1140
gggattacga cggaagagag atttgctgcg gcaaaaaaag tgtttcaggt ggctcaccgg 1200
tgttttctca atatatagga tttatagaag tagagttagt tcaggagtgt cggtaggtgg 1260
tcccaatcca tcaggacgcg gtcactccct gggcacgtcc tgttggcttg gcaccaccca 1320
tgtggcgtct ggtctcctcc aaagctttca tttcttattt ttgtccagaa aaaatcgtta 1380
aaaacttccg ttgcatttgg acttcgtttg atactgattt tctgaaaagc caaaaaaaca 1440
cagaaaacaa caactacatg tccagaaggt gatcaaggct aatgtggacg gtgctctttg 1500
aaaagaccag ggctcgggag ttctggtctt gttcttcgga atagccatgg cggattcatt 1560
gcacatgcat gccatttttt cccgtagctg ccaatgttga ggtgacagag ctccttgcgt 1620
gtatacgagc cattgttctt gcacaagaac tacatgccca gaaggtgatc gtagagacgg 1680
gctcgcaagt ggtggcaaga aaagtagtat ctattcaaaa agatctctga gctaatgggt 1740
aactaggtga ggagatcaaa gtgttgcttg gagcttttga tgagtttcgc gttgtttggg 1800
ggcgacggtc catgaataaa gtcacgtata ttttagttag aaaaggttgt tgcaactcct 1860
tatgtaaaac ttggctccat gttccatcga agtgtattcg ctcggaggta ggagacgagg 1920
ggccgtgaac tttgaaattt gaataaattg acaacatttt ctaaaataca acaaaaacat 1980
ttacacgttg aattattttc ttacttttat tttatttaaa atatcaaaaa tatttatcat 2040
acactatctt ttaataggct catccaaccg gcaagattga cacccttata agattgttgg 2100
aggtatacaa gggttttatt tgtattacta ttacaagaca tccaactact cgacacacct 2160
gtatgttcat agacttacac attgatttct cacttacgaa tgatgtctat cactatcact 2220
tgatacaagc cgacatacga aaagagtgga gacgaccaat tcagatgatt ttggtgcgac 2280
ttcacttgtt atcaaggagt ttccttgttg gtttttggtt tatgtgttcc ttaccttaac 2340
tgtgctatct tactcgcgg 2359

<210> SEQ ID NO 56
<211> LENGTH: 2047
<212> TYPE: DNA
<213> ORGANISM: Brassica napus
<220> FEATURE:
<221> NAME/KEY: misc_feature
<222> LOCATION: (850)..(869)
<223> OTHER INFORMATION: n is a, c, g, or t

<400> SEQUENCE: 56
acaaaggaag aaaccccccct acacgagtct ctcttattca gagagattcc gatcgcatct 60
caactgatcc agaaaccgat cggattaagc tcgctcgaaa ccctaatttg ctagcgagat 120
cgatcggagc tagagagaaa caaacctatt gacgaacgaa ttcgaaatca acaagaaaga 180
gatcgaaatc gagagaggga ggatcttgat ttctttcgag attagaaaac cctaaatcga 240
gtaatgagag aagaaaggga tgaaaagggc ttttgcgcaa gatatatata ttcaagcgaa 300
ccgaatacga taccgttttc ctccgtccag cttttcggac aactgacacg gggatccccg 360
ctacgtgtga ttcgtttact ccattaagct ttatacggcg tcgttttaca ctttatcatg 420
ggctggacag atggaaacaa aataagccca tgatataaga ctgggcccaa ccatcagcta 480
tgcacgggtt taagccccca ctatggaggg gttcgctttc ttatactttc aagtttcaac 540
tctaccttct cactactatc catggtatat atcaaaacac attacaatta gtcatataca 600
aaaacaaaat acaaatatat tcttctttta tgattgtagt aaggaaaaac tatggtttgt 660
caagaaaata aatatgataa taaaatctat ctatctactt atttaatgaa tctactcaat 720
gaaatgcatg tgatctatgc aaagatacaa atttattctt cttttttttct ttagccatca 780 cacgctaatt taaaaactaa atgtagaaat tttggttgtt tgggtttgag tttgttaatt 840
ggatgaagan nnnnnnnnnn nnnnnnnnnt tttgcctaat atgtcttgca aaataagcaa 900
agatatttat tctcaactag ggtattgtcc ctctactata tattctaccc gagtacaaac 960
ccattctaca cattctttta ccatttacgc tgatgaaaca ttacaaatgg ttttagctga 1020
tgaaactgtt agttctataa tatttgtatt tttttttga attttataaa gtagactttg 1080
agcaaaatca tcttttccta tttttgaatg tttttttgta acttagtttc attattattt 1140
ttggtttgtc taaataatgt atttgttttc aaaaatttca ataaaatatt tgaactttat 1200
attcaacttt taaataaaat atttataatt taatttaata aaaccccaaa tatacttaaa 1260
cctccgatac tttactattt aatttaccaa ataaactaaa taaaaataca ataaaagaaa 1320
aacacaatct catagtttaa aaatgatggc taatcatatt gaacaagaca caccgaaatc 1380
aaacctgaaa aacatatgaa tctataacat aataagtata aacaattaaa tttatcaaat 1440
tttcaaaagt taaaaatata tgattatgaa aaacaaaatc atcctttttt gaacaagaag 1500
aaagccccca cgttctgtct tggatggtat taccaatatt tcacattctt tatctaatgg 1560
aaacgaagaa acaacaacaa acatacatcg tgatatcaat caagaggata atgattttgt 1620
taaaggatga tgattttatt catagccttt gaataaatta atttccgtaa aagttatacc 1680
ttatttatct atttcatata tcatactaac tcataattct ttatttcatc atattttaat 1740
ggttttcaat agaaatgtgg tccaaattaa attaccttat cacagtatga tcaattttgt 1800
tgccaccgtg tgatcaaatt atgttacagc aatatttgta ttatgtgatg tatttttgtc 1860
attatttgta ttaaaatttt gatatattat ataatggtgt aaaaaatttt aattacatta 1920
agtaaacaga aaaaaaacac ccgcccggtc gggcgggacc agatctagtt actattcatt 1980
tataagtcca atttgaacaa aagttcccaa gacaatttat tacattctag gtagatagtt 2040
tctaatg 2047

<210> SEQ ID NO 57
<211> LENGTH: 2041
<212> TYPE: DNA
<213> ORGANISM: Brassica napus

<400> SEQUENCE: 57
acaaaggaag aaacccctcc acacgagtct ctcttattca gagagattcc gatcgcatct 60
caactgatcc agaaaccgat cggattaagc tcgctcgaaa ccctaatttg ctagcgagat 120
cgataggagc tagagagaaa caaagctatt gatgaacgaa ttcgaaatca acgcaaaagg 180
ggctacgaga tcgaaatcga gagaggaagg aaggaggatc ttgatttctt tcgagattag 240
aaaaccctaa atcgagtaat gagagaagaa agggatgaaa agggcttttg cgcaaaatat 300
atagattcaa gcgaagcgaa tacgataccg ttttcctccg tccagctttt cggacaagac 360
tgacacgggg atccccgcta cgtgtgattc gtttactcca ttaagcttaa tacggtgtcg 420
ttttacactt tatcatgggc tggacagatg gaaacaaaat aagcccaaga tataaggctg 480
ggcccaacca tcagccatag atatctgcaa gcttgcacgg gtttaagccc ccactatgat 540
ggaggttcgc tttcttatac tttcaactct accttctcac tacgatccat ggactatata 600
acacattagt cattacaatt atatatatga tctatgcaaa gatacaaata tattcttctt 660
ttatgattgt agtaaggaaa aactatggtt tgttaagaaa ataaatatga taataaaatc 720
tatttatcta cttatttaaa tgaatctact caacgaaatg caggtgatct atgcaaagat 780
acaaatttat tcttcttttt ttctttagcc atcacacgct aatttaaaat ctaaatgtag 840
aaattttggt tgtttgggtt tgagtttgtt aatcggatga agacatatat aaattattgt 900
acatatttta taaaaaaaac atgacagtat ataatacatt agtttctttt atacgtgtgc 960
ccttgtttgg aacttacaga tttttttaat atatatatat acatattaat ttaacccgaa 1020
aaacagaaat tacgattcat ttataaatcc aatttgaaca taccaaaagg gaaaaaatcg 1080
tcggtacgtc gtcggaataa cgttattccg acgacgtacc gacgattttt tccctttttgg 1140 tatgttcaaa ttggatttat aaatgaatcg taatttctgt ttttcgggtt aaattaatat 1200
gtatatatat atattaaaaa aatctgtaag ttccaaacaa gggcacacgt ataaaagaaa 1260
ctaatgtatt atatactgtc atgttttttt tataaaatat gtacaataat ttatatatgt 1320
cttcatccga ttaacaaact caaacccaaa caaccaaaat ttctacattt agattttaaa 1380
ttagcgtgtg atggctaaag aaaaaaagaa gaataaattt gtatctttgc atagatcacc 1440
tgcatttcgt tgagtagatt catttaaata agtagataaa tagattttat tatcatattt 1500
attttcttaa caaaccatag tttttcctta ctacaatcat aaaagaagaa tatatttgta 1560
tctttgcata gatcatatat ataattgtaa tgactaatgt gttatatagt ccatggatcg 1620
tagtgagaag gtagagttga aagtataaga aagcgaacct ccatcatagt gggggcttaa 1680
acccgtgcaa gcttgcagat atctatggct gatggttggg cccagcctta tatcttgggc 1740
ttattttgtt tccatctgtc cagcccatga taaagtgtaa aacgacaccg tattaagctt 1800
aatggagtaa acgaatcaca cgtagcgggg atccccgtgt cagttcttgt ccgaaaagct 1860
ggacggagga aaacggtatc gtattcgctt cgcttgaatc tatatatttt gcgcaaaagc 1920
ccttttcatc cctttcttct ctcattactc gatttagggt tttctaatct cgaaagaaat 1980
caagatcctc cttccttcct ctctcgattt cgatctcgta gccccttttg cgttgatttc 2040
g 2041

<210> SEQ ID NO 58
<211> LENGTH: 3240
<212> TYPE: DNA
<213> ORGANISM: Triticum aestivum

<400> SEQUENCE: 58
tgttgccgcc gtcggccggg aagtccatcg ggggctgcgg ggcgggcggg gagaggacga 60
cggagcggcg ggcgcgggtg ggcgcggggt gtgcgggggt gggggtcggg ctagggttag 120
ggttggggcg ggcgcgcttg gaggagcggg ccgaggagga ggaggtcggg gtggtggagg 180
aagacgacga ggcttccgcc cgcttgcggc tgcgcgtttc catacaaggg ggaggagggg 240
gaggggggcg gcggccgcct cgtcggaggc ggtggctgcg gcgcggcggc taggaggcgg 300
tgggcgtcgg gggaggaggc atcgatgggc gatcggagga gatctgggtg gggattttgt 360
tgattgattt ggggagggga gcagggaggc ggtgcgggtg gggactgcgg ctgcgggggc 420
ggcgacgcga gataagagag agagagagag acccgaggcc tttgccggat ggaacgcgtg 480
agcgtgagga gggccgcttg ggcttttgcg gggttgttcg gctctgccca cgagcaccgc 540
accgcaccgc accgccctcc ctcgacctaa gaaaaagaag aagaaaacaa aatctcctca 600
gaaaggtctc tcaaaagata aaatactccc tccgagtaat tccgaataaa gaaagtattt 660
gtttaaatac atccgtatct agattatcta gacatgtttt ggcattagat gcattcatat 720
ctagaaaaaa ttatgacatg taggagtaat ttggaacgga ggtaataaca taaaccgaaa 780
attcaatgta ctgagttaac cgaaattgtt tgtctctctc ttctaaagaa agaaaaatgc 840
tatcgaggga cgtggatagc acaaggtaag ataaggaaca cgcaagccgg aaaaatagca 900
aggaaactcc ttggtaagag ctgaagtcgc atcaaaatcg tctgaattgg tcgtcctcat 960
tcttcccttg tgcgaggtaa atttgttttg gcattgatac tctggccatg catgtctaac 1020
tctgacaatg tatatctaga gatttgtggc gaggttttat ctgtgtgtat ctagtagatg 1080
aatccattca tgattctacc aaaggaaagc tgtgctcgtg atctccaacc tgaggcgtcg 1140
ccggagcttt cggccaaggg agaacatatg aaagtgcatt gtttcttcga tggtattctc 1200
gtgttgatga caatgggtgc tagtgaggac tagtgtagat gacatgtgct aaaggtgtaa 1260
tagttggggc tccctcgtat gttggtttgt agcaagtgag taaatgtctt cccttcatga 1320
taaacccaac aatctataga gatgcaatag ttggatgtct ttaacatcaa taaaaccctc 1380
ttatgccctc aacaacacaa taaggatgtc aatcattgct agtcttgcta gttgaacaag 1440
cctattaaaa gataatgtgt gataaatatt tttggtattt tcagaataaa atgaacatga 1500
aaataaaaca atgtgtaaat attttttaac acggtacaga gcatacgctt atacatatgc 1560

-continued atatacaccc aaccttatga acgcacgcac gcatatcctg tccatatgag cacatccgag 1620
agaccaagct gacacattat cttagattga cgaagtgcca cagacgcctt catagttgac 1680
tgaaacgtct ctcccactaa acgcacatca ccgaaaagtg aaataaattc agaaaatgcg 1740
atcaccaatg tcaagtctag aacttgaact ctggtggtag aggataccac tgacatccta 1800
accatccaac catagctccg ttcacatgta taaatgttgt tggattgtga ttctaatgat 1860
ggaaactgaa ctgaggttca cgggttcacc aagtgtaact ctcaacgcat aaaactgtga 1920
atgttaactt tctcatgtgt aaaagtgcaa tggaaaactc atgttcatgt cagacaagta 1980
aagtcatgag aagatatata gacagtacat ccataacacc aaagatcgag accttcgcat 2040
gcatcttcag ctaaataact ctttcataga ccgacacact ccttatcact tgcacgttaa 2100
ctataaacac gggtaattat atttagcaca atgacatact gttaagacta gaggattatt 2160
tatcctctac taacccttaa tccttagtgg ccggcaacaa ttcttgcagg cctttttcat 2220 ttttttgtc actatggaag attatctaca agatttgaac ctatctaatg cataccactt 2280
ccattattgg ctaccgttct aaactggaaa agtgtagtca aataactaga aaaaaatatg 2340
catctatata cctctccatc tccttcctcg tttttcacct ccagccacca tatctggatt 2400
gtacgctcca gatccaacgg ctccaagcac cccagttcat ctccactcct gcagcccatt 2460
agccctcaca taagtatgtg ttgatttgca gataacacgg aatcacaccg tgaaagaccc 2520
gccaaacact gcactataaa aaagataaaa acacactcca ttatctcccc cacccgccaa 2580
accaaatagt cccccagttt caatataaga tgtatttgtt ttctgatgaa aagtcaaatt 2640
tctttaactt tgatgaagtt caaaaatgga cattcacaat gctaaacaaa taaatagaaa 2700
aaacatttca tggtgaatcc aacgatacca aattgattac aagtaggtca aataatgggt 2760
ttgacttttc aaaaaactaa tacaccttac attttaaaac tgaaggagta acaaaattat 2820
gaaaaaaatc aacaacacca acaacacagc aaagcgcgac caacccttct agtatgttgt 2880
ctaactaaga gctatacttg agttgagcta aactagatta tttatattct atcttttgaa 2940
caaaaatgca ggaatggaac caaacacaga atgaggttcc actatagttg accatttcgt 3000
ttaggaacga agtggaatgg aatgtcatgg ttccatggat aacctccgcc cccttagccg 3060
caatcccccc ttcgacgtct cttttcattt ctccgccgag cgattcacgt cattttccct 3120
ctctcgtaga tccatggcag gaggtgctca aggacgtggg ggcgcggcgg tgaaagcaca 3180
agtgctccct gggtggtttt ggtaattaat gtcaacatat cttttgttgg actaatactt 3240

<210> SEQ ID NO 59
<211> LENGTH: 2587
<212> TYPE: DNA
<213> ORGANISM: Triticum aestivum

<400> SEQUENCE: 59
ggagaccttt gatccgctat ggtccaatgt ttatccggga acagtagagg atccaaaatc 60
tgaactacat ctacaactgc aatgacgtca aggctttgtg gatgcttcga atgaaaagag 120
caccatttgc caggcttgtc gagaccttca ggagcagggg gttgcacaag ataacatcaa 180
caccagtgtg gaagagcaag tggccatgtt cctccatgtt gttggccata accaaaggtt 240
cagggtcatt cacaacacgt tcaggagatc aaatggagac cacctctagg tacttcaagc 300
aggtgctttt tgctgttggg gagcttagag gaaagatgat caggagacca tctgtccgga 360
ctccacccaa gattcgcgga agcccaagat ggtatccata tttcaaggtg agcattgata 420

-continued

```
atatacactt ttcatggctt gatatgcttg tattgttcaa gttgagcact aacacaggct    480

tgtgatacca ttttcaggat tgcattgggg caatagatgg tactcatgtc actgccagag    540

ttcttaggtc acagtctgca gcatacaagg ggaggaagca ctacacaagc cagaatgtgc    600

ttgttgttgt tgactttgat atgaagttca catatgtgct ggctagctgg gaggggtcag    660

cacatgatgc taacattctc aatgacaaca tgagtcgacc tgatgggatc aacatccccg    720

acggtaggtt ctaccttgaa gatgttggct atgcatgtcc gggtgttgtt tcacccttca    780

ggaaaaccaa gtaccatctc aacgagtttt ctggtaggaa ctatcctagg acaacacatg    840

cgttgtttaa tctcagacac tccaacctta gtgtaactgt tgagagggca tttggagctc    900

tgaagaatag atttaaaatc ttggatcaga agccattcca cccatactcc actcaggtta    960

agcttgttct tgcttgttgc attctgcata actggatcct ccagtggggc tttgatgaac   1020

acatgccaga ggaggaagag gtcaagcctg acgatgttgt tagctccggc catggtgtgg   1080

aggcatttga caatgacgct tggaagaaca aaaggttgga gtgggcagat gcaatgtggc   1140

ttaacagagg tcagtgccag atttgaagaa gaggaagacg aagaagcagc agcacaagaa   1200

gaagcaaaag cagaagcaga agcagaagaa gaggaagatg aagatctggt agcagcaaca   1260

ccaatgaact atcccctatt tagccaatgg cttaataatt tgttctgtca tttgatagta   1320

gttaggatga attgtcattt gtttaactag ctgacactat atgttcagat tatgtgtggt   1380

aagctcatca ctagttagaa atggtgacaa caccttatac gggttgcaac caaacatcat   1440

gtcatatgtg cgtccaatgc aatgcgggca accaaacacc gggccaaaaa tggttgtctc   1500

atgcaactaa ggtacatgca ggcaaccaaa ctatgtgcat ctggagtctt tttgtctgca   1560

tcccctcaaa ccggctcact agagccaggc tcaccgggcc agactcaatt gacaatgtaa   1620

ccaaacacgc ccttatatgt tctcccttgg cccgaagctc cgacggcgtc tcatgccgga   1680

aaccacgagc accgctttcc atcggcagaa tcatgaatgg gttctctact ggatacacac   1740

ggatgaagcc tcgccataaa tctccagata tacatacaca cggatgaagc ctcgccacaa   1800

atttcggtta actcagtata ttgaattttc atttttatga tattacctcc gtcccaaact   1860

gcatcttaaa tttgtccgga tacagatata tctaacacta aaacatgtct agatacggga   1920

cattcgtata tatctacaca aatagtagtt tcttggtccg gaattgctcg gagggagtat   1980

tttatctttt gagagacttt tcttgagaag atttttgttt tcttcttctt tttcttaggt   2040

cgagggaggg cggtgcgggg cggtgctctg ctcgtgggca gagagccgaa caaccccgca   2100

aaagcccaag cggccctcct cgcgctcacg cgtcccatcc ggcctctctc tctctctctt   2160

atctcgcgtc gccgccccccg cagccgcagt ccccaccgcc tcccctgccc cccaaatcaa   2220

tcaacaaaat ccccacccag atctccgccg atcgcccatc gatgccccct cccccgccgc   2280

ccaccgcctc ctagccgccg cgccgcaccc accgcctccg acgaggcggc cgccgcaccc   2340

accgcctccg acgaggcggc cgccgccccc tccccctcct cccccgtgta tggaaacgcg   2400

cagccgcaag cgggcggaag cctcgtcgtc ttcctccacc accccgacct cctcctcctc   2460

ggcccgctcc tccaagcgcg cccgccccaa ccctaaccct agccccgccc ccgccgcgcc   2520

cgcacacccc gcgccccgcg cccgccgctc cgtcctcctc tccccgcccg ccccgcagcc   2580

cccgatg                                                             2587
```

<210> SEQ ID NO 60
<211> LENGTH: 2458
<212> TYPE: DNA
<213> ORGANISM: Triticum aestivum

<400> SEQUENCE: 60
tacaaaatct gaggcgtctg aaggaagctt cctacacata ttggcagctg tagataacgc 60
aactctctgt atacattcca ccaaaaaaac aactgtgagt agtaataaaa atgtagtaca 120
gtatgtgtac aacaaaaaga tagtgatatg acaaattagt atgtcccaat ttctaaatgg 180
tgcaaaaaaa taacgtaagt attgagaatg ttatgtctaa atgctggaaa aacatagaag 240
tatttagaaa aattacttga acaccggtgg agaagaagtc aagatatgat agcactgcca 300
ttagcgcgcc agccctcaag caggcagttg gatgctcctg ggatatcttc ttgagtgctt 360
gtaaggacta aaatacacag agaaggcata agaaaatatt agtaacacat caagatctag 420
caatgataga ttcttcctgc agcatatttt aaacgacaaa acaaaacaag gaaagtggct 480
aatctaaagt gccacagaag caatacaata tcaaaatcta agaaagtaat tcaaatgtcc 540
taggtgctaa acctaatagt tgtagatact actcaataac atattgtgga gcagcaaact 600
agattcaatt gcacaaaggg ttacaaagga attcaaacag atgatatcaa gttaattcac 660
attgttttga attagaccca agagaagtag aagtataata tccatataag atgggaaggc 720
agagaagaaa cacagccaga aaccggttac atgaatctta gcatctgatt tccaacccac 780
ttcttagtat ttcagatgga tcattacagt agcacataca caggcgtgaa atcagaccct 840
gagctagaaa tatttcagat gaaaaacatg ttcaaatagc tagcttagtc atgcacaaat 900
aggtgatttg gcacacagca aaaccgtgtt aaatggcacc caggtgctcg gcaggaacac 960
caccatgatc aggcctagaa agtcttctaa ggggcagatg aggtccttag atggatttga 1020
gttcgctggt gaggatttgg agcccgagtc ctccggcggc accagaggaa gggaagacat 1080
ctccatgccc acaagctccc taaggcttta aggcatcacg tgcattggga catgctttca 1140
tctaaccatt ttttctttca tgtgtctcct atcctcagct tcttcctccc agagcgacca 1200
gtgactagac cctaggcagg ccccaaggct gctaagggat caccttctgc ctaactctct 1260
agatatttct tgtaacatca ttaaatggtg agctactgaa ataggcaata tttggtactt 1320
gccaagtgaa caatcaaaca agctatttca aatatatagt tccttgaaaa ctgattatac 1380
acaatatttc aaacttaata ttaactgagg ctaacttaca actaccacat ctgtacaggt 1440
caccgaaact tgagtcagaa acataacata gaaagcatac agtggaactt ctcgagtatg 1500
ggcacaacgc caacaaaaat catgttctta accttctcat ccatatttgt tttagcacta 1560
aaatgggaaa aaaacacagc tacacaaaag gcaaactact catgagcaag tccaaatact 1620
ataaatgatc tgcaacacta aaaggaaact catgtaatgt aggttaaggc tctatggaca 1680
gcataatcat gcataataca gtacacaaga atggttcact aagcattgat ctggatcagg 1740
caacatgata aagaagcagc atgtactata aaccaaacaa gcgatgcagc agaacagtgc 1800
tcacctgctc cgcaaggtcc atatattcaa tggtgagaag ccgggcgcag aagcatgcca 1860
cggcgccata gtgcacaacg gcagagcagg acgacggcag cacgtcacag aggtgggtca 1920
gggcccgcgc agcgagcagc atgatgtcag ggttgctctc gtggttgagc agcccgacca 1980
gaacaggcac gaatgagtcc accgagaacc cggcgagggt gtcctcggtg ccgatggaca 2040
gcatctcaca gagctgggtc agcgcctcca cctggcgccc ctcctccccg tcggcacgga 2100
gacccgcgag catgctcttc atccgcgcgc cgttcggccc agacatggac gacgaggagg 2160
cagccgcggc ggcggcggag agggcggacg acggcagcat gtcgtccagg ccggcgccga 2220
gcttcctgag cagcccctgc agggcgctgc tggcggaggt gaggccgtgg gggaaggccc 2280

```
cgtggccctc gtcgtcgtcg tccatgccgt cgaagctgag gcccagcatc cgctcggcct   2340

cgcgcacgcg ggagctctcc gagggctcct gctgctcctt gcccttgtcg gcgttggagg   2400

cgcggccgcc gcggcggcgg ggcgggggt tgttgccgcc gtcggccggg aagtccat     2458


<210> SEQ ID NO 61
<211> LENGTH: 284
<212> TYPE: DNA
<213> ORGANISM: Brassica napus

<400> SEQUENCE: 61

tatttccgca tgttgctaaa ccgggagaat atatcaaatg caactgtcat gatccaacca     60

tcgctgacat catatacatt cagttcacca cctcagccag ctttgcggct tctattgcag    120

ccgacagaat tcttctgtta gatgcatatt tcagtgttgt tgtcttccat ggaatgacaa    180

tagcacaatg gcgaaacatg ggttatcatc atcaggctga acatgaggca tttgatagtc    240

cgggagcgtt tccctgtccc gagattagtt gtgtgtgatc aaca                     284


<210> SEQ ID NO 62
<211> LENGTH: 329
<212> TYPE: DNA
<213> ORGANISM: Brassica napus

<400> SEQUENCE: 62

tatttccgca tgttgctaaa ccgggagaat atatcaaatg caactgtcat gattcaacca     60

tcgctgacat catatacatt cagttcacca cctcagccag ctttgctgga cgtggcttcc    120

attgcagccg acagaattct cctgttagat gcatatttca gtgttgttgt cttccatgga    180

atgacaatwg cacaatggcg aaacatgggt tatcatcatc aggctgaaca tgaggcattt    240

gctcagctat tgcaagctcc tcaagaagat tcccagatga tagtccggga gcgtttcccw    300

gtcccgagat tagttgtgtg tgatcaaca                                      329


<210> SEQ ID NO 63
<211> LENGTH: 24
<212> TYPE: DNA
<213> ORGANISM: Artificial Sequence
<220> FEATURE:
<223> OTHER INFORMATION: UPL3 fwd primer

<400> SEQUENCE: 63

gtagctctca tcaacctcaa atgc                                            24


<210> SEQ ID NO 64
<211> LENGTH: 22
<212> TYPE: DNA
<213> ORGANISM: Artificial Sequence
<220> FEATURE:
<223> OTHER INFORMATION: UPL3 rev primer

<400> SEQUENCE: 64

agggagctta aggtagttgg gg                                              22


<210> SEQ ID NO 65
<211> LENGTH: 24
<212> TYPE: DNA
<213> ORGANISM: Artificial Sequence
<220> FEATURE:
<223> OTHER INFORMATION: UPL3 (2) fwd primer

<400> SEQUENCE: 65

gtagctctca tcaacctcaa atgc                                            24
```

-continued

<210> SEQ ID NO 66
<211> LENGTH: 22
<212> TYPE: DNA
<213> ORGANISM: Artificial Sequence
<220> FEATURE:
<223> OTHER INFORMATION: UPL3 (2) rev primer

<400> SEQUENCE: 66
agggagctta aggtagttgg gg 22

<210> SEQ ID NO 67
<211> LENGTH: 29
<212> TYPE: DNA
<213> ORGANISM: Artificial Sequence
<220> FEATURE:
<223> OTHER INFORMATION: C03 genome promoter variant fwd primer

<400> SEQUENCE: 67
tataggcctg gacgtttggg tcatcgctc 29

<210> SEQ ID NO 68
<211> LENGTH: 31
<212> TYPE: DNA
<213> ORGANISM: Artificial Sequence
<220> FEATURE:
<223> OTHER INFORMATION: C03 genome promoter variant rev primer

<400> SEQUENCE: 68
tatctcgaga caaaggaaga aacccctcca c 31

<210> SEQ ID NO 69
<211> LENGTH: 43
<212> TYPE: DNA
<213> ORGANISM: Artificial Sequence
<220> FEATURE:
<223> OTHER INFORMATION: UPL3 (3) fwd primer

<400> SEQUENCE: 69
caccatatgg cgcgcctatc tcgagatgga aactcggagc cgc 43

<210> SEQ ID NO 70
<211> LENGTH: 34
<212> TYPE: DNA
<213> ORGANISM: Artificial Sequence
<220> FEATURE:
<223> OTHER INFORMATION: UPL3 (3) rev primer

<400> SEQUENCE: 70
tatggcgcgc cggcagagat tcttcaaatc agaa 34

<210> SEQ ID NO 71
<211> LENGTH: 21
<212> TYPE: DNA
<213> ORGANISM: Artificial Sequence
<220> FEATURE:
<223> OTHER INFORMATION: UPL3 (4) fwd primer

<400> SEQUENCE: 71
tagggacttg catggacgta c 21

<210> SEQ ID NO 72
<211> LENGTH: 21
<212> TYPE: DNA
<213> ORGANISM: Artificial Sequence
<220> FEATURE:

<223> OTHER INFORMATION: UPL3 (4) rev primer

<400> SEQUENCE: 72
gatatgtcag ctgttgaggg c 21

<210> SEQ ID NO 73
<211> LENGTH: 19
<212> TYPE: DNA
<213> ORGANISM: Artificial Sequence
<220> FEATURE:
<223> OTHER INFORMATION: T-DNA insertion sequence rev primer

<400> SEQUENCE: 73
attttgccga tttcggaac 19

<210> SEQ ID NO 74
<211> LENGTH: 21
<212> TYPE: DNA
<213> ORGANISM: Artificial Sequence
<220> FEATURE:
<223> OTHER INFORMATION: EIF4a fwd primer

<400> SEQUENCE: 74
ctggaggttt tgaggctggt a 21

<210> SEQ ID NO 75
<211> LENGTH: 21
<212> TYPE: DNA
<213> ORGANISM: Artificial Sequence
<220> FEATURE:
<223> OTHER INFORMATION: EIF4a rev primer

<400> SEQUENCE: 75
ccaagggtga aagcaagaag a 21

<210> SEQ ID NO 76
<211> LENGTH: 22
<212> TYPE: DNA
<213> ORGANISM: Artificial Sequence
<220> FEATURE:
<223> OTHER INFORMATION: LEC2 fwd primer

<400> SEQUENCE: 76
cgagaacaca ggagaatttg tg 22

<210> SEQ ID NO 77
<211> LENGTH: 23
<212> TYPE: DNA
<213> ORGANISM: Artificial Sequence
<220> FEATURE:
<223> OTHER INFORMATION: LEC2 rev primer

<400> SEQUENCE: 77
tcgactcatt ttctcttcct tca 23

<210> SEQ ID NO 78
<211> LENGTH: 21
<212> TYPE: DNA
<213> ORGANISM: Artificial Sequence
<220> FEATURE:
<223> OTHER INFORMATION: TTG1 fwd primer

<400> SEQUENCE: 78
catcctccgg tccacagaat c 21

<210> SEQ ID NO 79
<211> LENGTH: 20
<212> TYPE: DNA
<213> ORGANISM: Artificial Sequence
<220> FEATURE:
<223> OTHER INFORMATION: TTG1 rev primer

<400> SEQUENCE: 79
tttcggctct acatcgttcc 20

<210> SEQ ID NO 80
<211> LENGTH: 22
<212> TYPE: DNA
<213> ORGANISM: Artificial Sequence
<220> FEATURE:
<223> OTHER INFORMATION: AP2 fwd primer

<400> SEQUENCE: 80
aggaactcaa tgccgagtca tc 22

<210> SEQ ID NO 81
<211> LENGTH: 21
<212> TYPE: DNA
<213> ORGANISM: Artificial Sequence
<220> FEATURE:
<223> OTHER INFORMATION: AP2 rev primer

<400> SEQUENCE: 81
gttcatcctg agccgcatat c 21

<210> SEQ ID NO 82
<211> LENGTH: 16
<212> TYPE: DNA
<213> ORGANISM: Artificial Sequence
<220> FEATURE:
<223> OTHER INFORMATION: LEC1 fwd primer

<400> SEQUENCE: 82
ggcgccggtg acaaga 16

<210> SEQ ID NO 83
<211> LENGTH: 19
<212> TYPE: DNA
<213> ORGANISM: Artificial Sequence
<220> FEATURE:
<223> OTHER INFORMATION: LEC2 rev primer

<400> SEQUENCE: 83
gccacacatg gtggttgct 19

<210> SEQ ID NO 84
<211> LENGTH: 23
<212> TYPE: DNA
<213> ORGANISM: Artificial Sequence
<220> FEATURE:
<223> OTHER INFORMATION: WRI1 fwd primer

<400> SEQUENCE: 84
cacaaaggaa ttggaagaaa tgc 23

<210> SEQ ID NO 85
<211> LENGTH: 20
<212> TYPE: DNA
<213> ORGANISM: Artificial Sequence
<220> FEATURE:
<223> OTHER INFORMATION: WRI1 rev primer

<400> SEQUENCE: 85
tcccatcttc cgttgtggtg 20

<210> SEQ ID NO 86
<211> LENGTH: 25
<212> TYPE: DNA
<213> ORGANISM: Artificial Sequence
<220> FEATURE:
<223> OTHER INFORMATION: MYB118 fwd primer

<400> SEQUENCE: 86
gtctcagatt gctaagatgc ttcaa 25

<210> SEQ ID NO 87
<211> LENGTH: 23
<212> TYPE: DNA
<213> ORGANISM: Artificial Sequence
<220> FEATURE:
<223> OTHER INFORMATION: MYB118 rev primer

<400> SEQUENCE: 87
catccatctt tcttgatatc ggg 23

<210> SEQ ID NO 88
<211> LENGTH: 27
<212> TYPE: DNA
<213> ORGANISM: Artificial Sequence
<220> FEATURE:
<223> OTHER INFORMATION: AT2S3 promoter fwd primer

<400> SEQUENCE: 88
cacctagatt ccaaacaaaa accctcg 27

<210> SEQ ID NO 89
<211> LENGTH: 27
<212> TYPE: DNA
<213> ORGANISM: Artificial Sequence
<220> FEATURE:
<223> OTHER INFORMATION: AT2S3 promoter rev primer

<400> SEQUENCE: 89
gttttgctat ttgtgtatgt tttcttg 27

<210> SEQ ID NO 90
<211> LENGTH: 177
<212> TYPE: DNA
<213> ORGANISM: Brassica napus

<400> SEQUENCE: 90
tctttgcata gatcacctgc atttcgttga gtagattcat ttaaataagt agataaatag 60
attttattat catatttatt ttcttaacca tagtttttcc ttactacaat cataaaagaa 120
gaatatattt gtatctttgc atagatcata tatataatgt gaatgactaa tgtgtta 177

<210> SEQ ID NO 91
<211> LENGTH: 177
<212> TYPE: DNA
<213> ORGANISM: Brassica napus

<400> SEQUENCE: 91
tctttgcata gatcacctgc atttcgttga gtagattcat ttaaataagt agataaatag 60
attttattat catatttatt ttcttaacca tagtttttcc ttactacaat cataaaagaa 120
gaatatattt gtatctttgc atagatcata tatataatgt gaatgactaa tgtgtta 177

-continued

<210> SEQ ID NO 92
<211> LENGTH: 257
<212> TYPE: DNA
<213> ORGANISM: Brassica napus

<400> SEQUENCE: 92

```
tctttgcata gatcacctgc atttcattga gtagattcat ttaaataagt agatagatag     60

attttattat catatttatt ttcttaacca tcataaaaga agaatatatt tgtatctttg    120

catagatcat atatataatt gtaatgacta attattttct cgacaaacca tagtttttcc    180

ttactacaat cataaaagaa gaatatattt gtatctttgc atagatcata tatataatgt    240

gaatgagtaa tgtgtta                                                   257
```

<210> SEQ ID NO 93
<211> LENGTH: 257
<212> TYPE: DNA
<213> ORGANISM: Brassica napus

<400> SEQUENCE: 93

```
tctttgcata gatcacctgc atttcattga gtagattcat ttaaataagt agatagatag     60

attttattat catatttatt ttcttaacca tcataaaaga agaatatatt tgtatctttg    120

catagatcat atatataatt gtaatgacta attattttct cgacaaacca tagtttttcc    180

ttactacaat cataaaagaa gaatatattt gtatctttgc atagatcata tatataatgt    240

gaatgagtaa tgtgtta                                                   257
```

<210> SEQ ID NO 94
<211> LENGTH: 257
<212> TYPE: DNA
<213> ORGANISM: Brassica napus

<400> SEQUENCE: 94

```
tctttgcata gatcacctgc atttcattga gtagattcat ttaaataagt agatagatag     60

attttattat catatttatt ttcttaacca tcataaaaga agaatatatt tgtatctttg    120

catagatcat atatataatt gtaatgacta attattttct cgacaaacca tagtttttcc    180

ttactacaat cataaaagaa gaatatattt gtatctttgc atagatcata tatataatgt    240

gaatgagtaa tgtgtta                                                   257
```